US012358915B2

(12) United States Patent
Blackaby et al.

(10) Patent No.: US 12,358,915 B2
(45) Date of Patent: Jul. 15, 2025

(54) METTL3 INHIBITORY COMPOUNDS

(71) Applicant: STORM THERAPEUTICS LTD., Cambridge (GB)

(72) Inventors: Wesley Peter Blackaby, Cambridge (GB); David James Hardick, Cambridge (GB); Elizabeth Jane Thomas, Cambridge (GB); Frederick Arthur Brookfield, Abingdon (GB); Christian Bubert, Abingdon (GB); Jon Shepherd, Abingdon (GB); Mark Peter Ridgill, Abingdon (GB)

(73) Assignee: STORM THERAPEUTICS LTD., Cambridge (GB)

( * ) Notice: Subject to any disclaimer, the term of this patent is extended or adjusted under 35 U.S.C. 154(b) by 850 days.

(21) Appl. No.: 17/601,292

(22) PCT Filed: Apr. 3, 2020

(86) PCT No.: PCT/GB2020/050898
§ 371 (c)(1),
(2) Date: Oct. 4, 2021

(87) PCT Pub. No.: WO2020/201773
PCT Pub. Date: Oct. 8, 2020

(65) Prior Publication Data
US 2023/0085408 A1 Mar. 16, 2023

(30) Foreign Application Priority Data

Apr. 5, 2019 (GB) .................................... 1904848
Sep. 2, 2019 (GB) .................................... 1912603
Dec. 20, 2019 (GB) .................................... 1919095

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................... C07D 471/04
See application file for complete search history.

(56) References Cited

U.S. PATENT DOCUMENTS

| | | | |
|---|---|---|---|
| 3,946,031 A | 3/1976 | Beard | |
| 11,725,010 B2 * | 8/2023 | Blackaby | C07D 403/14 514/259.5 |
| 2003/0144281 A1 | 7/2003 | Cywin et al. | |
| 2009/0163488 A1 | 6/2009 | Oguro et al. | |
| 2010/0029619 A1 | 2/2010 | Uchikawa et al. | |

FOREIGN PATENT DOCUMENTS

| | | |
|---|---|---|
| WO | 2001010380 A2 | 2/2001 |
| WO | 2002044156 A2 | 6/2002 |
| WO | 2007095588 A1 | 8/2007 |
| WO | 2009106749 A2 | 9/2009 |
| WO | 2011113606 A | 9/2011 |
| WO | 2018169994 A1 | 9/2018 |

OTHER PUBLICATIONS

PCT Search Report and Written Opinion completed by the ISA/EP on May 13, 2020 and issued in connection with PCT/GB2020/050898.
Search Report dated Oct. 23, 2019 and issued in connection with GB Patent Application No. 1904848.7.
Akhtar, et al., "Design, synthesis, docking and QSAR study of substituted benzimidazole linked oxadiazole as cytotoxic agents, EGFR and erbB2 receptor inhibitors", European Journal of Medicinal Chemistry, vol. 126, 2017, pp. 853-869.
Guraiah et al., "Synthesis, characterization and biological activity of some novel benzimidazole linked 1,3,4-oxadiazoles".Heterocyclic letters, vol. 9(1), 2019, pp. 85-92.
Herath, Ananda, et al., "Continuous-flow synthesis of highly functionalized imidazo-oxadiazoles facilitated by microfluidic extraction", Beilstein Journal of Organic Chemistry, vol. 13, Jan. 6, 2017 (Jan. 6, 2017), p. 239-246.
Ukhin, L. Yu, et al., "Synthesis of phthalimidines linked to quinoline derivatives by an amide bridge", Russian Chemical Bulletin, Kluwer Academic Publishers—Plenum Publishers, NE,vol. 59, No. 5, Nov. 17, 2010 (Nov. 17, 2010), p. 1023-1030.
Ambinter Stock Collection catalogue, Oct. 2018, Compound of CAS registry number 1252380-76-9. See CHEMCATS accession No. 1602865722.
Registry Mar. 2, 2018 (Mar. 2, 2018), Database accession No. 2183120-12-7 Retrieved from the Internet: Url:Chemical Abstracts Service, Columbus, Ohio, US XP002798988, abstract.
Registry Feb. 21, 2018 (Feb. 21, 2018), Database accession No. 2177960-21-1 Retrieved from the Internet: URL:Chemical Abstracts Service, Columbus, Ohio, US XP002798989, abstract.
Registry Nov. 10, 2010 (Nov. 10, 2010), Database accession No. 125238-76-9 Retrieved from the Internet: URL:Chemical Abstracts Service, Columbus, Ohio, US XP002798990, abstract.
Registry Mar. 15, 2006 (Mar. 15, 2006), Database accession No. 876940-30-6 Retrieved from the Internet: URL:Chemical Abstracts Service, Columbus, Ohio, US XP002798992, abstract.

(Continued)

*Primary Examiner* — Golam M Shameem
(74) *Attorney, Agent, or Firm* — Barnes & Thornburg LLP

(57) ABSTRACT

The present invention relates to compounds of formula (I) that function as inhibitors of METTL3 (N6-adenosine-methyltransferase 70 kDa subunit) enzyme activity: X—Y—Z5 (I) wherein X, Y and Z are each as defined herein. The present invention also relates to processes for the preparation of these compounds, to pharmaceutical compositions comprising them, and to their use in the treatment of proliferative disorders, such as cancer, and autoimmune diseases, as well as other diseases or conditions in which METTL3 activity 10 is implicated.

18 Claims, 3 Drawing Sheets

(56) References Cited

OTHER PUBLICATIONS

Registry Feb. 25, 2009 (Feb. 25, 2009), Database accession No. 1111584-55-4 Retrieved from the Internet: URL:Chemical Abstracts Service, Columbus, Ohio, US XP002798991, abstract.
Registry Sep. 29, 2004 (Sep. 29, 2004), Database accession No. 753467-34-4 Retrieved from the Internet: URL:Chemical Abstracts Service, Columbus, Ohio, US XP002798993, abstract.
RegistryDatabase accession No. 879162-99-9 Retrieved from the Internet: URL:Chemical Abstracts Service, Columbus, Ohio, US XP002798994, abstract.
Registry Jul. 7, 2011 (Jul. 7, 2011), Database accession No. 1311663-16-7 Retrieved from the Internet: URL:Chemical Abstracts Service, Columbus, Ohio, US XP002798995, abstract.
Registry Sep. 15, 2010 (Sep. 15, 2010), Database accession No. 1241196-40-6 Retrieved from the Internet: URL:Chemical Abstracts Service, Columbus, Ohio, US XP002798996, abstract.
Registry Jul. 1, 2007 (Jul. 1, 2007), Database accession No. 924179-82-8 Retrieved from the Internet: URL:Chemical Abstracts Service, Columbus, Ohio, US XP002798997, abstract.
Barbieri, I., et al. Promoter-bound METTL3 maintains myeloid leukaemia by m6A-dependent translation control. Nature. Dec. 7, 2017; 552(7683): pp. 126-131.
Chandola, U., et al. Role of the N6-methyladenosine RNA mark in gene regulation and its implications on development and disease. Brief Funct Genomics. May 2015;14(3): pp. 169-179.
Cheng, M., et al. The m6A methyltransferase METTL3 promotes bladder cancer progression via AFF4/NF-κB/MYC signaling network. Oncogene (2019) 38: pp. 3667-3680. (Published: Jan. 18, 2019, e-publication ahead of print).
Fry, N.J., et al. N6-methyladenosine contributes to cellular phenotype in a genetically-defined model of breast cancer progression. Oncotarget. Jul. 27, 2018; 9(58): pp. 31231-31243.
Koranda, J.L., et al. Mettl14 Is Essential for Epitranscriptomic Regulation of Striatal Function and Learning. Neuron. Jul. 25, 2018; 99(2): pp. 283-292.
Li, H.B., et al. m6A mRNA methylation controls T cell homeostasis by targeting the IL-7/STAT5/SOCS pathways. Nature. Aug. 17, 2017; 548 (7667): pp. 338-342.
Li, X., et al. The M6A methyltransferase METTL3: acting as a tumor suppressor in renal cell carcinoma. Oncotarget. Oct. 10, 2017; 8(56): pp. 96103-96116.
Li, Y., et al. Genome-wide detection of high abundance N6-methyladenosine sites by microarray. RNA. Aug. 2015; 21 (8): pp. 1511-1518.
Lin, S., et al. The m6A Methyltransferase METTL3 Promotes Translation in Human Cancer Cells. Mol Cell. May 5, 2016; 62(3): pp. 335-345.
Liu J., et al. A METTL3-METTL14 complex mediates mammalian nuclear RNA N6-adenosine methylation. Nat Chem Biol. Feb. 2014; 10(2): pp. 93-95.
Meyer, K.D., et al. 50 UTR m6A Promotes Cap-Independent Translation. Cell. Nov. 5, 2015; 163(4): pp. 999-1010.
Meyer, K.D., et al. The dynamic epitranscriptome: N6-methyladenosine and gene expression control. Nat Rev Mol Cell Biol. May 2014; 15(5): pp. 313-326.
Meyer, K.D., et al. Comprehensive Analysis of mRNA Methylation Reveals Enrichment in 30 UTRs and near Stop Codons. Cell. Jun. 22, 2012;149(7): pp. 1635-1646.
Ping, X.L., et al. Mammalian WTAP is a regulatory subunit of the RNA N6-methyladenosine methyltransferase. Cell Res.Feb. 2014;24(2): pp. 177-189.
Śledź, P. and Jinek, M. Structural insights into the molecular mechanism of the m6A writer complex. Elife. Sep. 14, 2016;5. 16 pages.
Vu, L.P., et al. The N6-methyladenosine (m6A)-forming enzyme METTL3 controls myeloid differentiation of normal hematopoietic and leukemia cells. Nat Med. Nov. 2017;23(11): pp. 1369-1376.
Wang, X., et al. Structural basis of N6-adenosine methylation by the METTL3-METTL14 complex. Nature. Jun. 23, 2016;534(7608): pp. 575-578.
Wang, P., et al. Structural Basis for Cooperative Function of Mettl3 and Mettl14 Methyltransferases. Mol Cell. Jul. 21, 2016;63(2): pp. 306-317.
Winkler, R., et al. m6A modification controls the innate immune response to infection by targeting type I interferons. Nature Immunology. Feb. 2019. vol. 20. pp. 173-182. (Published: Dec. 17, 2018, e-publication ahead of print).
Yue, Y., et al. RNA N6-methyladenosine methylation in post-transcriptional gene expression regulation. Genes Dev. Jul. 1, 2015;29(13): pp. 1343-1355.
Niu, Y., et al. N6-methyl-adenosine (m6A) in RNA: An Old Modification with a Novel Epigenetic Function. Genomics Proteomics Bioinformatics. Feb. 2013;11(1): pp. 8-17.
Registry Database Entries, cited in CN202080040641A. 10 entries. Chemical Abstracts Service, Columbus, Ohio, US. pp. 1-3.
Registry Database Entries (XP093038056), List of relevant ChemCats Compounds cited in EP20718757A. 106 entries. Chemical Abstracts Service, Columbus, Ohio, US. pp. 1-49.
Registry Database Entries, cited in JP2021560410A. 9 entries. Chemical Abstracts Service, Columbus, Ohio, US. pp. 1-5.

* cited by examiner

METTL3 INHIBITORY COMPOUNDS

CROSS-REFERENCE TO RELATED CASES

This application is a U.S. national counterpart application of international application serial No. PCT/GB2020/050898 filed Apr. 3, 2020, which claims priority to Great Britain Patent Application Nos. 1904848.7, filed Apr. 5, 2019, 1912603.6, filed Sep. 2, 2019, and 1919095.8 filed Dec. 20, 2019, the contents of each are incorporated herein by reference.

FIELD OF THE INVENTION

The present invention relates to certain compounds that function as inhibitors of METTL3 (N6-adenosine-methyltransferase 70 kDa subunit) activity. The present invention also relates to processes for the preparation of these compounds, to pharmaceutical compositions comprising them, and to their use in the treatment of proliferative disorders, such as cancer, autoimmune, neurological, infectious and inflammatory diseases, as well as other diseases or conditions in which METTL3 activity is implicated.

BACKGROUND OF THE INVENTION

N6-methyladenosine (m6A) is the most common and abundant covalent modification of messenger RNA, modulated by 'writers', 'erasers' and 'readers' of this mark (Meyer & Jaffrey 2014, Niu Y et al, 2013, Yue et al 2015). Approximately 0.1 to 0.5% of all mRNA adenosines are m6A modified (Li Y et al 2015). In vitro data have shown that m6A influences fundamental aspects of mRNA biology, mainly mRNA expression, splicing, stability, localisation and translation (Meyer et al, 2015; Sledz & Jinek 2016). M6A modifications are tissue specific and there is significant variability in their occurrence profiles in non-diseased tissues (eg brain, heart, kidney) and diseased tissues and cells (lung, renal, breast, and leukeamic cancer cells) (Meyer et al 2012).

The m6A modifications and its erasers and writers such as FTO, ALKBH5, methyltransferese like 3 (METTL3) and METTL14 are associated with major diseases such as solid organ cancers, leukaemia, type 2 diabetes, neuropsychiatric behavioural and depressive disorders (Chandola et al 2015; Koranda et al 2018).

The RNA methyltransferase, METTL3, is the major, but not the sole enzyme, that catalyses m6A modification of RNA. It exists as a hetero-trimeric complex with METTL14 (Liu et al 2014, Wang et al 2016) and Wilm's Tumour Associated Protein (WTAP) (Ping et al 2014). Catalytic activity resides in METTL3, which transfers a methyl group from the co-factor S-adenosyl methionine to the substrate RNA and METTL14 facilitates substrate RNA binding. WTAP localises the complex in specific nuclear regions and also localises RNA substrates to the complex (Wang X et al 2016).

METTL3 has been reported to play a role in many aspects of the development of cancer (Fry et al 2018). Genetic knockdown of METTL3 in lung cancer cell lines (A549, H1299 and H1792) and HeLa cells leads to decreased growth, survival and invasion of human lung cancer cells (Lin S et al 2016). METTL3 is significantly up-regulated in human bladder cancer (Cheng et al 2019). Knockdown of METTL3 drastically reduced bladder cancer cell proliferation, invasion, and survival in vitro and tumorigenicity in vivo. AF4/FMR2 family member 4 (AFF4), two key regulators of NF-κB pathway (IKBKB and RELA) and MYC were further identified as direct targets of METTL3-mediated m6A modification. In renal carcinoma cell lines (CAK-1, CAK-2 and ACHN), genetic knockdown reduced cell proliferation via the phosphatidinylinositol 3-kinase (PI3K)/AKT/mammalian target of rapamycin (mTOR) signalling pathway (Li X et al 2017).

Recently Barbieri et al (2017), defined a set of RNA-modifying enzymes that are necessary for AML leukaemia and identified a key leukaemic pathway for the METTL3 RNA methyltransferase. In this pathway, METTL3 is stably recruited by the CCAAT-box binding transcription factor CEBPZ to promoters of a specific set of active genes, resulting in m6A methylation of the respective mRNAs and increased translation. One important target is SP1, an oncogene in several cancers, which regulates c-MYC expression. Consistent with these findings, it has been reported that METTL3 can methylate its targets co-transcriptionally.

The pathway described by Barbieri et al., is critical for AML leukaemia, as three of its components are required for AML cell growth: (i) the m6A RNA methyltransferase METTL3; (ii) the transcription factor CEBPZ, which targets this enzyme to promoters; and (iii) SP1, whose translation is dependent upon the m6A modification by METTL3. Together, the observations of Barbieri et al define METTL3 enzymatic activity as a new candidate target for the treatment of AML.

In separate, independent studies it has been reported that METTL3 plays an essential role in controlling myeloid differentiation of mammalian normal hematopoietic and leukemic cells (Vu et al 2017). Forced expression of wild type METTL3, but not a mutant METTL3 (with defect in catalytic activity), significantly promotes cell proliferation and inhibits cell differentiation of human cord blood-derived CD34+ haematopoietic stem/progenitor cells (HSPCs). Genetic knockdown of METTL3 has the opposite effects. METTL3 is highly expressed in AML compared to normal HSPCs or other types of cancers. Knockdown of METTL3 in human AML cell lines significantly induces cell differentiation and apoptosis and inhibits leukemia progression in mice xeno-transplanted with MOLM-13 AML cells. The biological function of METTL3 is likely attributed to the promotion of translation of its mRNA targets such as MYC, BCL-2, and PTEN in an m6A-dependent manner.

Recently, METTL3 mediated m6A modification has been demonstrated to play an important role in T cell homeostasis and signal dependent induction of mRNA degradation in CD4 positive T cell lineages (Li et al 2017). Deletion of METTL3 in mouse T cells disrupts T cell homeostasis and differentiation. In a lymphopenic mouse adoptive transfer model, naive Mettl3-deficient T cells failed to undergo homeostatic expansion and remained in the naive state for up to 12 weeks, thereby preventing colitis. Consistent with these observations, the mRNAs of SOCS family genes encoding the STAT signalling inhibitory proteins SOCS1, SOCS3 and CISH were marked by m6A, exhibited slower mRNA decay and showed increased mRNAs and levels of protein expression in Mettl3-deficient naive T cells. This increased SOCS family activity consequently inhibited IL-7-mediated STAT5 activation and T cell homeostatic proliferation and differentiation. Thus METTL3 mediated m6A methylation has important roles for inducible degradation of Socs mRNAs in response to IL-7 signalling in order to reprogram naive T cells for proliferation and differentiation, pointing to a role in auto-immunity.

Recent studies have revealed that depletion of METTL3 leads to alterations in the propagation of diverse viruses (Winkler et al). Following viral infection or stimulation of cells with an inactivated virus, deletion of the m6A 'writer' METTL3 led to an increase in the induction of interferon-stimulated genes. Consequently, propagation of different viruses was suppressed in an interferon-signaling-dependent manner. Significantly, the mRNA of IFNB, was m6A modified and was stabilized following repression of METTL3. m6A serves as a negative regulator of interferon response by dictating the fast turnover of interferon mRNAs and consequently facilitating viral propagation. Therefore METTL3 inhibitors may provide a novel therapeutic approach to a range of infectious and inflammatory diseases.

REFERENCES

Barbieri I, Tzelepis K, Pandolfini L, Shi J, Millán-Zambrano G, Robson S C, Aspris D, Migliori V, Bannister A J, Han N, De Braekeleer E, Ponstingl H, Hendrick A, Vakoc C R, Vassiliou G S, Kouzarides T. Nature. 2017 Dec. 7; 552 (7683):126-131.
Chandola U, Das R, Panda B. Brief Funct Genomics. 2015 May; 14(3):169-79.
Cheng M, Gao Q, Wu M, Liang Y, Zhu F, Zhang Y, Zhang X, Li Y, Sheng L, Zhang H, Xiong Q, Yuan Q, Oncogene (2019; e-publication ahead of print).
Fry N J, Law B A, Ilkayeva O R, Carraway K R, Holley C L, Mansfield K D. Oncotarget. 2018 Jul. 27; 9(58):31231-31243.
Koranda J L, Dore L, Shi H, Patel M J, Vaasjo L O, Rao M N, Chen K, Lu Z, Yi Y, Chi W, He C, Zhuang X. Neuron. 2018 Jul. 25; 99(2): 283-292.
Li H B, Tong J, Zhu S, Batista P J, Duffy E E, Zhao J, Bailis W, Cao G, Kroehling L, Chen Y, Wang G, Broughton J P, Chen Y G, Kluger Y, Simon M D, Chang H Y, Yin Z, Flavell R A. Nature. 2017 Aug. 17; 548 (7667):338-342
Li X, Tang J, Huang W, Wang F, Li P, Qin C, Qin Z, Zou Q, Wei J, Hua L, Yang H, Wang Z. Oncotarget. 2017 Oct. 10; 8(56):96103-96116.
Li Y, Wang Y, Zhang Z, Zamudio A V, Zhao J C. RNA. 2015 August; 21(8):1511-8.
Lin S, Choe J, Du P, Triboulet R, Gregory R I. Mol Cell. 2016 May 5; 62(3):335-345.
Liu J, Yue Y, Han D, Wang X, Fu Y, Zhang L, Jia G, Yu M, Lu Z, Deng X, Dai Q, Chen W, He C. Nat Chem Biol. 2014 February; 10(2):93-5.
Meyer K D, Patil D P, Zhou J, Zinoviev A, Skabkin M A, Elemento O, Pestova T A, Qian S B, Jaffrey S R. Cell. 2015 Nov. 5; 163(4): 999-1010.
Meyer K D, Jaffrey S R. Nat Rev Mol Cell Biol. 2014 May; 15(5):313-26.
Meyer K D, Saletore Y, Zumbo P, Elemento O, Mason C E, Jaffrey S R. Cell. 2012 Jun. 22; 149(7):1635-46.
Niu Y, Zhao X, Wu Y S, Li M M, Wang X J, Yang Y G. Genomics Proteomics Bioinformatics. 2013 February; 11(1):8-17.
Ping X L, Sun B F, Wang L, Xiao W, Yang X, Wang W J, Adhikari S, Shi Y, Lv Y, Chen Y S, Zhao X, Li A, Yang Y, Dahal U, Lou X M, Liu X, Huang J, Yuan W P, Zhu X F, Cheng T, Zhao Y L, Wang X, Rendtlew Danielsen J M, Liu F, Yang Y G. Cell Res. 2014 February; 24(2):177-89.
Śledź P, Jinek M. Elife. 2016 Sep. 14; 5.
Vu L P, Pickering B F, Cheng Y, Zaccara S, Nguyen D, Minuesa G, Chou T, Chow A, Saletore Y, MacKay M, Schulman J, Famulare C, Patel M, Klimek V M, Garrett-Bakelman F E, Melnick A, Carroll M, Mason C E, Jaffrey S R, Kharas M G. Nat Med. 2017 November; 23(11): 1369-1376.
Wang X, Feng J, Xue Y, Guan Z, Zhang D, Liu Z, Gong Z, Wang Q, Huang J, Tang C, Zou T, Yin P. Nature. 2016 Jun. 23; 534(7608):575-8
Wang P, Doxtader K A, Nam Y. Mol Cell. 2016 Jul. 21; 63(2):306-317.
Winkler R, Gillis E, Lasman L, Safra M, Geula S, Soyris C, Nachshon A, Tai-Schmiedel J, Friedman N, Le-Trilling Vu T K, Trilling M, Mandelboim M, Hanna, J H, Schwartz S, Stern-Ginossar N. Nature Immunology (2018, e-publication ahead of print).
Yue Y, Liu J, He C. Genes Dev. 2015 Jul. 1; 29(13):1343-55

An object of this invention is to provide inhibitors of METTL3 activity.

SUMMARY OF THE INVENTION

In one aspect, the present invention provides a compound as defined herein, or a pharmaceutically acceptable salt thereof.

In another aspect, the present invention provides a pharmaceutical composition as defined herein which comprises a compound as defined herein, or a pharmaceutically acceptable salt thereof, and one or more pharmaceutically acceptable excipients.

In another aspect, the present invention provides a compound as defined herein, or a pharmaceutically acceptable salt thereof, or a pharmaceutical composition as defined herein, for use in therapy.

In another aspect, the present invention provides a compound as defined herein, or a pharmaceutically acceptable salt thereof, or a pharmaceutical composition as defined herein, for use in the treatment of a proliferative condition.

In another aspect, the present invention provides a compound as defined herein, or a pharmaceutically acceptable salt thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt thereof, or a pharmaceutical composition as defined herein, for use in the inhibition of METTL3 activity.

In another aspect, the present invention provides a compound as defined herein, or a pharmaceutically acceptable salt thereof, or a pharmaceutical composition as defined herein, for use in the treatment of an autoimmune disease.

In another aspect, the present invention provides a compound as defined herein, or a pharmaceutically acceptable salt thereof, or a pharmaceutical composition as defined herein, for use in the treatment of a neurological disease.

In another aspect, the present invention provides a compound as defined herein, or a pharmaceutically acceptable salt thereof, or a pharmaceutical composition as defined herein, for use in the treatment of an infectious disease.

In another aspect, the present invention provides a compound as defined herein, or a pharmaceutically acceptable salt thereof, or a pharmaceutical composition as defined herein, for use in the treatment of an inflammatory disease.

In another aspect, the present invention provides the use of a compound as defined herein, or a pharmaceutically acceptable salt thereof, in the manufacture of a medicament for use in the treatment of a proliferative condition.

In another aspect, the present invention provides the use of a compound as defined herein, or a pharmaceutically acceptable salt thereof, in the manufacture of a medicament for use in the treatment of cancer. In a particular embodiment, the medicament is for use in the treatment of human cancers.

In another aspect, the present invention provides the use of a compound as defined herein, or a pharmaceutically acceptable salt thereof, in the manufacture of a medicament for the inhibition of METTL3 activity.

In another aspect, the present invention provides the use of a compound as defined herein, or a pharmaceutically acceptable salt thereof, in the manufacture of a medicament for use in the treatment of an autoimmune disease.

In another aspect, the present invention provides the use of a compound as defined herein, or a pharmaceutically acceptable salt thereof, in the manufacture of a medicament for use in the treatment of a neurological disease.

In another aspect, the present invention provides the use of a compound as defined herein, or a pharmaceutically acceptable salt thereof, in the manufacture of a medicament for use in the treatment of an infectious disease.

In another aspect, the present invention provides the use of a compound as defined herein, or a pharmaceutically acceptable salt thereof, in the manufacture of a medicament for use in the treatment of an inflammatory disease.

In another aspect, the present invention provides a method of inhibiting METTL3 activity in vitro or in vivo, said method comprising contacting a cell with an effective amount of a compound as defined herein, or a pharmaceutically acceptable salt thereof, or a pharmaceutical composition as defined herein.

In another aspect, the present invention provides a method of inhibiting cell proliferation in vitro or in vivo, said method comprising contacting a cell with an effective amount of a compound as defined herein, or a pharmaceutically acceptable salt, or a pharmaceutical composition as defined herein.

In another aspect, the present invention provides a method of inhibiting metastasis in vitro or in vivo, said method comprising contacting a cell with an effective amount of a compound as defined herein, or a pharmaceutically acceptable salt, or a pharmaceutical composition as defined herein.

In another aspect, the present invention provides a method of treating a proliferative disorder, said method comprising administering to a subject in need thereof a therapeutically effective amount of a compound as defined herein, or a pharmaceutically acceptable salt, or a pharmaceutical composition as defined herein.

In another aspect, the present invention provides a method of treating cancer, said method comprising administering to a subject in need thereof a therapeutically effective amount of a compound as defined herein, or a pharmaceutically acceptable salt, or a pharmaceutical composition as defined herein.

In another aspect, the present invention provides a method of treating an autoimmune disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating a neurological disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating an infectious disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating an inflammatory disease, said method comprising administering to a subject in need thereof a therapeutically effective amount of a compound as defined herein, or a pharmaceutically acceptable salt, or a pharmaceutical composition as defined herein.

In one aspect, the present invention provides a combination comprising a compound as defined herein, or a pharmaceutically acceptable salt thereof, with one or more additional therapeutic agents.

The present invention further provides a method of synthesising a compound, or a pharmaceutically acceptable salt, as defined herein.

In another aspect, the present invention provides a compound as defined herein, or a pharmaceutically acceptable salt, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

BRIEF DESCRIPTION OF THE DRAWINGS

For a better understanding of the invention, and to show how embodiments of the same are put into effect, reference is now made, by way of example, to the following figures, in which.

DETAILED DESCRIPTION OF THE INVENTION

Definitions

Figure 1:
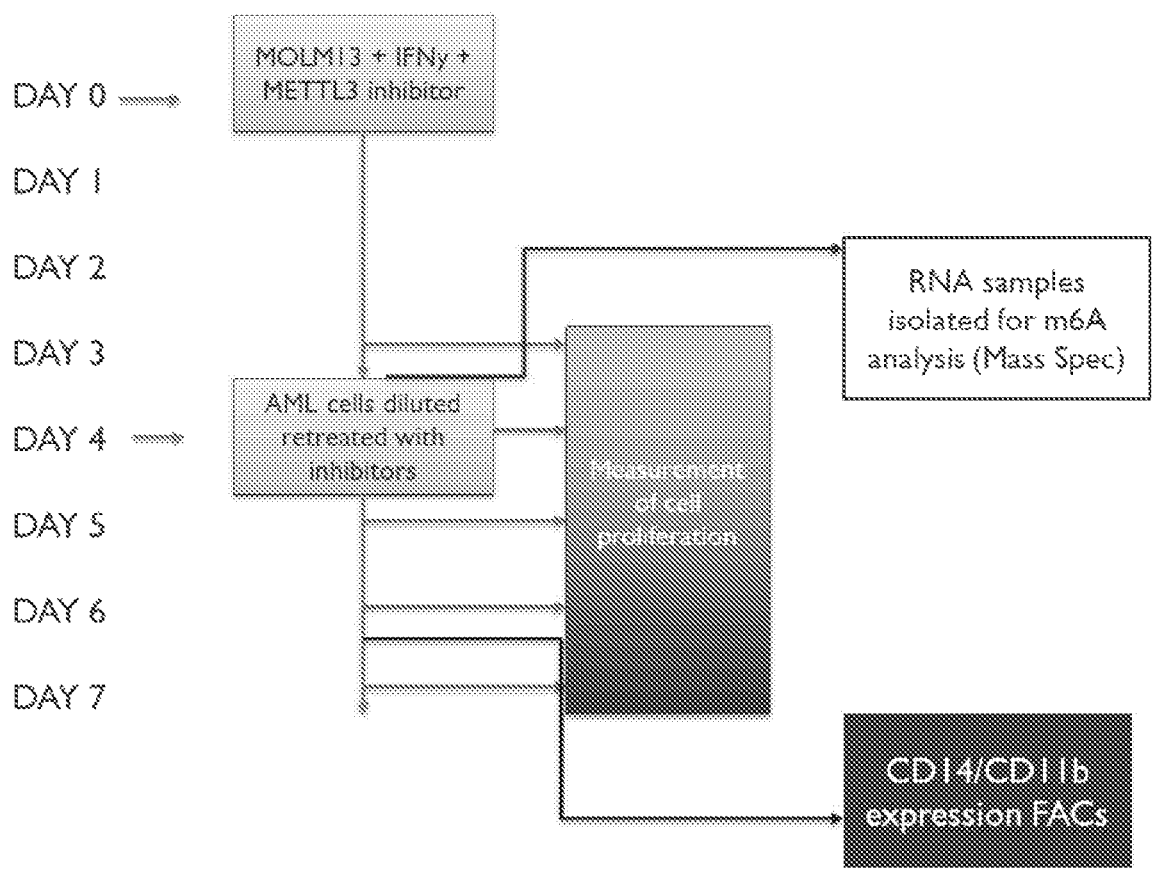
FIG. 1: Schematic of the MOLM13 AML proliferation assay with measurement of m6A levels

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl($C_{1-6}$alkyl)" includes phenyl($C_{1-4}$alkyl), benzyl, 1-phenylethyl and 2-phenylethyl.

The term "(m-nC)" or "Cm-n", or "(m-nC) group" or "Cm-n" used alone or as a prefix, refers to any group having m to n carbon atoms.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

An "alkylene" group is an alkyl group that is positioned between and serves to connect two other chemical groups. Thus, "$C_{1-3}$alkylene" means a linear saturated divalent hydrocarbon radical of one to three carbon atoms or a branched saturated divalent hydrocarbon radical of three atoms, for example, methylene, ethylene, propylene, and the like.

The term "$C_{m-n}$cycloalkyl" means a hydrocarbon ring containing from m to n carbon atoms, for example "$C_{3-6}$cycloalkyl" means a hydrocarbon ring containing from 3 to 6 carbon atoms, for example, cyclopropyl, cyclobutyl, cyclopentyl, cyclohexyl. The term "$C_{m-n}$cycloalkyl" also encompasses non-aromatic saturated or partially saturated monocyclic, fused, bridged, or spiro bicyclic carbocyclic ring system(s). The term "$C_{m-n}$cycloalkyl" includes both monovalent species and divalent species. Monocyclic "$C_{m-n}$cycloalkyl" rings contain from about 3 to 12 (suitably from 3 to 8, most suitably from 5 to 6) ring carbon atoms. Bicyclic "$C_{m-n}$cycloalkyl" contain from 7 to 17 ring carbon atoms, suitably 7 to 12 ring carbon atoms. Bicyclic "$C_{m-n}$cycloalkyl" rings may be fused, spiro (e.g. spiro[3,3]heptane), or bridged ring systems (e.g. bicyclo[2.2.1]hept-2-ene and bicyclo[1.1.1]pentanyl).

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7, most suitably from 5 to 6) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxo-imidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, quinuclidine, 6-azabicyclo[3.1.1]heptane, 8-azabicyclo[3.2.1]octane, bicyclo[3.2.1]octane, 7-oxabicyclo[2.2.1]hept-2-ene and 3-oxa-8-azabicyclo[3.2.1]octane.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds of the formula (I), or a pharmaceutically acceptable salt thereof, $$X-Y-Z \quad (I)$$

wherein:
X is selected from:

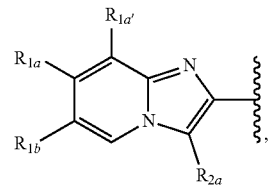

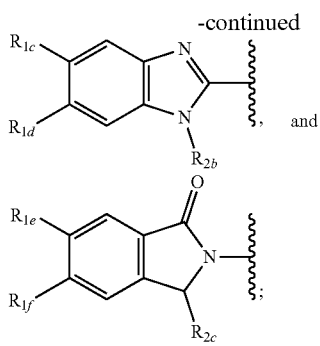

wherein:

$R_{1a}$, $R_{1b}$, $R_{1c}$, $R_{1d}$, $R_{1e}$ and $R_{1f}$ are independently selected from hydrogen, cyano, halo or a group of the formula:

-$L_{1a}$-$L_{1b}$-$Q_1$ wherein $L_{1a}$ is absent or selected from $C_{1-3}$alkylene and $C_{3-5}$cycloalkylene, wherein $C_{1-3}$alkylene and $C_{3-5}$cycloalkylene are optionally substituted by one or more substituents selected from aryl, aryl-(1-2C)alkyl, heteroaryl, aryl-(1-2C)alkyl, $C_{1-3}$alkyl, cyano, $C_{1-3}$alkoxy, halo, hydroxy, $C_{1-3}$haloalkoxy, —O—$C_{3-4}$cycloalkyl, $NH_2$ or oxo; wherein any —O—$C_{3-6}$cycloalkyl aryl, aryl-(1-2C)alkyl, heteroaryl, aryl-(1-2C)alkyl or $C_{1-3}$alkyl is optionally further substituted by one or more substituents selected from cyano, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally further substituted with halo, cyano or hydroxy; or $C_{1-3}$alkylene is optionally spiro-fused to a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$L_{1b}$ is absent or selected from O, S, SO, $SO_2$, $N(R_r)$, C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or $C_{1-3}$alkyl, wherein $C_{1-3}$alkyl is optionally further substituted by cyano, hydroxy, $C_{1-2}$alkoxy, halo, $C_{1-2}$haloalkoxy, $NH_2$, $C_{3-6}$-cycloalkyl or a 3 to 6 membered heterocyclyl, wherein the $C_{3-6}$cycloalkyl or a 3 to 6 membered heterocyclyl in turn are optionally further substituted by halo, hydroxy, $C_{1-2}$alkoxy or $C_{1-2}$haloalkoxy; and $Q_1$ is hydrogen, cyano, $C_{1-6}$alkyl, $C_{3-6}$cycloalkyl (including a spirocyclic carbocyclic and a bridged $C_{3-6}$cycloalkyl), $C_{2-3}$alkenyl, $C_{2-3}$alkynyl, aryl, heterocyclyl (including a mono- or bicyclic-heterocyclic ring system, a spirocyclic heterocyclic ring system, or a bridged heterocyclic ring system) or heteroaryl; and wherein $Q_1$ is optionally substituted by one or more substituents selected from $C_{1-4}$alkyl, halo, trifluoromethyl, trifluoromethoxy, amino, oxo, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, —S(O)$_{0-2}$R$_t$R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein $C_{1-4}$alkyl is in turn optionally substituted by one more substituents selected from cyano, hydroxy, $C_{1-2}$alkoxy, halo, $C_{1-2}$haloalkoxy, —O—$C_3$cycloalkyl, wherein —O—$C_3$cycloalkyl is optionally substituted with halo, cyano or hydroxy; and wherein $R_t$ and $R_u$ are each independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), C(O)N(R$_v$), N(R$_v$)C(O), N(R$_v$)C(O)N(R$_w$), S(O)$_2$N(R$_v$), or N(R$_v$)SO$_2$, wherein R$_v$ and R$_w$ are each independently selected from hydrogen or $C_{1-2}$alkyl; and $Z_1$ is $C_{3-8}$cycloalkyl (including a spirocyclic carbocyclic and a bridged $C_{3-8}$cycloalkyl), heterocyclyl (including a mono- or bicyclic-heterocyclic ring system, a spirocyclic heterocyclic ring system, or a bridged heterocyclic ring system), aryl or heteroaryl, wherein $Z_1$ is optionally substituted by one or more substituents selected from $C_{1-4}$alkyl, $C_{3-6}$cycloalkyl, heterocyclyl, halo, $C_{1-4}$haloalkyl, $C_{1-4}$haloalkoxy, $C_{1-4}$alkoxy, cyano, hydroxyl, NR$_{t1}$R$_{u1}$, OR$_{t1}$, C(O)R$_{t1}$, C(O)OR$_{t1}$, OC(O)R$_{t1}$, C(O)N(R$_{t1}$)R$_{u1}$, N(R$_{t1}$)C(O)R$_{u1}$, —S(O)$_{0-2}$R$_{t1}$R$_{u1}$, S(O)$_y$R$_{t1}$ (where y is 0, 1 or 2), SO$_2$N(R$_{t1}$)R$_{u1}$, N(R$_{t1}$)SO$_2$R$_{u1}$ or (CH$_2$)$_z$NR$_{t1}$R$_{u1}$ (where z is 1, 2 or 3), wherein R$_{t1}$ and R$_{u1}$ are each independently selected from hydrogen or $C_{1-4}$alkyl; and when $Z_1$ is $C_{3-6}$cycloalkyl or heterocyclyl, $Z_1$ is optionally spiro-fused to a $C_{3-6}$cycloalkyl or heterocyclyl ring;

$R_{1a'}$ is selected from hydrogen, halo and methyl;

$R_{2a}$, $R_{2b}$ and $R_{2c}$ are selected from hydrogen, halo or a group of the formula:

-$L_{2a}$-$L_{2b}$-$Q_2$ wherein $L_{2a}$ is absent or $C_{1-3}$alkylene optionally substituted by $C_{1-2}$ alkyl or oxo;

$L_{2b}$ is absent or selected from O, S, SO, $SO_2$, $N(R_n)$, C(O), C(O)O, OC(O), C(O)N($R_n$), N($R_n$)C(O), N($R_n$)C(O)N($R_o$), S(O)$_2$N($R_n$), or N($R_n$)SO$_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, NR$_p$R$_q$, OR$_p$, C(O)R$_p$, C(O)OR$_p$, OC(O)R$_p$, C(O)N(R$_p$)R$_q$, N(R$_r$)C(O)R$_p$, S(O)$_y$R$_p$ (where y is 0, 1 or 2), SO$_2$N(R$_p$)R$_q$, N(R$_r$)SO$_2$R$_p$ or (CH$_2$)$_z$NR$_p$R$_q$ (where z is 1, 2 or 3), wherein R$_p$ and R$_q$ are each independently selected from hydrogen or $C_{1-4}$alkyl;

Y is selected from:

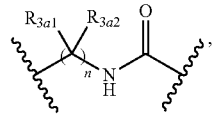 , 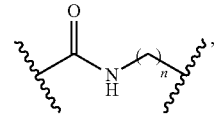 ,

-continued

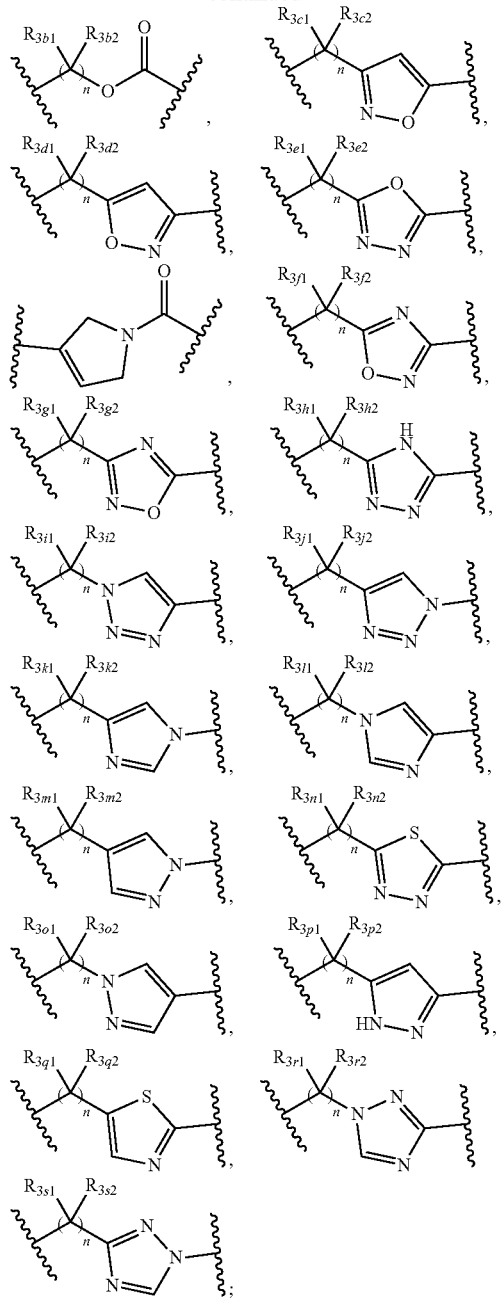

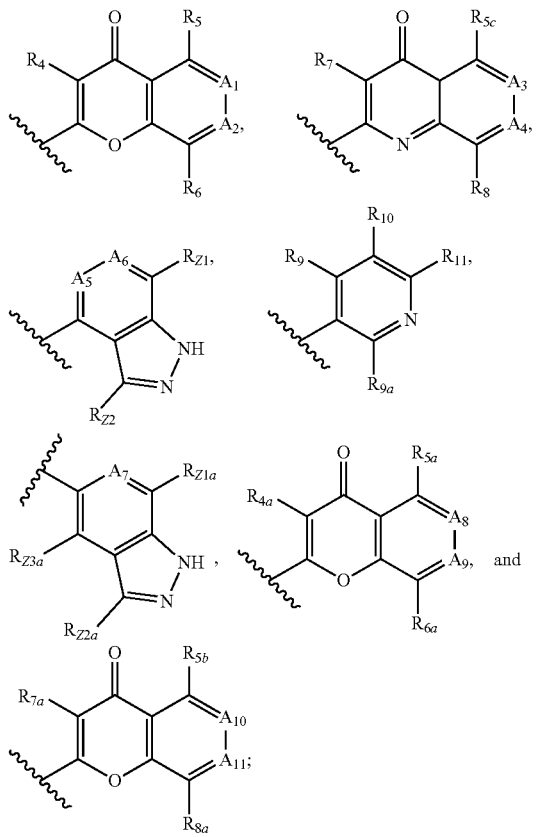

wherein:
R$_{3a1}$, R$_{3b1}$, R$_{3c1}$, R$_{3d1}$, R$_{3e1}$, R$_{3f1}$, R$_{3g1}$, R$_{3h1}$, R$_{3i1}$, R$_{3j1}$, R$_{3k1}$, R$_{3l1}$, R$_{3m1}$, R$_{3n1}$, R$_{3o1}$, R$_{3p1}$, R$_{3q1}$, R$_{3r1}$ and R$_{3s1}$ are independently selected from hydrogen (including deuterium), C$_{1-6}$alkyl, C$_{3-4}$ cycloalkyl, hydroxy, and halo; and wherein C$_{1-6}$alkyl, or C$_{3-4}$ cycloalkyl is optionally substituted with one or more substituents selected from halo, amino, cyano, and hydroxy;

R$_{3a2}$, R$_{3b2}$, R$_{3c2}$, R$_{3d2}$, R$_{3e2}$, R$_{3f2}$, R$_{3g2}$, R$_{3h2}$, R$_{3i2}$, R$_{3j2}$, R$_{3k2}$, R$_{3l2}$, R$_{3m2}$, R$_{3n2}$, R$_{3o2}$, R$_{3p2}$, R$_{3q2}$, R$_{3r2}$ and R$_{3s2}$ are hydrogen or halo;

with the proviso that R$_{3a1}$, R$_{3b1}$, R$_{3i1}$, R$_{3l1}$, R$_{3o1}$, R$_{3r1}$, R$_{3a2}$, R$_{3b2}$, R$_{3i2}$, R$_{3l2}$, R$_{3o2}$ and R$_{3s1}$ cannot be halo when n=1 or when n=2 and the carbon atom to which they are attached is linked to an oxygen or nitrogen atom;

or R$_{3a1}$ and R$_{3a2}$, R$_{3b1}$ and R$_{3b2}$, R$_{3c1}$ and R$_{3c2}$, R$_{3d1}$ and R$_{3d2}$, R$_{3e1}$ and R$_{3e2}$, R$_{3f1}$ and R$_{3f2}$, R$_{3g1}$ and R$_{3g2}$, R$_{3h1}$ and R$_{3h2}$, R$_{3i1}$ and R$_{3i2}$, R$_{3j1}$ and R$_{3j2}$, R$_{3k1}$ and R$_{3k2}$, R$_{3l1}$ and R$_{3l2}$, R$_{3m1}$ and R$_{3m2}$, R$_{3n1}$ and R$_{3n2}$, R$_{3o1}$ and R$_{3o2}$, R$_{3p1}$ and R$_{3p2}$, R$_{3q1}$ and R$_{3q2}$, or R$_{3r1}$ and R$_{3r2}$ or R$_{3s1}$ and R$_{3s2}$ may be linked such that, together with the carbon atom to which they are attached, they form a spiro-fused C$_{3-4}$cycloalkyl which is optionally substituted with one or more substituents selected from halo, methyl, amino, cyano, and hydroxy;

Z is selected from:

wherein:
R$_4$, R$_7$, R$_{4a}$ and R$_{7a}$ are independently selected from hydrogen, halo, cyano and methyl;
R$_5$, R$_{5a}$, R$_{5b}$ and R$_{5c}$ are independently selected from hydrogen, halo, cyano and methyl;
R$_6$, R$_8$, R$_{6a}$ and R$_{8a}$ are independently selected from hydrogen, halo, cyano and methyl;
R$_9$, R$_{9a}$, R$_{10}$ and R$_{11}$ are independently selected from hydrogen, NH$_2$, halo, cyano, and C$_{1-6}$ alkyl; or
R$_9$ and R$_{10}$ may be linked together to form a fused 5- or 6-membered saturated or unsaturated ring system or R$_{10}$ and R$_{11}$ may be linked together to form a fused 5- or 6-membered saturated or unsaturated ring system; wherein either of the fused 5- or 6-membered saturated or unsaturated ring system may be optionally substituted by one or more substituents selected from C$_{1-2}$alkyl, cyano, C$_{1-2}$haloalkyl, hydroxy, $C_{1-2}$ alkoxy, halo, $C_{1-2}$haloalkoxy, $NR_{1ia}R_{1ja}$ or $—S(O)_{0-2}R_{1ia}R_{1ja}$, wherein $R_{1ia}$ and $R_{1ja}$ are H or $C_{1-2}$alky;

$R_{Z1}$ and $R_{Z1a}$ are selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and $—O—C_{3-6}$cycloalkyl, wherein $C_{3-6}$cycloalkyl and $—O—C_{3-6}$cycloalkyl are optionally substituted by one or more of halo, methyl or methoxy;

$R_{Z2}$ and $R_{Z2a}$ are selected from hydrogen, $C_{1-4}$alkyl, cyano, halo, $NH_2$ and $C_{1-4}$alkoxy;

$R_{Z3a}$ is selected from hydrogen, $C_{1-4}$alkyl, cyano, halo, $NH_2$ and $C_{1-4}$alkoxy $A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;
$R_{12}$ and $R_{14}$ are independently selected from hydrogen, halo, cyano and $C_{1-4}$ alkyl;
$R_{13}$ is selected from hydrogen, halo, cyano, methoxy and methyl;
$R_{15}$ is selected from hydrogen, halo, cyano methoxy and methyl;
$R_{16}$ is selected from hydrogen, halo, cyano, $C_{1-4}$ alkyl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;
$R_{17}$ is selected from hydrogen, hydroxy, halo, cyano, $C_{1-5}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, $—O—C_{3-6}$cycloalkyl, heterocyclyl, —O-heterocyclyl (carbon-linked), $—(OCH_2CH_2)_m—NR_qR_r$, $—(OCH_2CH_2)_m—OCH_3$ wherein m is an integer from 1 to 6, $NR_qR_r$, $—C(O)—NR_qR_r$, $—C(O)OR_q$; wherein $R_q$ and $R_r$ are each independently hydrogen, $C_{1-5}$ alkyl, $C_{3-6}$cycloalkyl, a 3- to 6-membered carbon-linked heterocyclyl, wherein $C_{1-5}$ alkyl, $C_{3-6}$cycloalkyl, a 3- to 6-membered carbon-linked heterocyclyl may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or $—S(O)_{0-2}R_{1ea}R_{1fa}$, wherein $R_{1ea}$ and $R_{1fa}$ are H or $C_{1-2}$alkyl;

or $R_q$ and $R_r$ are linked together such that, together with the nitrogen atom to which they are attached, they form a 3- to 6-membered heterocyclic ring, which may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy;

wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, $—O—C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or $—S(O)_{0-2}R_{1ea}R_{1fa}$, wherein $R_{1ea}$ and $R_{1fa}$ are H or $C_{1-2}$alkyl;

$R_{18}$ is selected from hydrogen, halo, cyano, $C_{1-4}$ alkyl, $C_{2-4}$ alkenyl, $C_{2-4}$ alkynyl, a 5- or 6-membered heteroaryl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;

$R_{19}$, $R_{20}$, $R_{25}$ and $R_{26}$ are selected from hydrogen, halo, cyano and $C_{1-4}$ alkyl;

$R_{22}$ and $R_{23}$ are selected from hydrogen, halo, cyano and methyl;

$R_{28}$ and $R_{29}$ are selected from hydrogen, methoxy and methyl;

$R_{21}$, $R_{24}$, $R_{27}$ and $R_{30}$ are hydrogen; and n is 0, 1 or 2;

with the proviso that the compound is not:
2-((1H-benzo[d]imidazol-2-yl)methyl)-5-(pyridin-3-yl)-1,3,4-oxadiazole;
2-((6-chloro-1-phenyl-1H-benzo[d]imidazol-2-yl)methyl)-5-(pyridin-3-yl)-1,3,4-oxadiazole;
N-({6-methylimidazo[1,2-a]pyridin-2-yl}methyl)-1H-indazole-5-carboxamide.

In one aspect, the present invention relates to compounds of the formula (I), or a pharmaceutically acceptable salt thereof, $$X—Y—Z \quad (I)$$

wherein:
X is selected from:

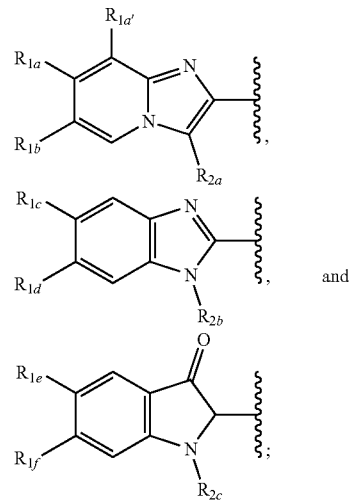

wherein:
$R_{1a}$, $R_{1b}$, $R_{1c}$, $R_{1d}$, $R_{1e}$ and $R_{1f}$ are independently selected from hydrogen, cyano, halo or a group of the formula:

$-L_{1a}-L_{1b}-Q_1$ wherein
$L_{1a}$ is absent or $C_{1-3}$alkylene, $C_{3-4}$cycloalkylene, optionally substituted by one or more substituents selected from aryl, aryl-(1-2C)alkyl, heteroaryl, aryl-(1-2C)alkyl, $C_{1-2}$alkyl, cyano, halo, hydroxy, or oxo; wherein any aryl, aryl-(1-2C)alkyl, heteroaryl, aryl-(1-2C)alkyl or $C_{1-2}$alkyl is optionally further substituted by one or more substituents selected from halo, cyano or hydroxy;

$L_{1b}$ is absent or selected from O, S, SO, $SO_2$, $N(R_r)$, C(O), C(O)O, OC(O), $C(O)N(R_r)$, $N(R_r)C(O)$, $N(R_r)C(O)N(R_s)$, $S(O)_2N(R_r)$, or $N(R_r)SO_2$, wherein $R_r$ and $R_s$ are each independently selected from hydrogen or $C_{1-2}$alkyl, wherein $C_{1-2}$alkyl is optionally further substituted by $C_{3-6}$cycloalkyl or a 3 to 6 membered heterocyclyl, which in turn are optionally further substituted by halo, hydroxy, $C_{1-2}$alkoxy or $C_{1-2}$haloalkoxy; and $Q_1$ is hydrogen, cyano, $C_{1-6}$alkyl, $C_{3-8}$cycloalkyl (e.g. $C_{3-6}$cycloalkyl), $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, oxo, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

$-L_{1c}-L_{1d}-Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), C(O)N($R_v$), N($R_v$)C(O), N($R_v$)C(O)N($R_w$), S(O)$_2$N($R_v$), or N($R_v$)SO$_2$, wherein $R_v$ and $R_w$ are each independently selected from hydrogen or $C_{1-2}$alkyl; and $Z_1$ is $C_{3-6}$cycloalkyl, heterocyclyl, phenyl or 5-6 membered heteroaryl; wherein $Z_1$ is optionally substituted by one or more substituents selected from $C_{1-4}$alkyl, $C_{3-6}$ cycloalkyl, heterocyclyl, halo, $C_{1-4}$haloalkyl, $C_{1-4}$haloalkoxy, $C_{1-4}$alkoxy, cyano, hydroxyl, $NR_{t1}R_{u1}$, $OR_{t1}$, $C(O)R_{t1}$, $C(O)OR_{t1}$, $OC(O)R_{t1}$, $C(O)N(R_{t1})R_{u1}$, $N(R_{t1})C(O)R_{u1}$, $S(O)_yR_{t1}$ (where y is 0, 1 or 2), $SO_2N(R_{t1})R_{u1}$, $N(R_{t1})SO_2R_{u1}$ or $(CH_2)_zNR_{t1}R_{u1}$ (where z is 1, 2 or 3), wherein $R_{t1}$ and $R_{u1}$ are each independently selected from hydrogen or $C_{1-4}$alkyl; and when $Z_1$ is $C_{3-6}$cycloalkyl or heterocyclyl, $Z_1$ is optionally spiro-fused to a $C_{3-6}$cycloalkyl or heterocyclyl ring;

$R_{1a'}$ is selected from hydrogen, halo and methyl;

$R_{2a}$, $R_{2b}$ and $R_{2c}$ are selected from hydrogen, halo or a group of the formula:

$-L_{2a}-L_{2b}-Q_2$ wherein $L_{2a}$ is absent or $C_{1-3}$alkylene optionally substituted by $C_{1-2}$ alkyl or oxo;

$L_{2b}$ is absent or selected from O, S, SO, SO$_2$, N($R_n$), C(O), C(O)O, OC(O), C(O)N($R_n$), N($R_n$)C(O), N($R_n$)C(O)N($R_o$), S(O)$_2$N($R_n$), or N($R_n$)SO$_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_p)C(O)R_q$, $S(O)_yR_p$ (where y is 0, 1 or 2), $SO_2N(R_p)R_q$, $N(R_p)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

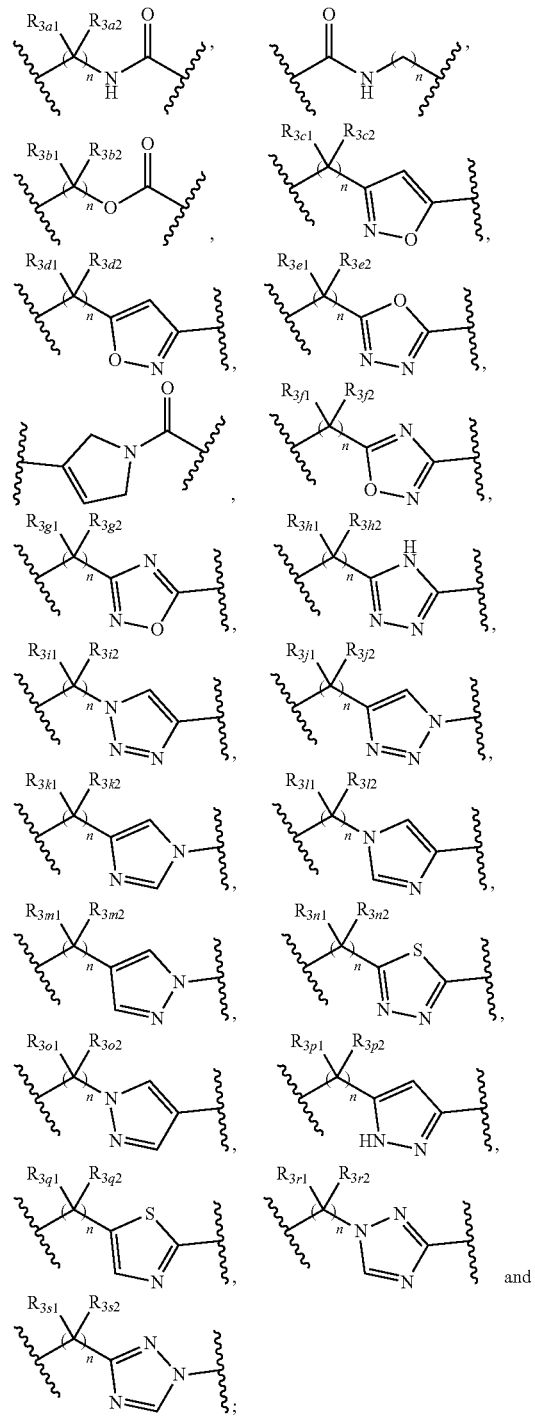

and wherein:

$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen (including deuterium), $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen or halo;

with the proviso that $R_{3a1}$, $R_{3b1}$, $R_{3i1}$, $R_{3l1}$, $R_{3o1}$, $R_{3r1}$, $R_{3a2}$, $R_{3b2}$, $R_{3i2}$, $R_{3l2}$, $R_{3o2}$ and $R_{3s2}$ cannot be halo when n=1 or when n=2 and the carbon atom to which they are attached is linked to an oxygen or nitrogen atom;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$, or $R_{3r1}$ and $R_{3r2}$ or $R_{3s1}$ and $R_{3s2}$ may be linked such that, together with the carbon atom to which they are attached, they form a spiro-fused $C_{3-4}$cycloalkyl which is optionally substituted with one or more substituents selected from halo, methyl, amino, cyano, and hydroxy;

Z is selected from:

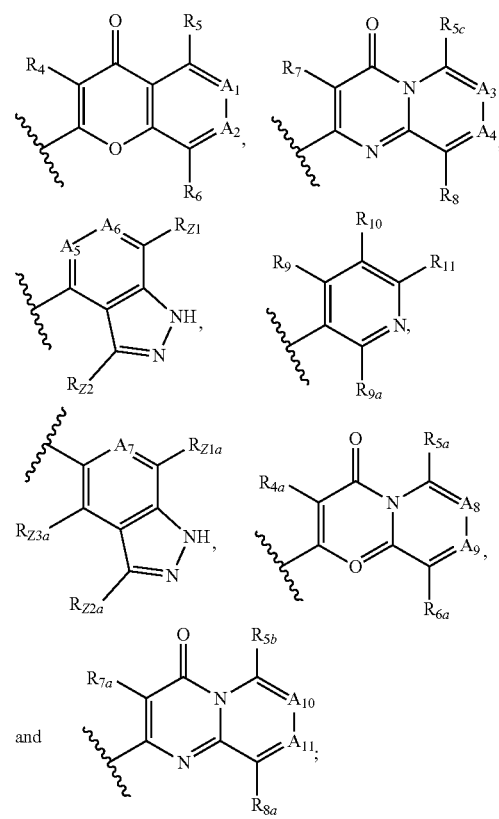

wherein:
$R_4$, $R_7$, $R_{4a}$ and $R_{7a}$ are independently selected from hydrogen, halo, cyano and methyl;
$R_5$, $R_{5a}$, $R_{5b}$ and $R_{5c}$ are independently selected from hydrogen, halo, cyano and methyl;
$R_6$, $R_8$, $R_{6a}$ and $R_{8a}$ are independently selected from hydrogen, halo, cyano and methyl;
$R_9$, $R_{9a}$, $R_{10}$ and $R_{11}$ are independently selected from hydrogen, $NH_2$, halo, cyano, and $C_{1-6}$ alkyl; or
$R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system; wherein either of the fused 5- or 6-membered saturated or unsaturated ring system may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ia}R_{1ja}$ or $-S(O)_{0-2}R_{1ia}R_{1ja}$, wherein $R_{1ia}$ and $R_{1ja}$ are H or $C_1$-2alky;

$R_{Z1}$ and $R_{Z1a}$ are selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and $-O-C_{3-6}$cycloalkyl, wherein $C_{3-6}$cycloalkyl and $-O-C_{3-6}$cycloalkyl are optionally substituted by one or more of halo, methyl or methoxy;

$R_{Z2}$ and $R_{Z2a}$ are selected from hydrogen, $C_{1-4}$alkyl, cyano, halo, $NH_2$ and $C_{1-4}$alkoxy;

$R_{Z3a}$ is selected from hydrogen, $C_{1-4}$alkyl, cyano, halo, $NH_2$ and $C_{1-4}$alkoxy $A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;

$R_{12}$ and $R_{14}$ are independently selected from hydrogen, halo, cyano and $C_{1-4}$ alkyl;

$R_{13}$ is selected from hydrogen, halo, cyano, methoxy and methyl;

$R_{15}$ is selected from hydrogen, halo, cyano methoxy and methyl;

$R_{16}$ is selected from hydrogen, halo, cyano, $C_{1-4}$ alkyl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;

$R_{17}$ is selected from hydrogen, hydroxy, halo, cyano, $C_{1-5}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, $-O-C_{3-6}$cycloalkyl, heterocyclyl, $-O$-heterocyclyl (carbon-linked), $-(OCH_2CH_2)_m-NR_qR_r$, $-(OCH_2CH_2)_m-OCH_3$ wherein m is an integer from 1 to 6, $NR_qR_r$, $-C(O)-NR_qR_r$, $-C(O)OR_q$; wherein $R_q$ and $R_r$ are each independently hydrogen, $C_{1-5}$ alkyl, $C_{3-6}$cycloalkyl, a 3- to 6-membered carbon-linked heterocyclyl, wherein $C_{1-5}$ alkyl, $C_{3-6}$cycloalkyl, a 3- to 6-membered carbon-linked heterocyclyl may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or $-S(O)_{0-2}R_{1ea}R_{1fa}$, wherein $R_{1ea}$ and $R_{1fa}$ are H or $C_{1-2}$alkyl; or $R_q$ and $R_r$ are linked together such that, together with the nitrogen atom to which they are attached, they form a 3- to 6-membered heterocyclic ring, which may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy;

wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, $-O-C_{3-6}$cycloalkyl, heterocyclyl or $-O$-heterocyclyl (carbon-linked) is optionally further substituted by one or more substituents selected from $C_{1-2}$-alkyl, cyano, $C_{1-2}$haloalkyl, hydroxy, $C_{1-2}$alkoxy, halo, $C_{1-2}$haloalkoxy, $NR_{1ea}R_{1fa}$ or $—S(O)_{0-2}R_{1ea}R_{1fa}$, wherein $R_{1ea}$ and $R_{1fa}$ are H or $C_{1-2}$alkyl;

$R_{18}$ is selected from hydrogen, halo, cyano, $C_{1-4}$ alkyl, $C_{2-4}$ alkenyl, $C_{2-4}$ alkynyl, a 5- or 6-membered heteroaryl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;

$R_{19}$, $R_{20}$, $R_{25}$ and $R_{26}$ are selected from hydrogen, halo, cyano and $C_{1-4}$ alkyl;

$R_{22}$ and $R_{23}$ are selected from hydrogen, halo, cyano and methyl;

$R_{28}$ and $R_{29}$ are selected from hydrogen, methoxy and methyl;

$R_{21}$, $R_{24}$, $R_{27}$ and $R_{30}$ are hydrogen; and n is 0, 1 or 2.

In one aspect, the present invention relates to compounds of the formula (I), or a pharmaceutically acceptable salt thereof, $$X—Y—Z \quad (I)$$

wherein:

X is selected from:

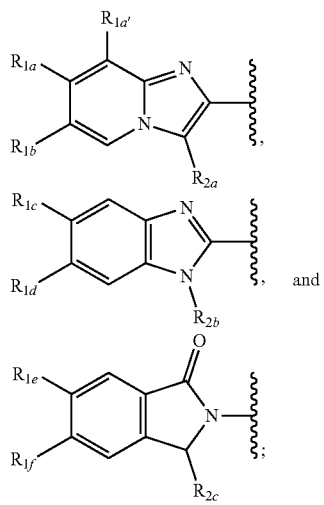

wherein:

$R_{1a}$, $R_{1b}$, $R_{1c}$, $R_{1d}$, $R_{1e}$ and $R_{1f}$ are independently selected from hydrogen, cyano, halo or a group of the formula:

-$L_{1a}$-$L_{1b}$-$Q_1$ wherein $L_{1a}$ is absent or $C_{1-3}$alkylene, $C_{3-4}$cycloalkylene, optionally substituted by one or more substituents selected from $C_{1-2}$alkyl, halo, hydroxy, or oxo;

$L_{1b}$ is absent or selected from O, S, SO, $SO_2$, $N(R_r)$, C(O), C(O)O, OC(O), C(O)N($R_r$), $N(R_r)$C(O), $N(R_r)$C(O)N($R_s$), $S(O)_2N(R_r)$, or $N(R_r)SO_2$, wherein $R_r$ and $R_s$ are each independently selected from hydrogen or $C_{1-2}$alkyl; and $Q_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), C(O)N($R_v$), $N(R_v)$C(O), $N(R_v)$C(O)N($R_w$), $S(O)_2N(R_v)$, or $N(R_v)SO_2$, wherein $R_v$ and $R_w$ are each independently selected from hydrogen or $C_{1-2}$alkyl; and $Z_1$ is $C_{3-8}$cycloalkyl, heterocyclyl, phenyl or 5-6 membered heteroaryl; wherein $Z_1$ is optionally substituted by one or more substituents selected from $C_{1-4}$alkyl, $C_{3-6}$ cycloalkyl, heterocyclyl, halo, $C_{1-4}$haloalkyl, $C_{1-4}$haloalkoxy, $C_{1-4}$alkoxy, cyano, hydroxyl, $NR_{t1}R_{u1}$, $OR_{t1}$, $C(O)R_{t1}$, $C(O)OR_{t1}$, $OC(O)R_{t1}$, $C(O)N(R_{t1})R_{u1}$, $N(R_{t1})C(O)R_{u1}$, $S(O)_yR_{t1}$ (where y is 0, 1 or 2), $SO_2N(R_{t1})R_{u1}$, $N(R_{t1})SO_2R_{u1}$ or $(CH_2)_zNR_{t1}R_{u1}$ (where z is 1, 2 or 3), wherein $R_{t1}$ and $R_{u1}$ are each independently selected from hydrogen or $C_{1-4}$alkyl; and when $Z_1$ is $C_{3-8}$cycloalkyl or heterocyclyl, $Z_1$ is optionally spiro-fused to a $C_{3-6}$cycloalkyl or heterocyclyl ring;

$R_{1a'}$ is selected from hydrogen and methyl;

$R_{2a}$, $R_{2b}$ and $R_{2c}$ are selected from hydrogen or a group of the formula:

-$L_{2a}$-$L_{2b}$-$Q_2$ wherein $L_{2a}$ is absent or $C_{1-3}$alkylene optionally substituted by $C_{1-2}$ alkyl or oxo;

$L_{2b}$ is selected from O, S, SO, $SO_2$, $N(R_n)$, C(O), C(O)O, OC(O), C(O)N($R_n$), $N(R_n)$C(O), $N(R_n)$C(O)N($R_o$), $S(O)_2N(R_n)$, or $N(R_n)SO_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

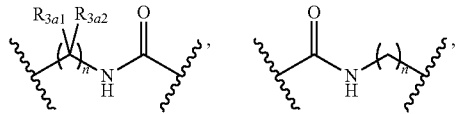

-continued

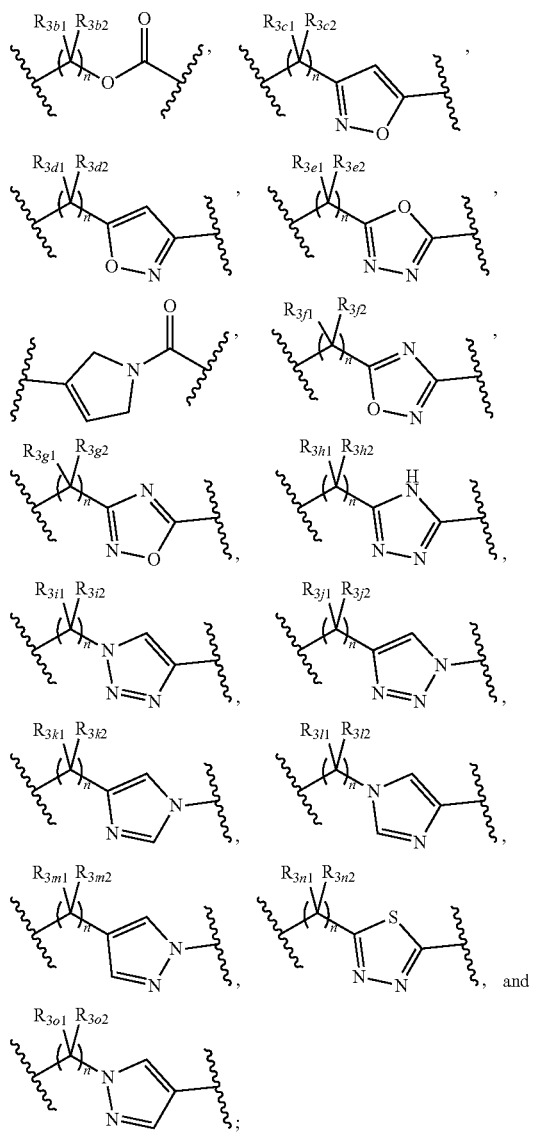

wherein:

$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$, are independently selected from hydrogen, $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$, are hydrogen;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$ may be linked to form a spiro-fused $C_{3-4}$cycloalkyl which is optionally substituted with one or more substituents selected from halo, amino, cyano, and hydroxy;

Z is selected from:

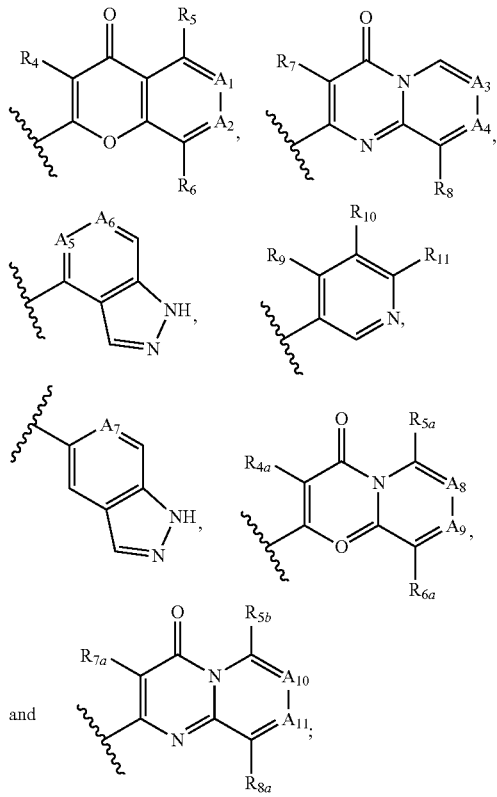

and wherein:

$R_4$, $R_7$ $R_{4a}$ and $R_{7a}$ are independently selected from hydrogen and methyl;

$R_5$, $R_{5a}$ and $R_{5b}$ are independently selected from hydrogen and halo;

$R_6$, $R_8$, $R_{6a}$ and $R_{8a}$ are independently selected from hydrogen, halo and methyl;

$R_9$, $R_{10}$ and $R_{11}$ are independently selected from hydrogen, $NH_2$, halo, cyano, and $C_{1-6}$ alkyl; or $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system;

$A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;
$R_{12}$ and $R_{14}$ are independently selected from hydrogen, halo, cyano and $C_{1-4}$ alkyl;
$R_{13}$ is selected from hydrogen, halo, cyano and methyl;
$R_{15}$ is selected from hydrogen, methoxy and methyl;
$R_{16}$ is selected from hydrogen, halo, cyano and $C_{1-4}$ alkyl;
$R_{17}$ is selected from hydrogen, halo, cyano, $C_{1-4}$ alkyl, $C_{2-4}$ alkenyl, $C_{2-4}$ alkynyl and a 5- or 6-membered heteroaryl;

R₁₈ is selected from hydrogen, halo, cyano, $C_{1-4}$ alkyl, $C_{2-4}$ alkenyl, $C_{2-4}$ alkynyl and a 5- or 6-membered heteroaryl;

$R_{19}$, $R_{20}$, $R_{25}$ and $R_{26}$ are selected from hydrogen, halo, cyano and $C_{1-4}$ alkyl;

$R_{22}$ and $R_{23}$ are selected from hydrogen, halo, cyano and methyl;

$R_{28}$ and $R_{29}$ are selected from hydrogen, methoxy and methyl;

$R_{21}$, $R_{24}$, $R_{27}$ and $R_{30}$ are hydrogen; and n is 0, 1 or 2.

In one aspect, the present invention relates to compounds of formula (I) shown below, or a pharmaceutically acceptable salt thereof:

$$X—Y—Z \quad (I)$$

wherein:
X is selected from:

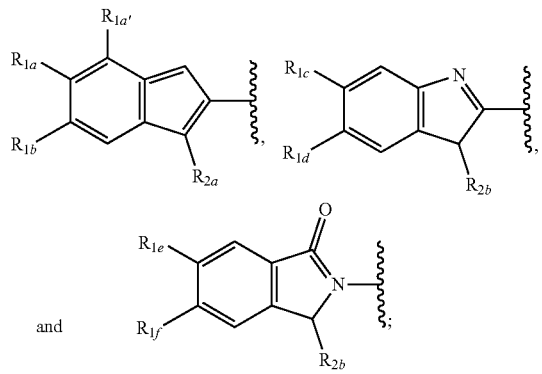

and wherein:
$R_{1a}$, $R_{1b}$, $R_{1c}$, $R_{1d}$, $R_{1e}$ and $R_{1f}$ are independently selected from hydrogen, cyano, halo or a group of the formula:

$$-L_{1a}-L_{1b}-Q_1$$

wherein
$L_{1a}$ is absent or $C_{1-3}$alkylene, $C_{3-4}$cycloalkylene, optionally substituted by one or more substituents selected from $C_{1-2}$alkyl, halo, hydroxy, or oxo;

$L_{1b}$ is absent or selected from O, S, SO, $SO_2$, $N(R_r)$, C(O), C(O)O, OC(O), $C(O)N(R_r)$, $N(R_r)C(O)$, $N(R_r)C(O)N(R_s)$, $S(O)_2N(R_r)$, or $N(R_r)SO_2$, wherein $R_r$ and $R_s$ are each independently selected from hydrogen or $C_{1-2}$alkyl; and $Q_1$ is hydrogen, cyano, $C_{1-6}$alkyl, $C_{3-8}$cycloalkyl (e.g. $C_{3-6}$cycloalkyl), $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

$$-L_{1c}-L_{1d}-Z_1$$

wherein
$L_{1c}$ is absent or $C_{1-3}$alkylene optionally substituted by $C_{1-2}$alkyl or oxo;

$L_{1d}$ is absent or selected from C(O), C(O)O, OC(O), $C(O)N(R_v)$, $N(R_v)C(O)$, $N(R_v)C(O)N(R_w)$, $S(O)_2N(R_v)$, or $N(R_v)SO_2$, wherein Ry and R, are each independently selected from hydrogen or $C_{1-2}$alkyl; and $Z_1$ is phenyl or 5-6 membered heteroaryl; wherein $Z_1$ is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl;

$R_{1a'}$ is selected from hydrogen and methyl;

$R_{2a}$, $R_{2b}$ and $R_{2c}$ are selected from hydrogen or a group of the formula:

$$-L_{2a}-L_{2b}-Q_2$$

wherein
$L_{2a}$ is absent or $C_{1-3}$alkylene optionally substituted by $C_{1-2}$ alkyl or oxo;

$L_{2b}$ is selected from O, S, SO, $SO_2$, $N(R_n)$, C(O), C(O)O, OC(O), $C(O)N(R_n)$, $N(R_n)C(O)$, $N(R_n)C(O)N(R_o)$, $S(O)_2N(R_n)$, or $N(R_n)SO_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

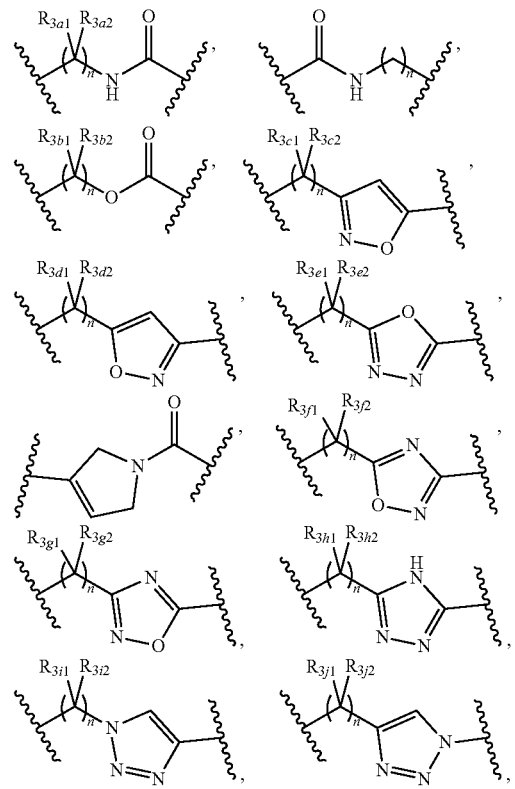

-continued

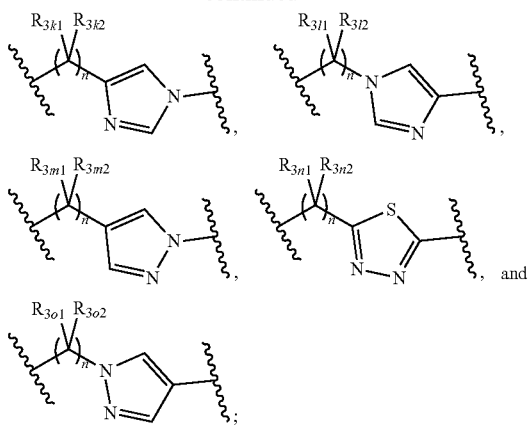

wherein:

$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen, $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$, are hydrogen;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$ may be linked to form a spiro-fused $C_{3-4}$cycloalkyl which is optionally substituted with one or more substituents selected from halo, amino, cyano, and hydroxy;

Z is selected from:

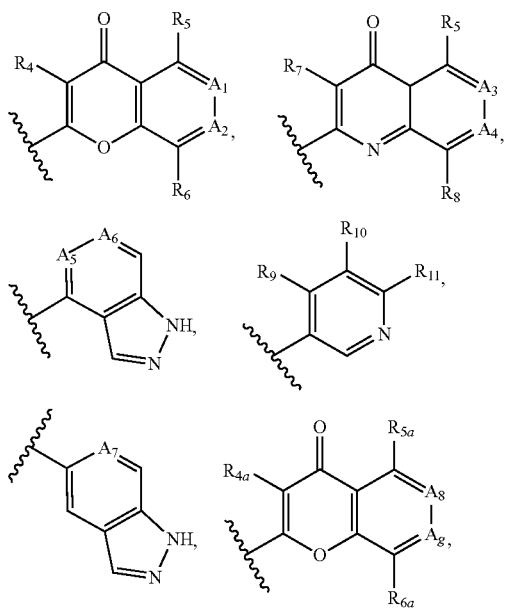

and

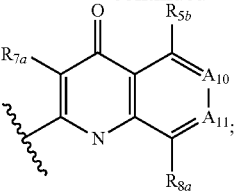

wherein:

$R_4$, $R_7$, $R_{4a}$ and $R_{7a}$ are independently selected from hydrogen and methyl;

$R_5$, $R_{5a}$ and $R_{5b}$ are independently selected from hydrogen and halo;

$R_6$, $R_8$, $R_{6a}$ and $R_{8a}$ are independently selected from hydrogen, halo and methyl;

$R_9$, $R_{10}$ and $R_{11}$ are independently selected from hydrogen, $NH_2$, halo, cyano, and $C_{1-6}$ alkyl; or $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system;

$A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;

$R_{12}$ and $R_{14}$ are independently selected from hydrogen, halo, cyano and $C_{1-4}$ alkyl;

$R_{13}$ is selected from hydrogen, halo, cyano and methyl;

$R_{15}$ is selected from hydrogen, methoxy and methyl;

$R_{16}$ is selected from hydrogen, halo, cyano and $C_{1-4}$ alkyl;

$R_{17}$ is selected from hydrogen, halo, cyano, $C_{1-4}$ alkyl, $C_{2-4}$ alkenyl, $C_{2-4}$ alkynyl and a 5- or 6-membered heteroaryl;

$R_{18}$ is selected from hydrogen, halo, cyano, $C_{1-4}$ alkyl, $C_{2-4}$ alkenyl, $C_{2-4}$ alkynyl and a 5- or 6-membered heteroaryl;

$R_{19}$, $R_{20}$, $R_{25}$ and $R_{26}$ are selected from hydrogen, halo, cyano and $C_{1-4}$ alkyl;

$R_{22}$ and $R_{23}$ are selected from hydrogen, halo, cyano and methyl;

$R_{28}$ and $R_{29}$ are selected from hydrogen, methoxy and methyl;

$R_{21}$, $R_{24}$, $R_{27}$ and $R_{30}$ are hydrogen; and n is 0, 1 or 2.

Particular compounds of the invention include, for example, compounds of formula (I), or pharmaceutically acceptable salts thereof, wherein, unless otherwise stated, each of X, Y, Z, $R_{1a}$, $R_{1b}$, $R_{1c}$, $R_{1d}$, $R_{1e}$, $R_{1f}$, $R_{1a'}$, $R_{2a}$, $R_{2b}$, $R_{2c}$, $R_{3a1}$, $R_{3a2}$, $R_{3b1}$, $R_{3b2}$, $R_{3c1}$, $R_{3c2}$, $R_{3d1}$, $R_{3d2}$, $R_{3e1}$, $R_{3e2}$, $R_{3f1}$, $R_{3f2}$, $R_{3g1}$, $R_{3g2}$, $R_{3h1}$, $R_{3h2}$, $R_{3i1}$, $R_{3i2}$, $R_{3j1}$, $R_{3j2}$, $R_{3k1}$, $R_{3k2}$, $R_{3l1}$, $R_{3l2}$, $R_{3m1}$, $R_{3m2}$, $R_{3n1}$, $R_{3n2}$, $R_{3o1}$, $R_{3o2}$, n, $R_4$, $R_{4a}$, $R_5$, $R_{5a}$, $R_{5b}$, $R_{5e}$, $R_6$, $R_{6a}$, $R_7$, $R_{7a}$, $R_8$, $R_{8a}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $A_1$, $A_2$, $A_3$, $A_4$, $A_5$, $A_6$, $A_7$, $A_8$, $A_9$, $A_{10}$ and $A_{11}$ and any associated substituent groups has any of the meanings defined hereinbefore or in any one of paragraphs (1) to (111b) hereinafter:—

(1) One of $R_{1a}$ and $R_{1b}$, $R_{1c}$ and $R_{1d}$, $R_{1e}$ and $R_{1f}$ is selected from hydrogen, halo, $C_{1-6}$-alkyl, $C_{2-3}$alkenyl or —O—$C_{1-6}$alkyl, and the other is selected from hydrogen, cyano, halo or a group of the formula:

-$L_{1a}$-$L_{1b}$-$Q_1$ wherein $L_{1a}$ is absent or $C_{1-3}$alkylene, $C_{3-4}$cycloalkylene, optionally substituted by one or more substituents selected from $C_{1-2}$alkyl, halo, hydroxy, or oxo;

$L_{1b}$ is absent or selected from O, S, SO, $SO_2$, N($R_r$), C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or $C_{1-2}$alkyl; and $Q_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and R$_u$ are each independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), C(O)O, OC(O), C(O)N(R$_v$), N(R$_v$)C(O), N(R$_v$)C(O)N(R$_w$), S(O)$_2$N(R$_v$), or N(R$_v$)SO$_2$, wherein R$_v$ and R$_w$ are each independently selected from hydrogen or $C_{1-2}$alkyl; and $Z_1$ is phenyl or 5-6 membered heteroaryl; wherein $Z_1$ is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl;

(1a) One of $R_{1a}$ and $R_{1b}$, $R_{1c}$ and $R_{1d}$, $R_{1e}$ and $R_{1f}$ is selected from hydrogen, halo, $C_{1-6}$-alkyl, $C_{2-3}$alkenyl or —O—$C_{1-6}$alkyl, and the other is selected from hydrogen, cyano, halo or a group of the formula:

-$L_{1a}$-$L_{1b}$-$Q_1$ wherein $L_{1a}$ is absent or $C_{1-3}$alkylene, $C_{3-4}$cycloalkylene, optionally substituted by one or more substituents selected from $C_{1-2}$alkyl, halo, hydroxy, or oxo; $L_{1b}$ is absent or selected from O, S, SO, $SO_2$, N($R_r$), C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or $C_{1-2}$alkyl; and $Q_1$ is hydrogen, cyano, $C_{1-6}$alkyl, $C_{3-8}$cycloalkyl (e.g. $C_{3-6}$cycloalkyl), $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and R$_u$ are each independently selected from hydrogen or $C_{1-4}$alkyl;

or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), C(O)N(R$_v$), N(R$_v$)C(O), N(R$_v$)C(O)N(R$_w$), S(O)$_2$N(R$_v$), or N(R$_v$)SO$_2$, wherein R$_v$ and R$_w$ are each independently selected from hydrogen or $C_{1-2}$alkyl; and $Z_1$ is $C_{3-6}$cycloalkyl (including a spirocyclic carbocyclic and a bridged $C_{3-6}$cycloalkyl), heterocyclyl (including a mono- or bicyclic-heterocyclic ring system, a spirocyclic heterocyclic ring system, or a bridged heterocyclic ring system), phenyl or 5-6 membered heteroaryl; wherein $Z_1$ is optionally substituted by one or more substituents selected from $C_{1-4}$alkyl, $C_{3-6}$cycloalkyl, heterocyclyl, halo, $C_{1-4}$haloalkyl, $C_{1-4}$haloalkoxy, $C_{1-4}$alkoxy, cyano, hydroxyl, NR$_{t1}$R$_{u1}$, OR$_{t1}$, C(O)R$_{t1}$, C(O)OR$_{t1}$, OC(O)R$_{t1}$, C(O)N(R$_{t1}$)R$_{u1}$, N(R$_{t1}$)C(O)R$_{u1}$, S(O)$_y$R$_{t1}$ (where y is 0, 1 or 2), SO$_2$N(R$_{t1}$)R$_{u1}$, N(R$_{t1}$)SO$_2$R$_{u1}$ or (CH$_2$)$_z$NR$_{t1}$R$_{u1}$ (where z is 1, 2 or 3), wherein R$_{t1}$ and R$_{u1}$ are each independently selected from hydrogen or $C_{1-4}$alkyl; and when $Z_1$ is $C_{3-8}$ cycloalkyl or heterocyclyl, $Z_1$ is optionally spiro-fused to a $C_{3-6}$cycloalkyl or heterocyclyl ring;

(1b) One of $R_{1a}$ and $R_{1b}$, $R_{1c}$ and $R_{1d}$, $R_{1e}$ and $R_{1f}$ is selected from hydrogen, halo, $C_{1-6}$-alkyl, $C_{2-3}$alkenyl or —O—$C_{1-6}$alkyl, and the other is selected from hydrogen, cyano, halo or a group of the formula:

-$L_{1a}$-$L_{1b}$-$Q_1$ wherein $L_{1a}$ is absent or $C_{1-3}$alkylene, $C_{3-4}$cycloalkylene, optionally substituted by one or more substituents selected from aryl, aryl-(1-2C)alkyl, heteroaryl, aryl-(1-2C)alkyl, $C_{1-2}$alkyl, cyano, halo, hydroxy, or oxo, wherein any aryl, aryl-(1-2C)alkyl, heteroaryl, aryl-(1-2C)alkyl or $C_{1-2}$alkyl is optionally further substituted by one or more substituents selected from halo, cyano or hydroxy;

$L_{1b}$ is absent or selected from O, S, SO, $SO_2$, N($R_r$), C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or $C_{1-2}$alkyl, wherein $C_{1-2}$alkyl is optionally further substituted by $C_{3-6}$cycloalkyl or a 3 to 6 membered heterocyclyl, which in turn are optionally further substituted by halo, hydroxy, $C_{1-2}$alkoxy or $C_{1-2}$haloalkoxy; and $Q_1$ is hydrogen, cyano, $C_{1-6}$alkyl, $C_{3-6}$cycloalkyl (e.g. $C_{3-6}$cycloalkyl), $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, oxo cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

$-L_{1c}-L_{1d}-Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), $C(O)N(R_v)$, $N(R_v)C(O)$, $N(R_v)C(O)N(R_w)$, $S(O)_2N(R_v)$, or $N(R_v)SO_2$, wherein $R_v$ and $R_w$ are each independently selected from hydrogen or $C_{1-2}$alkyl; and $Z_1$ is $C_{3-8}$cycloalkyl (including a spirocyclic carbocyclic and a bridged $C_{3-8}$cycloalkyl), heterocyclyl (including a mono- or bicyclic-heterocyclic ring system, a spirocyclic heterocyclic ring system, or a bridged heterocyclic ring system), phenyl or 5-6 membered heteroaryl; wherein $Z_1$ is optionally substituted by one or more substituents selected from $C_{1-4}$alkyl, $C_{3-6}$cycloalkyl, heterocyclyl, halo, $C_{1-4}$haloalkyl, $C_{1-4}$haloalkoxy, $C_{1-4}$alkoxy, cyano, hydroxyl, $NR_{t1}R_{u1}$, $OR_{t1}$, $C(O)R_{t1}$, $C(O)OR_{t1}$, $OC(O)R_{t1}$, $C(O)N(R_{t1})R_{u1}$, $N(R_{t1})C(O)R_{u1}$, $S(O)_yR_{t1}$ (where y is 0, 1 or 2), $SO_2N(R_{t1})R_{u1}$, $N(R_{t1})SO_2R_{u1}$ or $(CH_2)_zNR_{t1}R_{u1}$ (where z is 1, 2 or 3), wherein $R_{t1}$ and $R_{u1}$ are each independently selected from hydrogen or $C_{1-4}$alkyl; and when $Z_1$ is $C_{3-8}$ cycloalkyl or heterocyclyl, $Z_1$ is optionally spiro-fused to a $C_{3-6}$cycloalkyl or heterocyclyl ring;

(2) $R_{1a}$, $R_{1c}$ and $R_{1e}$ are selected from hydrogen, halo, $C_{1-6}$alkyl, $C_{2-3}$alkenyl or $-O-C_{1-6}$alkyl and $R_{1b}$, $R_{1d}$, and $R_{1f}$ are selected from hydrogen, cyano, halo or a group of the formula:

$-L_{1a}-L_{1b}-Q_1$ wherein $L_{1a}$ is absent or $C_{1-3}$alkylene, $C_{3-4}$cycloalkylene, optionally substituted by one or more substituents selected from $C_{1-2}$alkyl, halo, hydroxy, or oxo;

$L_{1b}$ is absent or selected from O, S, SO, $SO_2$, $N(R_r)$, C(O), C(O)O, OC(O), $C(O)N(R_r)$, $N(R_r)C(O)$, $N(R_r)C(O)N(R_s)$, $S(O)_2N(R_r)$, or $N(R_r)SO_2$, wherein $R_r$ and $R_s$ are each independently selected from hydrogen or $C_{1-2}$alkyl; and $Q_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

$-L_{1c}-L_{1d}-Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), $C(O)N(R_v)$, $N(R_v)C(O)$, $N(R_v)C(O)N(R_w)$, $S(O)_2N(R_v)$, or $N(R_v)SO_2$, wherein $R_v$ and $R_w$ are each independently selected from hydrogen or $C_{1-2}$alkyl; and $Z_1$ is phenyl or 5-6 membered heteroaryl; wherein $Z_1$ is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl;

(3) $R_{1a}$, $R_{1c}$ and $R_{1e}$ are selected from hydrogen, halo, $C_{1-4}$alkyl, $C_{2-3}$alkenyl and $-O-C_{1-4}$alkyl;

(4) $R_{1a}$, $R_{1c}$ and $R_{1e}$ are selected from hydrogen, fluoro, bromo, chloro, methyl, ethyl, propyl, butyl, ethenyl, —O-methyl, —O-ethyl, —O-propyl and —O-butyl;

(5) $R_{1a}$, $R_{1c}$ and $R_{1e}$ are selected from hydrogen, fluoro, bromo, chloro, methyl, ethyl, —O— methyl, ethenyl and —O-ethyl;

(6) $R_{1a}$, $R_{1c}$ and $R_{1e}$ are selected from hydrogen, fluoro, bromo, methyl, ethenyl and —O— methyl;

(6a) $R_{1b}$, $R_{1d}$ and $R_{1f}$ are selected from hydrogen, cyano, halo or a group of the formula:

$-L_{1a}-L_{1b}-Q_1$ wherein $L_{1a}$ is absent or $C_{1-3}$alkylene, $C_{3-4}$cycloalkylene, optionally substituted by one or more substituents selected from $C_{1-2}$alkyl, halo, hydroxy, or oxo;

$L_{1b}$ is absent or selected from O, S, SO, $SO_2$, $N(R_r)$, C(O), C(O)O, OC(O), $C(O)N(R_r)$, $N(R_r)C(O)$, $N(R_r)C(O)N(R_s)$, $S(O)_2N(R_r)$, or $N(R_r)SO_2$, wherein $R_r$ and $R_s$ are each independently selected from hydrogen or $C_{1-2}$alkyl; and $Q_1$ is hydrogen, cyano, $C_{1-6}$alkyl, $C_{3-8}$cycloalkyl (e.g. $C_{3-6}$cycloalkyl), $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

$-L_{1c}-L_{1d}-Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), $C(O)N(R_v)$, $N(R_v)C(O)$, $N(R_v)C(O)N(R_w)$, $S(O)_2N(R_v)$, or $N(R_v)SO_2$, wherein $R_v$ and $R_w$ are each independently selected from hydrogen or $C_{1-2}$alkyl; and $Z_1$ is $C_{3-8}$cycloalkyl (including a spirocyclic carbocyclic and a bridged $C_{3-8}$cycloalkyl), heterocyclyl (including a mono- or bicyclic-heterocyclic ring system, a spirocyclic heterocyclic ring system, or a bridged heterocyclic ring system), phenyl or 5-6 membered heteroaryl; wherein $Z_1$ is optionally substituted by one or more substituents selected from $C_{1-4}$alkyl, $C_{3-6}$cycloalkyl, heterocyclyl, halo, $C_{1-4}$haloalkyl, $C_{1-4}$haloalkoxy, $C_{1-4}$alkoxy, cyano, hydroxyl, $NR_{t1}R_{u1}$, $OR_{t1}$, $C(O)R_{t1}$, $C(O)OR_{t1}$, OC(O)R$_{t1}$, C(O)N(R$_{t1}$)R$_{u1}$, N(R$_{t1}$)C(O)R$_{u1}$, S(O)$_y$R$_{t1}$ (where y is 0, 1 or 2), SO$_2$N(R$_{t1}$)R$_{u1}$, N(R$_{t1}$)SO$_2$R$_{u1}$ or (CH$_2$)$_z$NR$_{t1}$R$_{u1}$ (where z is 1, 2 or 3), wherein R$_{t1}$ and R$_{u1}$ are each independently selected from hydrogen or C$_{1-4}$alkyl; and when Z$_1$ is C$_{3-8}$ cycloalkyl or heterocyclyl, Z$_1$ is optionally spiro-fused to a C$_{3-6}$cycloalkyl or heterocyclyl ring;

(6b) R$_{1b}$, R$_{1d}$ and R$_{1f}$ are selected from hydrogen, cyano, halo or a group of the formula:

-L$_{1a}$-L$_{1b}$-Q$_1$ wherein

L$_{1a}$ is absent or C$_{1-3}$alkylene, C$_{3-4}$cycloalkylene, optionally substituted by one or more substituents selected from aryl, aryl-(1-2C)alkyl, heteroaryl, aryl-(1-2C)alkyl, C$_{1-2}$alkyl, cyano, halo, hydroxy, or oxo, wherein any aryl, aryl-(1-2C)alkyl, heteroaryl, aryl-(1-2C)alkyl or C$_{1-2}$alkyl is optionally further substituted by one or more substituents selected from halo, cyano or hydroxy;

L$_{1b}$ is absent or selected from O, S, SO, SO$_2$, N(R$_r$), C(O), C(O)O, OC(O), C(O)N(R$_r$), N(R$_r$)C(O), N(R$_r$)C(O)N(R$_s$), S(O)$_2$N(R$_r$), or N(R$_r$)SO$_2$, wherein R$_r$ and R$_s$ are each independently selected from hydrogen or C$_{1-2}$alkyl, wherein C$_{1-2}$alkyl is optionally further substituted by C$_{3-6}$cycloalkyl or a 3 to 6 membered heterocyclyl, which in turn are optionally further substituted by halo, hydroxy, C$_{1-2}$alkoxy or C$_{1-2}$haloalkoxy; and Q$_1$ is hydrogen, cyano, C$_{1-6}$alkyl, C$_{3-8}$cycloalkyl (e.g. C$_{3-6}$cycloalkyl), C$_{2-3}$alkenyl, C$_{2-3}$alkynyl, aryl, heterocyclyl or heteroaryl; and wherein Q$_1$ is optionally substituted by one or more substituents selected from C$_{1-4}$alkyl, halo, trifluoromethyl, trifluoromethoxy, amino, oxo, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and R$_u$ are each independently selected from hydrogen or C$_{1-4}$alkyl; or Q$_1$ is optionally substituted by one or more groups of the formula:

-L$_{1c}$-L$_{1d}$-Z$_1$ wherein

L$_{1c}$ is absent or C$_{1-3}$alkylene optionally substituted by C$_{1-2}$alkyl or oxo;

L$_{1d}$ is absent or selected from C(O), O, C(O)O, OC(O), C(O)N(R$_v$), N(R$_v$)C(O), N(R$_v$)C(O)N(R$_w$), S(O)$_2$N(R$_v$), or N(R$_v$)SO$_2$, wherein R$_v$ and R$_w$ are each independently selected from hydrogen or C$_{1-2}$alkyl; and Z$_1$ is C$_{3-8}$cycloalkyl (including a spirocyclic carbocyclic and a bridged C$_{3-8}$cycloalkyl), heterocyclyl (including a mono- or bicyclic-heterocyclic ring system, a spirocyclic heterocyclic ring system, or a bridged heterocyclic ring system), phenyl or 5-6 membered heteroaryl; wherein Z$_1$ is optionally substituted by one or more substituents selected from C$_{1-4}$alkyl, C$_{3-6}$cycloalkyl, heterocyclyl, halo, C$_{1-4}$haloalkyl, C$_{1-4}$haloalkoxy, C$_{1-4}$alkoxy, cyano, hydroxyl, NR$_{t1}$R$_{u1}$, OR$_t$, C(O)R$_{t1}$, C(O)OR$_{t1}$, OC(O)R$_{t1}$, C(O)N(R$_{t1}$)R$_{u1}$, N(R$_{t1}$)C(O)R$_{u1}$, S(O)$_y$R$_{t1}$ (where y is 0, 1 or 2), SO$_2$N(R$_{t1}$)R$_{u1}$, N(R$_{t1}$)SO$_2$R$_{u1}$ or (CH$_2$)$_z$NR$_{t1}$R$_{u1}$ (where z is 1, 2 or 3), wherein R$_{t1}$ and R$_{u1}$ are each independently selected from hydrogen or C$_{1-4}$alkyl; and when Z$_1$ is C$_{3-8}$ cycloalkyl or heterocyclyl, Z$_1$ is optionally spiro-fused to a C$_{3-6}$cycloalkyl or heterocyclyl ring;

(7) R$_{1b}$, R$_{1d}$ and R$_{1f}$ are selected from hydrogen, cyano, halo or a group of the formula:

-L$_{1a}$-L$_{1b}$-Q$_1$ wherein

L$_{1a}$ is absent or C$_{1-3}$alkylene, C$_{3-4}$cycloalkylene, optionally substituted by one or more substituents selected from C$_{1-2}$alkyl, halo, hydroxy, or oxo;

L$_{1b}$ is absent or selected from O, S, SO, SO$_2$, N(R$_r$), C(O), C(O)O, OC(O), C(O)N(R$_r$), N(R$_r$)C(O), N(R$_r$)C(O)N(R$_s$), S(O)$_2$N(R$_r$), or N(R$_r$)SO$_2$, wherein R$_r$ and R$_s$ are each independently selected from hydrogen or C$_{1-2}$alkyl; and Q$_1$ is hydrogen, cyano, C$_{1-6}$alkyl, C$_{3-6}$cycloalkyl, C$_{2-3}$alkenyl, C$_{2-3}$alkynyl, aryl, heterocyclyl or heteroaryl; and wherein Q$_1$ is optionally substituted by one or more substituents selected from C$_{1-4}$alkyl, halo, trifluoromethyl, trifluoromethoxy, amino, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and R$_u$ are each independently selected from hydrogen or C$_{1-4}$alkyl; or Q$_1$ is optionally substituted by one or more groups of the formula:

-L$_{1c}$-L$_{1d}$-Z$_1$ wherein

L$_{1c}$ is absent or C$_{1-3}$alkylene optionally substituted by C$_{1-2}$alkyl or oxo;

L$_{1d}$ is absent or selected from C(O), C(O)O, OC(O), C(O)N(R$_v$), N(R$_v$)C(O), N(R$_v$)C(O)N(R$_w$), S(O)$_2$N(R$_v$), or N(R$_v$)SO$_2$, wherein R$_v$ and R$_w$ are each independently selected from hydrogen or C$_{1-2}$alkyl; and Z$_1$ is phenyl or 5-6 membered heteroaryl; wherein Z$_1$ is optionally substituted by one or more substituents selected from C$_{1-4}$alkyl, halo, C$_{1-4}$haloalkyl, C$_{1-4}$haloalkoxy, C$_{1-4}$alkoxy, C$_{1-4}$alkylamino, amino, cyano, hydroxyl, carboxy, carbamoyl or sulphamoyl;

(7a) R$_{1b}$, R$_{1d}$ and R$_{1f}$ are selected from hydrogen, cyano, halo or a group of the formula:

-L$_{1a}$-L$_{1b}$-Q$_1$ wherein

L$_{1a}$ is absent or C$_{1-3}$alkylene, C$_{3-4}$cycloalkylene, optionally substituted by one or more substituents selected from C$_{1-2}$alkyl, halo, hydroxy, or oxo;

L$_{1b}$ is absent or selected from O, S, SO, SO$_2$, N(R$_r$), C(O), C(O)O, OC(O), C(O)N(R$_r$), N(R$_r$)C(O), N(R$_r$)C(O)N(R$_s$), S(O)$_2$N(R$_r$), or N(R$_r$)SO$_2$, wherein R$_r$ and R$_s$ are each independently selected from hydrogen or C$_{1-2}$alkyl; and Q$_1$ is hydrogen, cyano, C$_{1-6}$alkyl, C$_{3-8}$cycloalkyl (e.g. C$_{3-6}$cycloalkyl), C$_{2-3}$alkenyl, C$_{2-3}$alkynyl, aryl, heterocyclyl or heteroaryl; and wherein Q$_1$ is optionally substituted by one or more substituents selected from C$_{1-4}$alkyl, halo, trifluoromethyl, trifluoromethoxy, amino, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein $R_t$ and $R_u$ are each independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), C(O)N($R_v$), N($R_v$)C(O), N($R_v$)C(O)N($R_w$), S(O)$_2$N ($R_v$), or N($R_v$)SO$_2$, wherein $R_v$ and $R_w$ are each independently selected from hydrogen or $C_{1-2}$alkyl; and $Z_1$ is $C_{3-8}$cycloalkyl (including a spirocyclic carbocyclic and a bridged $C_{3-8}$cycloalkyl), heterocyclyl (including a mono- or bicyclic-heterocyclic ring system, a spirocyclic heterocyclic ring system, or a bridged heterocyclic ring system), phenyl or 5-6 membered heteroaryl; wherein $Z_1$ is optionally substituted by one or more substituents selected from $C_{1-4}$alkyl, $C_{3-6}$cycloalkyl, heterocyclyl, halo, $C_{1-4}$haloalkyl, $C_{1-4}$haloalkoxy, $C_{1-4}$alkoxy, cyano, hydroxyl, $NR_{t1}R_{u1}$, $OR_{t}$, C(O)$R_{t1}$, C(O)O$R_{t1}$, OC(O)$R_{t1}$, C(O)N($R_{t1}$)$R_{u1}$, N($R_{t1}$)C(O)$R_{u1}$, S(O)$_y$$R_{t1}$ (where y is 0, 1 or 2), SO$_2$N($R_{t1}$)$R_{u1}$, N($R_{t1}$)SO$_2$$R_{u1}$ or (CH$_2$)$_z$NR$_{t1}$R$_{u1}$ (where z is 1, 2 or 3), wherein $R_{t1}$ and $R_{u1}$ are each independently selected from hydrogen or $C_{1-4}$alkyl; and when $Z_1$ is $C_{3-8}$ cycloalkyl or heterocyclyl, $Z_1$ is optionally spiro-fused to a $C_{3-6}$cycloalkyl or heterocyclyl ring;

(7b) $R_{1b}$, $R_{1d}$ and $R_{1f}$ are selected from hydrogen, cyano, halo or a group of the formula:

-$L_{1a}$-$L_{1b}$-$Q_1$ wherein $L_{1a}$ is absent or $C_{1-3}$alkylene, $C_{3-4}$cycloalkylene, optionally substituted by one or more substituents selected from aryl, aryl-(1-2C)alkyl, heteroaryl, aryl-(1-2C)alkyl, $C_{1-2}$alkyl, cyano, halo, hydroxy, or oxo, wherein any aryl, aryl-(1-2C)alkyl, heteroaryl, aryl-(1-2C)alkyl or $C_{1-2}$alkyl is optionally further substituted by one or more substituents selected from halo, cyano or hydroxy; $L_{1b}$ is absent or selected from O, S, SO, SO$_2$, N($R_r$), C(O), C(O)O, OC(O), C(O)N ($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or $C_{1-2}$alkyl, wherein $C_{1-2}$alkyl is optionally further substituted by $C_{3-6}$cycloalkyl or a 3 to 6 membered heterocyclyl, which in turn are optionally further substituted by halo, hydroxy, $C_{1-2}$alkoxy or $C_{1-2}$haloalkoxy; and $Q_1$ is hydrogen, cyano, $C_{1-6}$alkyl, $C_{3-8}$cycloalkyl (e.g. $C_{3-6}$cycloalkyl), $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, oxo, cyano, hydroxy, carboxy, carbamoyl, sulphamoyl, $NR_tR_u$, $OR_t$, C(O)$R_t$, C(O)O$R_t$, OC(O)$R_t$, C(O)N($R_t$)$R_u$, N($R_t$)C(O)$R_u$, S(O)$_y$$R_t$ (where y is 0, 1 or 2), SO$_2$N($R_t$)$R_u$, N($R_t$)SO$_2$$R_u$ or (CH$_2$)$_z$NR$_t$R$_u$ (where z is 1, 2 or 3), wherein $R_t$ and $R_u$ are each independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), C(O)N($R_v$), N($R_v$)C(O), N($R_v$)C(O)N($R_w$), S(O)$_2$N ($R_v$), or N($R_v$)SO$_2$, wherein $R_v$ and $R_w$ are each independently selected from hydrogen or $C_{1-2}$alkyl; and $Z_1$ is $C_{3-8}$cycloalkyl (including a spirocyclic carbocyclic and a bridged $C_{3-8}$cycloalkyl), heterocyclyl (including a mono- or bicyclic-heterocyclic ring system, a spirocyclic heterocyclic ring system, or a bridged heterocyclic ring system), phenyl or 5-6 membered heteroaryl; wherein $Z_1$ is optionally substituted by one or more substituents selected from $C_{1-4}$alkyl, $C_{3-6}$cycloalkyl, heterocyclyl, halo, $C_{1-4}$haloalkyl, $C_{1-4}$haloalkoxy, $C_{1-4}$alkoxy, cyano, hydroxyl, $NR_{t1}R_{u1}$, $OR_{t}$, C(O)$R_{t1}$, C(O)O$R_{t1}$, OC(O)$R_{t1}$, C(O)N($R_{t1}$)$R_{u1}$, N($R_{t1}$)C(O)$R_{u1}$, S(O)$_y$$R_{t1}$ (where y is 0, 1 or 2), SO$_2$N($R_{t1}$)$R_{u1}$, N($R_{t1}$)SO$_2$$R_{u1}$ or (CH$_2$)$_z$NR$_{t1}$R$_{u1}$ (where z is 1, 2 or 3), wherein $R_{t1}$ and $R_{u1}$ are each independently selected from hydrogen or $C_{1-4}$alkyl; and when $Z_1$ is $C_{3-8}$ cycloalkyl or heterocyclyl, $Z_1$ is optionally spiro-fused to a $C_{3-6}$cycloalkyl or heterocyclyl ring;

(8) $R_{1b}$, $R_{1d}$ and $R_{1f}$ are selected from hydrogen, halo, cyano or from a group of formula:

-$L_{1a}$-$L_{1b}$-$Q_1$ wherein $L_{1a}$ is absent or $C_{1-3}$alkylene, optionally substituted by one or more hydroxy;

$L_{1b}$ is absent or N($R_r$) wherein $R_r$ is hydrogen; and $Q_1$ is $C_{1-6}$alkyl, $C_{2-3}$alkenyl, $C_{3-8}$cycloalkyl (e.g. $C_{3-6}$cycloalkyl), aryl, heterocyclyl or heteroaryl; and wherein $Q_1$ is optionally substituted by one or more substituents selected from halo, carboxy, trifluoromethyl, $NR_tR_u$, $OR_t$ wherein $R_t$ and $R_u$ are independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent;

$L_{1d}$ is absent; and $Z_1$ is phenyl or 5-6 membered heteroaryl; wherein $Z_1$ is optionally substituted by one or more $C_{1-4}$alkyl;

(8a) $R_{1b}$, $R_{1d}$ and $R_{1f}$ are selected from hydrogen, halo, cyano or from a group of formula:

-$L_{1a}$-$L_{1b}$-$Q_1$ wherein $L_{1a}$ is absent or $C_{1-3}$alkylene, optionally substituted by one or more hydroxy;

$L_{1b}$ is absent or N($R_r$) wherein $R_r$ is hydrogen or $C_{1-4}$alkyl; and $Q_1$ is $C_{1-6}$alkyl, $C_{2-3}$alkenyl, $C_{3-6}$cycloalkyl, aryl, heterocyclyl or heteroaryl; and wherein $Q_1$ is optionally substituted by one or more substituents selected from halo, carboxy, trifluoromethyl, $NR_tR_u$, $OR_t$ wherein $R_t$ and $R_u$ are independently selected from hydrogen or $C_{1-4}$alkyl; or $Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is phenyl, 5-6 membered heteroaryl, $C_{3-8}$cycloalkyl (including a spirocyclic carbocyclic and a bridged $C_{3-8}$cycloalkyl) or heterocyclyl (including a mono- or bicyclic-heterocyclic ring system, a spirocyclic heterocyclic ring system, or a bridged heterocyclic ring system); wherein $Z_1$ is optionally substituted by one or more substituents selected from $C_{1-4}$alkyl, $C_{3-6}$cycloalkyl, heterocyclyl, halo, $C_{1-4}$haloalkyl, $OR_{t1}$, $C(O)R_{t1}$, $C(O)OR_{t1}$, $OC(O)R_{t1}$, wherein $R_{t1}$ and $R_{u1}$ are each independently selected from hydrogen or $C_{1-4}$alkyl; and $Z_1$ is optionally spiro-fused to a $C_{3-6}$ cycloalkyl or heterocyclyl ring;

(8b) $R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is $C_{1-3}$alkylene;
$L_{1b}$ is $N(R_r)$ wherein $R_r$ is hydrogen or $C_{1-4}$alkyl; and
$Q_1$ is $C_{1-6}$alkyl, heterocyclyl or heteroaryl; and wherein $Q_1$ is optionally substituted by one or more substituents selected from halo, carboxy, trifluoromethyl, $NR_tR_u$, $OR_t$ wherein $R_t$ and $R_u$ are independently selected from hydrogen or $C_{1-4}$alkyl; or
$Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is $C_{3-8}$cycloalkyl (including a spirocyclic carbocyclic and a bridged $C_{3-8}$cycloalkyl) or heterocyclyl (including a mono- or bicyclic-heterocyclic ring system, a spirocyclic heterocyclic ring system, or a bridged heterocyclic ring system); wherein $Z_1$ is optionally substituted by one or more substituents selected from $C_{1-4}$alkyl, $C_{3-6}$cycloalkyl, heterocyclyl, halo, $C_{1-4}$haloalkyl, $OR_t$, $C(O)R_{t1}$, $C(O)OR_{t1}$, $OC(O)R_{t1}$, wherein $R_{t1}$ is selected from hydrogen or $C_{1-4}$alkyl; and $Z_1$ is optionally spiro-fused to a $C_{3-6}$cycloalkyl or heterocyclyl ring;

(8c) $R_{1b}$, $R_{1d}$ and $R_{1f}$ are selected from hydrogen or from a group of formula:

-$L_{1a}$-$L_{1b}$-$Q_1$ wherein
$L_{1a}$ is $C_{1-3}$alkylene;
$L_{1b}$ is $N(R_r)$ wherein $R_r$ is hydrogen or $C_{1-4}$alkyl; and
$Q_1$ is $C_{1-6}$alkyl; and wherein $Q_1$ is optionally substituted by one or more substituents selected from halo, carboxy, trifluoromethyl, $NR_tR_u$, $OR_t$ wherein $R_t$ and $R_u$ are independently selected from hydrogen or $C_{1-4}$alkyl; or
$Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is $C_{3-8}$cycloalkyl (including a spirocyclic carbocyclic and a bridged $C_{3-8}$cycloalkyl); wherein $Z_1$ is optionally substituted by one or more substituents selected from $C_{1-4}$alkyl, $C_{3-6}$cycloalkyl, heterocyclyl, halo, $C_{1-4}$haloalkyl, $OR_{t1}$ or $C(O)OR_{t1}$, wherein $R_{t1}$ is selected from hydrogen or $C_{1-4}$alkyl; and $Z_1$ is optionally spiro-fused to a $C_{3-6}$cycloalkyl or heterocyclyl ring;

(8d) $R_{1b}$, $R_{1d}$ and $R_{1f}$ are selected from hydrogen or from a group of formula:

-$L_{1a}$-$L_{1b}$-$Q_1$ wherein
$L_{1a}$ is $C_{1-3}$alkylene;
$L_{1b}$ is $N(R_r)$ wherein $R_r$ is hydrogen; and
$Q_1$ is $C_{1-6}$alkyl; and wherein $Q_1$ is optionally substituted by one or more substituents selected from halo, carboxy, trifluoromethyl, $NR_tR_u$, $OR_t$ wherein $R_t$ and $R_u$ are independently selected from hydrogen or $C_{1-4}$alkyl; or
$Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is $C_{3-6}$cycloalkyl (including a spirocyclic carbocyclic and a bridged $C_{3-6}$cycloalkyl); wherein $Z_1$ is optionally substituted by one or more substituents selected from $C_{1-4}$alkyl or halo, $C_{1-4}$haloalkyl, $OR_{t1}$ or $C(O)OR_{t1}$, wherein $R_{t1}$ is selected from hydrogen or $C_{1-4}$alkyl;

(8e) $R_{1b}$, $R_{1d}$ and $R_{1f}$ are selected from hydrogen or from a group of formula:

-$L_{1a}$-$L_{1b}$-$Q_1$ wherein
$L_{1a}$ is $C_{1-3}$alkylene;
$L_{1b}$ is $N(R_r)$ wherein $R_r$ is hydrogen; and
$Q_1$ is $C_{1-6}$alkyl substituted by one or more groups of the formula:

-$L_{1c}$-$L_{1d}$-$Z_1$ wherein
$L_{1c}$ is absent;
$L_{1d}$ is absent; and
$Z_1$ is $C_{3-8}$cycloalkyl (including a spirocyclic carbocyclic and a bridged $C_{3-8}$cycloalkyl) that is optionally substituted by one or more substituents selected from $C_{1-4}$alkyl or halo;

(9) $R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent or $C_{1-3}$alkylene;
$L_{1b}$ is absent or $N(R_r)$ wherein $R_r$ is hydrogen; and
$Q_1$ is $C_{1-6}$alkyl, and wherein
$Q_1$ is substituted by a group of the formula:

-$L_{1c}$-$L_{1d}$-$Z_1$ wherein
$L_{1c}$ is absent;
$L_{1d}$ is absent; and
$Z_1$ is phenyl;

(9a) $R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent or $C_{1-3}$alkylene, optionally substituted by one or more hydroxy;
$L_{1b}$ is absent; and
$Q_1$ is a 5- or 6-membered aryl, a 5- or 6-membered heteroaryl, a 5- or 6-membered heterocyclyl or a 7, 8 or 9 membered bridged heterocycle, wherein $Q_1$ is optionally substituted by one or more substituents selected from halo, $NR_tR_u$, $OR_t$, wherein $R_t$ and $R_u$ are independently selected from hydrogen or $C_{1-4}$alkyl; or $Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is 5-6 membered heteroaryl; wherein $Z_1$ is optionally substituted by one or more $C_{1-4}$alkyl;

(10) $R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent or $C_{1-3}$alkylene, optionally substituted by one or more hydroxy;
$L_{1b}$ is absent or $N(R_r)$ wherein $R_r$ is hydrogen; and
$Q_1$ is a 5- or 6-membered aryl, a 5- or 6-membered heteroaryl, or a 5- or 6-membered heterocyclyl, wherein $Q_1$ is optionally substituted by one or more substituents selected from halo, $NR_tR_u$, $OR_t$ wherein $R_t$ and $R_u$ are independently selected from hydrogen or $C_{1-4}$alkyl; or
$Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is 5-6 membered heteroaryl; wherein $Z_1$ is optionally substituted by one or more $C_{1-4}$alkyl;

(11) $R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent or $C_{1-3}$alkylene optionally substituted by one hydroxy;
$L_{1b}$ is absent or $N(R_r)$ wherein $R_r$ is hydrogen; and
$Q_1$ is phenyl, pyrazolyl, piperazinyl or pyrindinyl, wherein $Q_1$ is optionally substituted by one or more substituents selected from chloro and methoxy;

(12) $R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent;
$L_{1b}$ is absent or $N(R_r)$ wherein $R_r$ is hydrogen; and
$Q_1$ is $C_{1-6}$alkyl optionally substituted with 5-6 membered heteroaryl; wherein 5-6 membered heteroaryl is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl;

(13) $R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent;
$L_{1b}$ is absent or $N(R_r)$ wherein $R_r$ is hydrogen; and
$Q_1$ is $C_{1-6}$alkyl optionally substituted with piperazinyl, imidazolyl or pyridyl, wherein the imidazolyl is optionally substituted with $C_{1-4}$alkyl;

(14) $R_{1b}$, $R_{1d}$ and $R_{1f}$ are selected from hydrogen; halo; cyano; hydroxy; $C_{1-6}$alkyl optionally substituted with $OH$, $NH_2$, a 5-6 membered aryl, carboxy and/or a 5-6 membered heterocyclyl; $C_{1-6}$alkyloxy; $C_{2-3}$alkenyl; $C_{3-6}$cycloalkyl; —$C_{1-3}$alkylene-NH—$C_{1-6}$alkyl wherein the $C_{1-6}$alkyl is optionally substituted with $OH$, trifluoromethyl, carboxy or phenyl; —NH-heteroaryl wherein the heteroaryl is a 5- or 6-membered heteroaryl; 5- or 6-membered heteroaryl; 5- or 6-membered heterocyclic; 5- or 6-membered aryl optionally substituted with —$OC_{1-4}$alkyl or halo; and —NH—$C_{1-6}$alkyl wherein the $C_{1-6}$alkyl is optionally substituted with a 5- or 6-membered heteroaryl and wherein the 5- or 6-membered heteroaryl is optionally substituted with $C_{1-4}$alkyl;

(14a) $R_{1b}$, $R_{1d}$ and $R_{1f}$ are independently selected from hydrogen, halo, cyano, hydroxy, $C_{1-4}$alkyl, $C_{1-4}$alkoxy, $C_{1-4}$haloalkoxy, or a group of the formula:

—$(CR_{1c'}R_{1d'})_p$—$NR_{1e'}R_{1f'}$;

wherein
p is an integer selected from 1 or 2;
$R_{1c'}$ and $R_{1d'}$ are independently selected from:
(i) hydrogen (including deuterium),
(ii) $C_{1-3}$alkyl which is optionally substituted by one more substituents selected from cyano, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally substituted with halo, cyano or hydroxy,
(iii) or $R_{1c'}$ and $R_{1d'}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;
$R_{1e'}$ is selected from:
(i) hydrogen (including deuterium);
(ii) $C_{1-3}$alkyl which is optionally substituted by one more substituents selected from cyano, hydroxy, $C_{1-2}$alkoxy, halo, $C_{1-2}$haloalkoxy and $NH_2$;
$R_{1f'}$ is a group with the formula:

—$(CR_{1g}R_{1h})_q$-$T_1$ wherein:
q is 0, 1 or 2 (e.g. q is 1 or 2);
$R_{1g}$ and $R_{1h}$ are independently selected from:
a) hydrogen (including deuterium); or
b) $C_{1-3}$alkyl, which is optionally substituted by one more substituents selected from cyano, hydroxy, $C_{1-2}$alkoxy, halo, $C_{1-2}$haloalkoxy, —O—$C_3$cycloalkyl, wherein —O—$C_3$cycloalkyl is optionally substituted with halo, cyano or hydroxy;

and $T_1$ is selected from $C_{3-6}$cycloalkyl, aryl, heterocyclyl, heteroaryl, a spirocyclic carbocyclic or heterocyclic ring system, a bridged $C_{3-6}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

or $R_{1e'}$ and $R_{1f'}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1i}R_{1j}$ or $-S(O)_{0-2}R_{1i}R_{1j}$, wherein $R_{1i}$ and $R_{1j}$ are H or $C_{1-2}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, cyano, hydroxy, $C_{1-2}$alkoxy, halo, $C_{1-2}$haloalkoxy, $NR_{1i}R_{1j}$ or $-S(O)_{0-2}R_{1i}R_{1j}$, wherein $R_{1i}$ and $R_{1j}$ are H or $C_{1-2}$alkyl.

(14b) $R_{1d}$ and $R_{1f}$ are independently selected from hydrogen, halo, cyano, hydroxy, $C_{1-4}$-alkyl, $C_{1-4}$alkoxy and $C_{1-4}$haloalkoxy; and $R_{1b}$ is a group of the formula:

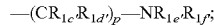

wherein
p is an integer selected from 1 or 2;
$R_{1c'}$ and $R_{1d'}$ are independently selected from:
(i) hydrogen (including deuterium) or
(ii) $C_{1-3}$alkyl which is optionally substituted by one more substituents selected from cyano, hydroxy, $C_{1-2}$alkoxy, halo, $C_{1-2}$haloalkoxy, $-O-C_3$cycloalkyl;
$R_{1e'}$ is selected from hydrogen (including deuterium) or $C_{1-2}$alkyl; and
$R_{1f'}$ is a group with the formula:

wherein:
q is 0, 1 or 2 (e.g. q is 1 or 2); $R_{1g}$ and $R_{1h}$ are independently selected from:
a) hydrogen (including deuterium); or
b) $C_{1-2}$alkyl, which is optionally substituted by one more substituents selected from cyano, hydroxy, $C_{1-2}$alkoxy, halo or $C_{1-2}$haloalkoxy;
and $T_1$ is selected from $C_{3-6}$cycloalkyl, aryl, heterocyclyl, heteroaryl, a spirocyclic carbocyclic or heterocyclic ring system, a bridged $C_{3-6}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

or $R_{1e'}$ and $R_{1f'}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

(14c) $R_{1d}$ and $R_{1f}$ are independently selected from hydrogen, halo, cyano, hydroxy, $C_{1-4}$-alkyl, $C_{1-4}$alkoxy and $C_{1-4}$haloalkoxy; and $R_{1b}$ is a group of the formula:

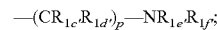

wherein
p is an integer selected from 1 or 2;
$R_{1c'}$ and $R_{1d'}$ are independently selected from hydrogen (including deuterium) or $C_{1-2}$alkyl;
$R_{1e'}$ is selected from hydrogen (including deuterium) or $C_{1-2}$alkyl; and
$R_{1f'}$ is a group with the formula:

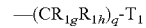

wherein:
q is 0, 1 or 2 (e.g. q is 1 or 2); $R_{1g}$ and $R_{1h}$ are independently selected from hydrogen (including deuterium) or $C_{1-2}$alkyl;
and $T_1$ is selected from $C_{3-4}$cycloalkyl, heterocyclyl, a spirocyclic carbocyclic or heterocyclic ring system, a bridged $C_{3-6}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

or $R_{1e'}$ and $R_{1f'}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

(14d) $R_{1d}$ and $R_{1f}$ are independently selected from hydrogen, halo, cyano, hydroxy, methyl and methoxy; and $R_{1b}$ is a group of the formula:

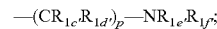

wherein
p is 1;
$R_{1c'}$ and $R_{1d'}$ are independently selected from hydrogen (including deuterium) or $C_{1-2}$alkyl;
$R_{1e'}$ is selected from hydrogen (including deuterium) or $C_{1-2}$alkyl; and
$R_{1f'}$ is a group with the formula:

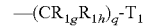

wherein:
q is 0, 1 or 2 (e.g. q is 1 or 2); $R_{1g}$ and $R_{1h}$ are independently selected from hydrogen (including deuterium) or $C_{1-2}$alkyl;
and $T_1$ is selected from $C_{3-4}$cycloalkyl, heterocyclyl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

or $R_{1e'}$ and $R_{1f'}$ are linked such that, together with the nitrogen atom to which they are attached, they form a mono- or bicyclic-heterocyclic ring, which is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy, and/or the mono- or bicyclic heterocyclic ring formed by R$_{1e}$ and R$_{1f}$ is optionally spiro-fused to a C$_{3-6}$cycloalkyl or a heterocyclic ring; which in turn is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy.

(14e) R$_{1d}$ and R$_{1f}$ are independently selected from hydrogen, halo, cyano, hydroxy, methyl and methoxy; and R$_{1b}$ is a group of the formula:

—(CR$_{1c'}$R$_{1d'}$)$_p$—NR$_{1e'}$R$_{1f'}$;

wherein
p is 1;
R$_{1c'}$ and R$_{1d'}$ are independently selected from hydrogen (including deuterium) or C$_{1-2}$alkyl;
R$_{1e'}$ is selected from hydrogen (including deuterium) or C$_{1-2}$alkyl; and
R$_{1f'}$ is a group with the formula:

—(CR$_{1g}$R$_{1h}$)$_q$-T$_1$ wherein:
q is 1;
R$_{1g}$ and R$_{1h}$ are independently selected from hydrogen (including deuterium) or C$_{1-2}$alkyl;
and T$_1$ is selected from C$_{3-4}$cycloalkyl, heterocyclyl, a spirocyclic carbocyclic or heterocyclic ring system, a bridged C$_{3-8}$cycloalkyl, or a bridged heterocyclic ring system, each of which is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy.

(14f) R$_{1d}$ and R$_{1f}$ are independently selected from hydrogen, halo, cyano, hydroxy, methyl and methoxy; and R$_{1b}$ is a group of the formula:

—(CR$_{1c'}$R$_{1d'}$)$_p$—NR$_{1e'}$R$_{1f'}$;

wherein
p is 1;
R$_{1c'}$ and R$_{1d'}$ are independently selected from hydrogen (including deuterium) or C$_{1-2}$alkyl; and
R$_{1e'}$ and R$_{1f'}$ are linked such that, together with the nitrogen atom to which they are attached, they form a mono- or bicyclic-heterocyclic ring, which is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy, and/or the mono- or bicyclic heterocyclic ring formed by R$_{1e'}$ and R$_{1f'}$ is optionally spiro-fused to a C$_{3-6}$cycloalkyl or a heterocyclic ring, which in turn is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy.

(14 g) R$_{1d}$ and R$_{1f}$ are independently selected from hydrogen, halo, cyano, hydroxy, methyl and methoxy; and R$_{1b}$ is a group of the formula wherein T$_1$ is selected from C$_{3-4}$cycloalkyl, heterocyclyl, a spirocyclic carbocyclic or heterocyclic ring system, a bridged C$_{3-8}$cycloalkyl, or a bridged heterocyclic ring system, each of which is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy.

(15) R$_{1b}$, R$_{1d}$ and R$_{1f}$ are selected from hydrogen; bromo; chloro; fluoro; cyano; methyl; hydroxy; methoxy;

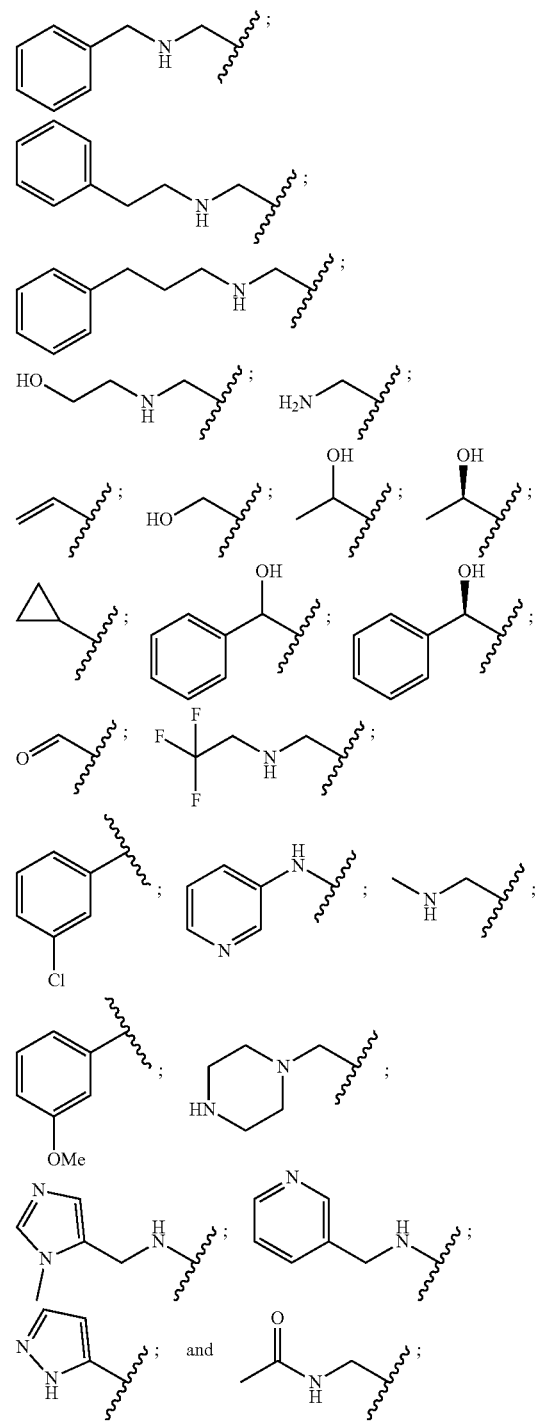

(15a) $R_{1d}$ and $R_{1f}$ are selected from hydrogen; bromo; chloro; fluoro; cyano; methyl; methoxy;
and $R_{1b}$ is selected from:
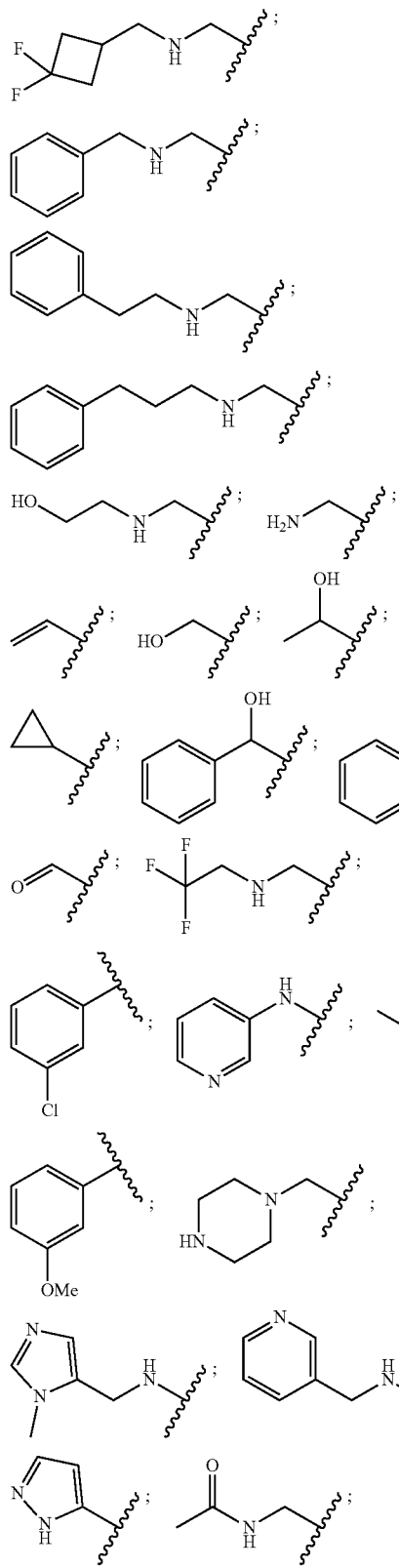
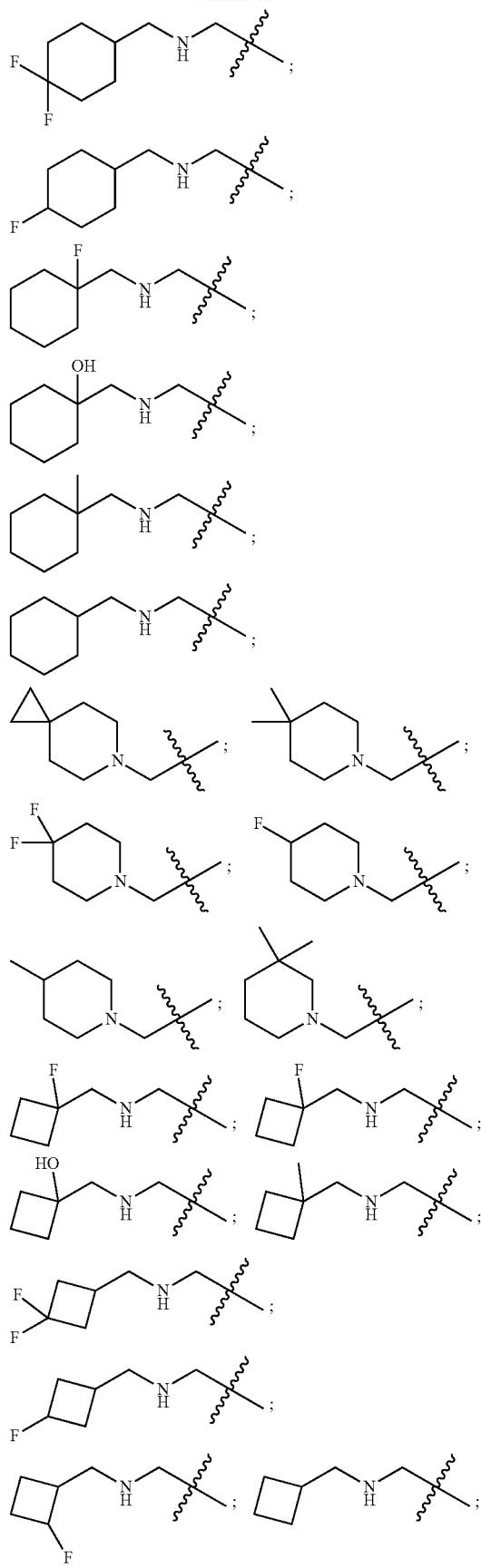

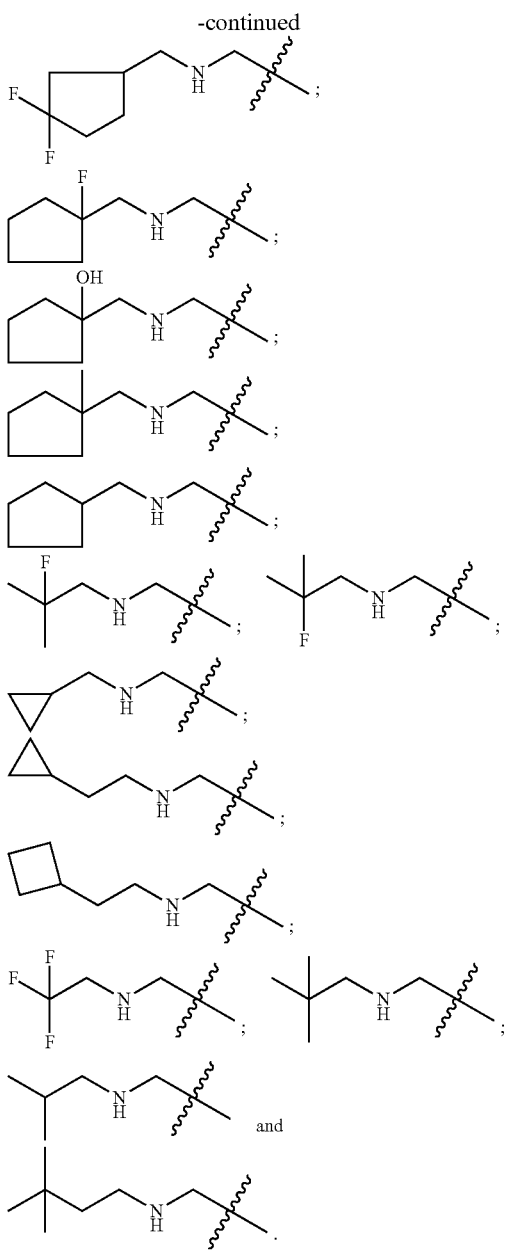
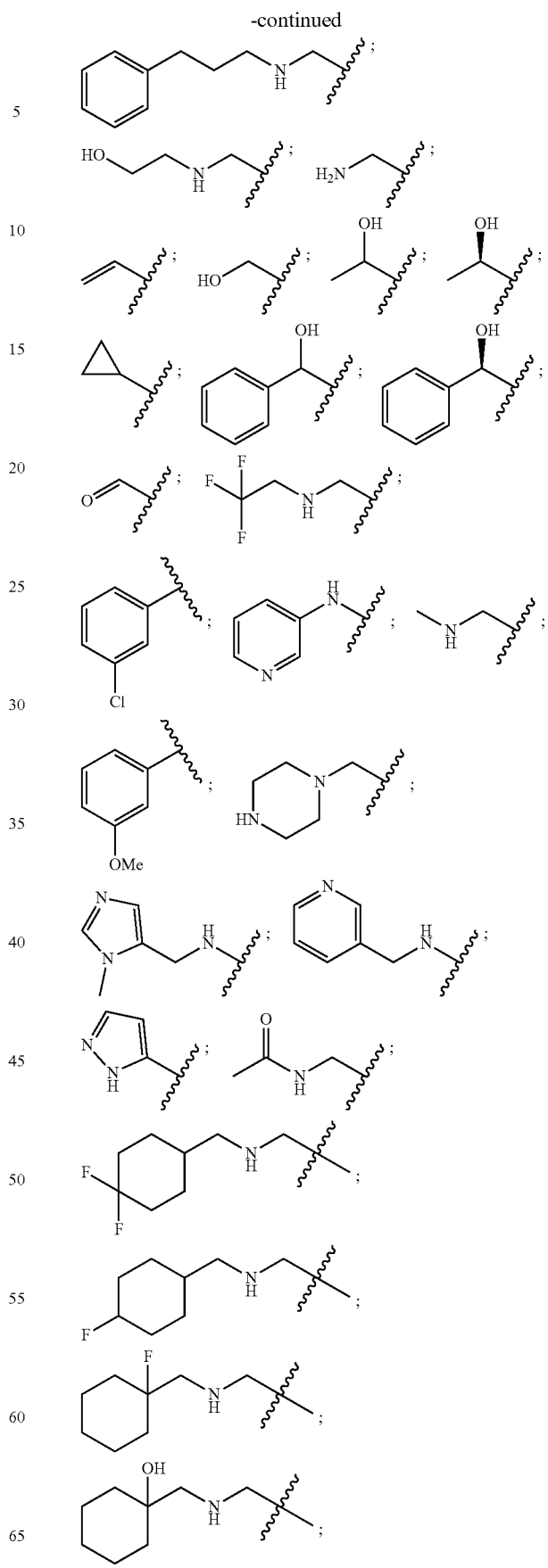
(15b) $R_{1b}$, $R_{1d}$ and $R_{1f}$ are selected from hydrogen; bromo; chloro; fluoro; cyano; methyl; methoxy,
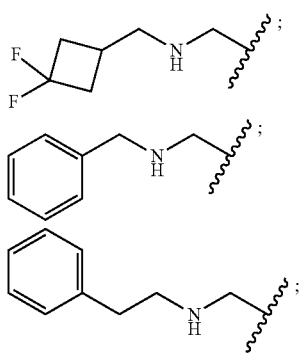

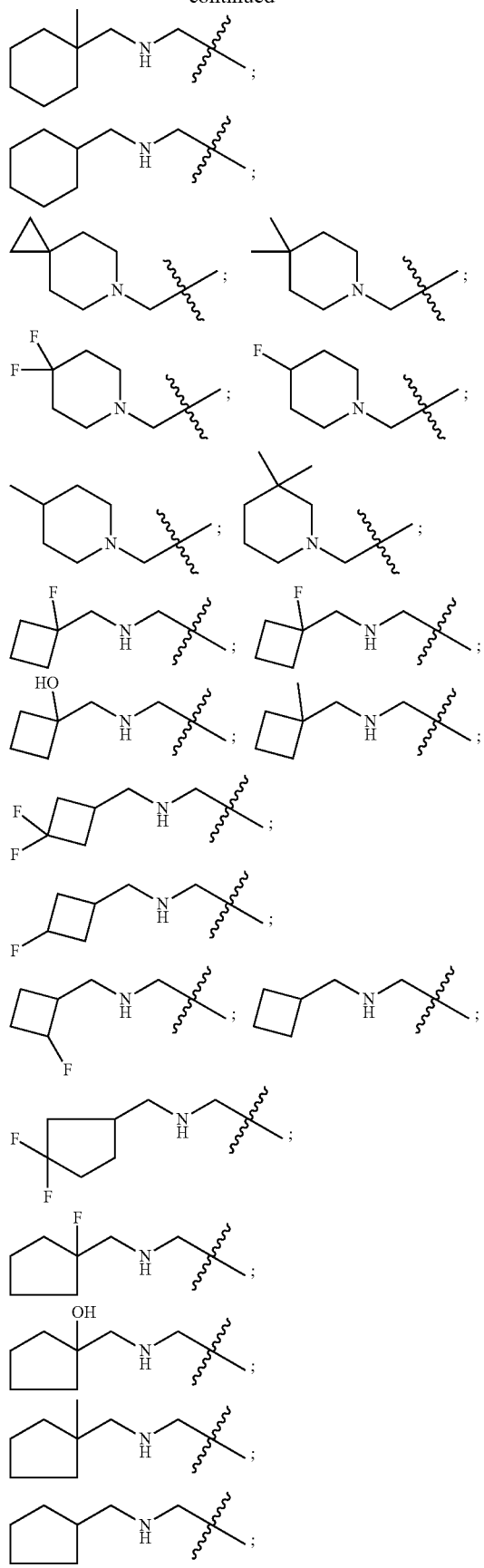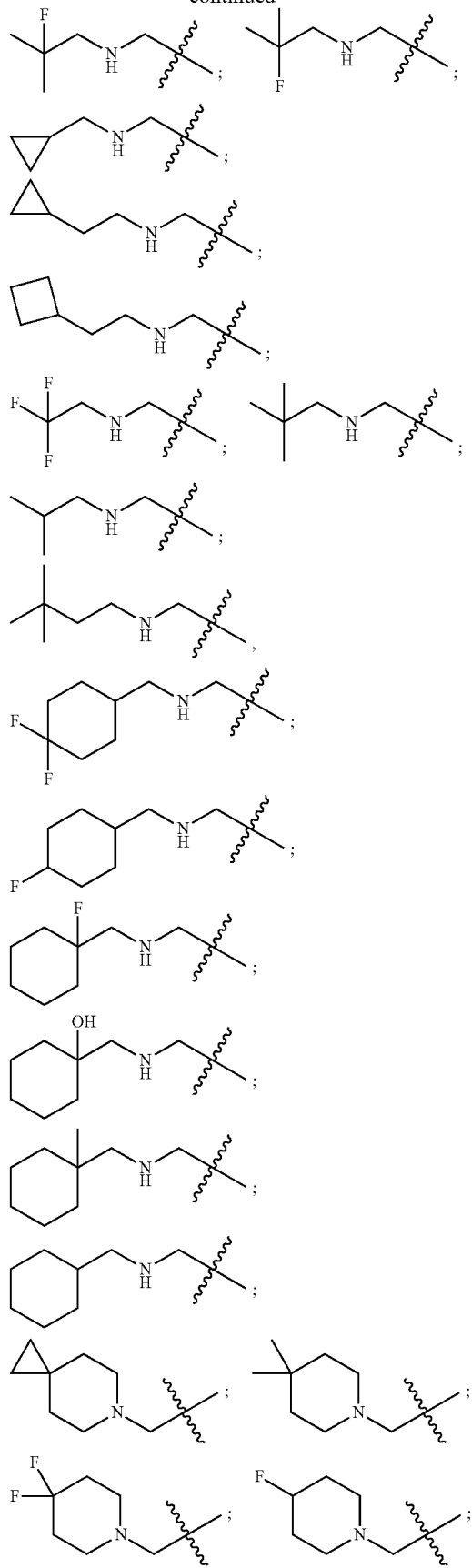

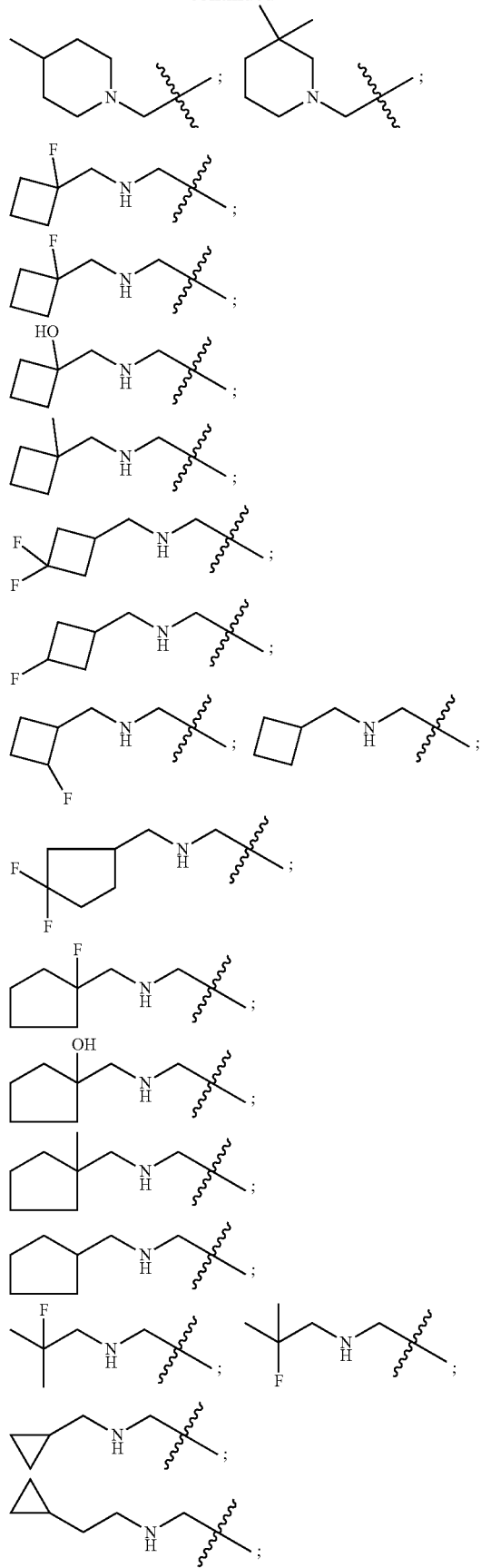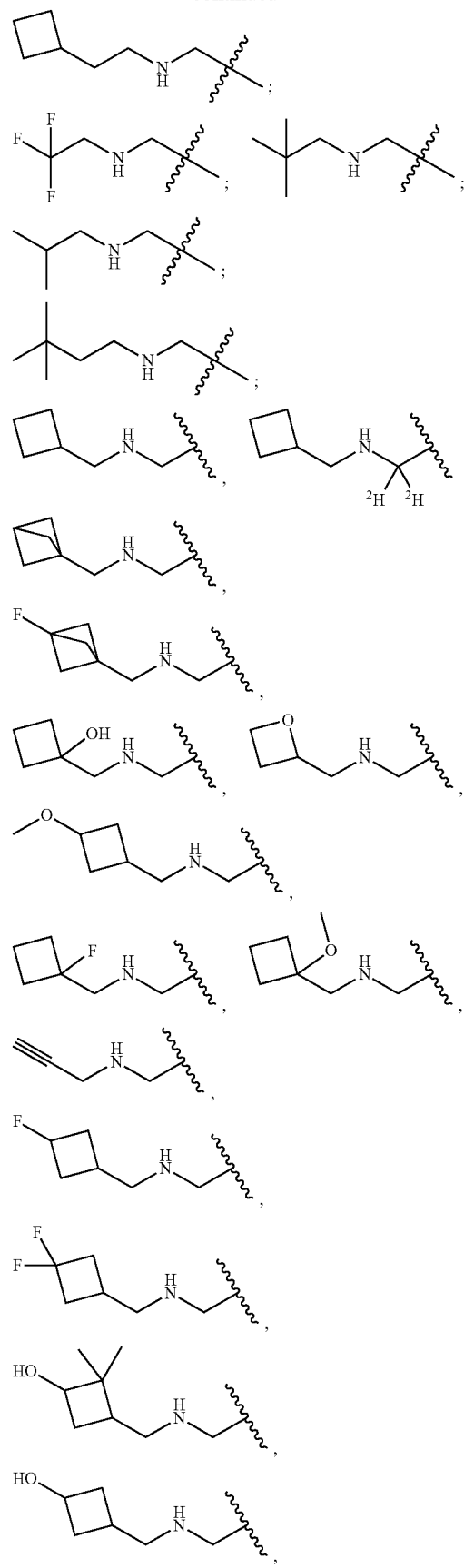

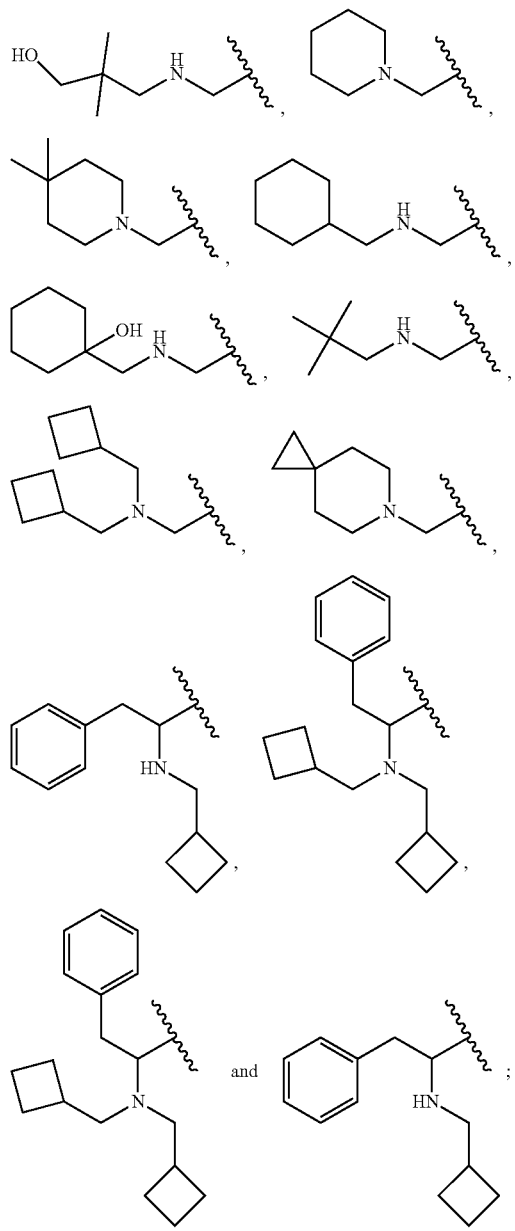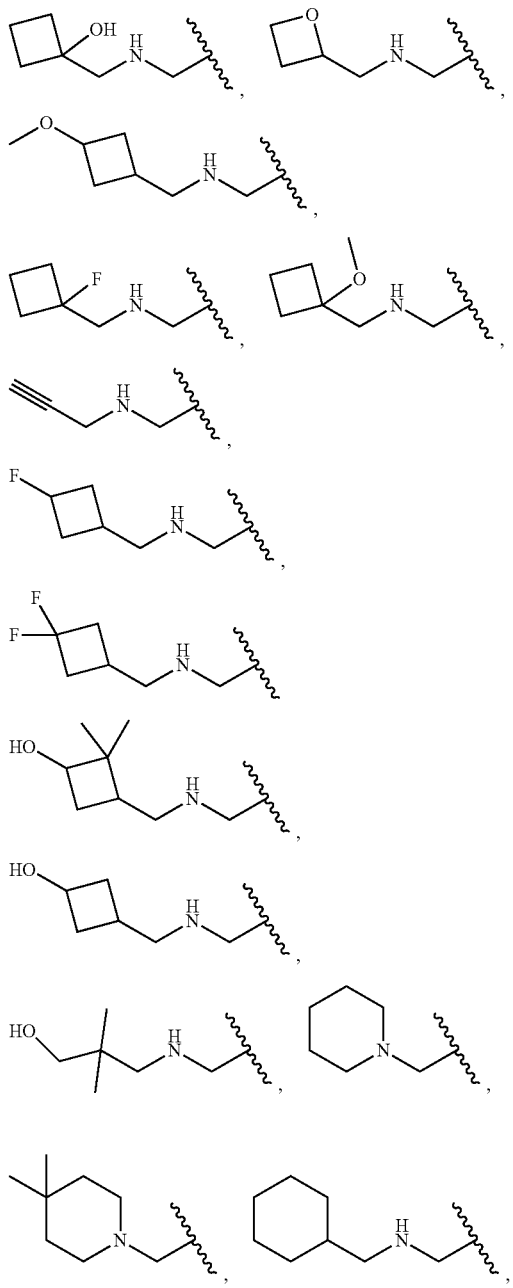
(15c) $R_{1b}$, $R_{1d}$ and $R_{1f}$ are selected from hydrogen; bromo; chloro; fluoro; cyano; methyl; methoxy,
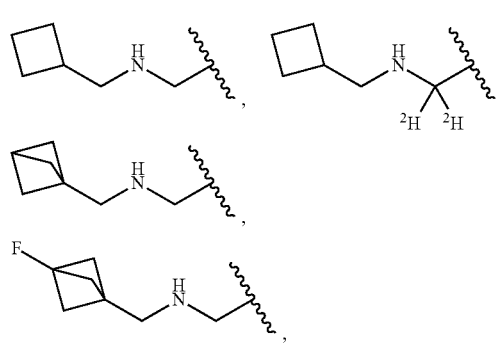

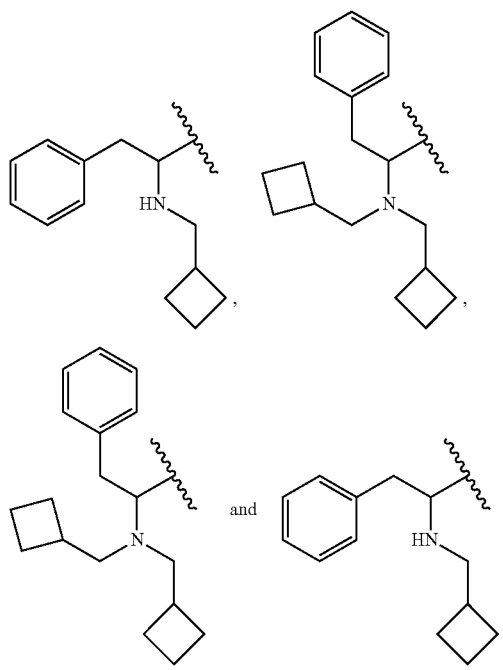
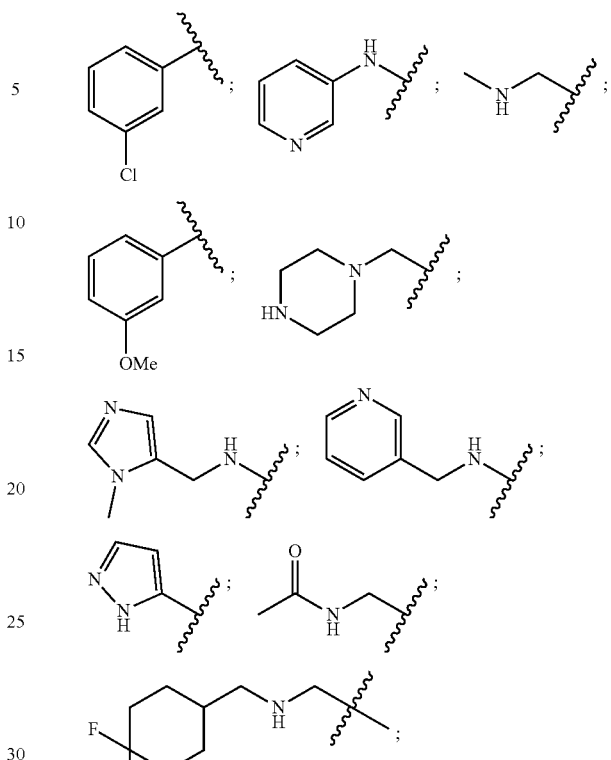
(15d) $R_{1b}$, $R_{1d}$ and $R_{1f}$ are selected from:
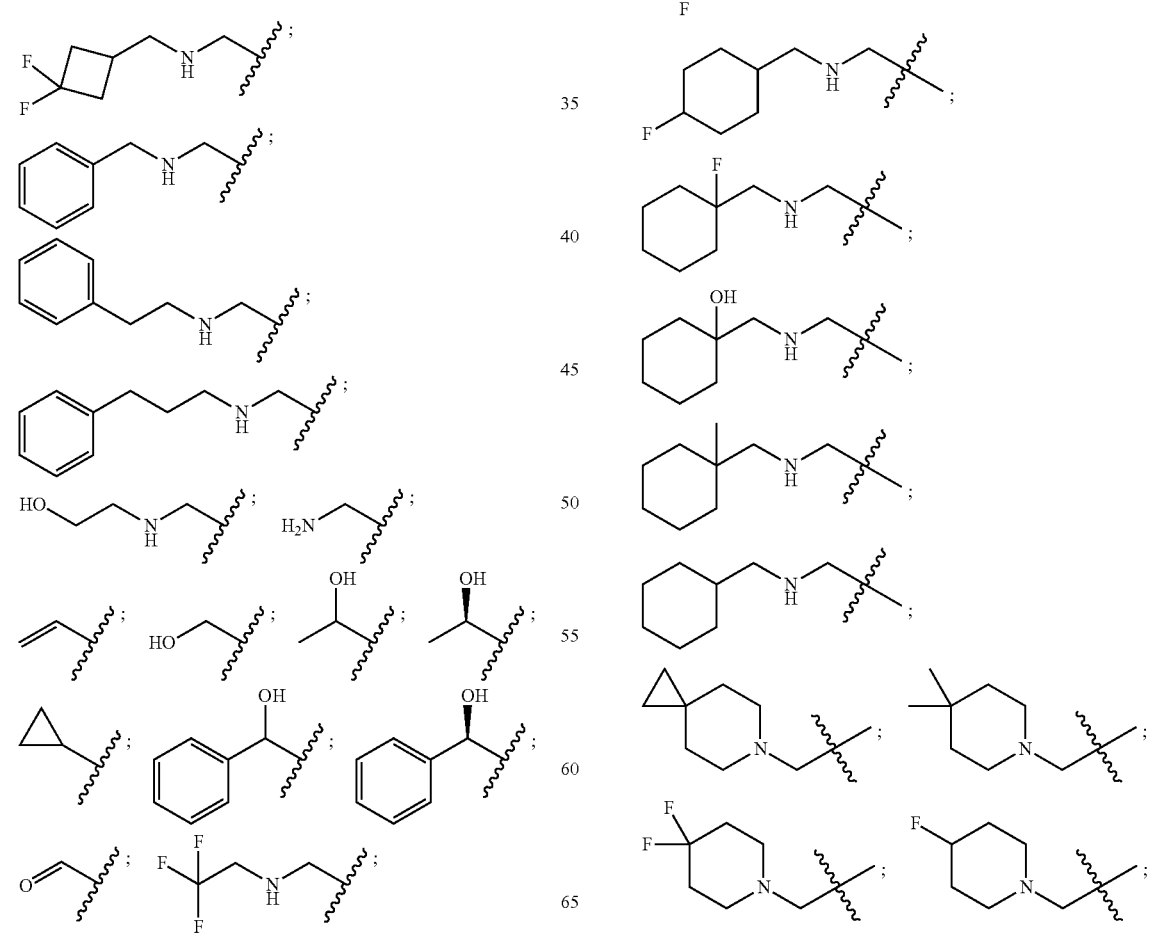

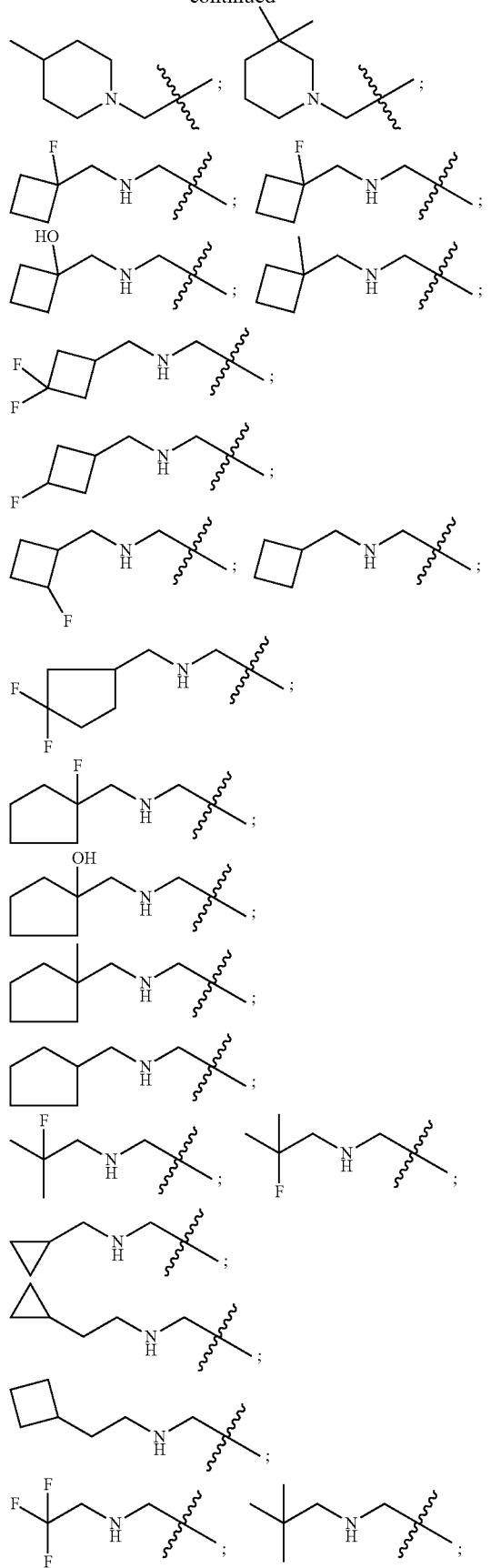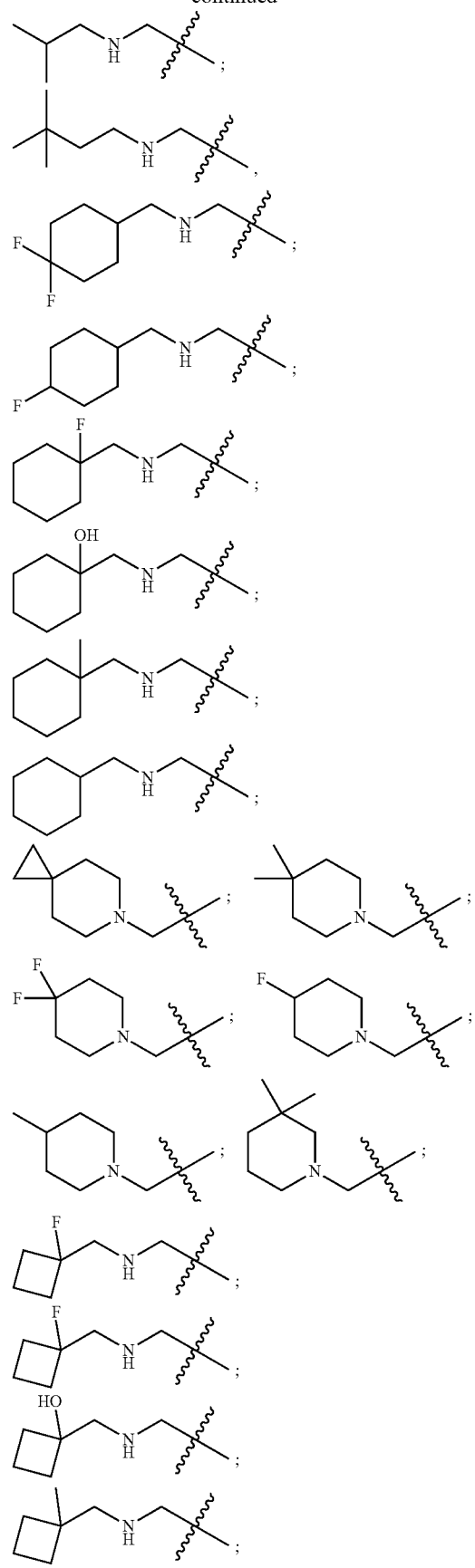

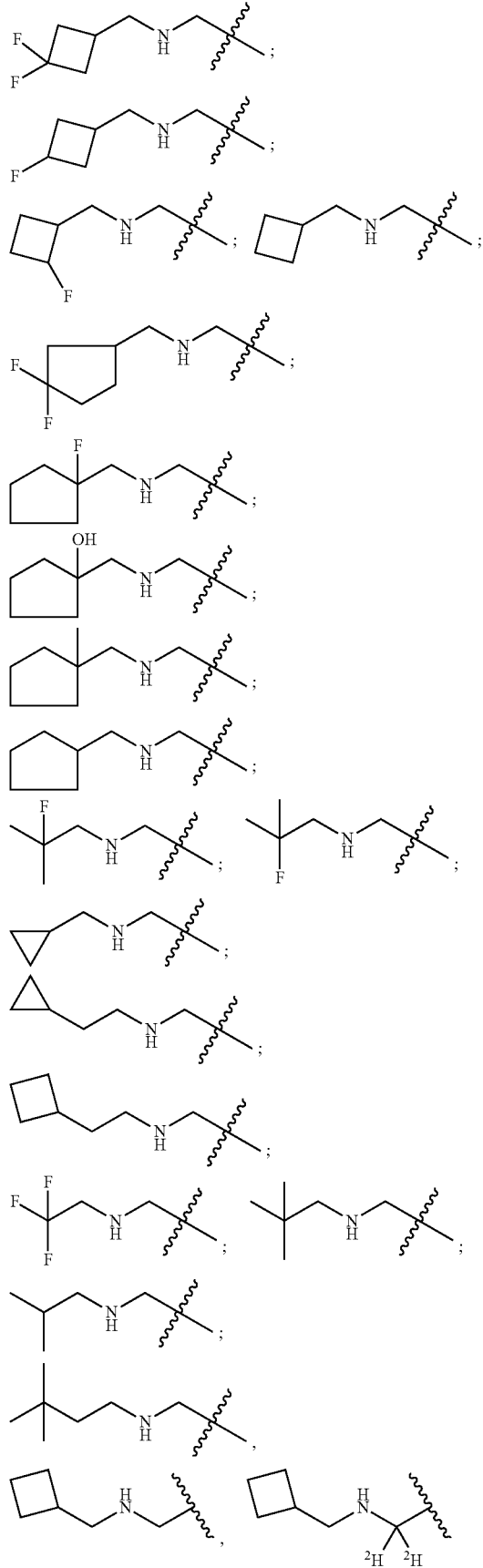
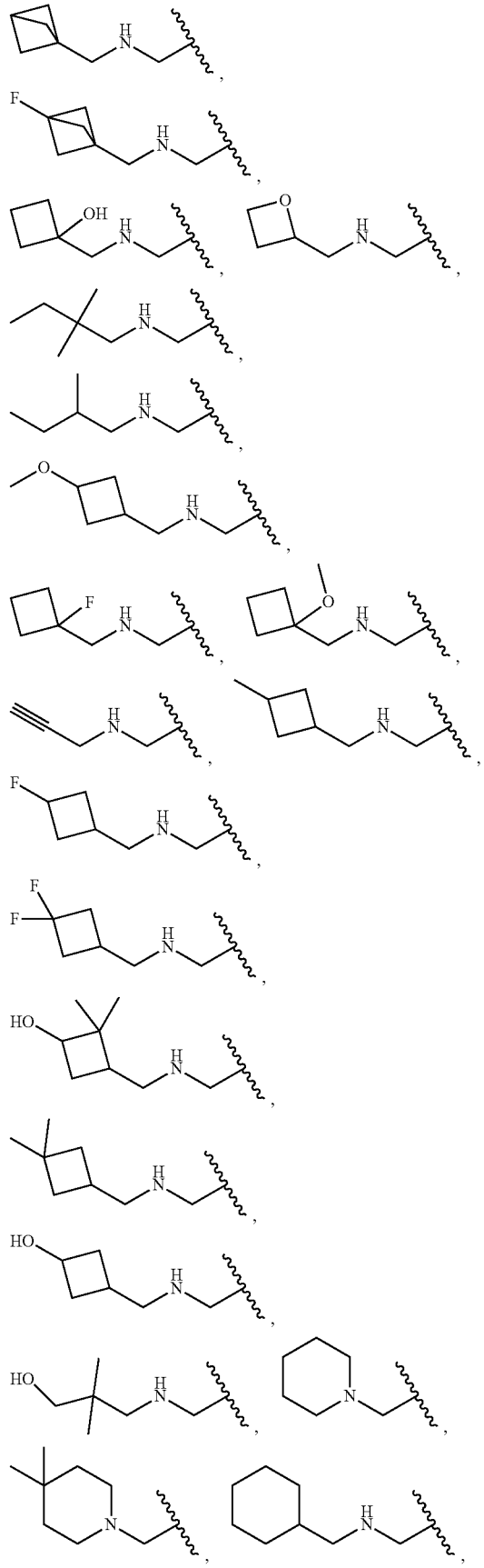

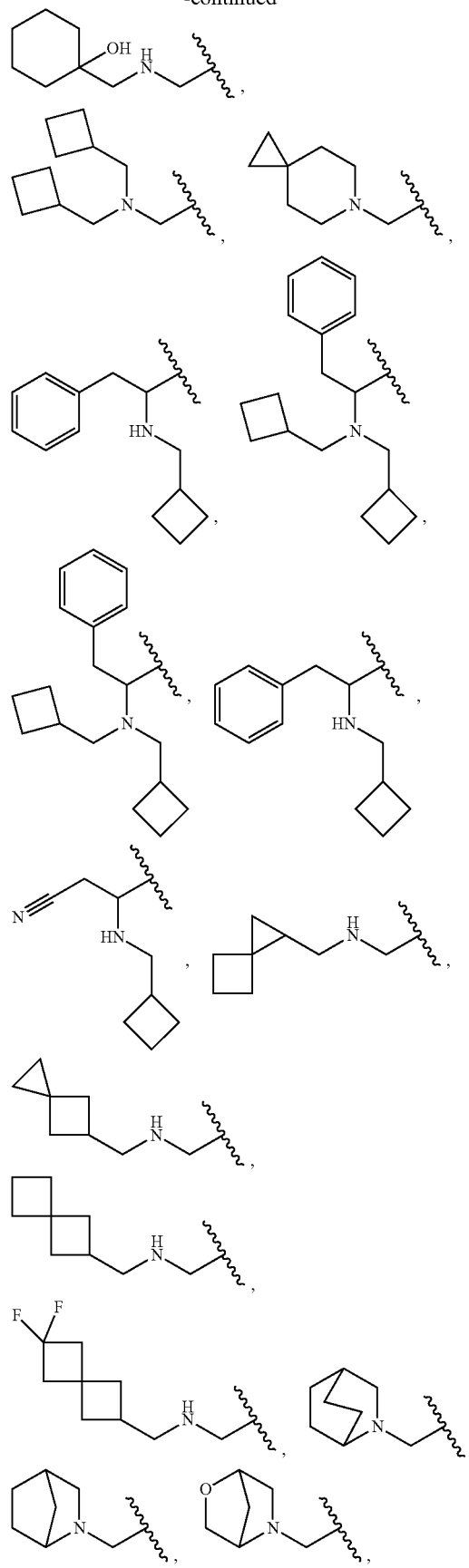
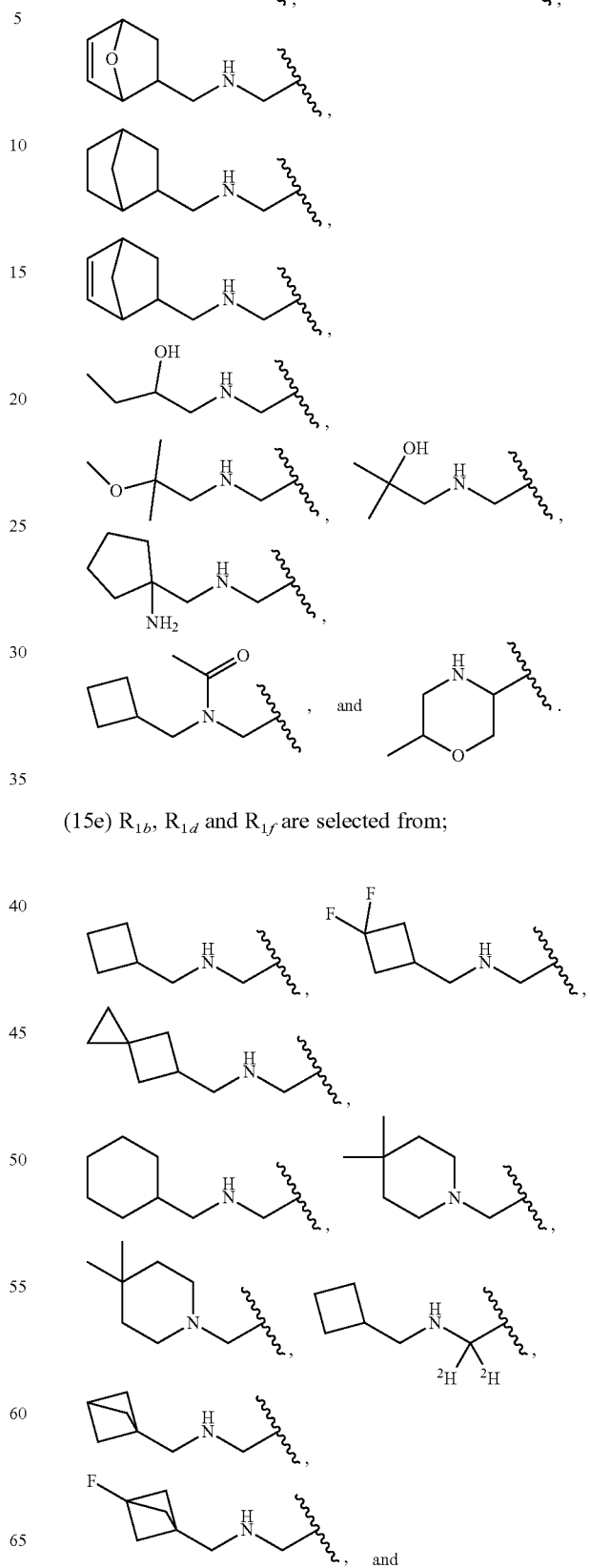
(15e) $R_{1b}$, $R_{1d}$ and $R_{1f}$ are selected from;

-continued

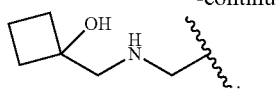

(15f) $R_{1b}$, $R_{1d}$ and $R_{1f}$ are selected from;

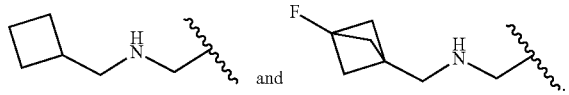 [SMILES: *CNCC1CCC1 ; *CNCC12CC(F)(C1)C2]

(15 g) $R_{1b}$, $R_{1d}$ and $R_{1f}$ are;

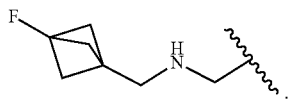

(16) $R_{1a'}$ is selected from hydrogen, halo and methyl;
(16a) $R_{1a'}$ is selected from hydrogen and methyl;
(17) $R_{1a'}$ is hydrogen;
(18) $R_{2a}$, $R_{2b}$ and $R_{2c}$ are selected from hydrogen, halo or a group of the formula:

-$L_{2a}$-$L_{2b}$-$Q_2$ wherein $L_{2a}$ is absent or $C_{1-3}$alkylene optionally substituted by $C_{1-2}$ alkyl or oxo;

$L_{2b}$ is absent or selected from O, S, SO, $SO_2$, $N(R_n)$, C(O), C(O)O, OC(O), $C(O)N(R_n)$, $N(R_n)C(O)$, $N(R_n)C(O)N(R_o)$, $S(O)_2N(R_n)$, or $N(R_n)SO_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

(19) $R_{2a}$, $R_{2b}$ and $R_{2c}$ are hydrogen;
(20) X is

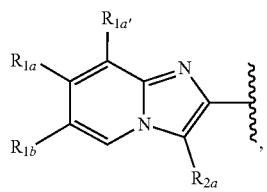

wherein $R_{1a}$, $R_{1b}$, $R_{1a'}$ and $R_{2a}$ are as herein defined;
(21) X is

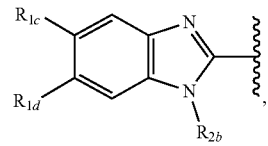

wherein $R_{1c}$, $R_{1d}$ and $R_{2b}$ are as herein defined;
(22) X is

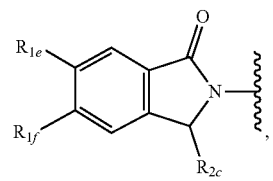

wherein $R_{1e}$, $R_{1f}$ and $R_{2c}$ are as herein defined;
(23) X is selected from

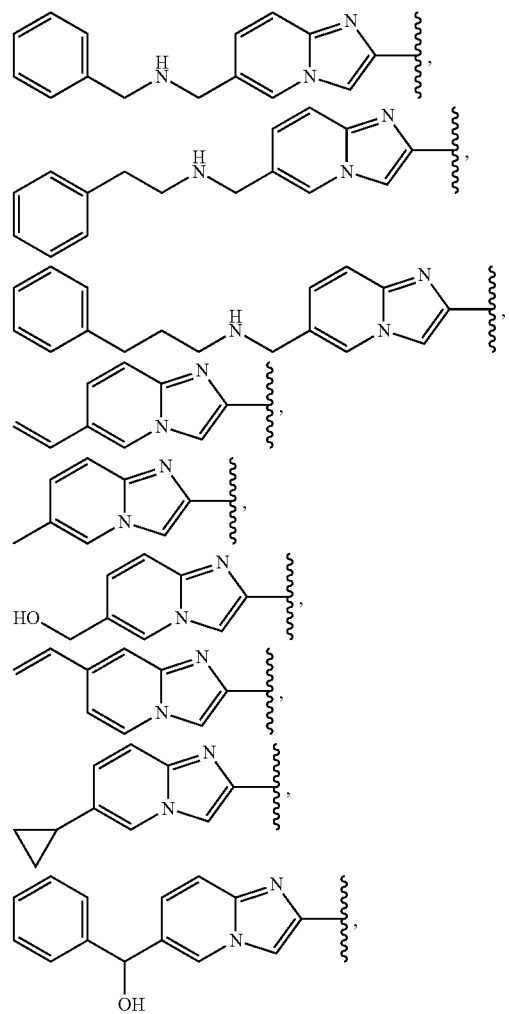

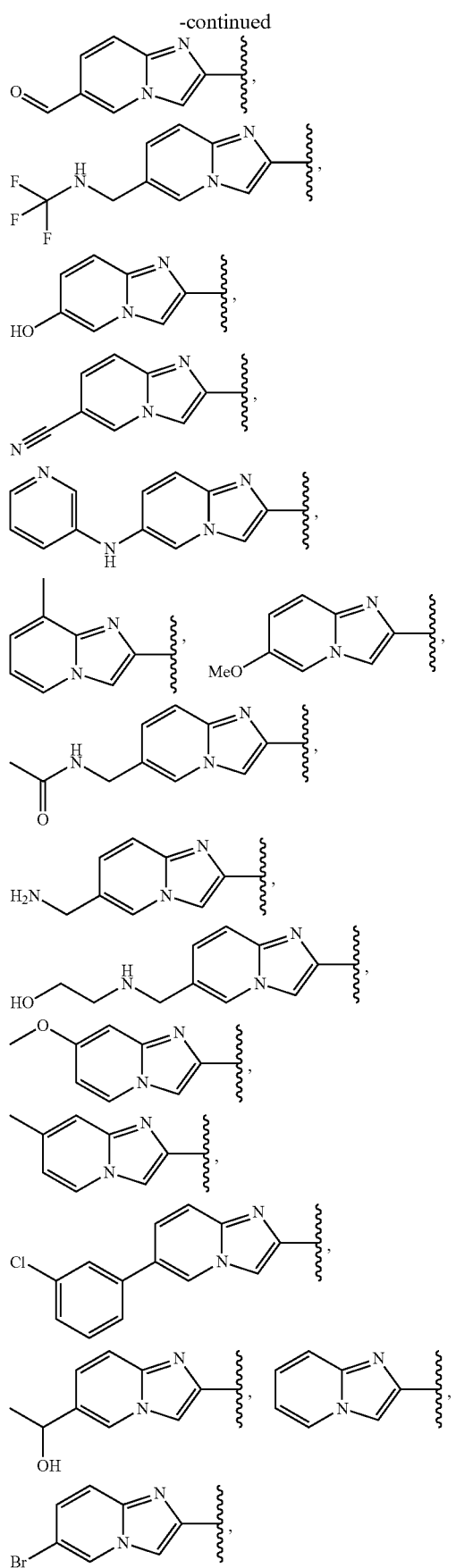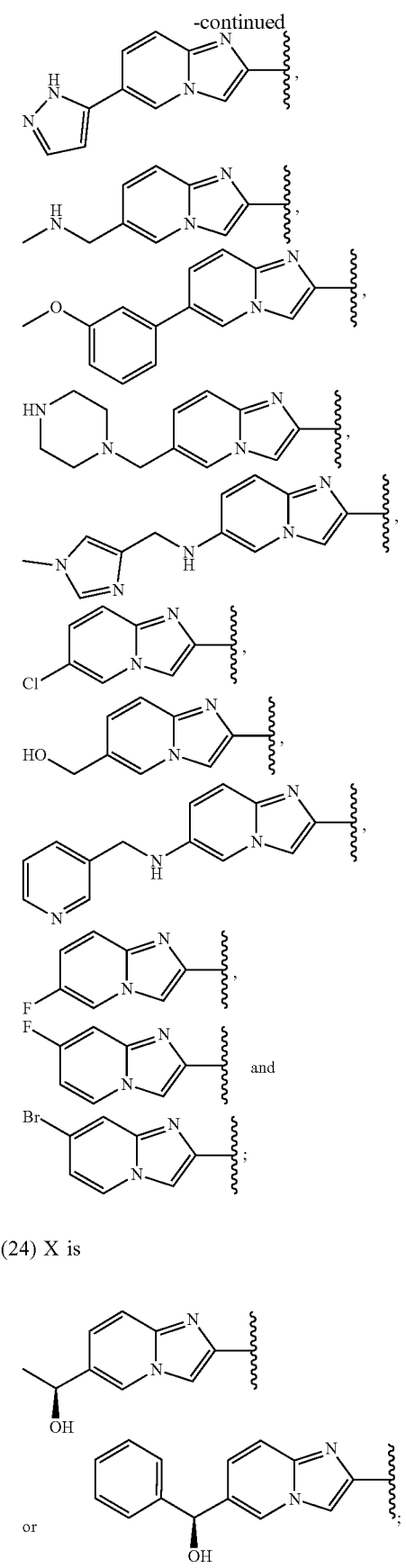
(24) X is (24a) X is

(25) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen, $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy; and $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$ are hydrogen;

(25a) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$ and $R_{3q1}$ are independently selected from hydrogen, $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy; and $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$ and $R_{3q2}$ are hydrogen;

(25b) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen, $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy; and $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$ $R_{3q2}$, $R_{3r2}$ and $R_{3s2}$ are hydrogen;

(26) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen and $C_{1-6}$alkyl; and wherein $C_{1-6}$alkyl is optionally substituted with one or more hydroxy substituents;

(26a) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$ and $R_{3q1}$ are independently selected from hydrogen and $C_{1-6}$alkyl; and wherein $C_{1-6}$alkyl is optionally substituted with one or more hydroxy substituents;

(26b) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3g1}$, $R_{3r1}$ and $R_{3s1}$ are independently selected from hydrogen and $C_{1-6}$alkyl; and wherein $C_{1-6}$alkyl is optionally substituted with one or more hydroxy substituents;

(27) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen and methyl; and wherein methyl is optionally substituted with one or more hydroxy substituents;

(27a) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$ and $R_{3q1}$ are independently selected from hydrogen and methyl; and wherein methyl is optionally substituted with one or more hydroxy substituents;

(27b) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$ and $R_{3q1}$ are independently selected from hydrogen and methyl; and wherein methyl is optionally substituted with one or more hydroxy substituents;

(28) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen and methyl; and wherein methyl is substituted with a hydroxy substituent;

(28a) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$ and $R_{3q1}$ are independently selected from hydrogen and methyl; and wherein methyl is substituted with a hydroxy substituent;

(28b) $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3g1}$, $R_{3r1}$ and $R_{3s1}$ are independently selected from hydrogen and methyl; and wherein methyl is substituted with a hydroxy substituent;

(29) $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$ are hydrogen;

(29a) $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$ and $R_{3q2}$ are hydrogen;

(29b) $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen;

(30) $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, or $R_{3o1}$ and $R_{3o2}$ are hydrogen;

(30a) $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$ are hydrogen.

(30b) $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3a1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$, $R_{3r1}$ and $R_{3r2}$, and $R_{3s1}$ and $R_{3s2}$ are hydrogen.

(31) $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k2}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$ may be linked to form a spiro-fused $C_{3-4}$cycloalkyl which is optionally substituted with one or more substituents selected from halo, amino, cyano, and hydroxy;

(31a) $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3a1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$ may be linked to form a spiro-fused $C_{3-4}$cycloalkyl which is optionally substituted with one or more substituents selected from halo, amino, cyano, and hydroxy;

(31b) $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3a1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, and $R_{3q1}$ and $R_{3q2}$, may be linked to form a spiro-fused $C_{3-4}$cycloalkyl which is optionally substituted with one or more substituents selected from halo, amino, cyano, and hydroxy;

(32) n is 0, 1 or 2;
(33) n is 1;
(34) Y is

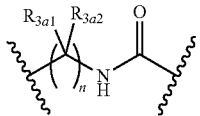

wherein $R_{3a1}$, $R_{3a2}$ and n are as herein defined;
(34a) Y is

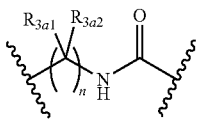

wherein n is 1, and $R_{3a1}$, $R_{3a2}$ are as herein defined
(35) Y is

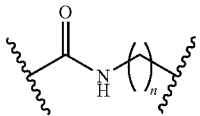

wherein n is herein defined;
(36) Y is

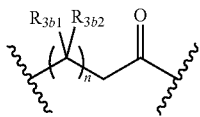

wherein $R_{3b1}$, $R_{3b2}$ and n are as herein defined;
(37) Y is

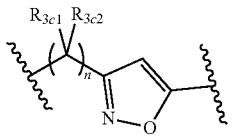

wherein $R_{3c1}$, $R_{3c2}$ and n are as herein defined;
(38) Y is

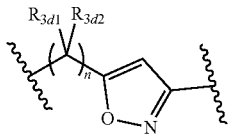

wherein $R_{3d1}$, $R_{3d2}$ and n are as herein defined;
(39) Y is

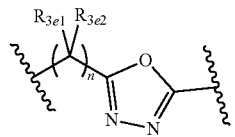

wherein $R_{3e1}$, $R_{3e2}$ and n are as herein defined;
(40) Y is

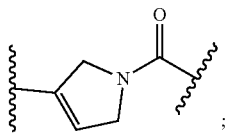 [SMILES: *C(=O)N1CC=C(*)C1]

;

(41) Y is

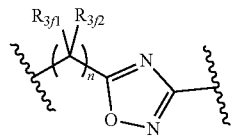

wherein $R_{3f1}$, $R_{3f2}$ and n are as herein defined;
(42) Y is

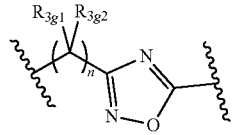

wherein $R_{3g1}$, $R_{3g2}$ and n are as herein defined;
(43) Y is

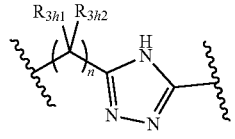

wherein $R_{3h1}$, $R_{3h2}$ and n are as herein defined
(44) Y is

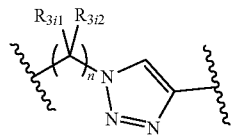

wherein R_{3i1}, R_{3i2} and n are as herein defined;
(45) Y is

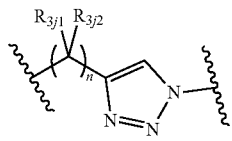

wherein R_{3j1}, R_{3j2} and n are as herein defined;
(46) Y is

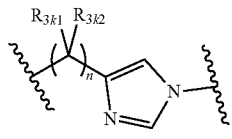

wherein R_{3k1}, R_{3k2} and n are as herein defined;
(47) Y is

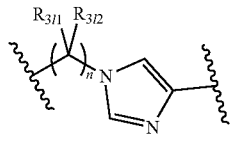

wherein R_{3l1}, R_{3l2} and n are as herein defined;
(48) Y is

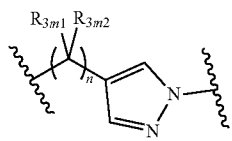

wherein R_{3m1}, R_{3m2} and n are as herein defined;
(49) Y is

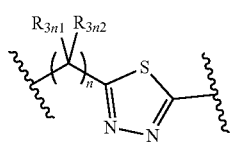

wherein R_{3n1}, R_{3n2} and n are as herein defined;
(50) Y is

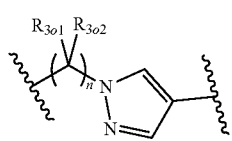

wherein R_{3o1}, R_{3o2} and n are as herein defined;
(50a) Y is

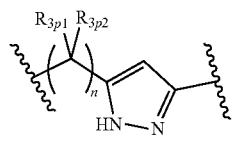

wherein R_{3p1}, R_{3p2} and n are as herein defined;
(50b) Y is

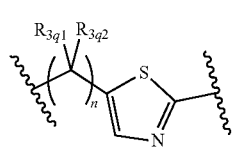

wherein R_{3q1}, R_{3q2} and n are as herein defined;
(50c) Y is

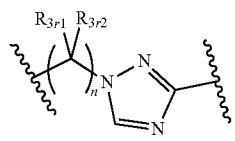

wherein R_{3r1}, R_{3r2} and n are as herein defined;
(50d) Y is

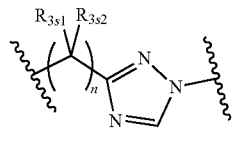

wherein R_{3s1}, R_{3s2} and n are as herein defined;
(51) Y is selected from

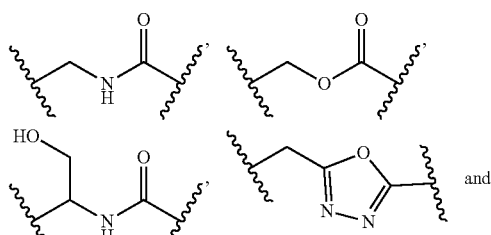

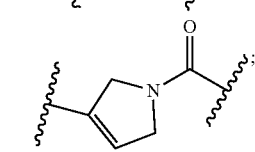

(52) Y is

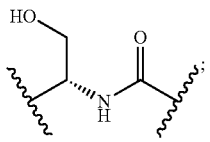 [SMILES: *C(=O)N[C@H](*)CO]

(52a) Y is selected from

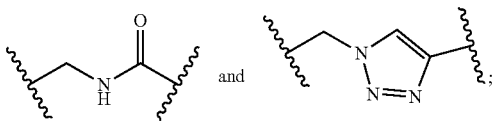 [SMILES: *CNC(*)=O ; *Cn1cc(*)nn1]

(53) $R_4$ is selected from hydrogen and methyl;
(54) $R_4$ is hydrogen;
(55) $R_5$ is selected from hydrogen and halo;
(56) $R_5$ is hydrogen;
(57) $R_6$ is selected from hydrogen, halo and methyl;
(58) $R_6$ is hydrogen;
(59) $R_4$, $R_5$ and $R_6$ are hydrogen;
(60) $A_1$ is selected from $CR_{12}$ and N, wherein $R_{12}$ is selected from hydrogen, halo, cyano and $C_{1-4}$ alkyl;
(61) $A_1$ is CH;
(62) $A_2$ is selected from $CR_{13}$ and N, wherein $R_{13}$ is selected from hydrogen, halo, cyano and methyl;
(63) Suitably $A_2$ is CH;
(64) $A_1$ is CH and $A_2$ is CH;
(65) $R_7$ is selected from hydrogen, halo and methyl;
(65a) $R_7$ is selected from hydrogen and methyl;
(66) $R_7$ is hydrogen;
(67) $R_8$ is selected from hydrogen, halo and methyl;
(68) $R_8$ is hydrogen;
(69) $R_7$ and $R_8$ are hydrogen;
(70) $A_3$ is selected from $CR_{14}$ and N, wherein $R_{14}$ is selected from hydrogen, halo, cyano and $C_{1-4}$ alkyl;
(71) $A_3$ is $CR_{14}$, wherein $R_{14}$ is selected from hydrogen and chloro;
(72) $A_3$ is CH;
(73) $A_4$ is selected from $CR_{15}$ and N, wherein $R_{15}$ is selected from hydrogen, methoxy and methyl;
(74) $A_4$ is CH;
(75) $A_3$ is CH and $A_4$ is CH;
(76) $A_5$ is selected from $CR_{16}$ and N, wherein $R_{16}$ is selected from hydrogen, halo, cyano and $C_{1-4}$ alkyl;
(76a) $A_5$ is selected from $CR_{16}$ and N, wherein $R_{16}$ is selected from hydrogen, halo, cyano, $C_{1-4}$ alkyl, $C_{1-4}$ alkoxy, $C_{1-4}$haloalkyl, $C_{1-4}$haloalkoxy and $C_{3-4}$cycloalkoxy;
(76b) $A_5$ is selected from $CR_{16}$ and N, wherein $R_{16}$ is selected from hydrogen, halo, cyano, $C_{1-4}$ alkyl, $C_{1-4}$ alkoxy, $C_{1-4}$haloalkyl and $C_{1-4}$haloalkoxy;
(76c) $A_5$ is selected from $CR_{16}$ and N, wherein $R_{16}$ is selected from hydrogen, halo, cyano and $C_{1-4}$ alkoxy;
(77) $A_5$ is CH;
(78) $A_6$ is selected from $CR_{17}$ and N, wherein $R_{17}$ is selected from hydrogen, halo, cyano, $C_{1-4}$ alkyl, $C_{2-4}$ alkenyl, $C_{2-4}$ alkynyl and a 5- or 6-membered heteroaryl;
(78a) $A_6$ is selected from $CR_{17}$ and N, wherein $R_{17}$ is selected from hydrogen, halo, cyano, $C_{1-5}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, —O—$C_{3-6}$cycloalkyl, heterocyclyl, —O— heterocyclyl (carbon-linked), —(OCH$_2$CH$_2$)$_m$—OCH$_3$ wherein m is an integer from 1 to 6, $NR_qR_r$,
wherein $R_q$ and $R_r$ are each independently hydrogen, $C_{1-5}$ alkyl, $C_{3-6}$cycloalkyl, a 3- to 6-membered carbon-linked heterocyclyl, wherein $C_{1-5}$ alkyl, $C_{3-6}$cycloalkyl, a 3- to 6-membered carbon-linked heterocyclyl may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or —S(O)$_{0-2}R_{1ea}R_{1fa}$, wherein $R_{1ea}$ and $R_{1fa}$ are H or $C_{1-2}$alkyl;
or $R_q$ and $R_r$ are linked together such that, together with the nitrogen atom to which they are attached, they form a 3- to 6-membered heterocyclic ring which may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy;
wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or —S(O)$_{0-2}R_{1ea}R_{1fa}$, wherein $R_{1ea}$ and $R_{1fa}$ are H or $C_{1-2}$alkyl.
(78b) $A_6$ is selected from $CR_{17}$ and N, wherein $R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl a 5- or 6-membered or heteroaryl, $C_{3-6}$cycloalkyl, —O—$C_{3-6}$cycloalkyl, heterocyclyl, —O— heterocyclyl (carbon-linked), —(OCH$_2$CH$_2$)$_m$—OCH$_3$ wherein m is an integer from 1 to 6, $NR_qR_r$, wherein $R_q$ and $R_r$ are each independently hydrogen, $C_{1-2}$ alkyl or $R_q$ and $R_r$ are linked together such that, together with the nitrogen atom to which they are attached, they form a 3- to 6-membered heterocyclic ring;
wherein any $C_1$alkyl, $C_{2-4}$ alkenyl, $C_{2-4}$ alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or —S(O)$_{0-2}R_{1ea}R_{1fa}$, wherein $R_{1ea}$ and $R_{1fa}$ are H or $C_{1-2}$alkyl.
(78c) $A_6$ is selected from $CR_{17}$ and N, wherein $R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered heteroaryl, $C_{3-6}$cycloalkyl, —O—$C_{3-6}$cycloalkyl, heterocyclyl, —O— heterocyclyl (carbon-linked), —(OCH$_2$CH$_2$)$_m$—OCH$_3$ wherein m is 1, 2 or 3, $NR_qR_r$, wherein $R_q$ and $R_r$ are each independently hydrogen, $C_{1-4}$ alkyl;
or $R_q$ and $R_r$ are linked together such that, together with the nitrogen atom to which they are attached, they form a 3- to 6-membered heterocyclic ring;
wherein any $C_{1-4}$ alkyl, $C_{2-4}$ alkenyl, $C_{2-4}$ alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, $C_{1-2}$haloalkyl, cyano, hydroxy, $C_{1-2}$alkoxy, halo and $C_{1-2}$haloalkoxy.

(78d) $A_6$ is selected from $CR_{17}$ and N, wherein $R_{17}$ is selected from selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{3-6}$cycloalkyl, —O—$C_{3-4}$cycloalkyl, heterocyclyl, —(OCH$_2$CH$_2$)$_m$—OCH$_3$ wherein m is 1, 2 or 3, $NR_qR_r$, wherein $R_q$ and $R_r$ are each independently hydrogen or $C_{1-2}$ alkyl;
wherein any $C_{1-4}$ alkyl, $C_{2-4}$ alkenyl, $C_{2-4}$ alkynyl, $C_{3-6}$cycloalkyl, —O—$C_{3-4}$cycloalkyl, heterocyclyl, system is optionally further substituted by one or more substituents selected from $C_{1-2}$alkyl, $C_{1-2}$haloalkyl, cyano, hydroxy, $C_{1-2}$alkoxy, halo and $C_{1-2}$-haloalkoxy.

(79) $A_6$ is $CR_{17}$, wherein $R_{17}$ is selected from hydrogen, halo, $C_{2-4}$ alkynyl and 5- or 6-membered heteroaryl;

(79a) $A_6$ is $CR_{17}$, wherein $R_{17}$ is selected from hydrogen, halo, $C_{1-4}$alkyl, $C_{1-4}$ alkoxy, $C_{1-4}$ haloalkoxy, $C_{2-4}$ alkynyl and 5- or 6-membered heteroaryl;

(79b) $A_6$ is $CR_{17}$, wherein $R_{17}$ is selected from hydrogen, halo, $C_{1-4}$ alkoxy or $C_{1-4}$ haloalkoxy;

(80) $A_6$ is $CR_{17}$, wherein $R_{17}$ is selected from hydrogen, bromo, ethynyl, and pyrazolyl;

(80a) $A_6$ is $CR_{17}$, wherein $R_{17}$ is selected from hydrogen, methoxy, bromo, ethynyl, and pyrazolyl;

(81) $A_5$ is CH and $A_6$ is $CR_{17}$, wherein $R_{17}$ is selected from hydrogen, halo, $C_{2-4}$ alkynyl and 5- or 6-membered heteroaryl;

(82) $R_9$, $R_{10}$ and $R_{11}$ are independently selected from hydrogen, $NH_2$, halo, cyano, and $C_{1-6}$ alkyl;

(82a) $R_9$, $R_{9a}$, $R_{10}$ and $R_{11}$ are independently selected from hydrogen, $NH_2$, halo, cyano, and $C_{1-6}$ alkyl (82c) $R_9$, $R_{10}$ and $R_{11}$ are independently selected from hydrogen, $NH_2$, halo, cyano, and $C_{1-6}$ alkyl; and $R_{9a}$ is hydrogen;

(83) $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system;

(83a) $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system; wherein either of the fused 5- or 6-membered saturated or unsaturated ring system may be optionally substituted by one or more substituents selected from $C_{1-2}$alkyl, cyano, $C_{1-2}$haloalkyl, hydroxy, $C_{1-2}$ alkoxy, halo, $C_{1-2}$haloalkoxy, $NR_{1ia}R_{1ja}$ or —S(O)$_{0-2}R_{1ia}R_{1ja}$, wherein $R_{1ia}$ and $R_{1ja}$ are H or $C_{1-2}$alky;

(84) $A_7$ is selected from $CR_{13}$ and N, wherein $R_{13}$ is selected from hydrogen, halo, cyano, $C_{1-4}$ alkyl, $C_{2-4}$ alkenyl, $C_{2-4}$ alkynyl and a 5- or 6-membered heteroaryl;

(85a) $A_7$ is selected from $CR_{13}$ and N, wherein $R_{13}$ is selected from hydrogen, halo, cyano, $C_{1-4}$ alkyl, $C_{1-4}$ alkoxy, $C_{1-4}$haloalkyl, $C_{1-4}$haloalkoxy and $C_{3-4}$cycloalkoxy;

(85b) $A_7$ is selected from $CR_{13}$ and N, wherein $R_{13}$ is selected from hydrogen, halo, cyano, $C_{1-4}$ alkyl, $C_{1-4}$ alkoxy, $C_{1-4}$haloalkyl and $C_{1-4}$haloalkoxy;

(85c) $A_7$ is selected from $CR_{13}$ and N, wherein $R_{13}$ is selected from hydrogen, halo, cyano and $C_{1-4}$ alkoxy;

(85) $A_7$ is CH;

(86) $R_{4a}$ is selected from hydrogen, halo and methyl;

(86a) $R_{4a}$ is selected from hydrogen and methyl;

(87) $R_{4a}$ is hydrogen;

(88) $R_{5a}$ is selected from hydrogen and halo;

(89) $R_{5a}$ is hydrogen;

(90) $R_{6a}$ is selected from hydrogen, halo and methyl;

(91) $R_{6a}$ is hydrogen;

(92) $R_{4a}$, $R_{5a}$ and $R_{6a}$ are hydrogen;

(93) $A_8$ is selected from $CR_{19}R_{20}$ and $NR_{21}$, wherein $R_{19}$ and $R_{20}$ are selected from hydrogen, halo, cyano and $C_{1-4}$ alkyl, and $R_{21}$ is hydrogen;

(94) $A_9$ is selected from $CR_{22}R_{23}$ and $NR_{24}$, wherein $R_{22}$ and $R_{23}$ are selected from hydrogen, halo, cyano and methyl, and $R_{24}$ is hydrogen;

(95) $R_{5b}$ is selected from hydrogen and halo;

(96) $R_{5b}$ is hydrogen;

(96a) $R_{5c}$ is selected from hydrogen and halo;

(96b) $R_{5c}$ is hydrogen;

(97) $R_{7a}$ is selected from hydrogen, halo and methyl;

(97a) $R_{7a}$ is selected from hydrogen and methyl;

(98) $R_{7a}$ is hydrogen;

(99) $R_{8a}$ is selected from hydrogen, halo and methyl;

(100) $R_{8a}$ is hydrogen;

(101) $R_{5b}$, $R_{7a}$ and $R_{8a}$ are hydrogen;

(102) $A_{10}$ is selected from $CR_{25}R_{26}$ and $NR_{27}$, wherein $R_{25}$ and $R_{26}$ are selected from hydrogen, halo, cyano and $C_{1-4}$ alkyl, and $R_{27}$ is hydrogen;

(103) $A_{11}$ is selected from $CR_{28}R_{29}$ and $NR_{30}$, wherein $R_{28}$ and $R_{29}$ are selected from hydrogen, methoxy and methyl, and $R_{30}$ is hydrogen;

(104a) $R_{Z1}$ and $R_{Z1a}$ are selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-6}$cycloalkyl, wherein $C_{3-6}$cycloalkyl and —O—$C_{3-6}$cycloalkyl are optionally substituted by one or more of halo, methyl or methoxy;

(104b) $R_{Z1}$ and $R_{Z1a}$ are selected from selected from hydrogen, $C_{1-2}$alkyl, cyano, halo, $C_{1-2}$haloalkyl, $C_{1-2}$haloalkoxy, $C_{1-2}$alkoxy;

(104c) $R_{Z1}$ and $R_{Z1a}$ are selected from selected from hydrogen, $C_{1-2}$alkyl, cyano and halo;

(104d) $R_{Z1}$ and $R_{Z1a}$ are hydrogen;

(104e) $R_{Z2}$ and $R_{Z2a}$ are selected from hydrogen, $C_{1-4}$alkyl, cyano, halo or $C_{1-4}$alkoxy;

(104f) $R_{Z2}$ and $R_{Z2a}$ are selected from hydrogen, cyano or halo;

(104 g) $R_{Z2}$ and $R_{Z2a}$ are hydrogen;

(104 h) $R_{Z3a}$ is selected from hydrogen, $C_{1-4}$alkyl, cyano, halo or $C_{1-4}$alkoxy;

(104i) $R_{Z3a}$ is selected from hydrogen, cyano or halo;

(104j) $R_{Z3a}$ is hydrogen;

(104k) Z is selected from:

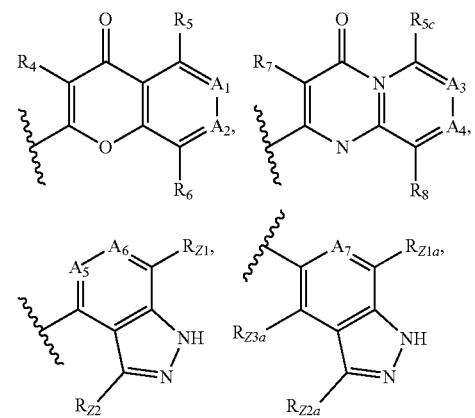

-continued

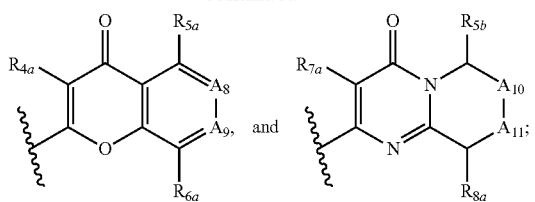
and wherein $R_4$, $R_{4a}$, $R_5$, $R_{5a}$, $R_{5b}$, $R_{5c}$, $R_6$, $R_{6a}$, $R_7$, $R_{7a}$, $R_8$, $R_{8a}$, $R_{Z1}$, $R_{Z1a}$, $R_{Z2}$, $R_{Z2a}$, $R_{Z3a}$, $A_1$, $A_2$, $A_3$, $A_4$, $A_5$, $A_6$, $A_7$, $A_8$, $A_9$, $A_{10}$ and $A_{11}$ are as herein defined.

(104) Z is

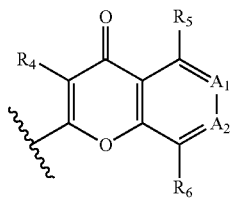

wherein $R_4$, $R_5$, $R_6$, $A_1$ and $A_2$ are as herein defined;
(105) Z is

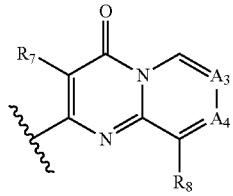

wherein $R_7$, $R_8$, $A_3$ and $A_4$ are as herein defined;
(105a) Z is

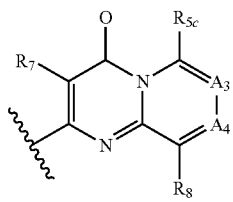

wherein $R_{5c}$, $R_7$, $R_8$, $A_3$ and $A_4$ are as herein defined
(106) Z is

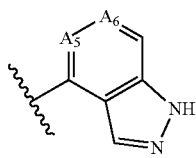

wherein $A_5$ and $A_6$ are as herein defined;
(106a) Z is

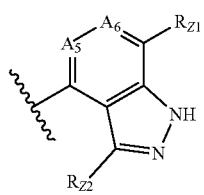

wherein $R_{Z1}$, $R_{Z2}$, $A_5$ and $A_6$ are as herein defined;
(107) Z is

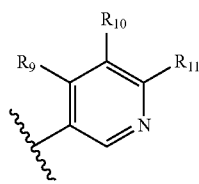

wherein $R_9$, $R_{10}$ and $R_{11}$ are as herein defined;
(107a) Z is

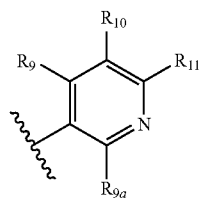

wherein $R_9$, $R_{9a}$, $R_{10}$ and $R_{11}$ are as herein defined;
(108) Z is

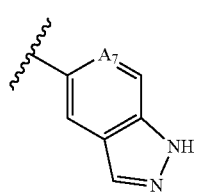

wherein $A_7$ is as herein defined;
(108a) Z is

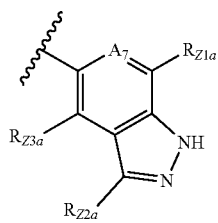

wherein $R_{Z1a}$, $R_{Z2a}$, $R_{Z3a}$ and $A_7$ is as herein defined;
(109) Z is
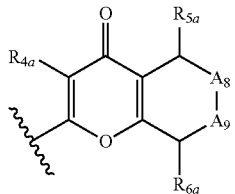
wherein $R_{4a}$, $R_{5a}$, $R_{6a}$, $A_8$ and $A_9$ are as herein defined;
(110) Z is
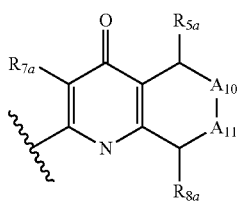
wherein $R_{5b}$, $R_{7a}$, $R_{8a}$, $A_{10}$ and $A_{11}$ are as herein defined;
(111) Z is selected from:
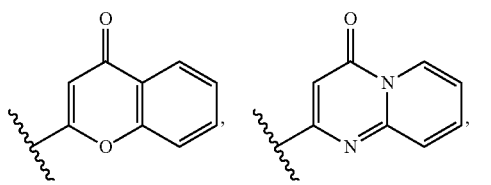
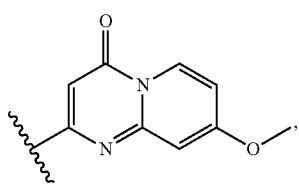
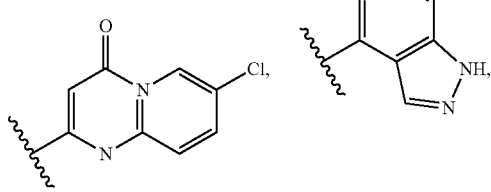
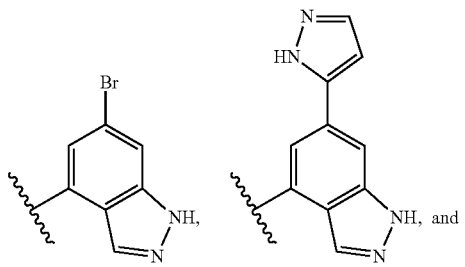
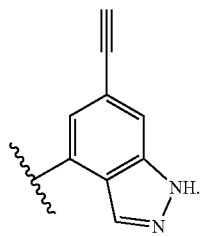
(111a) Z is selected from:
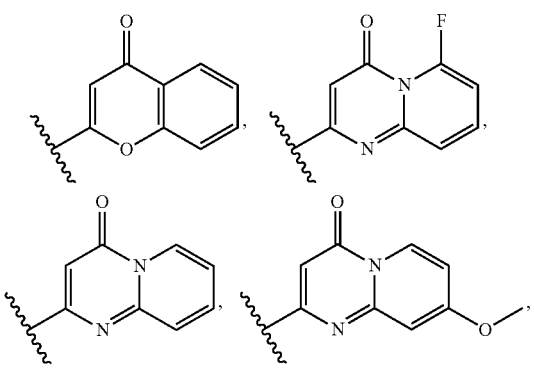
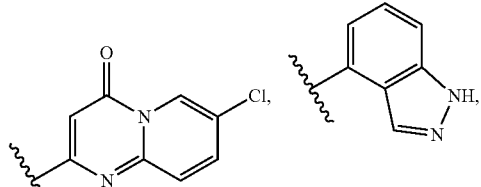
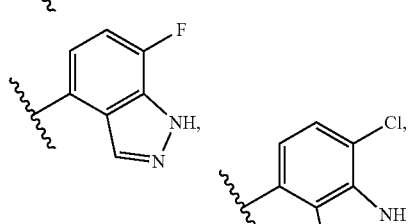
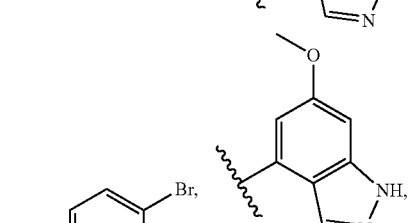
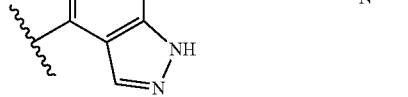
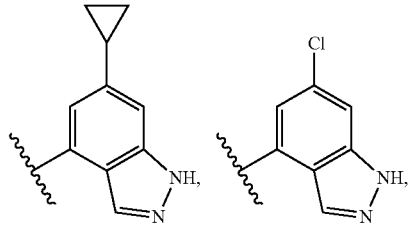

-continued

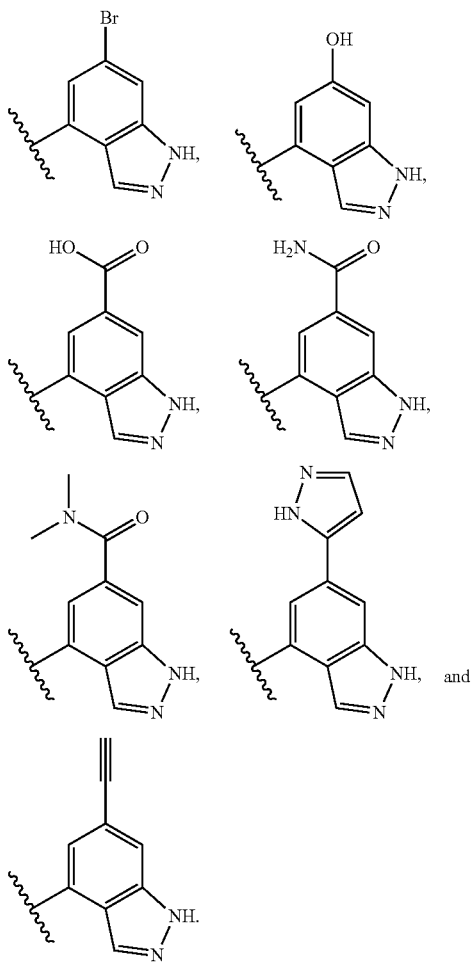

(111 b) Z is selected from:

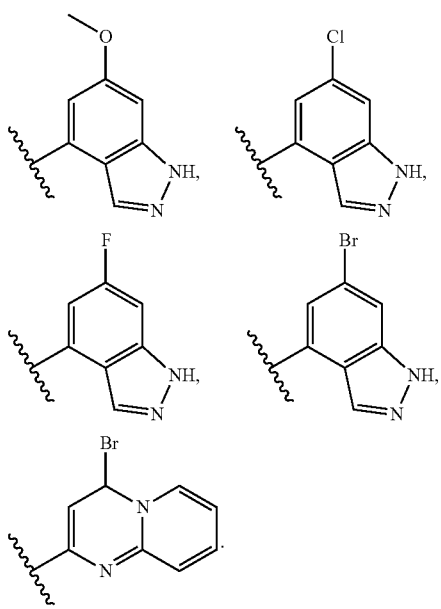

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably, an aryl group is phenyl.

Suitably, X is as defined in any one of paragraphs (20) to (24) above. Most suitably, X is as defined in paragraph (20).

Suitably, X is as defined in any one of paragraphs (20) to (24a) above. Most suitably, X is as defined in paragraph (20) or (24a).

Suitably, $R_{1a}$, $R_{1c}$ and $R_{1e}$ are as defined in any one of paragraphs (1) to (6) above. Most suitably, $R_{1a}$, $R_{1c}$ and $R_{1e}$ are as defined in paragraph (6).

Suitably, $R_{1b}$, $R_{1d}$ and $R_{1f}$ are as defined in any one of paragraphs (1), (2), and from paragraphs (7) to (15) above. Most suitably, $R_{1b}$, $R_{1d}$ and $R_{1f}$ are as defined in paragraph (15).

Suitably, $R_{1b}$, $R_{1d}$ and $R_{1f}$ are as defined in any one of paragraphs (1), (2), and from paragraphs (6a) to (15a) above. Most suitably, $R_{1b}$, $R_{1d}$ and $R_{1f}$ are as defined in paragraph (15a).

Suitably, $R_{1b}$, $R_{1d}$ and $R_{1f}$ are as defined in any one of paragraphs (14a) to (15c) above. Suitably, $R_{1b}$, $R_{1d}$ and $R_{1f}$ are as defined in any one of paragraphs (14d) to (15c). Suitably, $R_{1b}$, $R_{1d}$ and $R_{1f}$ are as defined in paragraph (15c).

Suitably, $R_{1b}$, $R_{1d}$ and $R_{1f}$ are as defined in any one of paragraphs (14a) to (15 g) above. Suitably, $R_{1b}$, $R_{1d}$ and $R_{1f}$ are as defined in any one of paragraphs (14a) to (14 g).

Suitably, $R_{1b}$, $R_{1d}$ and $R_{1f}$ are as defined in any one of paragraphs (15d) to (15 g). Most suitably, $R_{1b}$, $R_{1d}$ and $R_{1f}$ are as defined in paragraph (15 g).

Suitably, $R_{1a'}$ is as defined in paragraphs (16) and (17) above. Most suitably, $R_{1a'}$ is as defined in paragraph (17) above.

Suitably, $R_{2a}$, $R_{2b}$ and $R_{2e}$ are as defined in any one of paragraphs (18) and (19) above. Most suitably, $R_{2a}$, $R_{2b}$ and $R_{2e}$ are as defined in paragraph (19).

Suitably, Y is as defined in any one of paragraphs (34) to (52) above. Suitably, Y is as defined in paragraphs (34), (34a), (36), (39), (40), (43) and (50c). Suitably, Y is as defined in paragraphs (34a) or (43) above. Most suitably, Y is as defined in paragraph (52a)

Suitably, n is as defined in any one of paragraphs (32) and (33) above. Most suitably, n is as defined in paragraph (33).

Suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are as defined in any one of paragraphs (25) to (28), and paragraphs (30) to (31) above. Most suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are as defined in paragraph (28).

Suitably, $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$ are as defined in any one of paragraphs (25), (29), (30) and (31) above. Most suitably, $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$ are as defined in paragraph (29).

Suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$ and $R_{3q1}$ are as defined in any one of paragraphs (25) to (28a), and paragraphs (30) to (31a) above. Most suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$ and $R_{3q1}$ are as defined in paragraph (28a).

Suitably, $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$ and $R_{3q2}$ are as defined in any one of paragraphs (25), (25a), (29), (29a) (30), (30a), (31) and (31a) above. Most suitably, $R_{3a2}$, $R_{3b2}$, $R_{3c2}$, $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$ and $R_{3q2}$ are as defined in paragraph (29a).

Suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3S1}$ are as defined in any one of paragraphs (25) to (28b), and paragraphs (30a) to (31b) above. Most suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3S1}$ are as defined in paragraph (28b).

Suitably, $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are as defined in any one of paragraphs (25), (25a), (25b), (29), (29a), (29b), (30), (30a), (30b), (31), (31a) and (31b) above. Most suitably, $R_{3a2}$, $R_{3b2}$, $R_{3c2}$, $R_{3d2}$, $R_{3e2}$, $R_{3f2}$, $R_{3g2}$, $R_{3h2}$, $R_{3}12$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are as defined in paragraph (29b).

Suitably, Z is as defined in any one of paragraphs from (104k) and (104) to (111b) above. Suitably, Z is as defined in any one of paragraphs from (104) to (111a) above. Suitably, Z is as defined in any one of paragraphs from (104) to (111) above. Suitably, Z is as defined in any one of paragraphs (104) to (106a). Suitably, Z is as defined in paragraphs (104), (105a) and (106a). Most suitably, Z is as defined in any one of paragraphs (104) to (106). Most suitably, Z is as defined in paragraph (111b) above.

Suitably, $R_4$ is as defined in any one of paragraphs (53), (54) and (59) above. Most suitably, $R_4$ is as defined in paragraph (54).

Suitably, $R_5$ is as defined in any one of paragraphs (55), (56) and (59) above. Most suitably, $R_5$ is as defined in paragraph (56).

Suitably, $R_6$ is as defined in any one of paragraphs (57), (58) and (59) above. Most suitably, $R_6$ is as defined in paragraph (58).

Suitably, $A_1$ is as defined in any one of paragraphs (60), (61) and (64) above. Most suitably, $A_1$ is as defined in paragraph (61).

Suitably, $A_2$ is as defined in any one of paragraphs (62), (63) and (64) above. Most suitably, $A_1$ is as defined in paragraph (63).

Suitably, $R_7$ is as defined in any one of paragraphs (65), (66) and (69) above. Most suitably, $R_7$ is as defined in paragraph (66).

Suitably, $R_3$ is as defined in any one of paragraphs (67), (68) and (69) above. Most suitably, $R_3$ is as defined in paragraph (68).

Suitably, $A_3$ is as defined in any one of paragraphs (70), (71), (72) and (75) above. Most suitably, $A_3$ is as defined in paragraph (71).

Suitably, $A_4$ is as defined in any one of paragraphs (73), (74) and (75) above. Most suitably, $A_4$ is as defined in paragraph (74).

Suitably, $A_5$ is as defined in any one of paragraphs (76), (76a), (76b), (76c), (77) and (81) above. Suitably, $A_5$ is as defined in any one of paragraphs (76), (77) and (81) above. Most suitably, $A_5$ is as defined in paragraph (77).

Suitably, $A_6$ is as defined in any one of paragraphs from (78) to (81) above. Suitably, $A_6$ is as defined in paragraph (79). Suitably, $A_6$ is as defined in paragraphs (78a), (78b), (78c), (79a) and (79b). Most suitably, $A_6$ is as defined in paragraph (79b).

Suitably, $R_9$, $R_{10}$ and $R_{11}$ are as defined in any one of paragraphs (82) to (83a). Suitably, $R_9$, $R_{10}$ and $R_{11}$ are as defined in paragraphs (82) and (83).

Suitably, $A_7$ is as defined in any one of paragraphs (84) to (85c) above. Suitably, $A_7$ is as defined in any one of paragraphs (84) to (85) above.

Suitably $R_{4a}$ is as defined in any one of paragraphs (86), (86a), (87) and (92) above. Most suitably, $R_{4a}$ is as defined in paragraph (87).

Suitably $R_{5a}$ is as defined in any one of paragraphs (88), (89) and (92) above. Most suitably, $R_{5a}$ is as defined in paragraph (89).

Suitably $R_{6a}$ is as defined in any one of paragraphs (90) to (92) above. Most suitably, $R_{6a}$ is as defined in paragraph (91).

Suitably $A_8$ is as defined in any one of paragraphs (93) above.

Suitably $A_9$ is as defined in any one of paragraphs (94) above.

Suitably $R_{5b}$ is as defined in any one of paragraphs (95) and (96) above. Most suitably, $R_{5b}$ is as defined in paragraph (96).

Suitably $R_{7a}$ is as defined in any one of paragraphs (97), (97a) and (98) above. Most suitably, $R_{7a}$ is as defined in paragraph (98).

Suitably $R_{8a}$ is as defined in any one of paragraphs (99) and (100) above. Most suitably, $R_{8a}$ is as defined in paragraph (100).

Suitably $A_{10}$ is as defined in any one of paragraphs (102) above.

Suitably $A_{11}$ is as defined in any one of paragraphs (103) above.

Suitably, $R_{Z1}$ and $R_{Z1a}$ are as defined in any one of paragraphs (104a) to (104d) above. Most suitably, $R_{Z1}$ and $R_{Z1a}$ are as defined in paragraph (104d).

Suitably, $R_{Z2}$ and $R_{Z2a}$ are as defined in any one of paragraphs (104e) to (104 g) above. Most suitably, $R_{Z2}$ and $R_{Z2a}$ are as defined in paragraph (104 g).

Suitably, $R_{Z3a}$ is as defined in any one of paragraphs (104 h) to (104j) above. Most suitably, $R_{Z3a}$ is as defined in paragraph (104j).

In a particular group of compounds of the invention, Y is as defined in paragraph (34), i.e. the compounds have the structural formula (II) (a sub-definition of formula (I)) shown below:

(II)

$$X \overbrace{\phantom{XX}}^{R_{3a1} \; R_{3a2}}_{n} \underset{H}{N} \overset{O}{\underset{\|}{C}} Z$$

wherein X, $R_{3a1}$, $R_{3a2}$, n and Z each having any one of the meanings defined herein; or a pharmaceutically acceptable salt thereof.

In an embodiment of the compounds of formula (II):

X is as defined in any one of paragraphs (20) to (24) above, suitably X is as defined in paragraph (24a);

$R_{3a1}$ is as defined in any one of paragraphs from (25) to (28), and paragraphs (30) and (31) above;

$R_{3a2}$ is as defined in any one of paragraphs (25), (29), (30) and (31) above;

n is as defined in any one of paragraphs (32) and (33) above; and

Z is as defined in any one of paragraphs (104) to (111b) above. Suitably, Z is as defined in any one of paragraphs (104) to (111) above.

In an embodiment of the compounds of formula (II):

X is as defined in paragraph (20) above;

$R_{3a1}$ is as defined in paragraph (28) above;

$R_{3a2}$ is as defined in paragraph (29) above;

n is as defined in paragraph (33) above; and

Z is as defined in any one of paragraphs (104) to (106) above.

In a particular group of the compounds of formula (II):

X is as defined in paragraph (20), (21) or (22) above and $R_{1b}$, $R_{1d}$ and $R_{1f}$ are each as defined in any one of paragraphs (8a) to (8e) above;

$R_{3a1}$ is as defined in paragraph (28) above;

$R_{3a2}$ is as defined in paragraph (29) above;

n is as defined in paragraph (33) above; and

Z is as defined in any one of paragraphs (104) to (106) above.

In a particular group of the compounds of formula (II):

X is as defined in paragraph (20) above and $R_{1b}$ is as defined in any one of paragraphs (14a) to (14 g) above; suitably $R_{1b}$ is as defined in any one of paragraphs (14a) to (15 g) above. Suitably, $R_{1b}$, is as defined in any one of paragraphs (15d) to (15 g). Most suitably, $R_{1b}$ is as defined in paragraph (15 g);

$R_{3a1}$ is as defined in paragraph (28) above;

$R_{3a2}$ is as defined in paragraph (29) above;

n is as defined in paragraph (33) above; and

Z is as defined in any one of paragraphs (104) to (106) above.

In a particular group of the compounds of formula (II):

X is as defined in paragraph (20) above and $R_{1b}$ is as defined in any one of paragraphs (8a) to (8e) above;

$R_{3a1}$ is as defined in paragraph (28) above;

$R_{3a2}$ is as defined in paragraph (29) above;

n is as defined in paragraph (33) above; and

Z is as defined in any one of paragraphs (104) to (106) above.

In a particular group of compounds of the invention, Y is as defined in paragraph (36), i.e. the compounds have the structural formula (III) (a sub-definition of formula (1)) shown below:

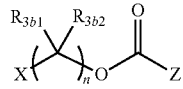

(III)

wherein X, $R_{3b1}$, $R_{3b2}$, n and Z each having any one of the meanings defined herein; or a pharmaceutically acceptable salt thereof.

In an embodiment of the compounds of formula (III):

X is as defined in any one of paragraphs (20) to (24) above;

$R_{3b1}$ is as defined in any one of paragraphs from (25) to (28), and paragraphs (30) and (31) above;

$R_{3b2}$ is as defined in any one of paragraphs (25), (29), (30) and (31) above;

n is as defined in any one of paragraphs (32) and (33) above; and

Z is as defined in any one of paragraphs (104) to (111) above.

In an embodiment of the compounds of formula (III):

X is as defined in paragraph (20) above;

$R_{3b1}$ is as defined in paragraph (28) above;

$R_{3b2}$ is as defined in paragraph (29) above;

n is as defined in paragraph (33) above; and

Z is as defined in any one of paragraphs (104) to (106) above.

In a particular group of the compounds of formula (III):

X is as defined in paragraph (20), (21) or (22) above and $R_{1b}$, $R_{1d}$ and $R_{1f}$ are each as defined in any one of paragraphs (8a) to (8e) above;

$R_{3a1}$ is as defined in paragraph (28) above;

$R_{3a2}$ is as defined in paragraph (29) above;

n is as defined in paragraph (33) above; and

Z is as defined in any one of paragraphs (104) to (106) above.

In a particular group of the compounds of formula (III):

X is as defined in paragraph (20) above and $R_{1b}$ is as defined in any one of paragraphs (8a) to (8e) above;

$R_{3a1}$ is as defined in paragraph (28) above;

$R_{3a2}$ is as defined in paragraph (29) above;

n is as defined in paragraph (33) above; and

Z is as defined in any one of paragraphs (104) to (106) above.

In a particular group of compounds of the invention, X is as defined in paragraph (20), i.e. the compounds have the structural formula (IV) (a sub-definition of formula (I)) shown below:

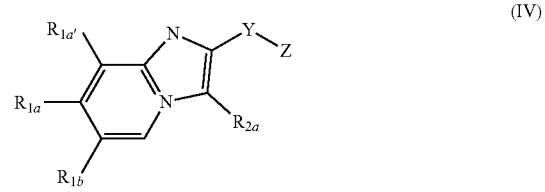

(IV)

wherein $R_{1a}$, $R_{1b}$, $R_{1a'}$, $R_{2a}$, Y and Z each having any one of the meanings defined herein; or a pharmaceutically acceptable salt thereof.

In an embodiment of the compounds of formula (IV):

$R_{1a}$ is as defined in any one of paragraphs (1) to (6) above;

$R_{1b}$ is as defined in any one of paragraphs (1), (2), from paragraphs (7) to (15a) above;

$R_{1a'}$ is as defined in paragraphs (16) and (17) above;

$R_{2a}$ is as defined in any one of paragraphs (18) to (19) above;

Y is as defined in any one of paragraphs (34) to (52); and

Z is as defined in any one of paragraphs (104) to (111) above.

In an embodiment of the compounds of formula (IV):

$R_{1a}$ is as defined in any one of paragraphs (1) to (6) above;

$R_{1b}$ is as defined in any one of paragraphs (14a) to (14 g) above;

$R_{1a'}$ is as defined in paragraphs (16) and (17) above;

$R_{2a}$ is as defined in any one of paragraphs (18) to (19) above;

Y is as defined in any one of paragraphs (34) to (52); and

Z is as defined in any one of paragraphs (104) to (111) above.

In an embodiment of the compounds of formula (IV):

$R_{1a}$ is as defined in paragraph (6) above;

$R_{1b}$ is as defined in paragraph (15) or (15a) above;

$R_{1a'}$ is as defined in paragraph (17) above;
$R_{2a}$ is as defined in paragraph (19) above;
Y is as defined in paragraphs (34), (36), (39) and (40) above; and
Z is as defined in any one of paragraphs (104) to (106) above.

In a particular group of the compounds of formula (IV):
$R_{1a}$ is as defined in any one of paragraphs (1) to (6) above;
$R_{1b}$ is as defined in any one of paragraphs (8a) to (8e) or (15a) above;
$R_{1a'}$ is as defined in paragraphs (16) and (17) above;
$R_{2a}$ is as defined in any one of paragraphs (18) to (19) above;
Y is as defined in any one of paragraphs (34) to (52); and
Z is as defined in any one of paragraphs (104) to (111) above.

In a particular group of the compounds of formula (IV):
$R_{1a}$ is as defined in paragraph (6) above;
$R_{1b}$ is as defined in paragraph (8e) or (15a) above;
$R_{1a'}$ is as defined in paragraph (17) above;
$R_{2a}$ is as defined in paragraph (19) above;
Y is as defined in paragraphs (34), (36), (39) and (40) above; and
Z is as defined in any one of paragraphs (104) to (111b) above.

In an embodiment of the compounds of formula (IV):
$R_{1a}$ is as defined in paragraph (6) above;
$R_{1b}$ is as defined in any one of paragraphs (14a) to (14 g) above; more suitably $R_{1b}$ is as defined in paragraphs (15a) to (15 g) above;
$R_{1a'}$ is as defined in paragraph (17) above;
$R_{2a}$ is as defined in paragraph (19) above;
Y is as defined in any one of paragraphs (34) to (52a); and
Z is as defined in any one of paragraphs (104) to (111b) above.

In a particular group of the compounds of formula (IV):
$R_{1a}$ is as defined in any one of paragraphs (1) to (6) above;
$R_{1b}$ is as defined in any one of paragraphs (15d), (15e), (15f) or (15 g) above;
$R_{1a'}$ is as defined in paragraphs (16) and (17) above;
$R_{2a}$ is as defined in any one of paragraphs (18) to (19) above;
Y is as defined in any one of paragraphs (34), (34a), (36), (39) and (40) above; and
Z is as defined in any one of paragraphs (104) to (111b) above.

In a particular group of the compounds of formula (IV):
$R_{1a}$ is as defined in paragraph (6) above;
$R_{1b}$ is as defined in paragraph (15 g) above;
$R_{1a'}$ is as defined in paragraph (17) above;
$R_{2a}$ is as defined in paragraph (19) above;
Y is as defined in any one of paragraphs (34), (36), (39) and (40) above; more suitably Y is as defined in paragraph (52a) above; and
Z is as defined in any one of paragraphs (111) to (111b) above; more suitably Z is as defined in paragraph (111b) above.

In a particular group of compounds of the invention, X is as defined in paragraph (20) and Y is as defined in paragraph (34), i.e. the compounds have the structural formula (V) (a sub-definition of formula (I)) shown below:

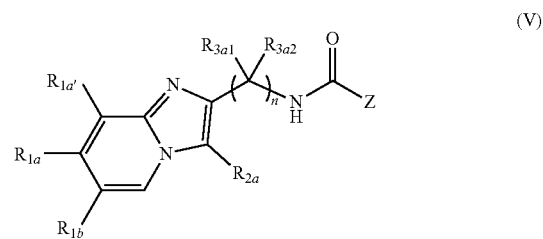

(V)

wherein $R_{1a}$, $R_{1b}$, $R_{1a'}$, $R_{2a}$, $R_{3a1}$, $R_{3a2}$, n and Z each having any one of the meanings defined herein; or a pharmaceutically acceptable salt thereof.

In an embodiment of the compounds of formula (V):
$R_{1a}$ is as defined in any one of paragraphs (1) to (6) above;
$R_{1b}$ is as defined in any one of paragraphs (1), (2), and from paragraphs (7) to (15 g) above;
$R_{1a'}$ is as defined in paragraphs (16) and (17) above;
$R_{2a}$ is as defined in any one of paragraphs (18) to (19) above;
$R_{3a1}$ is as defined in any one of paragraphs from (25) to (28), and paragraphs (30) and (31) above;
$R_{3a2}$ is as defined in any one of paragraphs (25), (29), (30) and (31) above;
n is as defined in any one of paragraphs (32) and (33) above; and
Z is as defined in any one of paragraphs (104) to (111) above.

In an embodiment of the compounds of formula (V):
$R_{1a}$ is as defined in paragraph (6) above;
$R_{1b}$ is as defined in paragraph (15) or (15a) above;
$R_{1a'}$ is as defined in paragraph (17) above;
$R_{2a}$ is as defined in paragraph (19) above;
$R_{3a1}$ is as defined in paragraph (28) above;
$R_{3a2}$ is as defined in paragraph (29) above;
n is as defined in paragraph (33) above; and
Z is as defined in any one of paragraphs (104) to (106) above.

In a particular group of the compounds of formula (V):
$R_{1a}$ is as defined in any one of paragraphs (1) to (6) above;
$R_{1b}$ is as defined in any one of paragraphs (8a) to (8e) or (15a) above;
$R_{1a'}$ is as defined in paragraphs (16) and (17) above;
$R_{2a}$ is as defined in any one of paragraphs (18) to (19) above;
$R_{3a1}$ is as defined in any one of paragraphs from (25) to (28), and paragraphs (30) and (31) above;
$R_{3a2}$ is as defined in any one of paragraphs (25), (29), (30) and (31) above;
n is as defined in any one of paragraphs (32) and (33) above; and
Z is as defined in any one of paragraphs (104) to (111) above.

In a particular group of the compounds of formula (V):
$R_{1a}$ is as defined in paragraph (6) above;
$R_{1b}$ is as defined in paragraph (8e) or (15a) above;
$R_{1a'}$ is as defined in paragraph (17) above;
$R_{2a}$ is as defined in paragraph (19) above;
$R_{3a1}$ is as defined in paragraph (28) above;
$R_{3a2}$ is as defined in paragraph (29) above;
n is as defined in paragraph (33) above; and
Z is as defined in any one of paragraphs (104) to (106) above.

In an embodiment of the compounds of formula (V):
$R_{1a}$ is as defined in paragraph (6) above;
$R_{1b}$ is as defined in paragraph (15 g) above;
$R_{1a'}$ is as defined in paragraph (17) above;
$R_{2a}$ is as defined in paragraph (19) above;
$R_{3a1}$ is as defined in paragraph (28) above;
$R_{3a2}$ is as defined in paragraph (29) above;
n is as defined in paragraph (33) above; and
Z is as defined in any one of paragraphs (104k) and (104) to (106) above.

In a particular group of the compounds of formula (V):
$R_{1a}$ is as defined in any one of paragraphs (1) to (6) above;
$R_{1b}$ is as defined in any one of paragraphs (15 g) above;
$R_{1a'}$ is as defined in paragraphs (16) and (17) above;
$R_{2a}$ is as defined in any one of paragraphs (18) to (19) above;
$R_{3a1}$ is as defined in any one of paragraphs from (25) to (28), and paragraphs (30) and (31) above;
$R_{3a2}$ is as defined in any one of paragraphs (25), (29), (30) and (31) above;
n is as defined in any one of paragraphs (32) and (33) above; and
Z is as defined in any one of paragraphs (104k) and (104) to (111) above.

In a particular group of the compounds of formula (V):
$R_{1a}$ is as defined in paragraph (6) above;
$R_{1b}$ is as defined in paragraph (15 g) above;
$R_{1a'}$ is as defined in paragraph (17) above;
$R_{2a}$ is as defined in paragraph (19) above;
$R_{3a1}$ is as defined in paragraph (28) above;
$R_{3a2}$ is as defined in paragraph (29) above;
n is as defined in paragraph (33) above; and
Z is as defined in paragraph (111b) above.

In a particular group of compounds of the invention, X is as defined in paragraph (20), $R_{1a'}$ is as defined in paragraph (17) and Y is as defined in paragraph (36), i.e. the compounds have the structural formula (VI) (a sub-definition of formula (I)) shown below:

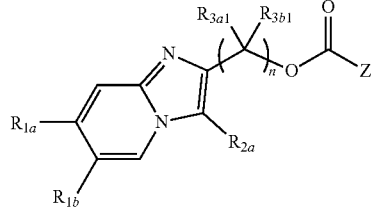

(VI)

wherein $R_{1a}$, $R_{1b}$, $R_{2a}$, $R_{3b1}$, $R_{3b2}$, n and Z each having any one of the meanings defined herein;
or a pharmaceutically acceptable salt thereof.

In an embodiment of the compounds of formula (VI):
$R_{1a}$ is as defined in any one of paragraphs (1) to (6) above;
$R_{1b}$ is as defined in any one of paragraphs (1), (2), and paragraphs (7) to (15 g) above;
$R_{2a}$ is as defined in any one of paragraphs (18) to (19) above;
$R_{3b1}$ is as defined in any one of paragraphs from (25) to (28) and paragraphs (30) to (31) above;
$R_{3b2}$ is as defined in any one of paragraphs (25), (29), (30) and (31) above;
n is as defined in any one of paragraphs (32) and (33) above; and
Z is as defined in any one of paragraphs (104k) or (104) to (111) above.

In an embodiment of the compounds of formula (VI):
$R_{1a}$ is as defined in paragraph (6) above;
$R_{1b}$ is as defined in paragraph (15) or (15a) above;
$R_{2a}$ is as defined in paragraph (19) above;
$R_{3b}$ is as defined in paragraph (28) above;
$R_{3b2}$ is as defined in paragraph (29) above;
n is as defined in paragraph (33) above; and
Z is as defined in any one of paragraphs (104) to (106) above.

In a particular group of the compounds of formula (VI):
$R_{1a}$ is as defined in any one of paragraphs (1) to (6) above;
$R_{1b}$ is as defined in any one of paragraphs (8a) to (8e) or (15a) above;
$R_{2a}$ is as defined in any one of paragraphs (18) to (19) above;
$R_{3b1}$ is as defined in any one of paragraphs from (25) to (28) and paragraphs (30) to (31) above;
$R_{3b2}$ is as defined in any one of paragraphs (25), (29), (30) and (31) above;
n is as defined in any one of paragraphs (32) and (33) above; and
Z is as defined in any one of paragraphs (104) to (111b) above.

In a particular group of the compounds of formula (VI):
$R_{1a}$ is as defined in paragraph (6) above;
$R_{1b}$ is as defined in paragraph (8e) or (15a) above;
$R_{2a}$ is as defined in paragraph (19) above;
$R_{3b1}$ is as defined in paragraph (28) above;
$R_{3b2}$ is as defined in paragraph (29) above;
n is as defined in paragraph (33) above; and
Z is as defined in any one of paragraphs (104) to (106) above.

In an embodiment of the compounds of formula (VI):
$R_{1a}$ is as defined in paragraph (6) above;
$R_{1b}$ is as defined in paragraph (15) to (15 g) above;
$R_{2a}$ is as defined in paragraph (19) above;
$R_{3b1}$ is as defined in paragraph (28) above;
$R_{3b2}$ is as defined in paragraph (29) above;
n is as defined in paragraph (33) above; and
Z is as defined in any one of paragraphs (104k), (104) to (106a) and (111) to (111b) above.

In a particular group of the compounds of formula (VI):
$R_{1a}$ is as defined in any one of paragraphs (1) to (6) above;
$R_{1b}$ is as defined in any one of paragraphs (15) to (15 g) above;
$R_{2a}$ is as defined in any one of paragraphs (18) to (19) above;
$R_{3b}$ is as defined in any one of paragraphs from (25) to (28) and paragraphs (30) to (31) above;
$R_{3b2}$ is as defined in any one of paragraphs (25), (29), (30) and (31) above;
n is as defined in any one of paragraphs (32) and (33) above; and
Z is as defined in any one of paragraphs (105) to (106a) and (111b) above.

In a particular group of the compounds of formula (VI):
$R_{1a}$ is as defined in paragraph (6) above;
$R_{1b}$ is as defined in paragraph (15 g) above;
$R_{2a}$ is as defined in paragraph (19) above;
$R_{3b}$ is as defined in paragraph (28) above;
$R_{3b2}$ is as defined in paragraph (29) above;
n is as defined in paragraph (33) above; and
Z is as defined in paragraph (111b) above.

In a particular group of compounds of the invention, Y is as defined in paragraph (34) and Z is defined as paragraph (106), i.e. the compounds have the structural formula (VII) (a sub-definition of formula (I)) shown below:

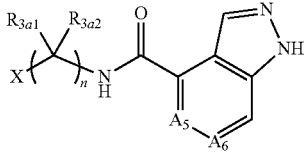

(VII)

wherein X, $R_{3a1}$, $R_{3a2}$, n, $A_5$ and $A_6$ each having any one of the meanings defined herein; or a pharmaceutically acceptable salt thereof.

In an embodiment of the compounds of formula (VII):
X is as defined in any one of paragraphs (20) to (24) above;
$R_{3a1}$ is as defined in any one of paragraphs from (25) to (28), and paragraphs (30) to (31) above;
$R_{3a2}$ is as defined in any one of paragraphs (25), (29), (30) and (31) above;
n is as defined in any one of paragraphs (32) and (33) above;
$A_5$ is as defined in any one of paragraphs (76), (77) and (81) above; and
$A_6$ is as defined in any one of paragraphs from (78) to (81) above.

In an embodiment of the compounds of formula (VII):
X is as defined in paragraph (20) above;
$R_{3a1}$ is as defined in paragraph (28) above;
$R_{3a2}$ is as defined in paragraph (29) above;
n is as defined in paragraph (33) above;
$A_5$ is as defined in paragraph (77) above;
$A_6$ is as defined in paragraph (79) above or $A_6$ is as defined in paragraph (79a) above.

In a particular group of the compounds of formula (VII):
X is as defined in any one of paragraphs (20) to (22) above and $R_{1b}$, $R_{1d}$ and $R_{1f}$ are each as defined in any one of paragraphs (8a) to (8e) above;
$R_{3a1}$ is as defined in any one of paragraphs from (25) to (28), and paragraphs (30) to (31) above;
$R_{3a2}$ is as defined in any one of paragraphs (25), (29), (30) and (31) above;
n is as defined in any one of paragraphs (32) and (33) above;
$A_5$ is as defined in any one of paragraphs (76), (77) and (81) above; and
$A_6$ is as defined in any one of paragraphs from (78) to (81) above.

In a particular group of the compounds of formula (VII):
X is as defined in paragraph (20) above and $R_{1b}$ is as defined in any one of paragraphs (8a) to (8e) above;
$R_{3a1}$ is as defined in paragraph (28) above;
$R_{3a2}$ is as defined in paragraph (29) above;
n is as defined in paragraph (33) above;
$A_5$ is as defined in paragraph (77) above;
$A_6$ is as defined in paragraph (79) above.

In a particular group of the compounds of formula (VII):
X is as defined in paragraph (20) above, $R_{1a}$, $R_{1b}$, $R_{1a'}$ and $R_{2a}$ are hydrogen, and $R_{1b}$ is as defined in any one of paragraphs (15e) to (15 g) above, suitably $R_{1b}$ is as defined in paragraph (15 g);
$R_{3a1}$ is as defined in paragraph (28) above;
$R_{3a2}$ is as defined in paragraph (29) above;
n is as defined in paragraph (33) above;

$A_3$ is as defined in paragraph (71) above;
$A_4$ is as defined in paragraph (74) above;
$R_7$ is as defined in paragraph (66) above; and
$R_3$ is as defined in paragraph (68) above.

In a particular group of compounds of the invention, Y is as defined in paragraph (34) and Z is defined as paragraph (105), i.e. the compounds have the structural formula (VIII) (a sub-definition of formula (I)) shown below:

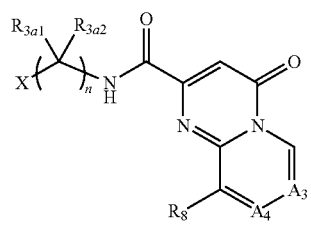

(VIII)

wherein X, $R_{3a1}$, $R_{3a2}$, n, $A_3$, $A_4$, $R_7$ and $R_8$ each having any one of the meanings defined herein; or a pharmaceutically acceptable salt thereof.

In an embodiment of the compounds of formula (VIII):
X is as defined in any one of paragraphs (20) to (24) and (24a) above;
$R_{3a1}$ is as defined in any one of paragraphs from (25) to (28), and paragraphs (30) to (31) above;
$R_{3a2}$ is as defined in any one of paragraphs (25), (29), (30) and (31) above;
n is as defined in any one of paragraphs (32) and (33) above;
$A_3$ is as defined in any one of paragraphs (70), (71), (72) and (75) above;
$A_4$ is as defined in any one of paragraphs from (73) to (75) above;
$R_7$ is as defined in any one of paragraphs (65), (66) and (69) above; and
$R_8$ is as defined in any one of paragraphs (67), (68) and (69) above.

In an embodiment of the compounds of formula (VIII):
X is as defined in paragraph (20) above;
$R_{3a1}$ is as defined in paragraph (28) above;
$R_{3a2}$ is as defined in paragraph (29) above;
n is as defined in paragraph (33) above;
$A_3$ is as defined in paragraph (71) above;
$A_4$ is as defined in paragraph (74) above;
$R_7$ is as defined in paragraph (66) above; and
$R_8$ is as defined in paragraph (68) above.

In a particular group of compounds of formula (VIII):
X is as defined in any one of paragraphs (20) to (22) above and $R_{1b}$, $R_{1d}$ and $R_{1f}$ are each as defined in any one of paragraphs (8a) to (8e) above;
$R_{3a1}$ is as defined in any one of paragraphs from (25) to (28), and paragraphs (30) to (31) above;
$R_{3a2}$ is as defined in any one of paragraphs (25), (29), (30) and (31) above;
n is as defined in any one of paragraphs (32) and (33) above;
$A_3$ is as defined in any one of paragraphs (70), (71), (72) and (75) above;
$A_4$ as defined in any one of paragraphs from (73) to (75) above;
$R_7$ is as defined in any one of paragraphs (65), (66) and (69) above; and R$_8$ is as defined in any one of paragraphs (67), (68) and (69) above.

In a particular group of the compounds of formula (VIII):
X is as defined in paragraph (20) above and R$_{1b}$ is as defined in any one of paragraphs (8a) to (8e) above;
R$_{3a1}$ is as defined in paragraph (28) above;
R$_{3a2}$ is as defined in paragraph (29) above;
n is as defined in paragraph (33) above;
A$_3$ is as defined in paragraph (71) above;
A$_4$ is as defined in paragraph (74) above;
R$_7$ is as defined in paragraph (66) above; and
R$_8$ is as defined in paragraph (68) above.

In a particular group of the compounds of formula (VIII):
X is as defined in paragraph (20) above, R$_{1a}$, R$_{1b}$, R$_{1a'}$ and R$_{2a}$ are hydrogen, and R$_{1b}$ is as defined in any one of paragraphs (15e) to (15 g) above, suitably R$_{1b}$ is as defined in paragraph (15 g);
R$_{3a1}$ is as defined in paragraph (28) above;
R$_{3a2}$ is as defined in paragraph (29) above;
n is as defined in paragraph (33) above;
A$_3$ is as defined in paragraph (71) above;
A$_4$ is as defined in paragraph (74) above;
R$_7$ is as defined in paragraph (66) above; and
R$_8$ is as defined in paragraph (68) above.

Particular compounds of the present invention include any of the compounds exemplified in the present application, or a pharmaceutically acceptable salt thereof, and, in particular, any of the following:

N-({6-methylimidazo[1,2-a]pyridin-2-yl}methyl)-1H-indazole-4-carboxamide;
N-({7-bromoimidazo[1,2-a]pyridin-2-yl}methyl)-1H-indazole-4-carboxamide;
N-({6-bromoimidazo[1,2-a]pyridin-2-yl}methyl)-1H-indazole-4-carboxamide;
N-({6-chloroimidazo[1,2-a]pyridin-2-yl}methyl)-1H-indazole-4-carboxamide;
N-({7-fluoroimidazo[1,2-a]pyridin-2-yl}methyl)-1H-indazole-4-carboxamide;
N-({6-fluoroimidazo[1,2-a]pyridin-2-yl}methyl)-1H-indazole-4-carboxamide;
N-({7-methoxyimidazo[1,2-a]pyridin-2-yl}methyl)-1H-indazole-4-carboxamide;
N-({6-methylimidazo[1,2-a]pyridin-2-yl}methyl)-6-(1H-pyrazol-5-yl)-1H-indazole-4-carboxamide;
N-({7-methylimidazo[1,2-a]pyridin-2-yl}methyl)-1H-indazole-4-carboxamide;
6-bromo-N-({6-methylimidazo[1,2-a]pyridin-2-yl}methyl)-1H-indazole-4-carboxamide;
6-bromo-N-({7-methylimidazo[1,2-a]pyridin-2-yl}methyl)-1H-indazole-4-carboxamide;
N-({6-methylimidazo[1,2-a]pyridin-2-yl}methyl)-4-oxo-4H-chromene-2-carboxamide;
N-({imidazo[1,2-a]pyridin-2-yl}methyl)-4-oxo-4H-chromene-2-carboxamide;
6-ethynyl-N-({6-methylimidazo[1,2-a]pyridin-2-yl}methyl)-1H-indazole-4-carboxamide;
N-({6-methylimidazo[1,2-a]pyridin-2-yl}methyl)-4-oxo-4H-pyrido[1,2-a]pyrimidine-2-carboxamide;
N-({7-methylimidazo[1,2-a]pyridin-2-yl}methyl)-4-oxo-4H-chromene-2-carboxamide;
N-({7-methylimidazo[1,2-a]pyridin-2-yl}methyl)-4-oxo-4H-pyrido[1,2-a]pyrimidine-2-carboxamide;
N-({6-cyanoimidazo[1,2-a]pyridin-2-yl}methyl)-4-oxo-4H-pyrido[1,2-a]pyrimidine-2-carboxamide;
8-methoxy-N-({6-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-indazole-5-carboxamide;
7-chloro-N-({6-methylimidazo[1,2-a]pyridin-2-yl}methyl)-4-oxo-4H-pyrido[1,2-a]pyrimidine-2-carboxamide;
N-({6-fluoroimidazo[1,2-a]pyridin-2-yl}methyl)-4-oxo-4H-pyrido[1,2-a]pyrimidine-2-carboxamide;
N-({6-bromoimidazo[1,2-a]pyridin-2-yl}methyl)-4-oxo-4H-pyrido[1,2-a]pyrimidine-2-carboxamide;
N-({6-methoxyimidazo[1,2-a]pyridin-2-yl}methyl)-4-oxo-4H-pyrido[1,2-a]pyrimidine-2-carboxamide;
N-({7-methoxyimidazo[1,2-a]pyridin-2-yl}methyl)-4-oxo-4H-pyrido[1,2-a]pyrimidine-2-carboxamide;
N-({imidazo[1,2-a]pyridin-2-yl}methyl)-4-oxo-4H-pyrido[1,2-a]pyrimidine-2-carboxamide;
N-({8-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-pyrazolo[4,3-c]pyridine-4-carboxamide;
N-({7-bromoimidazo[1,2-a]pyridin-2-yl}methyl)-4-oxo-4H-pyrido[1,2-a]pyrimidine-2-carboxamide;
N-(2-hydroxy-1-{6-methylimidazo[1,2-a]pyridin-2-yl}ethyl)-1H-indazole-4-carboxamide;
4-(3-{imidazo[1,2-a]pyridin-2-yl}-2,5-dihydro-1H-pyrrole-1-carbonyl)-1H-indazole;
N-[(6-{[(pyridin-3-yl)methyl]amino}imidazo[1,2-a]pyridin-2-yl)methyl]-1H-indazole-4-carboxamide;
N-[(6-{[(1-methyl-1H-imidazol-4-yl)methyl]amino}imidazo[1,2a]pyridin-2-yl)methyl]-1H-indazole-4-carboxamide;
N-{[6-(3-methoxyphenyl)imidazo[1,2-a]pyridin-2-yl]methyl}-1H-indazole-4-carboxamide;
N-{[6-(1H-pyrazol-5-yl)imidazo[1,2-a]pyridin-2-yl]methyl}-1H-indazole-4-carboxamide;
N-[[6-(3-chlorophenyl)imidazo[1,2-a]pyridin-2-yl]methyl]-1H-indazole-4-carboxamide;
N-({6-[(pyridin-3-yl)amino]imidazo[1,2-a]pyridin-2-yl}methyl)-1H-indazole-4-carboxamide;
N-({6-[(piperazin-1-yl)methyl]imidazo[1,2-a]pyridin-2-yl}methyl)-1H-indazole-4-carboxamide;
N-{[6-(aminomethyl)imidazo[1,2-a]pyridin-2-yl]methyl}-1H-indazole-4-carboxamide;
N-{[6-(acetamidomethyl)imidazo[1,2-a]pyridin-2-yl]methyl}-1H-indazole-4-carboxamide;
{6-methylimidazo[1,2-a]pyridin-2-yl}methyl 1H-indazole-4-carboxylate;
{6-methylimidazo[1,2-a]pyridin-2-yl}methyl 1H-indazole-4-carboxylate hydrochloride;
N-{[6-(hydroxymethyl)imidazo[1,2-a]pyridin-2-yl]methyl}-1H-indazole-4-carboxamide;
N-({6-hydroxyimidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide dihydrochloride;
N-[(6-{[(2-hydroxyethyl)amino]methyl}imidazo[1,2-a]pyridin-2-yl)methyl]-1H-indazole-4-carboxamide;
N-[(6-{[(2,2,2-trifluoroethyl)amino]methyl}imidazo[1,2-a]pyridin-2-yl)methyl]-1H-indazole-4-carboxamide;
N-{[6-(1-hydroxyethyl)imidazo[1,2-a]pyridin-2-yl]methyl}-1H-indazole-4-carboxamide;
N-({6-[hydroxy(phenyl)methyl]imidazo[1,2-a]pyridin-2-yl}methyl)-1H-indazole-4-carboxamide;
N-({6-formylimidazo[1,2-a]pyridin-2-yl}methyl)-4-oxo-4H-pyrido[1,2-a]pyrimidine-2-carboxamide;
N-{[6-(aminomethyl)imidazo[1,2-a]pyridin-2-yl]methyl}-4-oxo-4H-pyrido[1,2-a]pyrimidine-2-carboxamide;

4-oxo-N-[(6-{[(2,2,2-trifluoroethyl)amino]methyl}imidazo[1,2-a]pyridin-2-yl)methyl]-4H-pyrido[1,2-a]pyrimidine-2-carboxamide;

N-[(6-{[(2-hydroxyethyl)amino]methyl}imidazo[1,2-a]pyridin-2-yl)methyl]-4-oxo-4H-pyrido[1,2-a]pyrimidine-2-carboxamide;

4-oxo-N-[(6-{[(2-phenylethyl)amino]methyl}imidazo[1,2-a]pyridin-2-yl)methyl]-4H-pyrido[1,2-a]pyrimidine-2-carboxamide;

N-({6-[(benzylamino)methyl]imidazo[1,2-a]pyridin-2-yl}methyl)-4-oxo-4H-pyrido[1,2-a]pyrimidine-2-carboxamide;

4-oxo-N-[(6-{[(3-phenylpropyl)amino]methyl}imidazo[1,2-a]pyridin-2-yl)methyl]-4H-pyrido[1,2-a]pyrimidine-2-carboxamide;

N-({6-[hydroxy(phenyl)methyl]imidazo[1,2-a]pyridin-2-yl}methyl)-4-oxo-4H-pyrido[1,2-a]pyrimidine-2-carboxamide;

N-{[6-(1-hydroxyethyl)imidazo[1,2-a]pyridin-2-yl]methyl}-4-oxo-4H-pyrido[1,2-a]pyrimidine-2-carboxamide;

N-({6-ethenylimidazo[1,2-a]pyridin-2-yl}methyl)-4-oxo-4H-pyrido[1,2-a]pyrimidine-2-carboxamide;

N-({6-cyclopropylimidazo[1,2-a]pyridin-2-yl}methyl)-4-oxo-4H-pyrido[1,2-a]pyrimidine-2-carboxamide;

N-({7-ethenylimidazo[1,2-a]pyridin-2-yl}methyl)-4-oxo-4H-pyrido[1,2-a]pyrimidine-2-carboxamide;

N-{[6-(hydroxymethyl)imidazo[1,2-a]pyridin-2-yl]methyl}-4-oxo-4H-pyrido[1,2-a]pyrimidine-2-carboxamide; and 2-(1H-indazol-4-yl)-5-[(6-methylimidazo[1,2-a]pyridin-2-yl)methyl]-1,3,4-oxadiazole.

Particular compounds of the present invention include any of the compounds exemplified in the present application, or a pharmaceutically acceptable salt thereof, and, in particular, any of the following:

N-({6-methylimidazo[1,2-a]pyridin-2-yl}methyl)-1H-indazole-4-carboxamide;

N-({7-bromoimidazo[1,2-a]pyridin-2-yl}methyl)-1H-indazole-4-carboxamide;

N-({6-bromoimidazo[1,2-a]pyridin-2-yl}methyl)-1H-indazole-4-carboxamide;

N-({6-chloroimidazo[1,2-a]pyridin-2-yl}methyl)-1H-indazole-4-carboxamide;

N-({7-fluoroimidazo[1,2-a]pyridin-2-yl}methyl)-1H-indazole-4-carboxamide;

N-({6-fluoroimidazo[1,2-a]pyridin-2-yl}methyl)-1H-indazole-4-carboxamide;

N-({7-methoxyimidazo[1,2-a]pyridin-2-yl}methyl)-1H-indazole-4-carboxamide;

N-({6-methylimidazo[1,2-a]pyridin-2-yl}methyl)-6-(1H-pyrazol-5-yl)-1H-indazole-4-carboxamide;

N-({7-methylimidazo[1,2-a]pyridin-2-yl}methyl)-1H-indazole-4-carboxamide;

6-bromo-N-({6-methylimidazo[1,2-a]pyridin-2-yl}methyl)-1H-indazole-4-carboxamide;

6-bromo-N-({7-methylimidazo[1,2-a]pyridin-2-yl}methyl)-1H-indazole-4-carboxamide;

N-({6-methylimidazo[1,2-a]pyridin-2-yl}methyl)-4-oxo-4H-chromene-2-carboxamide;

N-({imidazo[1,2-a]pyridin-2-yl}methyl)-4-oxo-4H-chromene-2-carboxamide;

6-ethynyl-N-({6-methylimidazo[1,2-a]pyridin-2-yl}methyl)-1H-indazole-4-carboxamide;

N-({6-methylimidazo[1,2-a]pyridin-2-yl}methyl)-4-oxo-4H-pyrido[1,2-a]pyrimidine-2-carboxamide;

N-({7-methylimidazo[1,2-a]pyridin-2-yl}methyl)-4-oxo-4H-chromene-2-carboxamide;

N-({7-methylimidazo[1,2-a]pyridin-2-yl}methyl)-4-oxo-4H-pyrido[1,2-a]pyrimidine-2-carboxamide;

N-({6-cyanoimidazo[1,2-a]pyridin-2-yl}methyl)-4-oxo-4H-pyrido[1,2-a]pyrimidine-2-carboxamide;

8-methoxy-N-({6-methylimidazo[1,2-a]pyridin-2-yl}methyl)-4-oxo-4H-pyrido[1,2-a]pyrimidine-2-carboxamide;

N-({6-methylimidazo[1,2-a]pyridin-2-yl}methyl)-1H-indazole-5-carboxamide;

7-chloro-N-({6-methylimidazo[1,2-a]pyridin-2-yl}methyl)-4-oxo-4H-pyrido[1,2-a]pyrimidine-2-carboxamide;

N-({6-fluoroimidazo[1,2-a]pyridin-2-yl}methyl)-4-oxo-4H-pyrido[1,2-a]pyrimidine-2-carboxamide;

N-({6-bromoimidazo[1,2-a]pyridin-2-yl}methyl)-4-oxo-4H-pyrido[1,2-a]pyrimidine-2-carboxamide;

N-({6-methoxyimidazo[1,2-a]pyridin-2-yl}methyl)-4-oxo-4H-pyrido[1,2-a]pyrimidine-2-carboxamide;

N-({7-methoxyimidazo[1,2-a]pyridin-2-yl}methyl)-4-oxo-4H-pyrido[1,2-a]pyrimidine-2-carboxamide;

N-({imidazo[1,2-a]pyridin-2-yl}methyl)-4-oxo-4H-pyrido[1,2-a]pyrimidine-2-carboxamide;

N-({8-methylimidazo[1,2-a]pyridin-2-yl}methyl)-4-oxo-4H-pyrido[1,2-a]pyrimidine-2-carboxamide;

N-({6-methylimidazo[1,2-a]pyridin-2-yl}methyl)-1H-pyrazolo[4,3-c]pyridine-4-carboxamide;

N-({7-bromoimidazo[1,2-a]pyridin-2-yl}methyl)-4-oxo-4H-pyrido[1,2-a]pyrimidine-2-carboxamide;

N-(2-hydroxy-1-{6-methylimidazo[1,2-a]pyridin-2-yl}ethyl)-1H-indazole-4-carboxamide;

4-(3-{imidazo[1,2-a]pyridin-2-yl}-2,5-dihydro-1H-pyrrole-1-carbonyl)-1H-indazole;

N-[(6-{[(pyridin-3-yl)methyl]amino}imidazo[1,2-a]pyridin-2-yl)methyl]-1H-indazole-4-carboxamide;

N-[(6-{[(1-methyl-1H-imidazol-4-yl)methyl]amino}imidazo[1,2a]pyridin-2-yl)methyl]-1H-indazole-4-carboxamide;

N-{[6-(3-methoxyphenyl)imidazo[1,2-a]pyridin-2-yl]methyl}-1H-indazole-4-carboxamide;

N-{[6-(1H-pyrazol-5-yl)imidazo[1,2-a]pyridin-2-yl]methyl}-1H-indazole-4-carboxamide;

N-[[6-(3-chlorophenyl)imidazo[1,2-a]pyridin-2-yl]methyl]-1H-indazole-4-carboxamide;

N-({6-[(pyridin-3-yl)amino]imidazo[1,2-a]pyridin-2-yl}methyl)-1H-indazole-4-carboxamide;

N-({6-[(piperazin-1-yl)methyl]imidazo[1,2-a]pyridin-2-yl}methyl)-1H-indazole-4-carboxamide;

N-{[6-(aminomethyl)imidazo[1,2-a]pyridin-2-yl]methyl}-1H-indazole-4-carboxamide;

N-{[6-(acetamidomethyl)imidazo[1,2-a]pyridin-2-yl]methyl}-1H-indazole-4-carboxamide;

{6-methylimidazo[1,2-a]pyridin-2-yl}methyl 1H-indazole-4-carboxylate;

{6-methylimidazo[1,2-a]pyridin-2-yl}methyl 1H-indazole-4-carboxylate hydrochloride;

N-{[6-(hydroxymethyl)imidazo[1,2-a]pyridin-2-yl]methyl}-1H-indazole-4-carboxamide;

N-({6-hydroxyimidazo[1,2-a]pyridin-2-yl}methyl)-1H-indazole-4-carboxamide;

N-({6-[(methylamino)methyl]imidazo[1,2-a]pyridin-2-yl}methyl)-1H-indazole-4-carboxamide;

N-({6-[(methylamino)methyl]imidazo[1,2-a]pyridin-2-yl}methyl)-1H-indazole-4-carboxamide dihydrochloride;

N-[(6-{[(2-hydroxyethyl)amino]methyl}imidazo[1,2-a]pyridin-2-yl)methyl]-1H-indazole-4-carboxamide;

N-[(6-{[(2,2,2-trifluoroethyl)amino]methyl}imidazo[1,2-a]
pyridin-2-yl)methyl]-1H-indazole-4-carboxamide;
N-{[6-(1-hydroxyethyl)imidazo[1,2-a]pyridin-2-yl]
methyl}-1H-indazole-4-carboxamide;
N-({6-[hydroxy(phenyl)methyl]imidazo[1,2-a]pyridin-2-
yl}methyl)-1H-indazole-4-carboxamide;
N-({6-formylimidazo[1,2-a]pyridin-2-yl}methyl)-4-oxo-
4H-pyrido[1,2-a]pyrimidine-2-carboxamide;
N-{[6-(aminomethyl)imidazo[1,2-a]pyridin-2-yl]methyl}-
4-oxo-4H-pyrido[1,2-a]pyrimidine-2-carboxamide;
4-oxo-N-[(6-{[(2,2,2-trifluoroethyl)amino]methyl}imidazo
[1,2-a]pyridin-2-yl)methyl]-4H-pyrido[1,2-a]pyrimidine-
2-carboxamide;
N-[(6-{[(2-hydroxyethyl)amino]methyl}imidazo[1,2-a]
pyridin-2-yl)methyl]-4-oxo-4H-pyrido[1,2-a]pyrimidine-
2-carboxamide;
4-oxo-N-[(6-{[(2-phenylethyl)amino]methyl}imidazo[1,2-
a]pyridin-2-yl)methyl]-4H-pyrido[1,2-a]pyrimidine-2-
carboxamide;
N-({6-[(benzylamino)methyl]imidazo[1,2-a]pyridin-2-
yl}methyl)-4-oxo-4H-pyrido[1,2-a]pyrimidine-2-carbox-
amide;
4-oxo-N-[(6-{[(3-phenylpropyl)amino]methyl}imidazo[1,
2-a]pyridin-2-yl)methyl]-4H-pyrido[1,2-a]pyrimidine-2-
carboxamide;
N-({6-[hydroxy(phenyl)methyl]imidazo[1,2-a]pyridin-2-
yl}methyl)-4-oxo-4H-pyrido[1,2-a]pyrimidine-2-carbox-
amide;
N-{[6-(1-hydroxyethyl)imidazo[1,2-a]pyridin-2-yl]
methyl}-4-oxo-4H-pyrido[1,2-a]pyrimidine-2-carboxam-
ide;
N-({6-ethenylimidazo[1,2-a]pyridin-2-yl}methyl)-4-oxo-
4H-pyrido[1,2-a]pyrimidine-2-carboxamide;
N-({6-cyclopropylimidazo[1,2-a]pyridin-2-yl}methyl)-4-
oxo-4H-pyrido[1,2-a]pyrimidine-2-carboxamide;
N-({7-ethenylimidazo[1,2-a]pyridin-2-yl}methyl)-4-oxo-
4H-pyrido[1,2-a]pyrimidine-2-carboxamide;
N-{[6-(hydroxymethyl)imidazo[1,2-a]pyridin-2-yl]
methyl}-4-oxo-4H-pyrido[1,2-a]pyrimidine-2-carboxam-
ide;
2-(1H-indazol-4-yl)-5-[(6-methylimidazo[1,2-a]pyridin-2-
yl)methyl]-1,3,4-oxadiazole;
N-{[6-(2-aminoethyl)imidazo[1,2-a]pyridin-2-yl]methyl}-
4-oxo-4H-pyrido[1,2-a]pyrimidine-2-carboxamide;
N-({6-methylimidazo[1,2-a]pyridin-2-yl}methyl)-4-oxo-
4H,6H,7H,8H,9H-pyrido[1,2-a]pyrimidine-2-carboxam-
ide;
4-oxo-N-{[6-(trifluoromethyl)imidazo[1,2-a]pyridin-2-yl]
methyl}-4H-pyrido[1,2-a]pyrimidine-2-carboxamide;
tert-butyl N-(2-{2-[({4-oxo-4H-pyrido[1,2-a]pyrimidin-2-
yl}formamido)methyl]imidazo[1,2-a]pyridin-6-yl}ethyl)
carbamate;
N-benzyl-2-[({4-oxo-4H-pyrido[1,2-a]pyrimidin-2-
yl}formamido)methyl]imidazo[1,2-a]pyridine-6-carbox-
amide;
N-[(6-{[(cyclohexylmethyl)amino]methyl}imidazo[1,2-a]
pyridin-2-yl)methyl]-4-oxo-4H-chromene-2-carboxam-
ide;
7-chloro-N-[(6-{[(cyclohexylmethyl)amino]
methyl}imidazo[1,2-a]pyridin-2-yl)methyl]-4-oxo-4H-
chromene-2-carboxamide;
6-chloro-N-[(6-{[(cyclohexylmethyl)amino]
methyl}imidazo[1,2-a]pyridin-2-yl)methyl]-4-oxo-4H-
chromene-2-carboxamide;
N-[(6-{[(cyclohexylmethyl)amino]methyl}imidazo[1,2-a]
pyridin-2-yl)methyl]-4-oxo-4H,6H,7H,8H,9H-pyrido[1,
2-a]pyrimidine-2-carboxamide;
6-amino-N-[(6-{[(cyclohexylmethyl)amino]
methyl}imidazo[1,2-a]pyridin-2-yl)methyl]pyridine-3-
carboxamide;
N-({6-[(benzyloxy)methyl]imidazo[1,2-a]pyridin-2-
yl}methyl)-4-oxo-4H-pyrido[1,2-a]pyrimidine-2-carbox-
amide;
N-({6-[(benzylamino)methyl]imidazo[1,2-a]pyridin-2-
yl}methyl)-1H-indazole-4-carboxamide;
N-[(6-{[(cyclohexylmethyl)amino]methyl}imidazo[1,2-a]
pyridin-2-yl)methyl]-7-fluoro-4-oxo-4H-chromene-2-
carboxamide;
N-[(6-{[(cyclohexylmethyl)amino]methyl}imidazo[1,2-a]
pyridin-2-yl)methyl]-7-methyl-4-oxo-4H-chromene-2-
carboxamide;
N-[(6-{[(cyclohexylmethyl)amino]methyl}imidazo[1,2-a]
pyridin-2-yl)methyl]-1H-indazole-4-carboxamide;
8-chloro-N-[(6-{[(cyclohexylmethyl)amino]
methyl}imidazo[1,2-a]pyridin-2-yl)methyl]-4-oxo-4H-
chromene-2-carboxamide;
6-bromo-N-[(6-{[(cyclohexylmethyl)amino]
methyl}imidazo[1,2-a]pyridin-2-yl)methyl]-1H-inda-
zole-4-carboxamide;
N-[(6-{[(cyclohexylmethyl)amino]methyl}imidazo[1,2-a]
pyridin-2-yl)methyl]quinoline-3-carboxamide;
N-[(6-{1-[(cyclohexylmethyl)amino]ethyl}imidazo[1,2-a]
pyridin-2-yl)methyl]-4-oxo-4H-pyrido[1,2-a]pyrimidine-
2-carboxamide;
6-chloro-N-[(6-{[(cyclohexylmethyl)amino]
methyl}imidazo[1,2-a]pyridin-2-yl)methyl]-1H-inda-
zole-4-carboxamide;
4-[5-({6-methylimidazo[1,2-a]pyridin-2-yl}methyl)-1,3,4-
thiadiazol-2-yl]-1H-indazole;
4-[1-({6-methylimidazo[1,2-a]pyridin-2-yl}methyl)-1H-1,
2,3-triazol-4-yl]-1H-indazole;
N-[(6-{[(3-chlorophenyl)amino]methyl}imidazo[1,2-a]
pyridin-2-yl)methyl]-4-oxo-4H-pyrido[1,2-a]pyrimidine-
2-carboxamide;
N-[(6-{[(1-cyclohexyl-2-hydroxyethyl)amino]
methyl}imidazo[1,2-a]pyridin-2-yl)methyl]-4-oxo-4H-
pyrido[1,2-a]pyrimidine-2-carboxamide;
4-oxo-N-{[6-({[(pyridin-3-yl)methyl]amino}methyl)imi-
dazo[1,2-a]pyridin-2-yl]methyl}-4H-pyrido[1,2-a]py-
rimidine-2-carboxamide;
N-{[6-({[(4-methoxyphenyl)methyl]amino}methyl)imidazo
[1,2-a]pyridin-2-yl]methyl}-4-oxo-4H-pyrido[1,2-a]py-
rimidine-2-carboxamide;
N-[(6-{[(cyclohexylmethyl)amino]methyl}imidazo[1,2-a]
pyridin-2-yl)methyl]-4-oxo-4H-pyrido[1,2-a]pyrimidine-
2-carboxamide;
N-{[6-({[(4-chlorophenyl)methyl]amino}methyl)imidazo
[1,2-a]pyridin-2-yl]methyl}-4-oxo-4H-pyrido[1,2-a]py-
rimidine-2-carboxamide;
N-[(6-{[benzyl(methyl)amino]methyl}imidazo[1,2-a]pyri-
din-2-yl)methyl]-4-oxo-4H-pyrido[1,2-a]pyrimidine-2-
carboxamide;
4-oxo-N-{[6-({[(1R)-1-phenylethyl]amino}methyl)imidazo
[1,2-a]pyridin-2-yl]methyl}-4H-pyrido[1,2-a]pyrimi-
dine-2-carboxamide;
4-oxo-N-{[6-({[(1S)-1-phenylethyl]amino}methyl)imidazo
[1,2-a]pyridin-2-yl]methyl}-4H-pyrido[1,2-a]pyrimi-
dine-2-carboxamide;
N-{[6-({[(2-fluorophenyl)methyl]amino}methyl)imidazo
[1,2-a]pyridin-2-yl]methyl}-4-oxo-4H-pyrido[1,2-a]py-
rimidine-2-carboxamide;
4-oxo-N-[(6-{[(2-phenylpropan-2-yl)amino]
methyl}imidazo[1,2-a]pyridin-2-yl)methyl]-4H-pyrido
[1,2-a]pyrimidine-2-carboxamide;

N-{[6-({[(3-fluorophenyl)methyl]amino}methyl)imidazo[1,2-a]pyridin-2-yl]methyl}-4-oxo-4H-pyrido[1,2-a]pyrimidine-2-carboxamide;

N-{[6-({[(4-fluorophenyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(4,4,4-trifluorobutyl)amino]methyl}imidazo[1,2-a]pyridin-2-yl)methyl]-4H-pyrido[1,2-a]pyrimidine-2-carboxamide;

N-{[6-({[(oxan-4-yl)methyl]amino}methyl)imidazo[1,2-a]pyridin-2-yl]methyl}-4-oxo-4H-pyrido[1,2-a]pyrimidine-2-carboxamide;

N-{[6-({[(3,3-difluorocyclobutyl)methyl]amino}methyl)imidazo[1,2-a]pyridin-2-yl]methyl}-4-oxo-4H-pyrido[1,2-a]pyrimidine-2-carboxamide;

N-[(6-{[(cyclopropylmethyl)amino]methyl}imidazo[1,2-a]pyridin-2-yl)methyl]-4-oxo-4H-pyrido[1,2-a]pyrimidine-2-carboxamide;

4-oxo-N-[(6-{[(3,3,3-trifluoropropyl)amino]methyl}imidazo[1,2-a]pyridin-2-yl)methyl]-4H-pyrido[1,2-a]pyrimidine-2-carboxamide;

N-({6-[(cyclohexylamino)methyl]imidazo[1,2-a]pyridin-2-yl}methyl)-4-oxo-4H-pyrido[1,2-a]pyrimidine-2-carboxamide;

4-oxo-N-({6-[({[3-(trifluoromethyl)bicyclo[1.1.1]pentan-1-yl]methyl}amino)methyl]imidazo[1,2-a]pyridin-2-yl}methyl)-4H-pyrido[1,2-a]pyrimidine-2-carboxamide;

N-{[6-({[(oxan-2-yl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(3-phenyloxetan-3-yl)amino]methyl}imidazo[1,2-a]pyridin-2-yl)methyl]-4H-pyrido[1,2-a]pyrimidine-2-carboxamide;

N-{[6-({[(oxan-3-yl)methyl]amino}methyl)imidazo[1,2-a]pyridin-2-yl]methyl}-4-oxo-4H-pyrido[1,2-a]pyrimidine-2-carboxamide;

N-{[6-({[(1-fluorocyclohexyl)methyl]amino}methyl)imidazo[1,2-a]pyridin-2-yl]methyl}-4-oxo-4H-pyrido[1,2-a]pyrimidine-2-carboxamide;

N-{[6-({[(3-cyclopropylphenyl)methyl]amino}methyl)imidazo[1,2-a]pyridin-2-yl]methyl}-4-oxo-4H-pyrido[1,2-a]pyrimidine-2-carboxamide;

N-[(6-{[(3,3-dimethylbutyl)amino]methyl}imidazo[1,2-a]pyridin-2-yl)methyl]-4-oxo-4H-pyrido[1,2-a]pyrimidine-2-carboxamide;

4-oxo-N-{[6-({[2-(trifluoromethoxy)ethyl]amino}methyl)imidazo[1,2-a]pyridin-2-yl]methyl}-4H-pyrido[1,2-a]pyrimidine-2-carboxamide;

4-oxo-N-{[6-({[(oxolan-2-yl)methyl]amino}methyl)imidazo[1,2-a]pyridin-2-yl]methyl}-4H-pyrido[1,2-a]pyrimidine-2-carboxamide;

N-[(6-{[(2-methanesulfonylethyl)amino]methyl}imidazo[1,2-a]pyridin-2-yl)methyl]-4-oxo-4H-pyrido[1,2-a]pyrimidine-2-carboxamide;

4-oxo-N-({6-[(3-phenylpyrrolidin-1-yl)methyl]imidazo[1,2-a]pyridin-2-yl}methyl)-4H-pyrido[1,2-a]pyrimidine-2-carboxamide;

N-[(6-{[(1-cyclohexylcyclopropyl)amino]methyl}imidazo[1,2-a]pyridin-2-yl)methyl]-4-oxo-4H-pyrido[1,2-a]pyrimidine-2-carboxamide;

4-oxo-N-{[6-({[(1,3-thiazol-5-yl)methyl]amino}methyl)imidazo[1,2-a]pyridin-2-yl]methyl}-4H-pyrido[1,2-a]pyrimidine-2-carboxamide;

tert-butyl 3-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;

N-{[6-({[(4,4-difluorocyclohexyl)methyl]amino}methyl)imidazo[1,2-a]pyridin-2-yl]methyl}-4-oxo-4H-pyrido[1,2-a]pyrimidine-2-carboxamide;

tert-butyl 2-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;

N-[(6-{[(2-cyclopropylethyl)amino]methyl}imidazo[1,2-a]pyridin-2-yl)methyl]-4-oxo-4H-pyrido[1,2-a]pyrimidine-2-carboxamide;

4-oxo-N-({6-[(piperidin-1-yl)methyl]imidazo[1,2-a]pyridin-2-yl}methyl)-4H-pyrido[1,2-a]pyrimidine-2-carboxamide;

4-oxo-N-({6-[({[1-(2,2,2-trifluoroethyl)-1H-pyrazol-3-yl]methyl}amino)methyl]imidazo[1,2-a]pyridin-2-yl}methyl)-4H-pyrido[1,2-a]pyrimidine-2-carboxamide;

N-{[6-({[(1-methylcyclohexyl)methyl]amino}methyl)imidazo[1,2-a]pyridin-2-yl]methyl}-4-oxo-4H-pyrido[1,2-a]pyrimidine-2-carboxamide;

4-oxo-N-{[6-({[2-(pyridin-3-yl)ethyl]amino}methyl)imidazo[1,2-a]pyridin-2-yl]methyl}-4H-pyrido[1,2-a]pyrimidine-2-carboxamide;

N-{[6-({[(1,4-dioxan-2-yl)methyl]amino}methyl)imidazo[1,2-a]pyridin-2-yl]methyl}-4-oxo-4H-pyrido[1,2-a]pyrimidine-2-carboxamide;

N-({6-[(cyclopropylamino)methyl]imidazo[1,2-a]pyridin-2-yl}methyl)-4-oxo-4H-pyrido[1,2-a]pyrimidine-2-carboxamide;

N-[(6-{[(3,3-difluorocyclobutyl)amino]methyl}imidazo[1,2-a]pyridin-2-yl)methyl]-4-oxo-4H-pyrido[1,2-a]pyrimidine-2-carboxamide;

N-{[6-({[(oxetan-3-yl)methyl]amino}methyl)imidazo[1,2-a]pyridin-2-yl]methyl}-4-oxo-4H-pyrido[1,2-a]pyrimidine-2-carboxamide;

4-oxo-N-{[6-({[(1R,2R)-2-(trifluoromethyl)cyclopropyl]amino}methyl)imidazo[1,2-a]pyridin-2-yl]methyl}-4H-pyrido[1,2-a]pyrimidine-2-carboxamide;

N-[(6-{[(2,2-dimethylpropyl)amino]methyl}imidazo[1,2-a]pyridin-2-yl)methyl]-4-oxo-4H-pyrido[1,2-a]pyrimidine-2-carboxamide;

N-[(6-{[(cyclohexylmethyl)(methyl)amino]methyl}imidazo[1,2-a]pyridin-2-yl)methyl]-4-oxo-4H-pyrido[1,2-a]pyrimidine-2-carboxamide;

N-[(6-{[(4,4-difluorocyclohexyl)amino]methyl}imidazo[1,2-a]pyridin-2-yl)methyl]-4-oxo-4H-pyrido[1,2-a]pyrimidine-2-carboxamide;

N-({6-[({bicyclo[1.1.1]pentan-1-yl}amino)methyl]imidazo[1,2-a]pyridin-2-yl}methyl)-4-oxo-4H-pyrido[1,2-a]pyrimidine-2-carboxamide;

4-oxo-N-({6-[({[(2S)-oxolan-2-yl]methyl}amino)methyl]imidazo[1,2-a]pyridin-2-yl}methyl)-4H-pyrido[1,2-a]pyrimidine-2-carboxamide;

4-oxo-N-({6-[({[(2R)-oxolan-2-yl]methyl}amino)methyl]imidazo[1,2-a]pyridin-2-yl}methyl)-4H-pyrido[1,2-a]pyrimidine-2-carboxamide;

N-[(6-{[(2,2-difluoroethyl)amino]methyl}imidazo[1,2-a]pyridin-2-yl)methyl]-4-oxo-4H-pyrido[1,2-a]pyrimidine-2-carboxamide;

4-oxo-N-{[6-({[(oxolan-3-yl)methyl]amino}methyl)imidazo[1,2-a]pyridin-2-yl]methyl}-4H-pyrido[1,2-a]pyrimidine-2-carboxamide;

N-{[6-({[(1-methylcyclopropyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(oxolan-3-yl)amino]methyl}imidazo[1,2-a]pyridin-2-yl)methyl]-4H-pyrido[1,2-a]pyrimidine-2-carboxamide;

methyl 3-methyl-2-[({2-[({4-oxo-4H-pyrido[1,2-a]pyrimidin-2-yl}formamido)methyl]imidazo[1,2-a]pyridin-6-yl}methyl)amino]butanoate;

N-[(6-{[(oxan-3-yl)amino]methyl}imidazo[1,2-a]pyridin-2-yl)methyl]-4-oxo-4H-pyrido[1,2-a]pyrimidine-2-carboxamide;

4-oxo-N-{[6-({[(2S)-3,3,3-trifluoro-2-hydroxypropyl]amino}methyl)imidazo[1,2-a]pyridin-2-yl]methyl}-4H-pyrido[1,2-a]pyrimidine-2-carboxamide;

N-({6-[(cyclobutylamino)methyl]imidazo[1,2-a]pyridin-2-yl}methyl)-4-oxo-4H-pyrido[1,2-a]pyrimidine-2-carboxamide;

N-({6-[(tert-butylamino)methyl]imidazo[1,2-a]pyridin-2-yl}methyl)-4-oxo-4H-pyrido[1,2-a]pyrimidine-2-carboxamide;

N-[(6-{[(2-fluoroethyl)amino]methyl}imidazo[1,2-a]pyridin-2-yl)methyl]-4-oxo-4H-pyrido[1,2-a]pyrimidine-2-carboxamide;

N-({6-[(4,4-difluoropiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenylpiperazin-1-yl)methyl]imidazo[1,2-a]pyridin-2-yl}methyl)-4H-pyrido[1,2-a]pyrimidine-2-carboxamide;

4-oxo-N-({6-[(1,2,3,4-tetrahydroisoquinolin-2-yl)methyl]imidazo[1,2-a]pyridin-2-yl}methyl)-4H-pyrido[1,2-a]pyrimidine-2-carboxamide;

N-({6-[(diethylamino)methyl]imidazo[1,2-a]pyridin-2-yl}methyl)-4-oxo-4H-pyrido[1,2-a]pyrimidine-2-carboxamide;

4-oxo-N-({6-[(pyrrolidin-1-yl)methyl]imidazo[1,2-a]pyridin-2-yl}methyl)-4H-pyrido[1,2-a]pyrimidine-2-carboxamide;

4-oxo-N-[(6-{[3-(pyridin-2-yl)azetidin-1-yl]methyl}imidazo[1,2-a]pyridin-2-yl)methyl]-4H-pyrido[1,2-a]pyrimidine-2-carboxamide;

N-[(6-{[(dicyclopropylmethyl)amino]methyl}imidazo[1,2-a]pyridin-2-yl)methyl]-4-oxo-4H-pyrido[1,2-a]pyrimidine-2-carboxamide;

N-[(6-{[(cyclopropylmethyl)(methyl)amino]methyl}imidazo[1,2-a]pyridin-2-yl)methyl]-4-oxo-4H-pyrido[1,2-a]pyrimidine-2-carboxamide;

N-({6-[(4-methylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[4-(trifluoromethyl)piperidin-1-yl]methyl}imidazo[1,2-a]pyridin-2-yl)methyl]-4H-pyrido[1,2-a]pyrimidine-2-carboxamide;

N-({6-[(3-methylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[({spiro[2.2]pentan-1-yl}methyl)amino]methyl}imidazo[1,2-a]pyridin-2-yl)methyl]-4H-pyrido[1,2-a]pyrimidine-2-carboxamide;

N-({6-[(3,3-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[3-(trifluoromethyl)piperidin-1-yl]methyl}imidazo[1,2-a]pyridin-2-yl)methyl]-4H-pyrido[1,2-a]pyrimidine-2-carboxamide;

N-{[6-({[(5,5-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-({6-[(4-fluoropiperidin-1-yl)methyl]imidazo[1,2-a]pyridin-2-yl}methyl)-4-oxo-4H-pyrido[1,2-a]pyrimidine-2-carboxamide;

N-[(6-{[(3-methoxypropyl)amino]methyl}imidazo[1,2-a]pyridin-2-yl)methyl]-4-oxo-4H-pyrido[1,2-a]pyrimidine-2-carboxamide;

N-[(6-{[(1-methylcyclohexyl)amino]methyl}imidazo[1,2-a]pyridin-2-yl)methyl]-4-oxo-4H-pyrido[1,2-a]pyrimidine-2-carboxamide;

N-{[6-({[(4,4-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(1-methylcyclopentyl)amino]methyl}imidazo[1,2-a]pyridin-2-yl)methyl]-4-oxo-4H-pyrido[1,2-a]pyrimidine-2-carboxamide;

4-oxo-N-({6-[(propylamino)methyl]imidazo[1,2-a]pyridin-2-yl}methyl)-4H-pyrido[1,2-a]pyrimidine-2-carboxamide;

N-{[6-({[(3,3-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(2-methylpropyl)amino]methyl}imidazo[1,2-a]pyridin-2-yl)methyl]-4-oxo-4H-pyrido[1,2-a]pyrimidine-2-carboxamide;

N-{[6-({[2-(tert-butoxy)ethyl]amino}methyl)imidazo[1,2-a]pyridin-2-yl]methyl}-4-oxo-4H-pyrido[1,2-a]pyrimidine-2-carboxamide;

N-[(6-{[(4-chlorophenyl)amino]methyl}imidazo[1,2-a]pyridin-2-yl)methyl]-4-oxo-4H-pyrido[1,2-a]pyrimidine-2-carboxamide;

N-{[6-({[2-(oxan-2-yl)ethyl]amino}methyl)imidazo[1,2-a]pyridin-2-yl]methyl}-4-oxo-4H-pyrido[1,2-a]pyrimidine-2-carboxamide;

N-({6-[(4-benzylpiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenoxypiperidin-1-yl)methyl]imidazo[1,2-a]pyridin-2-yl}methyl)-4H-pyrido[1,2-a]pyrimidine-2-carboxamide;

N-{[6-({[(2,2-difluorocyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2,2-dimethylcyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2-methyloxolan-2-yl)methyl]amino}methyl)imidazo[1,2-a]pyridin-2-yl]methyl}-4-oxo-4H-pyrido[1,2-a]pyrimidine-2-carboxamide;

N-({6-[(4-tert-butylpiperidin-1-yl)methyl]imidazo[1,2-a]pyridin-2-yl}methyl)-4-oxo-4H-pyrido[1,2-a]pyrimidine-2-carboxamide;

N-[(6-{[(4-tert-butylcyclohexyl)amino]methyl}imidazo[1,2-a]pyridin-2-yl)methyl]-4-oxo-4H-pyrido[1,2-a]pyrimidine-2-carboxamide;

N-[(6-{[(2-cyclopentylethyl)amino]methyl}imidazo[1,2-a]pyridin-2-yl)methyl]-4-oxo-4H-pyrido[1,2-a]pyrimidine-2-carboxamide;

N-[(6-{[4-(2,2-dimethylpropanoyl)piperazin-1-yl]methyl}imidazo[1,2-a]pyridin-2-yl)methyl]-4-oxo-4H-pyrido[1,2-a]pyrimidine-2-carboxamide;

N-({6-[(4-acetylpiperazin-1-yl)methyl]imidazo[1,2-a]pyridin-2-yl}methyl)-4-oxo-4H-pyrido[1,2-a]pyrimidine-2-carboxamide;

N-{[6-({7-azabicyclo[2.2.1]heptan-7-yl}methyl)imidazo[1,2-a]pyridin-2-yl]methyl}-4-oxo-4H-pyrido[1,2-a]pyrimidine-2-carboxamide;

N-({6-[(4,4-dimethylpiperidin-1-yl)methyl]imidazo[1,2-a]pyridin-2-yl}methyl)-4-oxo-4H-pyrido[1,2-a]pyrimidine-2-carboxamide;

N-({6-[(2,2-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[(2,3,3-trimethylbutan-2-yl)amino]methyl}imidazo[1,2-a]pyridin-2-yl)methyl]-4H-pyrido[1,2-a]pyrimidine-2-carboxamide;

N-[(6-{[(5-fluoropyridin-2-yl)amino]methyl}imidazo[1,2-a]pyridin-2-yl)methyl]-4-oxo-4H-pyrido[1,2-a]pyrimidine-2-carboxamide;

N-({6-[({[1,1'-bi(cyclopropane)]-1-yl}amino)methyl]imidazo[1,2-a]pyridin-2-yl}methyl)-4-oxo-4H-pyrido[1,2-a]pyrimidine-2-carboxamide;

N-{[6-({[(1-fluorocyclopentyl)methyl]amino}methyl)imidazo[1,2-a]pyridin-2-yl]methyl}-4-oxo-4H-pyrido[1,2-a]pyrimidine-2-carboxamide;

N-({6-[(2,6-dimethylmorpholin-4-yl)methyl]imidazo[1,2-a]pyridin-2-yl}methyl)-4-oxo-4H-pyrido[1,2-a]pyrimidine-2-carboxamide;

methyl 1-({2-[({4-oxo-4H-pyrido[1,2-a]pyrimidin-2-yl}formamido)methyl]imidazo[1,2-a]pyridin-6-yl}methyl)piperidine-3-carboxylate;

N-[(6-{[(2-fluoro-2-methylpropyl)amino]methyl}imidazo[1,2-a]pyridin-2-yl)methyl]-4-oxo-4H-pyrido[1,2-a]pyrimidine-2-carboxamide;

N-[(6-{[(1-cyclohexylethyl)amino]methyl}imidazo[1,2-a]pyridin-2-yl)methyl]-4-oxo-4H-pyrido[1,2-a]pyrimidine-2-carboxamide;

N-[(6-{[(2-cyclopropylethyl)(methyl)amino]methyl}imidazo[1,2-a]pyridin-2-yl)methyl]-4-oxo-4H-pyrido[1,2-a]pyrimidine-2-carboxamide;

N-[(6-{[(2,2-dimethylpropyl)(methyl)amino]methyl}imidazo[1,2-a]pyridin-2-yl)methyl]-4-oxo-4H-pyrido[1,2-a]pyrimidine-2-carboxamide;

N-{[6-({[(1-fluorocyclobutyl)methyl]amino}methyl)imidazo[1,2-a]pyridin-2-yl]methyl}-4-oxo-4H-pyrido[1,2-a]pyrimidine-2-carboxamide;

N-({6-[(4-fluoro-4-methylpiperidin-1-yl)methyl]imidazo[1,2-a]pyridin-2-yl}methyl)-4-oxo-4H-pyrido[1,2-a]pyrimidine-2-carboxamide;

N-({6-[(3,3-difluoropiperidin-1-yl)methyl]imidazo[1,2-a]pyridin-2-yl}methyl)-4-oxo-4H-pyrido[1,2-a]pyrimidine-2-carboxamide;

N-{[6-({[(1-hydroxycyclohexyl)methyl]amino}methyl)imidazo[1,2-a]pyridin-2-yl]methyl}-4-oxo-4H-pyrido[1,2-a]pyrimidine-2-carboxamide;

N-[(6-{[(cyclopentylmethyl)amino]methyl}imidazo[1,2-a]pyridin-2-yl)methyl]-4-oxo-4H-pyrido[1,2-a]pyrimidine-2-carboxamide;

N-{[6-({[(3,3-difluorocyclopentyl)methyl]amino}methyl)imidazo[1,2-a]pyridin-2-yl]methyl}-4-oxo-4H-pyrido[1,2-a]pyrimidine-2-carboxamide;

N-[(6-{[(cyclobutylmethyl)amino]methyl}imidazo[1,2-a]pyridin-2-yl)methyl]-4-oxo-4H-pyrido[1,2-a]pyrimidine-2-carboxamide;

N-{[6-({[2-(3,3-difluorocyclobutyl)ethyl]amino}methyl)imidazo[1,2-a]pyridin-2-yl]methyl}-4-oxo-4H-pyrido[1,2-a]pyrimidine-2-carboxamide;

N-{[6-({[(2-fluorocyclobutyl)methyl]amino}methyl)imidazo[1,2-a]pyridin-2-yl]methyl}-4-oxo-4H-pyrido[1,2-a]pyrimidine-2-carboxamide;

N-{[6-({[(2S)-3,3-dimethylbutan-2-yl]amino}methyl)imidazo[1,2-a]pyridin-2-yl]methyl}-4-oxo-4H-pyrido[1,2-a]pyrimidine-2-carboxamide;

N-{[6-({6-azaspiro[2.5]octan-6-yl}methyl)imidazo[1,2-a]pyridin-2-yl]methyl}-4-oxo-4H-pyrido[1,2-a]pyrimidine-2-carboxamide;

4-oxo-N-({6-[({[(1r,3r)-3-fluorocyclobutyl]methyl}amino)methyl]imidazo[1,2-a]pyridin-2-yl}methyl)-4H-pyrido[1,2-a]pyrimidine-2-carboxamide;

4-oxo-N-({6-[(2-phenylethyl)amino]imidazo[1,2-a]pyridin-2-yl}methyl)-4H-pyrido[1,2-a]pyrimidine-2-carboxamide;

N-({6-[2-(benzylamino)ethyl]imidazo[1,2-a]pyridin-2-yl}methyl)-4-oxo-4H-pyrido[1,2-a]pyrimidine-2-carboxamide;

N-({6-[2-(cyclohexylamino)ethyl]imidazo[1,2-a]pyridin-2-yl}methyl)-4-oxo-4H-pyrido[1,2-a]pyrimidine-2-carboxamide;

4-oxo-N-({6-[(phenylformamido)methyl]imidazo[1,2-a]pyridin-2-yl}methyl)-4H-pyrido[1,2-a]pyrimidine-2-carboxamide;

N-({6-[(cyclohexylformamido)methyl]imidazo[1,2-a]pyridin-2-yl}methyl)-4-oxo-4H-pyrido[1,2-a]pyrimidine-2-carboxamide;

4-oxo-N-{[6-({[(piperidin-3-yl)methyl]amino}methyl)imidazo[1,2-a]pyridin-2-yl]methyl}-4H-pyrido[1,2-a]pyrimidine-2-carboxamide;

4-oxo-N-{[6-({[(piperidin-2-yl)methyl]amino}methyl)imidazo[1,2-a]pyridin-2-yl]methyl}-4H-pyrido[1,2-a]pyrimidine-2-carboxamide;

N-[(6-{[(azetidin-3-yl)amino]methyl}imidazo[1,2-a]pyridin-2-yl)methyl]-4-oxo-4H-pyrido[1,2-a]pyrimidine-2-carboxamide;

N-({6-[(cyclohexylamino)methyl]imidazo[1,2-a]pyridin-2-yl}methyl)-4-oxo-4H-chromene-2-carboxamide;

N-[(6-{[(2-cyclopropylethyl)amino]methyl}imidazo[1,2-a]pyridin-2-yl)methyl]-4-oxo-4H-chromene-2-carboxamide;

4-oxo-N-({6-[(piperidin-1-yl)methyl]imidazo[1,2-a]pyridin-2-yl}methyl)-4H-chromene-2-carboxamide;

N-{[6-({[(4-chlorophenyl)methyl]amino}methyl)imidazo[1,2-a]pyridin-2-yl]methyl}-4-oxo-4H-chromene-2-carboxamide;

N-({6-[(benzylamino)methyl]imidazo[1,2-a]pyridin-2-yl}methyl)-4-oxo-4H-chromene-2-carboxamide;

N-{[6-({[(1-methylcyclohexyl)methyl]amino}methyl)imidazo[1,2-a]pyridin-2-yl]methyl}-4-oxo-4H-chromene-2-carboxamide;

N-[(6-{[(2,2-dimethylpropyl)amino]methyl}imidazo[1,2-a]pyridin-2-yl)methyl]-4-oxo-4H-chromene-2-carboxamide;

4-oxo-N-[(7-{[(2-phenylethyl)amino]methyl}imidazo[1,2-a]pyridin-2-yl)methyl]-4H-pyrido[1,2-a]pyrimidine-2-carboxamide;

N-[(7-{[(cyclohexylmethyl)amino]methyl}imidazo[1,2-a]pyridin-2-yl)methyl]-4-oxo-4H-pyrido[1,2-a]pyrimidine-2-carboxamide;

N-[(7-{[(cyclopropylmethyl)amino]methyl}imidazo[1,2-a]pyridin-2-yl)methyl]-4-oxo-4H-pyrido[1,2-a]pyrimidine-2-carboxamide;

N-[(6-{1-[(cyclohexylmethyl)amino]cyclopropyl}imidazo[1,2-a]pyridin-2-yl)methyl]-4-oxo-4H-pyrido[1,2-a]pyrimidine-2-carboxamide;

N-{[6-(2-amino-3-phenylpropyl)imidazo[1,2-a]pyridin-2-yl]methyl}-4-oxo-4H-pyrido[1,2-a]pyrimidine-2-carboxamide;

(cyclohexylmethyl)[(2-{[4-(1H-indazol-4-yl)-1H-1,2,3-triazol-1-yl]methyl}imidazo[1,2-a]pyridin-6-yl)methyl]amine;

N-(cyclohexylmethyl)-2-{[4-(1H-indazol-4-yl)-1H-1,2,3-triazol-1-yl]methyl}imidazo[1,2-a]pyridine-6-carboxamide;

(2,2-dimethylpropyl)[(2-{[4-(1H-indazol-4-yl)-1H-1,2,3-triazol-1-yl]methyl}imidazo[1,2-a]pyridin-6-yl)methyl]amine;
4-[1-({6-[(4,4-dimethylpiperidin-1-yl)methyl]imidazo[1,2-a]pyridin-2-yl}methyl)-1H-1,2,3-triazol-4-yl]-1H-indazole;
[(2-{[4-(6-bromo-1H-indazol-4-yl)-1H-1,2,3-triazol-1-yl]methyl}imidazo[1,2-a]pyridin-6-yl)methyl][(3,3-difluorocyclobutyl)methyl]amine;
[(2-{[4-(6-bromo-1H-indazol-4-yl)-1H-1,2,3-triazol-1-yl]methyl}imidazo[1,2-a]pyridin-6-yl)methyl](2,2-dimethylpropyl)amine;
[(2-{[4-(6-bromo-1H-indazol-4-yl)-1H-1,2,3-triazol-1-yl]methyl}imidazo[1,2-a]pyridin-6-yl)methyl](cyclohexylmethyl)amine;
6-bromo-4-[1-({6-[(4,4-dimethylpiperidin-1-yl)methyl]imidazo[1,2-a]pyridin-2-yl}methyl)-1H-1,2,3-triazol-4-yl]-1H-indazole;
(2-{[4-(6-bromo-1H-indazol-4-yl)-1H-1,2,3-triazol-1-yl]methyl}imidazo[1,2-a]pyridin-6-yl)methanol;
(2,2-dimethylpropyl)[(2-{[4-(1H-indazol-5-yl)-1H-1,2,3-triazol-1-yl]methyl}imidazo[1,2-a]pyridin-6-yl)methyl]amine;
((cyclohexylmethyl)[1-(2-{[4-(1H-indazol-4-yl)-1H-1,2,3-triazol-1-yl]methyl}imidazo[1,2-a]pyridin-6-yl)ethyl]amine;
(2,2-dimethylpropyl)({2-[(4-{1H-pyrazolo[3,4-c]pyridin-4-yl}-1H-1,2,3-triazol-1-yl)methyl]imidazo[1,2-a]pyridin-6-yl}methyl)amine;
{2-[(4-{1H-pyrazolo[3,4-c]pyridin-4-yl}-1H-1,2,3-triazol-1-yl)methyl]imidazo[1,2-a]pyridin-6-yl}methanol;
N-({6-[(3R,5S)-5-tert-butylmorpholin-3-yl]imidazo[1,2-a]pyridin-2-yl}methyl)-4-oxo-4H-pyrido[1,2-a]pyrimidine-2-carboxamide;
N-({6-[(3S,5R)-5-tert-butylmorpholin-3-yl]imidazo[1,2-a]pyridin-2-yl}methyl)-4-oxo-4H-pyrido[1,2-a]pyrimidine-2-carboxamide;
N-({6-[(3S,5R)-5-cyclohexylmorpholin-3-yl]imidazo[1,2-a]pyridin-2-yl}methyl)-4-oxo-4H-pyrido[1,2-a]pyrimidine-2-carboxamide;
N-({6-[(3S,5R)-5-cyclohexylmorpholin-3-yl]imidazo[1,2-a]pyridin-2-yl}methyl)-1H-indazole-4-carboxamide;
N-({6-[(3S,5R)-5-cyclohexylmorpholin-3-yl]imidazo[1,2-a]pyridin-2-yl}methyl)-4-oxo-4H-chromene-2-carboxamide;
N-({6-[4-(2,2-dimethylpropyl)morpholin-3-yl]imidazo[1,2-a]pyridin-2-yl}methyl)-4-oxo-4H-pyrido[1,2-a]pyrimidine-2-carboxamide;
N-({6-[(3S,5R)-5-methylmorpholin-3-yl]imidazo[1,2-a]pyridin-2-yl}methyl)-4-oxo-4H-pyrido[1,2-a]pyrimidine-2-carboxamide; and
N-{[6-(9-methoxy-2,3,4,5-tetrahydro-1,4-benzoxazepin-3-yl)imidazo[1,2-a]pyridin-2-yl]methyl}-4-oxo-4H-pyrido[1,2-a]pyrimidine-2-carboxamide.

Particular compounds of the present invention include any of the compounds exemplified in the present application, or a pharmaceutically acceptable salt thereof, and, in particular, any of the following:

N-({6-methylimidazo[1,2-a]pyridin-2-yl}methyl)-1H-indazole-4-carboxamide;
N-({7-bromoimidazo[1,2-a]pyridin-2-yl}methyl)-1H-indazole-4-carboxamide;
N-({6-bromoimidazo[1,2-a]pyridin-2-yl}methyl)-1H-indazole-4-carboxamide;
N-({6-chloroimidazo[1,2-a]pyridin-2-yl}methyl)-1H-indazole-4-carboxamide;
N-({7-fluoroimidazo[1,2-a]pyridin-2-yl}methyl)-1H-indazole-4-carboxamide;
N-({6-fluoroimidazo[1,2-a]pyridin-2-yl}methyl)-1H-indazole-4-carboxamide;
N-({7-methoxyimidazo[1,2-a]pyridin-2-yl}methyl)-1H-indazole-4-carboxamide;
N-({6-methylimidazo[1,2-a]pyridin-2-yl}methyl)-6-(1H-pyrazol-5-yl)-1H-indazole-4-carboxamide;
N-({7-methylimidazo[1,2-a]pyridin-2-yl}methyl)-1H-indazole-4-carboxamide;
6-bromo-N-({6-methylimidazo[1,2-a]pyridin-2-yl}methyl)-1H-indazole-4-carboxamide;
6-bromo-N-({7-methylimidazo[1,2-a]pyridin-2-yl}methyl)-1H-indazole-4-carboxamide;
N-({6-methylimidazo[1,2-a]pyridin-2-yl}methyl)-4-oxo-4H-chromene-2-carboxamide;
N-({imidazo[1,2-a]pyridin-2-yl}methyl)-4-oxo-4H-chromene-2-carboxamide;
6-ethynyl-N-({6-methylimidazo[1,2-a]pyridin-2-yl}methyl)-1H-indazole-4-carboxamide;
N-({6-methylimidazo[1,2-a]pyridin-2-yl}methyl)-4-oxo-4H-pyrido[1,2-a]pyrimidine-2-carboxamide;
N-({7-methylimidazo[1,2-a]pyridin-2-yl}methyl)-4-oxo-4H-chromene-2-carboxamide;
N-({7-methylimidazo[1,2-a]pyridin-2-yl}methyl)-4-oxo-4H-pyrido[1,2-a]pyrimidine-2-carboxamide;
N-({6-cyanoimidazo[1,2-a]pyridin-2-yl}methyl)-4-oxo-4H-pyrido[1,2-a]pyrimidine-2-carboxamide;
8-methoxy-N-({6-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-indazole-5-carboxamide;
7-chloro-N-({6-methylimidazo[1,2-a]pyridin-2-yl}methyl)-4-oxo-4H-pyrido[1,2-a]pyrimidine-2-carboxamide;
N-({6-fluoroimidazo[1,2-a]pyridin-2-yl}methyl)-4-oxo-4H-pyrido[1,2-a]pyrimidine-2-carboxamide;
N-({6-bromoimidazo[1,2-a]pyridin-2-yl}methyl)-4-oxo-4H-pyrido[1,2-a]pyrimidine-2-carboxamide;
N-({6-methoxyimidazo[1,2-a]pyridin-2-yl}methyl)-4-oxo-4H-pyrido[1,2-a]pyrimidine-2-carboxamide;
N-({7-methoxyimidazo[1,2-a]pyridin-2-yl}methyl)-4-oxo-4H-pyrido[1,2-a]pyrimidine-2-carboxamide;
N-({imidazo[1,2-a]pyridin-2-yl}methyl)-4-oxo-4H-pyrido[1,2-a]pyrimidine-2-carboxamide;
N-({8-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-pyrazolo[4,3-c]pyridine-4-carboxamide;
N-({7-bromoimidazo[1,2-a]pyridin-2-yl}methyl)-4-oxo-4H-pyrido[1,2-a]pyrimidine-2-carboxamide;
N-(2-hydroxy-1-{6-methylimidazo[1,2-a]pyridin-2-yl}ethyl)-1H-indazole-4-carboxamide;
4-(3-{imidazo[1,2-a]pyridin-2-yl}-2,5-dihydro-1H-pyrrole-1-carbonyl)-1H-indazole;
N-[(6-{[(pyridin-3-yl)methyl]amino}imidazo[1,2-a]pyridin-2-yl)methyl]-1H-indazole-4-carboxamide;
N-[(6-{[(1-methyl-1H-imidazol-4-yl)methyl]amino}imidazo[1,2a]pyridin-2-yl)methyl]-1H-indazole-4-carboxamide;
N-{[6-(3-methoxyphenyl)imidazo[1,2-a]pyridin-2-yl]methyl}-1H-indazole-4-carboxamide;
N-{[6-(1H-pyrazol-5-yl)imidazo[1,2-a]pyridin-2-yl]methyl}-1H-indazole-4-carboxamide;
N-[[6-(3-chlorophenyl)imidazo[1,2-a]pyridin-2-yl]methyl]-1H-indazole-4-carboxamide;

N-({6-[(pyridin-3-yl)amino]imidazo[1,2-a]pyridin-2-yl}methyl)-1H-indazole-4-carboxamide;
N-({6-[(piperazin-1-yl)methyl]imidazo[1,2-a]pyridin-2-yl}methyl)-1H-indazole-4-carboxamide;
N-{[6-(aminomethyl)imidazo[1,2-a]pyridin-2-yl]methyl}-1H-indazole-4-carboxamide;
N-{[6-(acetamidomethyl)imidazo[1,2-a]pyridin-2-yl]methyl}-1H-indazole-4-carboxamide;
{6-methylimidazo[1,2-a]pyridin-2-yl}methyl 1H-indazole-4-carboxylate;
{6-methylimidazo[1,2-a]pyridin-2-yl}methyl 1H-indazole-4-carboxylate hydrochloride;
N-{[6-(hydroxymethyl)imidazo[1,2-a]pyridin-2-yl]methyl}-1H-indazole-4-carboxamide;
N-({6-hydroxyimidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide dihydrochloride;
N-[(6-{[(2-hydroxyethyl)amino]methyl}imidazo[1,2-a]pyridin-2-yl)methyl]-1H-indazole-4-carboxamide;
N-[(6-{[(2,2,2-trifluoroethyl)amino]methyl}imidazo[1,2-a]pyridin-2-yl)methyl]-1H-indazole-4-carboxamide;
N-{[6-(1-hydroxyethyl)imidazo[1,2-a]pyridin-2-yl]methyl}-1H-indazole-4-carboxamide;
N-({6-[hydroxy(phenyl)methyl]imidazo[1,2-a]pyridin-2-yl}methyl)-1H-indazole-4-carboxamide;
N-({6-formylimidazo[1,2-a]pyridin-2-yl}methyl)-4-oxo-4H-pyrido[1,2-a]pyrimidine-2-carboxamide;
N-{[6-(aminomethyl)imidazo[1,2-a]pyridin-2-yl]methyl}-4-oxo-4H-pyrido[1,2-a]pyrimidine-2-carboxamide;
4-oxo-N-[(6-{[(2,2,2-trifluoroethyl)amino]methyl}imidazo[1,2-a]pyridin-2-yl)methyl]-4H-pyrido[1,2-a]pyrimidine-2-carboxamide;
N-[(6-{[(2-hydroxyethyl)amino]methyl}imidazo[1,2-a]pyridin-2-yl)methyl]-4-oxo-4H-pyrido[1,2-a]pyrimidine-2-carboxamide;
4-oxo-N-[(6-{[(2-phenylethyl)amino]methyl}imidazo[1,2-a]pyridin-2-yl)methyl]-4H-pyrido[1,2-a]pyrimidine-2-carboxamide;
N-({6-[(benzylamino)methyl]imidazo[1,2-a]pyridin-2-yl}methyl)-4-oxo-4H-pyrido[1,2-a]pyrimidine-2-carboxamide;
4-oxo-N-[(6-{[(3-phenylpropyl)amino]methyl}imidazo[1,2-a]pyridin-2-yl)methyl]-4H-pyrido[1,2-a]pyrimidine-2-carboxamide;
N-({6-[hydroxy(phenyl)methyl]imidazo[1,2-a]pyridin-2-yl}methyl)-4-oxo-4H-pyrido[1,2-a]pyrimidine-2-carboxamide;
N-{[6-(1-hydroxyethyl)imidazo[1,2-a]pyridin-2-yl]methyl}-4-oxo-4H-pyrido[1,2-a]pyrimidine-2-carboxamide;
N-({6-ethenylimidazo[1,2-a]pyridin-2-yl}methyl)-4-oxo-4H-pyrido[1,2-a]pyrimidine-2-carboxamide;
N-({6-cyclopropylimidazo[1,2-a]pyridin-2-yl}methyl)-4-oxo-4H-pyrido[1,2-a]pyrimidine-2-carboxamide;
N-({7-ethenylimidazo[1,2-a]pyridin-2-yl}methyl)-4-oxo-4H-pyrido[1,2-a]pyrimidine-2-carboxamide;
N-{[6-(hydroxymethyl)imidazo[1,2-a]pyridin-2-yl]methyl}-4-oxo-4H-pyrido[1,2-a]pyrimidine-2-carboxamide;
2-(1H-indazol-4-yl)-5-[(6-methylimidazo[1,2-a]pyridin-2-yl)methyl]-1,3,4-oxadiazole;
N-{[6-(2-aminoethyl)imidazo[1,2-a]pyridin-2-yl]methyl}-4-oxo-4H-pyrido[1,2-a]pyrimidine-2-carboxamide;
N-({6-methylimidazo[1,2-a]pyridin-2-yl}methyl)-4-oxo-4H,6H,7H,8H,9H-pyrido[1,2-a]pyrimidine-2-carboxamide;
4-oxo-N-{[6-(trifluoromethyl)imidazo[1,2-a]pyridin-2-yl]methyl}-4H-pyrido[1,2-a]pyrimidine-2-carboxamide;
tert-butyl N-(2-{2-[({4-oxo-4H-pyrido[1,2-a]pyrimidin-2-yl}formamido)methyl]imidazo[1,2-a]pyridin-6-yl}ethyl)carbamate;
N-benzyl-2-[({4-oxo-4H-pyrido[1,2-a]pyrimidin-2-yl}formamido)methyl]imidazo[1,2-a]pyridine-6-carboxamide;
N-[(6-{[(cyclohexylmethyl)amino]methyl}imidazo[1,2-a]pyridin-2-yl)methyl]-4-oxo-4H-chromene-2-carboxamide;
7-chloro-N-[(6-{[(cyclohexylmethyl)amino]methyl}imidazo[1,2-a]pyridin-2-yl)methyl]-4-oxo-4H-chromene-2-carboxamide;
6-chloro-N-[(6-{[(cyclohexylmethyl)amino]methyl}imidazo[1,2-a]pyridin-2-yl)methyl]-4-oxo-4H-chromene-2-carboxamide;
N-[(6-{[(cyclohexylmethyl)amino]methyl}imidazo[1,2-a]pyridin-2-yl)methyl]-4-oxo-4H,6H,7H,8H,9H-pyrido[1,2-a]pyrimidine-2-carboxamide;
6-amino-N-[(6-{[(cyclohexylmethyl)amino]methyl}imidazo[1,2-a]pyridin-2-yl)methyl]pyridine-3-carboxamide;
N-({6-[(benzyloxy)methyl]imidazo[1,2-a]pyridin-2-yl}methyl)-4-oxo-4H-pyrido[1,2-a]pyrimidine-2-carboxamide;
N-({6-[(benzylamino)methyl]imidazo[1,2-a]pyridin-2-yl}methyl)-1H-indazole-4-carboxamide;
N-[(6-{[(cyclohexylmethyl)amino]methyl}imidazo[1,2-a]pyridin-2-yl)methyl]-7-fluoro-4-oxo-4H-chromene-2-carboxamide;
N-[(6-{[(cyclohexylmethyl)amino]methyl}imidazo[1,2-a]pyridin-2-yl)methyl]-7-methyl-4-oxo-4H-chromene-2-carboxamide;
N-[(6-{[(cyclohexylmethyl)amino]methyl}imidazo[1,2-a]pyridin-2-yl)methyl]-1H-indazole-4-carboxamide;
8-chloro-N-[(6-{[(cyclohexylmethyl)amino]methyl}imidazo[1,2-a]pyridin-2-yl)methyl]-4-oxo-4H-chromene-2-carboxamide;
6-bromo-N-[(6-{[(cyclohexylmethyl)amino]methyl}imidazo[1,2-a]pyridin-2-yl)methyl]-1H-indazole-4-carboxamide;
N-[(6-{[(cyclohexylmethyl)amino]methyl}imidazo[1,2-a]pyridin-2-yl)methyl]quinoline-3-carboxamide;
N-[(6-{1-[(cyclohexylmethyl)amino]ethyl}imidazo[1,2-a]pyridin-2-yl)methyl]-4-oxo-4H-pyrido[1,2-a]pyrimidine-2-carboxamide;
6-chloro-N-[(6-{[(cyclohexylmethyl)amino]methyl}imidazo[1,2-a]pyridin-2-yl)methyl]-1H-indazole-4-carboxamide;
4-[5-({6-methylimidazo[1,2-a]pyridin-2-yl}methyl)-1,3,4-thiadiazol-2-yl]-1H-indazole;
4-[1-({6-methylimidazo[1,2-a]pyridin-2-yl}methyl)-1H-1,2,3-triazol-4-yl]-1H-indazole;
N-[(6-{[(3-chlorophenyl)amino]methyl}imidazo[1,2-a]pyridin-2-yl)methyl]-4-oxo-4H-pyrido[1,2-a]pyrimidine-2-carboxamide;
N-[(6-{[(1-cyclohexyl-2-hydroxyethyl)amino]methyl}imidazo[1,2-a]pyridin-2-yl)methyl]-4-oxo-4H-pyrido[1,2-a]pyrimidine-2-carboxamide;
4-oxo-N-{[6-({[(pyridin-3-yl)methyl]amino}methyl)imidazo[1,2-a]pyridin-2-yl]methyl}-4H-pyrido[1,2-a]pyrimidine-2-carboxamide;

N-{[6-({[(4-methoxyphenyl)methyl]amino}methyl)imidazo[1,2-a]pyridin-2-yl]methyl}-4-oxo-4H-pyrido[1,2-a]pyrimidine-2-carboxamide;

N-[(6-{[(cyclohexylmethyl)amino]methyl}imidazo[1,2-a]pyridin-2-yl)methyl]-4-oxo-4H-pyrido[1,2-a]pyrimidine-2-carboxamide;

N-{[6-({[(4-chlorophenyl)methyl]amino}methyl)imidazo[1,2-a]pyridin-2-yl]methyl}-4-oxo-4H-pyrido[1,2-a]pyrimidine-2-carboxamide;

N-[(6-{[benzyl(methyl)amino]methyl}imidazo[1,2-a]pyridin-2-yl)methyl]-4-oxo-4H-pyrido[1,2-a]pyrimidine-2-carboxamide;

4-oxo-N-{[6-({[(1R)-1-phenylethyl]amino}methyl)imidazo[1,2-a]pyridin-2-yl]methyl}-4H-pyrido[1,2-a]pyrimidine-2-carboxamide;

4-oxo-N-{[6-({[(1S)-1-phenylethyl]amino}methyl)imidazo[1,2-a]pyridin-2-yl]methyl}-4H-pyrido[1,2-a]pyrimidine-2-carboxamide;

N-{[6-({[(2-fluorophenyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(2-phenylpropan-2-yl)amino]methyl}imidazo[1,2-a]pyridin-2-yl)methyl]-4H-pyrido[1,2-a]pyrimidine-2-carboxamide;

N-{[6-({[(3-fluorophenyl)methyl]amino}methyl)imidazo[1,2-a]pyridin-2-yl]methyl}-4-oxo-4H-pyrido[1,2-a]pyrimidine-2-carboxamide;

N-{[6-({[(4-fluorophenyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(4,4,4-trifluorobutyl)amino]methyl}imidazo[1,2-a]pyridin-2-yl)methyl]-4H-pyrido[1,2-a]pyrimidine-2-carboxamide;

N-{[6-({[(oxan-4-yl)methyl]amino}methyl)imidazo[1,2-a]pyridin-2-yl]methyl}-4-oxo-4H-pyrido[1,2-a]pyrimidine-2-carboxamide;

N-{[6-({[(3,3-difluorocyclobutyl)methyl]amino}methyl)imidazo[1,2-a]pyridin-2-yl]methyl}-4-oxo-4H-pyrido[1,2-a]pyrimidine-2-carboxamide;

N-[(6-{[(cyclopropylmethyl)amino]methyl}imidazo[1,2-a]pyridin-2-yl)methyl]-4-oxo-4H-pyrido[1,2-a]pyrimidine-2-carboxamide;

4-oxo-N-[(6-{[(3,3,3-trifluoropropyl)amino]methyl}imidazo[1,2-a]pyridin-2-yl)methyl]-4H-pyrido[1,2-a]pyrimidine-2-carboxamide;

N-({6-[(cyclohexylamino)methyl]imidazo[1,2-a]pyridin-2-yl}methyl)-4-oxo-4H-pyrido[1,2-a]pyrimidine-2-carboxamide;

4-oxo-N-({6-[({[3-(trifluoromethyl)bicyclo[1.1.1]pentan-1-yl]methyl}amino)methyl]imidazo[1,2-a]pyridin-2-yl}methyl)-4H-pyrido[1,2-a]pyrimidine-2-carboxamide;

N-{[6-({[(oxan-2-yl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(3-phenyloxetan-3-yl)amino]methyl}imidazo[1,2-a]pyridin-2-yl)methyl]-4H-pyrido[1,2-a]pyrimidine-2-carboxamide;

N-{[6-({[(oxan-3-yl)methyl]amino}methyl)imidazo[1,2-a]pyridin-2-yl]methyl}-4-oxo-4H-pyrido[1,2-a]pyrimidine-2-carboxamide;

N-{[6-({[(1-fluorocyclohexyl)methyl]amino}methyl)imidazo[1,2-a]pyridin-2-yl]methyl}-4-oxo-4H-pyrido[1,2-a]pyrimidine-2-carboxamide;

N-{[6-({[(3-cyclopropylphenyl)methyl]amino}methyl)imidazo[1,2-a]pyridin-2-yl]methyl}-4-oxo-4H-pyrido[1,2-a]pyrimidine-2-carboxamide;

N-[(6-{[(3,3-dimethylbutyl)amino]methyl}imidazo[1,2-a]pyridin-2-yl)methyl]-4-oxo-4H-pyrido[1,2-a]pyrimidine-2-carboxamide;

4-oxo-N-{[6-({[2-(trifluoromethoxy)ethyl]amino}methyl)imidazo[1,2-a]pyridin-2-yl]methyl}-4H-pyrido[1,2-a]pyrimidine-2-carboxamide;

4-oxo-N-{[6-({[(oxolan-2-yl)methyl]amino}methyl)imidazo[1,2-a]pyridin-2-yl]methyl}-4H-pyrido[1,2-a]pyrimidine-2-carboxamide;

N-[(6-{[(2-methanesulfonylethyl)amino]methyl}imidazo[1,2-a]pyridin-2-yl)methyl]-4-oxo-4H-pyrido[1,2-a]pyrimidine-2-carboxamide;

4-oxo-N-({6-[(3-phenylpyrrolidin-1-yl)methyl]imidazo[1,2-a]pyridin-2-yl}methyl)-4H-pyrido[1,2-a]pyrimidine-2-carboxamide;

N-[(6-{[(1-cyclohexylcyclopropyl)amino]methyl}imidazo[1,2-a]pyridin-2-yl)methyl]-4-oxo-4H-pyrido[1,2-a]pyrimidine-2-carboxamide;

4-oxo-N-{[6-({[(1,3-thiazol-5-yl)methyl]amino}methyl)imidazo[1,2-a]pyridin-2-yl]methyl}-4H-pyrido[1,2-a]pyrimidine-2-carboxamide;

tert-butyl 3-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;

N-{[6-({[(4,4-difluorocyclohexyl)methyl]amino}methyl)imidazo[1,2-a]pyridin-2-yl]methyl}-4-oxo-4H-pyrido[1,2-a]pyrimidine-2-carboxamide;

tert-butyl 2-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;

N-[(6-{[(2-cyclopropylethyl)amino]methyl}imidazo[1,2-a]pyridin-2-yl)methyl]-4-oxo-4H-pyrido[1,2-a]pyrimidine-2-carboxamide;

4-oxo-N-({6-[(piperidin-1-yl)methyl]imidazo[1,2-a]pyridin-2-yl}methyl)-4H-pyrido[1,2-a]pyrimidine-2-carboxamide;

4-oxo-N-({6-[({[1-(2,2,2-trifluoroethyl)-1H-pyrazol-3-yl]methyl}amino)methyl]imidazo[1,2-a]pyridin-2-yl}methyl)-4H-pyrido[1,2-a]pyrimidine-2-carboxamide;

N-{[6-({[(1-methylcyclohexyl)methyl]amino}methyl)imidazo[1,2-a]pyridin-2-yl]methyl}-4-oxo-4H-pyrido[1,2-a]pyrimidine-2-carboxamide;

4-oxo-N-{[6-({[2-(pyridin-3-yl)ethyl]amino}methyl)imidazo[1,2-a]pyridin-2-yl]methyl}-4H-pyrido[1,2-a]pyrimidine-2-carboxamide;

N-{[6-({[(1,4-dioxan-2-yl)methyl]amino}methyl)imidazo[1,2-a]pyridin-2-yl]methyl}-4-oxo-4H-pyrido[1,2-a]pyrimidine-2-carboxamide;

N-({6-[(cyclopropylamino)methyl]imidazo[1,2-a]pyridin-2-yl}methyl)-4-oxo-4H-pyrido[1,2-a]pyrimidine-2-carboxamide;

N-[(6-{[(3,3-difluorocyclobutyl)amino]methyl}imidazo[1,2-a]pyridin-2-yl)methyl]-4-oxo-4H-pyrido[1,2-a]pyrimidine-2-carboxamide;

N-{[6-({[(oxetan-3-yl)methyl]amino}methyl)imidazo[1,2-a]pyridin-2-yl]methyl}-4-oxo-4H-pyrido[1,2-a]pyrimidine-2-carboxamide;

4-oxo-N-{[6-({[(1R,2R)-2-(trifluoromethyl)cyclopropyl]amino}methyl)imidazo[1,2-a]pyridin-2-yl]methyl}-4H-pyrido[1,2-a]pyrimidine-2-carboxamide;

N-[(6-{[(2,2-dimethylpropyl)amino]methyl}imidazo[1,2-a]pyridin-2-yl)methyl]-4-oxo-4H-pyrido[1,2-a]pyrimidine-2-carboxamide;

N-[(6-{[(cyclohexylmethyl)(methyl)amino]methyl}imidazo[1,2-a]pyridin-2-yl)methyl]-4-oxo-4H-pyrido[1,2-a]pyrimidine-2-carboxamide;

N-[(6-{[(4,4-difluorocyclohexyl)amino]methyl}imidazo[1,2-a]pyridin-2-yl)methyl]-4-oxo-4H-pyrido[1,2-a]pyrimidine-2-carboxamide;

N-({6-[({bicyclo[1.1.1]pentan-1-yl}amino)methyl]imidazo[1,2-a]pyridin-2-yl}methyl)-4-oxo-4H-pyrido[1,2-a]pyrimidine-2-carboxamide;

4-oxo-N-({6-[({[(2S)-oxolan-2-yl]methyl}amino)methyl]imidazo[1,2-a]pyridin-2-yl}methyl)-4H-pyrido[1,2-a]pyrimidine-2-carboxamide;

4-oxo-N-({6-[({[(2R)-oxolan-2-yl]methyl}amino)methyl]imidazo[1,2-a]pyridin-2-yl}methyl)-4H-pyrido[1,2-a]pyrimidine-2-carboxamide;

N-[(6-{[(2,2-difluoroethyl)amino]methyl}imidazo[1,2-a]pyridin-2-yl)methyl]-4-oxo-4H-pyrido[1,2-a]pyrimidine-2-carboxamide;

4-oxo-N-{[6-({[(oxolan-3-yl)methyl]amino}methyl)imidazo[1,2-a]pyridin-2-yl]methyl}-4H-pyrido[1,2-a]pyrimidine-2-carboxamide;

N-{[6-({[(1-methylcyclopropyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(oxolan-3-yl)amino]methyl}imidazo[1,2-a]pyridin-2-yl)methyl]-4H-pyrido[1,2-a]pyrimidine-2-carboxamide;

methyl 3-methyl-2-[({2-[({4-oxo-4H-pyrido[1,2-a]pyrimidin-2-yl}formamido)methyl]imidazo[1,2-a]pyridin-6-yl}methyl)amino]butanoate;

N-[(6-{[(oxan-3-yl)amino]methyl}imidazo[1,2-a]pyridin-2-yl)methyl]-4-oxo-4H-pyrido[1,2-a]pyrimidine-2-carboxamide;

4-oxo-N-{[6-({[(2S)-3,3,3-trifluoro-2-hydroxypropyl]amino}methyl)imidazo[1,2-a]pyridin-2-yl]methyl}-4H-pyrido[1,2-a]pyrimidine-2-carboxamide;

N-({6-[(cyclobutylamino)methyl]imidazo[1,2-a]pyridin-2-yl}methyl)-4-oxo-4H-pyrido[1,2-a]pyrimidine-2-carboxamide;

N-({6-[(tert-butylamino)methyl]imidazo[1,2-a]pyridin-2-yl}methyl)-4-oxo-4H-pyrido[1,2-a]pyrimidine-2-carboxamide;

N-[(6-{[(2-fluoroethyl)amino]methyl}imidazo[1,2-a]pyridin-2-yl)methyl]-4-oxo-4H-pyrido[1,2-a]pyrimidine-2-carboxamide;

N-({6-[(4,4-difluoropiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenylpiperazin-1-yl)methyl]imidazo[1,2-a]pyridin-2-yl}methyl)-4H-pyrido[1,2-a]pyrimidine-2-carboxamide;

4-oxo-N-({6-[(1,2,3,4-tetrahydroisoquinolin-2-yl)methyl]imidazo[1,2-a]pyridin-2-yl}methyl)-4H-pyrido[1,2-a]pyrimidine-2-carboxamide;

N-({6-[(diethylamino)methyl]imidazo[1,2-a]pyridin-2-yl}methyl)-4-oxo-4H-pyrido[1,2-a]pyrimidine-2-carboxamide;

4-oxo-N-({6-[(pyrrolidin-1-yl)methyl]imidazo[1,2-a]pyridin-2-yl}methyl)-4H-pyrido[1,2-a]pyrimidine-2-carboxamide;

4-oxo-N-[(6-{[3-(pyridin-2-yl)azetidin-1-yl]methyl}imidazo[1,2-a]pyridin-2-yl)methyl]-4H-pyrido[1,2-a]pyrimidine-2-carboxamide;

N-[(6-{[(dicyclopropylmethyl)amino]methyl}imidazo[1,2-a]pyridin-2-yl)methyl]-4-oxo-4H-pyrido[1,2-a]pyrimidine-2-carboxamide;

N-[(6-{[(cyclopropylmethyl)(methyl)amino]methyl}imidazo[1,2-a]pyridin-2-yl)methyl]-4-oxo-4H-pyrido[1,2-a]pyrimidine-2-carboxamide;

N-({6-[(4-methylpiperidin-1-yl)methyl]imidazo[1,2-a]pyridin-2-yl}methyl)-4-oxo-4H-pyrido[1,2-a]pyrimidine-2-carboxamide;

4-oxo-N-({6-[{4-(trifluoromethyl)piperidin-1-yl]methyl}imidazo[1,2-a]pyridin-2-yl)methyl]-4H-pyrido[1,2-a]pyrimidine-2-carboxamide;

N-({6-[(3-methylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[({spiro[2.2]pentan-1-yl}methyl)amino]methyl}imidazo[1,2-a]pyridin-2-yl)methyl]-4H-pyrido[1,2-a]pyrimidine-2-carboxamide;

N-({6-[(3,3-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[3-(trifluoromethyl)piperidin-1-yl]methyl}imidazo[1,2-a]pyridin-2-yl)methyl]-4H-pyrido[1,2-a]pyrimidine-2-carboxamide;

N-{[6-({[(5,5-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-({6-[(4-fluoropiperidin-1-yl)methyl]imidazo[1,2-a]pyridin-2-yl}methyl)-4-oxo-4H-pyrido[1,2-a]pyrimidine-2-carboxamide;

N-[(6-{[(3-methoxypropyl)amino]methyl}imidazo[1,2-a]pyridin-2-yl)methyl]-4-oxo-4H-pyrido[1,2-a]pyrimidine-2-carboxamide;

N-[(6-{[(1-methylcyclohexyl)amino]methyl}imidazo[1,2-a]pyridin-2-yl)methyl]-4-oxo-4H-pyrido[1,2-a]pyrimidine-2-carboxamide;

N-{[6-({[(4,4-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(1-methylcyclopentyl)amino]methyl}imidazo[1,2-a]pyridin-2-yl)methyl]-4-oxo-4H-pyrido[1,2-a]pyrimidine-2-carboxamide;

4-oxo-N-({6-[(propylamino)methyl]imidazo[1,2-a]pyridin-2-yl}methyl)-4H-pyrido[1,2-a]pyrimidine-2-carboxamide;

N-{[6-({[(3,3-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(2-methylpropyl)amino]methyl}imidazo[1,2-a]pyridin-2-yl)methyl]-4-oxo-4H-pyrido[1,2-a]pyrimidine-2-carboxamide;

N-{[6-({[2-(tert-butoxy)ethyl]amino}methyl)imidazo[1,2-a]pyridin-2-yl]methyl}-4-oxo-4H-pyrido[1,2-a]pyrimidine-2-carboxamide;

N-[(6-{[(4-chlorophenyl)amino]methyl}imidazo[1,2-a]pyridin-2-yl)methyl]-4-oxo-4H-pyrido[1,2-a]pyrimidine-2-carboxamide;

N-{[6-({[2-(oxan-2-yl)ethyl]amino}methyl)imidazo[1,2-a]pyridin-2-yl]methyl}-4-oxo-4H-pyrido[1,2-a]pyrimidine-2-carboxamide;

N-({6-[(4-benzylpiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenoxypiperidin-1-yl)methyl]imidazo[1,2-a]pyridin-2-yl}methyl)-4H-pyrido[1,2-a]pyrimidine-2-carboxamide;

N-{[6-({[(2,2-difluorocyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2,2-dimethylcyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2-methyloxolan-2-yl)methyl]amino}methyl)imidazo[1,2-a]pyridin-2-yl]methyl}-4-oxo-4H-pyrido[1,2-a]pyrimidine-2-carboxamide;

N-({6-[(4-tert-butylpiperidin-1-yl)methyl]imidazo[1,2-a]pyridin-2-yl}methyl)-4-oxo-4H-pyrido[1,2-a]pyrimidine-2-carboxamide;

N-[(6-{[(4-tert-butylcyclohexyl)amino]methyl}imidazo[1,2-a]pyridin-2-yl)methyl]-4-oxo-4H-pyrido[1,2-a]pyrimidine-2-carboxamide;

N-[(6-{[(2-cyclopentylethyl)amino]methyl}imidazo[1,2-a]pyridin-2-yl)methyl]-4-oxo-4H-pyrido[1,2-a]pyrimidine-2-carboxamide;

N-[(6-{[4-(2,2-dimethylpropanoyl)piperazin-1-yl]methyl}imidazo[1,2-a]pyridin-2-yl)methyl]-4-oxo-4H-pyrido[1,2-a]pyrimidine-2-carboxamide;

N-({6-[(4-acetylpiperazin-1-yl)methyl]imidazo[1,2-a]pyridin-2-yl}methyl)-4-oxo-4H-pyrido[1,2-a]pyrimidine-2-carboxamide;

N-{[6-({7-azabicyclo[2.2.1]heptan-7-yl}methyl)imidazo[1,2-a]pyridin-2-yl]methyl}-4-oxo-4H-pyrido[1,2-a]pyrimidine-2-carboxamide;

N-({6-[(4,4-dimethylpiperidin-1-yl)methyl]imidazo[1,2-a]pyridin-2-yl}methyl)-4-oxo-4H-pyrido[1,2-a]pyrimidine-2-carboxamide;

N-({6-[(2,2-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[(2,3,3-trimethylbutan-2-yl)amino]methyl}imidazo[1,2-a]pyridin-2-yl)methyl]-4H-pyrido[1,2-a]pyrimidine-2-carboxamide;

N-[(6-{[(5-fluoropyridin-2-yl)amino]methyl}imidazo[1,2-a]pyridin-2-yl)methyl]-4-oxo-4H-pyrido[1,2-a]pyrimidine-2-carboxamide;

N-({6-[({[1,1'-bi(cyclopropane)]-1-yl}amino)methyl]imidazo[1,2-a]pyridin-2-yl}methyl)-4-oxo-4H-pyrido[1,2-a]pyrimidine-2-carboxamide;

N-{[6-({[(1-fluorocyclopentyl)methyl]amino}methyl)imidazo[1,2-a]pyridin-2-yl]methyl}-4-oxo-4H-pyrido[1,2-a]pyrimidine-2-carboxamide;

N-({6-[(2,6-dimethylmorpholin-4-yl)methyl]imidazo[1,2-a]pyridin-2-yl}methyl)-4-oxo-4H-pyrido[1,2-a]pyrimidine-2-carboxamide;

methyl 1-({2-[({4-oxo-4H-pyrido[1,2-a]pyrimidin-2-yl}formamido)methyl]imidazo[1,2-a]pyridin-6-yl}methyl)piperidine-3-carboxylate;

N-[(6-{[(2-fluoro-2-methylpropyl)amino]methyl}imidazo[1,2-a]pyridin-2-yl)methyl]-4-oxo-4H-pyrido[1,2-a]pyrimidine-2-carboxamide;

N-[(6-{[(1-cyclohexylethyl)amino]methyl}imidazo[1,2-a]pyridin-2-yl)methyl]-4-oxo-4H-pyrido[1,2-a]pyrimidine-2-carboxamide;

N-[(6-{[(2-cyclopropylethyl)(methyl)amino]methyl}imidazo[1,2-a]pyridin-2-yl)methyl]-4-oxo-4H-pyrido[1,2-a]pyrimidine-2-carboxamide;

N-[(6-{[(2,2-dimethylpropyl)(methyl)amino]methyl}imidazo[1,2-a]pyridin-2-yl)methyl]-4-oxo-4H-pyrido[1,2-a]pyrimidine-2-carboxamide;

N-{[6-({[(1-fluorocyclobutyl)methyl]amino}methyl)imidazo[1,2-a]pyridin-2-yl]methyl}-4-oxo-4H-pyrido[1,2-a]pyrimidine-2-carboxamide;

N-({6-[(4-fluoro-4-methylpiperidin-1-yl)methyl]imidazo[1,2-a]pyridin-2-yl}methyl)-4-oxo-4H-pyrido[1,2-a]pyrimidine-2-carboxamide;

N-({6-[(3,3-difluoropiperidin-1-yl)methyl]imidazo[1,2-a]pyridin-2-yl}methyl)-4-oxo-4H-pyrido[1,2-a]pyrimidine-2-carboxamide;

N-{[6-({[(1-hydroxycyclohexyl)methyl]amino}methyl)imidazo[1,2-a]pyridin-2-yl]methyl}-4-oxo-4H-pyrido[1,2-a]pyrimidine-2-carboxamide;

N-[(6-{[(cyclopentylmethyl)amino]methyl}imidazo[1,2-a]pyridin-2-yl)methyl]-4-oxo-4H-pyrido[1,2-a]pyrimidine-2-carboxamide;

N-{[6-({[(3,3-difluorocyclopentyl)methyl]amino}methyl)imidazo[1,2-a]pyridin-2-yl]methyl}-4-oxo-4H-pyrido[1,2-a]pyrimidine-2-carboxamide;

N-[(6-{[(cyclobutylmethyl)amino]methyl}imidazo[1,2-a]pyridin-2-yl)methyl]-4-oxo-4H-pyrido[1,2-a]pyrimidine-2-carboxamide;

N-{[6-({[2-(3,3-difluorocyclobutyl)ethyl]amino}methyl)imidazo[1,2-a]pyridin-2-yl]methyl}-4-oxo-4H-pyrido[1,2-a]pyrimidine-2-carboxamide;

N-{[6-({[(2-fluorocyclobutyl)methyl]amino}methyl)imidazo[1,2-a]pyridin-2-yl]methyl}-4-oxo-4H-pyrido[1,2-a]pyrimidine-2-carboxamide;

N-{[6-({[(2S)-3,3-dimethylbutan-2-yl]amino}methyl)imidazo[1,2-a]pyridin-2-yl]methyl}-4-oxo-4H-pyrido[1,2-a]pyrimidine-2-carboxamide;

N-{[6-({6-azaspiro[2.5]octan-6-yl}methyl)imidazo[1,2-a]pyridin-2-yl]methyl}-4-oxo-4H-pyrido[1,2-a]pyrimidine-2-carboxamide;

4-oxo-N-({6-[({[(1r,3r)-3-fluorocyclobutyl]methyl}amino)methyl]imidazo[1,2-a]pyridin-2-yl}methyl)-4H-pyrido[1,2-a]pyrimidine-2-carboxamide;

4-oxo-N-({6-[(2-phenylethyl)amino]imidazo[1,2-a]pyridin-2-yl}methyl)-4H-pyrido[1,2-a]pyrimidine-2-carboxamide;

N-({6-[2-(benzylamino)ethyl]imidazo[1,2-a]pyridin-2-yl}methyl)-4-oxo-4H-pyrido[1,2-a]pyrimidine-2-carboxamide;

N-({6-[2-(cyclohexylamino)ethyl]imidazo[1,2-a]pyridin-2-yl}methyl)-4-oxo-4H-pyrido[1,2-a]pyrimidine-2-carboxamide;

4-oxo-N-({6-[(phenylformamido)methyl]imidazo[1,2-a]pyridin-2-yl}methyl)-4H-pyrido[1,2-a]pyrimidine-2-carboxamide;

N-({6-[(cyclohexylformamido)methyl]imidazo[1,2-a]pyridin-2-yl}methyl)-4-oxo-4H-pyrido[1,2-a]pyrimidine-2-carboxamide;

4-oxo-N-{[6-({[(piperidin-3-yl)methyl]amino}methyl)imidazo[1,2-a]pyridin-2-yl]methyl}-4H-pyrido[1,2-a]pyrimidine-2-carboxamide;

4-oxo-N-{[6-({[(piperidin-2-yl)methyl]amino}methyl)imidazo[1,2-a]pyridin-2-yl]methyl}-4H-pyrido[1,2-a]pyrimidine-2-carboxamide;

N-[(6-{[(azetidin-3-yl)amino]methyl}imidazo[1,2-a]pyridin-2-yl)methyl]-4-oxo-4H-pyrido[1,2-a]pyrimidine-2-carboxamide;

N-({6-[(cyclohexylamino)methyl]imidazo[1,2-a]pyridin-2-yl}methyl)-4-oxo-4H-chromene-2-carboxamide;

N-[(6-{[(2-cyclopropylethyl)amino]methyl}imidazo[1,2-a]pyridin-2-yl)methyl]-4-oxo-4H-chromene-2-carboxamide;

4-oxo-N-({6-[(piperidin-1-yl)methyl]imidazo[1,2-a]pyridin-2-yl}methyl)-4H-chromene-2-carboxamide;

N-{[6-({[(4-chlorophenyl)methyl]amino}methyl)imidazo[1,2-a]pyridin-2-yl]methyl}-4-oxo-4H-chromene-2-carboxamide;

N-({6-[(benzylamino)methyl]imidazo[1,2-a]pyridin-2-yl}methyl)-4-oxo-4H-chromene-2-carboxamide;

N-{[6-({[(1-methylcyclohexyl)methyl]amino}methyl)imidazo[1,2-a]pyridin-2-yl]methyl}-4-oxo-4H-chromene-2-carboxamide;

N-[(6-{[(2,2-dimethylpropyl)amino]methyl}imidazo[1,2-a]pyridin-2-yl)methyl]-4-oxo-4H-chromene-2-carboxamide;

4-oxo-N-[(7-{[(2-phenylethyl)amino]methyl}imidazo[1,2-a]pyridin-2-yl)methyl]-4H-pyrido[1,2-a]pyrimidine-2-carboxamide;

N-[(7-{[(cyclohexylmethyl)amino]methyl}imidazo[1,2-a]pyridin-2-yl)methyl]-4-oxo-4H-pyrido[1,2-a]pyrimidine-2-carboxamide;

N-[(7-{[(cyclopropylmethyl)amino]methyl}imidazo[1,2-a]pyridin-2-yl)methyl]-4-oxo-4H-pyrido[1,2-a]pyrimidine-2-carboxamide;

N-[(6-{1-[(cyclohexylmethyl)amino]cyclopropyl}imidazo[1,2-a]pyridin-2-yl)methyl]-4-oxo-4H-pyrido[1,2-a]pyrimidine-2-carboxamide;

N-{[6-(2-amino-3-phenylpropyl)imidazo[1,2-a]pyridin-2-yl]methyl}-4-oxo-4H-pyrido[1,2-a]pyrimidine-2-carboxamide;

(cyclohexylmethyl)[(2-{[4-(1H-indazol-4-yl)-1H-1,2,3-triazol-1-yl]methyl}imidazo[1,2-a]pyridin-6-yl)methyl]amine;

N-(cyclohexylmethyl)-2-{[4-(1H-indazol-4-yl)-1H-1,2,3-triazol-1-yl]methyl}imidazo[1,2-a]pyridine-6-carboxamide;

(2,2-dimethylpropyl)[(2-{[4-(1H-indazol-4-yl)-1H-1,2,3-triazol-1-yl]methyl}imidazo[1,2-a]pyridin-6-yl)methyl]amine;

4-[1-({6-[(4,4-dimethylpiperidin-1-yl)methyl]imidazo[1,2-a]pyridin-2-yl}methyl)-1H-1,2,3-triazol-4-yl]-1H-indazole;

[(2-{[4-(6-bromo-1H-indazol-4-yl)-1H-1,2,3-triazol-1-yl]methyl}imidazo[1,2-a]pyridin-6-yl)methyl][(3,3-difluorocyclobutyl)methyl]amine;

[(2-{[4-(6-bromo-1H-indazol-4-yl)-1H-1,2,3-triazol-1-yl]methyl}imidazo[1,2-a]pyridin-6-yl)methyl](2,2-dimethylpropyl)amine;

[(2-{[4-(6-bromo-1H-indazol-4-yl)-1H-1,2,3-triazol-1-yl]methyl}imidazo[1,2-a]pyridin-6-yl)methyl](cyclohexylmethyl)amine;

6-bromo-4-[1-({6-[(4,4-dimethylpiperidin-1-yl)methyl]imidazo[1,2-a]pyridin-2-yl}methyl)-1H-1,2,3-triazol-4-yl]-1H-indazole;

(2-{[4-(6-bromo-1H-indazol-4-yl)-1H-1,2,3-triazol-1-yl]methyl}imidazo[1,2-a]pyridin-6-yl)methanol;

(2,2-dimethylpropyl)[(2-{[4-(1H-indazol-5-yl)-1H-1,2,3-triazol-1-yl]methyl}imidazo[1,2-a]pyridin-6-yl)methyl]amine;

((cyclohexylmethyl)[1-(2-{[4-(1H-indazol-4-yl)-1H-1,2,3-triazol-1-yl]methyl}imidazo[1,2-a]pyridin-6-yl)ethyl]amine;

(2,2-dimethylpropyl)({2-[(4-{1H-pyrazolo[3,4-c]pyridin-4-yl}-1H-1,2,3-triazol-1-yl)methyl]imidazo[1,2-a]pyridin-6-yl}methyl)amine;

{2-[(4-{1H-pyrazolo[3,4-c]pyridin-4-yl}-1H-1,2,3-triazol-1-yl)methyl]imidazo[1,2-a]pyridin-6-yl}methanol;

N-({6-[(3R,5S)-5-tert-butylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-tert-butylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-cyclohexylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-cyclohexylmorpholin-3-yl]imidazo[1,2-a]pyridin-2-yl}methyl)-1H-indazole-4-carboxamide;

N-({6-[(3S,5R)-5-cyclohexylmorpholin-3-yl]imidazo[1,2-a]pyridin-2-yl}methyl)-4-oxo-4H-chromene-2-carboxamide;

N-({6-[4-(2,2-dimethylpropyl)morpholin-3-yl]imidazo[1,2-a]pyridin-2-yl}methyl)-4-oxo-4H-pyrido[1,2-a]pyrimidine-2-carboxamide;

N-({6-[(3S,5R)-5-methylmorpholin-3-yl]imidazo[1,2-a]pyridin-2-yl}methyl)-4-oxo-4H-pyrido[1,2-a]pyrimidine-2-carboxamide;

N-{[6-(9-methoxy-2,3,4,5-tetrahydro-1,4-benzoxazepin-3-yl)imidazo[1,2-a]pyridin-2-yl]methyl}-4-oxo-4H-pyrido[1,2-a]pyrimidine-2-carboxamide;

4-[1-[[6-[(cyclobutylmethylamino)methyl]imidazo[1,2-a]pyridin-2-yl]methyl]triazol-4-yl]-1H-indazol-6-ol 4-[1-[[6-[[(1-hydroxycyclobutyl)methylamino]methyl]imidazo[1,2-a]pyridin-2-yl]methyl]triazol-4-yl]-1H-indazol-6-ol 1-[[[2-[[4-(5-methoxy-1H-indazol-4-yl)triazol-1-yl]methyl]imidazo[1,2-a]pyridin-6-yl]methylamino]methyl]cyclobutanol 1-[[[2-[[4-(6-methoxy-1H-indazol-4-yl)triazol-1-yl]methyl]imidazo[1,2-a]pyridin-6-yl]methylamino]methyl]cyclobutanol N-(cyclobutylmethyl)-1-[2-[[4-(6-methoxy-1H-indazol-4-yl)triazol-1-yl]methyl]imidazo[1,2-a]pyridin-6-yl]methanamine N-(cyclobutylmethyl)-1-[2-[[4-(5-methoxy-1H-indazol-4-yl)triazol-1-yl]methyl]imidazo[1,2-a]pyridin-6-yl]methanamine 4-[1-[(6-methylimidazo[1,2-a]pyridin-2-yl)methyl]triazol-4-yl]-1H-indazol-3-amine N-[[6-[[(1-methoxycyclobutyl)methylamino]methyl]imidazo[1,2-a]pyridin-2-yl]methyl]-4-oxo-pyrido[1,2-a]pyrimidine-2-carboxamide N-[[6-(1,4-oxazepan-3-yl)imidazo[1,2-a]pyridin-2-yl]methyl]-4-oxo-pyrido[1,2-a]pyrimidine-2-carboxamide N-[[6-[[(2-cyano-2-methyl-propyl)amino]methyl]imidazo[1,2-a]pyridin-2-yl]methyl]-4-oxo-pyrido[1,2-a]pyrimidine-2-carboxamide N-[[6-[[(3-fluoro-1-bicyclo[1.1.1]pentanyl)methylamino]methyl]imidazo[1,2-a]pyridin-2-yl]methyl]-4-oxo-pyrido[1,2-a]pyrimidine-2-carboxamide 4-oxo-N-[[6-[(spiro[3.3]heptan-2-ylmethylamino)methyl]imidazo[1,2-a]pyridin-2-yl]methyl]pyrido[1,2-a]pyrimidine-2-carboxamide 4-oxo-N-[[6-[(spiro[2.3]hexan-5-ylmethylamino)methyl]imidazo[1,2-a]pyridin-2-yl]methyl]pyrido[1,2-a]pyrimidine-2-carboxamide N-[[6-[(1-bicyclo[1.1.1]pentanylmethylamino)methyl]imidazo[1,2-a]pyridin-2-yl]methyl]-4-oxo-pyrido[1,2-a]pyrimidine-2-carboxamide 4-oxo-N-[[6-[(spiro[2.3]hexan-2-ylamino)methyl]imidazo[1,2-a]pyridin-2-yl]methyl]pyrido[1,2-a]pyrimidine-2-carboxamide N-[[6-[[(2-methoxy-2-methyl-propyl)amino]methyl]imidazo[1,2-a]pyridin-2-yl]methyl]-4-oxo-pyrido[1,2-a]pyrimidine-2-carboxamide N-[[6-[[(1-methylcyclobutyl)methylamino]methyl]imidazo[1,2-a]pyridin-2-yl]methyl]-4-oxo-pyrido[1,2-a]pyrimidine-2-carboxamide N-[[6-(butylaminomethyl)imidazo[1,2-a]pyridin-2-yl]methyl]-4-oxo-pyrido[1,2-a]pyrimidine-2-carboxamide N-[[6-[[(1-hydroxycyclopentyl)methylamino]methyl]imidazo[1,2-a]pyridin-2-yl]methyl]-4-oxo-pyrido[1,2-a]pyrimidine-2-carboxamide N-[[6-[(2-methylbutylamino)methyl]imidazo[1,2-a]pyridin-2-yl]methyl]-4-oxo-pyrido[1,2-a]pyrimidine-2-carboxamide N-[[6-[(2-cyclobutylethylamino)methyl]imidazo[1,2-a]pyridin-2-yl]methyl]-4-oxo-pyrido[1,2-a]pyrimidine-2-carboxamide N-[[6-[[(2-hydroxy-2-methyl-propyl)amino]methyl]imidazo[1,2-a]pyridin-2-yl]methyl]-4-oxo-pyrido[1,2-a]pyrimidine-2-carboxamide N-[[6-[[(1-hydroxycyclobutyl)methylamino]methyl]imidazo[1,2-a]pyridin-2-yl]methyl]-4-oxo-pyrido[1,2-a]pyrimidine-2-carboxamide N-[[6-[(2-hydroxybutylamino)methyl]imidazo[1,2-a]pyridin-2-yl]methyl]-4-oxo-pyrido[1,2-a]pyrimidine-2-carboxamide N-[[6-[[(3-methylcyclobutyl)methylamino]methyl]imidazo[1,2-a]pyridin-2-yl]methyl]-4-oxo-pyrido[1,2-a]pyrimidine-2-carboxamide N-[[6-[[(3,3-dimethylcyclobutyl)methylamino]methyl]imidazo[1,2-a]pyridin-2-yl]methyl]-4-oxo-pyrido[1,2-a]pyrimidine-2-carboxamide N-[[6-[(2,2-dimethylbutylamino)methyl]imidazo[1,2-a]pyridin-2-yl]methyl]-4-oxo-pyrido[1,2-a]pyrimidine-2-carboxamide N-[[6-[[[(2S)-2-methylbutyl]amino]methyl]imidazo[1,2-a]pyridin-2-yl]methyl]-4-oxo-pyrido[1,2-a]pyrimidine-2-carboxamide 1-[[[2-[[4-(6-bromo-1H-indazol-4-yl)triazol-1-yl]methyl]imidazo[1,2-a]pyridin-6-yl]methylamino]methyl]cyclohexanol 1-[[[2-[[4-(6-bromo-1H-indazol-4-yl)triazol-1-yl]methyl]imidazo[1,2-a]pyridin-6-yl]methylamino]methyl]cyclobutanol 1-[2-[[4-(6-bromo-1H-indazol-4-yl)triazol-1-yl]methyl]imidazo[1,2-a]pyridin-6-yl]-N-(cyclobutylmethyl)methanamine 4-[1-[[6-[(cyclobutylmethylamino)methyl]imidazo[1,2-a]pyridin-2-yl]methyl]triazol-4-yl]-1H-indazole-6-carboxylic acid 4-[1-[[6-[(cyclobutylmethylamino)methyl]imidazo[1,2-a]pyridin-2-yl]methyl]triazol-4-yl]-1H-indazole-6-carboxamide 4-[1-[[6-[(cyclobutylmethylamino)methyl]imidazo[1,2-a]pyridin-2-yl]methyl]triazol-4-yl]-N,N-dimethyl-1H-indazole-6-carboxamide

[4-[1-[[6-[(cyclobutylmethylamino)methyl]imidazo[1,2-a]pyridin-2-yl]methyl]triazol-4-yl]-1H-indazol-6-yl]-morpholino-methanone 4-[1-[[6-[(cyclobutylmethylamino)methyl]imidazo[1,2-a]pyridin-2-yl]methyl]triazol-4-yl]-N-(2-hydroxyethyl)-1H-indazole-6-carboxamide 1-[2-[[4-(6-chloro-1H-indazol-4-yl)triazol-1-yl]methyl]imidazo[1,2-a]pyridin-6-yl]-N-(cyclobutylmethyl)methanamine 1-[[[2-[[4-(6-chloro-1H-indazol-4-yl)triazol-1-yl]methyl]imidazo[1,2-a]pyridin-6-yl]methylamino]methyl]cyclobutanol N-[[2-[[4-(6-chloro-1H-indazol-4-yl)triazol-1-yl]methyl]imidazo[1,2-a]pyridin-6-yl]methyl]-2,2-dimethyl-propan-1-amine N-(cyclobutylmethyl)-1-[2-[[4-(7-fluoro-1H-indazol-4-yl)triazol-1-yl]methyl]imidazo[1,2-a]pyridin-6-yl]methanamine 1-[[[2-[[4-(7-fluoro-1H-indazol-4-yl)triazol-1-yl]methyl]imidazo[1,2-a]pyridin-6-yl]methylamino]methyl]cyclohexanol N-(cyclohexylmethyl)-1-[2-[[4-(7-fluoro-1H-indazol-4-yl)triazol-1-yl]methyl]imidazo[1,2-a]pyridin-6-yl]methanamine 1-[[[2-[[4-(7-fluoro-1H-indazol-4-yl)triazol-1-yl]methyl]imidazo[1,2-a]pyridin-6-yl]methylamino]methyl]cyclobutanol 1-[[[2-[[4-(7-fluoro-1H-indazol-4-yl)triazol-1-yl]methyl]imidazo[1,2-a]pyridin-6-yl]methylamino]methyl]cyclopentanamine N-[[6-[(4,4-dimethyl-1-piperidyl)methyl]imidazo[1,2-a]pyridin-2-yl]methyl]-5-fluoro-4-oxo-chromene-2-carboxamide N-(cyclobutylmethyl)-1-[2-[[4-(6-morpholino-1H-indazol-4-yl)triazol-1-yl]methyl]imidazo[1,2-a]pyridin-6-yl]methanamine 6-[2-(2-aminoethoxy)ethoxy]-N-[[6-[(4,4-dimethyl-1-piperidyl)methyl]imidazo[1,2-a]pyridin-2-yl]methyl]-1H-indazole-4-carboxamide N-[[6-[1-(cyclobutylmethylamino)-2-phenyl-ethyl]imidazo[1,2-a]pyridin-2-yl]methyl]-4-oxo-pyrido[1,2-a]pyrimidine-2-carboxamide N-[[6-[1-[bis(cyclobutylmethyl)amino]-2-phenyl-ethyl]imidazo[1,2-a]pyridin-2-yl]methyl]-4-oxo-pyrido[1,2-a]pyrimidine-2-carboxamide 1-[2-[[4-(7-chloro-1H-indazol-4-yl)triazol-1-yl]methyl]imidazo[1,2-a]pyridin-6-yl]-N-(cyclobutylmethyl)methanamine 1-[[[2-[[4-(7-chloro-1H-indazol-4-yl)triazol-1-yl]methyl]imidazo[1,2-a]pyridin-6-yl]methylamino]methyl]cyclobutanol

[2-[[4-(6-fluoro-1H-indazol-4-yl)triazol-1-yl]methyl]imidazo[1,2-a]pyridin-6-yl]methanol N-(cyclobutylmethyl)-1-[2-[[4-(6-fluoro-1H-indazol-4-yl)triazol-1-yl]methyl]imidazo[1,2-a]pyridin-6-yl]methanamine 1-[[[2-[[4-(6-fluoro-1H-indazol-4-yl)triazol-1-yl]methyl]imidazo[1,2-a]pyridin-6-yl]methylamino]methyl]cyclobutanol N-(cyclohexylmethyl)-1-[2-[[4-(6-fluoro-1H-indazol-4-yl)triazol-1-yl]methyl]imidazo[1,2-a]pyridin-6-yl]methanamine N-[[2-[[4-(6-cyclopropyl-1H-indazol-4-yl)triazol-1-yl]methyl]imidazo[1,2-a]pyridin-6-yl]methyl]-2,2-dimethyl-propan-1-amine N-[[6-[(cyclobutylmethylamino)methyl]imidazo[1,2-a]pyridin-2-yl]methyl]-1H-indazole-4-carboxamide N-(cyclobutylmethyl)-1-[2-[[4-(1H-pyrazolo[4,3-c]pyridin-4-yl)triazol-1-yl]methyl]imidazo[1,2-a]pyridin-6-yl]methanamine N-(cyclohexylmethyl)-1-[2-[[4-(1H-pyrazolo[4,3-c]pyridin-4-yl)triazol-1-yl]methyl]imidazo[1,2-a]pyridin-6-yl]methanamine 1-[[[2-[[4-(1H-pyrazolo[4,3-c]pyridin-4-yl)triazol-1-yl]methyl]imidazo[1,2-a]pyridin-6-yl]methylamino]methyl]cyclobutanol N-(cyclobutylmethyl)-1-[2-[[4-(1H-indazol-4-yl)triazol-1-yl]methyl]imidazo[1,2-a]pyridin-6-yl]methanamine 1-[[[2-[[4-(1H-indazol-4-yl)triazol-1-yl]methyl]imidazo[1,2-a]pyridin-6-yl]methylamino]methyl]cyclohexanol 2-[[4-(1H-indazol-4-yl)imidazol-1-yl]methyl]-6-methyl-imidazo[1,2-a]pyridine N-[[6-[2-cyano-1-(cyclobutylmethylamino)ethyl]imidazo[1,2-a]pyridin-2-yl]methyl]-4-oxo-pyrido[1,2-a]pyrimidine-2-carboxamide N-[[6-(6-methylmorpholin-3-yl)imidazo[1,2-a]pyridin-2-yl]methyl]-4-oxo-pyrido[1,2-a]pyrimidine-2-carboxamide N-[[6-(7-bromo-9-methoxy-2,3,4,5-tetrahydro-1,4-benzo-xazepin-3-yl)imidazo[1,2-a]pyridin-2-yl]methyl]-4-oxo-pyrido[1,2-a]pyrimidine-2-carboxamide 4-oxo-N-[(6-piperazin-2-ylimidazo[1,2-a]pyridin-2-yl)methyl]pyrido[1,2-a]pyrimidine-2-carboxamide N-[[6-(6-cyclohexyl-4-oxo-2-piperidyl)imidazo[1,2-a]pyridin-2-yl]methyl]-4-oxo-pyrido[1,2-a]pyrimidine-2-carboxamide 1-[2-(1H-indazol-4-yl)thiazol-5-yl]-1-(6-methylimidazo[1,2-a]pyridin-2-yl)ethanol 2-[[1-(1H-indazol-4-yl)triazol-4-yl]methyl]imidazo[1,2-a]pyridine N-[(3,3-difluorocyclobutyl)methyl]-1-[2-[[1-(1H-indazol-4-yl)triazol-4-yl]methyl]imidazo[1,2-a]pyridin-6-yl]methanamine 4-1-[[6-[(cyclobutylmethylamino)methyl]imidazo[1,2-a]pyridin-2-yl]methyl]triazol-4-yl]-1H-indazole-6-carbonitrile N-(cyclobutylmethyl)-1-[2-[[4-(1H-indazol-4-yl)imidazol-1-yl]methyl]imidazo[1,2-a]pyridin-6-yl]methanamine N-[[6-[[acetyl(cyclobutylmethyl)amino]methyl]imidazo[1,2-a]pyridin-2-yl]methyl]-4-oxo-pyrido[1,2-a]pyrimidine-2-carboxamide N-(cyclobutylmethyl)-1-[2-[[3-(1H-indazol-4-yl)-1,2,4-triazol-1-yl]methyl]imidazo[1,2-a]pyridin-6-yl]methanamine 2-[1-[[6-[(cyclobutylmethylamino)methyl]imidazo[1,2-a]pyridin-2-yl]methyl]triazol-4-yl]pyrido[1,2-a]pyrimidin-4-one N-[[6-[(2-bicyclo[2.2.1]hept-5-enylmethylamino)methyl]imidazo[1,2-a]pyridin-2-yl]methyl]-4-oxo-pyrido[1,2-a]pyrimidine-2-carboxamide N-[[6-[[[(1R,2R,4S)-norbornan-2-yl]methylamino]methyl]imidazo[1,2-a]pyridin-2-yl]methyl]-4-oxo-pyrido[1,2-a]pyrimidine-2-carboxamide N-[[6-[[[(1R,2S,4S)-norbornan-2-yl]methylamino]methyl]imidazo[1,2-a]pyridin-2-yl]methyl]-4-oxo-pyrido[1,2-a]pyrimidine-2-carboxamide N-[[6-(2-oxa-5-azabicyclo[2.2.1]heptan-5-ylmethyl)imidazo[1,2-a]pyridin-2-yl]methyl]-4-oxo-pyrido[1,2-a]pyrimidine-2-carboxamide N-[[6-(2-azabicyclo[2.2.1]heptan-2-ylmethyl)imidazo[1,2-a]pyridin-2-yl]methyl]-4-oxo-pyrido[1,2-a]pyrimidine-2-carboxamide N-[[6-(2-azabicyclo[2.2.2]octan-2-ylmethyl)imidazo[1,2-a]pyridin-2-yl]methyl]-4-oxo-pyrido[1,2-a]pyrimidine-2-carboxamide N-[[6-[[(2,2-difluorospiro[3.3]heptan-6-yl)amino]methyl]imidazo[1,2-a]pyridin-2-yl]methyl]-4-oxo-pyrido[1,2-a]pyrimidine-2-carboxamide 4-oxo-N-[[6-[[[rac-(1S,2S,4S)-7-oxabicyclo[2.2.1]hept-5-en-2-yl]methylamino]methyl]imidazo[1,2-a]pyridin-2-yl]methyl]pyrido[1,2-a]pyrimidine-2-carboxamide 4-oxo-N-[[6-[[[rac-(1S,2R,4S)-7-oxabicyclo[2.2.1]hept-5-en-2-yl]methylamino]methyl]imidazo[1,2-a]pyridin-2-yl]methyl]pyrido[1,2-a]pyrimidine-2-carboxamide; and N-[(1-methoxycyclobutyl)methyl]-1-[2-[[4-(6-methoxy-1H-indazol-4-yl)triazol-1-yl]methyl]imidazo[1,2-a]pyridin-6-yl]methanamine.

The various functional groups and substituents making up the compounds of the formula (I) are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the formula (I) (and compounds of formula (II), (III) and (IV)) may exist in solvated as well as unsolvated forms such as, for example, hydrated forms. It is to be understood that the invention encompasses all such solvated forms that possess antiproliferative activity.

It is also to be understood that certain compounds of the formula (I) (and compounds of formula (II), (III) and (IV))

may exhibit polymorphism, and that the invention encompasses all such forms that possess antiproliferative activity.

Compounds of the formula (I) (and compounds of formula (II), (III) and (IV)) may exist in a number of different tautomeric forms and references to compounds of the formula (I) include all such forms. For the avoidance of doubt, where a compound can exist in one of several tautomeric forms, and only one is specifically described or shown, all others are nevertheless embraced by formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

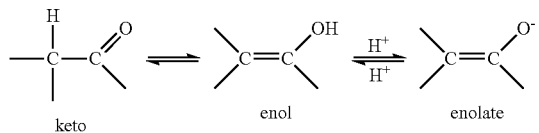

keto    enol    enolate

Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of formula (I) may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula (I) and in-vivo cleavable amide derivatives that may be formed at a carboxy group or an amino group in a compound of the formula (I).

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula (I) that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically acceptable pro-drug of a compound of the formula (I) is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula (I) that possesses a carboxy group is, for example, an in vivo cleavable ester thereof. An in vivo cleavable ester of a compound of the formula (I) containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-}$alkoxymethyl esters such as methoxymethyl esters, $C_{1-6}$alkanoyloxymethyl esters such as pivaloyloxymethyl esters, 3-phthalidyl esters, $C_{3-6}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula (I) that possesses a hydroxy group is, for example, an in vivo cleavable ester or ether thereof. An in vivo cleavable ester or ether of a compound of the formula (I) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula (I) that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethyl-amine, a $C_{1-4}$alkoxy-$C_{2-4}$alkylamine such as 2-methoxyethylamine, a phenyl-$C_{1-4}$ alkylamine such as benzylamine and amino acids such as glycine or an ester thereof.

A suitable pharmaceutically acceptable pro-drug of a compound of the formula (I) that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula (I) may be exerted in part by one or more metabolites that are formed within the human or animal body after administration of a compound of the formula (I). As stated hereinbefore, the in vivo effects of a compound of the formula (I) may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of the variable groups. Suitable processes for their preparation are described further in the accompanying Examples.

Once a compound of formula I has been synthesised by any one of the processes defined herein, the processes may then further comprise the additional steps of:
  (i) removing any protecting groups present;
  (ii) converting the compound formula I into another compound of formula I;
  (iii) forming a pharmaceutically acceptable salt, hydrate or solvate thereof; and/or
  (iv) forming a prodrug thereof.

The resultant compounds of formula I can be isolated and purified using techniques well known in the art.

Biological Activity

The METTL3 enzyme and cell assays described in accompanying Example section may be used to measure the pharmacological effects of the compounds of the present invention.

Although the pharmacological properties of the compounds of formula I vary with structural change, as expected, the compounds of the invention were found to be active in these METTL3 assays.

In general, the compounds of the invention demonstrate an $IC_{50}$ of 10 µM or less in the METTL3 enzyme assay described herein, with preferred compounds of the invention demonstrating an $IC_{50}$ of 5 µM or less and the most preferred compounds of the invention demonstrating an $IC_{50}$ of 2 µM or less.

In the METTL3 cell assay described in the Example section, the compounds of formula (I) suitably possess an activity of less than 10 µM, with preferred compounds of the invention demonstrating an $IC_{50}$ of 5 µM or less and the most preferred compounds demonstrating an activity of 2 µM or less.

Pharmaceutical Compositions

According to a further aspect of the invention there is provided a pharmaceutical composition which comprises a compound of the invention as defined hereinbefore, or a pharmaceutically acceptable salt thereof, and one or more pharmaceutically acceptable excipients.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition and/or treat or prevent an autoimmune disease referred to herein, slow its progression and/or reduce the symptoms associated with the condition and/or disease.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of METTL3 activity.

The present invention therefore provides a method of inhibiting METTL3 activity in vitro or in vivo, said method comprising contacting a cell with an effective amount of a compound, or a pharmaceutically acceptable salt thereof, or a pharmaceutical composition as defined herein.

The present invention also provides a method of treating a disease or disorder in which METTL3 activity is implicated in a patient in need of such treatment, said method comprising administering to said patient a therapeutically effective amount of a compound, or a pharmaceutically acceptable salt thereof, or a pharmaceutical composition as defined herein. Suitably, the disease or disorder in which METTL3 activity is implicated is cancer, such as lung cancer, renal cancer, solid organ cancer, pancreactic cancer or leukaemia, type 2 diabetes, a neuropsychiatric behavioural disorder or a depressive disorder.

The present invention provides a method of inhibiting cell proliferation, in vitro or in vivo, said method comprising contacting a cell with an effective amount of a compound, or a pharmaceutically acceptable salt thereof, as defined herein.

The present invention provides a method of treating a proliferative disorder, said method comprising administering to a subject in need thereof a therapeutically effective amount of a compound, or a pharmaceutically acceptable salt thereof, or a pharmaceutical composition as defined herein.

The present invention provides a method of treating cancer, said method comprising administering to a subject in need thereof a therapeutically effective amount of a compound, or a pharmaceutically acceptable salt thereof, or a pharmaceutical composition as defined herein. Suitably the cancer is lung cancer, renal cancer, solid organ cancer, pancreatic cancer or leukaemia suitably AML leukaemia or chronic myeloid leukaemia.

The present invention provides a method of treating leukaemia, said method comprising administering to a subject in need thereof a therapeutically effective amount of a compound, or a pharmaceutically acceptable salt thereof, or a pharmaceutical composition as defined herein.

The present invention provides a method of treating AML leukaemia, said method comprising administering to a subject in need thereof a therapeutically effective amount of a compound, or a pharmaceutically acceptable salt thereof, or a pharmaceutical composition as defined herein.

The present invention provides a method of treating an autoimmune disease, said method comprising administering to a subject in need thereof a therapeutically effective amount of a compound, or a pharmaceutically acceptable salt thereof, or a pharmaceutical composition as defined herein. Suitably the autoimmune disease is colitis, multiple sclerosis, rheumatoid arthritis, lupus, cirrhosis, or dermatitis.

The present invention provides a method of treating a neurological disease, said method comprising administering to a subject in need thereof a therapeutically effective amount of a compound, or a pharmaceutically acceptable salt thereof, or a pharmaceutical composition as defined herein.

The present invention provides a method of treating an infectious disease, said method comprising administering to a subject in need thereof a therapeutically effective amount of a compound, or a pharmaceutically acceptable salt thereof, or a pharmaceutical composition as defined herein.

The present invention provides a method of treating an inflammatory disease, said method comprising administering to a subject in need thereof a therapeutically effective amount of a compound, or a pharmaceutically acceptable salt thereof, or a pharmaceutical composition as defined herein.

The present invention provides a compound, or a pharmaceutically acceptable salt thereof, or a pharmaceutical composition as defined herein for use in therapy.

The present invention provides a compound, or a pharmaceutically acceptable salt thereof, or a pharmaceutical composition as defined herein for use in the treatment of a proliferative condition.

The present invention provides a compound, or a pharmaceutically acceptable salt thereof, or a pharmaceutical composition as defined herein for use in the treatment of cancer. In a particular embodiment, the cancer is human cancer. Suitably the cancer is lung cancer, renal cancer, solid organ cancer, pancreatic cancer or leukaemia suitably AML leukaemia or chronic myeloid leukaemia.

The present invention provides a compound, or a pharmaceutically acceptable salt thereof, or a pharmaceutical composition as defined herein for use in the treatment of leukaemia.

The present invention provides a compound, or a pharmaceutically acceptable salt thereof, or a pharmaceutical composition as defined herein for use in the treatment of AML leukaemia.

The present invention provides a compound, or a pharmaceutically acceptable salt thereof, or a pharmaceutical composition as defined herein for use in the inhibition of METTL3 activity.

The present invention provides a compound, or a pharmaceutically acceptable salt thereof, or a pharmaceutical composition as defined herein for use in the treatment of an autoimmune disease. Suitably the autoimmune disease is colitis, multiple sclerosis, rheumatoid arthritis, lupus, cirrhosis, or dermatitis.

The present invention provides a compound, or a pharmaceutically acceptable salt thereof, or a pharmaceutical composition as defined herein for use in the treatment of an neurological disease.

The present invention provides a compound, or a pharmaceutically acceptable salt thereof, or a pharmaceutical composition as defined herein for use in the treatment of an infectious disease.

The present invention provides a compound, or a pharmaceutically acceptable salt thereof, or a pharmaceutical composition as defined herein for use in the treatment of an inflammatory disease.

The present invention provides a compound, or a pharmaceutically acceptable salt thereof, as defined herein for use in the treatment of a disease or disorder in which METTL3 activity is implicated. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder or a depressive disorder.

The present invention provides a use of a compound, or a pharmaceutically acceptable salt thereof, as defined herein in the manufacture of a medicament for the treatment of a proliferative condition.

The present invention provides a use of a compound, or a pharmaceutically acceptable salt thereof, as defined herein in the manufacture of a medicament for the treatment of cancer. Suitably, the medicament is for use in the treatment of human cancers. Suitably the cancer is lung cancer, renal cancer, solid organ cancer, pancreatic cancer or leukaemia suitably AML leukaemia or chronic myeloid leukaemia.

The present invention provides a use of a compound, or a pharmaceutically acceptable salt thereof, as defined herein in the manufacture of a medicament for the treatment of leukaemia.

The present invention provides a use of a compound, or a pharmaceutically acceptable salt thereof, as defined herein in the manufacture of a medicament for the treatment of AML leukaemia.

The present invention provides a use of a compound, or a pharmaceutically acceptable salt thereof, as defined herein in the manufacture of a medicament for the treatment of an autoimmune disease. Suitably the autoimmune disease is colitis, multiple sclerosis, rheumatoid arthritis, lupus, cirrhosis, or dermatitis.

The present invention provides a use of a compound, or a pharmaceutically acceptable salt thereof, as defined herein in the manufacture of a medicament for the treatment of a neurological disease.

The present invention provides a use of a compound, or a pharmaceutically acceptable salt thereof, as defined herein in the manufacture of a medicament for the treatment of an inflammatory disease.

The present invention provides a use of a compound, or a pharmaceutically acceptable salt thereof, as defined herein in the manufacture of a medicament for the treatment of an infectious disease.

The present invention provides a use of a compound, or a pharmaceutically acceptable salt thereof, as defined herein in the manufacture of a medicament for the inhibition of METTL3 activity.

The present invention provides a use of a compound, or a pharmaceutically acceptable salt thereof, as defined herein in the manufacture of a medicament for the treatment of a disease or disorder in which METTL3 activity is implicated. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder or a depressive disorder.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain and skin.

The anti-proliferative effects of the compounds of the present invention have particular application in the treatment of human cancers (by virtue of their inhibition of METTL3 activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of antitumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan; (viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies; and (xi) Agents used to treat AML leukaemia, including for example, cytarabine, FLT3 inhibitors, BCL2 inhibitors or IDH1/2 inhibitors.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt thereof, and any one of the anti-tumour agents listed herein above.

In a further aspect of the invention there is provided a compound of the invention or a pharmaceutically acceptable salt thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt thereof, in combination with an anti-tumour agent (optionally selected from one listed herein above), in association with a pharmaceutically acceptable diluent or carrier.

In another embodiment, the invention relates to a therapeutic combination comprising a compound as defined herein and another agent used to treat AML leukeamia e.g., cytarabine, FLT3 inhibitors, BCL2 inhibitors or IDH1/2 inhibitors.

EXAMPLES

The following abbreviations have been used in the Examples:

HATU—[dimethylamino(triazolo[4,5-b]pyridin-3-yloxy)methylene]-dimethyl-ammonium; hexafluorophosphate DIPEA—N-ethyl-N-isopropyl-propan-2-amine DEAD—Diethylazodicarboxylate DMF—Dimethylformamide RT—Retention Time Phase sep cartridge—Telos phase separator 6 mL Example 1: Characterisation Methodology The following HPLC methodology was used:

Method 1:

| | |
|---|---|
| Column | Phenomenex Gemini -NX C18 Part No. 00D-4453-B0 2.0 × 100 mm, 3 μm column |
| Column Temp | 40° C. |
| Mobile Phase | A, 2 mM amm. bicarbonate, buffered to pH 10 B, Acetonitrile |

| | Time (mins) | % organic |
|---|---|---|
| Gradient | 0.00 | 5 |
| | 5.50 | 100 |
| | 5.90 | 100 |
| | 5.92 | 5 |
| | 7.00 | 5 |

| | |
|---|---|
| Flow rate | 0.5 ml/min |
| Injection Vol | 3 μl |
| | Detection |
| Signal | UV 215 |
| PDA Spectrum | Range: 210-420 nm step: 1 nm |

Method 2:

| | |
|---|---|
| Column | Phenomenex Gemini -NX C18 Part No. 00D-4453-B0 2.0 × 100 mm, 3 μm column |
| Column Temp | 40° C. |
| Mobile Phase | A, 2 mM amm. bicarbonate, buffered to pH 10 B, Acetonitrile |

| | Time (mins) | % organic |
|---|---|---|
| Gradient | 0.00 | 5 |
| | 5.50 | 100 |
| | 5.90 | 100 |
| | 5.92 | 5 |
| | 7.00 | 5 |

-continued

| | |
|---|---|
| Flow rate | 0.6 ml/min |
| Injection Vol | 3 μl |
| Detection | |
| Signal | UV 215 |
| PDA Spectrum | Range: 210-420 nm step: 1 nm |
| MSD Signal settings | Scan Pos 150-850 or 130-850 |

Method 3:

| | |
|---|---|
| Column | Phenomenex Kinetix-XB C18 Part No. 00D-4498-AN 2.1 × 100 mm, 1.7 μm |
| Column Temp | 40° C. |
| Mobile Phase | A, Water + 0.1% Formic acid B, Acetonitrile + 0.1% Formic acid |

| | Time (mins) | % organic |
|---|---|---|
| Gradient | 0.00 | 5 |
| | 5.30 | 100 |
| | 5.80 | 100 |
| | 5.82 | 5 |
| | 7.00 | 5 |

| | |
|---|---|
| Flow rate | 0.6 ml/min |
| Injection Vol | 1 μl |
| Detection | |
| Signal | UV 215 |
| PDA Spectrum | Range: 200-400 nm step: 1 nm |
| MSD Signal settings | Scan Pos: 150-850 |

Method 4:

| | |
|---|---|
| Column | Waters UPLC ® CSH ™ C18 Part No. 186005297 2.1 × 100 mm, 1.7 μm |
| Column Temp | 40° C. |
| Mobile Phase | A, 2 mM amm. bicarbonate, buffered to pH 10 B, Acetonitrile |

| | Time (mins) | % organic |
|---|---|---|
| Gradient | 0.00 | 5 |
| | 5.30 | 100 |
| | 5.80 | 100 |
| | 5.82 | 5 |
| | 7.00 | 5 |

| | |
|---|---|
| Flow rate | 0.6 ml/min |
| Injection Vol | 2 μl |
| Detection | |
| Signal | UV 215 |
| PDA Spectrum | Range: 200-400 nm step: 1 nm |
| MSD Signal settings | Scan Pos: 150-850 |

The following LCMS methodologies were used:

LCMS method A refers to low pH analysis using a mobile phase consisting of 0.1% formic acid in a gradient of 5-100% MeCN in water over 1.2 min at a flow rate of 1.2 mL/min. The stationary phase consisted of a Kinetex Core-Shell C18, 2.1 mm×50 mm, 5 μm. The experiment was run at 40° C.

LCMS Method B refers to high pH analysis using a mobile phase consisting of 2 mM ammonium bicarbonate, buffered to pH10 in a gradient of 5-100% MeCN in water over 2.1 min at a flow rate of 1.0 mL/min. The stationary phase consisted of a Phenomenex Gemini-NX C18, 2.0×50 mm, 3 μm. The experiment was run at 40° C.

LCMS Method C refers to high pH analysis using a mobile phase consisting of 2 mM ammonium bicarbonate, buffered to pH10 in a gradient of 5-100% MeCN in water over 5.8 min at a flow rate of 0.6 mL/min. The stationary phase consisted of a Waters UPLCO BEH™ C18, 2.1×100 mm, 1.7 μm. The experiment was run at 40° C.

LCMS Method D refers to high pH analysis using a mobile phase consisting of 2 mM ammonium bicarbonate, buffered to pH10 in a gradient of 5-100% MeCN in water over 5.9 min at a flow rate of 0.6 mL/min. The stationary phase consisted of a Phenomenex Gemini-NX C18, 2.0×100 mm, 3 μm. The experiment was run at 40° C.

LCMS method E refers to low pH analysis using a mobile phase consisting of 0.1% formic acid in a gradient of 5-100% MeCN in water over 5.3 min at a flow rate of 0.6 mL/min. The stationary phase consisted of a Phenomenex Kinetix-XB C18, 2.1 mm×100 mm, 1.7 μm. The experiment was run at 40° C.

LCMS method F refers to high pH analysis using a mobile phase consisting of 2 mM ammonium bicarbonate, buffered to pH10 in a gradient of 5-100% MeCN in water over 0.75 min at a flow rate of 1.0 mL/min. The stationary phase consisted of a Waters UPLC® BEH™ C18, 2.1×100 mm, 1.7 μm. The experiment was run at 40° C.

Method G refers to low pH analysis using a mobile phase consisting of 0.1% Formic acid in water (pH=2.70) in a gradient of 3-100% of 0.1% formic acid in water: acetonitrile (10:90) over 3.00 min at a flow rate of 0.8 mL/min. The stationary phase consisted of C18, 50*2.1 mm, 1.6 μm column. The experiment was run at 35° C.

Method H refers to a high pH analysis using a mobile phase consisting of 5 mM ammonium bicarbonate, (pH 7.35) in a gradient of MeCN in water over 3.0 min at a flow rate of 0.5 mL/min. The stationary phase consisted of C18, 50*2.1 mm, 2.5 μm. The experiment was run at 35° C.

Method I refers to a high pH analysis using a mobile phase consisting of 5 mM ammonium bicarbonate, (pH 7.35) in a gradient of MeCN in water over 3.0 min at a flow rate of 0.5 mL/min. The stationary phase consisted of C18, 50*2.1 mm, 2.5 μm. The experiment was run at 35° C.

The following preparative HPLC methodologies were used:

Preparative Method A refers to low pH purification using a mobile phase consisting of 0.1% Formic acid in a gradient of 10-95% MeCN in water over 14.4 min at a flow rate of 40 mL/min. The stationary phase consisted of a Waters Sunfire C18, 30×100 mm, 10 μm.

Preparative Method B refers to high pH purification using a mobile phase consisting of 0.2% ammonium hydroxide in a gradient of 30-95% MeCN in water over 10 min at a flow rate of 40 mL/min. The stationary phase consisted of a Waters XBridge™ C18 OBD™, 30×100 mm, 10 μm.

Example 2: Chemical Synthesis and Characterisation

Synthesis of Intermediate 1: 6-bromo-1-tetrahydropyran-2-yl-indazole-4-carboxylic acid

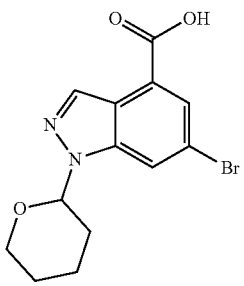 [SMILES: O=C(O)c1cc(Br)cc2c1cnn2C1CCCCO1]

Step 1: methyl 6-bromo-1-tetrahydropyran-2-yl-indazole-4-carboxylate

Methyl 6-bromo-1H-indazole-4-carboxylate (1.0 g, 3.92 mmol) and TsOH·H$_2$O (75 mg, 0.39 mmol) were combined in DCM (40 ml) and 3,4-dihydro-2H-pyran (1.07 ml, 11.8 mmol) was added. The mixture was stirred at room temperature for 20 minutes during which time the mixture darkened. The mixture was quenched with aqueous sodium hydrogen carbonate (sat, 100 ml) and the mixture was stirred vigorously for 5 minutes. The phases were separated, the aqueous phase was extracted with DCM (3×80 ml) and the combined organic extracts were dried over sodium sulfate and evaporated under vacuum. The residue was purified by chromatography on silica gel (Biotage 50 g eluting with 0-50% ethyl acetate/heptane) to afford the title compound (1.26 g, 92%) as a white solid.

LCMS Method A (electrospray): m/z=338.9/340.9 (M+H)$^+$, RT=1.34 min.

Step 2: 6-bromo-1-tetrahydropyran-2-yl-indazole-4-carboxylic acid A solution of methyl 6-bromo-1-tetrahydropyran-2-yl-indazole-4-carboxylate (600 mg, 1.77 mol) in THF (10 ml) and Water (10 ml) was treated with lithium hydroxide (132 mg, 5.31 mmol) and the mixture was heated at 60° C. for 90 minutes. The reaction mixture was cooled to room temperature and concentrated under vacuum. The residue was diluted with water (10 ml) and acidified to ~pH1 using 1M HCl(aq). The mixture was then extracted with chloroform/isopropanol (3:1, 4×30 ml) and the combined organic extracts were dried over sodium sulfate and evaporated under vacuum to afford the title compound (566 mg, 97%) as a white solid.

LCMS Method A (electrospray): m/z=324.9/326.9 (M+H)$^+$, RT=1.14 min.

Synthesis of Intermediate 2: 1-tetrahydropyran-2-yl-6-(2-tetrahydropyran-2-yl)pyrazol-3-yl)indazole-4-carboxylic acid

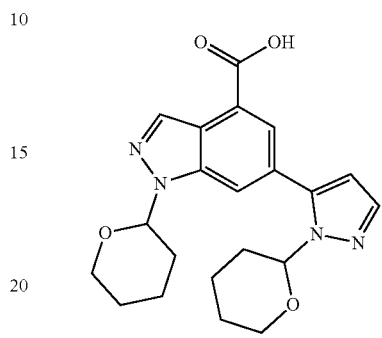

Step 1: methyl 1-tetrahydropyran-2-yl-6-(2-tetrahydropyran-2-ylpyrazol-3-yl)indazole-4-carboxylate Methyl 6-bromo-1-tetrahydropyran-2-yl-indazole-4-carboxylate Intermediate 1 Step 1 (300 mg, 0.88 mmol), 1-(tetrahydro-2H-pyran-2-yl)-5-(4,4,5,5-tetramethyl-1,3,2-dioxaborolan-2-yl)-1H-pyrazole (295 mg, 1.06 mmol) and aqueous K$_2$CO$_3$ (1.2M, 2.21 ml, 2.65 mmol) were combined in 1,4-Dioxane (6 ml) and the mixture was sparged with nitrogen for 5 mins. 1,1'-bis(di-tert-butylphosphanyl)ferrocene-dichloropalladium [Pd-118](58 mg, 0.09 mmol) was added and the mixture sparged for a further 5 mins. The vessel was sealed and the mixture heated at 100° C. for 2 hours. The reaction mixture was cooled to RT, diluted with aqueous Sodium hydrogen carbonate (sat, 30 ml) and extracted with ethyl acetate (2×50 ml). The combined organic extracts were washed with brine (4×30 ml), dried over sodium sulfate and evaporated under vacuum. The residue was purified by chromatography on silica gel (Biotage 25 g, eluting with 0-50% ethyl acetate/heptane) to afford the title compound (291 mg, 79%) as a yellow foam.

LCMS Method A (electrospray): m/z=433.1 (M+H)$^+$, RT=1.29 min.

Step 2: The title compound was prepared using the procedure described in Intermediate 1 Step 2 giving (175 mg, 62%) as an off-white solid.

LCMS Method A (electrospray): m/z=395.15 (M+H)$^+$, RT=1.11 min.

Synthesis of Intermediate 3: 6-ethynyl-1-(oxan-2-yl)-1H-indazole-4-carboxylic acid

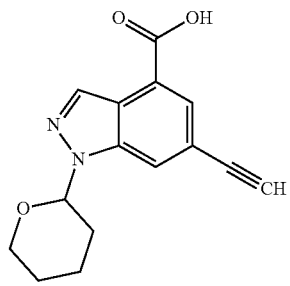 [SMILES: C#Cc1cc(C(=O)O)c2cnn(C3CCCCO3)c2c1]

Step 1: Methyl 1-tetrahydropyran-2-yl-6-(2-trimethylsilylethynyl)indazole-4-carboxylate

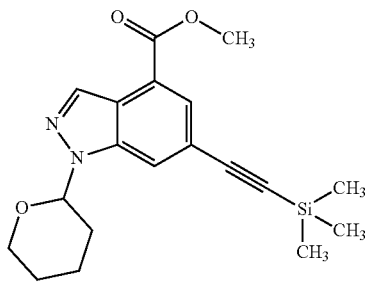 [SMILES: COC(=O)c1cc(C#C[Si](C)(C)C)cc2c1cnn2C1CCCCO1]

Methyl 6-bromo-1-tetrahydropyran-2-yl-indazole-4-carboxylate (500 mg, 1.47 mmol), PdCl$_2$(PPh$_3$)$_2$ (104 mg, 0.15 mmol), CuI (28 mg, 0.15 mmol) and triethylamine (1.03 ml, 7.37 mmol) were combined in DMF (3 ml) and the mixture sparged with nitrogen for 5 mins. Ethynyl(trimethyl)silane (1.0 ml, 7.37 mmol) was added, the mixture sparged briefly and the vessel sealed. The mixture was heated at 100° C. for 2.5 h. The reaction mixture was cooled to RT, diluted with ethyl acetate (50 ml) and washed with sat. aqueous Sodium hydrogen carbonate (50 ml) and brine (5×50 ml). The organic layer was dried over sodium sulfate and evaporated under vacuum. The residue was purified by Chromatography on silica gel [Biotage 50 g, eluting with 0-30% ethyl acetate/heptane] to afford the title compound (553 mg (99% yield) as a pale brown oil.

LCMS Method A (electrospray): m/z=357.1 (M+H)$^+$, RT=1.54 min.

Step 2: The title compound was prepared from methyl 1-tetrahydropyran-2-yl-6-(2-trimethylsilylethynyl)indazole-4-carboxylate using the method described in Intermediate 1 Step 2 giving (342 mg, 75%) as a pale brown solid.

LCMS Method A (electrospray): m/z=270.95 (M+H)$^+$, RT=1.10 min.

Synthesis of Intermediate 4: 4-oxo-4H-pyrido[1,2-a]pyrimidine-2-carboxylic acid hydrochloride

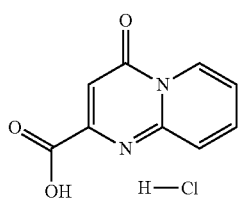

A suspension of methyl 4-oxopyrido[1,2-a]pyrimidine-2-carboxylate [Tetrahedron (2014), 70(17), 2761-2765](5 g, 24.5 mmol) in THF (150 ml) was treated with potassium trimethylsilanolate (6.28 g, 49.0 mmol) and the mixture was heated at reflux for an hour before HCl Solution (4M HCl in dioxane 15 ml) was added and the heating was continued for 15 mins before cooling to room temperature. The solid was collected by filtration, washed with diethyl ether and dried under suction to afford the title compound (7.98 g, 86%) as a pale yellow solid which contained ~40% residual KCl.

LCMS Method B (electrospray): m/z=191.2 (M+H)$^+$, RT=0.23 min.

Synthesis of Intermediate 5: 8-methoxy-4-oxo-4H-pyrido[1,2-a]pyrimidine-2-carboxylic acid

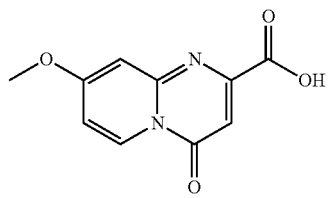 [SMILES: COc1ccn2c(=O)cc(C(=O)O)nc2c1]

Step 1: methyl 8-methoxy-4-oxo-4H-pyrido[1,2-a]pyrimidine-2-carboxylate

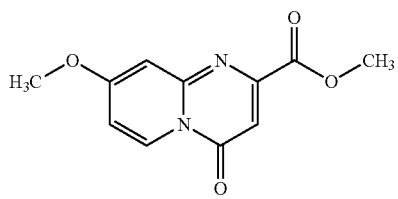

A suspension of 4-methoxypyridin-2-amine (2 g, 16.1 mmol) in Water (150 ml) was stirred vigorously whilst dimethyl but-2-ynedioate (2.38 ml, 19.3 mmol) was added slowly and the mixture was stirred at room temperature for 3 hours. The reaction mixture was diluted with DCM (100 ml) and allowed to stand at room temperature overnight. The phases were separated and the aqueous phase was extracted with DCM (2×80 ml), the combined organic extracts were dried over sodium sulfate and evaporated under vacuum to a residue which was purified by chromatography on silica gel [Biotage 50 g eluting with 50-100% ethyl acetate/heptane] to afford a crude material which was triturated with ethyl acetate/heptane. The solids were collected by filtration and washed with heptane to afford the title compound (850 mg (23%) as a beige solid.

LCMS Method B (electrospray): m/z=235.2 (M+H)$^+$, RT=1.20 min.

Step 2: The title compound was prepared from methyl 8-methoxy-4-oxo-4H-pyrido[1,2-a]pyrimidine-2-carboxylate using the method described in Intermediate 1 Step 2 giving (535 mg, 67%) as a white solid.

LCMS Method B (electrospray): m/z=221.2 (M+H)$^+$, RT=0.31 min.

Synthesis of Intermediate 6: 7-chloro-4-oxo-4H-pyrido[1,2-a]pyrimidine-2-carboxylic acid

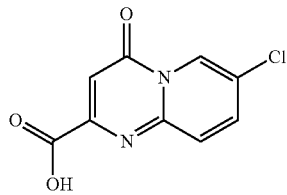 [SMILES: O=C(O)c1cc(=O)n2cc(Cl)ccc2n1]

The title compound was prepared from methyl 7-chloro-4-oxo-pyrido[1,2-a]pyrimidine-2-carboxylate [Tetrahedron (2014), 70(17), 2761-2765] using the method described in Intermediate 1 Step 2 giving (195 mg, 51%) as a pale yellow solid.

LCMS Method B (electrospray): m/z=225.1 (M+H)+, RT=0.31 min.

Synthesis of Intermediate 7: {7-bromoimidazo[1,2-a]pyridin-2-yl}methanamine

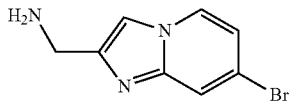

Step 1: 2-[(7-bromoimidazo[1,2-a]pyridin-2-yl)methyl]isoindoline-1,3-dione

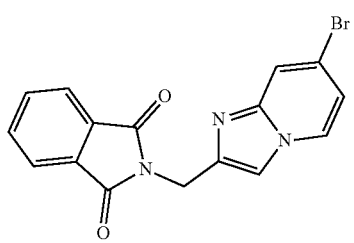 [SMILES: O=C1c2ccccc2C(=O)N1Cc1cn2ccc(Br)cc2n1]

A suspension of 4-bromopyridin-2-amine (2 g, 11.6 mmol) and 2-(3-bromo-2-oxo-propyl) isoindoline-1,3-dione (3.26 g, 11.6 mmol) (U.S. Pat. No. 7,105,508, 2006) in Ethanol (40 ml) was heated at reflux for 3 hours during which time the materials slow dissolved followed by a slow precipitation. The mixture was cooled to room temperature and the solids were collected by filtration, washed with MeOH followed by diethyl ether and dried under vacuum to afford the title compound (3.09 g, 51%) as a white solid.

LCMS Method B (electrospray): m/z=356.1/358.1 (M+H)+, RT=1.49 min.

Step 2: {7-bromoimidazo[1,2-a]pyridin-2-yl}methanamine

2-[(7-bromoimidazo[1,2-a]pyridin-2-yl)methyl]isoindoline-1,3-dione (3.09 g, 5.89 mmol) and hydrazine hydrate (2.9 ml, 59.0 mmol) were combined in Ethanol (40 ml) and the mixture was stirred at room temperature for 2 hours. The solids were collected by filtration and the filtrate was left standing overnight. Further solids were collected by filtration. The filtrates were evaporated directly onto silica gel (kp-NH) and the solids were deposited onto a short plug of kp-NH silica and the system eluted with 10% MeOH/DCM. The eluent was evaporated to afford the title compound (1.09 g 72% yield) as a pale yellow solid LCMS Method B: LC-MS (electrospray): m/z=226.1/228.1 (M+H)+, RT=1.25 min.

Synthesis of Intermediate 8: {6-chloroimidazo[1,2-a]pyridin-2-yl}methanamine

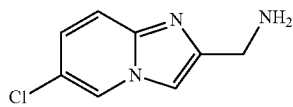 [SMILES: NCc1cn2cc(Cl)ccc2n1]

Step 1: 6-chloro-2-(chloromethyl)imidazo[1,2-a]pyridine

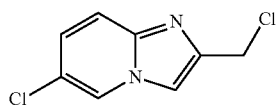 [SMILES: ClCc1cn2cc(Cl)ccc2n1]

A suspension of 5-chloropyridin-2-amine (1.0 g, 7.78 mmol) and 1,3-dichloropropan-2-one (0.71 mL, 7.8 mmol) in ethanol (7.4 mL) was heated to 80° C. for 3 hours. The mixture was cooled to room temperature and evaporated to dryness under vacuum. The residue was diluted with Sodium hydrogen carbonate (sat, 20 mL) and extracted with DCM (3×15 mL). The combined organics were evaporated under vacuum and the residue was purified by chromatography on silica gel (Biotage; 50 g KPNH eluting with 0-100% ethyl acetate/heptane) to afford the title compound (435 mg, 28% Yield) as an orange solid.

Method A: LC-MS (electrospray): m/z=200.85 (M+H)+, RT=0.64 min.

Step 2: (6-chloroimidazo[1,2-a]pyridin-2-yl)methanamine

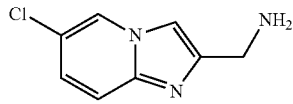 [SMILES: NCc1cn2cc(Cl)ccc2n1]

A solution of 6-chloro-2-(chloromethyl)imidazo[1,2-a]pyridine (750 mg, 3.73 mmol) in ammonia solution (7M in methanol, 5.3 mL, 37.3 mmol) was stirred at room temperature for 16 hours and at 60° C. for 3 hours. The mixture allowed to cool to room temperature and left standing for two days before it was evaporated under vacuum. The residue was purified by chromatography on silica gel [Biotage; KP—NH 28 g eluting with 0-10% MeOH in DCM] to give the title compound (83 mg, 9.2% Yield) as a yellow sticky solid.

Method A: LC-MS (electrospray): m/z=181.9 (M+H)+, RT=0.23 min.

Synthesis of Intermediates 9-13

The intermediates listed in table 1 were prepared in the same way as Intermediate 8 using the appropriate aminopyridine.

TABLE 1

| Intermediate | Name | Structure | LCMS method | LCMS Retention time | Mass ion |
|---|---|---|---|---|---|
| 9 | {7methylimidazo[1,2-a]pyridin-2-yl}methanamine | 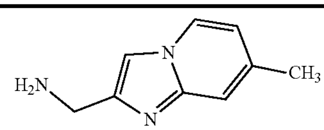 | B | 1.19 | 162.2 |
| 10 | {7-fluoroimidazo[1,2-a]pyridin-2-yl}methanamine | 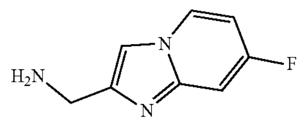 [SMILES: NCc1cn2ccc(F)cc2n1] | B | 1.09 | 166.2 |
| 11 | {6-fluoroimidazo[1,2-a]pyridin-2-yl}methanamine | 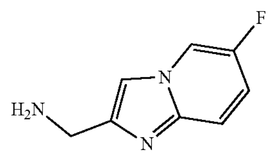 [SMILES: NCc1cn2cc(F)ccc2n1] | B | 1.10 | 166.2 |
| 12 | {7-methoxyimidazo[1,2-a]pyridin-2-yl}methanamine | 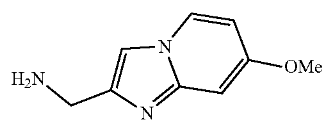 [SMILES: COc1ccn2cc(CN)nc2c1] | B | 1.26 | 178.3 |
| 13 | {6-methoxyimidazo[1,2-a]pyridin-2-yl}methanamine | 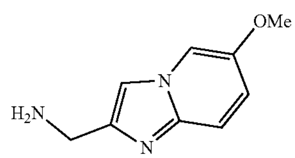 [SMILES: COc1ccc2nc(CN)cn2c1] | B | 1.25 | 178.2 |

Synthesis of Intermediate 14: N-[(6-bromoimidazo[1,2-a]pyridin-2-yl)methyl]-1-tetrahydropyran-2-yl-indazole-4-carboxamide

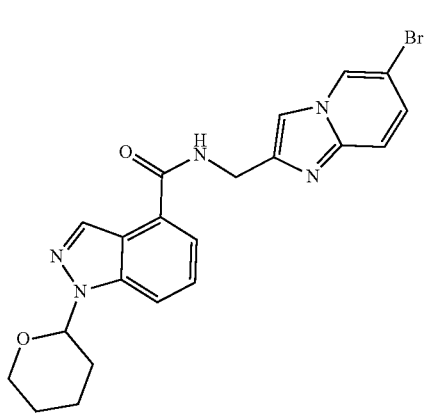 [SMILES: O=C(NCc1cn2cc(Br)ccc2n1)c1cccc2c1cnn2C1CCCCO1]

Prepared from 1-tetrahydropyran-2-ylindazole-4-carboxylic acid and (6-bromoimidazo[1,2-a]pyridin-2-yl)methanamine using the procedure described in Compound 1 and purified by chromatography on silica gel [Biotage 50 g eluting with 0-10% MeOH/DCM] to give the title compound (950 mg, 83%) as an orange solid.

LCMS Method B (electrospray): m/z=454.1456. (M+H)$^+$, RT=1.49 min.

Synthesis of Intermediate 15: 2-amino-2-(6-methyl-imidazo[1,2-a]pyridin-2-yl)ethanol

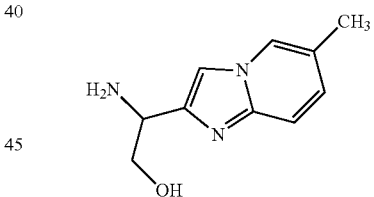

Step 1: 2-methyl-N-[(1Z)-{6-methylimidazo[1,2-a]pyridin-2-yl}methylidene]propane-2-sulfinamide

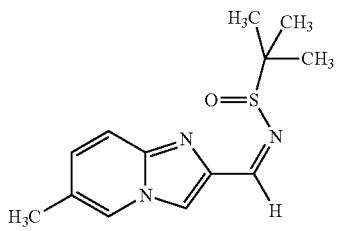 [SMILES: Cc1ccc2nc(/C=N\S(=O)C(C)(C)C)cn2c1]

A solution of 6-methylimidazo[1,2-a]pyridine-2-carbaldehyde (550 mg, 3.43 mmol) (Eur. J. Org. Chem. 2015 (18), 3957) and 2-methylpropane-2-sulfinamide (378 mg, 3.12 mmol) in DCM (20 mL), under a nitrogen atmosphere, was treated with CuSO₄·5H₂O (1.0 g, 6.24 mmol) and the resultant blue solution was stirred at room temperature for 85 hours. The dark green suspension was filtered through Celite washing with DCM and the filtrate was concentrated under vacuum and purified by chromatography on silica gel [Biotage 50 g eluting with 20-100% ethyl acetate/heptane] to give the title compound (553 mg, 67%) as an off white solid.

LCMS Method B (electrospray): m/z=264.2 (M+H)⁺, RT=1.37 min.

Step 2: N-[2-hydroxy-1-(6-methylimidazo[1,2-a]pyridin-2-yl)ethyl]-2-methyl-propane-2-sulfinamide

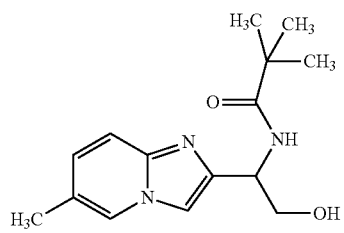 [SMILES: Cc1ccc2nc(C(CO)NC(=O)C(C)(C)C)cn2c1]

2-methyl-N-[(1Z)-{6-methylimidazo[1,2-a]pyridin-2-yl}methylidene]propane-2-sulfinamide (430 mg, 1.63 mmol), and potassium; 2-methylpropan-2-olate (550 mg, 4.90 mmol) were combined in a microwave vial, toluene (anhydrous, 2.9 mL) was added and the mixture was degassed via a stream of N₂ and the resultant suspension was heated at 50° C. for 16 hours. The mixture was cooled to room temperature, degassed via a stream of N₂, and heated at 100° C. for 3 hours. The purple mixture was quenched by the addition of NH₄Cl (sat) and extracted with DCM (phase sep cartridge) and the organic phase was evaporated under vacuum to a purple gum 332 mg. The gum was dissolved in THF/water (6:1) 3.5 mL and treated with NaBO₃·4H₂O (440 mg, 2.85 mml) and the mixture was stirred at room temperature for an hour. The mixture was diluted with water and extracted with DCM. The organics were dried (magnesium sulfate) and evaporated under vacuum to a residue which was purified by chromatography on silica gel [Biotage KPNH 11 g, eluting with 0-100% ethyl acetate/heptane] to give the title compound (mixture of diastereoisomers, 70 mg, 14%) as a dark gum.

LCMS Method B (electrospray): m/z=295.9 (M+H)⁺, RT=0.70/0.75 min.

Step 3: The title compound was prepared from N-[2-hydroxy-1-(6-methylimidazo[1,2-a]pyridin-2-yl)ethyl]-2-methyl-propane-2-sulfinamide using the procedure described in Compound 1 and purified by ion exchange [SCX-2] giving (50 mg 45%) as a dark gum.

LCMS Method B (electrospray): m/z=192.3 (M+H)⁺, RT=1.09 min.

Synthesis of Intermediate 16: N-[(6-cyanoimidazo[1,2-a]pyridin-2-yl)methyl]-1-tetrahydropyran-2-yl-indazole-4-carboxamide

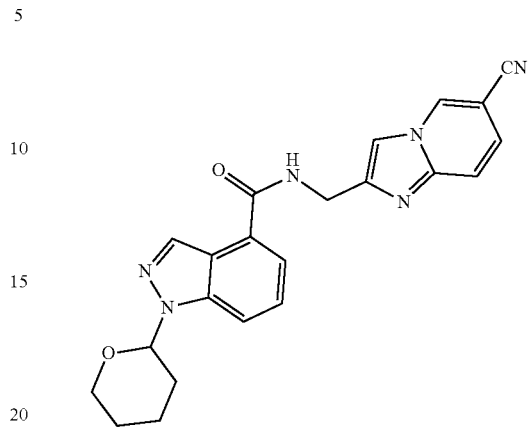

Prepared from 1-tetrahydropyran-2-ylindazole-4-carboxylic acid and (6-cyanoimidazo[1,2-a]pyridin-2-yl)methanamine (commercial) using the procedure described in Compound 1 and purified by trituration with cold ethyl acetate to give the title compound (3.8 g, 98%) as a light brown solid.

LCMS Method A (electrospray): m/z=401.1 (M+H)⁺, RT=0.92 min.

Synthesis of Intermediate 17: 3-{imidazo[1,2-a]pyridin-2-yl}-2,5-dihydro-1H-pyrrole dihydrochloride

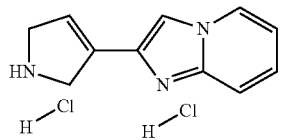

Step 1: tert-butyl 3-imidazo[1,2-a]pyridin-2-yl-2,5-dihydropyrrole-1-carboxylate

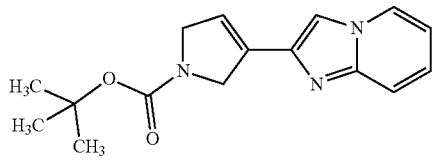 [SMILES: CC(C)(C)OC(=O)N1CC=C(c2cn3ccccc3n2)C1]

A mixture of 2-bromoimidazo[1,2-a]pyridine (520 mg, 2.64 mmol), tert-butyl 3-(4,4,5,5-tetramethyl-1,3,2-dioxaborolan-2-yl)-2,5-dihydropyrrole-1-carboxylate (935 mg, 3.17 mmol) and K₂CO₃ (1.2M aqueous solution, 6.6 ml, 7.92 mmol) were combined in 1,4-Dioxane (12 ml) and the mixture sparged with nitrogen for 5 mins. Pd-118 (86 mg, 0.13 mmol) was added and the mixture sparged for a further 5 mins. The vessel was sealed and the mixture heated at 100° C. for 2.5 h. The reaction mixture was cooled to room temperature diluted with ethyl acetate (100 ml), washed with aqueous sodium hydrogen carbonate (sat, 80 ml) and brine (3×80 ml). The organic layer was dried over sodium sulfate and evaporated under vacuum to a residue which was purified by chromatography on silica gel (Biotage 25 g, eluting with 50-100% ethyl acetate/heptane) to afford the title compound (669 mg, 89%) as a pale yellow solid Method A: LC-MS (electrospray): m/z=286.5 (M+H)⁺, RT=0.90 min.

Step 2: The title compound was prepared from tert-butyl 3-imidazo[1,2-a]pyridin-2-yl-2,5-dihydropyrrole-1-carboxylate using the procedure described in Compound 1 and purified by trituration with ethyl acetate/heptane giving (606 mg, 100%) as a white solid.

LCMS Method A (electrospray): m/z=186.0 (M+H)⁺, RT=0.14 min.

Synthesis of Intermediate 18: N-({6-formylimidazo [1,2-a]pyridin-2-yl}methyl)-1-(oxan-2-yl)-1H-indazole-4-carboxamide

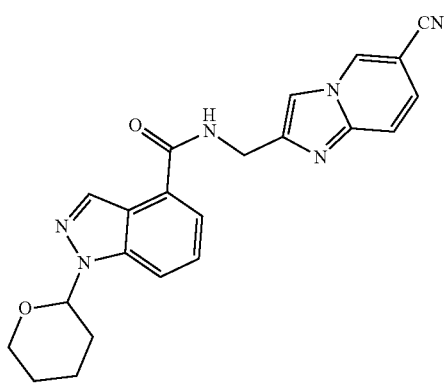

Isopropylmagnesium chloride lithium chloride complex (1.3M in THF, 4.1 mL, 5.35 mmol) was added dropwise to a solution of N-[(6-bromoimidazo[1,2-a]pyridin-2-yl) methyl]-1-tetrahydropyran-2-yl-indazole-4-carboxamide (Intermediate 14) (750 mg, 1.34 mmol) in THF (10 mL) at −78° C. Once the addition was complete the mixture was stirred at −78° C. for 10 minutes and allowed to warm to 5° C. over 3 hours. The mixture was then allowed to warm to room temperature and stirred for 30 minutes before it was cooled to −70° C. and treated with DMF (414 uL, 5.35 mmol) and allowed to slowly warm to room temperature overnight. The mixture was quenched by the addition of HCl (2M, 15 mL), basified with aqueous NaOH (2M) and extracted with ethyl acetate (2×15 mL). The combined organics were washed with brine, dried (magnesium sulfate) evaporated to dryness under reduced pressure to afford the title compound (460 mg, 42%, 1:1 mixture with N-({imidazo[1,2-a]pyridin-2-yl}methyl)-1-(oxan-2-yl)-1H-indazole-4-carboxamide) as a brown gum which was used without further purification.

LCMS Method A (electrospray): m/z=404.5 (M+H)⁺, RT=0.90 min.

Synthesis of Intermediate 19: 2-{6-methylimidazo [1,2-a]pyridin-2-yl}acetic acid

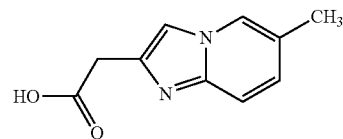

Step 1: ethyl 2-(6-methylimidazo[1,2-a]pyridin-2-yl)acetate

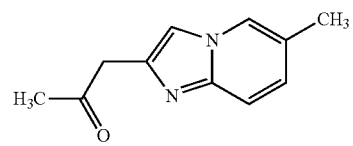

5-methylpyridin-2-amine (2 g, 18.5 mmol) and ethyl 4-chloro-3-oxo-butanoate (2.50 ml, 18.5 mmol) were combined in Ethanol (20 ml) and the mixture was heated at reflux for 3 hours and then stirred at room temperature for 16 hours. The reaction mixture was concentrated under vacuum, the residue was basified with aqueous sodium hydrogen carbonate (sat, 300 ml) and extracted with DCM (4×150 ml). The extracts were dried over sodium sulfate and evaporated under vacuum. The residue was purified by chromatography on silica gel (biotage 100 g, eluting with 0-100% ethyl acetate/heptane) to afford a dark brown oil which was further purified by chromatography on silica gel (biotage 55 g kp-NH, eluting with 0-100% ethyl acetate/ heptane) to afford the title compound 3.3 g, 40% at 50% purity) of as a pale brown oil.

LCMS Method B (electrospray): m/z=219.3 (M+H)⁺, RT=1.34 min.

Step 2: 2-{6-methylimidazo[1,2-a]pyridin-2-yl}acetic acid

The title compound was prepared from ethyl 2-(6-methylimidazo[1,2-a]pyridin-2-yl)acetate using the method described in Intermediate 1 Step 2 to give the title compound (1.35 g, 95% as a pale yellow solid.

LCMS Method A (electrospray): m/z=190.95 (M+H)⁺, RT=0.18 min.

Synthesis of Compound 1: N-({6-methylimidazo[1, 2-a]pyridin-2-yl}methyl)-1H-indazole-4-carboxamide

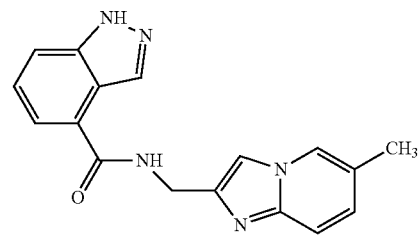 [SMILES: Cc1ccc2nc(CNC(=O)c3cccc4[nH]ncc34)cn2c1]

A solution of 1-tetrahydropyran-2-ylindazole-4-carboxylic acid (75 mg, 0.3 mmol) and DIPEA (271 uL, 1.52 mmol) in THF (10 mL) was treated with HATU (150 mg, 0.4 mmol) and the mixture was stirred at room temperature for 20 minutes before {6-methylimidazo[1,2-a]pyridin-2-yl}methanamine dihydrochloride (85 mg, 0.37 mmol) (commercially available) was added and the solution was stirred at room temperature for 3 hours. The brown solution was diluted with water and extracted with DCM (via a phase sep cartridge) and the extracts were evaporated under vacuum to a brown gum. The gum was dissolved in Methanol (5 mL), treated with 4 M 1,4-dioxane hydrochloride (0.76 mL, 3.05 mmol) and stirred at room temperature for 16 hours. The solution was evaporated under vacuum and the residue was purified by chromatography on silica gel [Biotage 25 g eluting with 0-100% ethyl acetate/Heptane] to give the title compound (72 mg, 93%) as a beige solid.

LCMS Method C (electrospray): m/z=306.1 (M+H)$^+$, RT=1.99 min.

Synthesis of Compounds 2-31

The compounds in Table 2 were prepared in a similar fashion to Compound 1 using the appropriate carboxylic acid and aminomethyl imidazopyridine intermediate, or commercially available materials, including deprotection where necessary.

TABLE 2

| Cpd No | Name | Structure | LCMS method | LCMS Retention time/mass ion | Intermediates |
|---|---|---|---|---|---|
| 2 | N-({7-bromoimidazo[1,2-a]pyridin-2-yl}methyl)-1H-indazole-4-carboxamide | 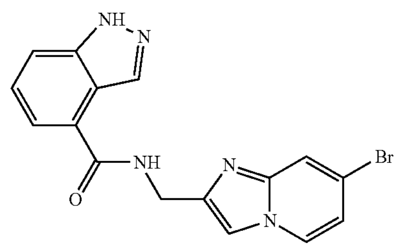 [SMILES: O=C(NCc1cn2ccc(Br)cc2n1)c1cccc2[nH]ncc12] | C | 3.35/370.1/372.1 | 7 |
| 3 | N-({6-bromoimidazo[1,2-a]pyridin-2-yl}methyl)-1H-indazole-4-carboxamide | 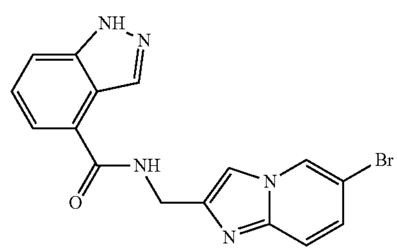 [SMILES: O=C(NCc1cn2cc(Br)ccc2n1)c1cccc2[nH]ncc12] | C | 3.38/370.1/372.1 | Commercially available |
| 4 | N-({6-chloroimidazo[1,2-a]pyridin-2-yl}methyl)-1H-indazole-4-carboxamide | 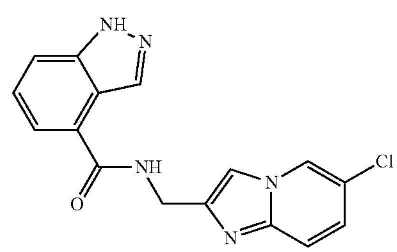 [SMILES: O=C(NCc1cn2cc(Cl)ccc2n1)c1cccc2[nH]ncc12] | D | 3.09/326.3 | 8 |
| 5 | N-({7-fluoroimidazo[1,2-a]pyridin-2-yl}methyl)-1H-indazole-4-carboxamide | 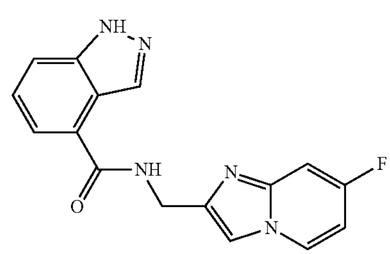 [SMILES: O=C(NCc1cn2ccc(F)cc2n1)c1cccc2[nH]ncc12] | D | 2.76/310.2 | 10 |

TABLE 2-continued

| Cpd No | Name | Structure | LCMS method | LCMS Retention time/mass ion | Inter mediates |
|---|---|---|---|---|---|
| 6 | N-({6-fluoroimidazo[1,2-a]pyridin-2-yl}methyl)-1H-indazole-4-carboxamide | 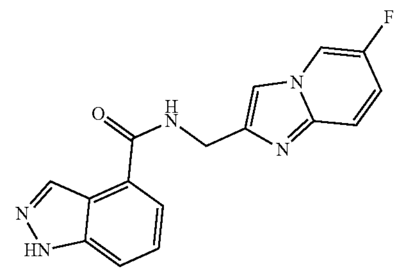 [SMILES: O=C(NCc1cn2cc(F)ccc2n1)c1cccc2[nH]ncc12] | D | 2.82/310.2 | 11 |
| 7 | N-({7-methoxyimidazo[1,2-a]pyridin-2-yl}methyl)-1H-indazole-4-carboxamide | 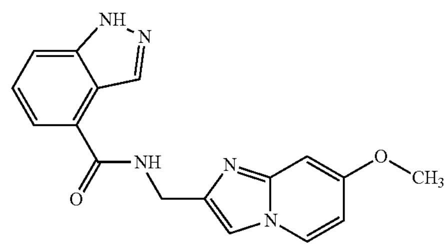 [SMILES: COc1ccn2cc(CNC(=O)c3cccc4[nH]ncc34)nc2c1] | D | 2.80/322.3 | 12 |
| 8 | N-({6-methylimidazo[1,2-a]pyridin-2-yl}methyl)-6-(1H-pyrazol-5-yl)-1H-indazole-4-carboxamide | 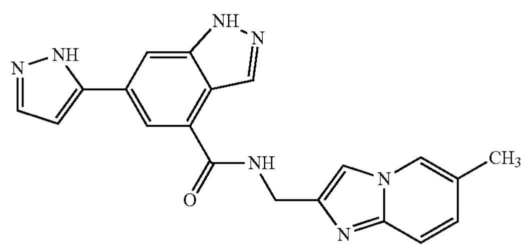 [SMILES: Cc1ccc2nc(CNC(=O)c3cc(-c4ccn[nH]4)cc4[nH]ncc34)cn2c1] | D | 1.17/372.2 | 2 |
| 9 | N-({7-methylimidazo[1,2-a]pyridin-2-yl}methyl)-1H-indazole-4-carboxamide | 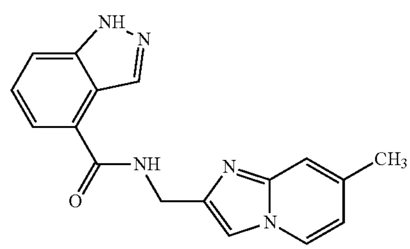 [SMILES: Cc1ccn2cc(CNC(=O)c3cccc4[nH]ncc34)nc2c1] | C | 1.96/306.9 | 9 |
| 10 | 6-bromo-N-({6-methylimidazo[1,2-a]pyridin-2-yl}methyl)-1H-indazole-4-carboxamide | 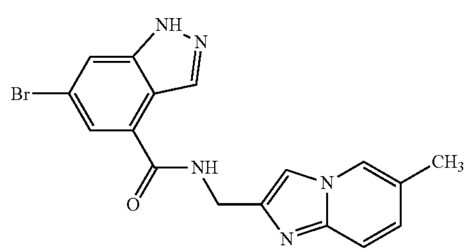 [SMILES: Cc1ccc2nc(CNC(=O)c3cc(Br)cc4[nH]ncc34)cn2c1] | D | 3.32/384.1/ 386.1 | 1 |
| 11 | 6-bromo-N-({7-methylimidazo[1,2-a]pyridin-2-yl}methyl)-1H-indazole-4-carboxamide | 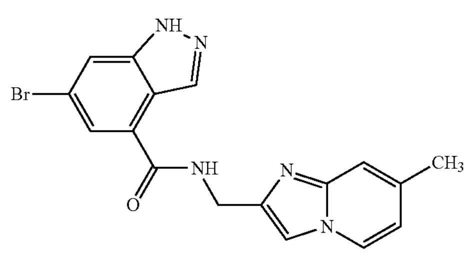 [SMILES: Cc1ccn2cc(CNC(=O)c3cc(Br)cc4[nH]ncc34)nc2c1] | D | 3.29/384.1/ 386.1 | 1, 9 |

TABLE 2-continued

| Cpd No | Name | Structure | LCMS method | LCMS Retention time/mass ion | Inter mediates |
|---|---|---|---|---|---|
| 12 | N-({6-methylimidazo[1,2-a]pyridin-2-yl}methyl)-4-oxo-4H-chromene-2-carboxamide | 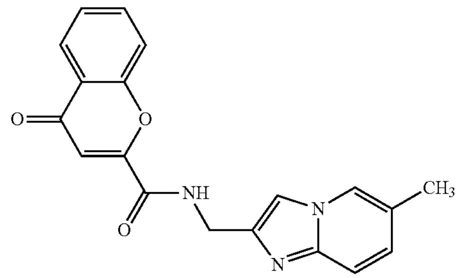 [SMILES: Cc1ccc2nc(CNC(=O)c3cc(=O)c4ccccc4o3)cn2c1] | E | 1.22/334.1 | Commercially available |
| 13 | N-aimidazo[1,2-a]pyridin-2-yl}methyl)-4-oxo-4H-chromene-2-carboxamide | 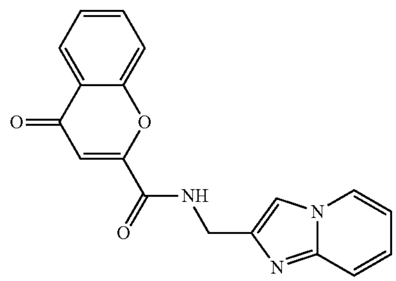 [SMILES: O=C(NCc1cn2ccccc2n1)c1cc(=O)c2ccccc2o1] | D | 3.00/320.2 | Commercially available |
| 14 | 6-ethynyl-N-({6-methylimidazo[1,2-a]pyridin-2-yl}methyl)-1H-indazole-4-carboxamide | 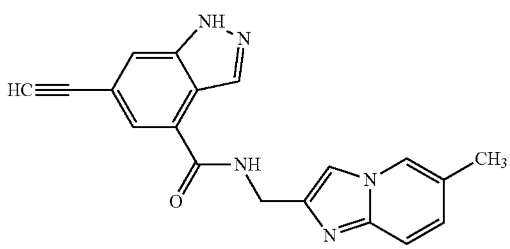 [SMILES: C#Cc1cc(C(=O)NCc2cn3cc(C)ccc3n2)c2cn[nH]c2c1] | D | 3.15/330.2 | 3 |
| 15 | N-({6-methylimidazo[1,2-a]pyridin-2-yl}methyl)-4-oxo-4H-pyrido[1,2-a]pyrimidine-2-carboxamide | 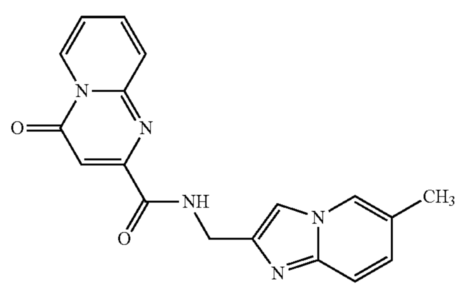 [SMILES: Cc1ccc2nc(CNC(=O)c3cc(=O)n4ccccc4n3)cn2c1] | D | 2.66/334.2 | 4 |
| 16 | N-({7-methylimidazo[1,2-a]pyridin-2-yl}methyl)-4-oxo-4H-chromene-2-carboxamide | 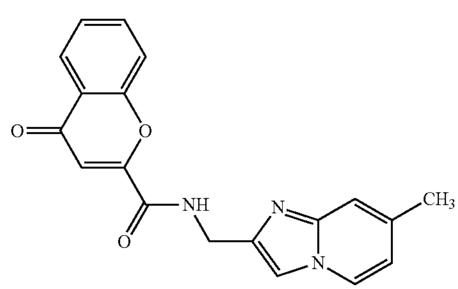 [SMILES: Cc1ccn2cc(CNC(=O)c3cc(=O)c4ccccc4o3)nc2c1] | D | 3.24/333.3 | 9 |

TABLE 2-continued

| Cpd No | Name | Structure | LCMS method | LCMS Retention time/mass ion | Intermediates |
|---|---|---|---|---|---|
| 17 | N-({7-methylimidazo[1,2-a]pyridin-2-yl}methyl)-4-oxo-4H-pyrido[1,2-a]pyrimidine-2-carboxamide | 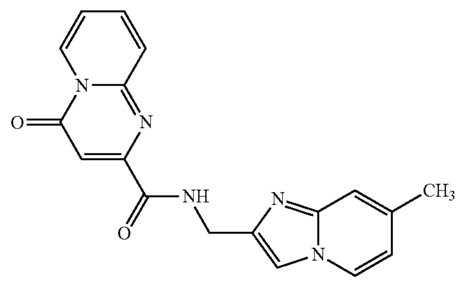 [SMILES: Cc1ccn2cc(CNC(=O)c3cc(=O)n4ccccc4n3)nc2c1] | D | 2.96/334.3 | 9 |
| 18 | N-({6-cyanoimidazo[1,2-a]pyridin-2-yl}methyl)-4-oxo-4H-pyrido[1,2-a]pyrimidine-2-carboxamide | 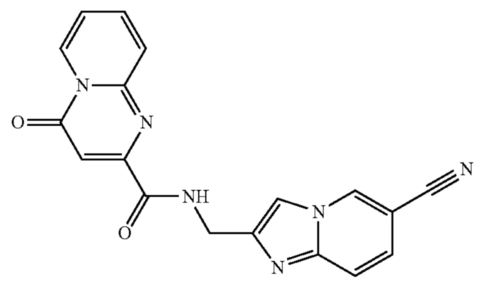 [SMILES: N#Cc1ccc2nc(CNC(=O)c3cc(=O)n4ccccc4n3)cn2c1] | E | 1.14/345.1 | Commercially available |
| 19 | 8-methoxy-N-({6-methylimidazo[1,2-a]pyridin-2-yl}methyl)-4-oxo-4H-pyrido[1,2-a]pyrimidine-2-carboxamide | 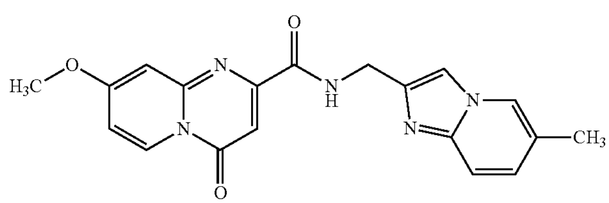 | D | 3.20/364.3 | 5 |
| 20 | N-({6-methylimidazo[1,2-a]pyridin-2-yl}methyl)-1H-indazole-5-carboxamide | 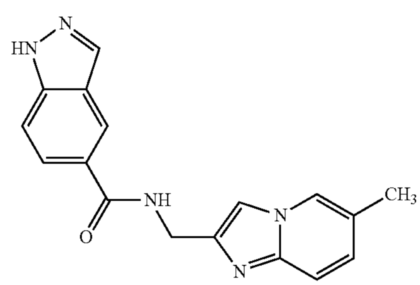 [SMILES: Cc1ccc2nc(CNC(=O)c3ccc4[nH]ncc4c3)cn2c1] | D | 2.84/306.3 | Commercially available |
| 21 | 7-chloro-N-({6-methylimidazo[1,2-a]pyridin-2-yl}methyl)-4-oxo-4H-pyrido[1,2-a]pyrimidine-2-carboxamide | 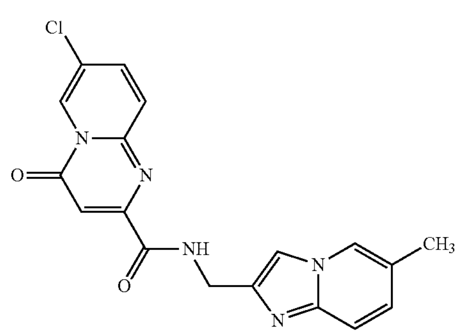 [SMILES: Cc1ccc2nc(CNC(=O)c3cc(=O)n4cc(Cl)ccc4n3)cn2c1] | D | 3.39/368.1 | 6 |

TABLE 2-continued

| Cpd No | Name | Structure | LCMS method | LCMS Retention time/mass ion | Intermediates |
|---|---|---|---|---|---|
| 22 | N-({6-fluoroimidazo[1,2-a]pyridin-2-yl}methyl)-4-oxo-4H-pyrido[1,2-a]pyrimidine-2-carboxamide | 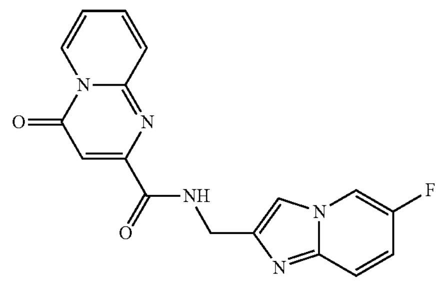 [SMILES: O=C(NCc1cn2cc(F)ccc2n1)c1cc(=O)n2ccccc2n1] | D | 2.93/338.2 | 11 |
| 23 | N-({6-bromoimidazo[1,2-a]pyridin-2-yl}methyl)-4-oxo-4H-pyrido[1,2-a]pyrimidine-2-carboxamide | 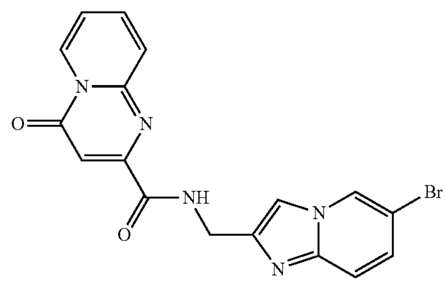 [SMILES: O=C(NCc1cn2cc(Br)ccc2n1)c1cc(=O)n2ccccc2n1] | C | 2.35/398.1/ 400.1 | Commercially available |
| 24 | N-({6-methoxyimidazo[1,2-a]pyridin-2-yl}methyl)-4-oxo-4H-pyrido[1,2-a]pyrimidine-2-carboxamide | 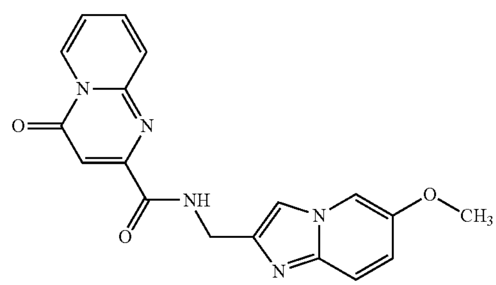 | D | 2.95/350.2 | 13 |
| 25 | N-({7-methoxyimidazo[1,2-a]pyridin-2-yl}methyl)-4-oxo-4H-pyrido[1,2-a]pyrimidine-2-carboxamide | 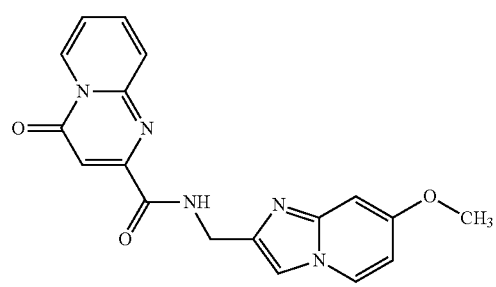 [SMILES: COc1ccn2cc(CNC(=O)c3cc(=O)n4ccccc4n3)nc2c1] | D | 2.55/350.3 | 12 |
| 26 | N-aimidazo[1,2-a]pyridin-2-yl}methyl)-4-oxo-4H-pyrido[1,2-a]pyrimidine-2-carboxamide | 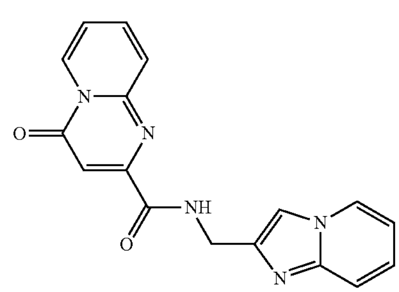 [SMILES: O=C(NCc1cn2ccccc2n1)c1cc(=O)n2ccccc2n1] | MS10 7 min | 2.72/320.2 | Commercially available |

TABLE 2-continued

| Cpd No | Name | Structure | LCMS method | LCMS Retention time/mass ion | Inter mediates |
|---|---|---|---|---|---|
| 27 | N-({8-methylimidazo[1,2-a]pyridin-2-yl}methyl)-4-oxo-4H-pyrido[1,2-a]pyrimidine-2-carboxamide | 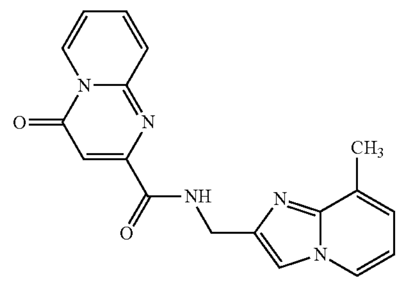 [SMILES: Cc1cccn2cc(CNC(=O)c3cc(=O)n4ccccc4n3)nc12] | D | 2.99/334.3 | Commercially available |
| 28 | N-({6-methylimidazo[1,2-a]pyridin-2-yl}methyl)-1H-pyrazolo[4,3-c]pyridine-4-carboxamide | 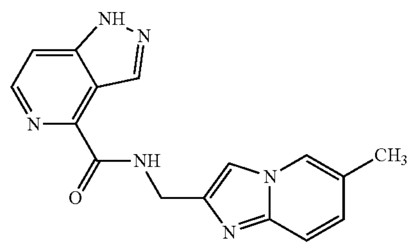 | D | 2.90/307.2 | Commercially available |
| 29 | N-({7-bromoimidazo[1,2-a]pyridin-2-yl}methyl)-4-oxo-4H-pyrido[1,2-a]pyrimidine-2-carboxamide | 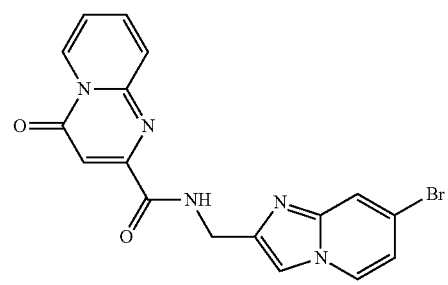 [SMILES: O=C(NCc1cn2ccc(Br)cc2n1)c1cc(=O)n2ccccc2n1] | D | 3.14/ 398.5/ 400.5 | 7 |
| 30 | N-(2-hydroxy-1-{6-methylimidazo[1,2-a]pyridin-2-yl}ethyl)-1H-indazole-4-carboxamide | 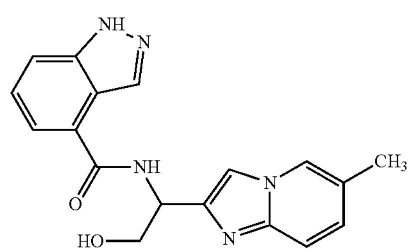 [SMILES: Cc1ccc2nc(C(CO)NC(=O)c3cccc4[nH]ncc34)cn2c1] | D | 2.81/336.2 | 15 |
| 31 | 4-(3-{imidazo[1,2-a]pyridin-2-yl}-2,5-dihydro-1H-pyrrole-1-carbonyl)-1H-indazole | 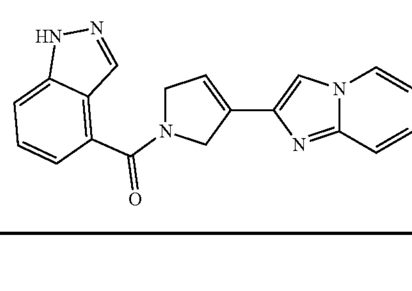 | D | 2.87/330.3 | 17 |

Synthesis of Compound 32: N-[(6-{[(pyridin-3-yl)methyl]amino}imidazo[1,2-a]pyridin-2-yl)methyl]-1H-indazole-4-carboxamide

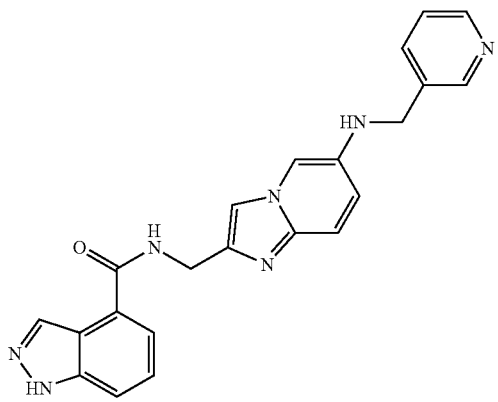

Step 1: N-[[6-(3-pyridylmethylamino)imidazo[1,2-a]pyridin-2-yl]methyl]-1-tetrahydropyran-2-yl-indazole-4-carboxamide dihydrochloride

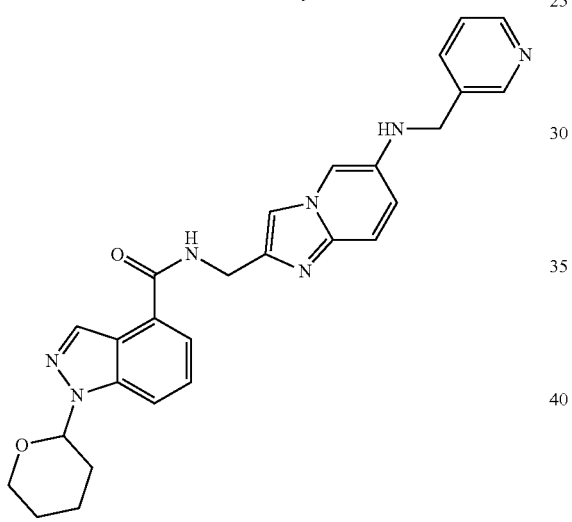

A mixture of N-[(6-bromoimidazo[1,2-a]pyridin-2-yl)methyl]-1-tetrahydropyran-2-yl-indazole-4-carboxamide (100 mg, 0.220 mmol), Intermediate 14, 3-pyridylmethanamine (273 uL, 2.20 mmol), copper iodide (6.3 mg, 0.0330 mmol), (2{S})-pyrrolidine-2-carboxylic acid (5.1 mg, 0.0440 mmol) and potassium carbonate (61 mg, 0.440 mmol) in DMSO (0.6 mL) was heated using microwave irradiation at 150° C. for 15 min. The reaction mixture was diluted with 10% MeOH in DCM (15 mL) and water (15 mL). The organic phase was collected and the aqueous phase was extracted with 10% MeOH in DCM (2×15 mL). The combined organics were evaporated to dryness under reduced pressure and purified by preparative HPLC (Method A) to afford the title compound (22 mg, 21%) as a yellow solid.

LCMS Method A (electrospray): m/z=482.2 (M+H)$^+$, RT=0.77 min.

Step 2: N-[(6-{[(pyridin-3-yl)methyl]amino}imidazo[1,2-a]pyridin-2-yl)methyl]-1H-indazole-4-carboxamide dihydrochloride

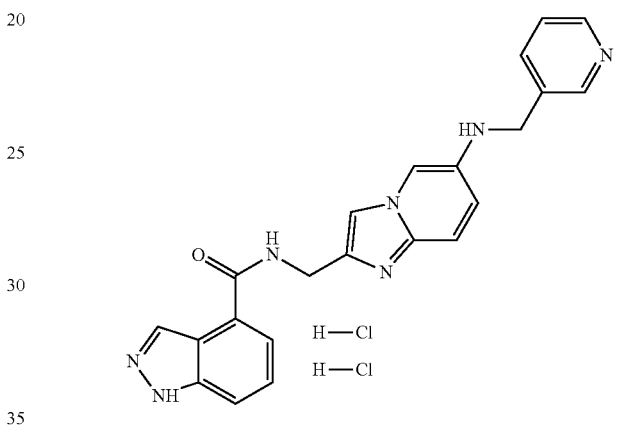

The title compound was prepared from N-[[6-(3-pyridylmethylamino)imidazo[1,2-a]pyridin-2-yl]methyl]-1-tetrahydropyran-2-yl-indazole-4-carboxamide using the procedure described in Compound 1 giving (21 mg 96%) as a light brown solid.

LCMS Method D (electrospray): m/z=398.3 (M+H)$^+$, RT=2.76 min.

Synthesis of Compound 33: N-[(6-{[(1-methyl-1H-imidazol-4-yl)methyl]amino}imidazo[1,2a]pyridin-2-yl)methyl]-1H-indazole-4-carboxamide The compound in table 3 was prepared in the same manner as Compound 32

TABLE 3

| Cpd No | Name | Structure | LCMS method | LCMS Retention time | Mass ion |
|---|---|---|---|---|---|
| 33 | N-[(6-{[(1-methyl-1H-imidazol-4-yl)methyl]amino}imidazo[1,2a]pyridin-2-yl)methyl]-1H-indazole-4-carboxamide | 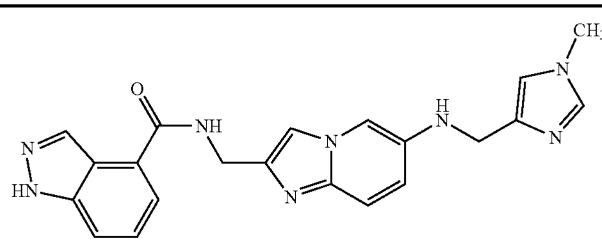 | D | 2.53 | 401.3 |

Synthesis of Compound 34: N-{[6-(3-methoxyphenyl)imidazo[1,2-a]pyridin-2-yl]methyl}-1H-indazole-4-carboxamide

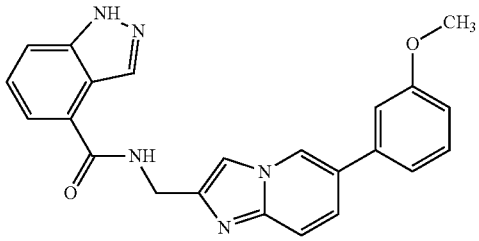 [SMILES: COc1cccc(-c2ccc3nc(CNC(=O)c4cccc5[nH]ncc45)cn3c2)c1]

Step 1: N-[[6-(3-methoxyphenyl)imidazo[1,2-a]pyridin-2-yl]methyl]-1-tetrahydropyran-2-yl-indazole-4-carboxamide

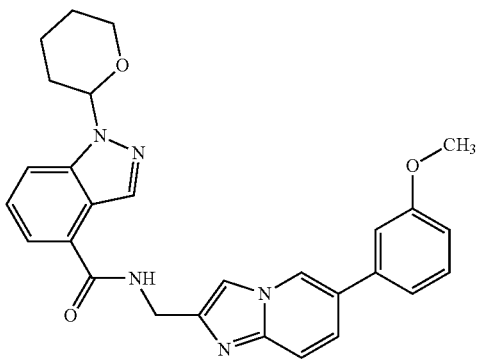 [SMILES: COc1cccc(-c2ccc3nc(CNC(=O)c4cccc5c4cnn5C4CCCCO4)cn3c2)c1]

N-[(6-bromoimidazo[1,2-a]pyridin-2-yl)methyl]-1-tetrahydropyran-2-yl-indazole-4-carboxamide (120 mg, 0.25 mmol), Intermediate 14, (3-methoxyphenyl)boronic acid (45 mg, 0.29 mmol) and $K_2CO_3$ (1.2M aqueous, 0.61 ml, 0.74 mmol) were combined in 1,4-Dioxane (4 ml) and the mixture sparged with nitrogen for 5 mins. Dichloro[1,1'-bis(di-t-butylphosphino)ferrocene]palladium(II) (16 mg, 0.02 mmol) was added and the mixture sparged for a further 5 mins. The vessel was sealed and the mixture heated at 100° C. for 2 h. The reaction mixture was cooled to room temperature and diluted with ethyl acetate (30 ml). The mixture was washed with sat. Sodium hydrogen carbonate (aq) (30 ml) and brine (2×30 ml) and the organic layer dried over sodium sulfate and evaporated under vacuum. The residue was purified by chromatography on silica gel [Biotage 28 g kp-NH, eluting with 0-100% ethyl acetate/heptane 0-100%] to afford N-[[6-(3-methoxyphenyl)imidazo[1,2-a]pyridin-2-yl]methyl]-1-tetrahydropyran-2-yl-indazole-4-carboxamide (113 mg, 96%) as a white solid.

LCMS Method A (electrospray): m/z=482.25 (M+H)$^+$, RT=1.04 min.

The title compound was prepared from N-[[6-(3-methoxyphenyl)imidazo[1,2-a]pyridin-2-yl]methyl]-1-tetrahydropyran-2-yl-indazole-4-carboxamide using the procedure described in Compound 1 giving (51 mg, 54%) as a white solid.

LCMS Method D (electrospray): m/z=398.2 (M+H)$^+$, RT=3.50 min.

Synthesis of Compounds 35-36

The compounds in Table 4 were prepared by in a similar fashion to Compound 34.

TABLE 4

| Cpd No | Name | Structure | LCMS method | LCMS Retention time | Mass ion |
|---|---|---|---|---|---|
| 35 | N-{[6-(1H-pyrazol-5-yl)imidazo[1,2-a]pyridin-2-yl]methyl}-1H-indazole-4-carboxamide | 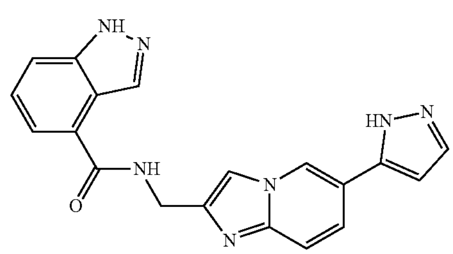 [SMILES: O=C(NCc1cn2cc(-c3ccn[nH]3)ccc2n1)c1cccc2[nH]ncc12] | D | 2.64 | 358.2 |
| 36 | N-[[6-(3-chlorophenyl)imidazo 1,2-a]pyridin-2-yl]methyl]-1H-indazole-4-carboxamide | 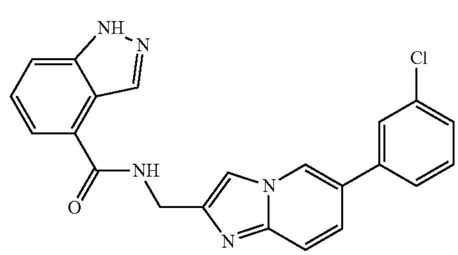 [SMILES: O=C(NCc1cn2cc(-c3cccc(Cl)c3)ccc2n1)c1cccc2[nH]ncc12] | D | 3.76 | 402.2 |

Synthesis of Compound 37: N-({6-[(pyridin-3-yl)amino]imidazo[1,2-a]pyridin-2-yl}methyl)-1H-indazole-4-carboxamide

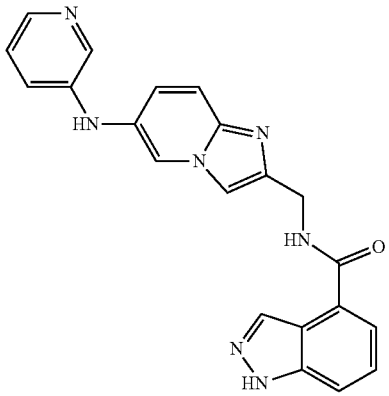 [SMILES: O=C(NCc1cn2cc(Nc3cccnc3)ccc2n1)c1cccc2[nH]ncc12]

Step 1: 1-(oxan-2-yl)-N-({6-[(pyridin-3-yl)amino]imidazo[1,2-a]pyridin-2-yl}methyl)-1H-indazole-4-carboxamide

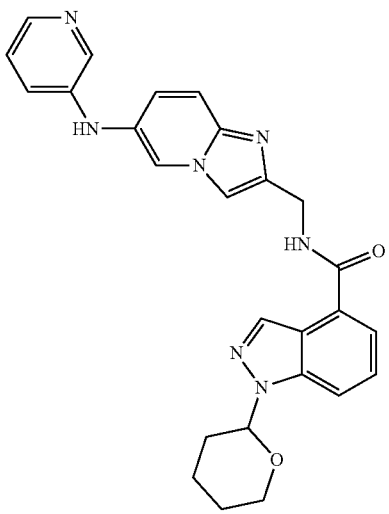 [SMILES: O=C(NCc1cn2cc(Nc3cccnc3)ccc2n1)c1cccc2c1cnn2C1CCCCO1]

A solution of N-[(6-bromoimidazo[1,2-a]pyridin-2-yl)methyl]-1-tetrahydropyran-2-yl-indazole-4-carboxamide (75 mg, 0.165 mmol), Intermediate 14, cesium carbonate (161 mg, 0.495 mmol), pyridin-3-amine (19 mg, 0.198 mmol) and XPhos Pd G3 (14 mg, 0.0165 mmol) in 1,4-Dioxane (2 mL) was stirred at 110° C. for 2 h. More pyridin-3-amine (19 mg, 0.198 mmol) and XPhos Pd G3 (14 mg, 0.0165 mmol) were added and the reaction mixture was stirred at 110° C. for 2 h. The reaction mixture was cooled to rt. diluted with water (25 mL) and extracted with ethyl acetate (2×25 mL). The combined organics were evaporated to dryness and purified by preparative HPLC [method B, followed by method A] to afford N-[[6-(3-pyridylamino)imidazo[1,2-a]pyridin-2-yl]methyl]-1-tetrahydropyran-2-yl-indazole-4-carboxamide as a yellow solid.

LCMS Method A (electrospray): m/z=468.2 (M+H)$^+$, RT=0.8 min

Step 2: The title compound was prepared from N-[[6-(3-methoxyphenyl)imidazo[1,2-a]pyridin-2-yl]methyl]-1-tetrahydropyran-2-yl-indazole-4-carboxamide using the procedure described in Compound 1 giving (7.5 mg, 92%) as a white solid.

LCMS Method D (electrospray): m/z=384.3 (M+H)$^+$, RT=2.75 min

Synthesis of Compound 38: N-({6-[(piperazin-1-yl)methyl]imidazo[1,2-a]pyridin-2-yl}methyl)-1H-indazole-4-carboxamide

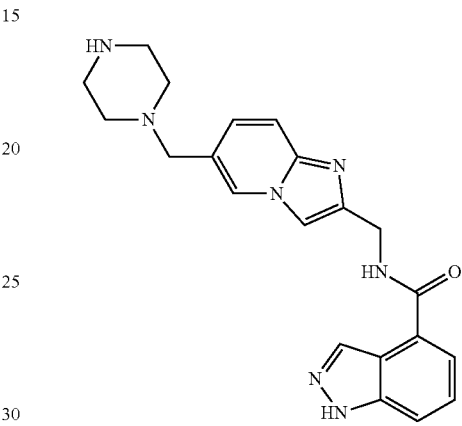

Step 1: tert-butyl 4-[[2-[[(1-tetrahydropyran-2-ylindazole-4-carbonyl)amino]methyl]imidazo[1,2-a]pyridin-6-yl]methyl]piperazine-1-carboxylate

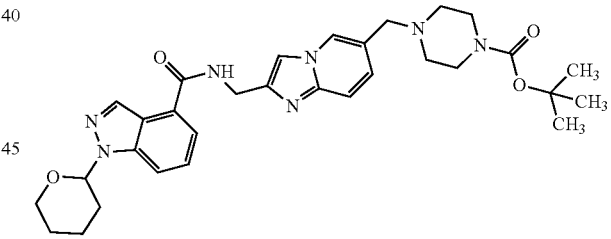

A solution of N-[(6-bromoimidazo[1,2-a]pyridin-2-yl)methyl]-1-tetrahydropyran-2-yl-indazole-4-carboxamide (50 mg, 0.110 mmol), Intermediate 14, potassium; (4-tert-butoxycarbonylpiperazin-1-yl)methyl-trifluoro-borohydride (37 mg, 0.121 mmol), cesium carbonate (108 mg, 0.330 mmol) and Pd-118 (3.6 mg, 5.50 µmol) in THF (3.2 mL) and Water (0.8 mL), under a nitrogen atmosphere, was stirred at 85° C. overnight. The reaction mixture was diluted with water (10 mL) and extracted with ethyl acetate (3×10 mL). The combined organics were evaporated to dryness under reduced pressure and purified by preparative HPLC [method A) to afford the title compound (30 mg, 48%) as a white solid.

LCMS Method A (electrospray): m/z=574.4 (M+H)$^+$, RT=0.88 min.

Step 2: The title compound was prepared from: tert-butyl 4-[[2-[[(1-tetrahydropyran-2-ylindazole-4-carbonyl)amino]methyl]imidazo[1,2-a]pyridin-6-yl]methyl]piperazine-1-carboxylate using the procedure described in Compound 1 giving (7.5 mg, 92%) as a white solid.

Method C: LC-MS (electrospray): m/z=390.3 (M+H)$^+$, RT=1.55 min.

Synthesis of Compound 39: N-{[6-(aminomethyl)imidazo[1,2-a]pyridin-2-yl]methyl}-1H-indazole-4-carboxamide

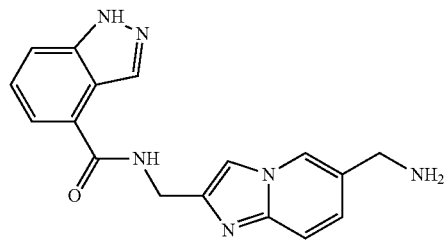 [SMILES: NCc1ccc2nc(CNC(=O)c3cccc4[nH]ncc34)cn2c1]

Step 1: tert-butyl N-[[2-[[(1-tetrahydropyran-2-ylindazole-4-carbonyl)amino]methyl]imidazo[1,2-a]pyridin-6-yl]methyl]carbamate and N-{[6-(aminomethyl)imidazo[1,2-a]pyridin-2-yl]methyl}-1-(oxan-2-yl)-1H-indazole-4-carboxamide

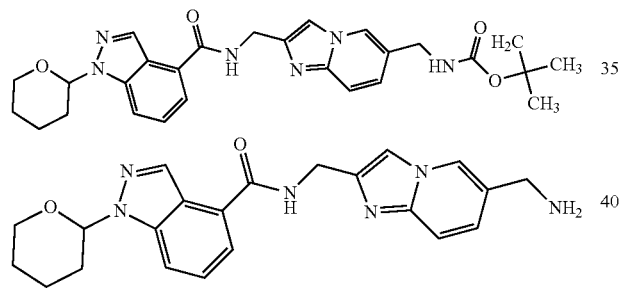

A solution of N-[(6-cyanoimidazo[1,2-a]pyridin-2-yl)methyl]-1-tetrahydropyran-2-yl-indazole-4-carboxamide (500 mg, 1.25 mmol) (Intermediate 16) and tert-butoxycarbonyl tert-butyl carbonate (545 mg, 2.50 mmol) in methanol (10 mL) was cooled to 0° C. and treated with nickel (II) chloride (164 mg, 1.25 mmol) followed by the addition of sodium borohydride (425 mg, 11.2 mmol) in small portions. Further NaBH$_4$ (212 mg, 5.5 mmol) was added in portions and the stirring was continued for an hour at 0° C. before the crude reaction was evaporated under vacuum and purified by chromatography on silica gel [Biotage; 25 g KP—NH, eluting with 40-100% ethyl acetate in heptane) to afford tert-butyl N-[[2-[[(1-tetrahydropyran-2-ylindazole-4-carbonyl)amino]methyl]imidazo[1,2-a]pyridin-6-yl]methyl]carbamate (180 mg, 0.357 mmol, 50%) as a white solid.

LCMS Method A (electrospray): m/z=505.2 (M+H)$^+$, RT=0.96 min.

Flushing the column with 0-20% MeOH in ethyl acetate afforded N-[[6-(aminomethyl)imidazo[1,2-a]pyridin-2-yl]methyl]-1-tetrahydropyran-2-yl-indazole-4-carboxamide (90 mg, 0.129 mmol, 18%) as a white solid.

LCMS Method A: LC-MS (electrospray): m/z=405.1 (M+H)$^+$, RT=0.85 min.

Step 2: N-{[6-(aminomethyl)imidazo[1,2-a]pyridin-2-yl]methyl}-1H-indazole-4-carboxamide hydrochloride

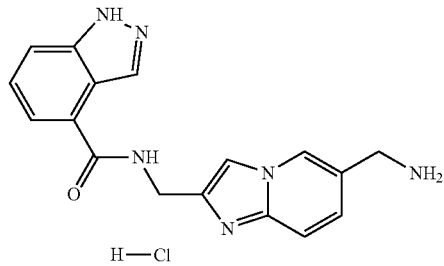 [SMILES: NCc1ccc2nc(CNC(=O)c3cccc4[nH]ncc34)cn2c1 ; Cl]

Tert-butyl N-[[2-[[(1-tetrahydropyran-2-ylindazole-4-carbonyl)amino]methyl]imidazo[1,2-a]pyridin-6-yl]methyl]carbamate (180 mg, 0.36 mmol) was treated with HCl (4M in dioxane 0.5 mL) and the mixture was stirred at room temperature for 65 hours. The mixture was evaporated to dryness and triturated from MeOH/ethyl acetate to afford the title compound (98 mg, 70%) as a white powder.

LCMS Method D (electrospray): m/z=321.2 (M+H)$^+$, RT=2.38 min.

Synthesis of Compound 40: N-{[6-(acetamidomethyl)imidazo[1,2-a]pyridin-2-yl]methyl}-1H-indazole-4-carboxamide

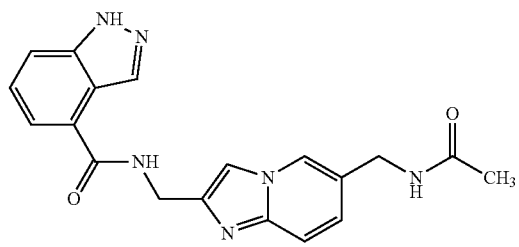 [SMILES: CC(=O)NCc1ccc2nc(CNC(=O)c3cccc4[nH]ncc34)cn2c1]

The title compound was prepared using the method described in Compound 39 substituting acetic anhydride for tert-butoxycarbonyl tert-butyl carbonate to give (32 mg, 31%) as a white solid.

LCMS Method D: LC-MS (electrospray): m/z=363.2 (M+H)$^+$, RT=2.36 min.

Synthesis of Compound 41: {6-methylimidazo[1,2-a]pyridin-2-yl}methyl 1H-indazole-4-carboxylate hydrochloride

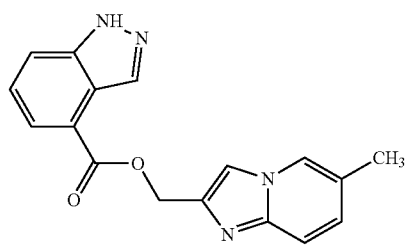 [SMILES: Cc1ccc2nc(COC(=O)c3cccc4[nH]ncc34)cn2c1]

167

Step 1: (6-methylimidazo[1,2-a]pyridin-2-yl)methanol

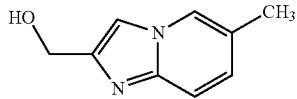

6-methylimidazo[1,2-a]pyridine-2-carbaldehyde (Eur. J. Org. Chem. 2015 (18), 3957) (165 mg, 1.03 mmol) was dissolved in methanol (20 ml) and cooled in an ice/water bath. NaBH$_4$ (195 mg, 5.15 mmol) was added in a single portion and the effervescent mixture stirred under cooling for 30 minutes. The reaction mixture was quenched with sodium hydrogen carbonate (Sat, 30 ml) and warmed to RT. The mixture was extracted with 3:1 chloroform/isopropanol (4×30 ml) and the combined organic extracts were dried over sodium sulfate and evaporated under vacuum. The residue was purified by Chromatography on silica gel [Biotage 28 g kp-NH, eluting with 0-20% MeOH/DCM) to afford the title compound (137 mg, 80% yield, 98%) as a bright yellow oily residue.

LCMS Method B (electrospray): m/z=163.2 (M+H)$^+$, RT=1.11 min

Step 2: The title compound was prepared from (6-methylimidazo[1,2-a]pyridin-2-yl)methanol using the procedure described in Compound 1 giving (187 mg, 90%) as a white solid.

LCMS Method B: LC-MS (electrospray): m/z=163.2 (M+H)$^+$, RT=1.11 min

Synthesis of Compound 42: {N-{[6-(hydroxymethyl)imidazo[1,2-a]pyridin-2-yl]methyl}-1H-indazole-4-carboxamide

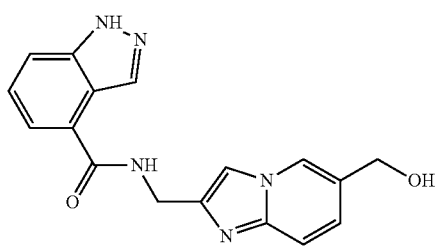 [SMILES: O=C(NCc1cn2cc(CO)ccc2n1)c1cccc2[nH]ncc12]

168

Step 1: N-[[6-(hydroxymethyl)imidazo[1,2-a]pyridin-2-yl]methyl]-1-tetrahydropyran-2-yl-indazole-4-carboxamide

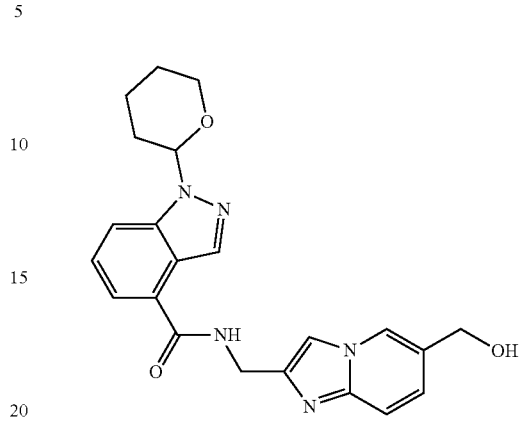

A solution of N-[(6-formylimidazo[1,2-a]pyridin-2-yl)methyl]-1-tetrahydropyran-2-yl-indazole-4-carboxamide (Intermediate 18) (50% purity with N-(imidazo[1,2-a]pyridin-2-ylmethyl)-1-tetrahydropyran-2-yl-indazole-4-carboxamide, 92 mg, 0.114 mmol) in ethanol (4 mL), under a nitrogen atmosphere was treated with sodium borohydride (13 mg, 0.342 mmol) and the resultant mixture was stirred at room temperature for an hour. The reaction mixture was quenched by the addition of sodium hydrogen carbonate(sat) and concentrated under vacuum. The residue was extracted with DCM (phase sep) and the extracts were evaporated under vacuum to a residue which was purified by chromatography on silica gel [Biotage KPNH 11 g, eluting with 20-80% (10% MeOH in DCM/DCM) to give the title compound (44 mg, 95%).

LCMS Method B (electrospray): m/z=406.4 (M+H)$^+$, RT=1.27 min

The title compound was prepared from N-[[6-(hydroxymethyl)imidazo[1,2-a]pyridin-2-yl]methyl]-1-tetrahydropyran-2-yl-indazole-4-carboxamide using the procedure described in Compound 1 giving (24 mg, 68%) as a beige solid.

LCMS Method D (electrospray): m/z=322.3 (M+H)$^+$, RT=2.30 min

Synthesis of Compound 43: N-({6-hydroxyimidazo[1,2-a]pyridin-2-yl}methyl)-1H-indazole-4-carboxamide

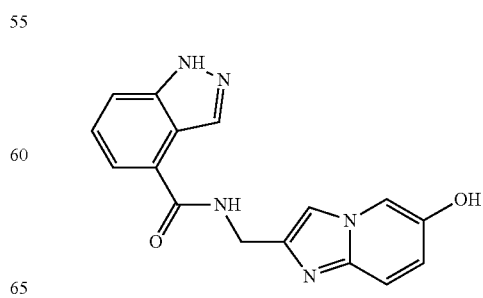

169

Step 1: N-({6-hydroxyimidazo[1,2-a]pyridin-2-yl}methyl)-1-(oxan-2-yl)-1H-indazole-4-carboxamide

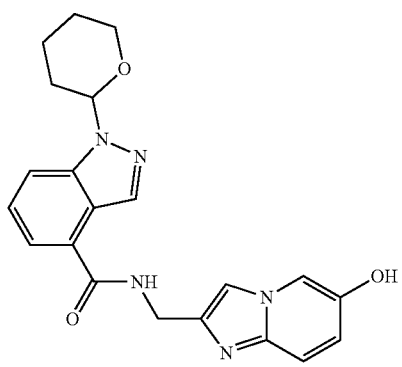 [SMILES: O=C(NCc1cn2cc(O)ccc2n1)c1cccc2c1cnn2C1CCCCO1]

A solution of N-[(6-bromoimidazo[1,2-a]pyridin-2-yl)methyl]-1-tetrahydropyran-2-yl-indazole-4-carboxamide (Intermediate 14) (100 mg, 0.220 mmol), 4,4,5,5-tetramethyl-2-(4,4,5,5-tetramethyl-1,3,2-dioxaborolan-2-yl)-1,3,2-dioxaborolane (126 mg, 0.495 mmol), Pd(dppf)Cl$_2$·CH$_2$Cl$_2$ (18 mg, 0.0220 mmol) and potassium acetate (65 mg, 0.660 mmol) in 1,4-Dioxane (3 mL) was stirred at 100° C. for 2 hours. The mixture was cooled to room temperature before acetic acid (25 uL, 0.440 mmol) and Water (0.06 mL) were added. The mixture was stirred for 1 hour before hydrogen peroxide (30%, 2.86 mL, 28.0 mmol) was added and the mixture was stirred for 3 hours. The mixture was quenched with sodium thiosulfate solution (sat, 15 mL), diluted with water (15 mL), extracted with ethyl acetate (2×25 mL) and evaporated to dryness under reduced pressure. The residue was purified by preparative HPLC [method B] to afford the title compound (25 mg, 27%) as a white powder.

LCMS Method A (electrospray): m/z=392.1 (M+H)$^+$, RT=0.85 min

Step 2: The title compound was prepared from N-({6-hydroxyimidazo[1,2-a]pyridin-2-yl}methyl)-1-(oxan-2-yl)-1H-indazole-4-carboxamide using the procedure described in Compound 1 giving (7.3 mg, 37%) as a brown powder.

LCMS Method C (electrospray): m/z=308.1 (M+H)$^+$, RT=1.04 min

170

Synthesis of Compound 44: N-({6-[(methylamino)methyl]imidazo[1,2-a]pyridin-2-yl}methyl)-1H-indazole-4-carboxamide dihydrochloride

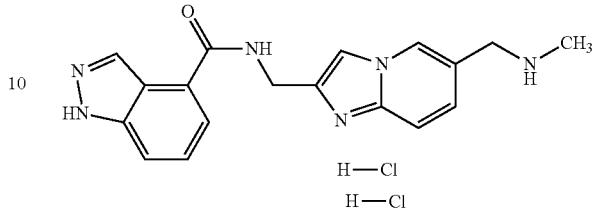

Step 1: N-({6-[(methylamino)methyl]imidazo[1,2-a]pyridin-2-yl}methyl)-1-(oxan-2-yl)-1H-indazole-4-carboxamide

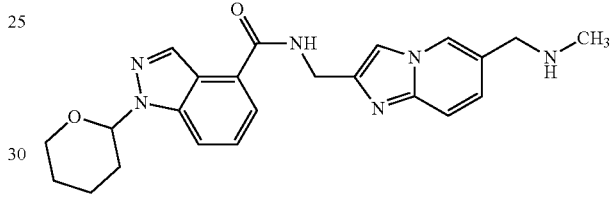

A solution of N-[(6-formylimidazo[1,2-a]pyridin-2-yl)methyl]-1-tetrahydropyran-2-yl-indazole-4-carboxamide (Intermediate 18) (50%, 100 mg, 0.114 mmol), STAB (48 mg, 0.228 mmol) and methylamine (8M in ethanol, 16 uL, 0.125 mmol) in DCM (1 mL) was stirred at rt for 3 h.

More methylamine (8M in ethanol, 16 uL, 0.125 mmol) and STAB (48 mg, 0.228 mmol) were added in portions over 48 hours whilst stirring the reaction mixture at rt. The reaction mixture was evaporated to dryness and purified by ion exchange [SCX-2] followed by preparative HPLC [method A] to afford the title compound (46 mg, 96%) as a yellow solid.

LCMS Method A (electrospray): m/z=419.1 (M+H)$^+$, RT=0.74 min

Step 2: The title compound was prepared from N-[[6-(hydroxymethyl)imidazo[1,2-a]pyridin-2-yl]methyl]-1-tetrahydropyran-2-yl-indazole-4-carboxamide using the procedure described in Compound 1 giving (25 mg, 58%) as a beige solid.

LCMS Method C (electrospray): m/z=390.3 (M+H)$^+$, RT=1.58 min

Synthesis of Compounds 45-46

The compounds in table 4 was prepared in the same manner as Compound 44

TABLE 4

| Cpd No | Name | Structure | LCMS method | LCMS Retention time | Mass ion |
|---|---|---|---|---|---|
| 45 | N-[(6-{[(2-hydroxyethyl)amino]methyl{imidazo[1,2-a]pyridin-2-2-yl)methyl]-1H-indazole-4-carboxamide | 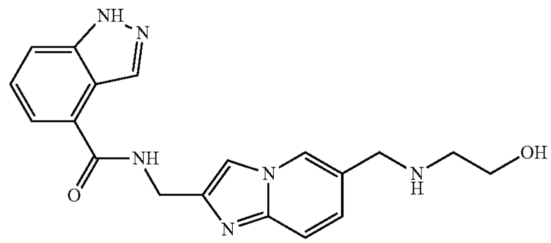 [SMILES: O=C(NCc1cn2cc(CNCCO)ccc2n1)c1cccc2[nH]ncc12] | C | 1.40 | 365.2 |
| 46 | N-[(6-{[(2,2,2-trifluoroethyl)amino]methyl}imidazo[1,2-a]pyridin-yl)methyl]-1H-indazole-4-carboxamide | 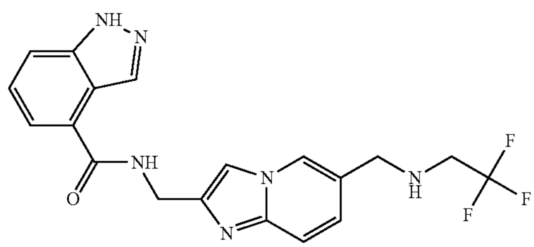 [SMILES: O=C(NCc1cn2cc(CNCC(F)(F)F)ccc2n1)c1cccc2[nH]ncc12] | D | 3.05 | 403.1 |

Synthesis of Compound 47: N-{[6-(1-hydroxyethyl)imidazo[1,2-a]pyridin-2-yl]methyl}-1H-indazole-4-carboxamide

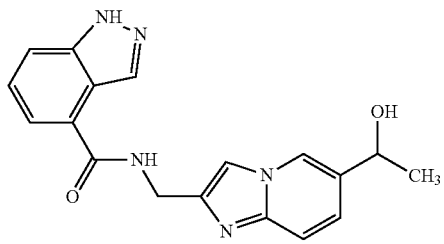 [SMILES: CC(O)c1ccc2nc(CNC(=O)c3cccc4[nH]ncc34)cn2c1]

Step 1: N-{[6-(1-hydroxyethyl)imidazo[1,2-a]pyridin-2-yl]methyl}-1-(oxan-2-yl)-1H-indazole-4-carboxamide

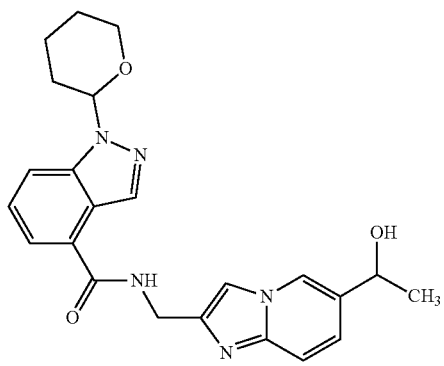 [SMILES: CC(O)c1ccc2nc(CNC(=O)c3cccc4c3cnn4C3CCCCO3)cn2c1]

A solution of magnesium bromide in ether (3M, 74 uL, 0.22 mmol) was added dropwise over 1 min to a solution of N-[(6-formylimidazo[1,2-a]pyridin-2-yl)methyl]-1-tetrahydropyran-2-yl-indazole-4-carboxamide (intermediate 18) (75 mg, 0.186 mmol) in THF (1 mL) at −30° C. The reaction mixture was then warmed to 0° C. and stirred for 2 h. The reaction mixture was quenched by the addition of sat. aq. NH$_4$Cl (10 mL) and extracted with ethyl acetate (3×15 mL). The combined organics were dried and evaporated to dryness and the residue was purified by preparative HPLC (method B) to afford the title compound (31 mg, 40%) as an orange solid.

The title compound was prepared from N-{[6-(1-hydroxyethyl)imidazo[1,2-a]pyridin-2-yl]methyl}-1-(oxan-2-yl)-1H-indazole-4-carboxamide using the procedure described in Compound 1 giving (14.6 mg, 59%) as a white powder.

Method C: LC-MS (electrospray): m/z=336.2 (M+H)$^+$, RT=1.56 min

Synthesis of Compound 48

The compound in table 5 was prepared in the same manner as Compound 47

TABLE 5

| Cpd No | Name | Structure | LCMS method | LCMS Retention time | Mass ion |
|---|---|---|---|---|---|
| 48 | N-({6-[hydroxy(phenyl)methyl]imidazo[1,2-a]pyridin-2-yl}methyl)-1H-indazole-4-carboxamide | 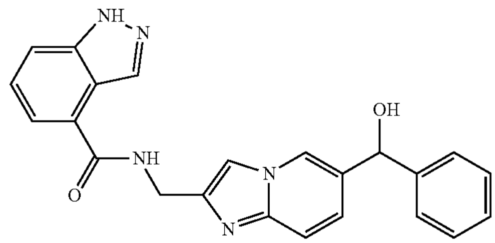 [SMILES: O=C(NCc1cn2cc(C(O)c3ccccc3)ccc2n1)c1cccc2[nH]ncc12] | D | 3.05 | 398.2 |

Synthesis of Compound 49: N-({6-formylimidazo[1,2-a]pyridin-2-yl}methyl)-4-oxo-4H-pyrido[1,2-a]pyrimidine-2-carboxamide

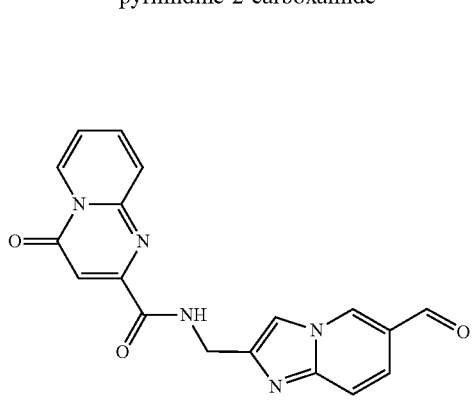

A suspension of N-[(6-cyanoimidazo[1,2-a]pyridin-2-yl)methyl]-4-oxo-pyrido[1,2-a]pyrimidine-2-carboxamide (Compound 18) (400 mg, 1.16 mmol), in a mixture of water (6 mL), pyridine (12 mL) and acetic acid (3 mL) was treated with sodium phosphinate hydrate (985 mg, 9.29 mmol) followed by Raney nickel (50%, 1.20 g, 10.2 mmol) and the mixture was heated at 100° C., under a nitrogen atmosphere, for 4.5 hours. Further Raney nickel (50%, 0.6 g, 5.1 mmol) was added and the heating was continued for an hour. The suspension was cooled to room temperature and the Ni (R) was removed by filtration through a bed of celite (washing with water). The filtrate was extracted with DCM (×4) and the extracts were dried (magnesium sulfate) and evaporated under vacuum to a suspension which contained pyridine. Further evaporation under vacuum gave a solid residue which was suspended in water and the solids were collected by filtration, washed with water followed by ether and dried under vacuum to give the title compound (205 mg, 51%) as a buff solid. The aqueous was further extracted with IPA/CHCl$_3$ (1:3) and the extracts were evaporated under vacuum to dryness. The residue which was suspended in water and the solids were collected by filtration, washed with water followed by ether and dried under vacuum to give the title compound (61 mg, 15%) as a buff solid.

LCMS Method E (electrospray): m/z=348.1 (M+H)$^+$, RT=1.16 min

Synthesis of Compound 50: N-{[6-(aminomethyl)imidazo[1,2-a]pyridin-2-yl]methyl}-4-oxo-4H-pyrido[1,2-a]pyrimidine-2-carboxamide

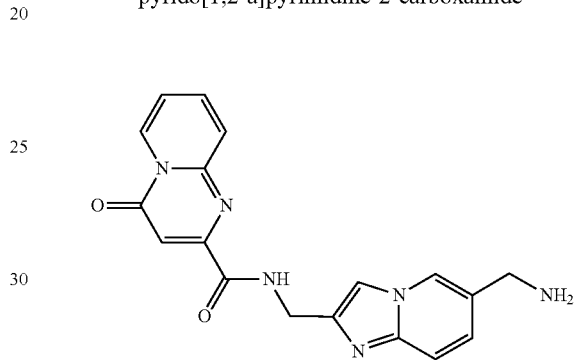

The residual aqueous solution from Compound 49 was concentrated under vacuum and the residue was dissolved in MeOH and purified by ion exchange (SCX-2, 5 g) and the eluted fraction was evaporated under vacuum to a beige solid which was purified by preparative HPLC [method B] to provide the title compound (7.5 mg, 2%) as an off white solid.

LCMS Method C (electrospray): m/z=349.2 (M+H)$^+$, RT=1.47 min

Synthesis of Compound 51: 4-oxo-N-[(6-{[(2,2,2-trifluoroethyl)amino]methyl}imidazo[1,2-a]pyridin-2-yl)methyl]-4H-pyrido[1,2-a]pyrimidine-2-carboxamide

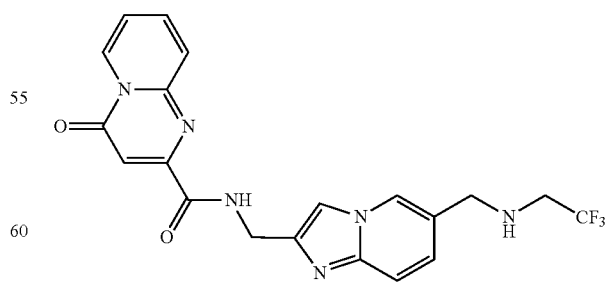

A solution of N-[(6-formylimidazo[1,2-a]pyridin-2-yl)methyl]-4-oxo-pyrido[1,2-a]pyrimidine-2-carboxamide (Compound 49) (50 mg, 0.144 mmol) and 2,2,2-trifluoroethanamine (29 mg, 0.288 mmol) in DCE (2 mL) was stirred at rt for 2 hours before STAB (92 mg, 0.432 mmol) was added and the reaction mixture was stirred at 50° C. for 18 h. The reaction mixture was cooled to RT, STAB (92 mg, 0.432 mmol) was added and the reaction mixture was stirred at 50° C. for 2 h. The reaction mixture was quenched with water (5 mL) and extracted with DCM (3×5 mL). The combined organics were dried, evaporated to dryness and purified by preparative HPLC [method B] to afford the title compound (34 mg, 53%) as a white powder.

LCMS Method E (electrospray): m/z=431.3 (M+H)$^+$, RT=1.18 min

Synthesis of Compounds 52-55

The compounds in table 6 was prepared in the same manner as Compound 47

TABLE 6

| Cpd No | Name | Structure | LCMS method | LCMS Retention time | Mass ion |
|---|---|---|---|---|---|
| 52 | N-[(6-{[(2-hydroxyethyl)amino]methyl}imidazo[1,2-a]pyridin-2-yl)methyl]-4-oxo-4H-pyrido[1,2-a]pyrimidine-2-carboxamide | 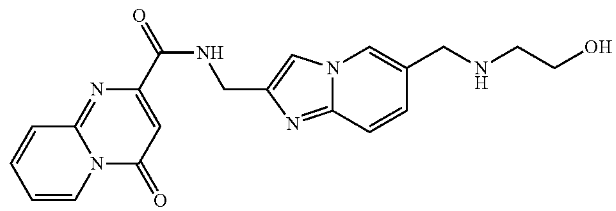 [SMILES: O=C(NCc1cn2cc(CNCCO)ccc2n1)c1cc(=O)n2ccccc2n1] | C | 1.47 | 393.2 |
| 53 | 4-oxo-N-[(6-{[(2-phenylethyl)amino]methyl}imidazo[1,2-a]pyridin-2-yl)methyl]-4H-pyrido[1,2-a]pyrimidine-2-carboxamide | 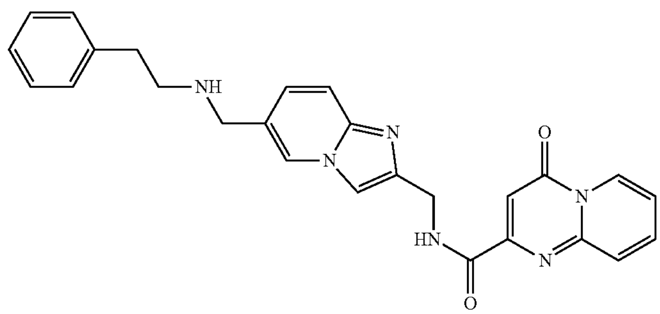 [SMILES: O=C(NCc1cn2cc(CNCCc3ccccc3)ccc2n1)c1cc(=O)n2ccccc2n1] | D | 3.43 | 453.3 |
| 54 | N-({6-[(benzylamino)methyl]imidazo[1,2-a]pyridin-2-yl}methyl)-4-oxo-4H-pyrido[1,2-a]pyrimidine-2-carboxamide | 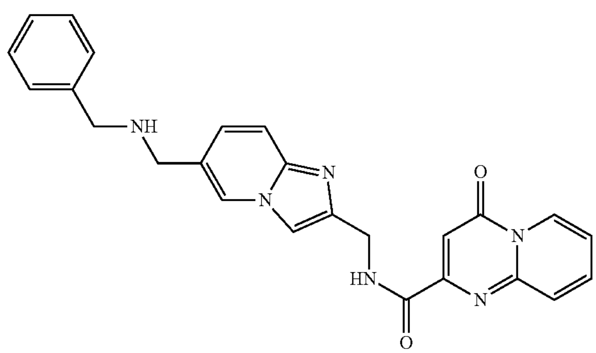 [SMILES: O=C(NCc1cn2cc(CNCc3ccccc3)ccc2n1)c1cc(=O)n2ccccc2n1] | D | 3.37 | 439.3 |
| 55 | 4-oxo-N-[(6-{[(3-phenylpropyl)amino]methyl}imidazo[1,2-a]pyridin-2-yl)methyl]-4H-pyrido[1,2-a]pyrimidine-2-carboxamide | 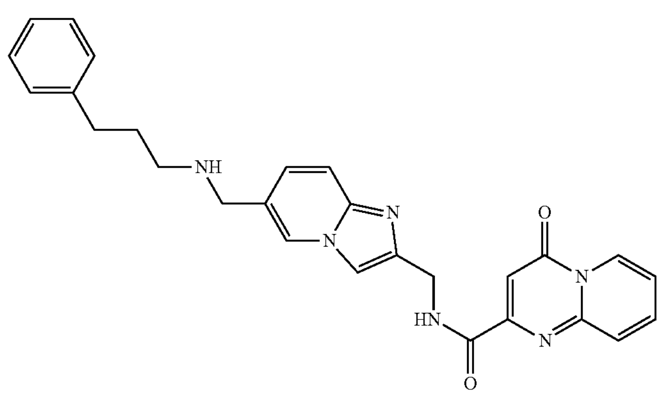 [SMILES: O=C(NCc1cn2cc(CNCCCc3ccccc3)ccc2n1)c1cc(=O)n2ccccc2n1] | D | 3.64 | 467.3 |

TABLE 6-continued

| Cpd No | Name | Structure | LCMS method | LCMS Retention time | Mass ion |
|---|---|---|---|---|---|
| 273 | N-[[6-[[(1-methoxycyclobutyl)methylamino]methyl]imidazo[1,2-a]pyridin-2-yl]methyl]-4-oxo-pyrido[1,2-a]pyrimidine-2-carboxamide | 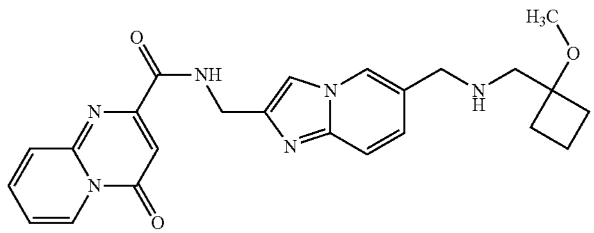 [SMILES: COC1(CNCc2ccc3nc(CNC(=O)c4cc(=O)n5ccccc5n4)cn3c2)CCC1] | D | 3.04 | 447.4 |
| 275 | N-[[6-[[(2-cyano-2-methyl-propyl)amino]methyl]imidazo[1,2-a]pyridin-2-yl]methyl]-4-oxo-pyrido[1,2-a]pyrimidine-2-carboxamide | 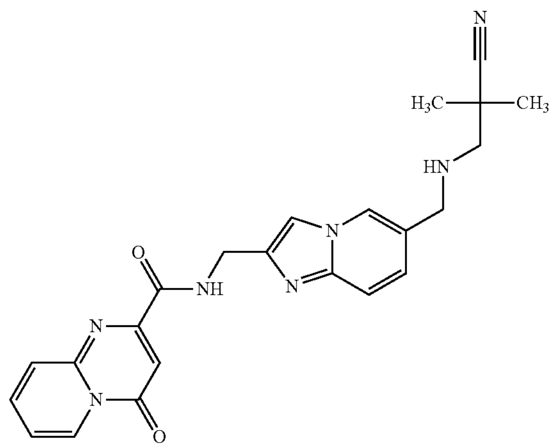 [SMILES: CC(C)(C#N)CNCc1ccc2nc(CNC(=O)c3cc(=O)n4ccccc4n3)cn2c1] | C | 2.19 | 430.1 |
| 276 | N-[[6-[[(3-fluoro-1-bicyclo[1.1.1]pentanyl)methylamino]methyl]imidazo[1,2-a]pyridin-2-yl]methyl]-4-oxo-pyrido[1,2-a]pyrimidine-2-carboxamide | 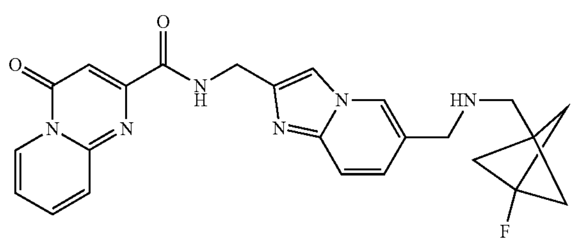 [SMILES: O=C(NCc1cn2cc(CNCC34CC(F)(C3)C4)ccc2n1)c1cc(=O)n2ccccc2n1] | C | 2.36 | 447.3 |
| 277 | 4-oxo-N-[[6-[(spiro[3.3]heptan-2-ylmethylamino)methyl]imidazo[1,2-a]pyridin-2-yl]methyl]pyrido[1,2-a]pyrimidine-2-carboxamide | 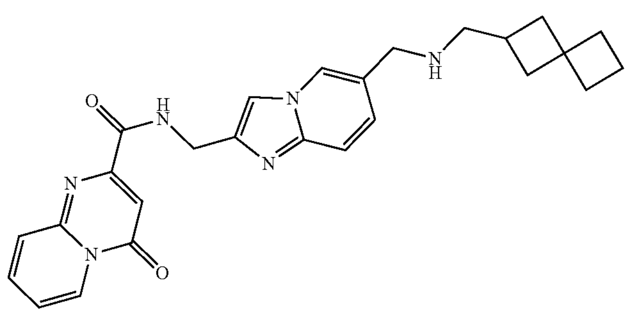 [SMILES: O=C(NCc1cn2cc(CNCC3CC4(CCC4)C3)ccc2n1)c1cc(=O)n2ccccc2n1] | C | 3.12 | 457.4 |
| 278 | 4-oxo-N-[[6-[(spiro[2.3]hexan-5-ylmethylamino)methyl]imidazo[1,2-a]pyridin-2-yl]methyl]pyrido[1,2-a]pyrimidine-2-carboxamide | 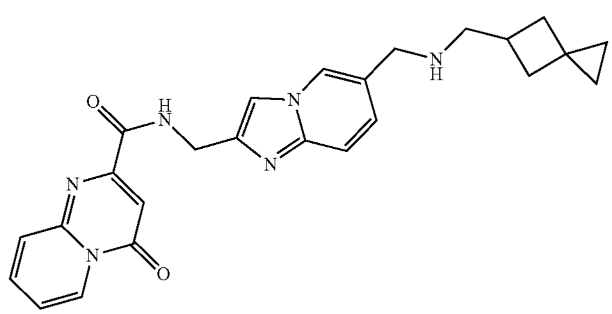 [SMILES: O=C(NCc1cn2cc(CNCC3CC4(CC4)C3)ccc2n1)c1cc(=O)n2ccccc2n1] | C | 2.79 | 443.4 |

TABLE 6-continued

| Cpd No | Name | Structure | LCMS method | LCMS Retention time | Mass ion |
|---|---|---|---|---|---|
| 279 | N-[[6-[(1-bicyclo[1.1.1]pentanyl ethylamino)methyl] imidazo[1,2-a] pyridin-2-yl]methyl]-4-oxo-pyrido[1,2-a] pyrimidine-2-carboxamide | 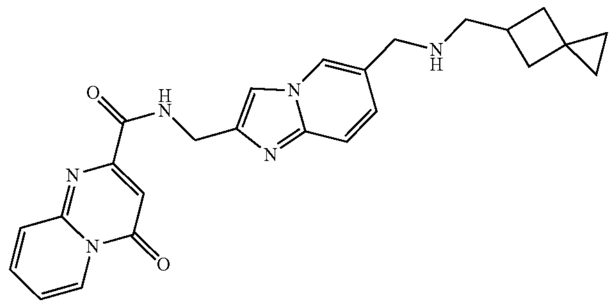 [SMILES: O=C(NCc1cn2cc(CNCC3CC4(CC4)C3)ccc2n1)c1cc(=O)n2ccccc2n1] | D | 3.33 | 429.4 |
| 280 | 4-oxo-N-[[6-[(spiro[2.3]hexan-2-ylamino)methyl]imidazo [1,2-a]pyridin-2-yl]methyl]pyrido[1,2-a]pyrimidine-2-carboxamide | 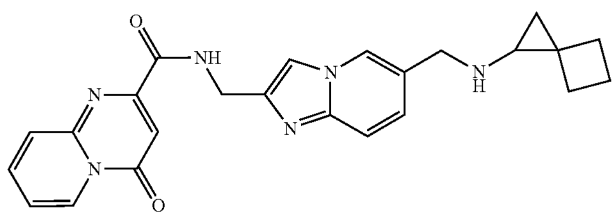 [SMILES: O=C(NCc1cn2cc(CNC3CC34CCC4)ccc2n1)c1cc(=O)n2ccccc2n1] | D | 3.37 | 429.3 |
| 281 | N-[[6-[[(2-methoxy-2-methyl-propyl)amino]methyl] imidazo[1,2-a] pyridin-2-yl]methyl]-4-oxo-pyrido[1,2-a] pyrimidine-2-carboxamide | 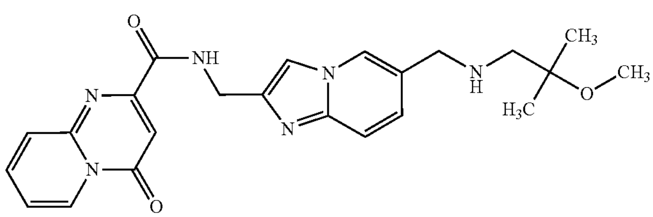 [SMILES: COC(C)(C)CNCc1ccc2nc(CNC(=O)c3cc(=O)n4ccccc4n3)cn2c1] | C | 2.09 | 435.4 |
| 282 | N-[[6-[[(1-methylcyclobutyl) methyl amino]methyl]imidazo [1,2-a]pyridin-2-yl]methyl]-4-oxo-pyrido [1,2-a]pyrimidine-2-carboxamide | 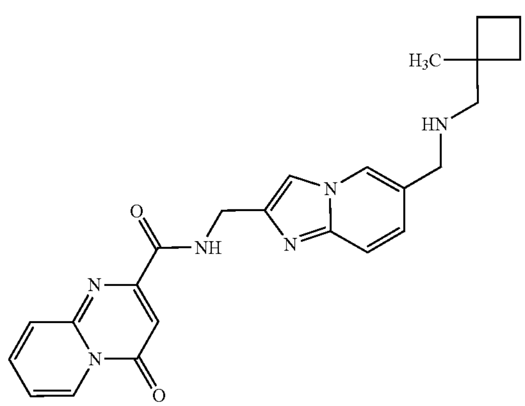 [SMILES: CC1(CNCc2ccc3nc(CNC(=O)c4cc(=O)n5ccccc5n4)cn3c2)CCC1] | D | 3.51 | 431.3 |
| 283 | N-[[6-(butylaminomethyl) imidazo[1,2-a]pyridin-2-yl]methyl]-4-oxo-pyrido[1,2-a] pyrimidine-2-carboxamide | 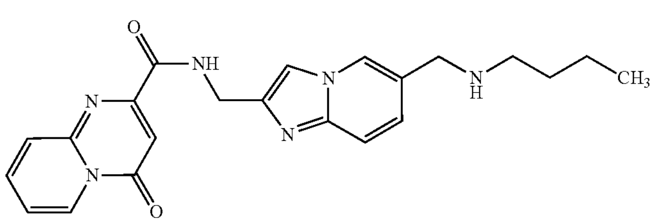 [SMILES: CCCCNCc1ccc2nc(CNC(=O)c3cc(=O)n4ccccc4n3)cn2c1] | D | 3.17 | 405.3 |

TABLE 6-continued

| Cpd No | Name | Structure | LCMS method | LCMS Retention time | Mass ion |
|---|---|---|---|---|---|
| 284 | N-[[6-[[(1-hydroxycyclopentyl)methylamino]methyl]imidazo[1,2-a]pyridin-2-yl]methyl]-4-oxo-pyrido[1,2-a]pyrimidine-2-carboxamide | 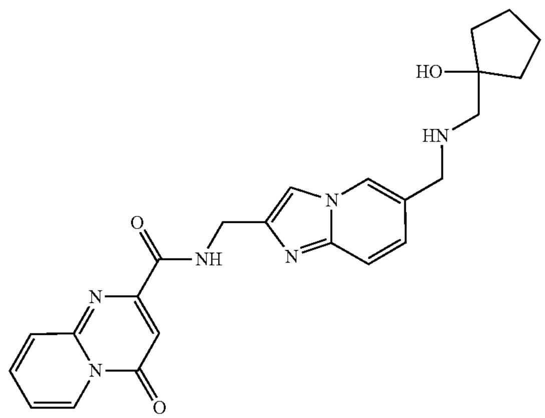 [SMILES: O=C(NCc1cn2cc(CNCC3(O)CCCC3)ccc2n1)c1cc(=O)n2ccccc2n1] | C | 2.06 | 447.4 |
| 285 | N-[[6-[(2-methylbutylamino)methyl]imidazo[1,2-a]pyridin-2-yl]methyl]-4-oxo-pyrido[1,2-a]pyrimidine-2-carboxamide | 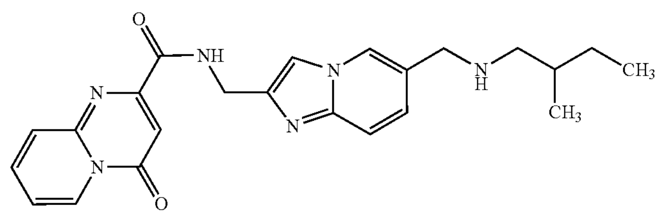 [SMILES: CCC(C)CNCc1ccc2nc(CNC(=O)c3cc(=O)n4ccccc4n3)cn2c1] | | 2.66 | 419.4 |
| 286 | N-[[6-[(2-cyclobutylethylamino)methyl]imidazo[1,2-a]pyridin-2-yl]methyl]-4-oxo-pyrido[1,2-a]pyrimidine-2-carboxamide | 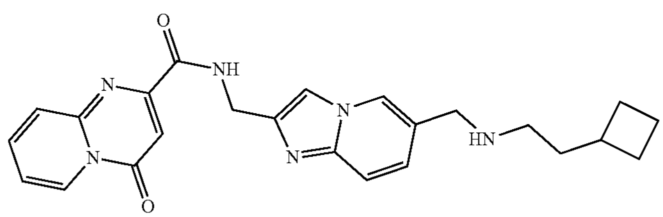 [SMILES: O=C(NCc1cn2cc(CNCCC3CCC3)ccc2n1)c1cc(=O)n2ccccc2n1] | C | 2.75 | 431.3 |
| 287 | N-[[6-[[(2-hydroxy-2-methyl-propyl)amino]methyl]imidazo[1,2-a]pyridin-2-yl]methyl]-4-oxo-pyrido[1,2-a]pyrimidine-2-carboxamide | 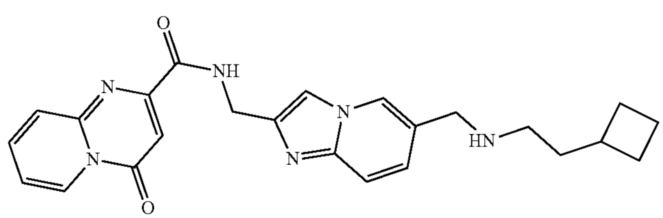 [SMILES: O=C(NCc1cn2cc(CNCCC3CCC3)ccc2n1)c1cc(=O)n2ccccc2n1] | C | 1.76 | 421.3 |
| 288 | N-[[6-[[(1-hydroxycyclobutyl)methylamino]methyl]imidazo[1,2-a]pyridin-2-yl]methyl]-4-oxo-pyrido[1,2-a]pyrimidine-2-carboxamide | 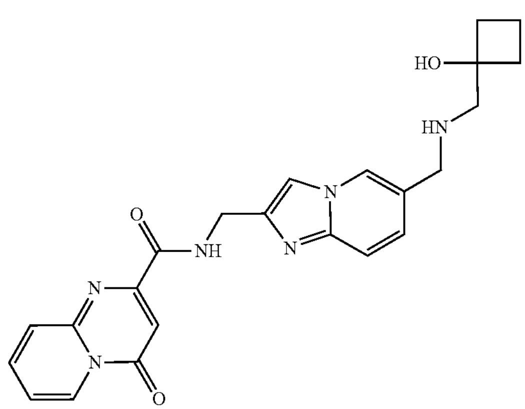 [SMILES: O=C(NCc1cn2cc(CNCC3(O)CCC3)ccc2n1)c1cc(=O)n2ccccc2n1] | C | 1.89 | 433.3 |

TABLE 6-continued

| Cpd No | Name | LCMS method | LCMS Retention time | Mass ion |
|---|---|---|---|---|
| 289 | N-[[6-[(2-hydroxputylamino)methyl]imidazo[1,2-a]pyridin-2-yl]methyl]-4-oxo-pyrido[1,2-a]pyrimidine-2-carboxamide | D | 2.65 | 421.3 |
| 290 | N-[[6-[[(3-methylcyclobutyl)methylamino]methyl]imidazo[1,2-a]pyridin-2-yl]methyl]-4-oxo-pyrido[1,2-a]pyrimidine-2-carboxamide | D | 3.59 | 431.2 |
| 291 | N-[[6-[[(3,3-dimethylcyclobutyl)methylamino]methyl]imidazo[1,2-a]pyridin-2-yl]methyl]-4-oxo-pyrido[1,2-a]pyrimidine-2-carboxamide | D | 3.84 | 445.3 |
| 292 | N-[[6-[(2,2-dimethylbutylamino)methyl]imidazo[1,2-a]pyridin-2-yl]methyl]-4-oxo-pyrido[1,2-a]pyrimidine-2-carboxamide | D | 3.74 | 433.3 |
| 293 | N-[[6-[[[(2S)-2-methylbutyl]amino]methyl]imidazo[1,2-a]pyridin-2-yl]methyl]-4-oxo-pyrido[1,2-a]pyrimidine-2-carboxamide | C | 2.66 | 419.3 |

TABLE 6-continued

| Cpd No | Name | Structure | LCMS method | LCMS Retention time | Mass ion |
|---|---|---|---|---|---|
| 346 | N-[(6-{[({bicyclo[2.2.1]hept-5-en-2-yl}methyl)amino]methyl}imidazo[1,2-a]pyridin-2-yl)methyl]-4-oxo-4H-pyrido[1,2-a]pyrimidine-2-carboxamide | 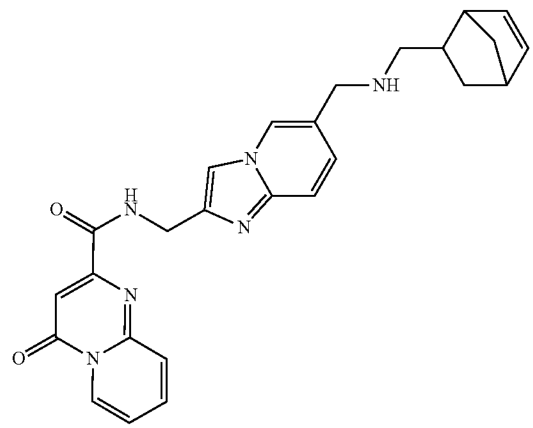 [SMILES: O=C(NCc1cn2cc(CNCC3CC4C=CC3C4)ccc2n1)c1cc(=O)n2ccccc2n1] | D | 3.61 | 455.3 |
| 347 | N-({6-[({[(1R,2R,4S)-bicyclo[2.2.1]heptan-2-yl]methyl}amino)methyl]imidazo[1,2-a]pyridin-2-yl}methyl)-4-oxo-4H-pyrido[1,2-a]pyrimidine-2-carboxamide | 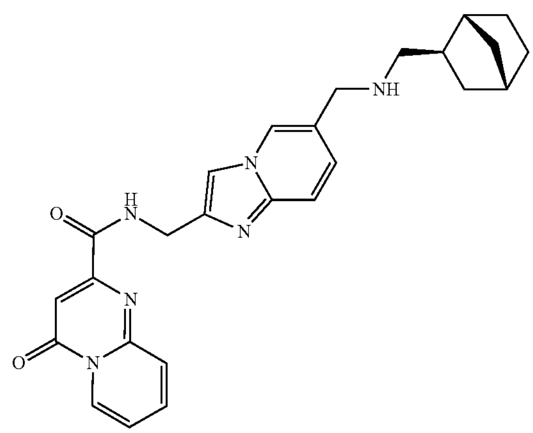 [SMILES: O=C(NCc1cn2cc(CNC[C@@H]3C[C@H]4CC[C@@H]3C4)ccc2n1)c1cc(=O)n2ccccc2n1] | C | 2.93 | 457.4 |
| 348 | N-({6-[({[(1R,2S,4S)-bicyclo[2.2.1]heptan-2-yl]methyl}amino)methyl]imidazo[1,2-a]pyridin-2-yl}methyl)-4-oxo-4H-pyrido[1,2-a]pyrimidine-2-carboxamide | 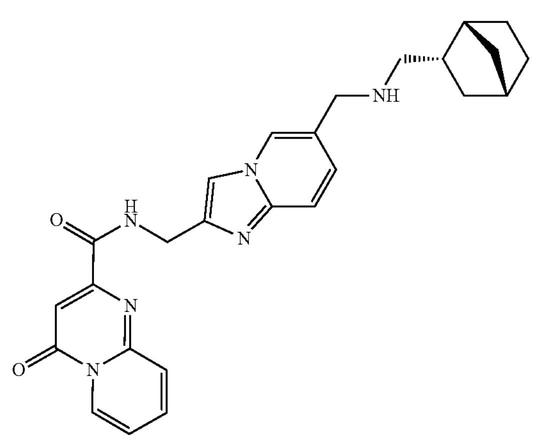 [SMILES: O=C(NCc1cn2cc(CNC[C@H]3C[C@H]4CC[C@@H]3C4)ccc2n1)c1cc(=O)n2ccccc2n1] | C | 3.00 | 457.4 |

TABLE 6-continued

| Cpd No | Name | Structure | LCMS method | LCMS Retention time | Mass ion |
|---|---|---|---|---|---|
| 349 | N-{[6-({2-oxa-5-azabicyclo[2.2.1]heptan-5-yl}methyl)imidazo[1,2-a]pyridin-2-yl]methyl}-4-oxo-4H-pyrido[1,2-a]pyrimidine-2-carboxamide | 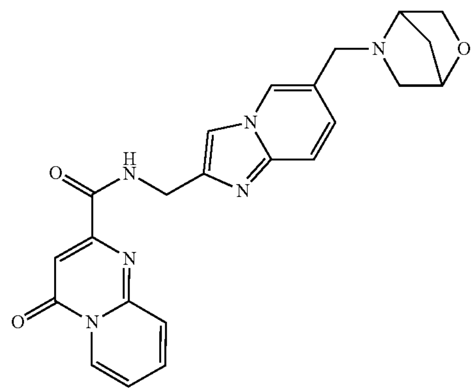 [SMILES: O=C(NCc1cn2cc(CN3CC4CC3CO4)ccc2n1)c1cc(=O)n2ccccc2n1] | C | 1.75 | 431.4 |
| 350 | N-{[6-({2-azabicyclo[2.2.1]heptan-2-yl}methyl)imidazo[1,2-a]pyridin-2-yl]methyl}-4-oxo-4H-pyrido[1,2-a]pyrimidine-2-carboxamide | 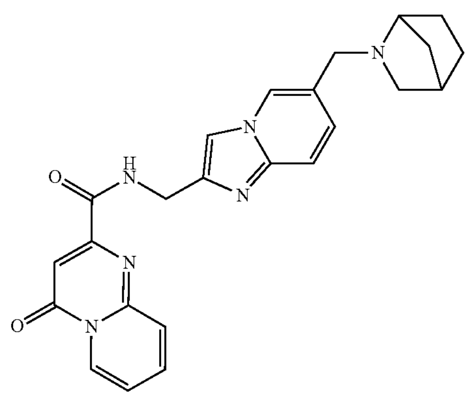 [SMILES: O=C(NCc1cn2cc(CN3CC4CCC3C4)ccc2n1)c1cc(=O)n2ccccc2n1] | C | 2.45 | 429.4 |
| 351 | N-{[6-({2-azabicyclo[2.2.2]octan-2-yl}methyl)imidazo[1,2-a]pyridin-2-yl]methyl}-4-oxo-4H-pyrido[1,2-a]pyrimidine-2-carboxamide | 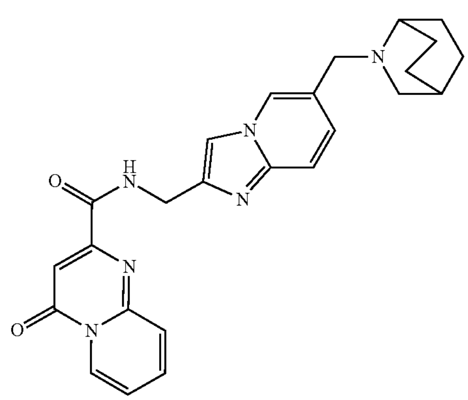 [SMILES: O=C(NCc1cn2cc(CN3CC4CCC3CC4)ccc2n1)c1cc(=O)n2ccccc2n1] | C | 2.80 | 443.3 |

TABLE 6-continued

| Cpd No | Name | Structure | LCMS method | LCMS Retention time | Mass ion |
|---|---|---|---|---|---|
| 352 | N-({6-[({6,6-difluorospiro[3.3]heptan-2-yl}amino)methyl]imidazo[1,2-a]pyridin-2-yl}methyl)-4-oxo-4H-pyrido[1,2-a]pyrimidine-2-carboxamide | 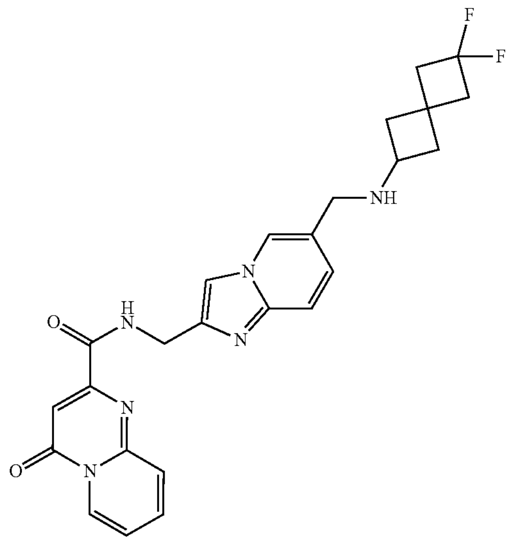 [SMILES: O=C(NCc1cn2cc(CNC3CC4(C3)CC(F)(F)C4)ccc2n1)c1cc(=O)n2ccccc2n1] | C | 2.55 | 479.3 |
| 353 | rac-N-({6-[({[(1R,2R,4R)-7-oxabicyclo[2.2.1]hept-5-en-2-yl]methyl}amino)methyl]imidazo[1,2-a]pyridin-2-yl}methyl)-4-oxo-4H-pyrido[1,2-a]pyrimidine-2-carboxamide | 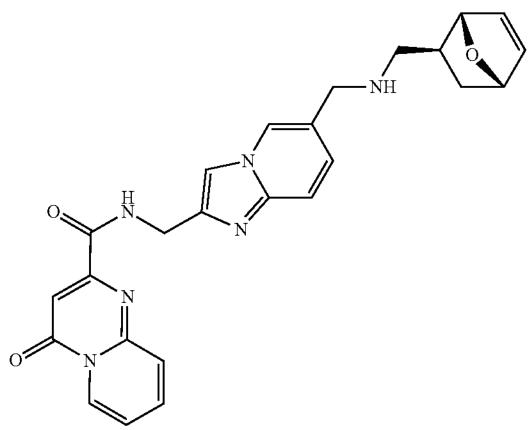 [SMILES: O=C(NCc1cn2cc(CNC[C@@H]3C[C@H]4C=C[C@@H]3O4)ccc2n1)c1cc(=O)n2ccccc2n1] | C | 1.97 | 457.4 |
| 354 | rac-N-({6-[({[(1R,2S,4R)-7-oxabicyclo[2.2.1]hept-5-en-2-yl]methyl}amino)methyl]imidazo[1,2-a]pyridin-2-yl}methyl)-4-oxo-4H-pyrido[1,2-a]pyrimidine-2-carboxamide | 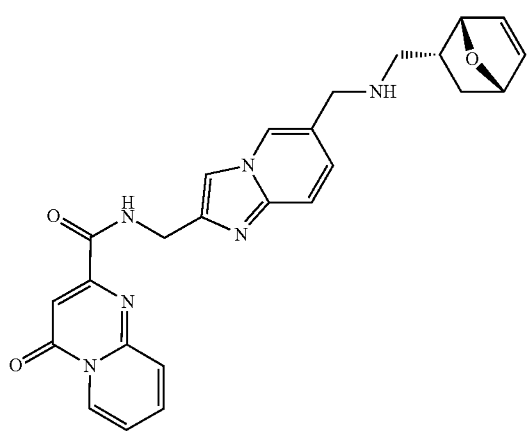 [SMILES: O=C(NCc1cn2cc(CNC[C@H]3C[C@H]4C=C[C@@H]3O4)ccc2n1)c1cc(=O)n2ccccc2n1] | C | 1.92 | 457.3 |

Synthesis of Compound 56: N-({6-[hydroxy(phenyl)methyl]imidazo[1,2-a]pyridin-2-yl}methyl)-4-oxo-4H-pyrido[1,2-a]pyrimidine-2-carboxamide Synthesis of Compound 58: N-({6-ethenylimidazo[1,2-a]pyridin-2-yl}methyl)-4-oxo-4H-pyrido[1,2-a]pyrimidine-2-carboxamide

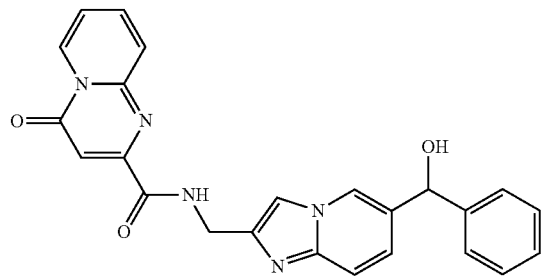 [SMILES: O=C(NCc1cn2cc(C(O)c3ccccc3)ccc2n1)c1cc(=O)n2ccccc2n1]

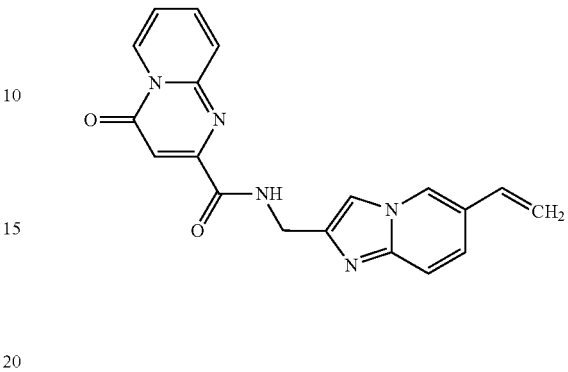

Phenyl magnesium bromide (1M in THF, 207 uL, 0.207 mmol) was added dropwise over 1 min to a solution of N-[(6-formylimidazo[1,2-a]pyridin-2-yl)methyl]-4-oxo-pyrido[1,2-a]pyrimidine-2-carboxamide (Compound 49) (30 mg, 0.0864 mmol) in THF (2 mL) at −30° C. The reaction mixture was then warmed to 0° C. and stirred for 2 hours. The stirring was continued for 16 hours during which time the reaction warmed to room temperature. The reaction mixture was re-cooled to −30° C. and treated with Phenyl magnesium bromide (1M in THF, 103 uL, 0.1 mmol) and the mixture was stirred at 0° C. for a further 30 minutes. The mixture was quenched by the addition of NH$_4$Cl (sat 10 mL) and extracted with DCM (3×15 mL) and the organics were dried and evaporated to dryness to afford a residue which was purified by Preparative HPLC [method B] and the fractions were freeze dried to afford the title compound (4.4 mg, 12%) as a white foam.

LCMS Method D (electrospray): m/z=426.2 (M+H)$^+$, RT=3.10 min

N-[(6-bromoimidazo[1,2-a]pyridin-2-yl)methyl]-4-oxo-pyrido[1,2-a]pyrimidine-2-carboxamide (Compound 23) (150 mg, 0.38 mmol), potassium ethenyl(trifluoro)borate (76 mg, 0.57 mmol) and K$_2$CO$_3$ (1.2M aqueous, 941 µl, 1.13 mmol) were combined in 1,4-Dioxane (4 ml) and the mixture was sparged with nitrogen for 5 mins. Pd-118 (25 mg, 0.04 mmol) was added and the mixture was sparged for a further 5 mins. The vessel was sealed and the mixture heated at 1000 for 2 hours. The reaction mixture was cooled to room temperature and diluted with sodium hydrogen carbonate (sat, 30 ml) and extracted with chloroform/isopropanol (3:1, 3×50 ml) and the combined organic extracts were dried over sodium sulfate and evaporated under vacuum. The residue was purified by chromatography on silica gel (Biotage 28 g kp-NH, eluting with 0-100% ethyl acetate/heptane). The residue after evaporation was triturated with ethyl acetate/heptane. The solids were collected by filtration, washed with heptane and dried under suction to afford the title compound (73 mg, 56% yield) as a white solid.

LCMS Method E (electrospray): m/z=346.1 (M+H)$^+$, RT=1.17 min

Synthesis of Compound 57

The compound in table 7 was prepared in a similar manner to Compound 56

Synthesis of Compounds 59-61

The compounds in table 8 was prepared in a similar manner to Compound 58

TABLE 7

| Compound No | Name | Structure | LCMS method | LCMS Retention time | Mass ion |
|---|---|---|---|---|---|
| 57 | N-{[6-(1-hydroxyethyl)imidazo[1,2-a]pyridin-2-yl]methyl}-oxo-4H-pyrido[1,2-a]pyrimidine-2-carboxamide | 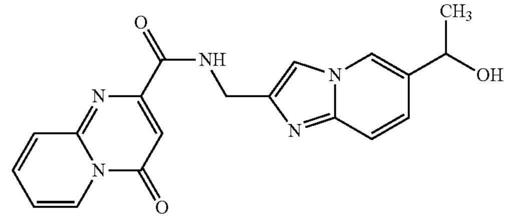 [SMILES: CC(O)c1ccc2nc(CNC(=O)c3cc(=O)n4ccccc4n3)cn2c1] | D | 2.54 | 364.2 |

TABLE 8

| Compound No | Name | Structure | LCMS method | LCMS Retention time | Mass ion | catalyst |
|---|---|---|---|---|---|---|
| 59 | N-({6-cyclopropyl-imidazo[1,2-a]pyridin-2-yl}methyl)-4-oxo-4H-pyrido[1,2-a]pyrimidine-2-carboxamide | 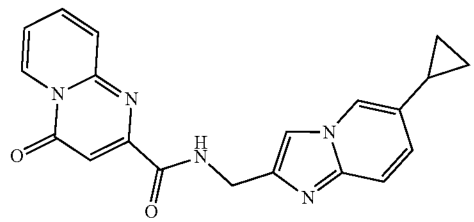 [SMILES: O=C(NCc1cn2cc(C3CC3)ccc2n1)c1cc(=O)n2ccccc2n1] | D | 3.27 | 360.3 | Pd118 Followed by PddppfCl2 |
| 60 | N-({7-ethenylimidazo[1,2-a]pyridin-2-yl}methyl)-4-oxo-4H-pyrido[1,2-a]pyrimidine-2-carboxamide | 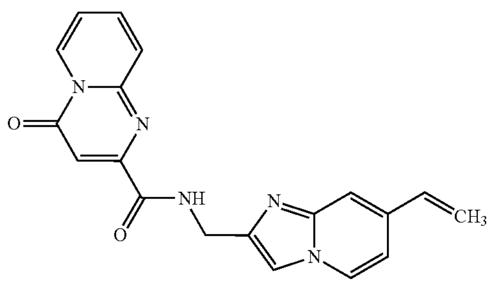 [SMILES: C=Cc1ccn2cc(CNC(=O)c3cc(=O)n4ccccc4n3)nc2c1] | D | 3.12 | 346.2 | |
| 61 | N-{[6-(hydroxymethyl)imidazo[1,2-a]pyridin-2-yl]methyl}-4-oxo-4H-pyrido[1,2-a]pyrimidine-2-carboxamide | 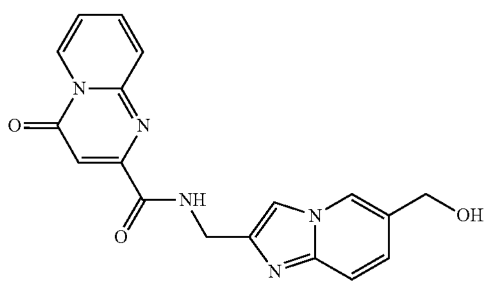 [SMILES: O=C(NCc1cn2cc(CO)ccc2n1)c1cc(=O)n2ccccc2n1] | D | 2.45 | 350.3 | Ruphos, Acetyl protected |

Synthesis of Compound 62: 2-(1H-indazol-4-yl)-5-[(6-methylimidazo[1,2-a]pyridin-2-yl)methyl]-1,3,4-oxadiazole

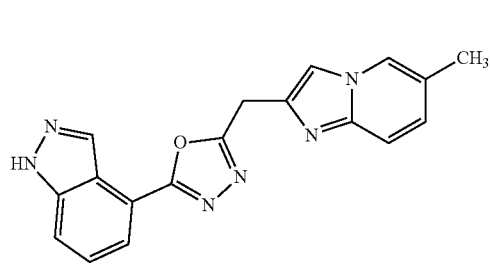 [SMILES: Cc1ccc2nc(Cc3nnc(-c4cccc5[nH]ncc45)o3)cn2c1]

Step 1: ({[(benzyloxy)carbonyl]amino}amino)[1-(oxan-2-yl)-1H-indazol-4-yl]methanone

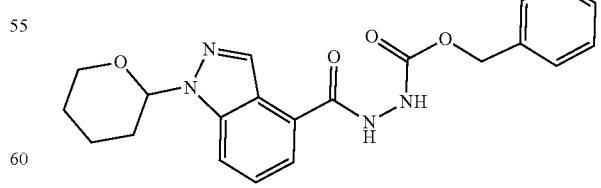

A solution of 1-tetrahydropyran-2-ylindazole-4-carboxylic acid (900 mg, 3.65 mmol), benzyl N-aminocarbamate (729 mg, 4.39 mmol) and triethylamine (1.53 ml, 11.0 mmol) were combined in DMF (10 ml), HATU (2.08 g, 5.48 mmol) was added and the mixture was stirred at room temperature for 7 hours. The reaction mixture was diluted with ethyl acetate (100 ml) and washed with sodium hydrogen carbonate (sat, 100 ml) and brine (4×100 ml). The organic layer was dried over sodium sulfate and evaporated under vacuum. The residue was purified by chromatography on silica gel (Biotage 50 g, eluting with 0-100% ethyl acetate/heptane) to afford the title compound (1.42 g, 91%) as a pale pink solid.

LCMS Method A (electrospray): m/z=393.15 (M–H)⁻, RT=1.09 min

Step 2: 1-(oxan-2-yl)-1H-indazole-4-carbohydrazide

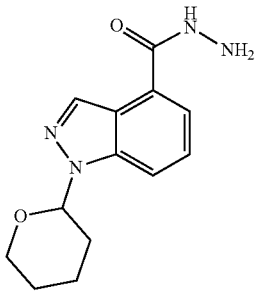 [SMILES: NNC(=O)c1cccc2c1cnn2C1CCCCO1]

A suspension of benzyl N-[(1-tetrahydropyran-2-ylindazole-4-carbonyl)amino]carbamate (500 mg, 1.17 mmol) and Palladium on carbon (10% wt, 124 mg, 0.12 mmol) were suspended in ethanol (50 ml) and the mixture stirred vigorously under an atmosphere of hydrogen (1 atm) at room temperature for 6 h. The catalyst was removed by filtration through Celite, washing with MeOH, then ammonia in MeOH (7M) and the filtrate evaporated under vacuum. The residue was purified by ion exchange [SCX-2, 10 g] and the residue triturated with ethyl acetate/heptane to afford the title compound (158 mg, 52%) as a pale yellow solid.

LCMS Method A (electrospray): m/z=261.0 (M+H)⁺, RT=0.84 min

Step 3: 2-{6-methylimidazo[1,2-a]pyridin-2-yl}-N'-[1-(oxan-2-yl)-1H-indazole-4-carbonyl]acetohydrazide

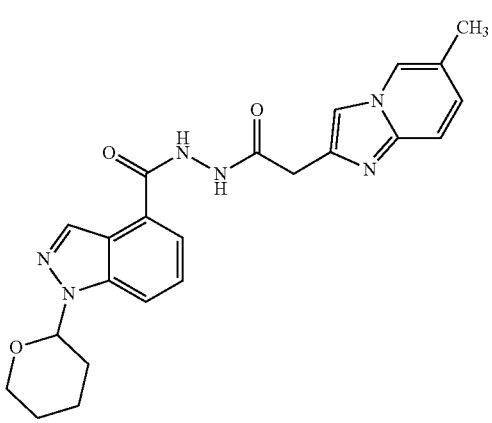 [SMILES: Cc1ccc2nc(CC(=O)NNC(=O)c3cccc4c3cnn4C3CCCCO3)cn2c1]

The title compound was prepared by coupling 1-(oxan-2-yl)-1H-indazole-4-carbohydrazide with Intermediate 19 using the coupling described in Compound 1 and DMF as solvent to give (178 mg, 67%) as yellow solid.

LCMS Method A (electrospray): m/z=433.2 (M+H)⁺, RT=0.84 min

Step 4: 4-[5-({6-methylimidazo[1,2-a]pyridin-2-yl}methyl)-1,3,4-oxadiazol-2-yl]-1H-indazole

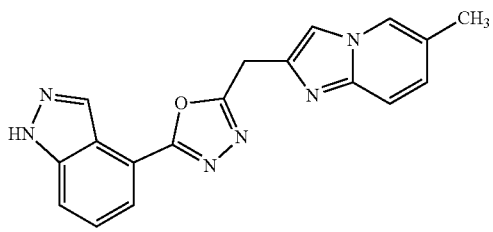 [SMILES: Cc1ccc2nc(Cc3nnc(-c4cccc5[nH]ncc45)o3)cn2c1]

A suspension of N'-[2-(6-methylimidazo[1,2-a]pyridin-2-yl)acetyl]-1-tetrahydropyran-2-yl-indazole-4-carbohydrazide (150 mg, 0.35 mmol) in phosphoryl trichloride (5 ml) was heated at 100° C. for 1.5 hours. The reaction mixture was cooled to room temperature and poured slowly onto a slurry of solid K₂CO₃ and ice. The mixture was stirred vigorously [gas evolution; significant exotherm] until the ice had melted. The mixture was extracted with chloroform/isopropanol (3:1, 4×80 ml). The extracts were dried over sodium sulfate and evaporated under vacuum. The residue was purified by ion exchange [SCX-2, 10 g]. The residue was purified by preparative HPLC (method B) and the residue was triturated with ethyl acetate/heptane, the solids were collected by filtration, washed with heptane and dried under vacuum to afford the title compound (21.3 mg, 19%) as an off-white solid.

LCMS Method D (electrospray): m/z=331.2 (M+H)⁺, RT=3.20 min

Further Organic Synthesis

Intermediate 20: tert-butyl N-{2-[2-(aminomethyl)imidazo[1,2-a]pyridin-6-yl]ethyl}carbamate

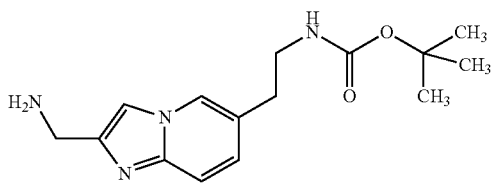 [SMILES: CC(C)(C)OC(=O)NCCc1ccc2nc(CN)cn2c1]

Step 1: tert-butyl N-[2-(6-nitro-3-pyridyl)ethyl]carbamate

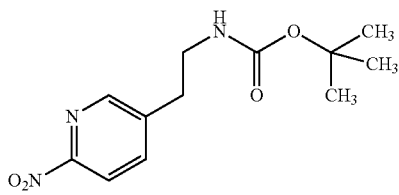 [SMILES: CC(C)(C)OC(=O)NCCc1ccc([N+](=O)[O-])nc1]

5-bromo-2-nitro-pyridine (1000 mg, 4.93 mmol), potassium; 2-(tert-butoxycarbonylamino)ethyl-trifluoro-boranuide (1.36 g, 5.41 mmol), cesium carbonate (4815 mg, 14.8 mmol) and [1,1'-Bis(diphenylphosphino)ferrocene]palladium(II) chloride dichloromethane complex (302 mg, 0.369 mmol) were combined in toluene (20 mL) and water (5 mL) and the mixture was heated at 80° C. for 16 hours. The reaction mixture was cooled to room temperature whereupon water (20 mL) was added and the aqueous were extracted with EtOAc (2×30 mL). The combined organic layer was washed with brine, dried over Na₂SO₄, filtered and evaporated under reduced pressure to give a brown gum, which was purified by chromatography on silica gel [Biotage 100 g, eluting by 10%-80% EtOAc in heptane] to provide the title compound (900 mg, 55%) as an off white solid.

Method A: LC-MS (electrospray): m/z=267.9 (M+H)⁺, RT=1.06 min.

Step 2: tert-butyl N-[2-(6-aminopyridin-3-yl)ethyl] carbamate

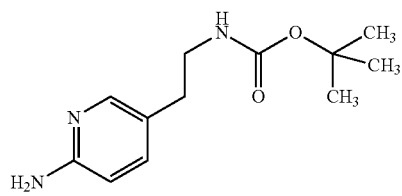

tert-butyl N-[2-(6-nitro-3-pyridyl)ethyl]carbamate (1.07 g, 4.00 mmol) and Pd/C (10%) were combined in EtOH (25 mL). The mixture placed under an atmosphere of hydrogen and the reaction mixture was stirred at room temperature for 4 hours. The catalyst was removed by filtration washing with methanol and the filtrate was evaporated under vacuum to provide the title compound (1000 mg, 95%) as a colourless oil.

Method A: LC-MS (electrospray): m/z=238.0 (M+H)⁺, RT=0.66 min.

Step 3: tert-butyl N-(2-{2-[(1,3-dioxo-2,3-dihydro-1H-isoindol-2-yl)methyl]imidazo[1,2-a]pyridin-6-yl}ethyl)carbamate

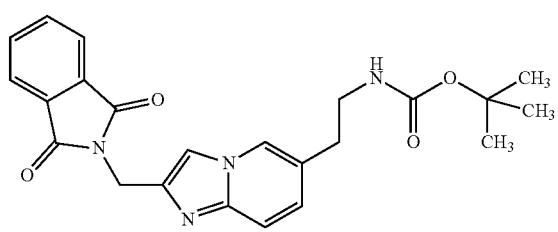 [SMILES: CC(C)(C)OC(=O)NCCc1ccc2nc(CN3C(=O)c4ccccc4C3=O)cn2c1]

The title compound was prepared using the method described for Intermediate 7 Step 1 and triturating with MeCN to provide the title compound (600 mg, 38%) as an off white solid.

Method A: LC-MS (electrospray): m/z=421.55 (M+H)⁺, RT=0.94 min.

Step 4: tert-butyl N-{2-[2-(aminomethyl)imidazo[1,2-a]pyridin-6-yl]ethyl}carbamate

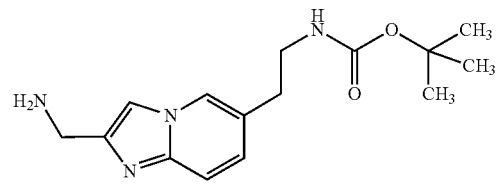 [SMILES: CC(C)(C)OC(=O)NCCc1ccc2nc(CN)cn2c1]

The title compound was prepared using the method described for Intermediate 7 Step 2 to provide the title compound (170 mg, 41%) as a yellow solid.

Method A: LC-MS (electrospray): m/z=291.10 (M+H)⁺, RT=0.70 min.

Intermediate 21: 4-oxo-6,7,8,9-tetrahydropyrido[1,2-a]pyrimidine-2-carboxylic acid hydrochloride

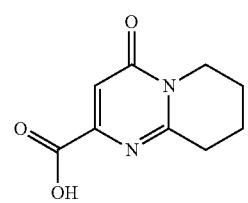

A suspension of rhodium (504 mg, 4.90 mmol) in ethanol (20 mL) was placed under a nitrogen atmosphere. 4-oxopyrido[1,2-a]pyrimidine-2-carboxylate hydrochloride (Intermediate 4, 60%, 1000 mg, 2.66 mmol) was added. The mixture was placed under an atmosphere of hydrogen and the mixture was stirred at room temperature for 4 hours. The catalyst was removed by filtration and the filtrate was evaporated under vacuum to afford a brown gum which crystallised on standing to give the title compound (600 mg, 97%) as beige solid.

Method B: LC-MS (electrospray): m/z=195.2 (M+H)⁺, RT=0.28 min.

Intermediate 22: 2-(aminomethyl)-N-benzylimidazo[1,2-a]pyridine-6-carboxamide

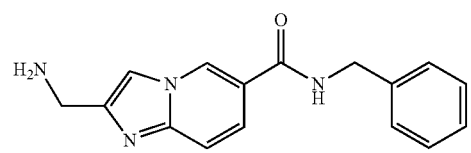 [SMILES: NCc1cn2cc(C(=O)NCc3ccccc3)ccc2n1]

Step 1: methyl 2-(chloromethyl)imidazo[1,2-a]pyridine-6-carboxylate

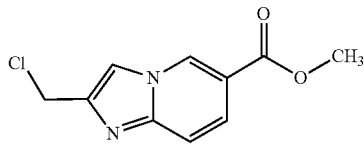

The title compound was prepared using the method described in Intermediate 8 Step 1, to provide (741 mg, 48%) as a white solid.

Method B: LC-MS (electrospray): m/z=225.1 (M+H)$^+$, RT=1.31 min.

Step 2: methyl 2-({bis[(tert-butoxy)carbonyl]amino}methyl)imidazo[1,2-a]pyridine-6-carboxylate

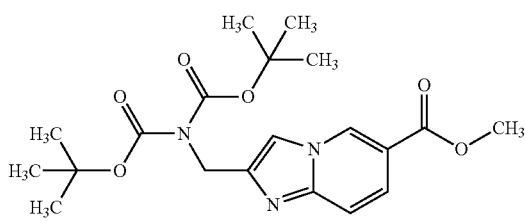 [SMILES: COC(=O)c1ccc2nc(CN(C(=O)OC(C)(C)C)C(=O)OC(C)(C)C)cn2c1]

A mixture of methyl 2-(chloromethyl)imidazo[1,2-a]pyridine-6-carboxylate (740 mg, 3.29 mmol), di-tert-butyl imidodicarbonate (1.07 g, 4.94 mmol), NaI (50 mg, 0.33 mmol) and K$_2$CO$_3$ (1.37 g, 9.88 mmol) were combined in acetonitrile (40 mL) and the mixture stirred at room temperature for an hour before water (1 mL) was added and the mixture heated at reflux for an hour. The reaction mixture was cooled to room temperature and concentrated under vacuum. The residue was suspended in saturated aqueous sodium hydrogen carbonate (50 mL) and extracted with DCM (4×80 mL). The combined organic extracts were dried over sodium sulfate and evaporated under vacuum. The residue was purified by chromatography on silica gel (Biotage 50 g kp-Sil, eluting with EtOAc/heptane 0-50%) to afford the title compound (1.13 g 77%, 91% purity) as a viscous yellow oil which solidified on standing.

Method B: LC-MS (electrospray): m/z=406.2 (M+H)$^+$, RT=1.72 min.

Step 3: 2-({bis[(tert-butoxy)carbonyl]amino}methyl)imidazo[1,2-a]pyridine-6-carboxylic acid A mixture of methyl 2-(chloromethyl)imidazo[1,2-a]pyridine-6-carboxylate (740 mg, 3.29 mmol), di-tert-butyl imidodicarbonate (1.07 g, 4.94 mmol), NaI (50 mg, 0.33 mmol) and K$_2$CO$_3$ (1.37 g, 9.88 mmol) were combined in Acetonitrile (40 mL) and the mixture stirred at room temperature for an hour before water (1 mL) was added and the mixture heated at reflux for an hour. The reaction mixture was cooled to room temperature and concentrated under vacuum. The residue was suspended in aqueous sodium hydrogen carbonate (sat, 50 mL) and extracted with DCM (4×80 mL). The combined organic extracts were dried over sodium sulfate and evaporated under vacuum. The residue was purified by chromatography on silica gel (Biotage 50 g kp-Sil, eluting with EtOAc/heptane 0-50%) to afford the title compound (1.13 g 77%, 91% purity) as a viscous yellow oil which solidified on standing.

Method B: LC-MS (electrospray): m/z=406.2 (M+H)$^+$, RT=1.72 min.

Step 3: 2-({bis[(tert-butoxy)carbonyl]amino}methyl)imidazo[1,2-a]pyridine-6-carboxylic acid

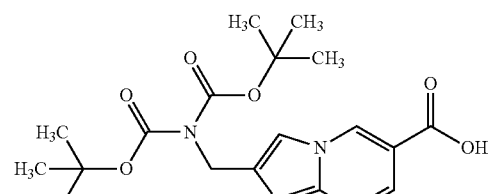

Methyl 2-[[bis(tert-butoxycarbonyl)amino]methyl]imidazo[1,2-a]pyridine-6-carboxylate (500 mg, 1.23 mmol) was dissolved in THF (25 mL) and water (10 mL), lithium hydroxide (240 mg, 5.98 mmol) was added which caused instant decolourisation of the yellow solution and the mixture was stirred at room temperature for 70 minutes. The reaction mixture was acidified with HCl (2M, pH-5) and extracted with chloroform/isopropanol (3:1, 3×80 mL). The combined organic extracts were dried over sodium sulfate and evaporated under vacuum to afford the title compound (405 mg, 84%) as a white solid.

Method B: LC-MS (electrospray): m/z=392.2 (M+H)$^+$, RT=1.17 min.

Step 4: tert-butyl N-{[6-(benzylcarbamoyl)imidazo[1,2-a]pyridin-2-yl]methyl}-N-[(tert-butoxy)carbonyl]carbamate

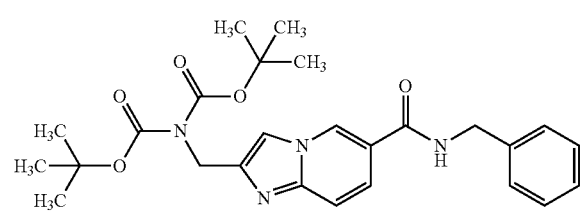 [SMILES: CC(C)(C)OC(=O)N(Cc1cn2cc(C(=O)NCc3ccccc3)ccc2n1)C(=O)OC(C)(C)C]

Prepared using the coupling conditions described in Example 1 and purified by chromatography on silica gel (Biotage 25 g kp-Sil, eluting with EtOAc/heptane 0-100%) to afford the title compound (493 mg, 99%) as a pink solid.

Method B: LC-MS (electrospray): m/z=481.25 (M+H)$^+$, RT=1.13 min.

Step 5: 2-(aminomethyl)-N-benzylimidazo[1,2-a]pyridine-6-carboxamide dihydrochloride

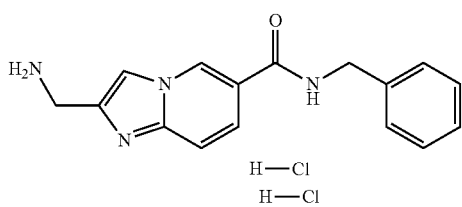

A solution of tert-butyl N-[[6-(benzylcarbamoyl)imidazo[1,2-a]pyridin-2-yl]methyl]-N-tert-butoxycarbonyl-carbamate (493 mg, 1.03 mmol) in methanol (20 mL) was treated with HCl (4M in Dioxane, 3 mL, 12 mmol) and the mixture was heated at 50° C. for an hour. The reaction mixture was cooled to room temperature and evaporated to dryness under vacuum to afford the title compound (346 mg, 95%) as a white solid.

Method B: LC-MS (electrospray): m/z=281.05 (M+H)$^+$, RT=0.71 min.

Intermediate 23: 2-(azidomethyl)-6-methylimidazo[1,2-a]pyridine

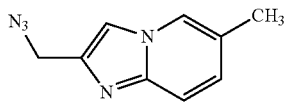

A suspension of 2-(chloromethyl)-6-methyl-imidazo[1,2-a]pyridine hydrochloride (532 mg, 2.45 mmol), triethylamine (1 mL, 7.35 mmol) and NaI (111 mg, 0.74 mmol) were suspended in DMF (5 mL) before sodium azide (175 mg, 2.70 mmol) was added and the mixture was stirred at room temperature For 16 hours. The reaction mixture was quenched with saturated aqueous sodium hydrogen carbonate (20 mL) and extracted with chloroform/isopropanol (3:1, 4×30 mL) and the combined organic extracts were dried over sodium sulfate and evaporated under vacuum. The residue was purified by chromatography on silica gel (Biotage 28 g kp-NH, eluting with EtOAc/heptane 0-100%) to afford the title compound (291 mg, 63%) as a colourless oil.

Method B: LC-MS (electrospray): m/z=188.2 (M+H)$^+$, RT=1.33 min.

Intermediate 24: 4-ethynyl-1-(oxan-2-yl)-1H-indazole

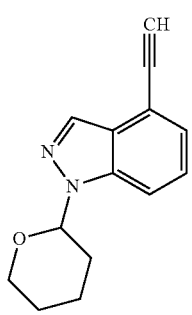

Step 1: 4-bromo-1-tetrahydropyran-2-yl-indazole

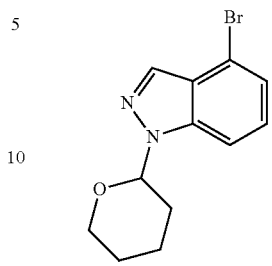

A solution of 4-bromo-1H-indazole (2.3 g, 11.7 mmol) and tosic acid monohydrate (444 mg, 2.33 mmol) in DCM (50 mL) was treated with 3,4-dihydro-2H-pyran (1.60 mL, 17.5 mmol) and the mixture was stirred at room temperature for 2 hours during which time the solution turned brown. The reaction mixture was quenched with saturated aqueous sodium hydrogen carbonate (50 mL) the phases were separated and the aqueous phase was extracted with DCM (2×80 mL) and the combined organic layers were dried over sodium sulfate and evaporated under vacuum. The residue was purified by chromatography on silica gel (Biotage 50 g kp-Sil, eluting with EtOAc/heptane 0-50%) to afford the title compound (3.4 g, 91%) as a pale yellow oil which solidified on standing to a white solid.

Method B: LC-MS (electrospray): m/z=281.1/283.1 (M+H)$^+$, RT=1.74 min.

Step 2: 1-(oxan-2-yl)-4-[2-(trimethylsilyl)ethynyl]-1H-indazole

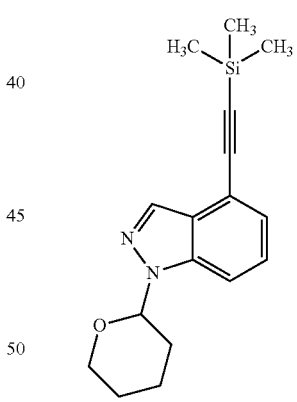

4-bromo-1-tetrahydropyran-2-yl-indazole (1 g, 3.56 mmol), CuI (68 mg, 0.36 mmol), PdCl$_2$(PPh$_3$)$_2$ (125 mg, 0.18 mmol) and triethylamine (1.5 mL, 3.03 mmol) were combined in anhydrous THF (7.5 mL) and the mixture sparged with nitrogen for 5 minutes. Ethynyl(trimethyl)silane (739 μl, 5.34 mmol) was added, the vessel was sealed and the mixture heated at 80° C. for 48 hours. The reaction mixture was cooled to room temperature and diluted with EtOAc (100 mL). The mixture was washed with saturated aqueous sodium hydrogen carbonate (80 mL) and brine (2×80 mL) and the organic phase was dried over sodium sulfate and evaporated under vacuum. The residue was purified by chromatography on silica gel (Biotage 50 g kp-Sil, eluting with EtOAc/heptane 0-50%) to afford the crude title compound contaminated with starting material (1.15 g, 52%, 48% purity) as a brown oil.

Method B: LC-MS (electrospray): m/z=299.0 (M+H)$^+$, RT=1.52 min.

Step 3: 4-ethynyl-1-(oxan-2-yl)-1H-indazole

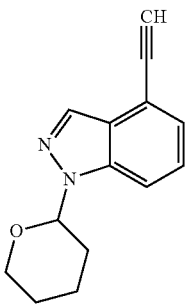

A solution of trimethyl-[2-(1-tetrahydropyran-2-ylindazol-4-yl)ethynyl]silane (1.15 g, 1.93 mmol) in methanol (30 mL) was treated with K$_2$CO$_3$ (100 mg, 0.72 mmol) and the mixture was stirred at room temperature for 16 hours. The reaction mixture was filtered and the filtrate were evaporated under vacuum. The resultant residue was purified by chromatography on silica gel (Biotage 25 g kp-Sil, eluting with TMBE/heptane 0-40%) to afford the title compound (207 mg, 39%) of as a pale yellow oil which slowly solidified on standing.

Method B: LC-MS (electrospray): m/z=226.95 (M+H)$^+$, RT=1.23 min.

Intermediate 25: (6-{[(cyclohexylmethyl)amino]methyl}imidazo[1,2-a]pyridin-2-yl)methanamine trihydrochloride

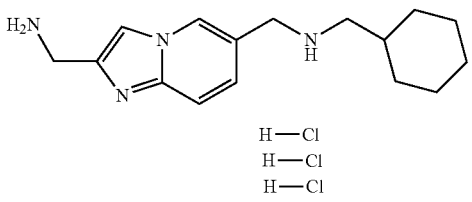

Step 1: tert-butyl N-({6-cyanoimidazo[1,2-a]pyridin-2-yl}methyl)carbamate

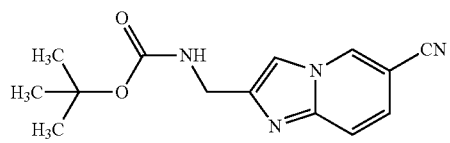

A suspension of 2-(aminomethyl)imidazo[1,2-a]pyridine-6-carbonitrile (2.60 g, 15.1 mmol) and N-ethyl-N-isopropylpropan-2-amine (3.7 mL, 20.9 mmol) in THF (35 mL) and DCM (35 mL) was treated with N,N-dimethylpyridin-4-amine (0.085 g, 0.697 mmol) and tert-butoxycarbonyl tert-butyl carbonate (3.40 g, 15.6 mmol) at 0° C. and the mixture was allowed to warm to room temperature and stirred at room temperature for 65 hours. The reaction mixture was concentrated under vacuum, the residue was suspended in water-CH$_3$CN (1:1, 15 mL), and sonicated for 20 min. The solid was filtered, and then treated with water-MeCN again. The obtained solid was dried under vacuum to give the title compound (2.78 g, 63%) as an off white solid. The filtrate was purified by reverse phase chromatography (Biotage 400 g eluting with 5-100% (0.1% formic acid in MeCN) in 0.1% formic acid to provide a further crop of title compound (414 mg, 10%).

Method B: LC-MS (electrospray): m/z=273.3 (M+H)$^+$, RT=1.38 min.

Step 2: tert-butyl N-({6-formylimidazo[1,2-a]pyridin-2-yl}methyl)carbamate

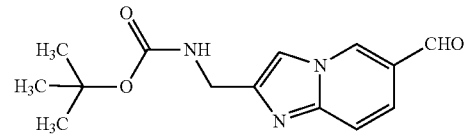

A suspension of tert-butyl N-[(6-cyanoimidazo[1,2-a]pyridin-2-yl)methyl]carbamate (5.00 g, 18.4 mmol) and sodium phosphinate hydrate (15.57 g, 0.147 mol) in a mixture of water (50 mL), Pyridine (100 mL) and Acetic acid (50 mL) was treated with Raney nickel (50%, 18.97 g, 0.162 mol) and the mixture was heated at 100° C. under a nitrogen atmosphere for an hour. The Raney nickel was removed by hot filtration through a bed of Celite (washing with water, followed by methanol). The filtrate was concentrated under vacuum to remove the methanol and the blue solution was extracted with DCM (50 mL×4). The extracts evaporated under vacuum to afford a beige gum which was triturated with water to furnish a white solid. The solid was collected by filtration, washed with water followed by ether and dried under vacuum overnight to provide the title compound (4.13 g, 82%) as an off white solid.

Method B: LC-MS (electrospray): m/z=276.2 (M+H)$^+$, RT=1.33 min.

Step 3: tert-butyl N-[(6-{[(cyclohexylmethyl)amino]methyl}imidazo[1,2-a]pyridin-2-yl)methyl]carbamate

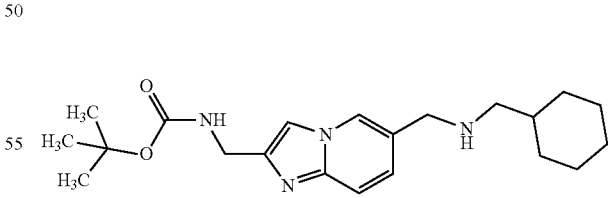

A solution of tert-butyl N-[(6-formylimidazo[1,2-a]pyridin-2-yl)methyl]carbamate (340 mg, 0.988 mmol) and cyclohexylmethanamine (224 mg, 1.98 mmol) in ethanol (6.8 mL) was stirred at 50° C. for an hour. The reaction mixture was cooled to 0° C. and NaBH$_4$ (75 mg, 1.98 mmol) was added in portions. The reaction mixture was allowed to warm to room temperature and stirring was continued for 2 hours. The reaction mixture was partitioned between DCM (80 mL) and saturated aqueous sodium hydrogen carbonate (30 mL). The organic layer was separated, washed with brine (30 mL), dried (MgSO₄), concentrated under reduced pressure. The residue was purified by column chromatography on silica gel (Biotage KP—NH 28 g, eluting with 0-20% methanol in EtOAc) to afford the title compound (360 mg, 97%) as a pale yellow oil.

Method B: LC-MS (electrospray): m/z=373.3 (M+H)⁺, RT=1.76 min.

Step 4: (6-{[(cyclohexylmethyl)amino]methyl}imidazo[1,2-a]pyridin-2-yl)methanamine trihydrochloride

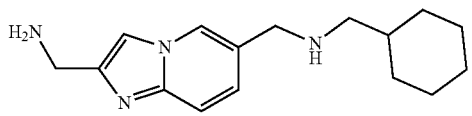

H—Cl
H—Cl
H—Cl

To a solution of tert-butyl N-[[6-[(cyclohexylmethylamino)methyl]imidazo[1,2-a]pyridin-2-yl]methyl]carbamate (360 mg, 0.908 mmol) in methanol (4.1379 mL) was added HCl (4M in dioxane, 2.4 mL, 9.6 mmol) at room temperature The solution was stirred at 50° C. for 1 hour. The solution was cooled to room temperature, and concentrated to dryness under reduced pressure. The residue (pale yellow glass) was dissolved in methanol (~3 mL) and diethyl ether (~20 mL) was added drop-wise to the stirred solution. The resulting precipitate was collected by filtration and dried in the vacuum oven at 40° C. for 4 hours to afford [the title compound (359 mg, 100%) as white solid.

Method B: LC-MS (electrospray): m/z=273.3 (M+H)⁺, RT=1.77 min.

Intermediate 28: {6-[(benzyloxy)methyl]imidazo[1,2-a]pyridin-2-yl}methanamine dihydrochloride

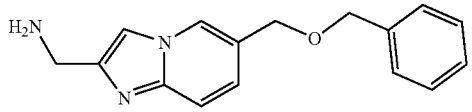

H—Cl
H—Cl

Step 1: Methyl 2-(chloromethyl)imidazo[1,2-a]pyridine-6-carboxylate

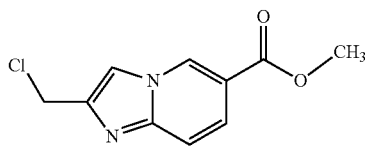

Methyl 6-aminopyridine-3-carboxylate (8.8 g, 57.8 mmol) and 1,3-dichloropropan-2-one (11.0 g, 86.8 mmol) were combined in acetonitrile (120 mL) and the mixture heated at reflux. The reaction mixture was cooled to room temperature and concentrated under vacuum. The residue was basified using saturated aqueous sodium hydrogen carbonate (~150 mL) and extracted with chloroform/isopropanol (3:1, 4×80 mL). The combined organic extracts were dried over sodium sulfate and evaporated under vacuum. The residue was purified by chromatography on silica gel (Biotage, 100 g kp-Sil, eluting with EtOAc/heptane 0-100%) to afford the title compound (6.33 g, 49%) of as an off-white solid.

Method B: LC-MS (electrospray): m/z=225.1 (M+H)⁺, RT=1.33 min.

Step 2: methyl 2-({bis[(tert-butoxy)carbonyl]amino}methyl)imidazo[1,2-a]pyridine-6-carboxylate

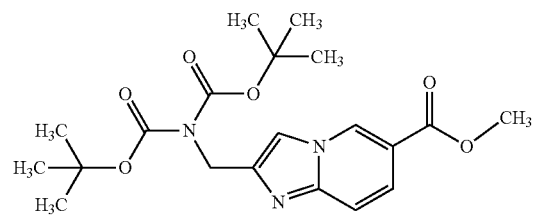 [SMILES: COC(=O)c1ccc2nc(CN(C(=O)OC(C)(C)C)C(=O)OC(C)(C)C)cn2c1]

Methyl 2-(chloromethyl)imidazo[1,2-a]pyridine-6-carboxylate (6.33 g, 28.2 mmol), di-tert-butyl imidodicarbonate (9.80 g, 45.1 mmol), NaI (425 mg, 2.82 mmol) and K₂CO₃ (11.7 g, 84.5 mmol) were combined in acetonitrile (200 mL) and water (5 mL) and the mixture heated at 70° C. for 3 hours.

The reaction mixture was cooled to room temperature and concentrated under vacuum. The residue was diluted with water (100 mL) and extracted with DCM (3×150 mL) and the combined organic extracts were dried over sodium sulfate and evaporated under vacuum. The residue was purified by chromatography on silica gel (Biotage 340 g kp-Sil, eluting with EtOAc/heptane 0-50%) to afford the title compound (8.51 g, 74%) as a very pale yellow oil.

Method B: LC-MS (electrospray): m/z=406.2 (M+H)⁺, RT=1.71 min.

Step 3: 2-({bis[(tert-butoxy)carbonyl]amino}methyl)imidazo[1,2-a]pyridine-6-carboxylic acid

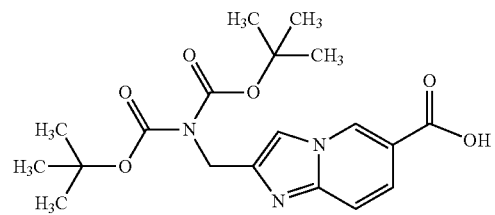 [SMILES: CC(C)(C)OC(=O)N(Cc1cn2cc(C(=O)O)ccc2n1)C(=O)OC(C)(C)C]

Methyl 2-[[bis(tert-butoxycarbonyl)amino]methyl]imidazo[1,2-a]pyridine-6-carboxylate (2.12 g, 5.23 mmol) was dissolved in THF (30 mL) and water (10 mL) and lithium hydroxide (455 mg, 18.2 mmol) was added. The mixture was stirred at room temperature for 2 hours. The reaction mixture was concentrated under vacuum to remove THF. The residue was acidified carefully using HCl (1M) to ~pH2 and extracted with chloroform/isopropanol (3:1, 3×80 mL). The combined organic extracts were dried over sodium sulfate and evaporated under vacuum to afford the title compound (1.99 g, 97%) as a white solid.

Method B: LC-MS (electrospray): m/z=392.3 (M+H)$^+$, RT=1.13 min.

Step 4: 2-({bis[(tert-butoxy)carbonyl]amino}methyl)imidazo[1,2-a]pyridine-6-carboxylic acid

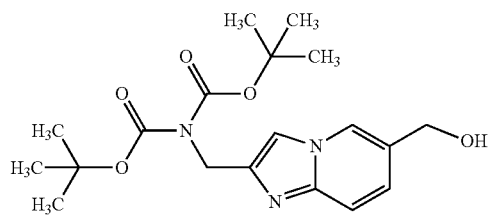 [SMILES: CC(C)(C)OC(=O)N(Cc1cn2cc(CO)ccc2n1)C(=O)OC(C)(C)C]

2-[[bis(tert-butoxycarbonyl)amino]methyl]imidazo[1,2-a]pyridine-6-carboxylic acid (800 mg, 2.04 mmol) was dissolved in THF (anhydrous, 40 mL) and borane in THF (1M, 4.7 mL, 4.7 mmol) was added. The mixture was stirred at room temperature. Further borane THF (1M, 4.7 mL, 4.7 mmol) added and stirring continued overnight. Yellow solution after 2nd addition. The reaction mixture was quenched with methanol (40 mL) and the mixture stirred at room temperature for 30 minutes and was heated at reflux for 24 hours. The reaction mixture was cooled to room temperature and evaporated under vacuum. The residue was suspended in saturated aqueous sodium hydrogen carbonate (50 mL) and extracted with chloroform/isopropanol (3:1 4×50 mL). The combined organic extracts were dried over sodium sulfate and evaporated under vacuum. The residue was purified by chromatography on silica gel (Biotage 28 g kp-NH, eluting with methanol/DCM 0-20%) to afford the title compound (356 mg, 44%) of the title compound as a colourless oily residue.

Method B: LC-MS (electrospray): m/z=378.3 (M+H)$^+$, RT=1.49 min.

Step 5: {6-[(benzyloxy)methyl]imidazo[1,2-a]pyridin-2-yl}methanamine dihydrochloride

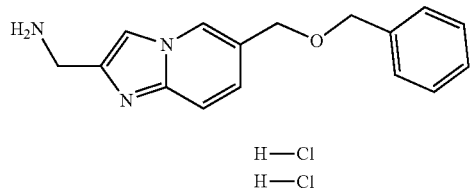

tert-butyl N-tert-butoxycarbonyl-N-[[6-(hydroxymethyl)imidazo[1,2-a]pyridin-2-yl]methyl]carbamate (350 mg, 0.93 mmol) was dissolved in THF (anhydrous 30 mL) and cooled in an ice/water bath. Sodium hydride (60% wt in mineral oil, 371 mg, 9.27 mmol) was added and the mixture stirred under cooling for 15 minutes. Benzyl bromide (220 μl, 1.85 mmol) was added and the mixture stirred whilst warming to room temperature. Further sodium hydride (60% wt in mineral oil, 371 mg, 9.27 mmol) was added and mixture continued to stir for 16 hours. The reaction mixture was slowly quenched with water (20 mL)—gas evolution— and the mixture stirred for 5 minutes, then extracted with chloroform/isopropanol (3:1, 4×30 mL) and the combined organic extracts dried over sodium sulfate and evaporated under vacuum. The residue was purified by chromatography on silica gel (Biotage 28 g kp-NH, eluting with EtOAc/heptane 0-100%) to afford the crude intermediate (356 mg, 37%, 41% purity) of as an amorphous solid. tert-butyl N-[[6-(benzyloxymethyl)imidazo[1,2-a]pyridin-2-yl]methyl]-N-tert-butoxycarbonyl-carbamate (356 mg, 0.31 mmol, 41% purity) was dissolved in methanol (5 mL) and HCl (4M in Dioxane 1 mL, 4 mmol) was added and the mixture was stirred at room temperature for an hour and at 60° C. for 3 hours. The reaction mixture was cooled to room temperature and evaporated under vacuum to afford the title compound (252 mg, 97%, 41% purity) as a colourless foamy residue which was used without further purification.

Method B: LC-MS (electrospray): m/z=268.3 (M+H)$^+$, RT=1.26 min.

Intermediate 29: {6-[(benzylamino)methyl]imidazo[1,2-a]pyridin-2-yl}methanamine dihydrochloride

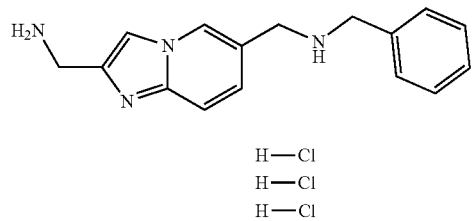

The title compound was prepared in the same manner as Intermediate 25 using benzylamine to provide (99 mg, 98%) as a white solid.

Method B: LC-MS (electrospray): m/z=267.2 (M+H)$^+$, RT=1.32 min.

Intermediate 30: N-({6-formylimidazo[1,2-a]pyridin-2-yl}methyl)-4-oxo-4H-chromene-2-carboxamide

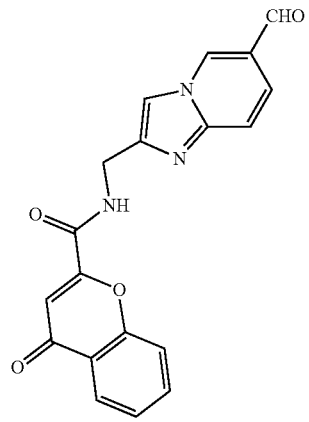 [SMILES: O=Cc1ccc2nc(CNC(=O)c3cc(=O)c4ccccc4o3)cn2c1]

The intermediate was prepared in the same manner as Compound 49 starting from 2-(aminomethyl)imidazo[1,2-a]pyridine-7-carbonitrile and acid giving (349 mg, 49%) as a beige solid.

Method B: LC-MS (electrospray): m/z=348.1 (M+H)⁺, RT=1.29 min.

Intermediate 31: N-({7-formylimidazo[1,2-a]pyridin-2-yl}methyl)-4-oxo-4H-pyrido[1,2-a]pyrimidine-2-carboxamide

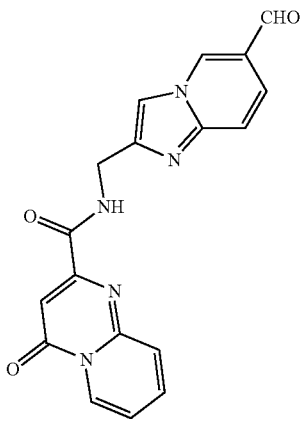 [SMILES: O=Cc1ccc2nc(CNC(=O)c3cc(=O)n4ccccc4n3)cn2c1]

The intermediate was prepared in the same manner as Compound 49 starting from 2-(aminomethyl)imidazo[1,2-a]pyridine-7-carbonitrile and coupling with Intermediate 4 to give the title compound as a beige solid.

Method B: LC-MS (electrospray): m/z=348.2 (M+H)⁺, RT=1.19 min.

Intermediate 32: tert-butyl N-{1-[2-(aminomethyl)imidazo[1,2-a]pyridin-6-yl]ethyl}-N-(cyclohexylmethyl) carbamate

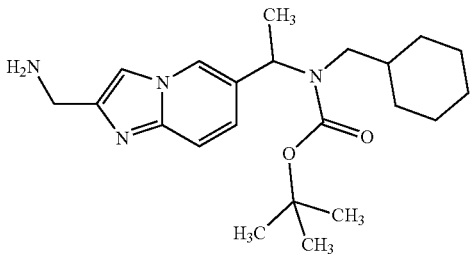 [SMILES: CC(c1ccc2nc(CN)cn2c1)N(CC1CCCCC1)C(=O)OC(C)(C)C]

Step 1: 5-{1-[(cyclohexylmethyl)amino]ethyl}pyridin-2-amine

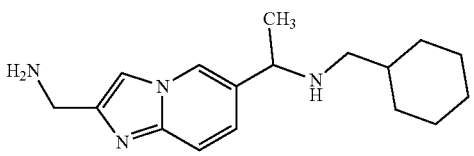 [SMILES: CC(NCC1CCCCC1)c1ccc2nc(CN)cn2c1]

A mixture of 1-(6-amino-3-pyridyl)ethanone (1.05 g, 7.71 mmol) and cyclohexylmethanamine (5.24 g, 46.3 mmol) in ethanol (20 mL) was stirred at 90° C. for 36 hours. The reaction mixture was cooled to 0° C., and then NaBH₄ (584 mg, 15.4 mmol) was added. The reaction mixture was stirred at room temperature for 2 hours. The reaction mixture was cooled to 0° C. and quenched with water and NaOH (1M). The aqueous were extracted with IPA-CHCl₃ (1:4, 3×30 mL). The combined organic layer was dried over Na₂SO₄, filtered and evaporated under reduced pressure to give a yellow gum, which was purified by acidic reverse phase chromatography (biotage 100 g) to give the title compound as a pale brown gum (1.00 g, 48%).

Method B: LC-MS (electrospray): m/z=234.3 (M+H)⁺, RT=1.51 min

Step 2: tert-butyl N-[1-[2-(chloromethyl)imidazo[1,2-a]pyridin-6-yl]ethyl]-N-(cyclohexylmethyl)carbamate

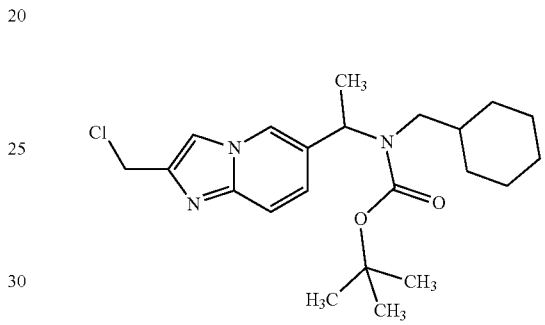

A solution of 1,3-dichloropropan-2-one (702 mg, 5.53 mmol) and 5-[1-(cyclohexylmethylamino)ethyl]pyridin-2-amine (1000 mg, 3.69 mmol) in acetonitrile (50 mL) was stirred at reflux for 2 hours. The reaction mixture was cooled to 0° C. and treated with tert-butoxycarbonyl tert-butyl carbonate (965 mg, 4.42 mmol), N,N-dimethylpyridin-4-amine (45 mg, 0.369 mmol) and N-ethyl-N-isopropyl-propan-2-amine (1.3 mL, 7.37 mmol) and the mixture was stirred at room temperature for 16 hours. The solvent was removed under vacuum and the residue was suspended in EtOAc (100 mL) and washed with water and brine, dried over Na₂SO₄, filtered and evaporated under reduced pressure to give a brown gum, which was purified by high pH reverse phases chromatography (biotage C18 Snap 100 g) to give the title compound (400 mg, 27%) as a white solid.

Method B: LC-MS (electrospray): m/z=406.3 (M+H)⁺, RT=1.97 min.

Step 3: tert-butyl N-[1-[2-(azidomethyl)imidazo[1,2-a]pyridin-6-yl]ethyl]-N-(cyclohexylmethyl)carbamate

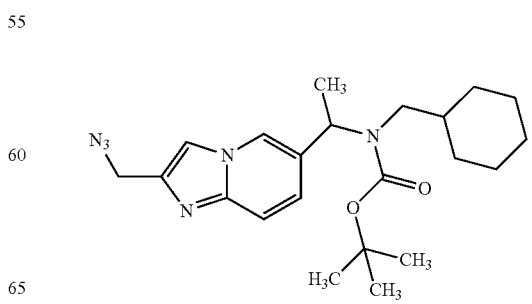

A suspension of tert-butyl N-[1-[2-(chloromethyl)imidazo[1,2-a]pyridin-6-yl]ethyl]-N-(cyclohexylmethyl)carbamate (400 mg, 0.985 mmol) in acetonitrile (15 mL) was treated with sodium azide (231 mg, 3.55 mmol) and sodium iodide (15 mg, 0.0985 mmol) at room temperature The mixture was stirred at reflux for 20 hours. The reaction mixture was cooled to 0° C. and quenched with water (50 mL). The mixture was extracted with DCM (3×15 mL). The combined organic layer was dried over Na$_2$SO$_4$, filtered and concentrated in vacuo to give the title compound (410 mg, 98%) as a dark brown solid.

Method B: LC-MS (electrospray): m/z=413.4 (M+H)$^+$, RT=1.98 min.

Step 4: tert-butyl N-[1-[2-(aminomethyl)imidazo[1,2-a]pyridin-6-yl]ethyl]-N-(cyclohexylmethyl)carbamate

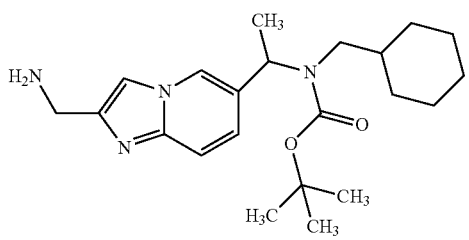 [SMILES: CC(c1ccc2nc(CN)cn2c1)N(CC1CCCCC1)C(=O)OC(C)(C)C]

tert-butyl N-[1-[2-(azidomethyl)imidazo[1,2-a]pyridin-6-yl]ethyl]-N-(cyclohexylmethyl)carbamate (300 mg, 0.727 mmol) and Pd/C (10%, 50 mg, 0.0470 mmol) were combined in EtOH (10 mL). The mixture was flushed three times with nitrogen, placed under a hydrogen atmosphere and stirred at room temperature for 16 hours. The reaction mixture was filtered through a pad of celite and the solid residue was washed with methanol. The filtrate was concentrated to dryness under vacuum to provide the title compound (280 mg, 100%) as yellow solid.

Method B: LC-MS (electrospray): m/z=387.3 (M+H)$^+$, RT=1.95 min.

Intermediate 33: 6-bromo-4-ethynyl-1-(oxan-2-yl)-1H-indazole

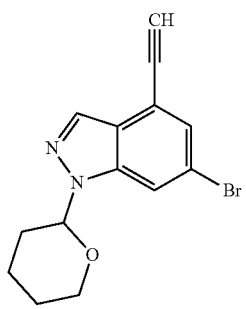 [SMILES: C#Cc1cc(Br)cc2c1cnn2C1CCCCO1]

The title compound starting from was prepared from 6-bromo-4-iodo-1H-indazole using the steps described in Intermediate 24 to give (737 mg, 96%).

Method A: LC-MS (electrospray): m/z=304.95/306.95 (M+H)$^+$, RT=1.39 min

Intermediate 34: 2-[[4-(1-tetrahydropyran-2-ylindazol-4-yl)triazol-1-yl]methyl]imidazo[1,2-a]pyridine-6-carbaldehyde

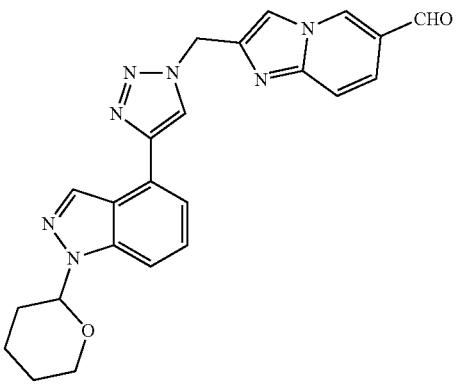 [SMILES: O=Cc1ccc2nc(Cn3cc(-c4cccc5c4cnn5C4CCCCO4)nn3)cn2c1]

Step 1: methyl 2-(chloromethyl)imidazo[1,2-a]pyridine-6-carboxylate

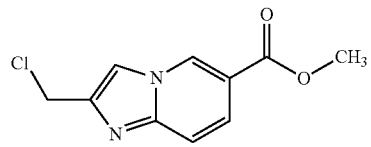

Methyl 6-aminopyridine-3-carboxylate (5.3 g, 34.8 mmol) and 1,3-dichloropropan-2-one (6.63 g, 52.3 mmol) were combined in acetonitrile (50 mL) and the mixture heated at reflux for 6 hours. The reaction mixture was cooled to room temperature and the residue suspended in saturated aqueous sodium hydrogen carbonate (80 mL). The mixture was extracted with 3:1 chloroform/isopropanol (3×100 mL) and the combined organic extracts dried over sodium sulfate and evaporated under vacuum. The residue was purified by Biotage Isolera™ chromatography (100 g kp-Sil, eluting with EtOAc/heptane 0-100%) to afford a crude material which was triturated with EtOAc/heptane. The solids were collected by filtration and dried under suction to afford 3.35 g (43%) of the title compound as a white solid.

Method B: LC-MS (electrospray): m/z=225.1 (M+H)$^+$, RT=1.32 min

Step 2: [2-(chloromethyl)imidazo[1,2-a]pyridin-6-yl]methanol

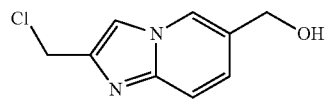 [SMILES: OCc1ccc2nc(CCl)cn2c1]

A solution of methyl 2-(chloromethyl)imidazo[1,2-a]pyridine-6-carboxylate (700 mg, 3.12 mmol) in anhydrous THF (20 mL) and cooled in an ice/water bath. DIBAL (1M in PhMe, 8.6 mL, 8.6 mmol) was added slowly to give a yellow solution and the mixture stirred under cooling for 2 hours.

The reaction mixture was quenched by dropwise addition of methanol (5 mL), then diluted with DCM (70 mL) and saturated aqueous sodium hydrogen carbonate (50 mL). The mixture was filtered through Celite and the residue rinsed well with DCM. The filtrates were phase-separated, the aqueous layer extracted with DCM (80 mL). The combined organic layers dried over sodium sulfate and evaporated under vacuum. The resultant residue was triturated with Et$_2$O and the solids collected by filtration to afford (384 mg 60%) of the title compound as a pale yellow solid MS16 IPC: LC-MS (electrospray): m/z=196.8 (M+H)$^+$, RT=0.31 min Step 3: [2-(azidomethyl)imidazo[1,2-a]pyridin-6-yl]methanol

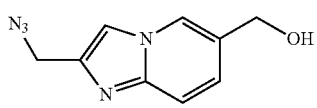

[2-(chloromethyl)imidazo[1,2-a]pyridin-6-yl]methanol (380 mg, 1.93 mmol), NaI (29 mg, 0.19 mmol) and NaN$_3$ (300 mg, 4.61 mmol) were combined in DMF (2 mL) and the mixture stirred at room temperature for 3 hours. The reaction mixture was diluted with saturated aqueous sodium hydrogen carbonate (30 mL) and extracted with DCM (3×50 mL). The combined organic extracts were dried over sodium sulfate and evaporated under vacuum. The solids were carefully triturated with EtOAc/heptane and the solids collected by filtration to afford 309 mg, 79%) of the title compound as a pale yellow solid Method B: LC-MS (electrospray): m/z=204.2 (M+H)$^+$, RT=1.10 min Step 4: [2-[[4-(1-tetrahydropyran-2-ylindazol-4-yl)triazol-1-yl]methyl]imidazo[1,2-a]pyridin-6-yl]methanol

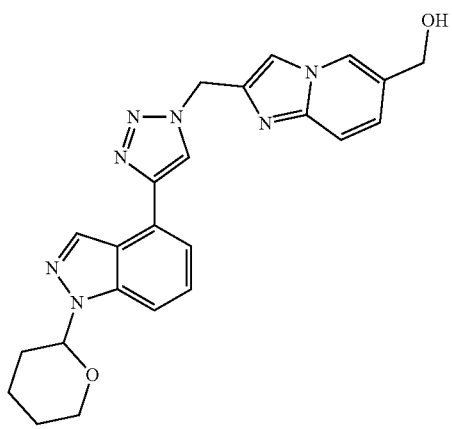 [SMILES: OCc1ccc2nc(Cn3cc(-c4cccc5c4cnn5C4CCCCO4)nn3)cn2c1]

4-ethynyl-1-tetrahydropyran-2-yl-indazole Intermediate 24 (280 mg, 1.19 mmol), [2-(azidomethyl)imidazo[1,2-a]pyridin-6-yl]methanol (265 mg, 1.31 mmol) and copper sulfate (40 mg, 0.25 mmol) were combined in DMF (3 mL) and water (1 mL), and sodium ascorbate (261 mg, 1.31 mmol) was added. The mixture was stirred at room temperature for 45 minutes. The reaction mixture was diluted with 3:1 chloroform/isopropanol (50 mL) and water (30 mL) and the phases separated. The aqueous phase was extracted with 3:1 chloroform/isopropanol (2×30 mL) and the combined organic layers dried over sodium sulfate and evaporated under vacuum. The residue was purified by chromatography on silica gel (Biotage, 28 g kp-NH, eluting with EtOAc/heptane 0-100% followed by 0-20% methanol/EtOAc) to afford a crude material which was triturated with methanol/Et$_2$O/heptane and the resultant flocculant solid collected by filtration to afford the title compound (376 mg (71%) of as a white solid.

Method B: LC-MS (electrospray): m/z=430.3 (M+H)$^+$, RT=1.38 min

Step 5: 2-[[4-(1-tetrahydropyran-2-ylindazol-4-yl)triazol-1-yl]methyl]imidazo[1,2-a]pyridine-6-carbaldehyde

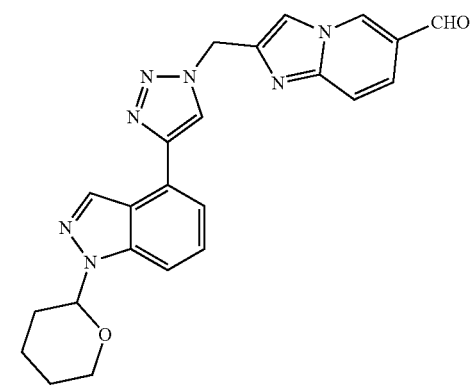 [SMILES: O=Cc1ccc2nc(Cn3cc(-c4cccc5c4cnn5C4CCCCO4)nn3)cn2c1]

[2-[[4-(1-tetrahydropyran-2-ylindazol-4-yl)triazol-1-yl]methyl]imidazo[1,2-a]pyridin-6-yl]methanol (380 mg, 0.88 mmol) was suspended in DCE (30 mL) and Dess-Martin periodinane (1.13 g, 2.65 mmol) was added. The mixture was stirred at 60° C. for 2 hours. The reaction mixture was cooled to room temperature, quenched with saturated aqueous sodium hydrogen carbonate (40 mL) and extracted with 3:1 chloroform/isopropanol (4×50 mL). The combined organic extracts were dried over sodium sulfate and evaporated under vacuum. The residue was triturated with EtOAc/heptane and the solids collected by filtration to afford the title compound (371 mg, 94%) as a beige solid Method B: LC-MS (electrospray): m/z=428.2 (M+H)$^+$, RT=1.45 min

Intermediate 35: 2-[[4-(6-bromo-1-tetrahydropyran-2-yl-indazol-4-yl)triazol-1-yl]methyl]imidazo[1,2-a]pyridine-6-carbaldehyde

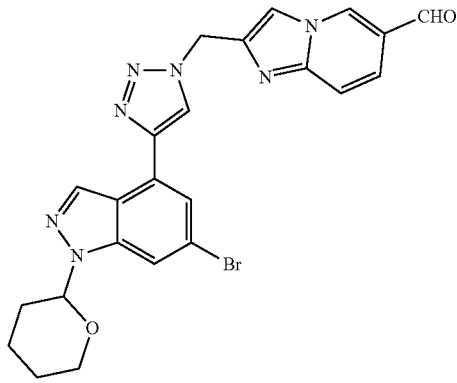 [SMILES: O=Cc1ccc2nc(Cn3cc(-c4cc(Br)cc5c4cnn5C4CCCCO4)nn3)cn2c1]

The title compound was prepared from Intermediate 33 in a similar fashion to Intermediate 34 giving (906 mg, 99%) as a pale yellow solid.

Method B: LC-MS (electrospray): m/z=506.2/508.2 (M+H)$^+$, RT=1.58 min

The title compound was prepared in a similar fashion to Intermediate 34 starting from 5-iodo-1H-indazole Method B: LC-MS (electrospray): m/z=428.2 (M+H)$^+$, RT=1.42 min

Intermediate 36: 5-ethynyl-1-(oxan-2-yl)-1H-indazole

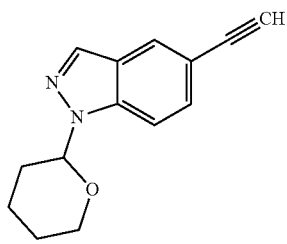 [SMILES: C#Cc1ccc2c(cnn2C2CCCCO2)c1]

The title compound was prepared from 5-iodo-1H-indazole using the steps described in Intermediate 24 giving (1.03 g, 94%) as a yellow oil.

Method A: LC-MS (electrospray): m/z=227.10 (M+H)$^+$, RT=1.22 min.

Intermediate 37: 2-({4-[1-(oxan-2-yl)-1H-indazol-5-yl]-1H-1,2,3-triazol-1-yl}methyl)imidazo[1,2-a]pyridine-6-carbaldehyde

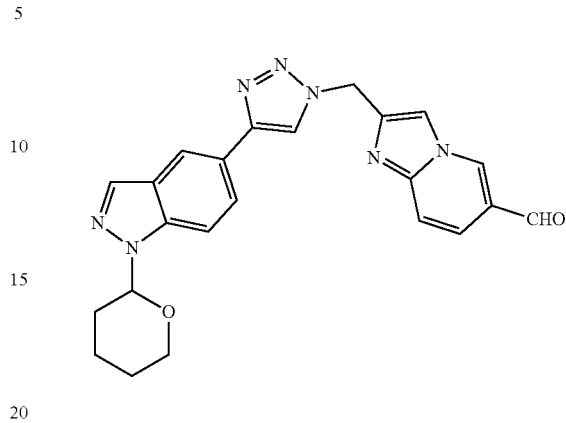

The title compound was prepared from Intermediate 36 using the steps described in Intermediate 24 giving (143 mg, 98%) as a pale yellow solid.

Method B: LC-MS (electrospray): m/z=428.2 (M+H)$^+$, RT=1.42 min

Intermediate 38: 4-ethynyl-1-(oxan-2-yl)-1H-pyrazolo[3,4-c]pyridine

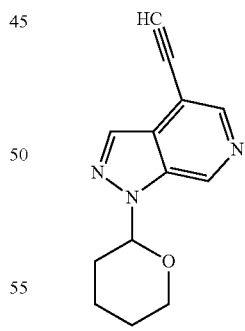

The title compound was prepared from 4-bromo-1H-pyrazolo[3,4-c]pyridine using the method described for Intermediate 24 giving Method A: LC-MS (electrospray): m/z=228.15 (M+H)$^+$, RT=1.078 min

Intermediate 39: [2-({4-[1-(oxan-2-yl)-1H-pyrazolo[3,4-c]pyridin-4-yl]-1H-1,2,3-triazol-1-yl}methyl)imidazo[1,2-a]pyridin-6-yl]methanol

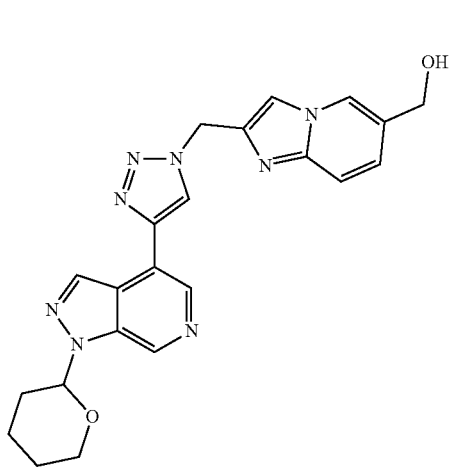

The intermediate was prepared from Intermediate 38 using the methods described in Intermediate 34 Step 4 giving (314 mg, 73%) as an off white solid.

Method A: LC-MS (electrospray): m/z=431.05 (M+H)$^+$, RT=0.78 min

Intermediate 40: 2-({4-[1-(oxan-2-yl)-1H-pyrazolo[3,4-c]pyridin-4-yl]-1H-1,2,3-triazol-1-yl}methyl)imidazo[1,2-a]pyridine-6-carbaldehyde

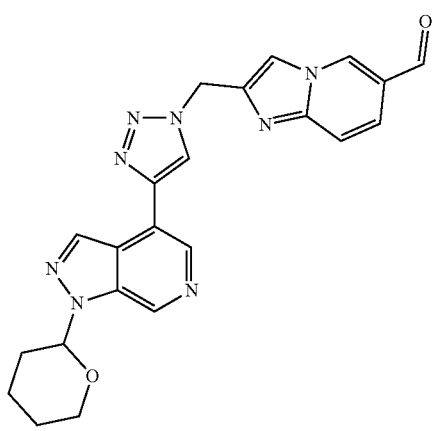 [SMILES: O=Cc1ccc2nc(Cn3cc(-c4cncc5c4cnn5C4CCCCO4)nn3)cn2c1]

The intermediate was prepared from Intermediate 39 using the methods described in Intermediate 34 Step 5 giving (249 mg, 77%) as a pale yellow solid.

Method A: LC-MS (electrospray): m/z=429.65 (M+H)$^+$, RT=0.95 min

Intermediate 42: (2,3,4,5,6-pentafluorophenyl) 3-phenylpropanoate

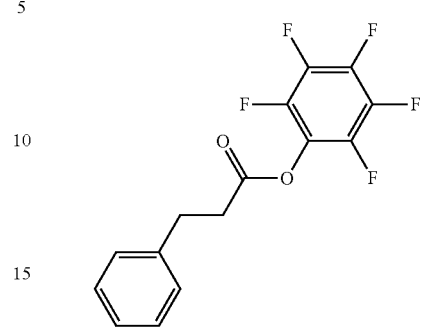

pentafluorophenol (135 mg, 0.732 mmol) was added to a mixture of 3-phenylpropanoic acid (100 mg, 0.666 mmol), N,N'-dicyclohexylmethanediimine (0.18 mL, 0.799 mmol) and N,N-dimethylpyridin-4-amine (8.1 mg, 0.0666 mmol) in anhydrous THF (4 mL) under nitrogen and the reaction mixture was stirred at room temperature for 24 hours. The reaction mixture was filtered and the filtrates concentrated under vacuum. The resultant residue was purified by chromatography on silica gel (Biotage kp-Sil, eluting with EtOAc/heptane 0-30%) to afford (135 mg, 64%) as a colourless oil.

Method A: LC-MS (electrospray): does not ionise, RT=1.46 min

Intermediate 43: {6-[(4,4-dimethylpiperidin-1-yl)methyl]imidazo[1,2-a]pyridin-2-yl}methanamine trihydrochloride

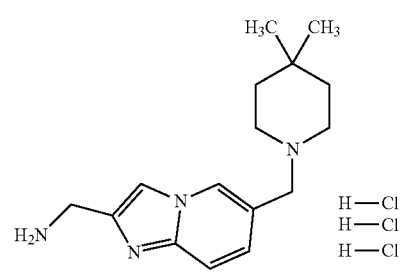

The intermediate was prepared in the same manner as Intermediate 29 to give the title compound (390 mg, 97%) as a white solid.

Method B: LC-MS (electrospray): m/z=273.3 (M+H)$^+$, RT=1.52 min

Intermediate 44: 1-Cyclohexyl-2-(tributylstannylmethoxy)ethanamine

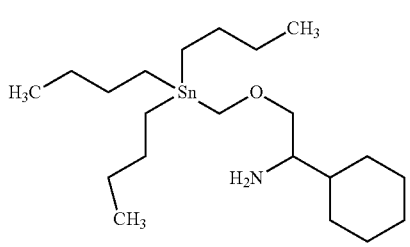 [SMILES: CCC[CH2][Sn]([CH2]CCC)([CH2]CCC)[CH2]OCC(N)C1CCCCC1]

To a solution of 2-amino-2-cyclohexyl-ethanol (150 mg, 1.05 mmol) in anhydrous THF (3 mL) was added potassium-2-methylpropan-2-olate (153 mg, 1.36 mmol) at room temperature. The mixture stirred for 30 minutes before a solution of tributyl(iodomethyl)stannane (451 mg, 1.05 mmol) in THF (2 mL) was added drop-wise and stirring was continued for 72 hours. The reaction mixture was cooled to 0° C. and slowly quenched with sat aq NH$_4$Cl (5 mL) before being poured onto a mixture of EtOAc/water (4:1, 50 mL). The layers were separated and the aqueous layer was extracted with EtOAc (2×20 mL). The combined organic layers were washed with water (2×15 mL), brine (30 mL), dried over Na$_2$SO$_4$, filtered, and concentrated under reduced pressure. The residue was purified by column chromatography on silica (Biotage KP-Sil 25 g; 0-10% 2M ammonia in methanol/DCM) to afford the title compound (330 mg, 64%) as yellow oil.

$^1$HNMR (500 MHz, Chloroform-d) δ 0.80-0.97 (m, 15H), 0.98-1.56 (m, 18H), 1.60-1.84 (m, 5H), 2.02 (s, 2H), 2.67-2.76 (m, 1H), 3.15-3.23 (m, 1H), 3.38 (dd, J=9.1, 3.6 Hz, 1H), 3.68 (d, J=10.3 Hz, 1H), 3.74 (d, J=10.3 Hz, 1H).

Intermediate 45: (2S)-3,3-Dimethyl-1-(tributylstannylmethoxy)butan-2-amine

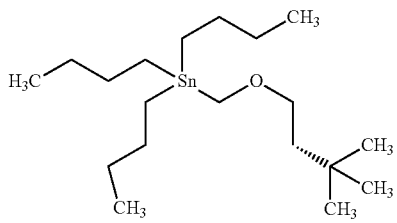

The title compound was prepared in the same manner as Intermediate 44 from (2S)-2-amino-3,3-dimethylbutan-1-ol giving (465 mg, 85%) as a yellow oil.

$^1$HNMR (500 MHz, Chloroform-d) δ 0.85-0.93 (m, 24H), 1.24-1.35 (m, 7H), 1.42-1.59 (m, 7H), 2.65 (dd, J=9.1, 2.9 Hz, 1H), 3.06-3.14 (m, 1H), 3.43 (dd, J=9.0, 2.9 Hz, 1H), 3.65-3.71 (m, 1H), 3.72-3.77 (m, 1H).

Intermediate 46: (2R)-3,3-Dimethyl-1-(tributylstannylmethoxy)butan-2-amine

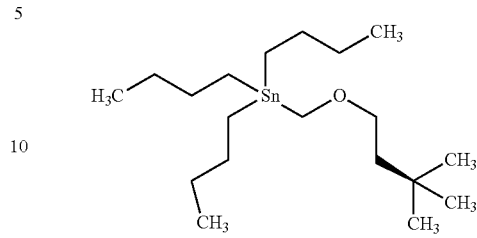

The title compound was prepared in the same manner as Intermediate 44 from (2R)-2-amino-3,3-dimethylbutan-1-ol giving (470 mg, 87%) as a yellow oil.

$^1$HNMR (500 MHz, Chloroform-d) δ 0.81-0.98 (m, 24H), 1.25-1.34 (m, 6H), 1.35-1.61 (m, 8H), 2.65 (dd, J=9.1, 2.9 Hz, 1H), 3.05-3.15 (m, 1H), 3.44 (dd, J=8.9, 2.9 Hz, 1H), 3.64-3.70 (m, 1H), 3.70-3.78 (m, 1H).

Intermediate 47: [6-[rac-(3S,5R)-5-Cyclohexylmorpholin-3-yl]imidazo[1,2-a]pyridin-2yl]methanamine trihydrochloride

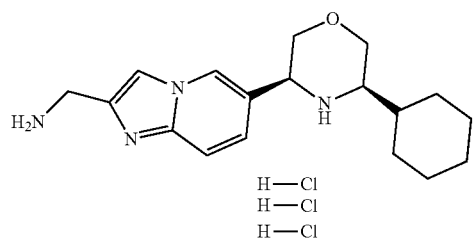

Step 1: tert-Butyl N-[[6-[rac-(3S,5R)-5-cyclohexylmorpholin-3-yl]imidazo[1,2-a]pyridin-2-yl]methyl]carbamate

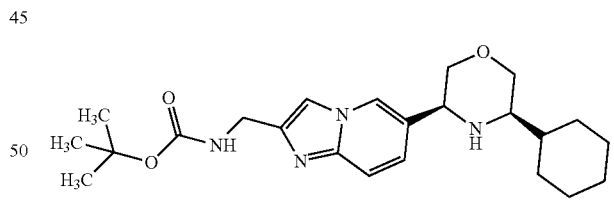

To a solution of tert-butyl N-[(6-formylimidazo[1,2-a]pyridin-2-yl)methyl]carbamate (Intermediate 25 step 2) (183 mg, 0.67 mmol) in 1,1,1,3,3,3-Hexafluoro-2-propanol (2.5 mL) was added a solution of 1-cyclohexyl-2-(tributylstannylmethoxy)ethanamine (90%, 330 mg, 0.665 mmol) in DCE (4 mL). The reaction mixture was stirred at 80° C. for 16 hours. Meanwhile a mixture of 2,6-dimethylpyridine (0.16 mL, 1.33 mmol), copper (2+) bis(trifluoromethanesulfonate) (484 mg, 1.33 mmol) and 1,1,1,3,3,3-Hexafluoro-2-propanol (2.5 mL) was stirred separately at room temperature for 1 hour. After cooling to room temperature, the solution of the imine was added drop-wise to the solution of the catalyst. The resulting mixture was stirred at room temperature for 3 hours forming a clear, dark green solution.

The reaction mixture was diluted with DCM (25 mL) and quenched with 10% aq. NH₄OH (10 mL) solution. The organic layer was separated, washed with brine (10 mL), dried (Na₂SO₄), filtered and concentrated under reduced pressure. The residue was purified by preparative HPLC (method B) to afford the title compound (152 mg, 55%) as pale yellow oil.

Method C: LC-MS (electrospray): m/z=415.4 (M+H)⁺, RT=3.66 min

Step 2: [6-[rac-(3S,5R)-5-Cyclohexylmorpholin-3-yl]imidazo[1,2-a]pyridin-2yl]methanamine trihydrochloride

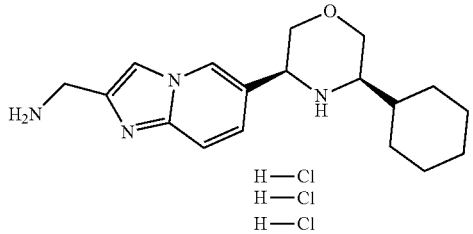

To a solution of tert-butyl N-[[6-[rac-(3S,5R)-5-cyclohexylmorpholin-3-yl]imidazo[1,2-a]pyridin-2-yl]methyl]carbamate (153 mg, 0.368 mmol) in methanol (2 mL) was added 4M HCl in dioxane (1 mL) at room temperature. The solution was stirred at 50° C. for 1 hour. After cooling to room temperature, the reaction mixture was concentrated to dryness under reduced pressure. The residue was dissolved in methanol (3 mL) and diethyl ether (20 mL) was added drop-wise to the stirred solution. The resulting precipitate was collected by filtration and dried in the vacuum oven at 40° C. for 4 hours to afford the title compound (129 mg, 78%) as an off-white solid.

Method C: LC-MS (electrospray): m/z=315.3 (M+H)⁺ for freebase, RT=2.80 min.

Intermediate 48: tert-butyl N-[[6-[rac-(3S,5R)-5-methylmorpholin-3-yl]imidazo[1,2-a]pyridin-2-yl]methyl]carbamate

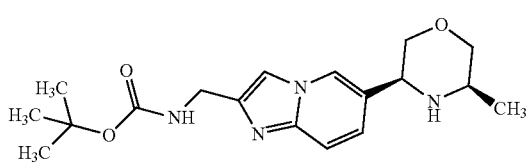 [SMILES: C[C@@H]1COC[C@H](c2ccc3nc(CNC(=O)OC(C)(C)C)cn3c2)N1]

A glass vial (40 mL clear, screw cap) was charged with tert-butyl N-[(6-formylimidazo[1,2-a]pyridin-2-yl)methyl]carbamate (Intermediate 25 step 2) (138 mg, 0.500 mmol) and loaded into a SYNPLEChem capsule based synthesizer, using a H007 3-Methylmorpholine cartridge. After the reaction mixture was complete (11 hour), the product containing solution was concentrated under reduced pressure. The residue was purified by preparative HPLC (method B) to afford the title compound (82 mg, 45%) as colourless oil.

Method C: LC-MS (electrospray): m/z=347.3 (M+H), RT=2.28 min.

Intermediate 49: tert-Butyl N-[[6-(9-methoxy-2,3,4,5-tetrahydro-1,4-benzoxazepin-3-yl)imidazo[1,2-a]pyridin-2-yl]methyl]carbamate

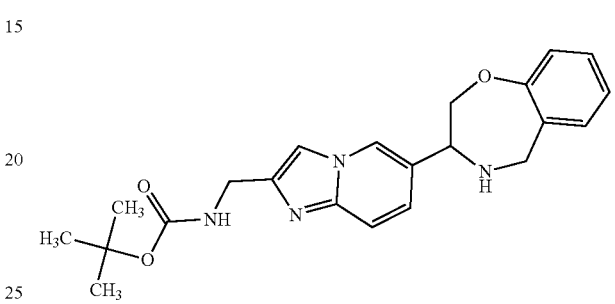

The intermediate was prepared in the same manner as Intermediate 48 to afford the title compound (105 mg, 49%) as colourless oil.

Method C: LC-MS (electrospray): m/z=425.3 (M+H), RT=2.75 min

Intermediate 50: [6-(trifluoromethyl)imidazo[1,2-a]pyridin-2-yl]methanamine

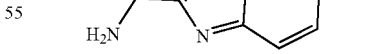

The title compound was prepared from 2-amino-5-(trifluoromethyl)pyridine in a similar manner to Intermediate 7 to give (650 mg, 65%) as a light brown solid. Method B: LC-MS (electrospray): m/z=216.2 (M+H)⁺, RT=1.29 min.

The compounds in Table 9 were prepared in a similar fashion to Compound 1 using the appropriate carboxylic acid and aminomethyl imidazopyridine intermediate, or commercially available materials, including deprotection where necessary.

TABLE 9

| Compound No | Name | Structure | LCMS method | LCMS Retention time/ mass ion | Intermediates |
|---|---|---|---|---|---|
| 63 | N-{[6-(2-aminoethyl)imidazo[1,2-a]pyridin-2-yl]methyl}-4-oxo-4H-pyrido[1,2-a]pyrimidine-2-carboxamide | 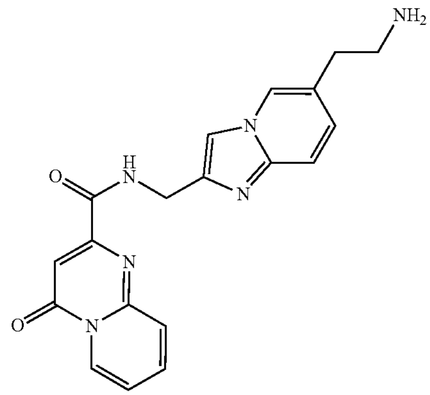 [SMILES: NCCc1ccc2nc(CNC(=O)c3cc(=O)n4ccccc4n3)cn2c1] | D | 2.69 | 20 |
| 64 | N-({6-methylimidazo[1,2-a]pyridin-2-yl}methyl)-4-oxo-4H,6H,7H,8H,9H-pyrido[1,2-a]pyrimidine-2-carboxamide | 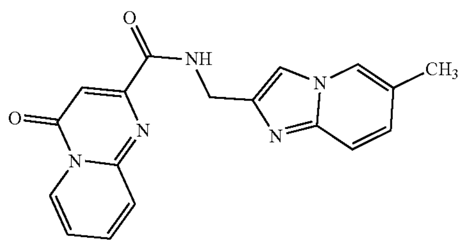 [SMILES: Cc1ccc2nc(CNC(=O)c3cc(=O)n4ccccc4n3)cn2c1] | C | 2.41/338.2 | 21 |
| 65 | 4-oxo-N-{[6-(trifluoromethyl)imidazo[1,2-a]pyridin-2-yl]methyl}-4H-pyrido[1,2-a]pyrimidine-2-carboxamide | 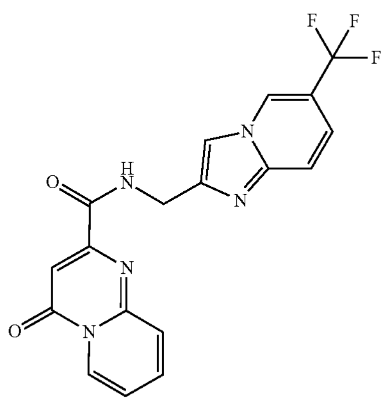 [SMILES: O=C(NCc1cn2cc(C(F)(F)F)ccc2n1)c1cc(=O)n2ccccc2n1] | C | 2.48/388.1 | 50 |
| 67 | tert-butyl N-(2-{2-[({4-oxo-4H-pyrido[1,2-a]pyrimidin-2-yl}formamido)methyl]imidazo[1,2-a]pyridin-6-yl}ethyl)carbamate | 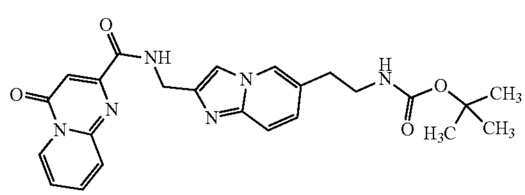 [SMILES: CC(C)(C)OC(=O)NCCc1ccc2nc(CNC(=O)c3cc(=O)n4ccccc4n3)cn2c1] | D | 3.34/463.2 | 20 |
| 68 | N-benzyl-2-[({4-oxo-4H-pyrido[1,2-a]pyrimidin-2-yl}formamido)methyl]imidazo[1,2-a]pyridine-6-carboxamide | 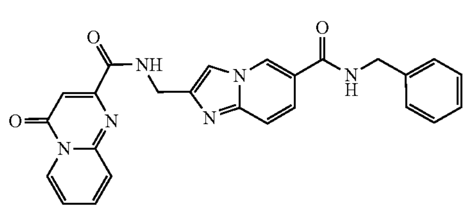 [SMILES: O=C(NCc1ccccc1)c1ccc2nc(CNC(=O)c3cc(=O)n4ccccc4n3)cn2c1] | D | 3.21/453.2 | 22 |

TABLE 9-continued

| Compound No | Name | Structure | LCMS method | LCMS Retention time/ mass ion | Intermediates |
|---|---|---|---|---|---|
| 170 | N-[(6-{[(cyclohexyl methyl)amino] methyl} imidazo[1,2-a]pyridin-2-yl)methyl]-4-oxo-4H-chromene-2-carboxamide | 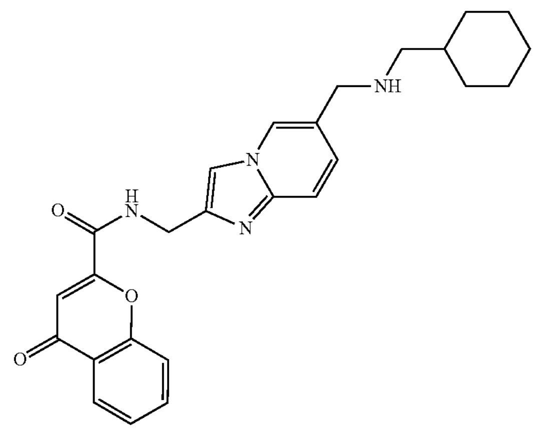 [SMILES: O=C(NCc1cn2cc(CNCC3CCCCC3)ccc2n1)c1cc(=O)c2ccccc2o1] | C | 3.20/445.4 | 25 |
| 171 | 7-chloro-N-[(6-{[(cyclohexyl methyl)amino] methyl} imidazo[1,2-a]pyridin-2-yl)methyl]-4-oxo-4H-chromene-2-carboxamide | 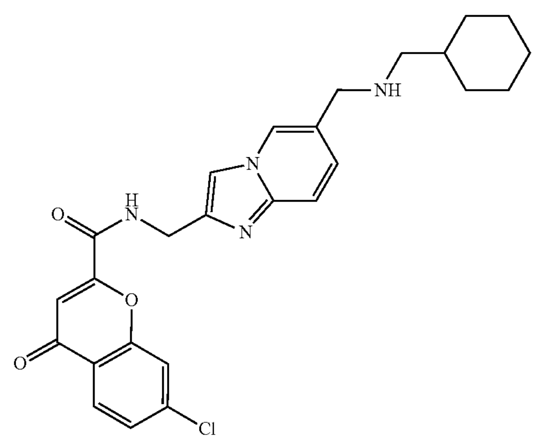 [SMILES: O=C(NCc1cn2cc(CNCC3CCCCC3)ccc2n1)c1cc(=O)c2ccc(Cl)cc2o1] | C | 3.56/479.3 | 25 |
| 172 | 6-chloro-N-[(6-{[(cyclohexyl methyl)amino] methyl} imidazo[1,2-a]pyridin-2-yl)methyl]-4-oxo-4H-chromene-2-carboxamide | 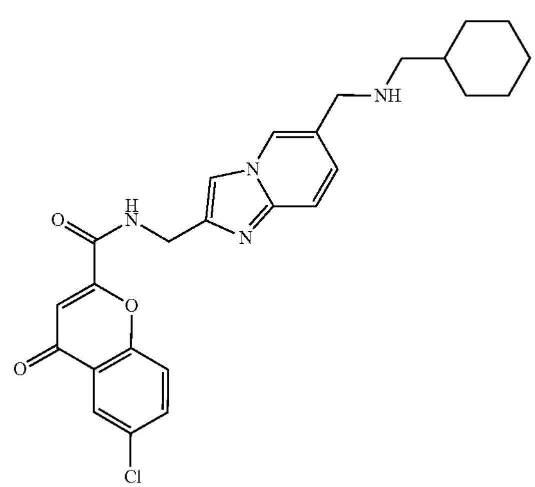 [SMILES: O=C(NCc1cn2cc(CNCC3CCCCC3)ccc2n1)c1cc(=O)c2cc(Cl)ccc2o1] | C | 3.59/479.2 | 25 |

TABLE 9-continued

| Compound No | Name | Structure | LCMS method | LCMS Retention time/ mass ion | Intermediates |
|---|---|---|---|---|---|
| 175 | N-[(6-{[(cyclohexyl methyl)amino] methyl} imidazo[1,2-a]pyridin-2-yl)methyl]-4-oxo-4H,6H,7H,8H,9H-pyrido[1,2-a]pyrimidine-2-carboxamide | 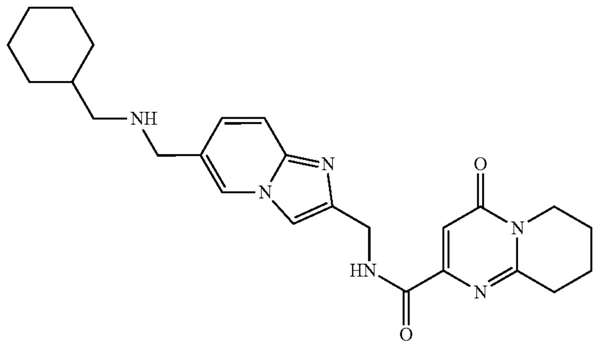 [SMILES: O=C(NCc1cn2cc(CNCC3CCCCC3)ccc2n1)c1cc(=O)n2c(n1)CCCC2] | C | 2.97/449.4 | 175 |
| 176 | 6-amino-N-[(6-{[(cyclohexyl methyl)amino] methyl} imidazo[1,2-a]pyridin-2-yl)methyl] pyridine-3-carboxamide | 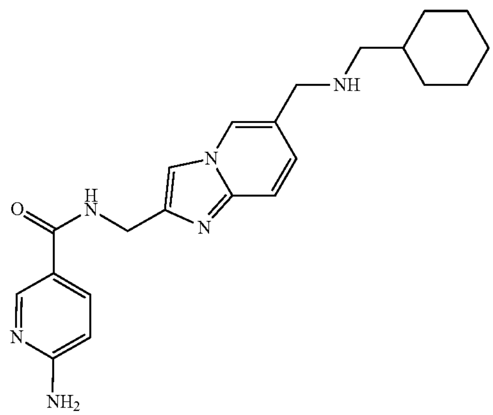 [SMILES: Nc1ccc(C(=O)NCc2cn3cc(CNCC4CCCCC4)ccc3n2)cn1] | D | 3.41/ 393.3 | 176 |
| 177 | N-({6-[(benzyloxy) methyl]imidazo [1,2-a]pyridin-2-yl]methyl)-4-oxo-4H-pyrido[1,2-a]pyrimidine-2-carboxamide | 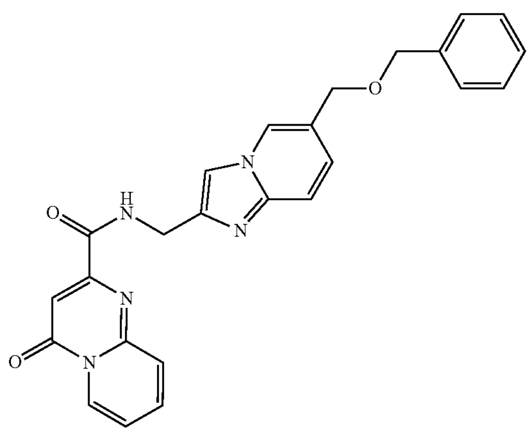 [SMILES: O=C(NCc1cn2cc(COCc3ccccc3)ccc2n1)c1cc(=O)n2ccccc2n1] | D | 3.68/440.1 | 28 |
| 178 | N-({6-[(benzylamino) methyl]imidazo [1,2-a]pyridin-2-yl}methyl)-1H-indazole-4-carboxamide | 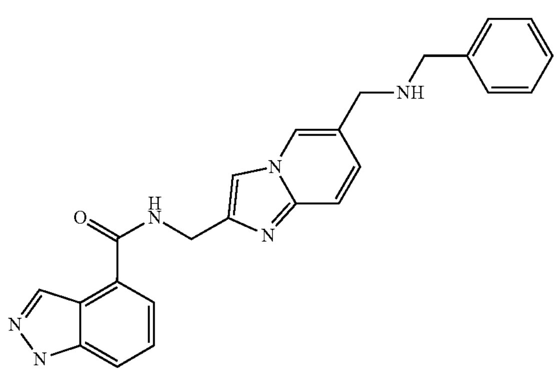 [SMILES: O=C(NCc1cn2cc(CNCc3ccccc3)ccc2n1)c1cccc2[nH]ncc12] | C | 2.39/411.3 | 29 |

TABLE 9-continued

| Compound No | Name | Structure | LCMS method | LCMS Retention time/ mass ion | Intermediates |
|---|---|---|---|---|---|
| 180 | N-[(6-{[(cyclohexyl methyl)amino] methyl}imidazo [1,2-a]pyridin-2- yl)methyl]-7-fluoro-4-oxo-4H-chromene-2-carboxamide | 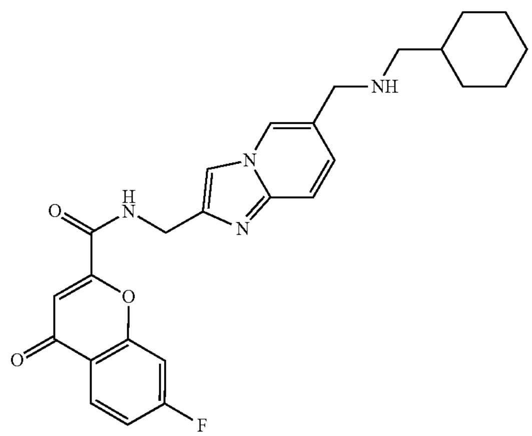 [SMILES: O=C(NCc1cn2cc(CNCC3CCCCC3)ccc2n1)c1cc(=O)c2ccc(F)cc2o1] | C | 3.33/463.4 | 25 |
| 181 | N-[(6-{[(cyclohexyl methyl)amino] methyl} imidazo[1,2-a]pyridin-2-yl)methyl]-7-methyl-4-oxo-4H-chromene-2-carboxamide | 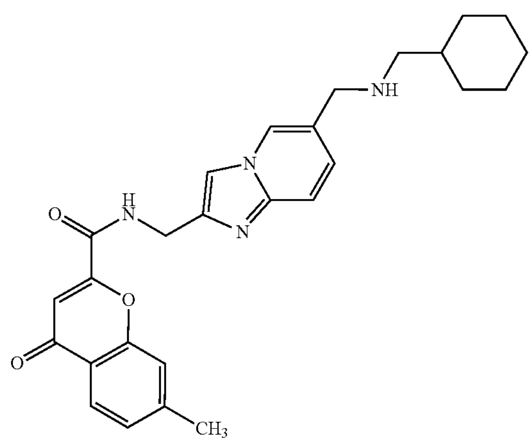 [SMILES: Cc1ccc2c(=O)cc(C(=O)NCc3cn4cc(CNCC5CCCCC5)ccc4n3)oc2c1] | C | 3.39/459.4 | 25 |
| 182 | N-[(6-{[(cyclohexyl-methyl) amino]methyl} imidazo[1,2-a]pyridin-2-yl)methyl]-1H-indazole-4-carboxamide | 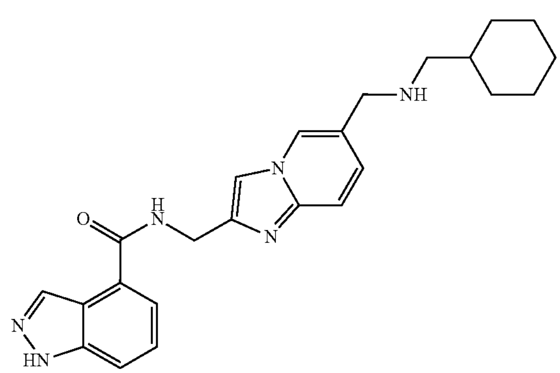 [SMILES: O=C(NCc1cn2cc(CNCC3CCCCC3)ccc2n1)c1cccc2[nH]ncc12] | E | 0.93/417.3 | 25 |

TABLE 9-continued

| Compound No | Name | Structure | LCMS method | LCMS Retention time/ mass ion | Intermediates |
| --- | --- | --- | --- | --- | --- |
| 185 | 8-chloro-N-[(6-{[(cyclohexyl methyl)amino] methyl} imidazo[1,2-a]pyridin-2-yl)methyl]-4-oxo-4H-chromene-2-carboxamide | 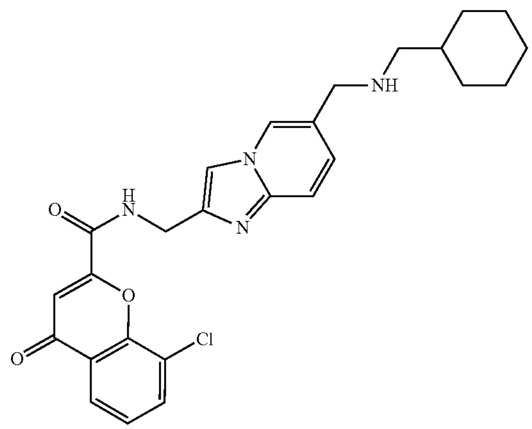 [SMILES: O=C(NCc1cn2cc(CNCC3CCCCC3)ccc2n1)c1cc(=O)c2cccc(Cl)c2o1] | C | 3.56/479.3 | |
| 187 | 6-bromo-N-[(6-{[(cyclohexyl methyl)amino] methyl} imidazo[1,2-a]pyridin-2-yl)methyl]-1H-indazole-4-carboxamide | 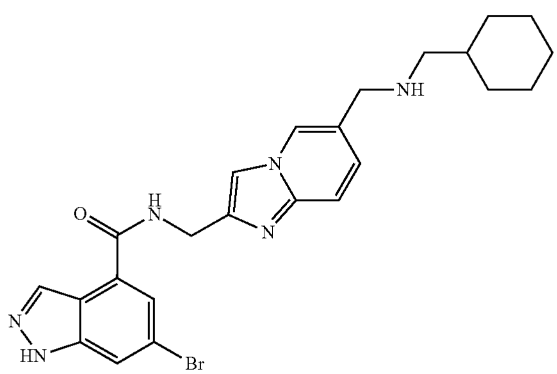 | D | 3.99/495.2/ 497.2 | 1, 25 |
| 188 | N-[(6-{[(cyclohexyl methyl)amino] methyl} imidazo[1,2-a]pyridin-2-yl)methyl] quinoline-3-carboxamide | 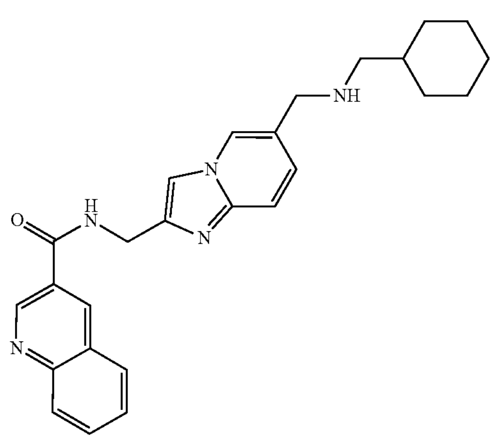 [SMILES: O=C(NCc1cn2cc(CNCC3CCCCC3)ccc2n1)c1cnc2ccccc2c1] | C | 3.14/428.4 | 25 |

TABLE 9-continued

| Compound No | Name | Structure | LCMS method | LCMS Retention time/ mass ion | Intermediates |
|---|---|---|---|---|---|
| 189 | N-[(6-{1-[(cyclohexyl-methyl)amino]ethyl}imidazo[1,2-a]pyridin-2-yl)methyl]-4-oxo-4H-pyrido[1,2-a]pyrimidine-2-carboxamide | 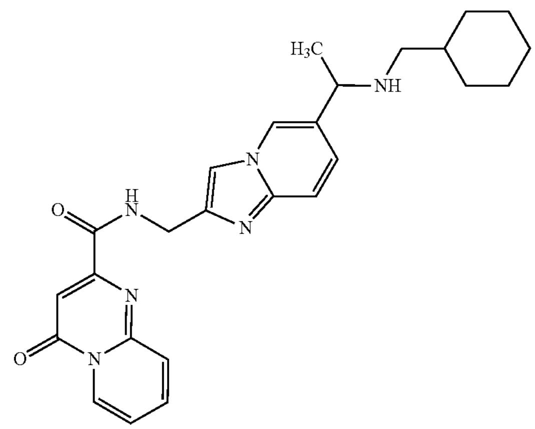 [SMILES: CC(NCC1CCCCC1)c1ccc2nc(CNC(=O)c3cc(=O)n4ccccc4n3)cn2c1] | D | 3.90/459.3 | 32 |
| 190 | 6-chloro-N-[(6-{[(cyclohexylmethyl)amino]methyl}imidazo[1,2-a]pyridin-2-yl)methyl]-1H-indazole-4-carboxamide | 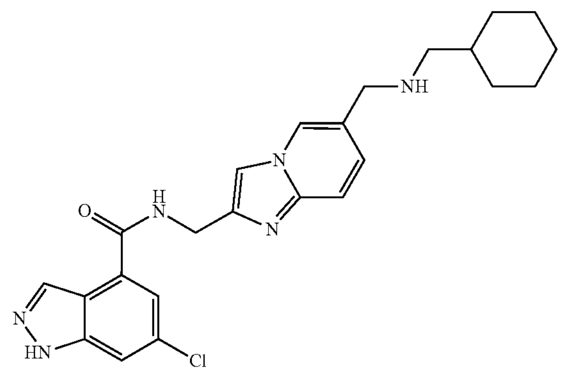 [SMILES: O=C(NCc1cn2cc(CNCC3CCCCC3)ccc2n1)c1cc(Cl)cc2[nH]ncc12] | D | 3.94/451.2 | 25 |

Compound 66: 4-[5-({6-methylimidazo[1,2-a]pyridin-2-yl}methyl)-1,3,4-thiadiazol-2-yl]-1H-indazole

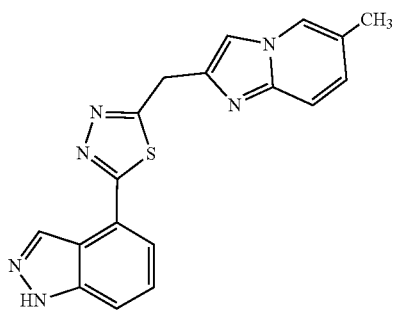

N'-[2-(6-methylimidazo[1,2-a]pyridin-2-yl)acetyl]-1-tetrahydropyran-2-yl-indazole-4-carbohydrazide (Compound 62 Step 3), (250 mg, 0.58 mmol) was suspended in 1,4-Dioxane (10 mL) and Lawesson's reagent (1.17 g, 2.89 mmol) was added. The vessel was sealed and the mixture heated at 110° C. and the solids dissolved upon heating. The reaction mixture was cooled to room temperature and left standing overnight. The reaction mixture was diluted with saturated aqueous sodium hydrogen carbonate (50 mL) and extracted with chloroform/isopropanol (3:1, 4×50 mL). The combined organic extracts were dried over sodium sulfate and evaporated under vacuum. The residue was purified by chromatography on silica gel (Biotage kp-NH 28 g, eluting with EtOAc/heptane 0-100% followed by 0-20% methanol/EtOAc) to afford a crude material which was triturated with EtOAc. The solids were collected by filtration and rinsed with heptane to afford the title compound (112 mg, 56%) as a white solid.

Method D: LC-MS (electrospray): m/z=347.2 (M+H)$^+$, RT=3.33 min

Compound 69: 4-[1-({6-methylimidazo[1,2-a]pyridin-2-yl}methyl)-1H-1,2,3-triazol-4-yl]-1H-indazole

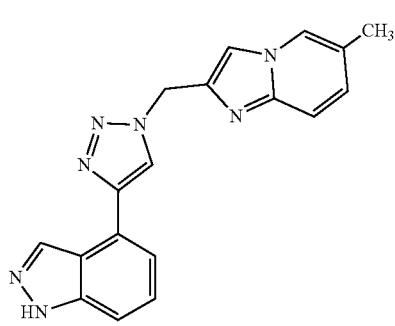

Step 1: 4-[1-({6-methylimidazo[1,2-a]pyridin-2-yl}methyl)-1H-1,2,3-triazol-4-yl]-1-(oxan-2-yl)-1H-indazole

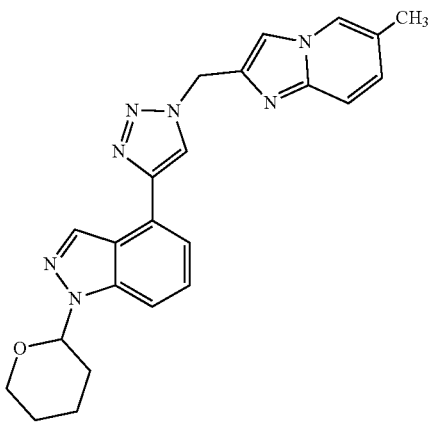

A solution of 2-(azidomethyl)-6-methyl-imidazo[1,2-a]pyridine (Intermediate 23, 120 mg, 0.64 mmol) and 4-ethynyl-1-tetrahydropyran-2-yl-indazole (intermediate 24, 189 mg, 0.83 mmol) in DMF (3 mL) and water (0.5 mL) was treated with $CuSO_4$ (31 mg, 0.19 mmol) and sodium ascorbate (38 mg, 0.19 mmol) and the mixture was stirred at room temperature for an hour. Precipitation noted within 30 minutes. The reaction mixture was diluted with water (20 mL), the solid was collected by filtration washed with water, then triturated successively with methanol, EtOAc and heptane and dried under suction to afford the title compound (209 mg, 79%) as a white solid.

Method D: LC-MS (electrospray): m/z=414.3 (M+H)$^+$, RT=3.93 min.

Step 2: 4-[1-({6-methylimidazo[1,2-a]pyridin-2-yl}methyl)-1H-1,2,3-triazol-4-yl]-1H-indazole

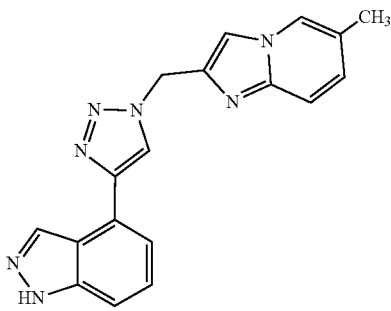

A suspension of 4-[1-[(6-methylimidazo[1,2-a]pyridin-2-yl)methyl]triazol-4-yl]-1-tetrahydropyran-2-yl-indazole (100 mg, 0.24 mmol) in methanol (5 mL) was treated with HCl (4M in Dioxane, 2 mL, 8 mmol)) which caused dissolution. The mixture was stirred at room temperature for two hours. The reaction mixture was evaporated under vacuum and the residue was triturated with methanol/EtOAc/heptane and the solids collected by filtration. The residue was purified by preparative HPLC (method B) and the fractions evaporated to afford the title compound (13 mg, 16%) as a white solid.

Method D: LC-MS (electrospray): m/z=330.2 (M+H)$^+$, RT=3.15 min.

Compound 158: N-[(6-{[(3-chlorophenyl)amino]methyl}imidazo[1,2-a]pyridin-2-yl)methyl]-4-oxo-4H-pyrido[1,2-a]pyrimidine-2-carboxamide

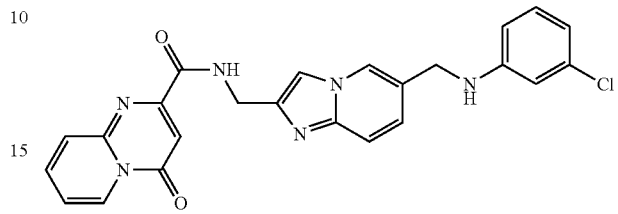

N-[(6-formylimidazo[1,2-a]pyridin-2-yl)methyl]-4-oxo-pyrido[1,2-a]pyrimidine-2-carboxamide (Compound 49) (70 mg, 0.20 mmol) and 3-chloroaniline (51 mg, 0.40 mmol) were combined in 1,1,1,3,3,3-Hexfluoro-2-propanol (2 mL) and the mixture stirred at room temperature. $NaBH_4$ (70 mg, 1.85 mmol) was added with a few drops of methanol-gas evolution—and the mixture stirred briefly at room temperature. The reaction mixture was quenched with methanol (20 mL)—gas evolution—and the mixture evaporated under vacuum. The residue was suspended in saturated aqueous sodium hydrogen carbonate (20 mL) and extracted with chloroform/isopropanol (3:1, 3×30 mL). The combined organic extracts were dried over sodium sulfate and evaporated under vacuum.

The residue was purified by preparative HPLC (method B) and the clean product-containing fractions combined and evaporated under vacuum. The residue was dried in the genevac and under vacuum at 40° C. to afford the title compound (47 mg, 50%) of as a pale yellow solid.

Method C: LC-MS (electrospray): m/z=459.3 (M+H)$^+$, RT=2.96 min.

Compound 168: N-[(6-{[(1-cyclohexyl-2-hydroxyethyl)amino]methyl}imidazo[1,2-a]pyridin-2-yl)methyl]-4-oxo-4H-pyrido[1,2-a]pyrimidine-2-carboxamide

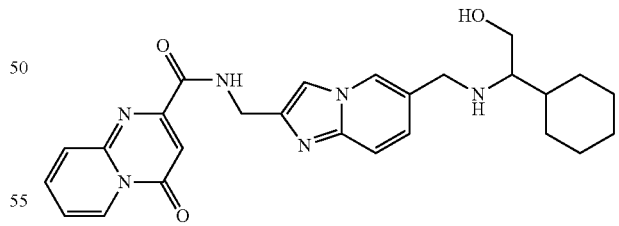

To a solution of N-[(6-formylimidazo[1,2-a]pyridin-2-yl)methyl]-4-oxo-pyrido[1,2-a]pyrimidine-2-carboxamide (Compound 49) (100 mg, 0.288 mmol) in 1,1,1,3,3,3-Hexafluoro-2-propanol (2 mL) was added 2-amino-2-cyclohexyl-ethanol (0.062 mL, 0.317 mmol) at room temperature. The mixture was stirred at room temperature overnight. The reaction mixture was concentrated under reduced pressure and the residue (pale yellow oil) was purified by preparative HPLC (Method B). The product containing fractions were combined and concentrated under reduced pressure to afford the intermediate imine (55 mg, 38%) as white solid. To a solution of the imine (52 mg, 0.105 mmol) in ethanol (3 mL) was added NaBH₄ (36 mg, 0.96 mmol) at room temperature. The mixture was stirred at room temperature for 3 hours. The reaction mixture was partitioned between ethyl acetate (40 mL) and Na2CO₃ (2M, 30 mL). The organic layer was separated, washed with brine (20 mL), dried (Na₂SO₄), filtered and concentrated under reduced pressure. The residue was purified by preparative HPLC (method B) to afford the title compound (16 mg, 31%) as white solid.

Method C: LC-MS (electrospray): m/z=475.3 (M+H)⁺, RT=2.56 min.

The compounds in table 10 was prepared in the same manner as Compounds 51, 158 or 168 and purified by method B.

TABLE 10

| Compound No | Name | Structure | LCMS method | LCMS Retention time | Mass ion |
|---|---|---|---|---|---|
| 70 | 4-oxo-N-{[6-({[(pyridin-3-yl)methyl]amino}methyl)imidazo[1,2-a]pyridin-2-yl]methyl}-4H-pyrido[1,2-a]pyrimidine-2-carboxamide | 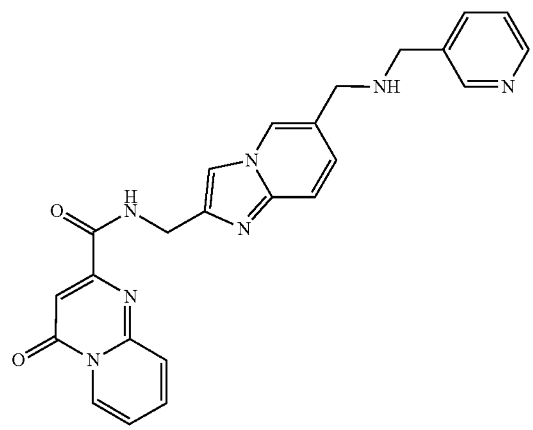 [SMILES: O=C(NCc1cn2cc(CNCc3cccnc3)ccc2n1)c1cc(=O)n2ccccc2n1] | D | 2.74 | 440.1 |
| 71 | N-{[6-({[(4-methoxyphenyl)methyl]amino}methyl)imidazo[1,2-a]pyridin-2-yl]methyl}-4-oxo-4H-pyrido[1,2-a]pyrimidine-2-carboxamide | 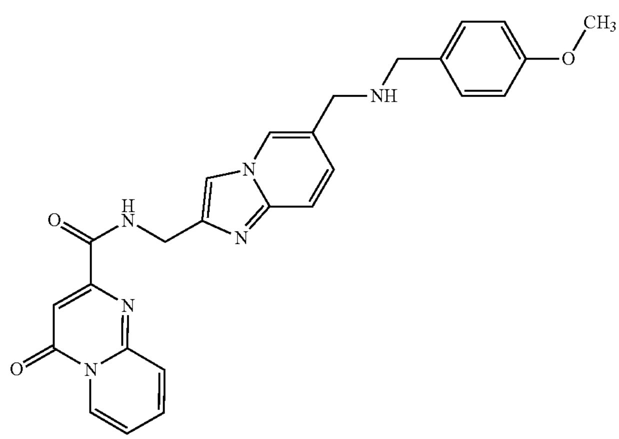 [SMILES: COc1ccc(CNCc2ccc3nc(CNC(=O)c4cc(=O)n5ccccc5n4)cn3c2)cc1] | D | 3.33 | 469.2 |
| 72 | N-[(6-{[(cyclohexylmethyl)amino]methyl}imidazo[1,2-a]pyridin-2-yl)methyl]-4-oxo-4H-pyrido[1,2-a]pyrimidine-2-carboxamide | 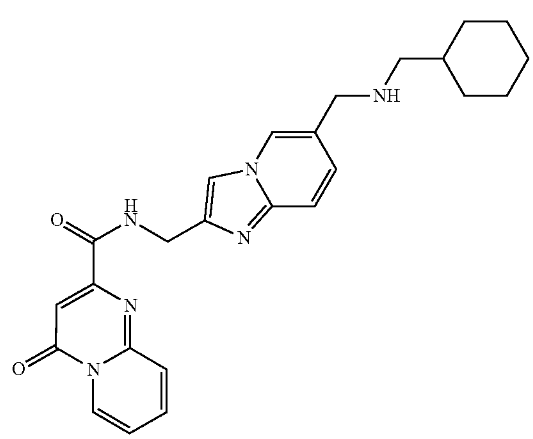 [SMILES: O=C(NCc1cn2cc(CNCC3CCCCC3)ccc2n1)c1cc(=O)n2ccccc2n1] | D | 3.84 | 445.2 |

TABLE 10-continued

| Compound No | Name | Structure | LCMS method | LCMS Retention time | Mass ion |
|---|---|---|---|---|---|
| 73 | N-{[6-({[(4-chlorophenyl)methyl]amino}methyl)imidazo[1,2-a]pyridin-2-yl]methyl}-4-oxo-4H-pyrido[1,2-a]pyrimidine-2-carboxamide | 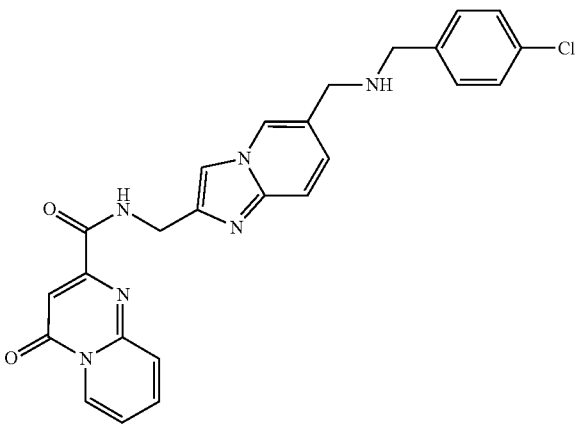 [SMILES: O=C(NCc1cn2cc(CNCc3ccc(Cl)cc3)ccc2n1)c1cc(=O)n2ccccc2n1] | D | 3.65 | 473.2 |
| 74 | N-[(6-{[benzyl(methyl)amino]methyl}imidazo[1,2-a]pyridin-2-yl)methyl]-4-oxo-4H-pyrido[1,2-a]pyrimidine-2-carboxamide | 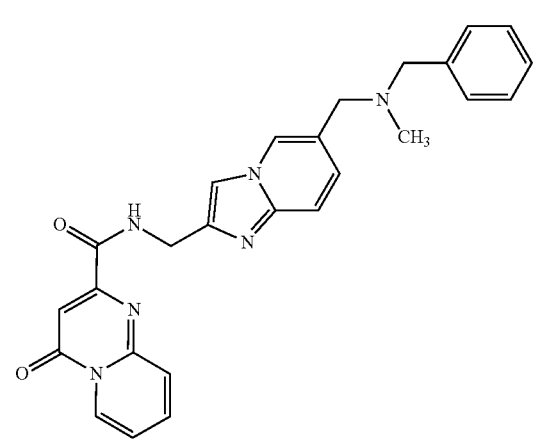 [SMILES: CN(Cc1ccccc1)Cc1ccc2nc(CNC(=O)c3cc(=O)n4ccccc4n3)cn2c1] | D | 3.80 | 453.3 |
| 75 | 4-oxo-N-{[6-({[(1R)-1-phenylethyl]amino}methyl)imidazo[1,2-a]pyridin-2-yl]methyl}-4H-pyrido[1,2-a]pyrimidine-2-carboxamide | 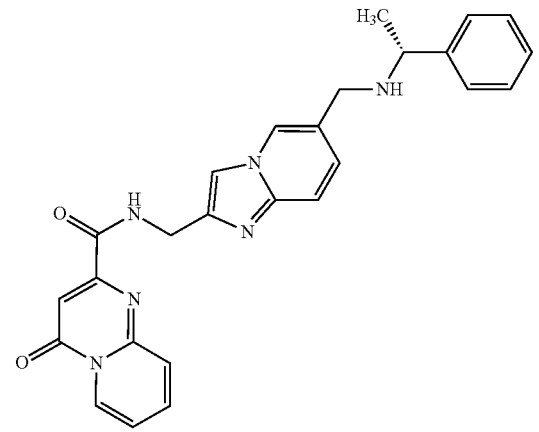 [SMILES: C[C@@H](NCc1ccc2nc(CNC(=O)c3cc(=O)n4ccccc4n3)cn2c1)c1ccccc1] | C | 2.76 | 453.3 |

TABLE 10-continued

| Compound No | Name | Structure | LCMS method | LCMS Retention time | Mass ion |
|---|---|---|---|---|---|
| 76 | 4-oxo-N-{[6-({[(1S)-1-phenylethyl]amino}methyl)imidazo[1,2-a]pyridin-2-yl]methyl}-4H-pyrido[1,2-a]pyrimidine-2-carboxamide | 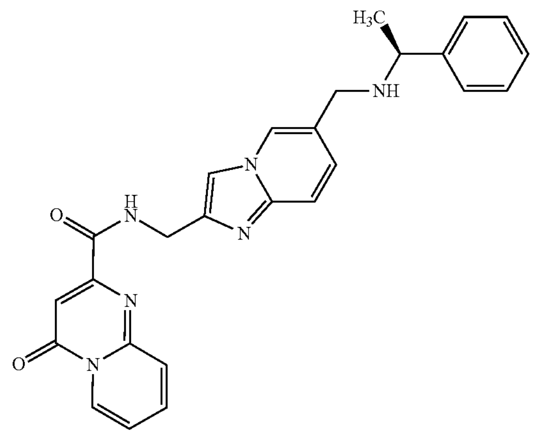 [SMILES: C[C@H](NCc1ccc2nc(CNC(=O)c3cc(=O)n4ccccc4n3)cn2c1)c1ccccc1] | C | 2.76 | 453.3 |
| 77 | N-{[6-({[(2-fluorophenyl)methyl]amino}methyl)imidazo[1,2-a]pyridin-2-yl]methyl}-4-oxo-4H-pyrido[1,2-a]pyrimidine-2-carboxamide | 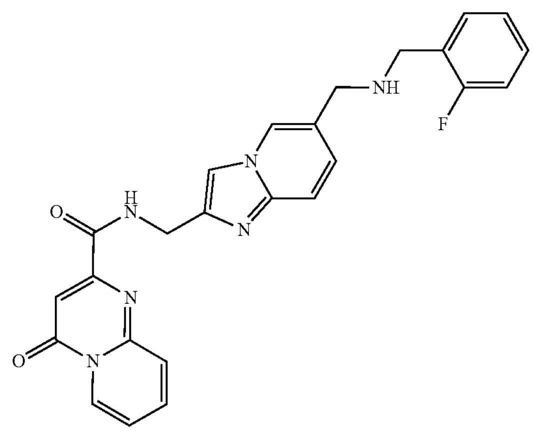 [SMILES: O=C(NCc1cn2cc(CNCc3ccccc3F)ccc2n1)c1cc(=O)n2ccccc2n1] | D | 3.40 | 457.1 |
| 78 | 4-oxo-N-[(6-{[(2-phenylpropan-2-yl)amino]methyl}imidazo[1,2-a]pyridin-2-yl)methyl]-4H-pyrido[1,2-a]pyrimidine-2-carboxamide | 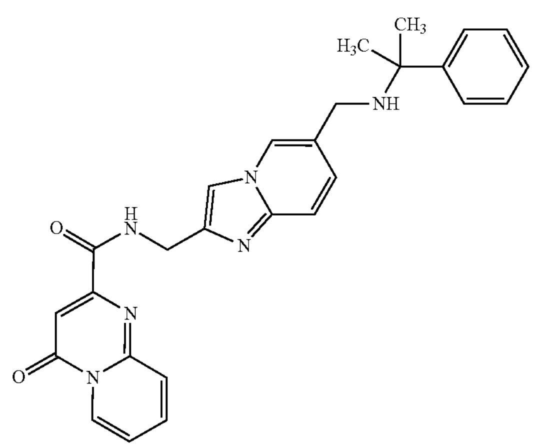 [SMILES: CC(C)(NCc1ccc2nc(CNC(=O)c3cc(=O)n4ccccc4n3)cn2c1)c1ccccc1] | D | 3.80 | 467.3 |

TABLE 10-continued

| Compound No | Name | Structure | LCMS method | LCMS Retention time | Mass ion |
|---|---|---|---|---|---|
| 79 | N-{[6-({[(3-fluorophenyl)methyl]amino}methyl)imidazo[1,2-a]pyridin-2-yl]methyl}-4-oxo-4H-pyrido[1,2-a]pyrimidine-2-carboxamide | 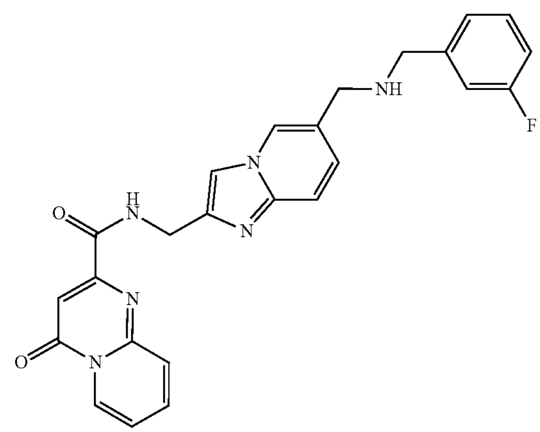 [SMILES: O=C(NCc1cn2cc(CNCc3cccc(F)c3)ccc2n1)c1cc(=O)n2ccccc2n1] | D | 3.47 | 457.1 |
| 80 | N-{[6-({[(4-fluorophenyl)methyl]amino}methyl)imidazo[1,2-a]pyridin-2-yl]methyl}-4-oxo-4H-pyrido[1,2-a]pyrimidine-2-carboxamide | 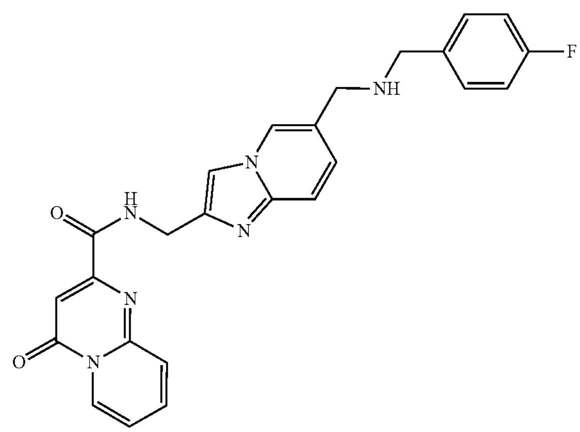 [SMILES: O=C(NCc1cn2cc(CNCc3ccc(F)cc3)ccc2n1)c1cc(=O)n2ccccc2n1] | D | 3.43 | 457.1 |
| 81 | 4-oxo-N-[(6-{[(4,4,4-trifluorobutyl)amino]methyl}imidazo[1,2-a]pyridin-2-yl)methyl]-4H-pyrido[1,2-a]pyrimidine-2-carboxamide | 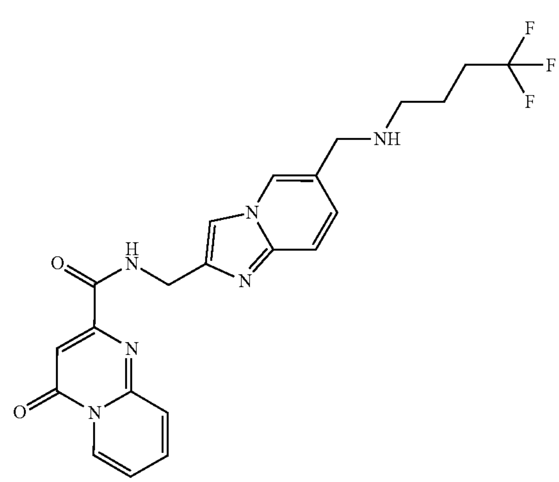 [SMILES: O=C(NCc1cn2cc(CNCCCC(F)(F)F)ccc2n1)c1cc(=O)n2ccccc2n1] | C | 2.44 | 459.3 |

TABLE 10-continued

| Compound No | Name | Structure | LCMS method | LCMS Retention time | Mass ion |
|---|---|---|---|---|---|
| 82 | N-{[6-({[(oxan-4-yl)methyl]amino}methyl)imidazo[1,2-a]pyridin-2-yl]methyl}-4-oxo-4H-pyrido[1,2-a]pyrimidine-2-carboxamide | 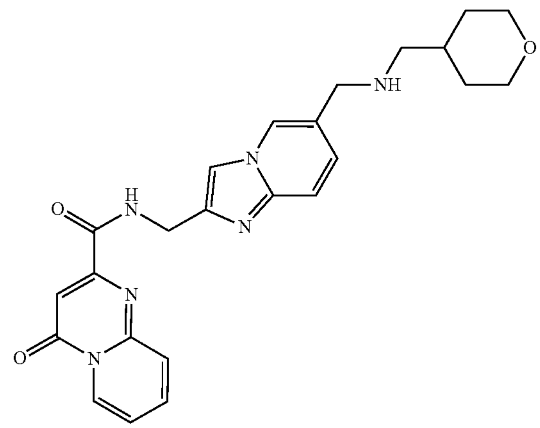 [SMILES: O=C(NCc1cn2cc(CNCC3CCOCC3)ccc2n1)c1cc(=O)n2ccccc2n1] | C | 1.91 | 447.3 |
| 83 | N-{[6-({[(3,3-difluorocyclobutyl)methyl]amino}methyl)imidazo[1,2-a]pyridin-2-yl]methyl}-4-oxo-4H-pyrido[1,2-a]pyrimidine-2-carboxamide | 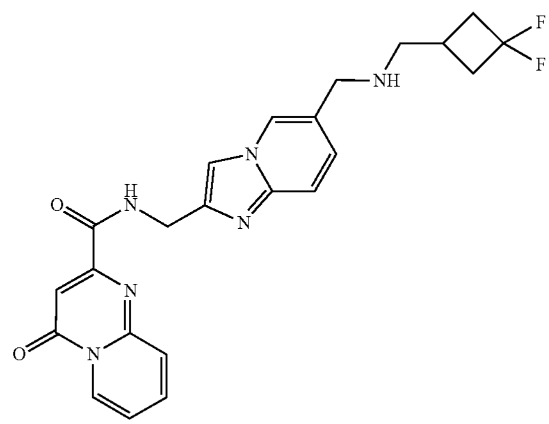 [SMILES: O=C(NCc1cn2cc(CNCC3CC(F)(F)C3)ccc2n1)c1cc(=O)n2ccccc2n1] | C | 2.33 | 453.3 |
| 84 | N-[(6-{[(cyclopropylmethyl)amino]methyl}imidazo[1,2-a]pyridin-2-yl)methyl]-4-oxo-4H-pyrido[1,2-a]pyrimidine-2-carboxamide | 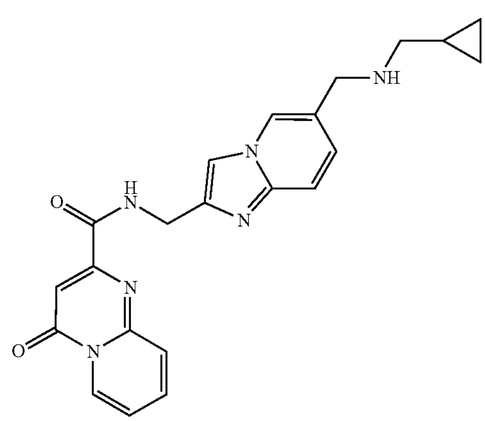 [SMILES: O=C(NCc1cn2cc(CNCC3CC3)ccc2n1)c1cc(=O)n2ccccc2n1] | D | 3.11 | 403.2 |

TABLE 10-continued

| Compound No | Name | Structure | LCMS method | LCMS Retention time | Mass ion |
|---|---|---|---|---|---|
| 85 | 4-oxo-N-[(6-{[(3,3,3-trifluoropropyl)amino]methyl}imidazo[1,2-a]pyridin-2-yl)methyl]-4H-pyrido[1,2-a]pyrimidine-2-carboxamide | 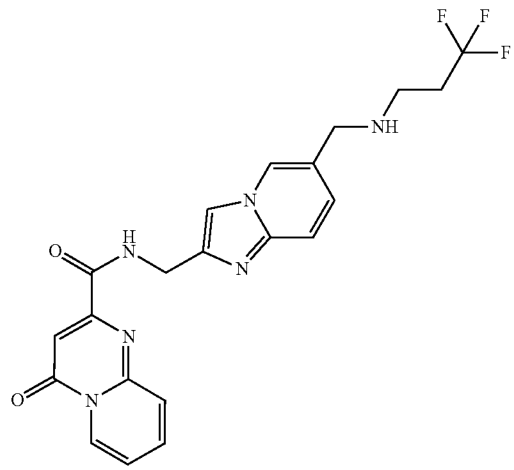 [SMILES: O=C(NCc1cn2cc(CNCCC(F)(F)F)ccc2n1)c1cc(=O)n2ccccc2n1] | C | 2.26 | 445.3 |
| 86 | N-({6-[(cyclohexylamino)methyl]imidazo[1,2-a]pyridin-2-yl}methyl)-4-oxo-4H-pyrido[1,2-a]pyrimidine-2-carboxamide | 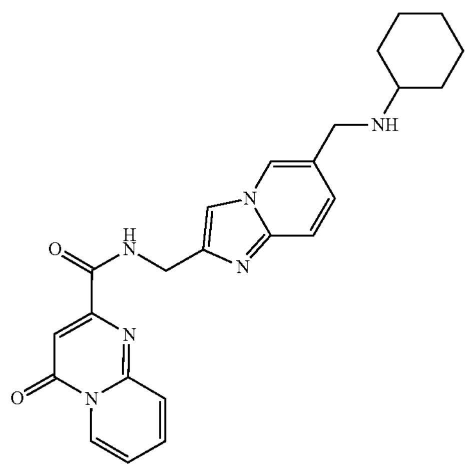 [SMILES: O=C(NCc1cn2cc(CNC3CCCCC3)ccc2n1)c1cc(=O)n2ccccc2n1] | D | 3.60 | 431.2 |
| 87 | 4-oxo-N-({6-[({[3-(trifluoromethyl)bicyclo[1.1.1]pentan-1-yl]methyl}amino)methyl]imidazo[1,2-a]pyridin-2-yl}methyl)-4H-pyrido[1,2-a]pyrimidine-2-carboxamide | 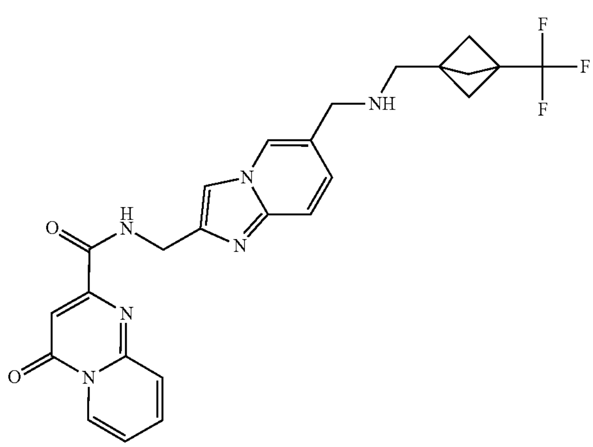 [SMILES: O=C(NCc1cn2cc(CNCC34CC(C(F)(F)F)(C3)C4)ccc2n1)c1cc(=O)n2ccccc2n1] | D | 3.75 | 497.2 |

TABLE 10-continued

| Compound No | Name | Structure | LCMS method | LCMS Retention time | Mass ion |
|---|---|---|---|---|---|
| 88 | N-{[6-({[(oxan-2-yl)methyl]amino}methyl)imidazo[1,2-a]pyridin-2-yl]methyl}-4-oxo-4H-pyrido[1,2-a]pyrimidine-2-carboxamide | 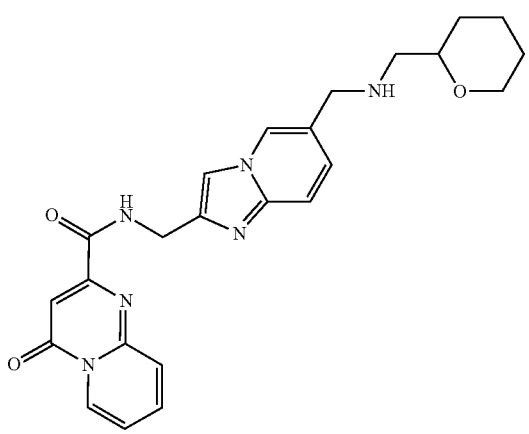 [SMILES: O=C(NCc1cn2cc(CNCC3CCCCO3)ccc2n1)c1cc(=O)n2ccccc2n1] | D | 3.05 | 447.2 |
| 89 | 4-oxo-N-[(6-{[(3-phenyloxetan-3-yl)amino]methyl}imidazo[1,2-a]pyridin-2-yl)methyl]-4H-pyrido[1,2-a]pyrimidine-2-carboxamide | 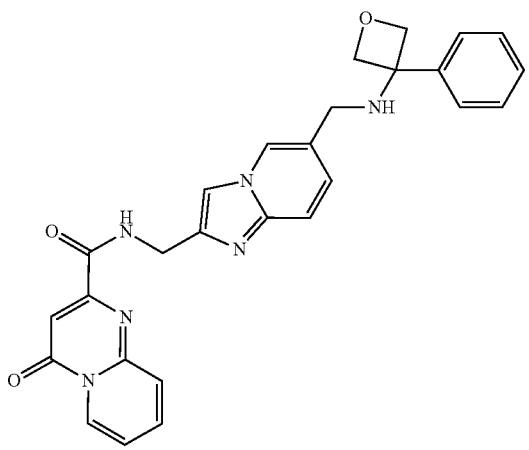 [SMILES: O=C(NCc1cn2cc(CNC3(c4ccccc4)COC3)ccc2n1)c1cc(=O)n2ccccc2n1] | C | 2.40 | 481.3 |
| 90 | N-{[6-({[(oxan-3-yl)methyl]amino}methyl)imidazo[1,2-a]pyridin-2-yl]methyl}-4-oxo-4H-pyrido[1,2-a]pyrimidine-2-carboxamide | 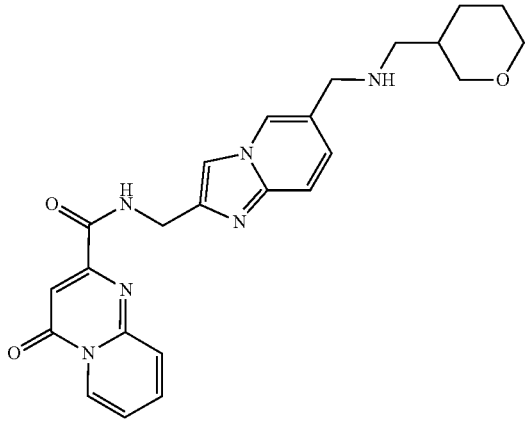 [SMILES: O=C(NCc1cn2cc(CNCC3CCCOC3)ccc2n1)c1cc(=O)n2ccccc2n1] | D | 2.90 | 447.2 |

TABLE 10-continued

| Compound No | Name | Structure | LCMS method | LCMS Retention time | Mass ion |
|---|---|---|---|---|---|
| 91 | N-{[6-({[(1-fluorocyclohexyl)methyl]amino}methyl)imidazo[1,2-a]pyridin-2-yl]methyl}-4-oxo-4H-pyrido[1,2-a]pyrimidine-2-carboxamide | 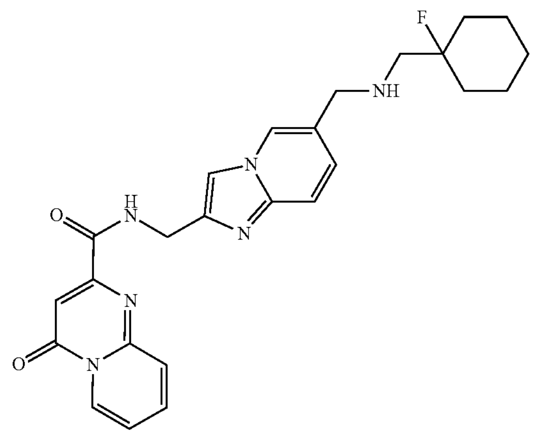 [SMILES: O=C(NCc1cn2cc(CNCC3(F)CCCCC3)ccc2n1)c1cc(=O)n2ccccc2n1] | C | 2.82 | 463.4 |
| 92 | N-{[6-({[(3-cyclopropylphenyl)methyl]amino}methyl)imidazo[1,2-a]pyridin-2-yl]methyl}-4-oxo-4H-pyrido[1,2-a]pyrimidine-2-carboxamide | 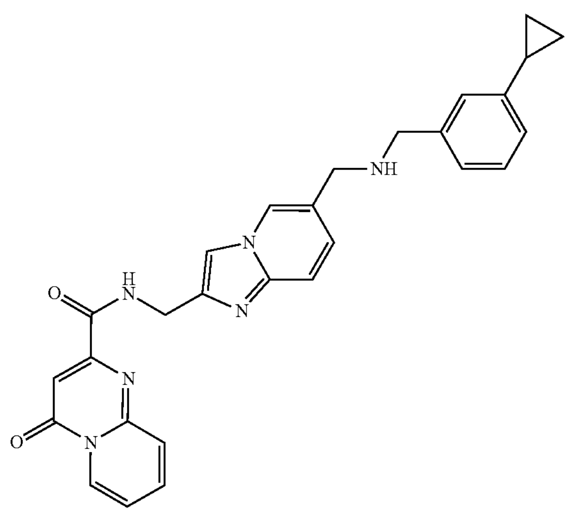 [SMILES: O=C(NCc1cn2cc(CNCc3cccc(C4CC4)c3)ccc2n1)c1cc(=O)n2ccccc2n1] | C | 2.96 | 479.4 |
| 93 | N-[(6-{[(3,3-dimethylbutyl)amino]methyl}imidazo[1,2-a]pyridin-2-yl)methyl]-4-oxo-4H-pyrido[1,2-a]pyrimidine-2-carboxamide | 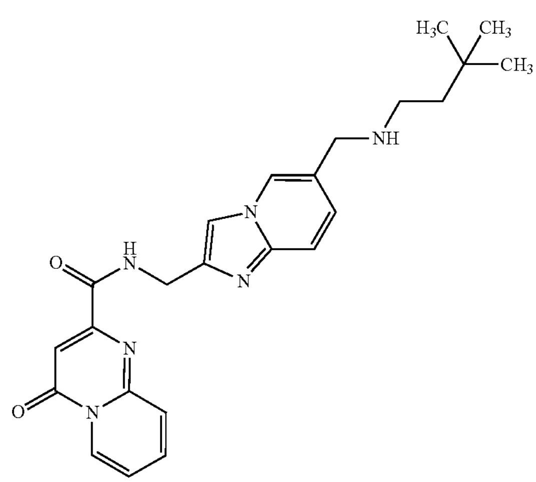 [SMILES: CC(C)(C)CCNCc1ccc2nc(CNC(=O)c3cc(=O)n4ccccc4n3)cn2c1] | C | 2.77 | 433.4 |

TABLE 10-continued

| Compound No | Name | Structure | LCMS method | LCMS Retention time | Mass ion |
|---|---|---|---|---|---|
| 94 | 4-oxo-N-{[6-({[2-(trifluoromethoxy)ethyl]amino}methyl)imidazo[1,2-a]pyridin-2-yl]methyl}-4H-pyrido[1,2-a]pyrimidine-2-carboxamide | 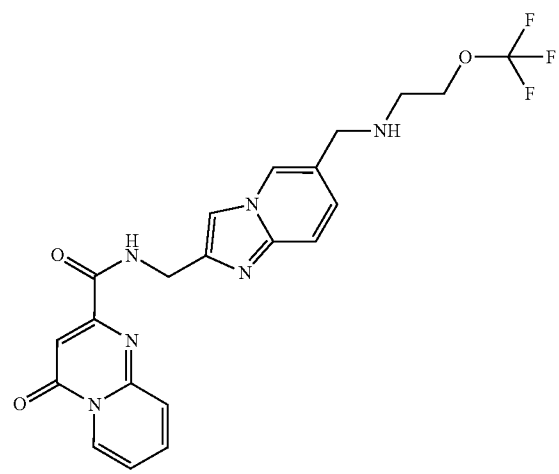 [SMILES: O=C(NCc1cn2cc(CNCCOC(F)(F)F)ccc2n1)c1cc(=O)n2ccccc2n1] | C | 2.37 | 461.3 |
| 95 | 4-oxo-N-{[6-({[(oxolan-2-yl)methyl]amino}methyl)imidazo[1,2-a]pyridin-2-yl]methyl}-4H-pyrido[1,2-a]pyrimidine-2-carboxamide | 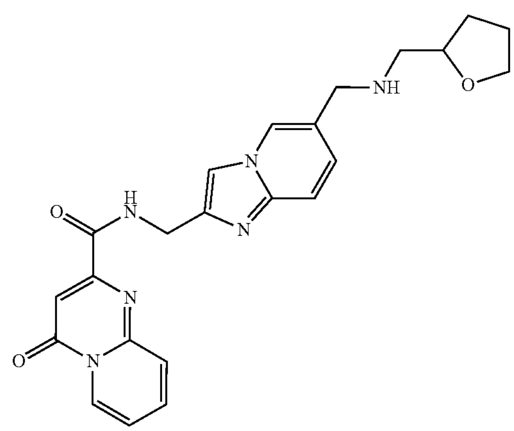 [SMILES: O=C(NCc1cn2cc(CNCC3CCCO3)ccc2n1)c1cc(=O)n2ccccc2n1] | C | 1.93 | 433.3 |
| 96 | N-[(6-{[(2-methanesulfonylethyl)amino]methyl}imidazo[1,2-a]pyridin-2-yl)methyl]-4-oxo-4H-pyrido[1,2-a]pyrimidine-2-carboxamide | 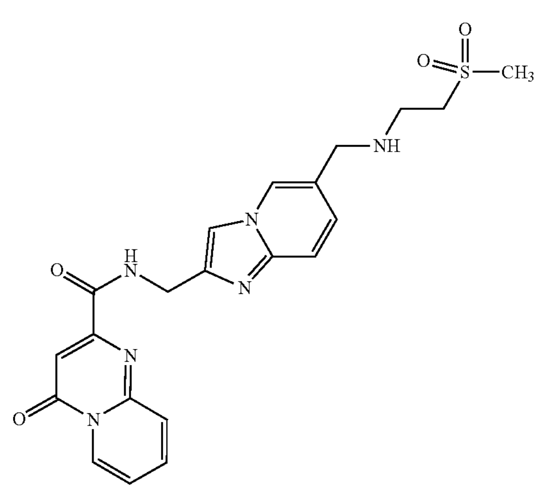 [SMILES: CS(=O)(=O)CCNCc1ccc2nc(CNC(=O)c3cc(=O)n4ccccc4n3)cn2c1] | C | 1.59 | 455.3 |

TABLE 10-continued

| Compound No | Name | Structure | LCMS method | LCMS Retention time | Mass ion |
|---|---|---|---|---|---|
| 97 | 4-oxo-N-({6-[(3-phenylpyrrolidin-1-yl)methyl]imidazo[1,2-a]pyridin-2-yl}methyl)-4H-pyrido[1,2-a]pyrimidine-2-carboxamide | 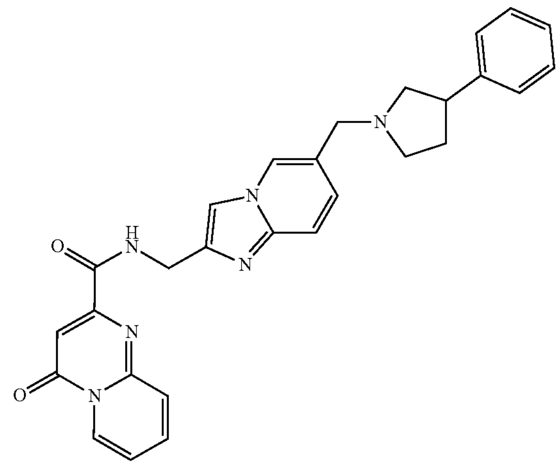 [SMILES: O=C(NCc1cn2cc(CN3CCC(c4ccccc4)C3)ccc2n1)c1cc(=O)n2ccccc2n1] | C | 3.36 | 479.4 |
| 98 | N-[(6-{[(1-cyclohexyl-cyclopropyl)amino]methyl}imidazo[1,2-a]pyridin-2-yl)methyl]-4-oxo-4H-pyrido[1,2-a]pyrimidine-2-carboxamide | 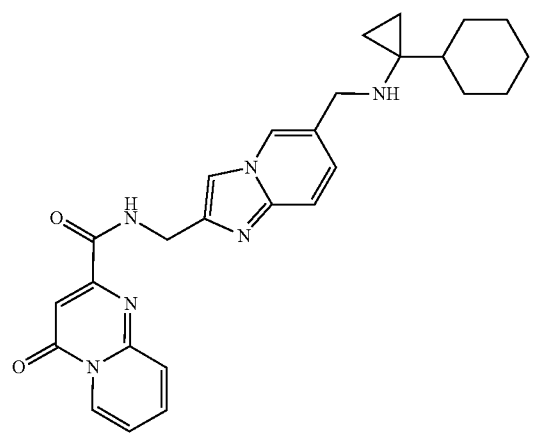 [SMILES: O=C(NCc1cn2cc(CNC3(C4CCCCC4)CC3)ccc2n1)c1cc(=O)n2ccccc2n1] | D | 4.35 | 471.2 |
| 99 | 4-oxo-N-{[6-({[(1,3-thiazol-5-yl)methyl]amino}methyl)imidazo[1,2-a]pyridin-2-yl]methyl}-4H-pyrido[1,2-a]pyrimidine-2-carboxamide | 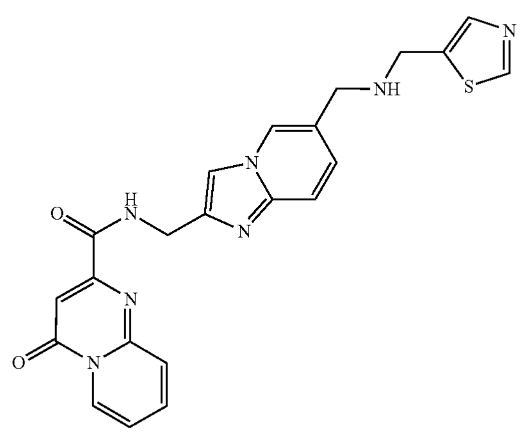 [SMILES: O=C(NCc1cn2cc(CNCc3cncs3)ccc2n1)c1cc(=O)n2ccccc2n1] | C | 1.83 | 446.2 |

TABLE 10-continued

| Compound No | Name | Structure | LCMS method | LCMS Retention time | Mass ion |
|---|---|---|---|---|---|
| 100 | tert-butyl 3-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate | 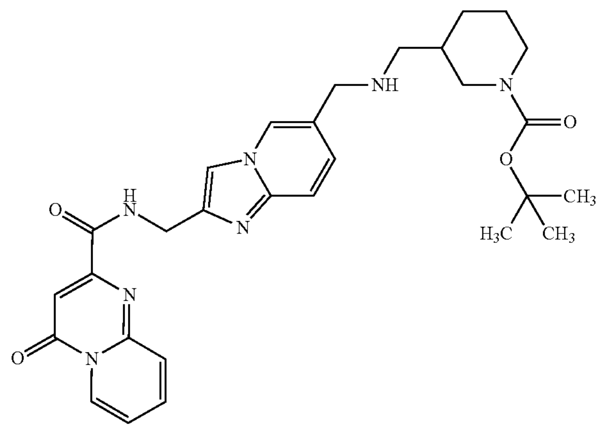 [SMILES: CC(C)(C)OC(=O)N1CCCC(CNCc2ccc3nc(CNC(=O)c4cc(=O)n5ccccc5n4)cn3c2)C1] | D | 3.63 | 546.3 |
| 101 | N-{[6-({[(4,4-difluorocyclohexyl)methyl]amino}methyl)imidazo[1,2-a]pyridin-2-yl]methyl}-4-oxo-4H-pyrido[1,2-a]pyrimidine-2-carboxamide | 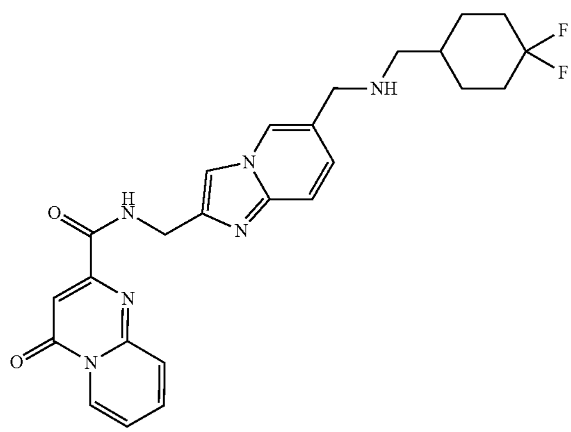 [SMILES: O=C(NCc1cn2cc(CNCC3CCC(F)(F)CC3)ccc2n1)c1cc(=O)n2ccccc2n1] | D | 3.48 | 481.2 |
| 102 | tert-butyl 2-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate | 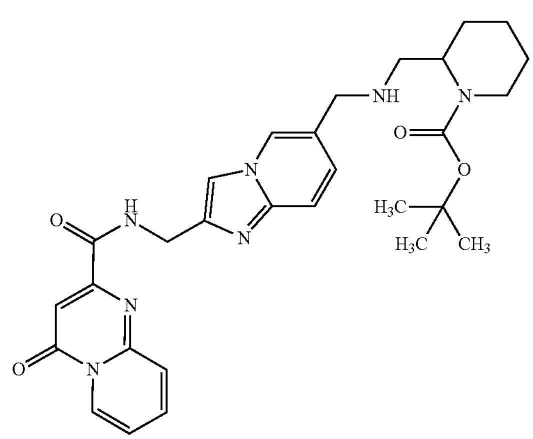 [SMILES: CC(C)(C)OC(=O)N1CCCCC1CNCc1ccc2nc(CNC(=O)c3cc(=O)n4ccccc4n3)cn2c1] | D | 3.68 | 546.3 |

| Compound No | Name | Structure | LCMS method | LCMS Retention time | Mass ion |
|---|---|---|---|---|---|
| 103 | N-[(6-{[(2-cyclopropylethyl)amino]methyl}imidazo[1,2-a]pyridin-2-yl)methyl]-4-oxo-4H-pyrido[1,2-a]pyrimidine-2-carboxamide | 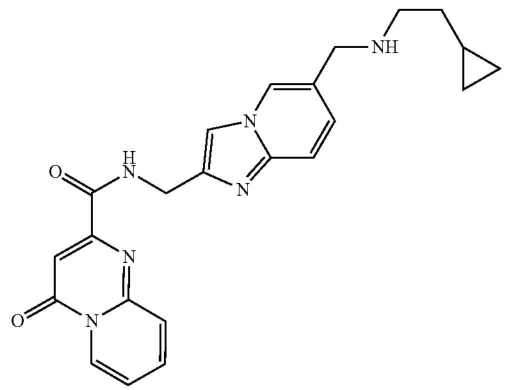 [SMILES: O=C(NCc1cn2cc(CNCCC3CC3)ccc2n1)c1cc(=O)n2ccccc2n1] | C | 2.38 | 417.3 |
| 104 | 4-oxo-N-({6-[(piperidin-1-yl)methyl]imidazo[1,2-a]pyridin-2-yl}methyl)-4H-pyrido[1,2-a]pyrimidine-2-carboxamide | 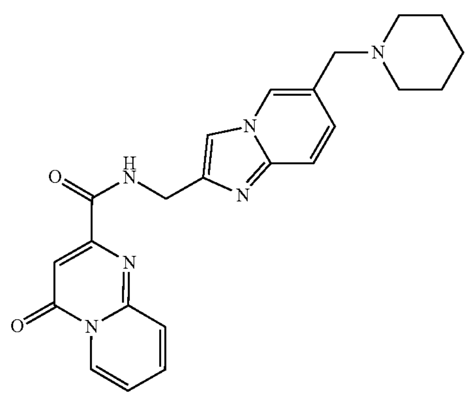 [SMILES: O=C(NCc1cn2cc(CN3CCCCC3)ccc2n1)c1cc(=O)n2ccccc2n1] | C | 2.49 | 417.3 |
| 105 | 4-oxo-N-({6-[({[1-(2,2,2-trifluoroethyl)-1H-pyrazol-3-yl]methyl}amino)methyl]imidazo[1,2-a]pyridin-2-yl}methyl)-4H-pyrido[1,2-a]pyrimidine-2-carboxamide | 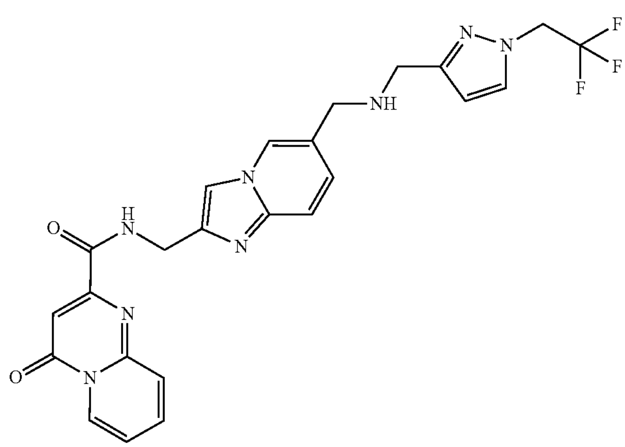 [SMILES: O=C(NCc1cn2cc(CNCc3ccn(CC(F)(F)F)n3)ccc2n1)c1cc(=O)n2ccccc2n1] | C | 2.13 | 511.3 |

TABLE 10-continued

| Compound No | Name | Structure | LCMS method | LCMS Retention time | Mass ion |
|---|---|---|---|---|---|
| 106 | N-{[6-({[(1-methylcyclohexyl)methyl]amino}methyl)imidazo[1,2-a]pyridin-2-yl]methyl}-4-oxo-4H-pyrido[1,2-a]pyrimidine-2-carboxamide | 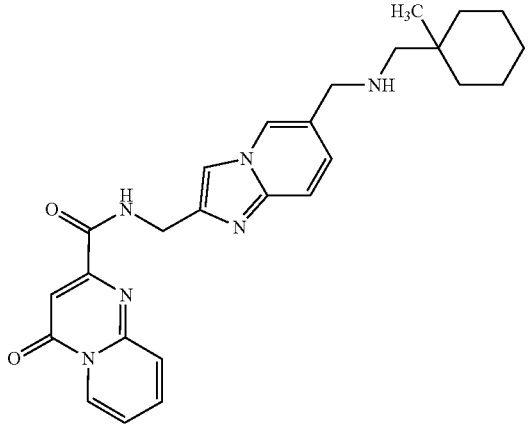 | C | 3.29 | 459.4 |
| 107 | 4-oxo-N-{[6-({[2-(pyridin-3-yl)ethyl]amino}methyl)imidazo[1,2-a]pyridin-2-yl]methyl}-4H-pyrido[1,2-a]pyrimidine-2-carboxamide | 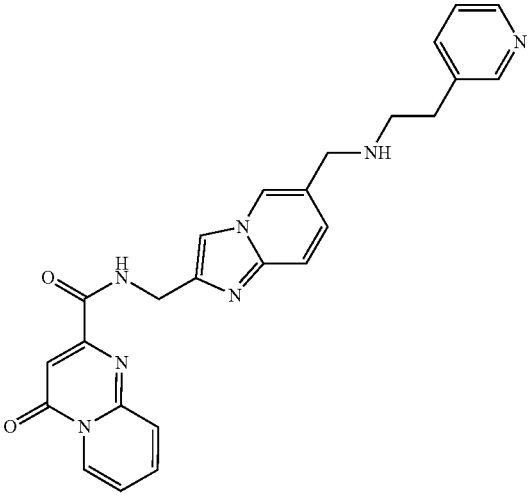 [SMILES: O=C(NCc1cn2cc(CNCCc3cccnc3)ccc2n1)c1cc(=O)n2ccccc2n1] | C | 1.88 | 454.3 |
| 108 | N-{[6-({[(1,4-dioxan-2-yl)methyl]amino}methyl)imidazo[1,2-a]pyridin-2-yl]methyl}-4-oxo-4H-pyrido[1,2-a]pyrimidine-2-carboxamide | 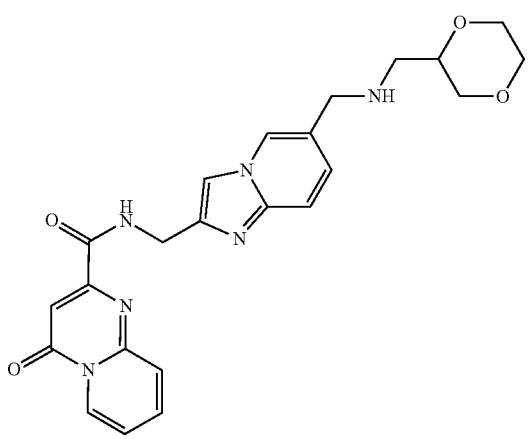 [SMILES: O=C(NCc1cn2cc(CNCC3COCCO3)ccc2n1)c1cc(=O)n2ccccc2n1] | C | 1.73 | 449.3 |

TABLE 10-continued

| Compound No | Name | Structure | LCMS method | LCMS Retention time | Mass ion |
|---|---|---|---|---|---|
| 109 | N-({6-[(cyclopropylamino)methyl]imidazo[1,2-a]pyridin-2-yl}methyl)-4-oxo-4H-pyrido[1,2-a]pyrimidine-2-carboxamide | 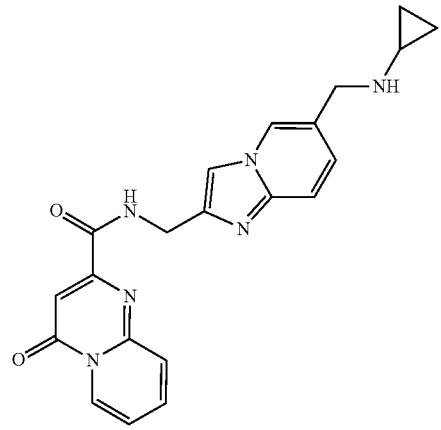 [SMILES: O=C(NCc1cn2cc(CNC3CC3)ccc2n1)c1cc(=O)n2ccccc2n1] | C | 1.97 | 389.2 |
| 110 | N-[(6-{[(3,3-difluorocyclobutyl)amino]methyl}imidazo[1,2-a]pyridin-2-yl)methyl]-4-oxo-4H-pyrido[1,2-a]pyrimidine-2-carboxamide | 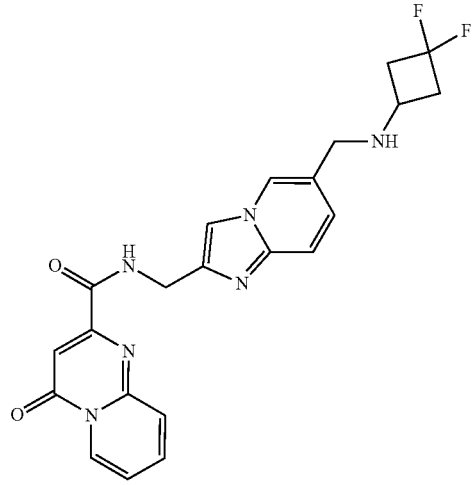 [SMILES: O=C(NCc1cn2cc(CNC3CC(F)(F)C3)ccc2n1)c1cc(=O)n2ccccc2n1] | C | 2.16 | 439.3 |
| 111 | N-{[6-({[(oxetan-3-yl)methyl]amino}methyl)imidazo[1,2-a]pyridin-2-yl]methyl}-4-oxo-4H-pyrido[1,2-a]pyrimidine-2-carboxamide | 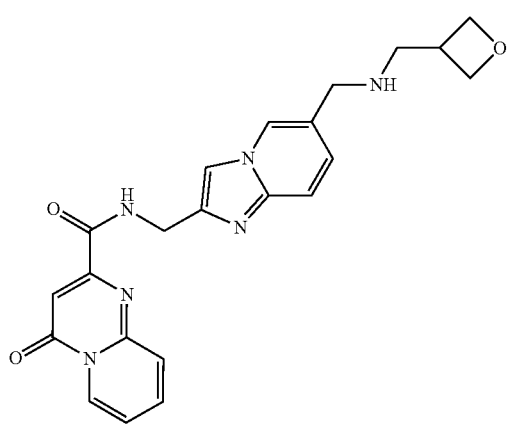 [SMILES: O=C(NCc1cn2cc(CNCC3COC3)ccc2n1)c1cc(=O)n2ccccc2n1] | C | 1.62 | 419.3 |

TABLE 10-continued

| Compound No | Name | Structure | LCMS method | LCMS Retention time | Mass ion |
|---|---|---|---|---|---|
| 112 | 4-oxo-N-{[6-({[(1R,2R)-2-(trifluoromethyl)cyclopropyl]amino}methyl)imidazo[1,2-a]pyridin-2-yl]methyl}-4H-pyrido[1,2-a]pyrimidine-2-carboxamide | 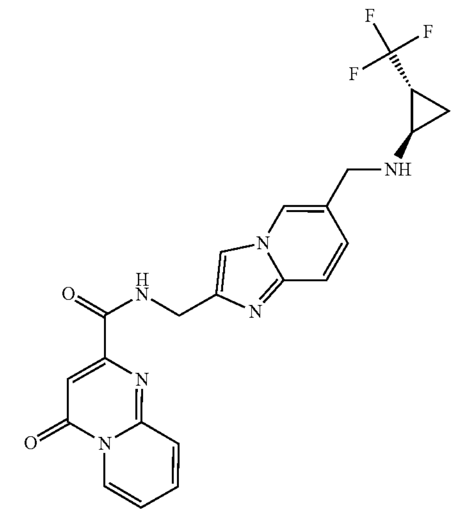 [SMILES: O=C(NCc1cn2cc(CN[C@@H]3C[C@H]3C(F)(F)F)ccc2n1)c1cc(=O)n2ccccc2n1] | C | 2.43 | 457.3 |
| 113 | N-[(6-{[(2,2-dimethylpropyl)amino]methyl}imidazo[1,2-a]pyridin-2-yl)methyl]-4-oxo-4H-pyrido[1,2-a]pyrimidine-2-carboxamide | 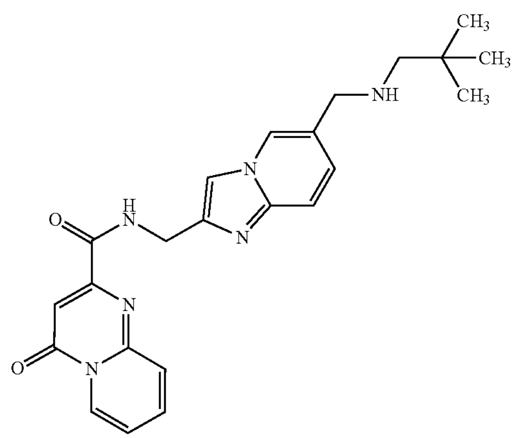 [SMILES: CC(C)(C)CNCc1ccc2nc(CNC(=O)c3cc(=O)n4ccccc4n3)cn2c1] | C | 2.70 | 419.3 |
| 114 | N-[(6-{[(cyclohexylmethyl)(methyl)amino]methyl}imidazo[1,2-a]pyridin-2-yl)methyl]-4-oxo-4H-pyrido[1,2-a]pyrimidine-2-carboxamide | 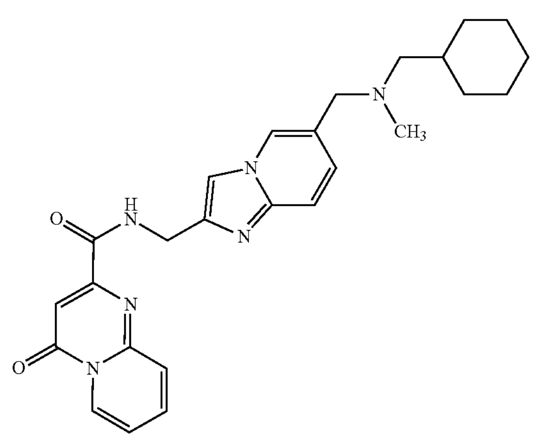 [SMILES: CN(Cc1ccc2nc(CNC(=O)c3cc(=O)n4ccccc4n3)cn2c1)CC1CCCCC1] | D | 4.43 | 459.3 |

TABLE 10-continued

| Compound No | Name | Structure | LCMS method | LCMS Retention time | Mass ion |
|---|---|---|---|---|---|
| 115 | N-[(6-{[(4,4-difluoro-cyclohexyl)amino]methyl}imidazo[1,2-a]pyridin-2-yl)methyl]-4-oxo-4H-pyrido[1,2-a]pyrimidine-2-carboxamide | 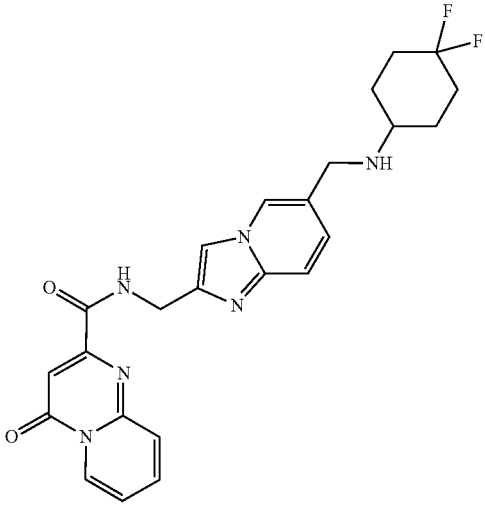 [SMILES: O=C(NCc1cn2cc(CNC3CCC(F)(F)CC3)ccc2n1)c1cc(=O)n2ccccc2n1] | C | 2.43 | 467.3 |
| 116 | N-({6-[({bicyclo[1.1.1]pentan-1-yl}amino)methyl]imidazo[1,2-a]pyridin-2-yl}methyl)-4-oxo-4H-pyrido[1,2-a]pyrimidine-2-carboxamide | 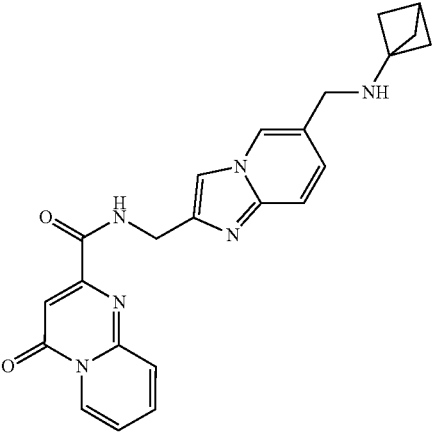 [SMILES: O=C(NCc1cn2cc(CNC34CC(C3)C4)ccc2n1)c1cc(=O)n2ccccc2n1] | C | 2.34 | 415.3 |
| 117 | 4-oxo-N-({6-[({[(2S)-oxolan-2-yl]methyl}amino)methyl]imidazo[1,2-a]pyridin-2-yl}methyl)-4H-pyrido[1,2-a]pyrimidine-2-carboxamide | 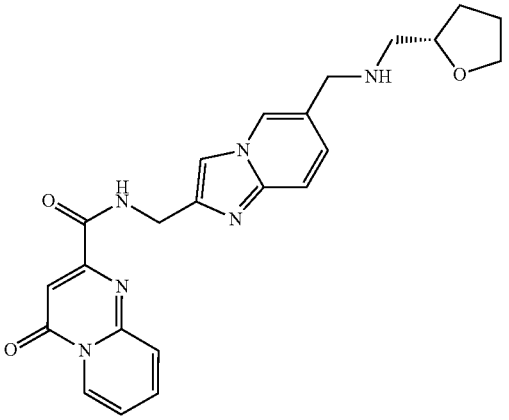 [SMILES: O=C(NCc1cn2cc(CNC[C@@H]3CCCO3)ccc2n1)c1cc(=O)n2ccccc2n1] | C | 1.93 | 433.3 |

TABLE 10-continued

| Compound No | Name | Structure | LCMS method | LCMS Retention time | Mass ion |
|---|---|---|---|---|---|
| 118 | 4-oxo-N-({6-[({[(2R)-oxolan-2-yl]methyl}amino)methyl]imidazo[1,2-a]pyridin-2-yl}methyl)-4H-pyrido[1,2-a]pyrimidine-2-carboxamide | 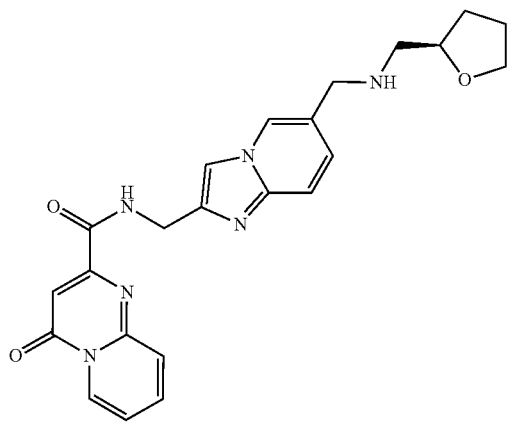 [SMILES: O=C(NCc1cn2cc(CNC[C@H]3CCCO3)ccc2n1)c1cc(=O)n2ccccc2n1] | C | 1.93 | 433.3 |
| 119 | N-[(6-{[(2,2-difluoroethyl)amino]methyl}imidazo[1,2-a]pyridin-2-yl)methyl]-4-oxo-4H-pyrido[1,2-a]pyrimidine-2-carboxamide | 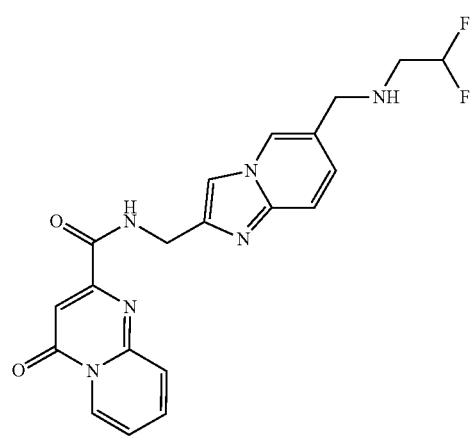 [SMILES: O=C(NCc1cn2cc(CNCC(F)F)ccc2n1)c1cc(=O)n2ccccc2n1] | C | 1.93 | 413.2 |
| 120 | 4-oxo-N-{[6-({[(oxolan-3-yl)methyl]amino}methyl)imidazo[1,2-a]pyridin-2-yl]methyl}-4H-pyrido[1,2-a]pyrimidine-2-carboxamide | 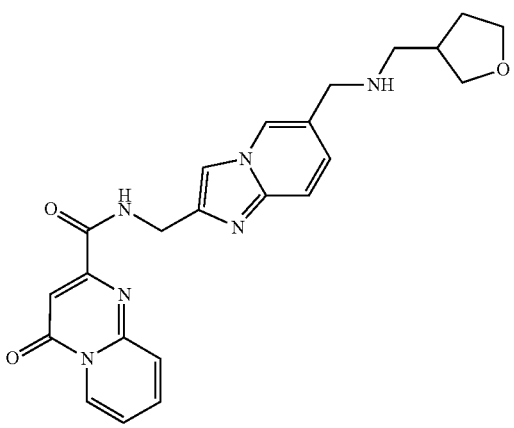 [SMILES: O=C(NCc1cn2cc(CNCC3CCOC3)ccc2n1)c1cc(=O)n2ccccc2n1] | D | 2.68 | 433.2 |

TABLE 10-continued

| Compound No | Name | Structure | LCMS method | LCMS Retention time | Mass ion |
|---|---|---|---|---|---|
| 121 | N-{[6-({[(1-methylcyclopropyl)methyl]amino}methyl)imidazo[1,2-a]pyridin-2-yl]methyl}-4-oxo-4H-pyrido[1,2-a]pyrimidine-2-carboxamide | 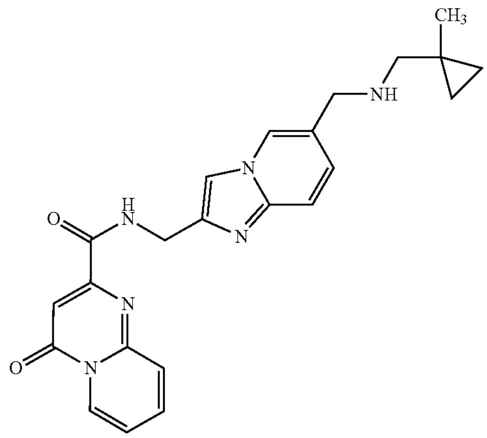 [SMILES: CC1(CNCc2ccc3nc(CNC(=O)c4cc(=O)n5ccccc5n4)cn3c2)CC1] | C | 2.43 | 417.3 |
| 122 | 4-oxo-N-[(6-{[(oxolan-3-yl)amino]methyl}imidazo[1,2-a]pyridin-2-yl)methyl]-4H-pyrido[1,2-a]pyrimidine-2-carboxamide | 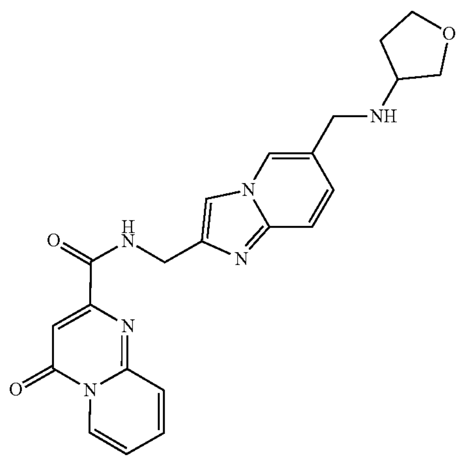 [SMILES: O=C(NCc1cn2cc(CNC3CCOC3)ccc2n1)c1cc(=O)n2ccccc2n1] | D | 2.58 | 419.3 |
| 123 | methyl 3-methyl-2-[({2-[({4-oxo-4H-pyrido[1,2-a]pyrimidin-2-yl}formamido)methyl]imidazo[1,2-a]pyridin-6-yl}methyl)amino]butanoate | 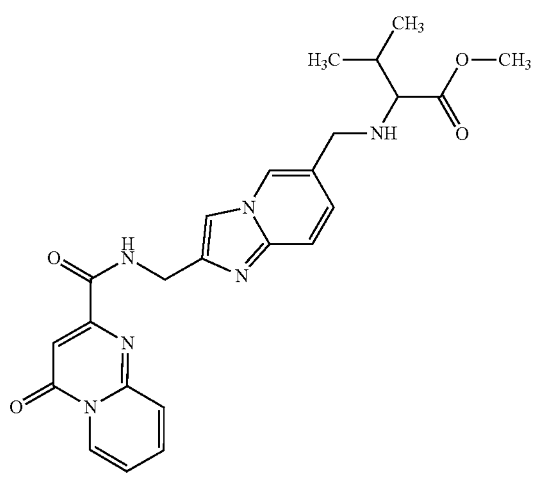 [SMILES: COC(=O)C(NCc1ccc2nc(CNC(=O)c3cc(=O)n4ccccc4n3)cn2c1)C(C)C] | C | 2.53 | 463.3 |

TABLE 10-continued

| Compound No | Name | Structure | LCMS method | LCMS Retention time | Mass ion |
|---|---|---|---|---|---|
| 124 | N-[(6-{[(oxan-3-yl)amino]methyl}imidazo[1,2-a]pyridin-2-yl)methyl]-4-oxo-4H-pyrido[1,2-a]pyrimidine-2-carboxamide | 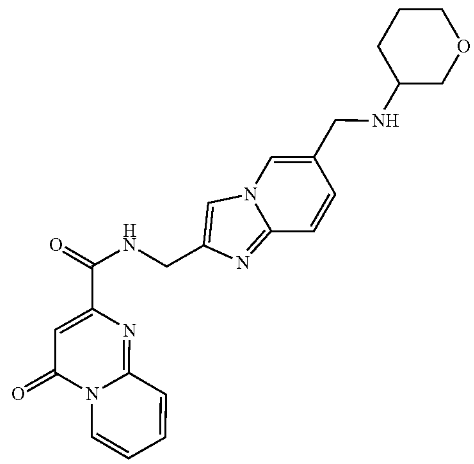 [SMILES: O=C(NCc1cn2cc(CNC3CCCOC3)ccc2n1)c1cc(=O)n2ccccc2n1] | D | 2.74 | 433.3 |
| 125 | 4-oxo-N-{6-({[(2S)-3,3,3-trifluoro-2-hydroxypropyl]amino}methyl)imidazo[1,2-a]pyridin-2-yl]methyl}-4H-pyrido[1,2-a]pyrimidine-2-carboxamide | 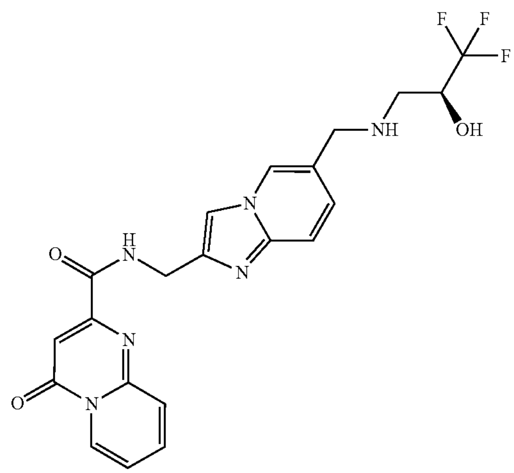 [SMILES: O=C(NCc1cn2cc(CNC[C@H](O)C(F)(F)F)ccc2n1)c1cc(=O)n2ccccc2n1] | C | 1.98 | 461.3 |
| 126 | N-({6-[(cyclobutylamino)methyl]imidazo[1,2-a]pyridin-2-yl}methyl)-4-oxo-4H-pyrido[1,2-a]pyrimidine-2-carboxamide | 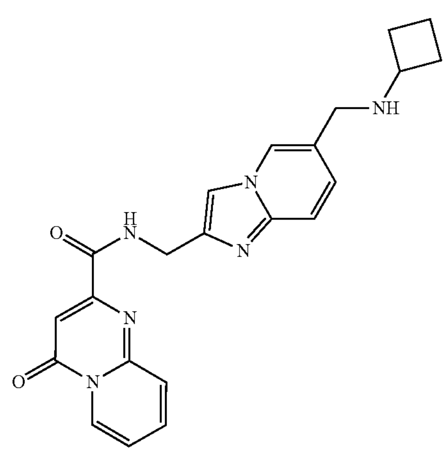 [SMILES: O=C(NCc1cn2cc(CNC3CCC3)ccc2n1)c1cc(=O)n2ccccc2n1] | C | 2.16 | 403.3 |

TABLE 10-continued

| Compound No | Name | Structure | LCMS method | LCMS Retention time | Mass ion |
|---|---|---|---|---|---|
| 127 | N-({6-[(tert-butylamino)methyl]imidazo[1,2-a]pyridin-2-yl}methyl)-4-oxo-4H-pyrido[1,2-a]pyrimidine-2-carboxamide | 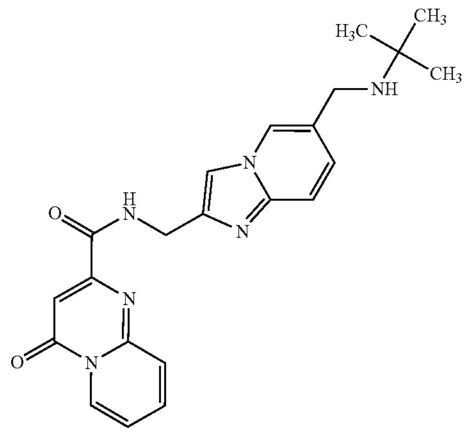 [SMILES: CC(C)(C)NCc1ccc2nc(CNC(=O)c3cc(=O)n4ccccc4n3)cn2c1] | C | 2.31 | 405.3 |
| 128 | N-[(6-{[(2-fluoroethyl)amino]methyl}imidazo[1,2-a]pyridin-2-yl)methyl]-4-oxo-4H-pyrido[1,2-a]pyrimidine-2-carboxamide | 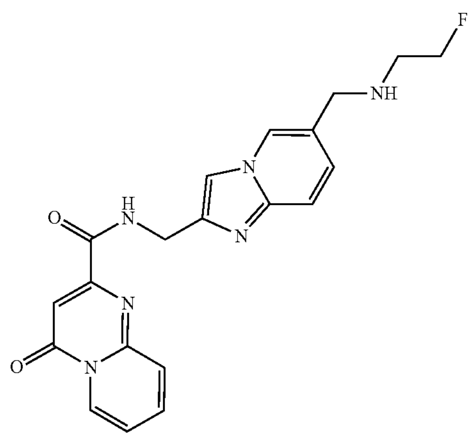 [SMILES: O=C(NCc1cn2cc(CNCCF)ccc2n1)c1cc(=O)n2ccccc2n1] | D | 2.67 | 395.3 |
| 129 | N-({6-[(4,4-difluoropiperidin-1-yl)methyl]imidazo[1,2-a]pyridin-2-yl}methyl)-4-oxo-4H-pyrido[1,2-a]pyrimidine-2-carboxamide | 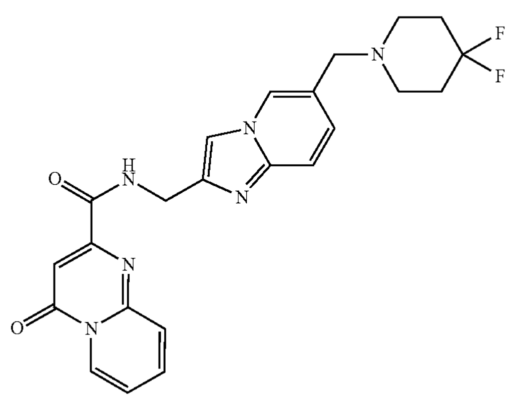 [SMILES: O=C(NCc1cn2cc(CN3CCC(F)(F)CC3)ccc2n1)c1cc(=O)n2ccccc2n1] | D | 3.36 | 453.3 |

TABLE 10-continued

| Compound No | Name | Structure | LCMS method | LCMS Retention time | Mass ion |
|---|---|---|---|---|---|
| 130 | 4-oxo-N-({6-[(4-phenylpiperazin-1-yl)methyl]imidazo[1,2-a]pyridin-2-yl}methyl)-4H-pyrido[1,2-a]pyrimidine-2-carboxamide | 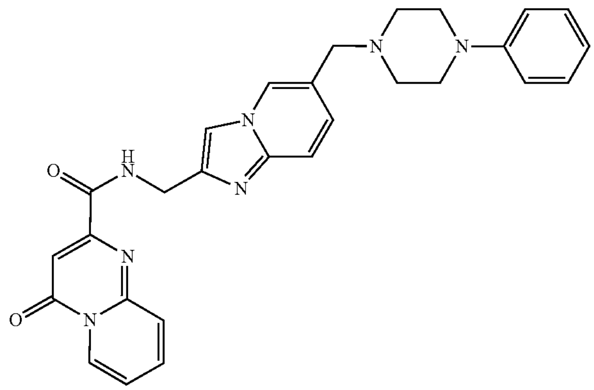 [SMILES: O=C(NCc1cn2cc(CN3CCN(c4ccccc4)CC3)ccc2n1)c1cc(=O)n2ccccc2n1] | C | 2.83 | 494.4 |
| 131 | 4-oxo-N-({6-[(1,2,3,4-tetrahydroisoquinolin-2-yl)methyl]imidazo[1,2-a]pyridin-2-yl}methyl)-4H-pyrido[1,2-a]pyrimidine-2-carboxamide | 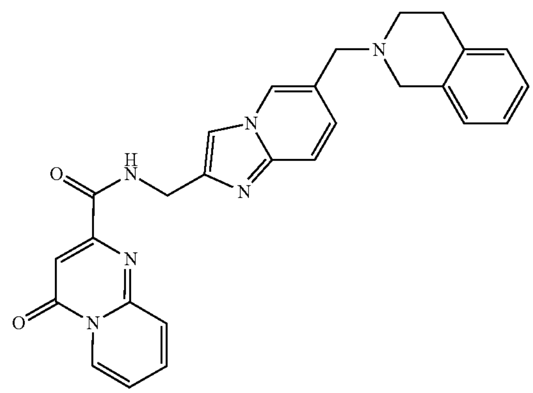 [SMILES: O=C(NCc1cn2cc(CN3CCc4ccccc4C3)ccc2n1)c1cc(=O)n2ccccc2n1] | C | 2.89 | 465.4 |
| 132 | N-({6-[(diethylamino)methyl]imidazo[1,2-a]pyridin-2-yl}methyl)-4-oxo-4H-pyrido[1,2-a]pyrimidine-2-carboxamide | 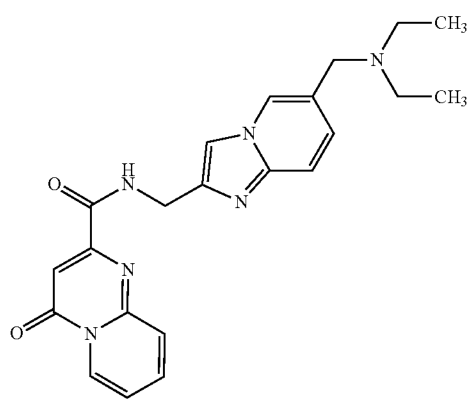 [SMILES: CCN(CC)Cc1ccc2nc(CNC(=O)c3cc(=O)n4ccccc4n3)cn2c1] | C | 2.43 | 405.3 |
| 133 | 4-oxo-N-({6-[(pyrrolidin-1-yl)methyl]imidazo[1,2-a]pyridin-2-yl}methyl)-4H-pyrido[1,2-a]pyrimidine-2-carboxamide | 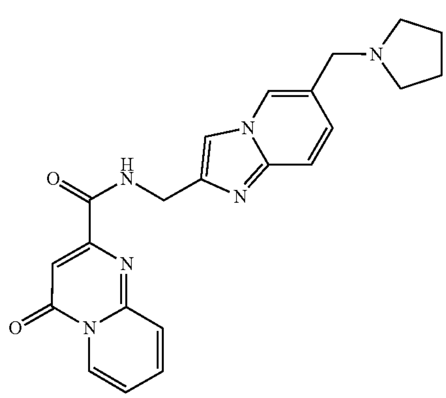 [SMILES: O=C(NCc1cn2cc(CN3CCCC3)ccc2n1)c1cc(=O)n2ccccc2n1] | C | 2.18 | 403.3 |

TABLE 10-continued

| Compound No | Name | Structure | LCMS method | LCMS Retention time | Mass ion |
|---|---|---|---|---|---|
| 134 | 4-oxo-N-[(6-{[3-(pyridin-2-yl)azetidin-1-yl]methyl}imidazo[1,2-a]pyridin-2-yl)methyl]-4H-pyrido[1,2-a]pyrimidine-2-carboxamide | 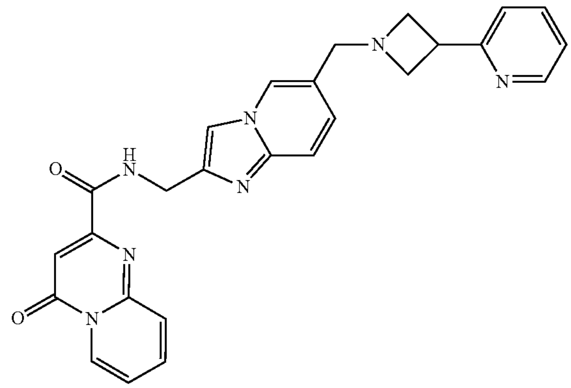 [SMILES: O=C(NCc1cn2cc(CN3CC(c4ccccn4)C3)ccc2n1)c1cc(=O)n2ccccc2n1] | D | 2.96 | 466.2 |
| 135 | N-[(6-{[(dicyclopropyl-methyl)amino]methyl}imidazo[1,2-a]pyridin-2-yl)methyl]-4-oxo-4H-pyrido[1,2-a]pyrimidine-2-carboxamide | 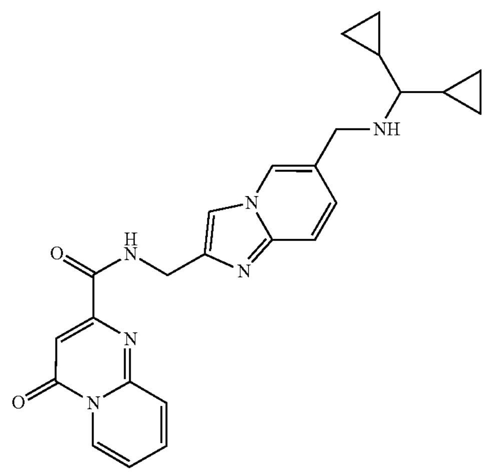 [SMILES: O=C(NCc1cn2cc(CNC(C3CC3)C3CC3)ccc2n1)c1cc(=O)n2ccccc2n1] | C | 2.63 | 443.3 |
| 136 | N-[(6-{[(cyclopropyl-methyl)(methyl)amino]methyl}imidazo[1,2-a]pyridin-2-yl)methyl]-4-oxo-4H-pyrido[1,2-a]pyrimidine-2-carboxamide | 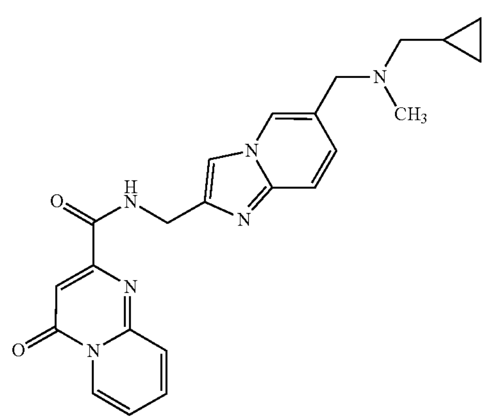 [SMILES: CN(Cc1ccc2nc(CNC(=O)c3cc(=O)n4ccccc4n3)cn2c1)CC1CC1] | C | 2.47 | 417.3 |

TABLE 10-continued

| Compound No | Name | Structure | LCMS method | LCMS Retention time | Mass ion |
|---|---|---|---|---|---|
| 137 | N-({6-[(4-methylpiperidin-1-yl)methyl]imidazo[1,2-a]pyridin-2-yl}methyl)-4-oxo-4H-pyrido[1,2-a]pyrimidine-2-carboxamide | 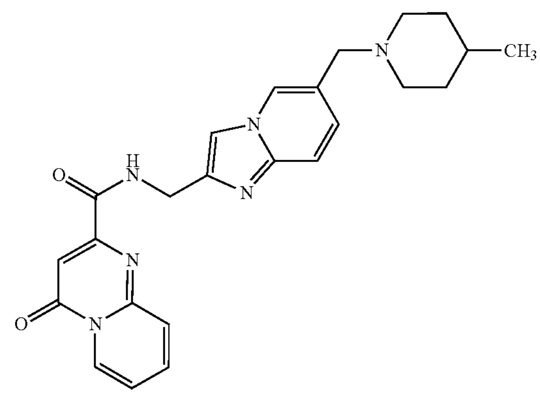 [SMILES: CC1CCN(Cc2ccc3nc(CNC(=O)c4cc(=O)n5ccccc5n4)cn3c2)CC1] | C | 2.80 | 431.3 |
| 138 | 4-oxo-N-[(6-{[4-(trifluoromethyl)piperidin-1-yl]methyl}imidazo[1,2-a]pyridin-2-yl)methyl]-4H-pyrido[1,2-a]pyrimidine-2-carboxamide | 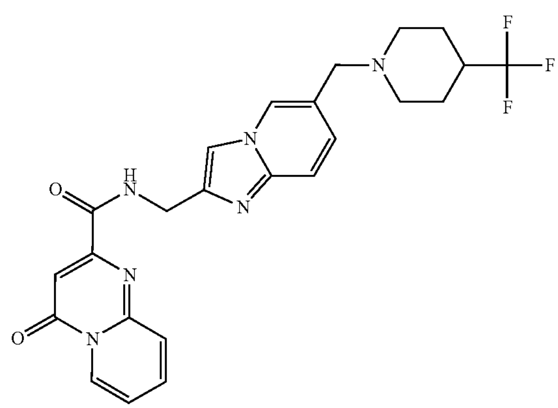 [SMILES: O=C(NCc1cn2cc(CN3CCC(C(F)(F)F)CC3)ccc2n1)c1cc(=O)n2ccccc2n1] | D | 3.69 | 485.3 |
| 139 | N-({6-[(3-methylpiperidin-1-yl)methyl]imidazo[1,2-a]pyridin-2-yl}methyl)-4-oxo-4H-pyrido[1,2-a]pyrimidine-2-carboxamide | 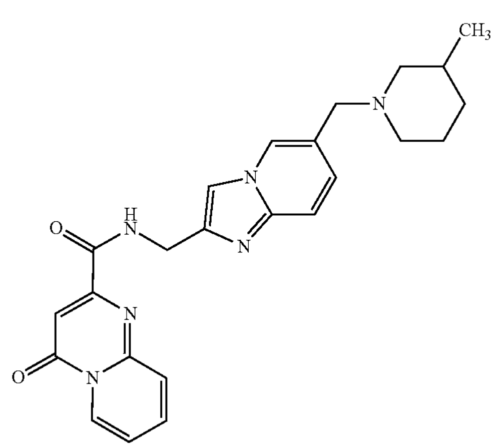 [SMILES: CC1CCCN(Cc2ccc3nc(CNC(=O)c4cc(=O)n5ccccc5n4)cn3c2)C1] | C | 2.80 | 431.4 |

TABLE 10-continued

| Compound No | Name | Structure | LCMS method | LCMS Retention time | Mass ion |
|---|---|---|---|---|---|
| 140 | 4-oxo-N-[(6-{R{spiro[2.2]pentan-1-yl}methyl)amino]methyl}imidazo[1,2-a]pyridin-2-yl)methyl]-4H-pyrido[1,2-a]pyrimidine-2-carboxamide | 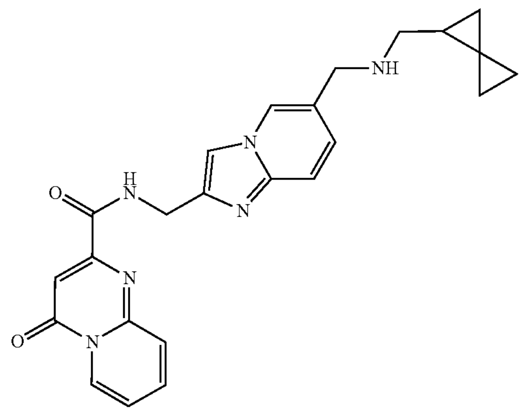 [SMILES: O=C(NCc1cn2cc(CNCC3CC34CC4)ccc2n1)c1cc(=O)n2ccccc2n1] | C | 2.53 | 429.3 |
| 141 | N-({6-[(3,3-dimethylpiperidin-1-yl)methyl]imidazo[1,2-a]pyridin-2-yl}methyl)-4-oxo-4H-pyrido[1,2-a]pyrimidine-2-carboxamide | 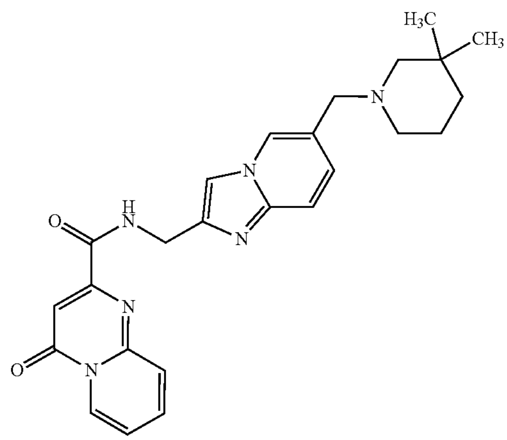 [SMILES: CC1(C)CCCN(Cc2ccc3nc(CNC(=O)c4cc(=O)n5ccccc5n4)cn3c2)C1] | C | 3.45 | 445.3 |
| 142 | 4-oxo-N-[(6-{[3-(trifluoromethyl)piperidin-1-yl]methyl}imidazo[1,2-a]pyridin-2-yl)methyl]-4H-pyrido[1,2-a]pyrimidine-2-carboxamide | 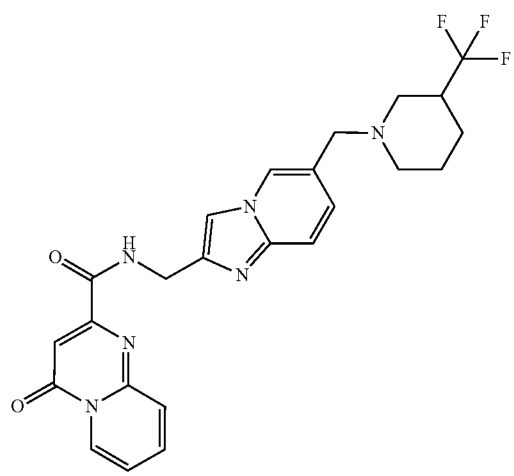 [SMILES: O=C(NCc1cn2cc(CN3CCCC(C(F)(F)F)C3)ccc2n1)c1cc(=O)n2ccccc2n1] | C | 2.94 | 485.3 |
| 143 | N-{[6-({[(5,5-dimethyloxolan-2-yl)methyl]amino}methyl)imidazo[1,2-a]pyridin-2-yl]methyl}-4-oxo-4H-pyrido[1,2-a]pyrimidine-2-carboxamide | 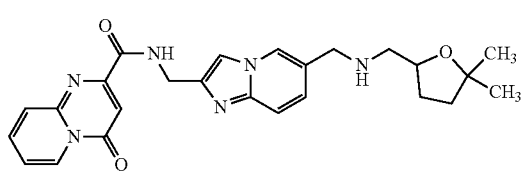 [SMILES: CC1(C)CCC(CNCc2ccc3nc(CNC(=O)c4cc(=O)n5ccccc5n4)cn3c2)O1] | C | 2.33 | 461.4 |

TABLE 10-continued

| Compound No | Name | Structure | LCMS method | LCMS Retention time | Mass ion |
|---|---|---|---|---|---|
| 144 | N-({6-[(4-fluoropiperidin-1-yl)methyl] imidazo[1,2-a]pyridin-2-yl} methyl)-4-oxo-4H-pyrido[1,2-a]pyrimidine-2-carboxamide | 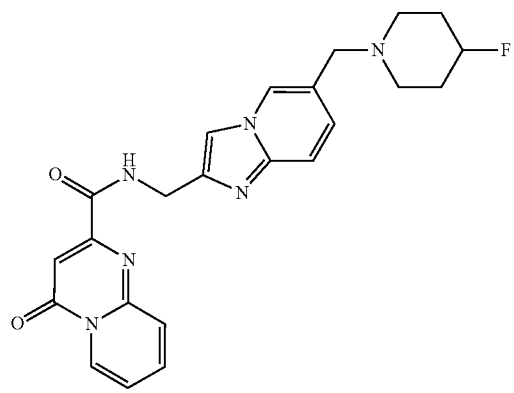 [SMILES: O=C(NCc1cn2cc(CN3CCC(F)CC3)ccc2n1)c1cc(=O)n2ccccc2n1] | D | 3.15 | 435.2 |
| 145 | N-[(6-{[(3-methoxypropyl) amino]methyl} imidazo[1,2-a] pyridin-2-yl) methyl]-4-oxo-4H-pyrido[1,2-a] pyrimidine-2-carboxamide | 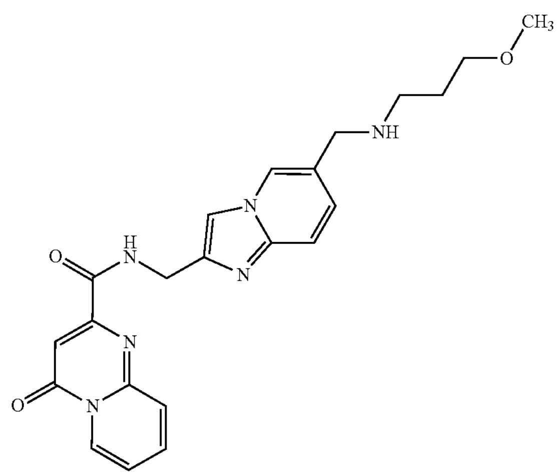 [SMILES: COCCCNCc1ccc2nc(CNC(=O)c3cc(=O)n4ccccc4n3)cn2c1] | C | 1.85 | 421.3 |
| 146 | N-[(6-{[(1-methylcyclohexyl) amino]methyl} imidazo[1,2-a]pyridin-2-yl) methyl]-4-oxo-4H-pyrido[1,2-a]pyrimidine-2-carboxamide | 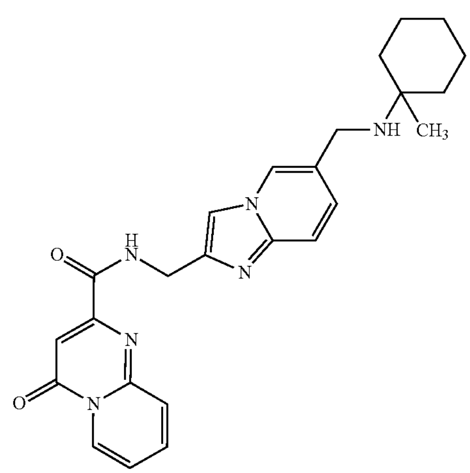 [SMILES: CC1(NCc2ccc3nc(CNC(=O)c4cc(=O)n5ccccc5n4)cn3c2)CCCCC1] | C | 3.04 | 445.3 |

TABLE 10-continued

| Compound No | Name | Structure | LCMS method | LCMS Retention time | Mass ion |
|---|---|---|---|---|---|
| 147 | N-{6-({[(4,4-dimethyloxolan-2-yl)methyl]amino}methyl)imidazo[1,2-a]pyridin-2-yl]methyl}-4-oxo-4H-pyrido[1,2-a]pyrimidine-2-carboxamide | 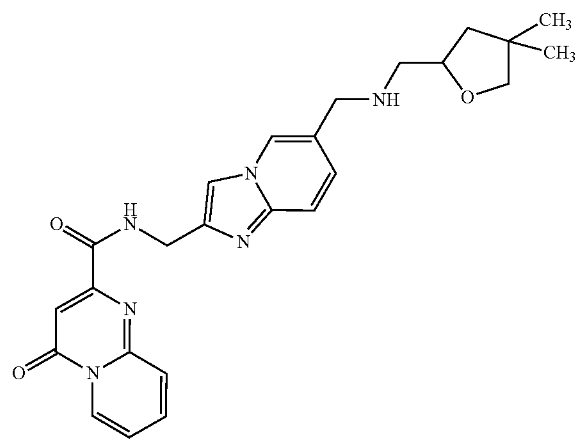 [SMILES: CC1(C)COC(CNCc2ccc3nc(CNC(=O)c4cc(=O)n5ccccc5n4)cn3c2)C1] | C | 2.39 | 461.4 |
| 148 | N-[(6-{[(1-methylcyclopentyl)amino]methyl}imidazo[1,2-a]pyridin-2-yl)methyl]-4-oxo-4H-pyrido[1,2-a]pyrimidine-2-carboxamide | 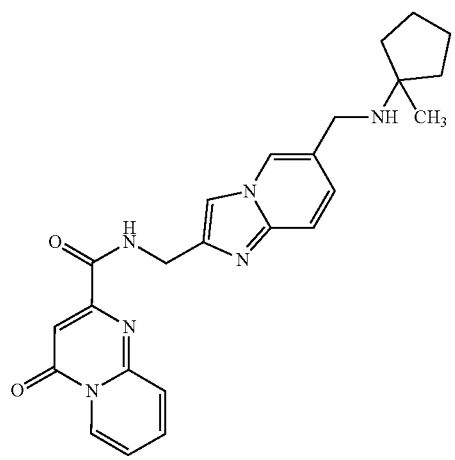 [SMILES: CC1(NCc2ccc3nc(CNC(=O)c4cc(=O)n5ccccc5n4)cn3c2)CCCC1] | C | 2.71 | 431.3 |
| 149 | 4-oxo-N-({6-[(propylamino)methyl]imidazo[1,2-a]pyridin-2-yl}methyl)-4H-pyrido[1,2-a]pyrimidine-2-carboxamide | 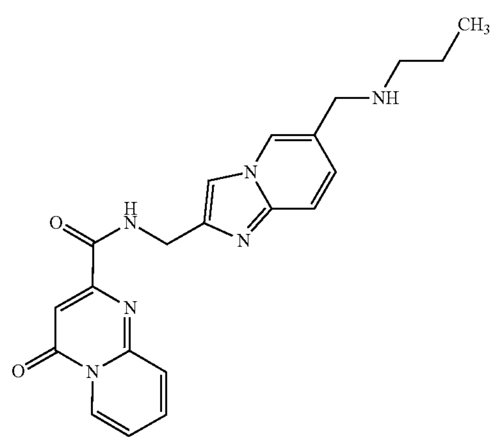 [SMILES: CCCNCc1ccc2nc(CNC(=O)c3cc(=O)n4ccccc4n3)cn2c1] | C | 2.10 | 391.3 |

TABLE 10-continued

| Compound No | Name | Structure | LCMS method | LCMS Retention time | Mass ion |
|---|---|---|---|---|---|
| 150 | N-{[6-({[(3,3-dimethyloxolan-2-yl)methyl]amino}methyl)imidazo[1,2-a]pyridin-2-yl]methyl}-4-oxo-4H-pyrido[1,2-a]pyrimidine-2-carboxamide | 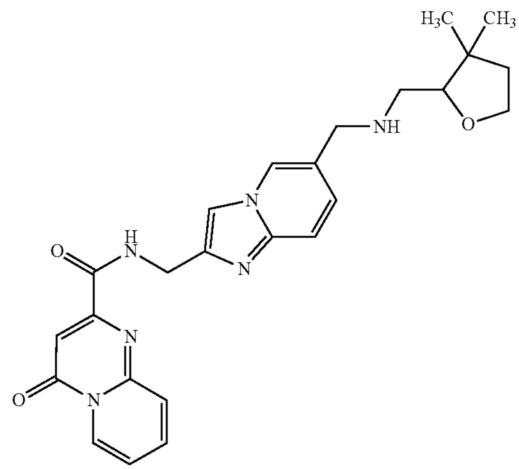 [SMILES: CC1(C)CCOC1CNCc1ccc2nc(CNC(=O)c3cc(=O)n4ccccc4n3)cn2c1] | C | 2.34 | 461.4 |
| 151 | N-[(6-{[(2-methylpropyl)amino]methyl}imidazo[1,2-a]pyridin-2-yl)methyl]-4-oxo-4H-pyrido[1,2-a]pyrimidine-2-carboxamide | 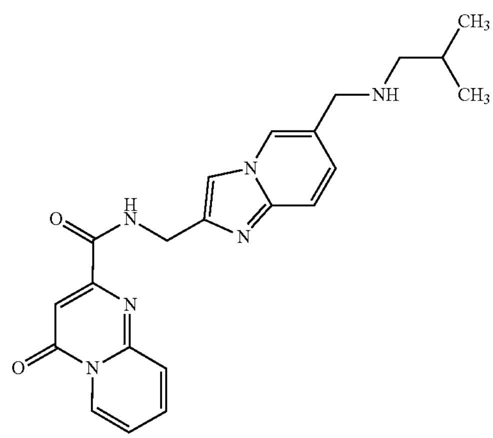 [SMILES: CC(C)CNCc1ccc2nc(CNC(=O)c3cc(=O)n4ccccc4n3)cn2c1] | C | 2.38 | 405.3 |
| 152 | N-{[6-({[2-(tert-butoxy)ethyl]amino}methyl)imidazo[1,2-a]pyridin-2-yl]methyl}-4-oxo-4H-pyrido[1,2-a]pyrimidine-2-carboxamide | 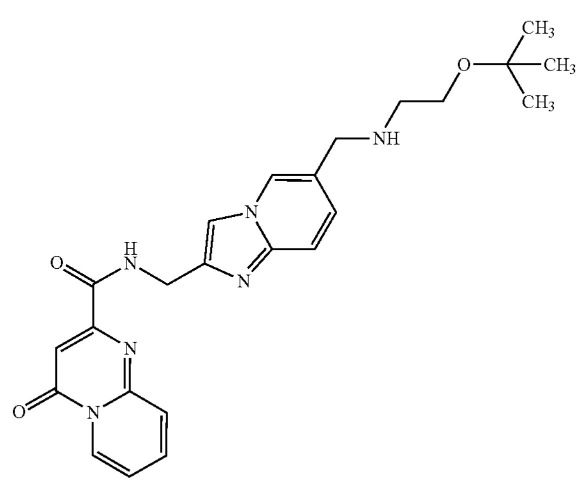 [SMILES: CC(C)(C)OCCNCc1ccc2nc(CNC(=O)c3cc(=O)n4ccccc4n3)cn2c1] | C | 2.31 | 449.4 |

TABLE 10-continued

| Compound No | Name | Structure | LCMS method | LCMS Retention time | Mass ion |
|---|---|---|---|---|---|
| 153 | N-[(6-{[(4-chlorophenyl)amino]methyl}imidazo[1,2-a]pyridin-2-yl)methyl]-4-oxo-4H-pyrido[1,2-a]pyrimidine-2-carboxamide | 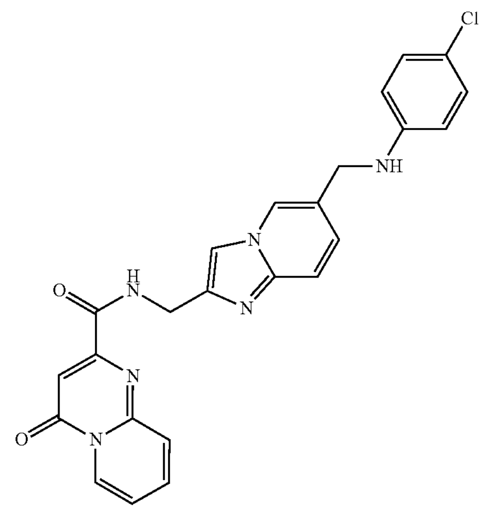 [SMILES: O=C(NCc1cn2cc(CNc3ccc(Cl)cc3)ccc2n1)c1cc(=O)n2ccccc2n1] | C | 2.95 | 459.3 |
| 154 | N-{[6-({[2-(oxan-2-yl)ethyl]amino}methyl)imidazo[1,2-a]pyridin-2-yl]methyl}-4-oxo-4H-pyrido[1,2-a]pyrimidine-2-carboxamide | 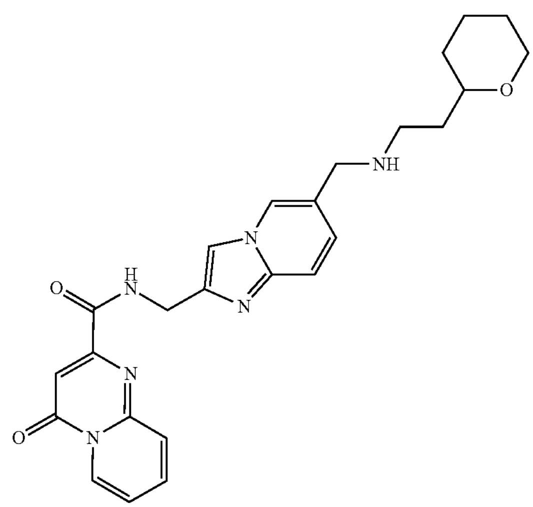 [SMILES: O=C(NCc1cn2cc(CNCCC3CCCCO3)ccc2n1)c1cc(=O)n2ccccc2n1] | C | 2.27 | 461.4 |
| 155 | N-({6-[(4-benzylpiperidin-1-yl)methyl]imidazo[1,2-a]pyridin-2-yl}methyl)-4-oxo-4H-pyrido[1,2-a]pyrimidine-2-carboxamide | 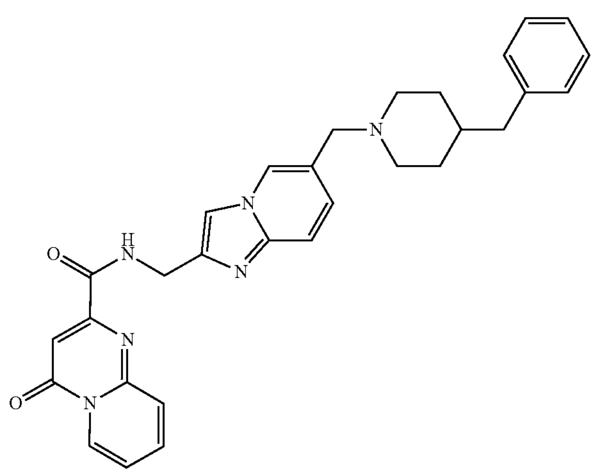 [SMILES: O=C(NCc1cn2cc(CN3CCC(Cc4ccccc4)CC3)ccc2n1)c1cc(=O)n2ccccc2n1] | D | 4.24 | 507.3 |

TABLE 10-continued

| Compound No | Name | Structure | LCMS method | LCMS Retention time | Mass ion |
|---|---|---|---|---|---|
| 156 | 4-oxo-N-({6-[(4-phenoxypiperidin-1-yl)methyl]imidazo[1,2-a]pyridin-2-yl}methyl)-4H-pyrido[1,2-a]pyrimidine-2-carboxamide | 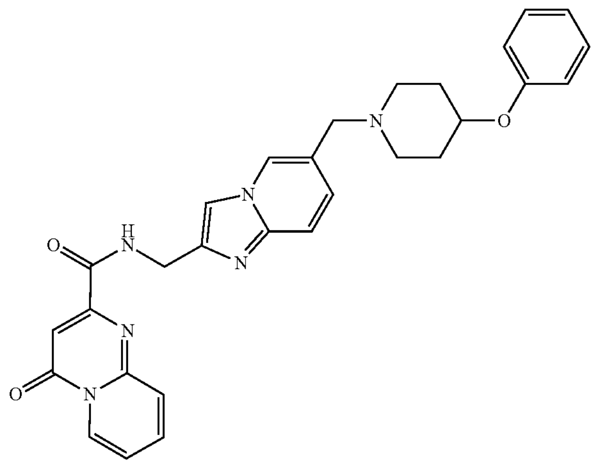 [SMILES: O=C(NCc1cn2cc(CN3CCC(Oc4ccccc4)CC3)ccc2n1)c1cc(=O)n2ccccc2n1] | D | 3.86 | 509.3 |
| 157 | N-{[6-({[(2,2-difluorocyclopropyl)methyl]amino}methyl)imidazo[1,2-a]pyridin-2-yl]methyl}-4-oxo-4H-pyrido[1,2-a]pyrimidine-2-carboxamide | 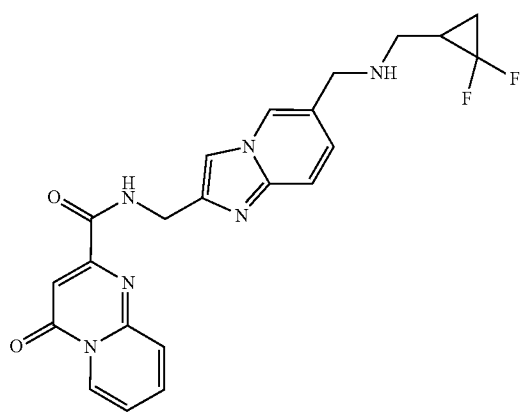 [SMILES: O=C(NCc1cn2cc(CNCC3CC3(F)F)ccc2n1)c1cc(=O)n2ccccc2n1] | D | 3.05 | 439.2 |
| 159 | N-{[6-({[(2,2-dimethylcyclopropyl)methyl]amino}methyl)imidazo[1,2-a]pyridin-2-yl]methyl}-4-oxo-4H-pyrido[1,2-a]pyrimidine-2-carboxamide | 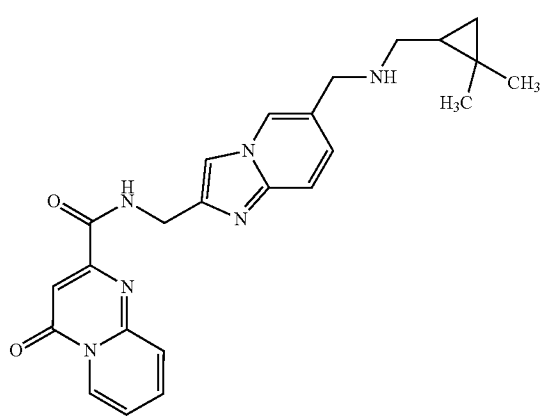 [SMILES: CC1(C)CC1CNCc1ccc2nc(CNC(=O)c3cc(=O)n4ccccc4n3)cn2c1] | D | 3.53 | 431.3 |

TABLE 10-continued

| Compound No | Name | Structure | LCMS method | LCMS Retention time | Mass ion |
|---|---|---|---|---|---|
| 160 | N-{[6-({[(2-methyloxolan-2-yl)methyl]amino}methyl)imidazo[1,2-a]pyridin-2-yl]methyl}-4-oxo-4H-pyrido[1,2-a]pyrimidine-2-carboxamide | 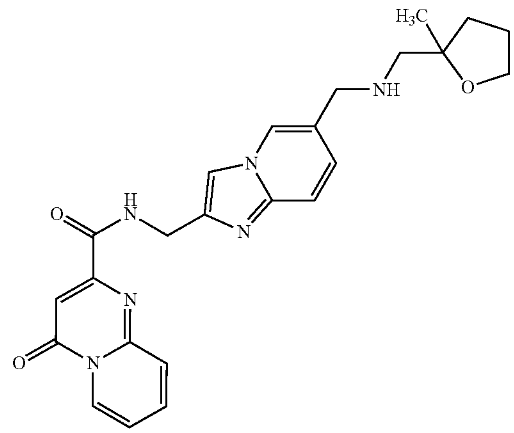 [SMILES: CC1(CNCc2ccc3nc(CNC(=O)c4cc(=O)n5ccccc5n4)cn3c2)CCCO1] | C | 2.13 | 447.3 |
| 161 | N-({6-[(4-tert-butylpiperidin-1-yl)methyl]imidazo[1,2-a]pyridin-2-yl}methyl)-4-oxo-4H-pyrido[1,2-a]pyrimidine-2-carboxamide | 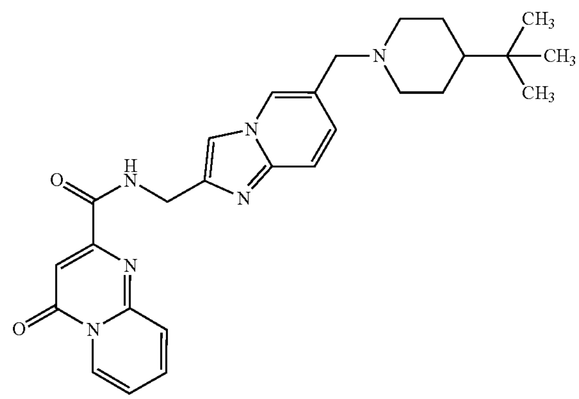 [SMILES: CC(C)(C)C1CCN(Cc2ccc3nc(CNC(=O)c4cc(=O)n5ccccc5n4)cn3c2)CC1] | C | 3.55 | 473.4 |
| 162 | N-[(6-{[(4-tert-butylcyclohexyl)amino]methyl}imidazo[1,2-a]pyridin-2-yl)methyl]-4-oxo-4H-pyrido[1,2-a]pyrimidine-2-carboxamide | 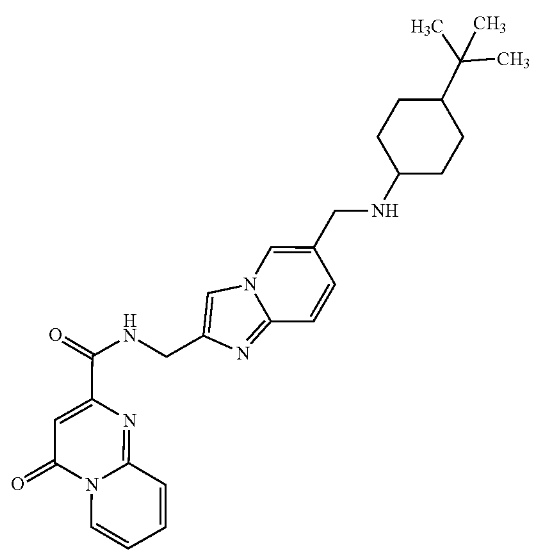 [SMILES: CC(C)(C)C1CCC(NCc2ccc3nc(CNC(=O)c4cc(=O)n5ccccc5n4)cn3c2)CC1] | C | 3.81 | 487.4 |

TABLE 10-continued

| Compound No | Name | Structure | LCMS method | LCMS Retention time | Mass ion |
|---|---|---|---|---|---|
| 163 | N-[(6-{[(2-cyclopentylethyl)amino]methyl}imidazo[1,2-a]pyridin-2-yl)methyl]-4-oxo-4H-pyrido[1,2-a]pyrimidine-2-carboxamide | 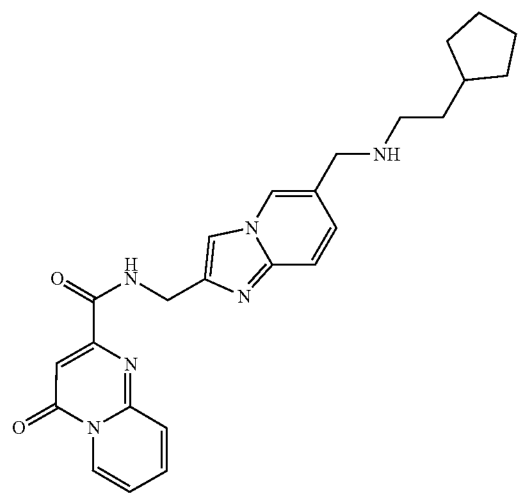 [SMILES: O=C(NCc1cn2cc(CNCCC3CCCC3)ccc2n1)c1cc(=O)n2ccccc2n1] | C | 2.95 | 445.4 |
| 166 | N-[(6-{[4-(2,2-dimethylpropanoyl)piperazin-1-yl]methyl}imidazo[1,2-a]pyridin-2-yl)methyl]-4-oxo-4H-pyrido[1,2-a]pyrimidine-2-carboxamide | 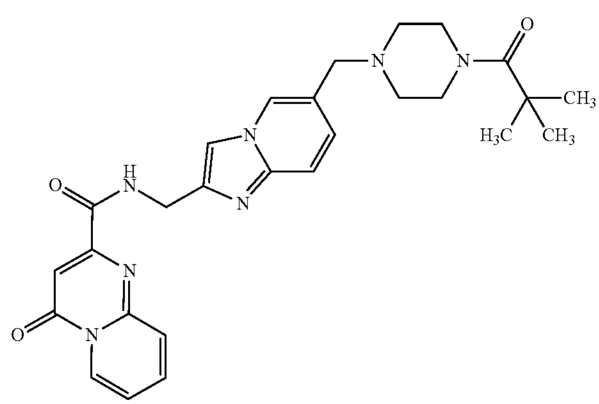 [SMILES: CC(C)(C)C(=O)N1CCN(Cc2ccc3nc(CNC(=O)c4cc(=O)n5ccccc5n4)cn3c2)CC1] | D | 3.15 | 502.2 |
| 167 | N-({6-[(4-acetylpiperazin-1-yl)methyl]imidazo[1,2-a]pyridin-2-yl}methyl)-4-oxo-4H-pyrido[1,2-a]pyrimidine-2-carboxamide | 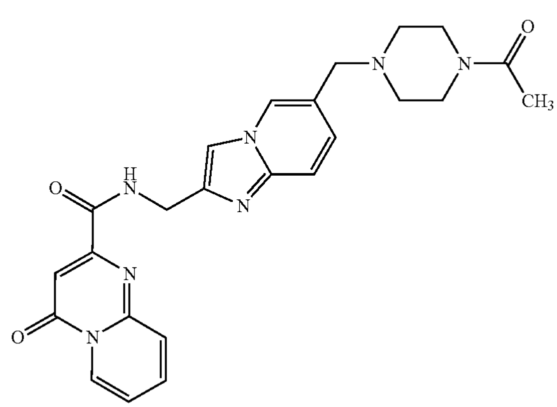 [SMILES: CC(=O)N1CCN(Cc2ccc3nc(CNC(=O)c4cc(=O)n5ccccc5n4)cn3c2)CC1] | D | 2.60 | 460.1 |

TABLE 10-continued

| Compound No | Name | Structure | LCMS method | LCMS Retention time | Mass ion |
|---|---|---|---|---|---|
| 169 | N-{[6-({7-azabicyclo[2.2.1]heptan-7-yl}methyl)imidazo[1,2-a]pyridin-2-yl]methyl}-4-oxo-4H-pyrido[1,2-a]pyrimidine-2-carboxamide | 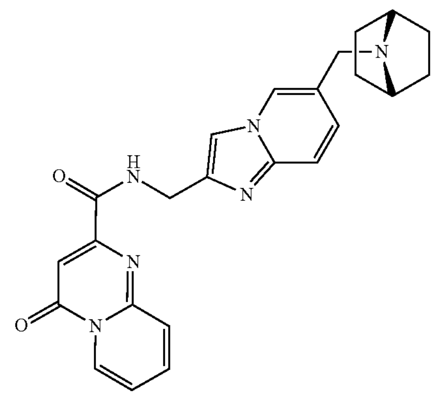 | C | 2.46 | 429.3 |
| 193 | N-({6-[(4,4-dimethylpiperidin-1-yl)methyl]imidazo[1,2-a]pyridin-2-yl}methyl)-4-oxo-4H-pyrido[1,2-a]pyrimidine-2-carboxamide | 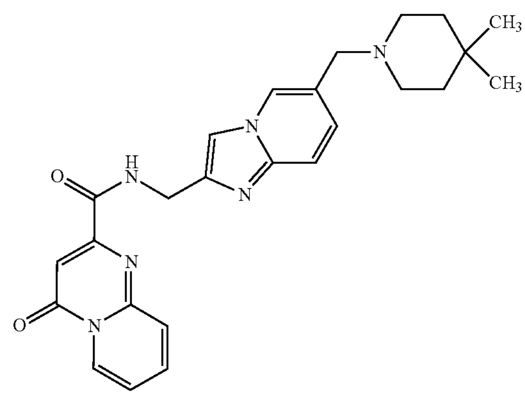 [SMILES: CC1(C)CCN(Cc2ccc3nc(CNC(=O)c4cc(=O)n5ccccc5n4)cn3c2)CC1] | C | 3.00 | 445.3 |
| 194 | N-({6-[(2,2-dimethylpiperidin-1-yl)methyl]imidazo[1,2-a]pyridin-2-yl}methyl)-4-oxo-4H-pyrido[1,2-a]pyrimidine-2-carboxamide | 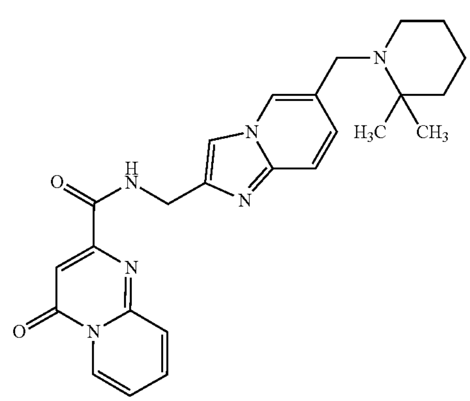 [SMILES: CC1(C)CCCCN1Cc1ccc2nc(CNC(=O)c3cc(=O)n4ccccc4n3)cn2c1] | C | 3.29 | 445.4 |

TABLE 10-continued

| Compound No | Name | Structure | LCMS method | LCMS Retention time | Mass ion |
|---|---|---|---|---|---|
| 195 | 4-oxo-N-[(6-{[(2,3,3-trimethylbutan-2-yl)amino]methyl}imidazo[1,2-a]pyridin-2-yl)methyl]-4H-pyrido[1,2-a]pyrimidine-2-carboxamide | 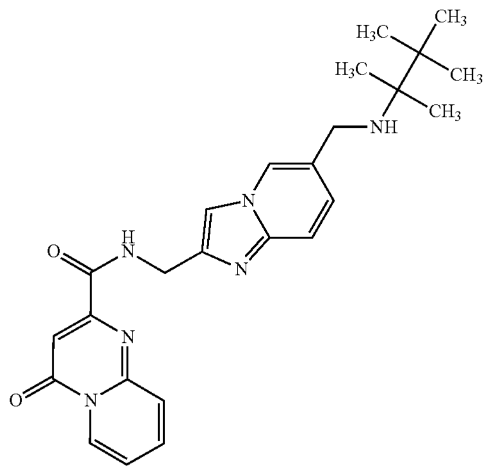 [SMILES: CC(C)(C)C(C)(C)NCc1ccc2nc(CNC(=O)c3cc(=O)n4ccccc4n3)cn2c1] | C | 3.54 | 447.4 |
| 196 | N-[(6-{[(5-fluoropyridin-2-yl)amino]methyl}imidazo[1,2-a]pyridin-2-yl)methyl]-4-oxo-4H-pyrido[1,2-a]pyrimidine-2-carboxamide | 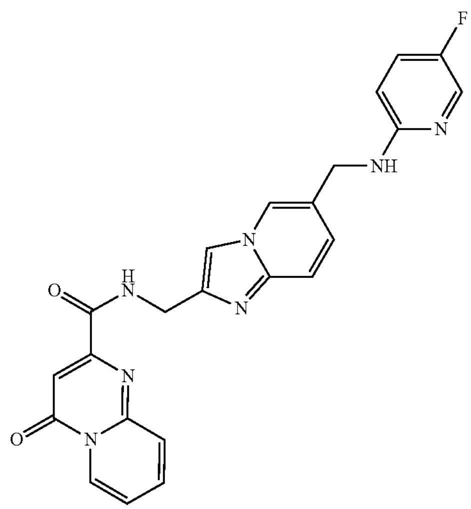 [SMILES: O=C(NCc1cn2cc(CNc3ccc(F)cn3)ccc2n1)c1cc(=O)n2ccccc2n1] | C | 2.32 | 444.3 |
| 197 | N-({6-[({[1,1'-bi(cyclopropane)]-1-yl}amino)methyl]imidazo[1,2-a]pyridin-2-yl}methyl)-4-oxo-4H-pyrido[1,2-a]pyrimidine-2-carboxamide | 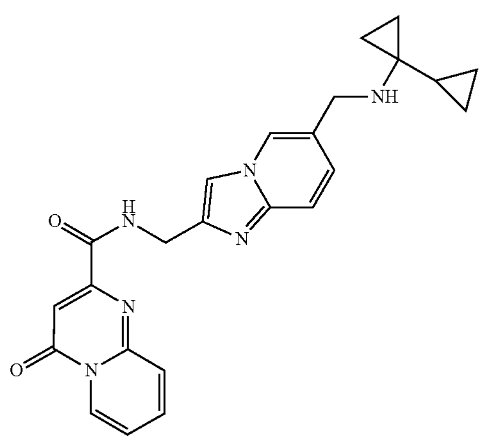 [SMILES: O=C(NCc1cn2cc(CNC3(C4CC4)CC3)ccc2n1)c1cc(=O)n2ccccc2n1] | C | 2.63 | 429.3 |

TABLE 10-continued

| Compound No | Name | Structure | LCMS method | LCMS Retention time | Mass ion |
|---|---|---|---|---|---|
| 198 | N-{[6-({[(1-fluorocyclopentyl)methyl]amino}methyl)imidazo[1,2-a]pyridin-2-yl]methyl}-4-oxo-4H-pyrido[1,2-a]pyrimidine-2-carboxamide | 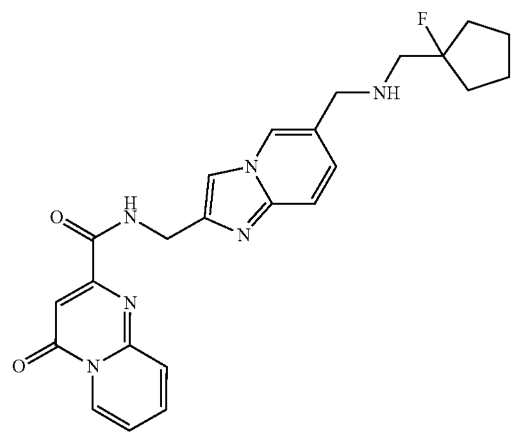 [SMILES: O=C(NCc1cn2cc(CNCC3(F)CCCC3)ccc2n1)c1cc(=O)n2ccccc2n1] | C | 2.56 | 449.4 |
| 199 | N-({6-[(2,6-dimethylmorpholin-4-yl)methyl]imidazo[1,2-a]pyridin-2-yl}methyl)-4-oxo-4H-pyrido[1,2-a]pyrimidine-2-carboxamide | 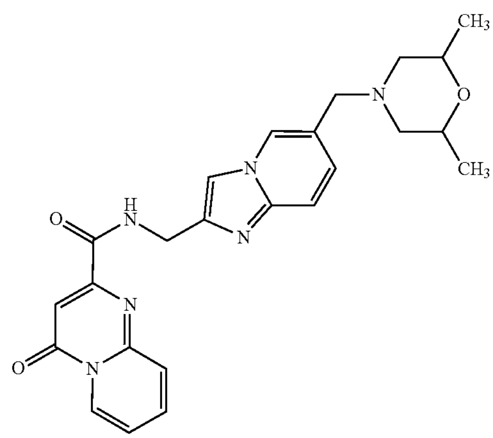 [SMILES: CC1CN(Cc2ccc3nc(CNC(=O)c4cc(=O)n5ccccc5n4)cn3c2)CC(C)O1] | D | 3.02 | 447.2 |
| 200 | methyl 1-({2-[({4-oxo-4H-pyrido[1,2-a]pyrimidin-2-yl}formamido)methyl]imidazo[1,2-a]pyridin-6-yl}methyl)piperidine-3-carboxylate | 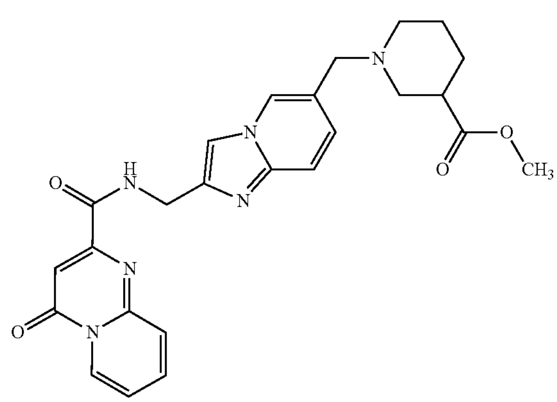 [SMILES: COC(=O)C1CCCN(Cc2ccc3nc(CNC(=O)c4cc(=O)n5ccccc5n4)cn3c2)C1] | D | 3.25 | 475.2 |

TABLE 10-continued

| Compound No | Name | Structure | LCMS method | LCMS Retention time | Mass ion |
|---|---|---|---|---|---|
| 202 | N-[(6-{[(2-fluoro-2-methylpropyl)amino]methyl}imidazo[1,2-a]pyridin-2-yl)methyl]-4-oxo-4H-pyrido[1,2-a]pyrimidine-2-carboxamide | 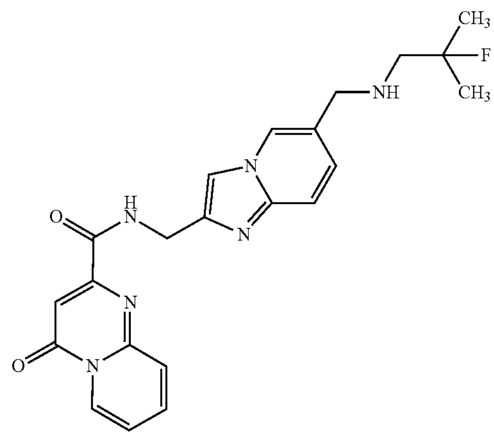 [SMILES: CC(C)(F)CNCc1ccc2nc(CNC(=O)c3cc(=O)n4ccccc4n3)cn2c1] | C | 2.26 | 423.3 |
| 203 | N-[(6-{[(1-cyclohexylethyl)amino]methyl}imidazo[1,2-a]pyridin-2-yl)methyl]-4-oxo-4H-pyrido[1,2-a]pyrimidine-2-carboxamide | 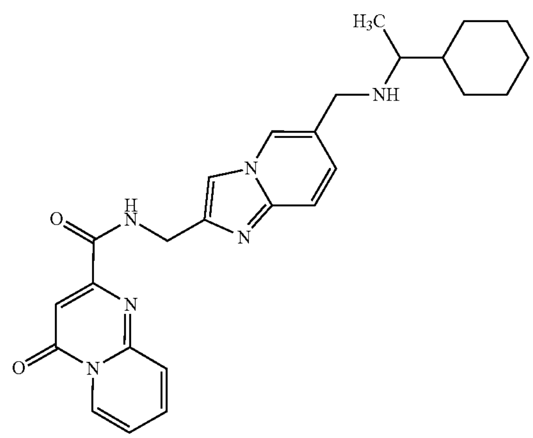 [SMILES: CC(NCc1ccc2nc(CNC(=O)c3cc(=O)n4ccccc4n3)cn2c1)C1CCCCC1] | C | 3.28 | 459.4 |
| 204 | N-[(6-{[(2-cyclopropylethyl)(methyl)amino]methyl}imidazo[1,2-a]pyridin-2-yl)methyl]-4-oxo-4H-pyrido[1,2-a]pyrimidine-2-carboxamide | 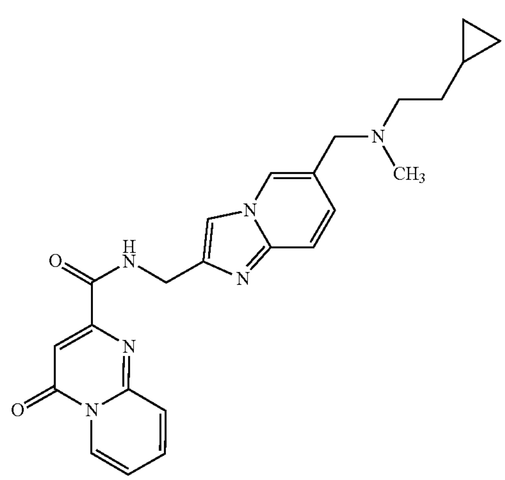 [SMILES: CN(CCC1CC1)Cc1ccc2nc(CNC(=O)c3cc(=O)n4ccccc4n3)cn2c1] | D | 3.61 | 431.2 |

TABLE 10-continued

| Compound No | Name | Structure | LCMS method | LCMS Retention time | Mass ion |
|---|---|---|---|---|---|
| 205 | N-[(6-{[(2,2-dimethylpropyl)(methyl)amino]methyl}imidazo[1,2-a]pyridin-2-yl)methyl]-4-oxo-4H-pyrido[1,2-a]pyrimidine-2-carboxamide | 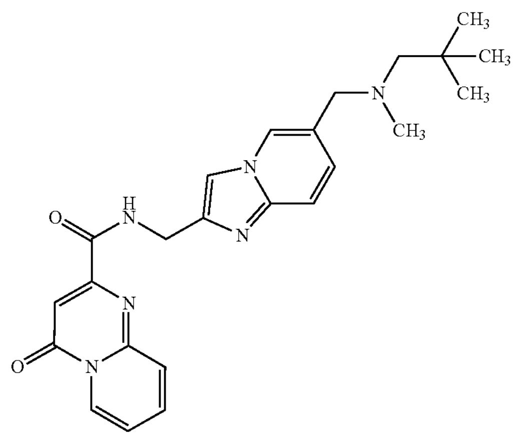 [SMILES: CN(Cc1ccc2nc(CNC(=O)c3cc(=O)n4ccccc4n3)cn2c1)CC(C)(C)C] | D | 4.27 | 433.3 |
| 206 | N-{[6-({[(1-fluorocyclobutyl)methyl]amino}methyl)imidazo[1,2-a]pyridin-2-yl]methyl}-4-oxo-4H-pyrido[1,2-a]pyrimidine-2-carboxamide | 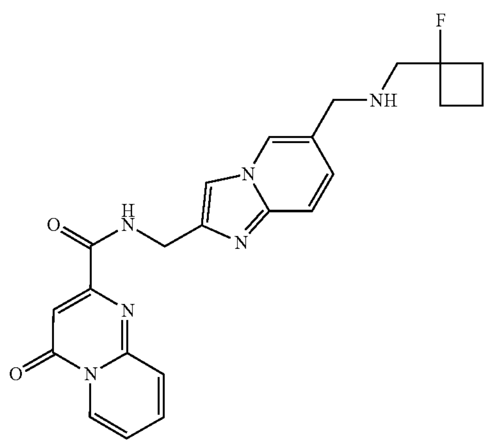 [SMILES: O=C(NCc1cn2cc(CNCC3(F)CCC3)ccc2n1)c1cc(=O)n2ccccc2n1] | C | 3.14 | 435.2 |
| 207 | N-({6-[(4-fluoro-4-methylpiperidin-1-yl)methyl]imidazo[1,2-a]pyridin-2-yl}methyl)-4-oxo-4H-pyrido[1,2-a]pyrimidine-2-carboxamide | 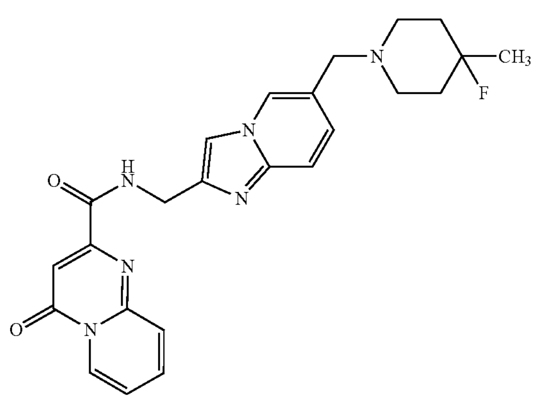 [SMILES: CC1(F)CCN(Cc2ccc3nc(CNC(=O)c4cc(=O)n5ccccc5n4)cn3c2)CC1] | C | 2.49 | 449.3 |

TABLE 10-continued

| Compound No | Name | Structure | LCMS method | LCMS Retention time | Mass ion |
|---|---|---|---|---|---|
| 208 | N-({6-[(3,3-difluoropiperidin-1-yl)methyl]imidazo[1,2-a]pyridin-2-yl}methyl)-4-oxo-4H-pyrido[1,2-a]pyrimidine-2-carboxamide | 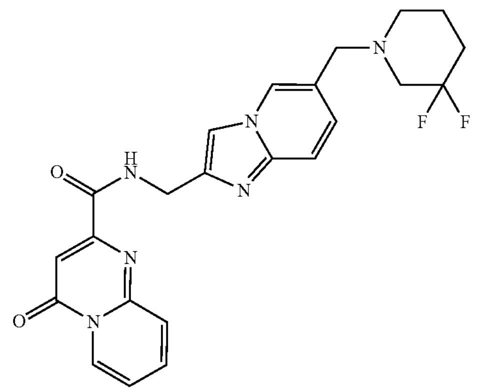 [SMILES: O=C(NCc1cn2cc(CN3CCCC(F)(F)C3)ccc2n1)c1cc(=O)n2ccccc2n1] | C | 2.52 | 453.3 |
| 209 | N-{[6-({[(1-hydroxycyclohexyl)methyl]amino}methyl)imidazo[1,2-a]pyridin-2-yl]methyl}-4-oxo-4H-pyrido[1,2-a]pyrimidine-2-carboxamide | 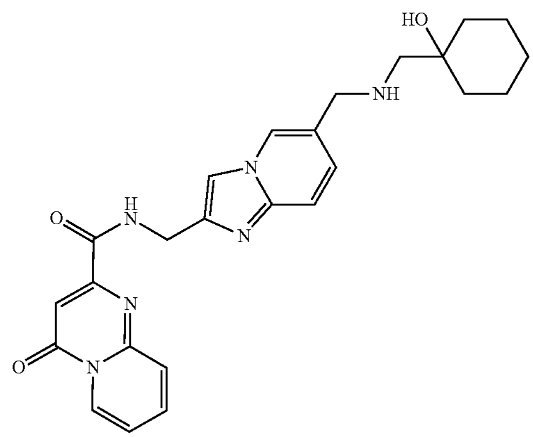 [SMILES: O=C(NCc1cn2cc(CNCC3(O)CCCCC3)ccc2n1)c1cc(=O)n2ccccc2n1] | C | 2.30 | 461.4 |
| 210 | N-[(6-{[(cyclopentylmethyl)amino]methyl}imidazo[1,2-a]pyridin-2-yl)methyl]-4-oxo-4H-pyrido[1,2-a]pyrimidine-2-carboxamide | 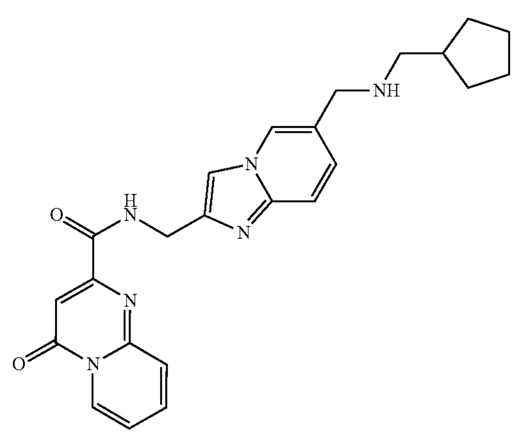 | C | 2.74 | 431.3 |

TABLE 10-continued

| Compound No | Name | Structure | LCMS method | LCMS Retention time | Mass ion |
|---|---|---|---|---|---|
| 211 | N-{[6-({[(3,3-difluorocyclopentyl)methyl]amino}methyl)imidazo[1,2-a]pyridin-2-yl]methyl}-4-oxo-4H-pyrido[1,2-a]pyrimidine-2-carboxamide | 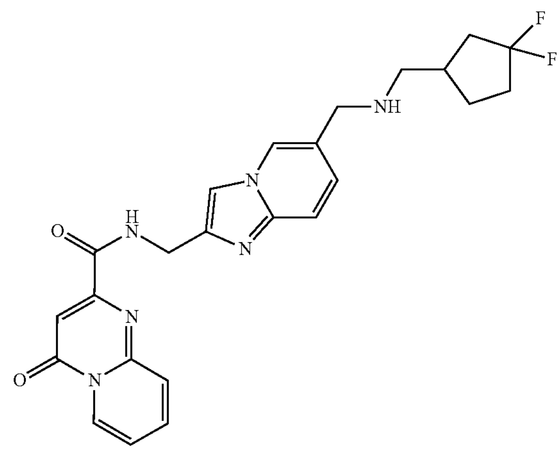 [SMILES: O=C(NCc1cn2cc(CNCC3CCC(F)(F)C3)ccc2n1)c1cc(=O)n2ccccc2n1] | D | 3.32 | 467.4 |
| 212 | N-[(6-{[(cyclobutylmethyl)amino]methyl}imidazo[1,2-a]pyridin-2-yl)methyl]-4-oxo-4H-pyrido[1,2-a]pyrimidine-2-carboxamide | 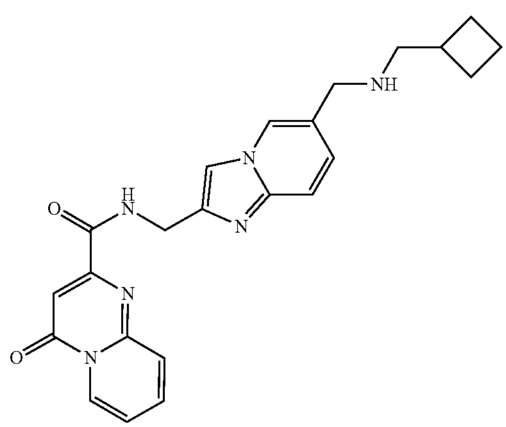 [SMILES: O=C(NCc1cn2cc(CNCC3CCC3)ccc2n1)c1cc(=O)n2ccccc2n1] | E | 0.82 | 417.3 |
| 213 | N-{[6-({[2-(3,3-difluorocyclobutyl)ethyl]amino}methyl)imidazo[1,2-a]pyridin-2-yl]methyl}-4-oxo-4H-pyrido[1,2-a]pyrimidine-2-carboxamide | 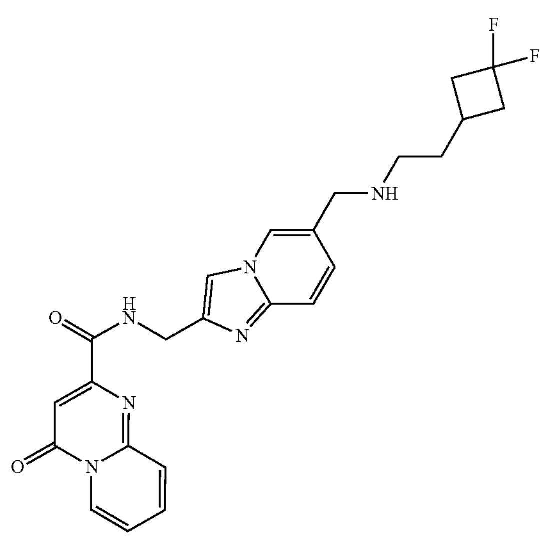 [SMILES: O=C(NCc1cn2cc(CNCCC3CC(F)(F)C3)ccc2n1)c1cc(=O)n2ccccc2n1] | D | 3.37 | 467.2 |

TABLE 10-continued

| Compound No | Name | Structure | LCMS method | LCMS Retention time | Mass ion |
|---|---|---|---|---|---|
| 214 | N-{[6-({[(2-fluorocyclobutyl)methyl]amino}methyl)imidazo[1,2-a]pyridin-2-yl]methyl}-4-oxo-4H-pyrido[1,2-a]pyrimidine-2-carboxamide | 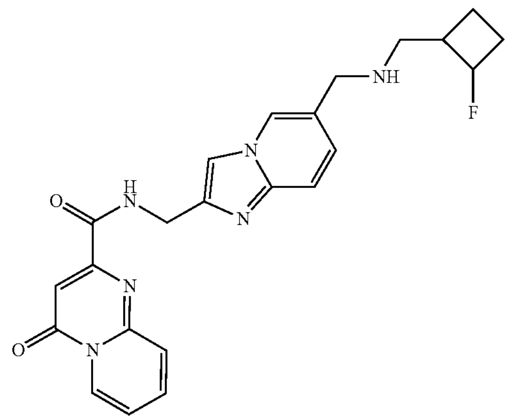 [SMILES: O=C(NCc1cn2cc(CNCC3CCC3F)ccc2n1)c1cc(=O)n2ccccc2n1] | D | 3.06 | 435.2 |
| 215 | N-{[6-({[(2S)-3,3-dimethylbutan-2-yl]amino}methyl)imidazo[1,2-a]pyridin-2-yl]methyl}-4-oxo-4H-pyrido[1,2-a]pyrimidine-2-carboxamide | 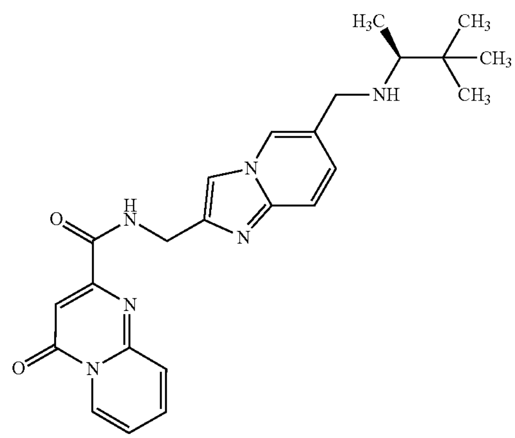 [SMILES: C[C@H](NCc1ccc2nc(CNC(=O)c3cc(=O)n4ccccc4n3)cn2c1)C(C)(C)C] | D | 3.69 | 433.2 |
| 216 | N-{[6-({6-azaspiro[2.5]octan-6-yl}methyl)imidazo[1,2-a]pyridin-2-yl]methyl}-4-oxo-4H-pyrido[1,2-a]pyrimidine-2-carboxamide | 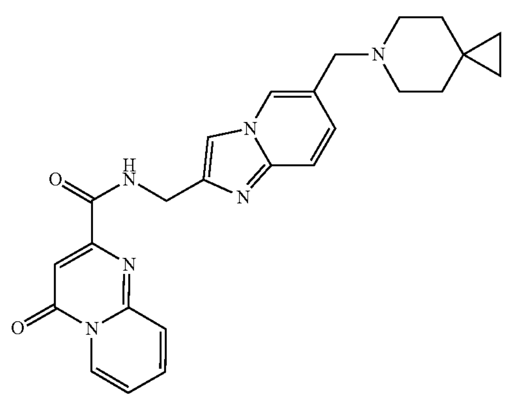 [SMILES: O=C(NCc1cn2cc(CN3CCC4(CC3)CC4)ccc2n1)c1cc(=O)n2ccccc2n1] | D | 3.63 | 443.3 |

TABLE 10-continued

| Compound No | Name | Structure | LCMS method | LCMS Retention time | Mass ion |
|---|---|---|---|---|---|
| 217 | 4-oxo-N-({6-[({[(1r,3r)-3-fluorocyclobutyl]methyl}amino)methyl]imidazo[1,2-a]pyridin-2-yl}methyl)-4H-pyrido[1,2-a]pyrimidine-2-carboxamide | 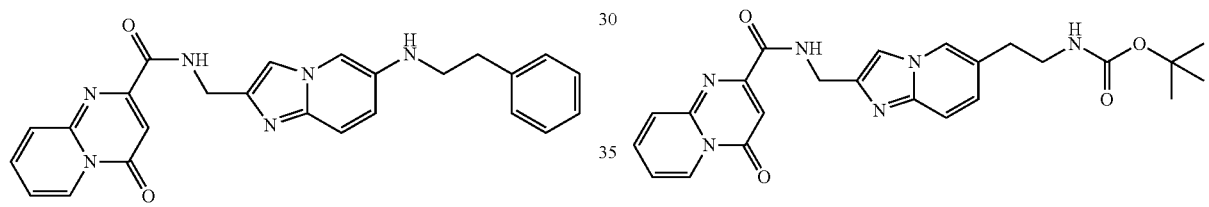 | C | 2.22 | 435.3 |

Compound 191: 4-oxo-N-({6-[(2-phenylethyl)amino]imidazo[1,2-a]pyridin-2-yl}methyl)-4H-pyrido[1,2-a]pyrimidine-2-carboxamide Step 1: tert-butyl N-(2-{2-[({4-oxo-4H-pyrido[1,2-a]pyrimidin-2-yl}formamido)methyl]imidazo[1,2-a]pyridin-6-yl}ethyl)carbamate The title compound was prepared from Compound 23 using the procedure described for Compound 32 and purified by preparative HPLC (Method A) to give (29 mg, 22%) as a brown solid.

Method E: LC-MS (electrospray): m/z=439.3 (M+H)$^+$, RT=1.83 min.

The title compound was prepared by the coupling of Intermediate 4 with intermediate 20 using the method described in Compound 1 and purified by reverse phase chromatography (400 g, High pH method) to provide (900 mg, 63%) as an off white solid. Method B: LC-MS (electrospray): m/z=463.3 (M+H)$^+$, RT=1.39 min.

Step 2: N-{[6-(2-aminoethyl)imidazo[1,2-a]pyridin-2-yl]methyl}-4-oxo-4H-pyrido[1,2-a]pyrimidine-2-carboxamide Compound 235: N-({6-[2-(benzylamino)ethyl]imidazo[1,2-a]pyridin-2-yl}methyl)-4-oxo-4H-pyrido[1,2-a]pyrimidine-2-carboxamide

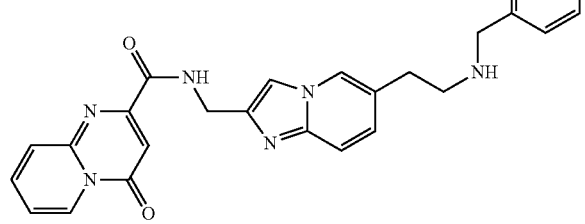

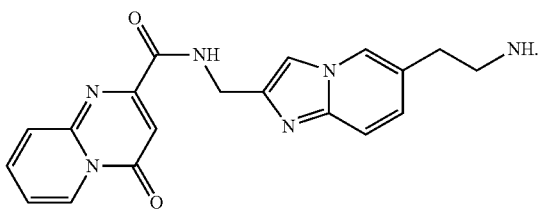

The title compound was prepared using the deprotection described in Intermediate 22 step 5 and purified by reverse phase chromatography (60 g, High pH method) to provide (100 mg, 12%) as a white solid.

Method D: LC-MS (electrospray): m/z=363.2 (M+H)$^+$, RT=2.67 min.

Step 3: N-({6-[2-(benzylamino)ethyl]imidazo[1,2-a]pyridin-2-yl}methyl)-4-oxo-4H-pyrido[1,2-a]pyrimidine-2-carboxamide

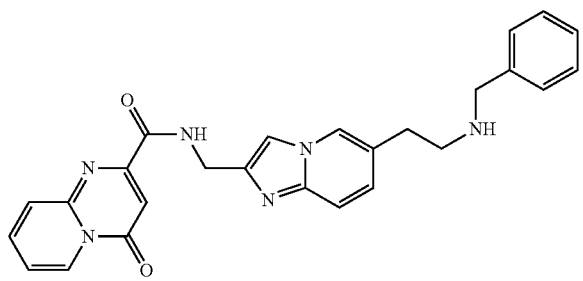 [SMILES: O=C(NCc1cn2cc(CCNCc3ccccc3)ccc2n1)c1cc(=O)n2ccccc2n1]

The title compound was prepared from benzaldehyde using the procedure described in Compound 51 and purified by preparative HPLC (method B) to give the title compound (7.8 mg, 8.9%) as a white solid.

Method D: LC-MS (electrospray): m/z=353.2 (M+H)$^+$, RT=3.44 min.

Compound 236: N-({6-[2-(cyclohexylamino)ethyl]imidazo[1,2-a]pyridin-2-yl}methyl)-4-oxo-4H-pyrido[1,2-a]pyrimidine-2-carboxamide

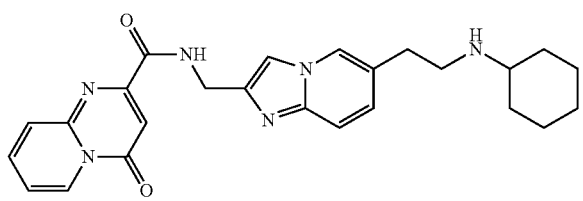 [SMILES: O=C(NCc1cn2cc(CCNC3CCCCC3)ccc2n1)c1cc(=O)n2ccccc2n1]

The title compound was prepared using the method described in Compound 51 and purified by preparative HPLC (method A) to give the title compound (48 mg, 56%) as an off white solid.

Method D: LC-MS (electrospray): m/z=445.3 (M+H)$^+$, RT=3.78 min.

Compound 237: 4-oxo-N-({6-[(phenylformamido)methyl]imidazo[1,2-a]pyridin-2-yl}methyl)-4H-pyrido[1,2-a]pyrimidine-2-carboxamide

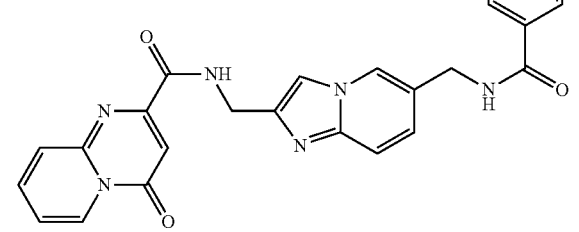

A stirred solution of HATU (140 mg, 0.368 mmol), benzoic acid (30 mg, 0.246 mmol) in DMF (1 mL) was treated with N-ethyl-N-isopropyl-propan-2-amine (0.128 mL, 0.737 mmol) at 0° C. under a nitrogen atmosphere for 30 min, and then a solution of N-[[6-(aminomethyl)imidazo[1,2-a]pyridin-2-yl]methyl]-4-oxo-pyrido[1,2-a]pyrimidine-2-carboxamide Compound 50 (122 mg, 0.245 mmol) in DMF (2 mL) was added and the reaction mixture was stirred at room temperature for 4 hours. The crude product was purified by reverse phase HPLC (method B) to provide the title product (25 mg, 21%) as an off white solid.

Method D: LC-MS (electrospray): m/z=453.1 (M+H)$^+$, RT=3.04 min.

Compound 238: N-({6-[(cyclohexylformamido)methyl]imidazo[1,2-a]pyridin-2-yl}methyl)-4-oxo-4H-pyrido[1,2-a]pyrimidine-2-carboxamide

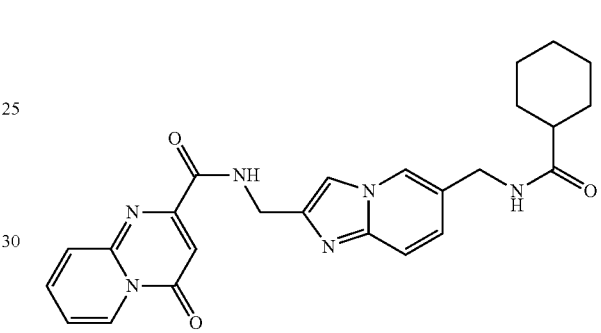

The title compound was prepared in the same manner as Compound 237 using cyclohexanecarboxylic acid to give the title compound (35.2 mg, 35%) as a white solid.

Method D: LC-MS (electrospray): m/z=459.2 (M+H)$^+$, RT=3.20 min.

Compound 239: 4-oxo-N-{[6-({[(piperidin-3-yl)methyl]amino}methyl)imidazo[1,2-a]pyridin-2-yl]methyl}-4H-pyrido[1,2-a]pyrimidine-2-carboxamide

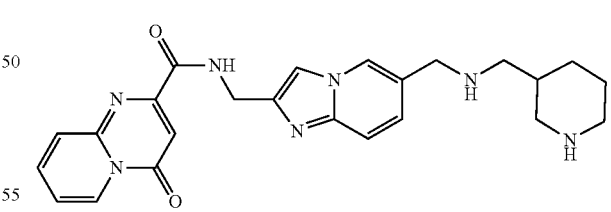

The title compound was prepared by deprotection of Compound 100 using the method described in Example 1 and the product was purified by preparative HPLC (method B) followed by ion exchange (SCX-2) giving (8 mg, 19%) as a white solid.

Method D: LC-MS (electrospray): m/z=446.2 (M+H)$^+$, RT=3.18 min.

Compound 240 4-oxo-N-{[6-({[(piperidin-2-yl)methyl]amino}methyl)imidazo[1,2-a]pyridin-2-yl]methyl}-4H-pyrido[1,2-a]pyrimidine-2-carboxamide

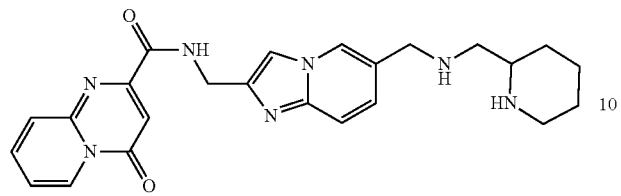

The title compound was prepared in the same manner as Compound 239 to give the title compound (8 mg, 19%) as a white solid.
Method D: LC-MS (electrospray): m/z=446.2 (M+H)$^+$, RT=3.18 min.

Compound 241 N-[(6-{[(azetidin-3-yl)amino]methyl}imidazo[1,2-a]pyridin-2-yl)methyl]-4-oxo-4H-pyrido[1,2-a]pyrimidine-2-carboxamide

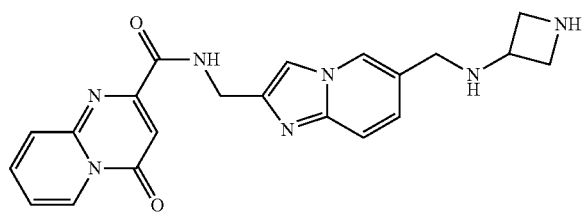 [SMILES: O=C(NCc1cn2cc(CNC3CNC3)ccc2n1)c1cc(=O)n2ccccc2n1]

The title compound was prepared in the same manner as Compound 1 starting tert-butyl 3-aminoazetidine-1-carboxylate and the deprotection outlined in Compound 239 was used to give the title compound (24 mg, 30%) as an off white solid.
Method D: LC-MS (electrospray): m/z=404.3 (M+H)$^+$, RT=2.83 min.

Compound 242: N-({6-[(cyclohexylamino)methyl]imidazo[1,2-a]pyridin-2-yl}methyl)-4-oxo-4H-chromene-2-carboxamide The title compound was prepared in a similar manner to Compound 51, using Intermediate 30 giving (16 mg, 33%) as a beige solid.
Method C: LC-MS (electrospray): m/z=431.4 (M+H)$^+$, RT=2.87 min.

The compounds in Table 10 were prepared in a similar manner to Compound 242 using the appropriate amine and Intermediate 30.

TABLE 10

| Compound No | Name | Structure | LCMS method | LCMS Retention time | Mass ion |
|---|---|---|---|---|---|
| 218 | N-[(6-{(2-cyclopropylethyl)amino]methyl}imidazo[1,2-a]pyridin-2-yl)methyl]-4-oxo-4H-chromene-2-carboxamide | 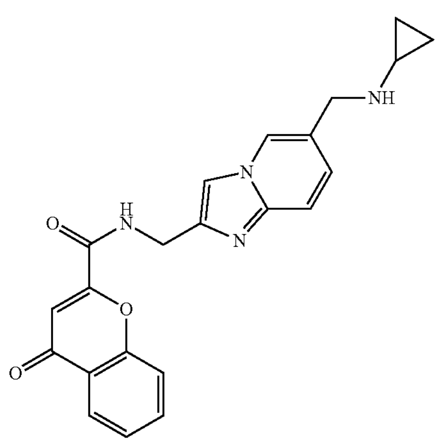 [SMILES: O=C(NCc1cn2cc(CNC3CC3)ccc2n1)c1cc(=O)c2ccccc2o1] | E | 1.00 | 417.2 |

TABLE 10-continued

| Compound No | Name | Structure | LCMS method | LCMS Retention time | Mass ion |
|---|---|---|---|---|---|
| 219 | 4-oxo-N-({6-[(piperidin-1-yl)methyl]imidazo[1,2-a]pyridin-2-yl}methyl)-4H-chromene-2-carboxamide | 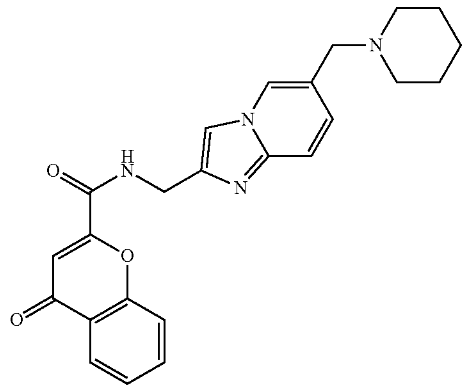 [SMILES: O=C(NCc1cn2cc(CN3CCCCC3)ccc2n1)c1cc(=O)c2ccccc2o1] | E | 0.87 | 417.2 |
| 220 | N-{[6-({[(4-chlorophenyl)methyl]amino}methyl)imidazo[1,2-a]pyridin-2-yl]methyl}-4-oxo-4H-chromene-2-carboxamide | 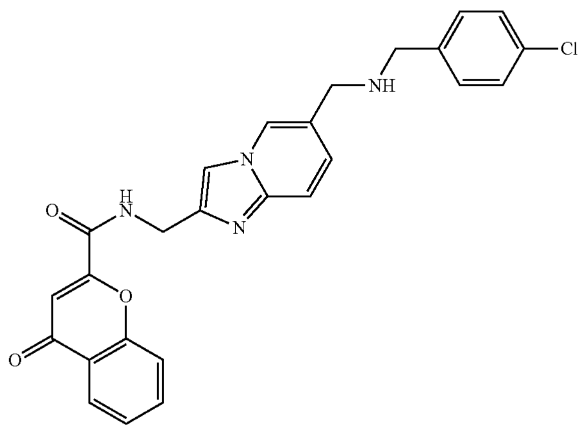 [SMILES: O=C(NCc1cn2cc(CNCc3ccc(Cl)cc3)ccc2n1)c1cc(=O)c2ccccc2o1] | E | 1.26 | 473.1 |
| 221 | N-({6-[(benzylamino)methyl]imidazo[1,2-a]pyridin-2-yl}methyl)-4-oxo-4H-chromene-2-carboxamide | 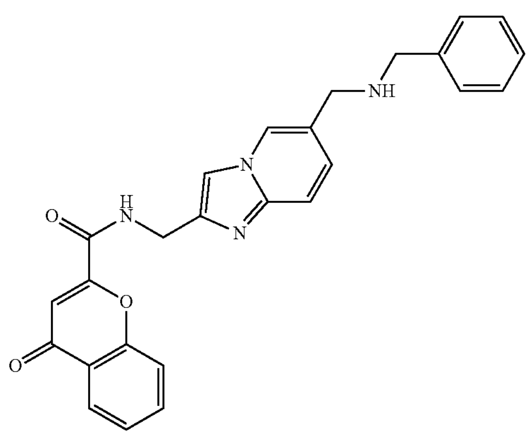 [SMILES: O=C(NCc1cn2cc(CNCc3ccccc3)ccc2n1)c1cc(=O)c2ccccc2o1] | E | 1.06 | 439.2 |

TABLE 10-continued

| Compound No | Name | Structure | LCMS method | LCMS Retention time | Mass ion |
|---|---|---|---|---|---|
| 222 | N-{[6-({[(1-methylcyclohexyl)methyl]amino}methyl)imidazo[1,2-a]pyridin-2-yl]methyl}-4-oxo-4H-chromene-2-carboxamide | 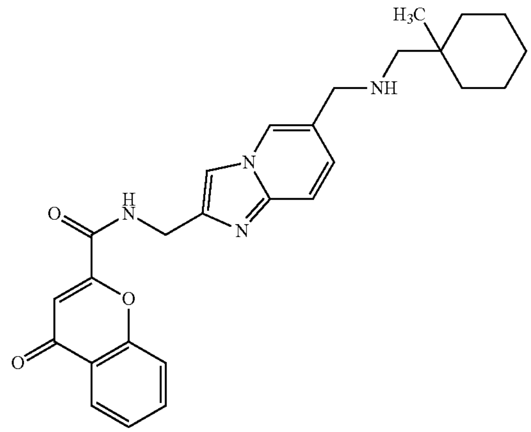 [SMILES: CC1(CNCc2ccc3nc(CNC(=O)c4cc(=O)c5ccccc5o4)cn3c2)CCCCC1] | E | 1.35 | 459.3 |
| 265 | N-[(6-{[(2,2-dimethylpropyl)amino]methyl}imidazo[1,2-a]pyridin-2-yl)methyl]-4-oxo-4H-chromene-2-carboxamide | 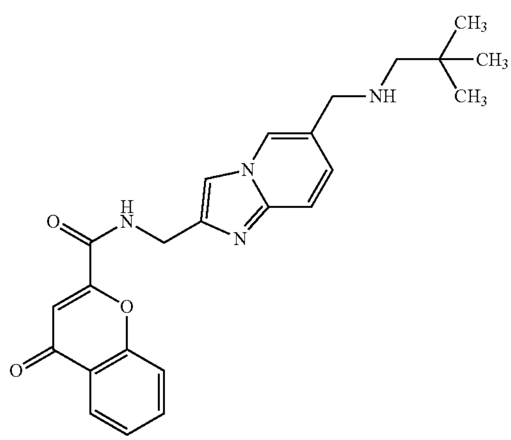 [SMILES: CC(C)(C)CNCc1ccc2nc(CNC(=O)c3cc(=O)c4ccccc4o3)cn2c1] | E | 1.08 | 419.2 |

Compound 243 4-oxo-N-[(7-{[(2-phenylethyl)amino]methyl}imidazo[1,2-a]pyridin-2-yl)methyl]-4H-pyrido[1,2-a]pyrimidine-2-carboxamide The title compound was prepared in a similar manner to Compound 51, using Intermediate 31 giving (45 mg, 69%) as a pale yellow solid.

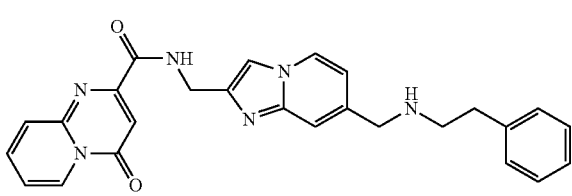 [SMILES: O=C(NCc1cn2ccc(CNCCc3ccccc3)cc2n1)c1cc(=O)n2ccccc2n1]

Method C: LC-MS (electrospray): m/z=453.3 (M+H)$^+$, RT=2.58 min.

The compounds in Table 11 were prepared in a similar manner to Compound 243 using the appropriate amine and Intermediate 31.

TABLE 11

| Compound No | Name | Structure | LCMS method | LCMS Retention time | Mass ion |
|---|---|---|---|---|---|
| 223 | N-[(7-{[(cyclohexylmethyl)amino]methyl}imidazo[1,2-a]pyridin-2-yl)methyl]-4-oxo-4H-pyrido[1,2-a]pyrimidine-2-carboxamide | 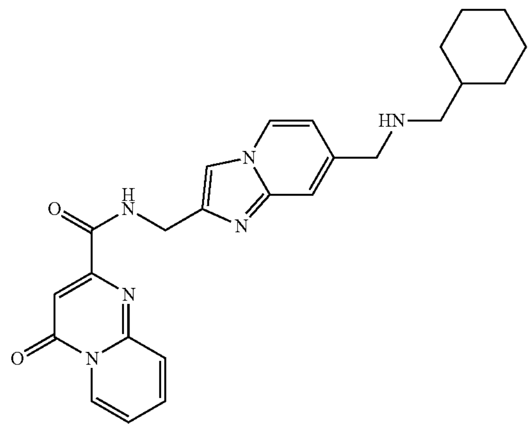 [SMILES: O=C(NCc1cn2ccc(CNCC3CCCCC3)cc2n1)c1cc(=O)n2ccccc2n1] | C | 2.94 | 445.3 |
| 224 | N-[(7-{[(cyclopropylmethyl)amino]methyl}imidazo[1,2-a]pyridin-2-yl)methyl]-4-oxo-4H-pyrido[1,2-a]pyrimidine-2-carboxamide | 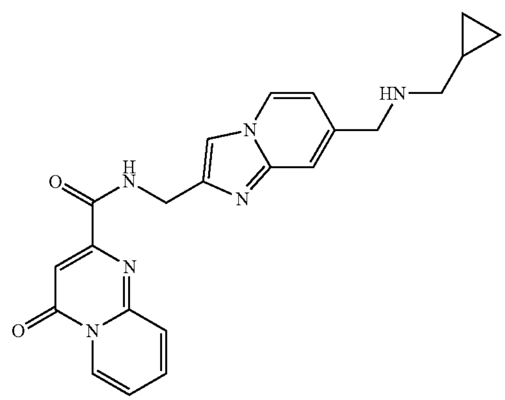 [SMILES: O=C(NCc1cn2ccc(CNCC3CC3)cc2n1)c1cc(=O)n2ccccc2n1] | C | 2.12 | 403.3 |

Compound 245: N-[(6-{1-[(cyclohexylmethyl)amino]cyclopropyl}imidazo[1,2-a]pyridin-2-yl)methyl]-4-oxo-4H-pyrido[1,2-a]pyrimidine-2-carboxamide

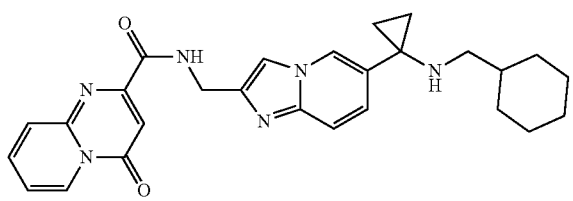 [SMILES: O=C(NCc1cn2cc(C3(NCC4CCCCC4)CC3)ccc2n1)c1cc(=O)n2ccccc2n1]

A 3 neck flask containing a suspension of N-[(6-cyano-imidazo[1,2-a]pyridin-2-yl)methyl]-4-oxo-pyrido[1,2-a]pyrimidine-2-carboxamide Compound 18 (300 mg, 0.871 mmol) in THF (24 mL) was cooled to −78° C. and treated with tetraisopropoxytitanium (634 µL, 2.09 mmol) followed by bromo(ethyl)magnesium (3M, 1336 µL, 4.01 mmol) and the mixture was stirred at −78° C. for 30 minutes before (diethyl ether)(trifluoro)boron (438 µL, 3.49 mmol) was added and the mixture was stirred at −78° C. for 30 minutes before the mixture was allowed to slowly warm to room temperature overnight. The brown mixture was cooled to −78° C. and dropwise treated with tetraisopropoxytitanium (634 µL, 2.09 mmol) followed by bromo(ethyl)magnesium (3M, 1336 µL, 4.01 mmol) and the mixture was stirred at −78° C. for 30 minutes before (diethyl ether)(trifluoro)boron (438 µL, 3.49 mmol) was added. The dark mixture was stirred at −78° C. for a further 30 minutes, allowed to warm to room temperature and left stirring for 7 days. The dark mixture was quenched by the addition of HCl (1M, 50 mL) and washed with DCM. The aqueous layer was basified (6M NaOH, pH~12) which caused Ti salts to precipitate. The suspension was filtered through Celite (washing with DCM followed by IPA/CHCl₃ (1:3) and the phases were separated. The extracts were evaporated under vacuum to afford a brown residue 500 mg which was further purified by ion exchange [SCX-2 washing with methanol followed by DCM and eluting with 2M ammonia in methanol]. The eluted fraction was evaporated under vacuum to afford a brown residue. The residue was suspended in DCE (2 mL) and treated with cyclohexanecarbaldehyde (17 µL, 0.128 mmol) followed by NaB(OAc)₃H (41 mg, 0.192 mmol) and the mixture was stirred at room temperature for 16 hours. The mixture was quenched by the addition of aqueous sodium hydrogen carbonate and extracted with DCM (phase separation cartridge). The organics were evaporated under vacuum and the residue was purified by preparative HPLC (method B) and the relevant fraction was evaporated under vacuum to give the title compound (2.9 mg, 9%) as a brown gum.

Method C: LC-MS (electrospray): m/z=471.4 (M+H)+, RT=3.31 min.

Compound 247: N-{[6-(2-amino-3-phenylpropyl)imidazo[1,2-a]pyridin-2-yl]methyl}-4-oxo-4H-pyrido[1,2-a]pyrimidine-2-carboxamide

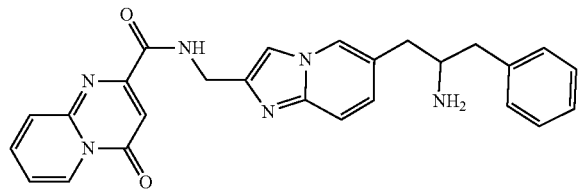

Step 1: (2-nitroethyl)benzene

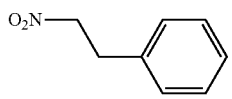

[(E)-2-nitrovinyl]benzene (1.50 g, 10.1 mmol) was added to a stirred suspension of Silica gel (604 mg, 10.1 mmol) in chloroform (75 mL) and IPA (22.5 mL). The yellow mixture was cooled to 0° C., and NaBH$_4$ (837 mg, 22.1 mmol) was added in 4 portions over 20 minutes. The resulting heterogeneous mixture was stirred vigorously at 0° C. for 30 minutes, then at room temperature for 30 minutes. The suspension was cooled to 0° C., and aqueous HCl (0.2M) was added carefully until no gas evolution was observed. The mixture was filtered and washed with DCM (30 mL). The filtrate was washed with water (50 mL), the organic phase was separated, and the aqueous phase was extracted with DCM (3×20 mL). The combined organic phases were washed with brine (2×30 mL), dried over MgSO$_4$ and concentrated to give the title compound (1.15 g, 61%) as a yellow oil.

Method A: LC-MS (electrospray): m/z=no mass ion (M+H)+, RT=1.13 min.

Step 2: N-[[6-[(E)-2-nitro-3-phenyl-prop-1-enyl]imidazo[1,2-a]pyridin-2-yl]methyl]-4-oxo-pyrido[1,2-a]pyrimidine-2-carboxamide

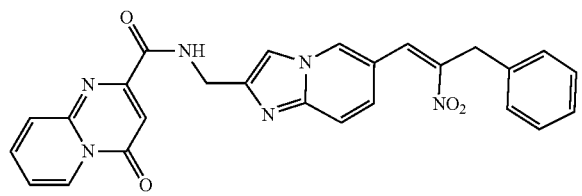

To a stirred suspension of N-[(6-formylimidazo[1,2-a]pyridin-2-yl)methyl]-4-oxo-pyrido[1,2-a]pyrimidine-2-carboxamide Compound 49 (100 mg, 0.288 mmol) and 2-nitroethylbenzene (82 mg, 0.432 mmol) in anhydrous methanol (1 mL) at 0° C. was added acetic acid (16 μL, 0.288 mmol) and butan-1-amine (28 μL, 0.288 mmol), and the reaction mixture was stirred at room temperature for 17 hours. The reaction mixture was stirred at 50° C. for 2 hours before 1,1,1,3,3,3-Hexafluoro-2-propanol (2.5 mL) was added and the solution was stirred overnight at 50° C. for 5 days. The mixture was retreated with butan-1-amine (28 μL, 0.288 mmol) and acetic acid (16 μL, 0.288 mmol), and was stirred at room temperature for 24 hours. The solvent was removed under vacuum. The mixture was diluted with water and extracted with EtOAc (4×10 mL), the organic layers were washed with brine, dried over MgSO$_4$ and concentrated under vacuum. The residue was purified by preparative HPLC (method A) to give the title compound (22 mg, 16%) as a yellow solid.

Method A: LC-MS (electrospray): m/z=481.2 (M+H)+, RT=1.00 min.

Step 3: N-[[6-(2-amino-3-phenyl-propyl)imidazo[1,2-a]pyridin-2-yl]methyl]-4-oxo-pyrido[1,2-a]pyrimidine-2-carboxamide

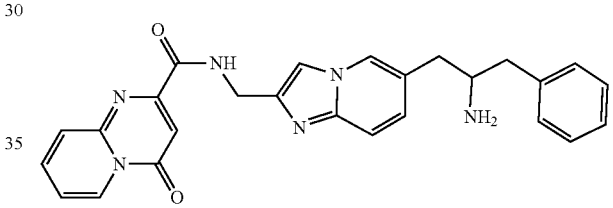

NaBH$_4$ (3.8 mg, 0.101 mmol) was dissolved in ethanol (1 mL) and cooled to 0° C. To this a solution of N-[[6-[(E)-2-nitro-3-phenyl-prop-1-enyl]imidazo[1,2-a]pyridin-2-yl]methyl]-4-oxo-pyrido[1,2-a]pyrimidine-2-carboxamide (22 mg, 0.05 mmol) in 1,4-Dioxane (1 mL) was added slowly, and stirred at 0° C. for 20 minutes, then at room temperature for 180 minutes. The mixture was cooled to 0° C. and was quenched with NH$_4$Cl (sat). The solvent was removed under vacuum, the mixture was diluted with EtOAc (10 mL) and water (10 mL), the layers were separated, the mixture was extracted with EtOAc (3×10 mL), the organic layers were washed with water (10 mL) and brine (10 mL), dried over MgSO$_4$ and concentrated to a yellow solid. Ammonium chloride (10 mg, 0.187 mmol) was then added to a mixture of N-[[6-(2-nitro-3-phenyl-propyl)imidazo[1,2-a]pyridin-2-yl]methyl]-4-oxo-pyrido[1,2-a]pyrimidine-2-carboxamide (18 mg, 0.0373 mmol) in methanol (1 mL) and water (0.5 mL), the mixture was heated at 50° C. Iron (10 mg, 0.187 mmol) was then added, and the reaction mixture was heated to 65° C. and stirred for 4.5 hours. The reaction mixture was allowed to cool to room temperature, was filtered through a pad of Celite, washed with EtOAc and the filtrate was concentrated. The mixture was purified by preparative HPLC (method A) to give the title compound (7.0 mg, 41%) as an off white solid.

Method D: LC-MS (electrospray): m/z=453.3 (M+H)+, RT=3.31 min.

Compound 248: (cyclohexylmethyl)[(2-{[4-(1H-indazol-4-yl)-1H-1,2,3-triazol-1-yl]methyl}imidazo[1,2-a]pyridin-6-yl)methyl]amine

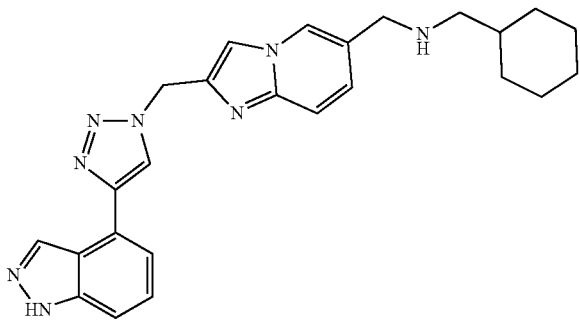

Step 1:
6-amino-N-(cyclohexylmethyl)pyridine-3-carboxamide

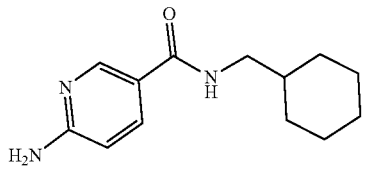 [SMILES: Nc1ccc(C(=O)NCC2CCCCC2)cn1]

6-aminopyridine-3-carboxylic acid (500 mg, 3.62 mmol), cyclohexylmethanamine (820 mg, 7.24 mmol) and triethylamine (1.51 mL, 10.9 mmol) were combined in DMF (3 mL) and HATU (2.06 g, 5.43 mmol) was added. The mixture was stirred at room temperature for 24 hours. The reaction mixture was quenched with saturated aqueous sodium hydrogen carbonate (30 mL) and extracted with 3:1 chloroform/isopropanol (3×80 mL). The combined organic extracts were dried over sodium sulfate and evaporated under vacuum. The residue was purified by Biotage Isolera™ chromatography (28 g kp-NH, eluting with EtOAc/heptane 0-100% followed by methanol/EtOAc 0-20%) to afford a crude material which was further purified by Biotage Isolera™ chromatography (60 g C18-Ultra, acetonitrile+0.1% NH₃/water+0.1% NH₃ 10-100%) to afford (298 mg, 35%) of the title compound as a white solid Method B: LC-MS (electrospray): m/z=234.3 (M+H)⁺, RT=1.36 min Step 2: 2-(chloromethyl)-N-(cyclohexylmethyl)imidazo[1,2-a]pyridine-6-carboxamide

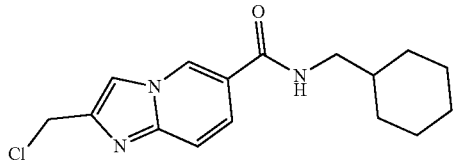 [SMILES: O=C(NCC1CCCCC1)c1ccc2nc(CCl)cn2c1]

6-amino-N-(cyclohexylmethyl)pyridine-3-carboxamide (290 mg, 1.24 mmol) and 1,3-dichloropropan-2-one (237 mg, 1.86 mmol) were combined in acetonitrile (10 mL) and the mixture heated at reflux for 3 days. The reaction mixture was cooled to room temperature and concentrated under vacuum. The residue was suspended in saturated aqueous sodium hydrogen carbonate (30 mL) and extracted with 3:1 chloroform/isopropanol (4×30 mL). The combined organic extracts were dried over sodium sulfate and evaporated under vacuum. The residue was purified by Biotage Isolera™ chromatography (25 g kp-Sil, eluting with EtOAc/heptane 0-100% followed by methanol/EtOAc 0-20%) to afford (143 mg, 38%) of the title compound as an off-white solid.
Method B: LC-MS (electrospray): m/z=306.3 (M+H)⁺, RT=1.52 min Step 3: 2-(azidomethyl)-N-(cyclohexylmethyl)imidazo[1,2-a]pyridine-6-carboxamide

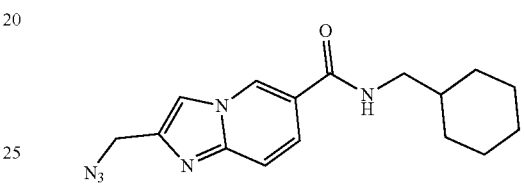

2-(chloromethyl)-N-(cyclohexylmethyl)imidazo[1,2-a]pyridine-6-carboxamide (140 mg, 0.46 mmol), sodium iodide (69 mg, 0.46 mmol) and NaN₃ (45 mg, 0.69 mmol) were combined in DMF (2 mL) and the mixture stirred at room temperature for 22 hours. The reaction mixture was quenched with saturated aqueous sodium hydrogen carbonate (30 mL) and extracted with 3:1 chloroform/isopropanol (3×30 mL). The combined organic extracts were dried over sodium sulfate and evaporated under vacuum. The residue was triturated with EtOAc/heptane and the solids collected by filtration to afford (100 mg, 70%) of the title compound as a white solid
Method B: LC-MS (electrospray): m/z=313.3 (M+H)⁺, RT=1.52 min Step 4: N-(cyclohexylmethyl)-2-[[4-(1-tetrahydropyran-2-ylindazol-4-yl)triazol-1-yl]methyl]imidazo[1,2-a]pyridine-6-carboxamide

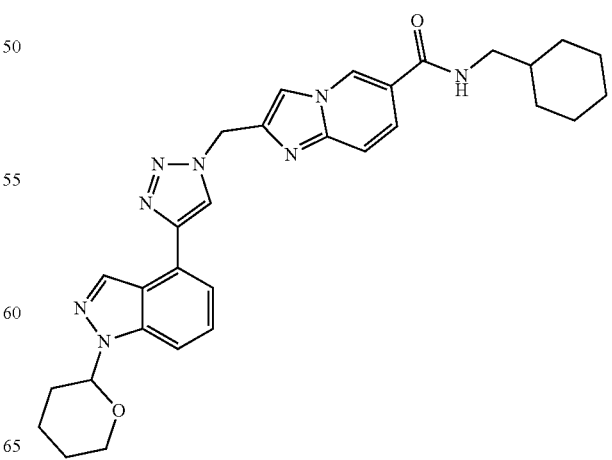

2-(azidomethyl)-N-(cyclohexylmethyl)imidazo[1,2-a]pyridine-6-carboxamide (100 mg, 0.32 mmol) and 4-ethynyl-1-tetrahydropyran-2-yl-indazole Intermediate 24 (101 mg, 0.32 mmol) were dissolved in DMF (3 mL) and water (0.5 mL) and copper sulfate (10 mg, 0.06 mmol) and sodium ascorbate (64 mg, 0.32 mmol) were added. The mixture was stirred at room temperature for 1 hour. The reaction mixture was diluted with 3:1 chloroform/isopropanol (30 mL) and washed with water (20 mL). The aqueous phase was extracted with 3:1 chloroform/isopropanol (2×30 mL) and the combined organic layers were dried over sodium sulfate and evaporated under vacuum. The residue was purified by chromatography on silica gel (Biotage, 11 g kp-NH, eluting with EtOAc/heptane 0-100% followed by methanol/EtOAc 0-20%) to afford the title compound (171 mg, 99%) as a white solid Method A: LC-MS (electrospray): m/z=589.3 (M+H)+, RT=1.18 min Step 5: N-(cyclohexylmethyl)-1-[2-[[4-(1H-indazol-4-yl)triazol-1-yl]methyl]imidazo[1,2-a]pyridin-6-yl]methanamine

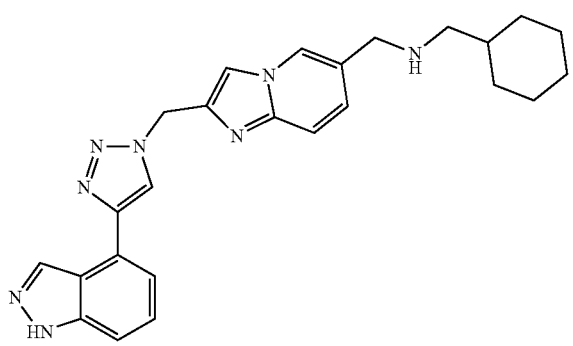 [SMILES: c1cc(-c2cn(Cc3cn4cc(CNCC5CCCCC5)ccc4n3)nn2)c2cn[nH]c2c1]

N-(cyclohexylmethyl)-2-[[4-(1-tetrahydropyran-2-ylindazol-4-yl)triazol-1-yl]methyl]imidazo[1,2-a]pyridine-6-carboxamide (80 mg, 0.15 mmol) and 2-fluoropyridine (53 µl, 0.62 mmol) were combined in DCM-Anhydrous (4 mL) and cooled in an ice/water bath. trifluoromethylsulfonyl trifluoromethanesulfonate (107 µl, 0.63 mmol) was added dropwise to give a yellow solution which was stirred briefly, then 1,1,3,3-tetramethyldisiloxane (160 µl, 0.91 mmol) and tris(pentafluorophenyl)borane (15 mg, 0.03 mmol) were added and the mixture stirred whilst warming to room temperature for 6 hours. $K_2CO_3$ (100 mg) and methanol (20 mL) were added and the mixture incubated at room temperature for 16 h and at reflux for 1 hour. The reaction mixture was cooled to room temperature and concentrated under vacuum. The residue was suspended in saturated aqueous sodium hydrogen carbonate (20 mL) and extracted with 3:1 chloroform/isopropanol (3×30 mL) and the combined organic extracts dried over sodium sulfate and evaporated under vacuum. The residue was triturated with EtOAc/heptane and the solids collected by filtration. The residue was purified by reverse phase chromatography (method B) and the clean product-containing fractions combined and evaporated under vacuum to afford the title compound (17 mg (26%) as a white solid.

Method C: LC-MS (electrospray): m/z=441.4 (M+H)+, RT=3.09 min

Compound 249: N-(cyclohexylmethyl)-2-{[4-(1H-indazol-4-yl)-1H-1,2,3-triazol-1-yl]methyl}imidazo[1,2-a]pyridine-6-carboxamide

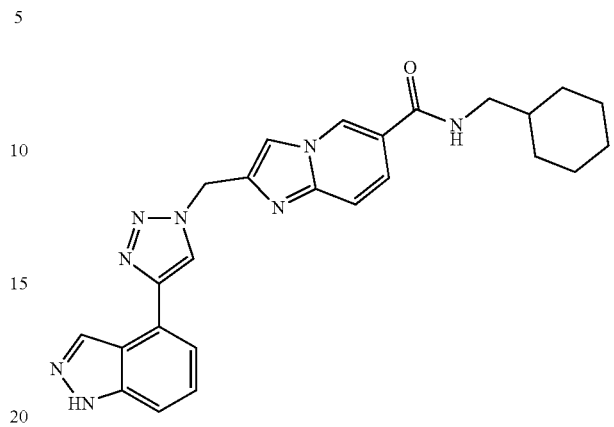

N-(cyclohexylmethyl)-2-[[4-(1-tetrahydropyran-2-ylindazol-4-yl)triazol-1-yl]methyl]imidazo[1,2-a]pyridine-6-carboxamide Compound 248 step 4 (40 mg, 0.07 mmol) was suspended in methanol (1 mL) and treated with 4M HCl in Dioxane (1 mL). The mixture was incubated at room temperature for 5 h, then evaporated under vacuum. The residue was loaded to an SCX-2 cartridge (2 g) and the cartridge rinsed with DCM and methanol, then eluted with 7M $NH_3$/methanol. The basic eluent was evaporated under vacuum and the residue dried in the Genevac to afford the title compound (8 mg (23%) as an off-white solid.

Method C: LC-MS (electrospray): m/z=455.3 (M+H)+, RT=2.88 min

Compound 250: (2,2-dimethylpropyl)[(2-{[4-(1H-indazol-4-yl)-1H-1,2,3-triazol-1-yl]methyl}imidazo[1,2-a]pyridin-6-yl)methyl]amine

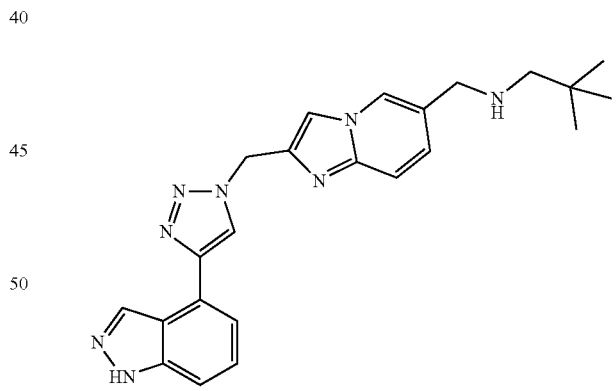

2-[[4-(1-tetrahydropyran-2-ylindazol-4-yl)triazol-1-yl]methyl]imidazo[1,2-a]pyridine-6-carbaldehyde (Intermediate 34) (70 mg, 0.16 mmol) and 2,2-dimethylpropan-1-amine (57 mg, 0.66 mmol) were combined in 1,1,1,3,3,3-Hexafluoroisopropanol (2 mL) and the mixture stirred at room temperature for 1 hour. $NaBH_4$ (70 mg, 1.85 mmol) was added with a few drops methanol then quenched with methanol (20 mL) and the mixture evaporated under vacuum. The residue was suspended in saturated aqueous sodium hydrogen carbonate (40 mL) and extracted with 3:1 chloroform/isopropanol (3×40 mL). The combined organic extracts were dried over sodium sulfate and evaporated under vacuum. The residue was dissolved in methanol (3 mL) and treated with 4M HCl in Dioxane (3 mL) and the mixture incubated at room temperature for 2 h, then evaporated under vacuum. The residue was redissolved in methanol and loaded to an SCX-2 cartridge (5 g). The system was rinsed with DCM and methanol, then eluted with 7N NH₃/methanol. The basic eluent was evaporated under vacuum. The residue was triturated with EtOAc/heptane and the solids collected by filtration to afford (45 mg, 64%) of the title compound as a white solid.

Method D: LC-MS (electrospray): m/z=415.3 (M+H)⁺, RT=3.69 min

Compound 251: 4-[1-({6-[(4,4-dimethylpiperidin-1-yl)methyl]imidazo[1,2-a]pyridin-2-yl}methyl)-1H-1,2,3-triazol-4-yl]-1H-indazole

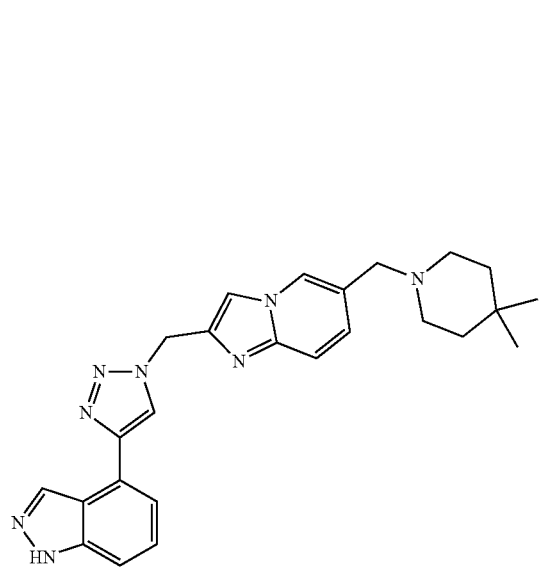 [SMILES: CC1(C)CCN(Cc2ccc3nc(Cn4cc(-c5cccc6[nH]ncc56)nn4)cn3c2)CC1]

Step 1: 4-[1-({6-[(4,4-dimethylpiperidin-1-yl) methyl]imidazo[1,2-a]pyridin-2-yl}methyl)-1H-1,2,3-triazol-4-yl]-1H-indazole A mixture of 2-[[4-(1-tetrahydropyran-2-ylindazol-4-yl)triazol-1-yl]methyl]imidazo[1,2-a]pyridine-6-carbaldehyde (Intermediate 34) (70 mg, 0.164 mmol) and 4,4-dimethylpiperidine (43 µL, 0.328 mmol) in DCE (1.8 mL) was stirred at 50° C. for 5 minutes, NaB(OAc)₃H (104 mg, 0.49 mmol) was added, and the mixture was stirred at 50° C. for 4 hours. The reaction mixture was quenched with aqueous sodium hydrogen carbonate, diluted with 3:1 CHCl₃/IPA and the phases were separated, the aqueous mixture was extracted with CHCl₃/IPA, the organic layers were dried by passage through a TELOS phase separation cartridge and concentrated under vacuum. The residue was dissolved in methanol (2.5 mL) and 4M HCl in dioxane (2.5 mL), and stirred at room temperature for 2 h, then evaporated under vacuum. The residue was purified by reverse phase chromatography (Method B) to afford the title compound (23 mg, 32%) as a white solid.

Method C: LC-MS (electrospray): m/z=441.4 (M+H)⁺, RT=3.17 min

Compound 252: [(2-{[4-(6-bromo-1H-indazol-4-yl)-1H-1,2,3-triazol-1-yl]methyl}imidazo[1,2-a]pyridin-6-yl)methyl][(3,3-difluorocyclobutyl)methyl]amine

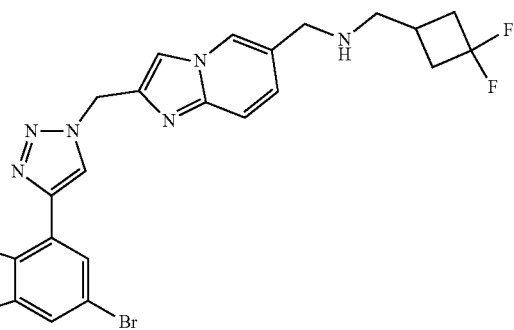

2-[[4-(6-bromo-1-tetrahydropyran-2-yl-indazol-4-yl)triazol-1-yl]methyl]imidazo[1,2-a]pyridine-6-carbaldehyde Intermediate 35 (70 mg, 0.12 mmol), (3,3-difluorocyclobutyl)methanamine hydrochloride (37 mg, 0.24 mmol) and triethylamine (50 µl, 0.36 mmol) were combined in 1,1,1,3,3,3-Hexafluoro-2-propanol (2 mL) and the mixture stirred at room temperature for 30 minutes. NaBH₄ (70 mg, 1.85 mmol) was added with a few drops methanol and the mixture stirred briefly, then quenched with methanol (20 mL) and the mixture evaporated under vacuum. The residue was suspended in saturated aqueous sodium hydrogen carbonate (30 mL) and extracted with 3:1 chloroform/isopropanol (3×30 mL). The combined organic extracts were dried over sodium sulfate and evaporated under vacuum. The residue was redissolved in methanol (3 mL), treated with 4M HCl in Dioxane (3 mL) and incubated at room temperature for 16 hours. The reaction mixture was evaporated under vacuum. The residue was loaded to an SCX-2 cartridge (2 g) and the system rinsed with DCM and methanol, then eluted with 7M NH₃/methanol. The basic eluent was evaporated under vacuum. The resultant residue was purified by reverse phase chromatography (Method B) to afford the title compound (17 mg, 27%) as an off-white solid.

Method D: LC-MS (electrospray): m/z=527.2/529.2 (M+H)⁺, RT=3.69 min

The compounds in Table 12 were prepared in a similar fashion to Compound 252

TABLE 12

| Cpd No | Name | Structure | LCMS method | LCMS Retention time | Mass ion | Reductive amination conditions |
|---|---|---|---|---|---|---|
| 225 | [(2-{[4-(6-bromo-1H-indazol-4-yl)-1H-1,2,3-triazol-1-yl]methyl}imidazo[1,2-a]pyridin-6-yl)methyl](2,2-dimethylpropyl)amine | 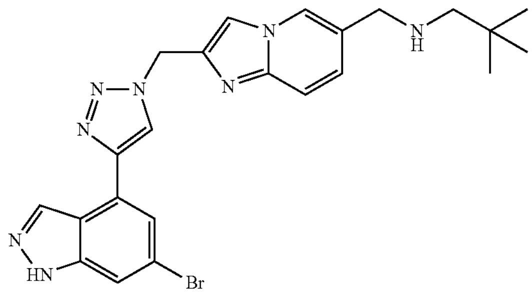 [SMILES: CC(C)(C)CNCc1ccc2nc(Cn3cc(-c4cc(Br)cc5[nH]ncc45)nn3)cn2c1] | D | 4.09 | 493.2/ 495.2 | 252 |
| 226 | [(2-{[4-(6-bromo-1H-indazol-4-yl)-1H-1,2,3-triazol-1-yl]methyl}imidazo[1,2-a]pyridin-6-yl)methyl](cyclohexylmethyl)amine | 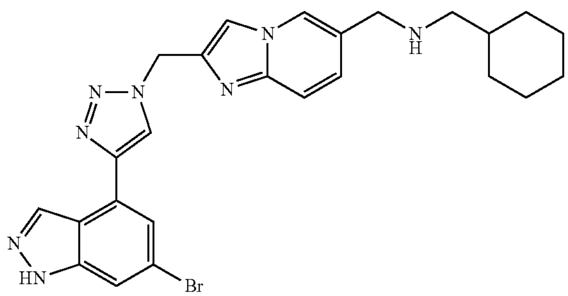 [SMILES: Brc1cc(-c2cn(Cc3cn4cc(CNCC5CCCCC5)ccc4n3)nn2)c2cn[nH]c2c1] | C | 3.54 | 519.3/ 521.3 | Compound 252 |
| 227 | 6-bromo-4-[1-({6-[(4,4-dimethylpiperidin-1-yl)methyl]imidazo[1,2-a]pyridin-2-yl}methyl)-1H-1,2,3-triazol-4-yl]-1H-indazole | 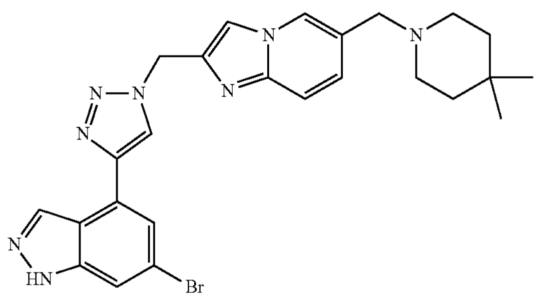 [SMILES: CC1(C)CCN(Cc2ccc3nc(Cn4cc(-c5cc(Br)cc6[nH]ncc56)nn4)cn3c2)CC1] | C | 1.64 | 519.2/ 521.2 | Compound 251 |

Compound 253: (2-{[4-(6-bromo-1H-indazol-4-yl)-1H-1,2,3-triazol-1-yl]methyl}imidazo[1,2-a]pyridin-6-yl)methanol Step 1: [2-({4-[6-bromo-1-(oxan-2-yl)-1H-indazol-4-yl]-1H-1,2,3-triazol-1-yl}methyl)imidazo[1,2-a]pyridin-6-yl]methanol

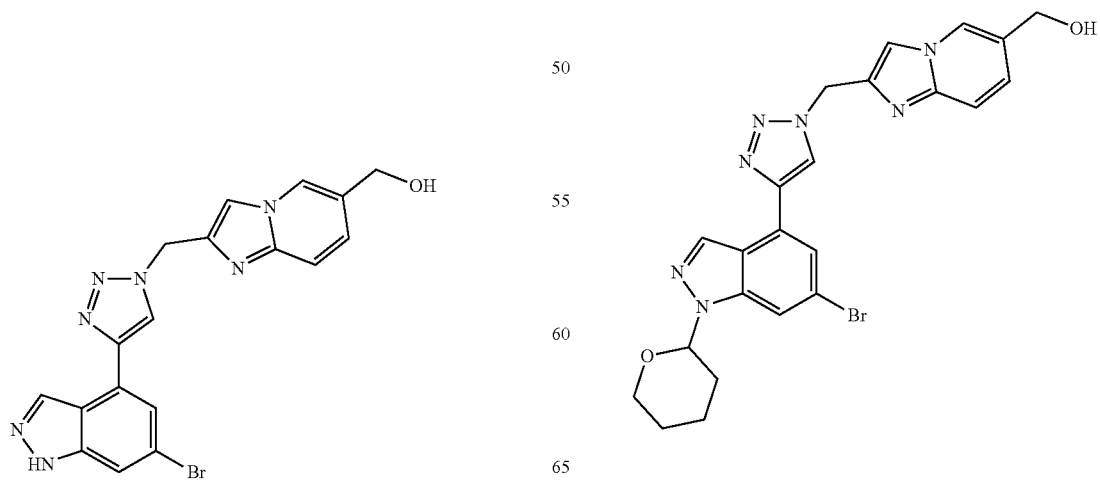

The title compound was prepared in the same manner as Intermediate 34 Step 4 to give (795 mg, 68%) as a grey solid.

Method A: LC-MS (electrospray): m/z=508.15/510.15 (M+H)+, RT=1.00 min

Step 2: (2-{[4-(6-bromo-1H-indazol-4-yl)-1H-1,2,3-triazol-1-yl]methyl}imidazo[1,2-a]pyridin-6-yl)methanol

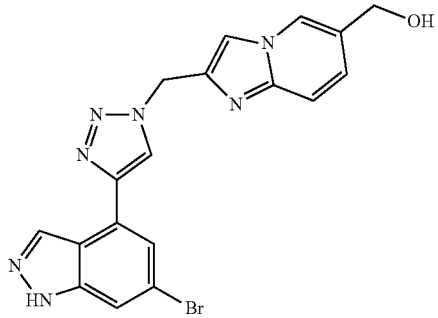 [SMILES: OCc1ccc2nc(Cn3cc(-c4cc(Br)cc5[nH]ncc45)nn3)cn2c1]

[2-[[4-(6-bromo-1-tetrahydropyran-2-yl-indazol-4-yl)triazol-1-yl]methyl]imidazo[1,2-a]pyridin-6-yl]methanol (87 mg, 0.17 mmol) was suspended in methanol (3 mL) and treated with HCl (4M in Dioxane, 3 mL, 12 mmol). The mixture was stirred at room temperature for 1 h, then evaporated under vacuum. The residue was triturated with methanol/Et$_2$O and the solids collected by filtration. The residue was purified by preparative HPLC (method B) to afford the title compound (14 mg, 19%) as an off-white solid.

Method C: LC-MS (electrospray): m/z=424.1/426.1 (M+H)+, RT=2.14 min

Compound 254: (2,2-dimethylpropyl)[(2-{[4-(1H-indazol-5-yl)-1H-1,2,3-triazol-1-yl]methyl}imidazo[1,2-a]pyridin-6-yl)methyl]amine

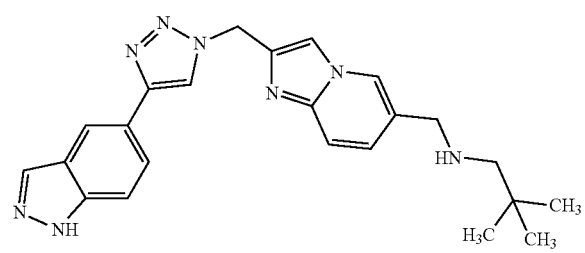 [SMILES: CC(C)(C)CNCc1ccc2nc(Cn3cc(-c4ccc5[nH]ncc5c4)nn3)cn2c1]

The title compound was prepared from intermediate 37 using the method described in Compound 250 giving (42 mg, 65%) as an off white solid.

Method D: LC-MS (electrospray): m/z=415.3 (M+H)+, RT=3.57 min

Compound 255: ((cyclohexylmethyl)[1-(2-{[4-(1H-indazol-4-yl)-1H-1,2,3-triazol-1-yl]methyl}imidazo[1,2-a]pyridin-6-yl)ethyl]amine

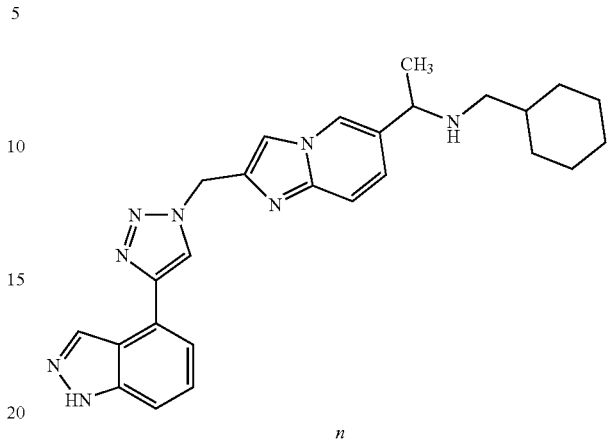

The title compound was prepared from Intermediate 32 Step 3 and Intermediate 24 using the method described in Compound 248 giving (27 mg, 25%) as an off-white solid.

Method D: LC-MS (electrospray): m/z=455.4 (M+H)+, RT=4.03 min.

Compound 256: (2,2-dimethylpropyl)({2-[(4-{1H-pyrazolo[3,4-c]pyridin-4-yl}-1H-1,2,3-triazol-1-yl)methyl]imidazo[1,2-a]pyridin-6-yl}methyl)amine

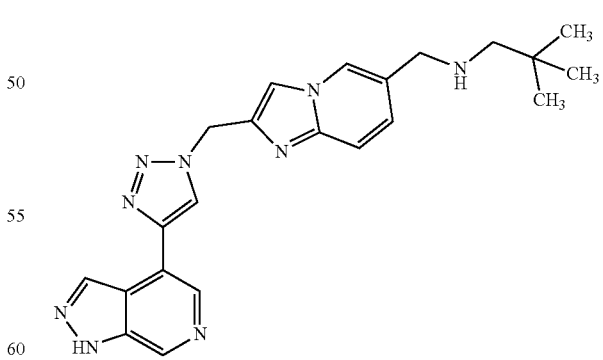

The title compound was prepared from Intermediate 40 using the procedure described (Compound 250) giving (31 mg, 32%) as a pale yellow solid.

Method D: LC-MS (electrospray): m/z=416.3 (M+H)+, RT=3.09 min

Compound 257: {2-[(4-{1H-pyrazolo[3,4-c]pyridin-4-yl}-1H-1,2,3-triazol-1-yl)methyl]imidazo[1,2-a]pyridin-6-yl}methanol

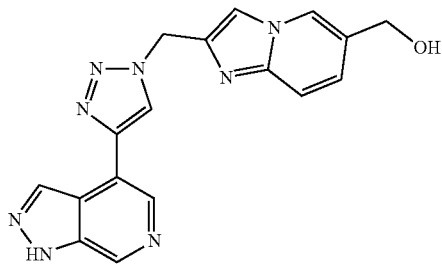 [SMILES: OCc1ccc2nc(Cn3cc(-c4cncc5[nH]ncc45)nn3)cn2c1]

The title compound was prepared from Intermediate 39 using the procedure described in Compound 253 giving (1 mg, 2%) as a white solid.
Method D: LC-MS (electrospray): m/z=347.2 (M+H)$^+$, RT=2.30 min.
μμ

Compound 263: N-{[6-(morpholin-3-yl)imidazo[1,2-a]pyridin-2-yl]methyl}-4-oxo-4H-pyrido[1,2-a]pyrimidine-2-carboxamide

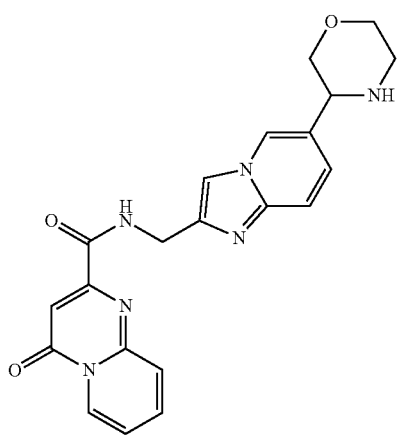 [SMILES: O=C(NCc1cn2cc(C3COCCN3)ccc2n1)c1cc(=O)n2ccccc2n1]

To solution of N-[(6-formylimidazo[1,2-a]pyridin-2-yl)methyl]-4-oxo-pyrido[1,2-a]pyrimidine-2-carboxamide (Compound 49) (119 mg, 0.343 mmol) in 1,1,1,3,3,3-Hexafluoro-2-propanol (0.5 mL) was added a solution of [(2-aminoethoxy)methyl]tributylstannane (125 mg, 0.343 mmol) in DCE (4 mL). The mixture was stirred at 80° C. for 2 hours. Meanwhile a mixture of 2,6-dimethylpyridine (0.080 mL, 0.685 mmol), copper(II) bis(trifluoromethanesulfonate) (249 mg, 0.685 mmol) and 1,1,1,3,3,3-Hexafluoro-2-propanol (2 mL) was stirred separately at room temperature for 1 hour. After cooling to room temperature, the solution of the imine was added drop-wise to the solution of the catalyst. The resulting mixture was stirred at room temperature for 3 hours forming a clear, dark green solution. The reaction mixture was diluted with DCM (25 mL) and quenched with 10% aq. NH$_4$OH (10 mL) solution. The organic layer was separated, washed with brine (10 mL), dried (Na$_2$SO$_4$), filtered and concentrated under reduced pressure. The residue was purified by preparative HPLC (method B) to afford the title compound (39 mg, 28%) as greenish solid.

Method C: LC-MS (electrospray): m/z=405.3 (M+H)$^+$, RT=1.59 min

The compounds in Table 12 were prepared in the same manner as Compound 263

TABLE 13

| Compound No | Name | Structure | LCMS method | LCMS Retention time | Mass ion |
|---|---|---|---|---|---|
| 228 | N-({6-[(3R,5S)-5-tert-butylmorpholin-3-yl]imidazo[1,2-a]pyridin-2-yl}methyl)-4-oxo-4H-pyrido[1,2-a]pyrimidine-2-carboxamide | 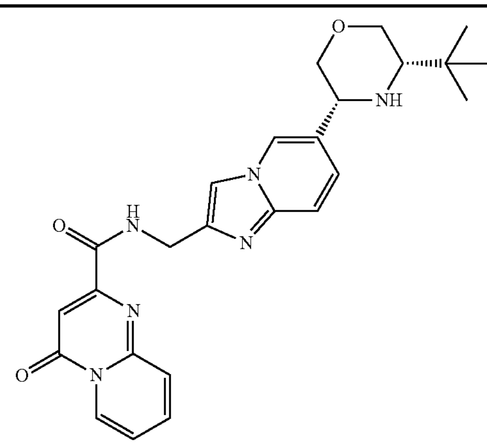 | C | 2.91 | 461.4 |

TABLE 13-continued

| Compound No | Name | Structure | LCMS method | LCMS Retention time | Mass ion |
|---|---|---|---|---|---|
| 229 | N-({6-[(3S,5R)-5-tert-butylmorpholin-3-yl]imidazo[1,2-a]pyridin-2-yl}methyl)-4-oxo-4H-pyrido[1,2-a]pyrimidine-2-carboxamide | 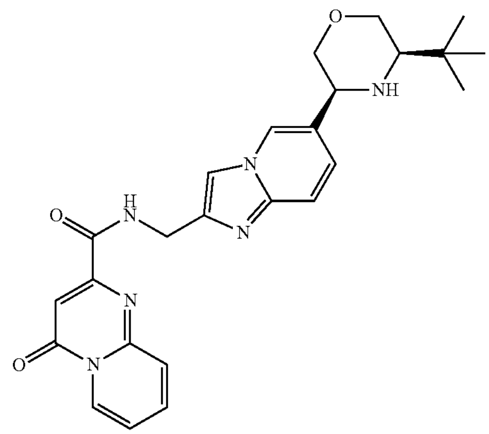 [SMILES: CC(C)(C)[C@@H]1COC[C@H](c2ccc3nc(CNC(=O)c4cc(=O)n5ccccc5n4)cn3c2)N1] | C | 2.89 | 461.4 |
| 230 | N-({6-[(3S,5R)-5-cyclohexyl-morpholin-3-yl]imidazo[1,2-a]pyridin-2-yl}methyl)-4-oxo-4H-pyrido[1,2-a]pyrimidine-2-carboxamide | 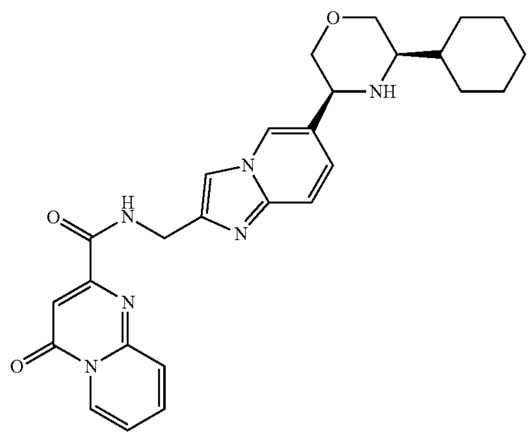 [SMILES: O=C(NCc1cn2cc([C@H]3COC[C@@H](C4CCCCC4)N3)ccc2n1)c1cc(=O)n2ccccc2n1] | C | 3.05 | 487.4 |

Compound 231: N-({6-[(3S,5R)-5-cyclohexylmorpholin-3-yl]imidazo[1,2-a]pyridin-2-yl}methyl)-1H-indazole-4-carboxamide

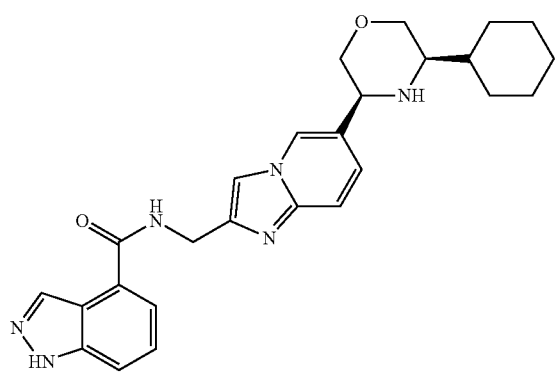 [SMILES: O=C(NCc1cn2cc([C@H]3COC[C@@H](C4CCCCC4)N3)ccc2n1)c1cccc2[nH]ncc12]

Trans Racemate

To a solution of 1-[rac-(2R)-tetrahydropyran-2-yl]indazole-4-carboxylic acid (35 mg, 0.142 mmol)), [6-[rac-(3S,5R)-5-cyclohexylmorpholin-3-yl]imidazo[1,2-a]pyridin-2-yl]methanamine trihydrochloride (Intermediate 47) (60 mg, 0.142 mmol) and DIPEA (0.12 mL, 0.708 mmol) in DMF (3 mL) was added HATU (65 mg, 0.170 mmol). The reaction mixture was stirred at room temperature overnight. The reaction mixture was partitioned between EtOAc (30 mL) and saturated aqueous sodium hydrogen carbonate (20 mL). The organic layer was separated, washed with brine (10 mL), dried ($Na_2SO_4$), filtered and concentrated under reduced pressure to dryness. The residue was dissolved in methanol (3 mL) and 4M HCl in dioxane (1 mL) was added. The mixture was stirred at room temperature overnight. The volatiles were removed under reduced pressure and the residue was purified by preparative HPLC (method B) to afford the title compound (30 mg, 46%) as white solid.

Method C: LC-MS (electrospray): m/z=459.4 $(M+H)^+$, RT=2.96 min

Compound 264: N-({6-[(3S,5R)-5-cyclohexylmorpholin-3-yl]imidazo[1,2-a]pyridin-2-yl}methyl)-4-oxo-4H-chromene-2-carboxamide

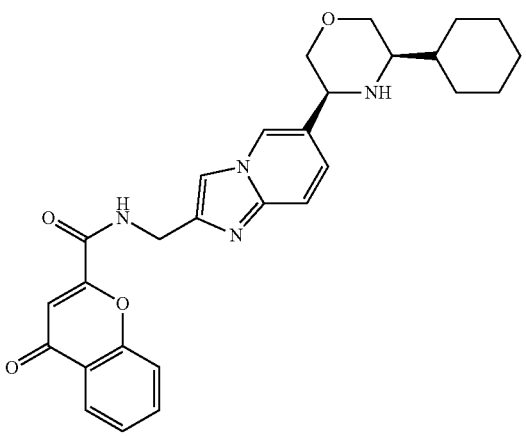 [SMILES: O=C(NCc1cn2cc([C@H]3COC[C@@H](C4CCCCC4)N3)ccc2n1)c1cc(=O)c2ccccc2o1]

To a solution of 4-oxochromene-2-carboxylic acid (22 mg, 0.118 mmol)), [6-[rac-(3S,5R)-5-cyclohexylmorpholin-3-yl]imidazo[1,2-a]pyridin-2-yl]methanamine-trihydrochloride (50 mg, 0.118 mmol) and DIPEA (0.10 mL, 0.590 mmol) in DMF (1 mL) was added HATU (54 mg, 0.142 mmol). The reaction mixture was stirred at room temperature overnight. The reaction mixture was partitioned between EtOAc (30 mL) and saturated aqueous sodium hydrogen carbonate (20 mL). The organic layer was separated, washed with brine (10 mL), dried (Na$_2$SO$_4$), filtered and concentrated under reduced pressure. The residue was purified by preparative HPLC (method B) to afford the title compound (15 mg, 26%) as off-white solid.

Method C: LC-MS (electrospray): m/z=487.4 (M+H)$^+$, RT=3.33 min

Compound 232: N-({6-[4-(2,2-dimethylpropyl)morpholin-3-yl]imidazo[1,2-a]pyridin-2-yl}methyl)-4-oxo-4H-pyrido[1,2-a]pyrimidine-2-carboxamide

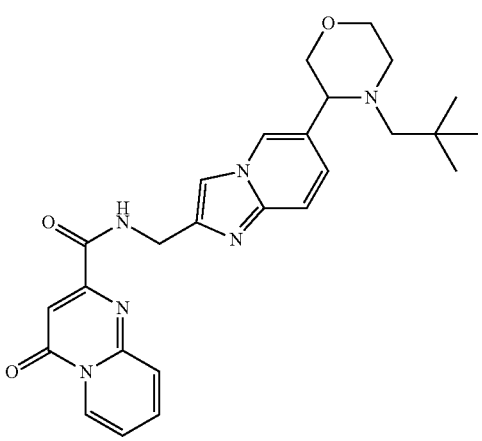 [SMILES: CC(C)(C)CN1CCOCC1c1ccc2nc(CNC(=O)c3cc(=O)n4ccccc4n3)cn2c1]

To a solution of N-[(6-morpholin-3-ylimidazo[1,2-a]pyridin-2-yl)methyl]-4-oxo-pyrido[1,2-a]pyrimidine-2-carboxamide (Compound 263) (38 mg, 0.09 mmol) in DCE (1.5 mL) was added 2,2-dimethylpropanal (0.04 mL, 0.38 mmol) and acetic acid (0.011 mL, 0.188 mmol) at room temperature. The mixture was stirred for 15 minutes before NaB(OAc)$_3$H (100 mg, 0.470 mmol) was added in small portions over a period of 2 hours. The reaction mixture was then stirred at 40° C. overnight. More 2,2-dimethylpropanal (0.041 mL, 0.376 mmol) and NaB(OAc)$_3$H (100 mg, 0.470 mmol) were added and the reaction mixture was stirred for another 24 hours at 40° C. The reaction mixture was diluted with DCE (20 mL), washed with saturated aqueous sodium hydrogen carbonate (10 mL) and brine (10 mL), dried (Na$_2$SO$_4$), filtered and concentrated under reduced pressure. The residue was purified by preparative HPLC (method B) to afford the title compound (14 mg, 31%) as off-white solid.

Method C: LC-MS (electrospray): m/z=475.4 (M+H)$^+$, RT=3.17 min

Compound 233: N-({6-[(3S,5R)-5-methylmorpholin-3-yl]imidazo[1,2-a]pyridin-2-yl}methyl)-4-oxo-4H-pyrido[1,2-a]pyrimidine-2-carboxamide

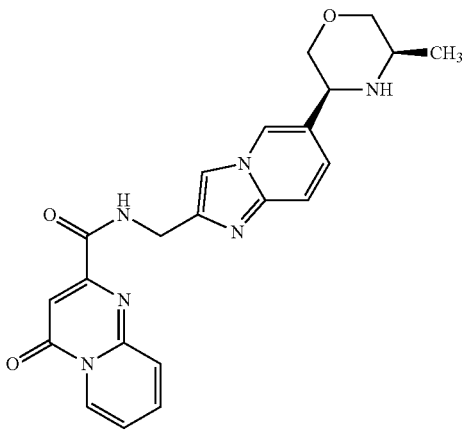 [SMILES: C[C@@H]1COC[C@H](c2ccc3nc(CNC(=O)c4cc(=O)n5ccccc5n4)cn3c2)N1]

To a solution of tert-butyl N-[[6-[rac-(3S,5R)-5-methylmorpholin-3-yl]imidazo[1,2-a]pyridin-2-yl]methyl]carbamate (Intermediate 48) (80 mg, 0.231 mmol) in methanol (1 mL) was added HCl (4M in dioxane, 1 mL, 4 mmol) at room temperature. The solution was stirred at 50° C. for 1 hour. After cooling to room temperature, the reaction mixture was concentrated to dryness under reduced pressure. To the residue was added DMF (2 mL), 4-oxopyrido[1,2-a]pyrimidine-2-carboxylic acid Intermediate 4 (60%, 73 mg, 0.231 mmol) and N-ethyl-N-isopropyl-propan-2-amine (0.20 mL, 1.15 mmol). The mixture was stirred for 15 minutes at room temperature before HATU (105 mg, 0.277 mmol) was added and stirring was continued overnight. The reaction mixture was then diluted with EtOAc (30 mL), washed with saturated aqueous sodium hydrogen carbonate (20 mL) and brine (10 mL), dried (Na$_2$SO$_4$), filtered and concentrated under reduced pressure. The residue was purified by preparative HPLC (method B) to afford the title compound (41 mg, 42%) as white solid.

Method C: LC-MS (electrospray): m/z=419.3 (M+H)$^+$, RT=1.81 min

Compound 234: N-{[6-(9-methoxy-2,3,4,5-tetra-hydro-1,4-benzoxazepin-3-yl)imidazo[1,2-a]pyridin-2-yl]methyl}-4-oxo-4H-pyrido[1,2-a]pyrimidine-2-carboxamide

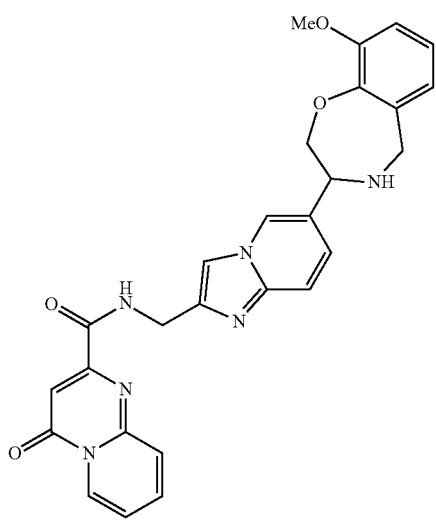 [SMILES: COc1cccc2c1OCC(c1ccc3nc(CNC(=O)c4cc(=O)n5ccccc5n4)cn3c1)NC2]

The title compound was prepared in a similar manner to Compound 233 using Intermediate 49 to afford the title compound (415 mg, 38%) as white solid.

Method C: LC-MS (electrospray): m/z=497.3 (M+H)$^+$, RT=2.27 min

Improved synthesis of Intermediate 4: 4-oxopyrido[1,2-a]pyrimidine-2-carboxylic acid

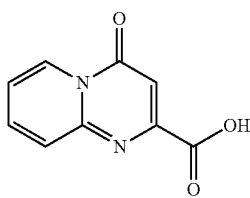 [SMILES: O=C(O)c1cc(=O)n2ccccc2n1]

Step 1: methyl 4-oxopyrido[1,2-a]pyrimidine-2-carboxylate

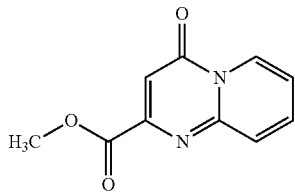

Dimethyl but-2-ynedioate (16 mL, 0.126 mol) was added slowly to a vigorously stirred solution of pyridin-2-amine (10.00 g, 0.105 mol) in water (1000 mL), and the reaction mixture was stirred at room temperature for 18 hours.

The mixture was worked up in two batches. Each half of the material was extracted with DCM (3×100 mL), passed through a TELOS phase separator and concentrated.

The material was also purified in two batches. One half of the material was dry loaded onto KP—NH silica, loaded onto a plug of KP—NH silica, and was eluted, with EtOAc in heptane, 50%, 70% and 100% and the yellow solution was concentrated to give a pale yellow solid.

The second half of the material was diluted with DCM (150 mL), treated with loose silica, stirred for 5 minutes, then filtered. The filter cake was washed with DCM (~1 L) and the filtrate was concentrated to give a pale yellow solid.

The two batches were combined, triturated with Et$_2$O and the solid was collected by filtration to give the title compound (6.57 g, 30%) as an off-white solid.

Method A: LC-MS (electrospray): m/z=205.1 (M+H)+, RT=0.79 min

Step 2: 4-oxopyrido[1,2-a]pyrimidine-2-carboxylic acid

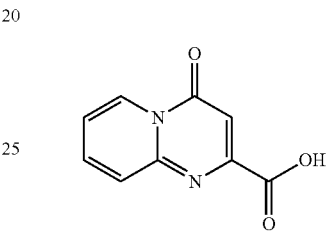

Methyl 4-oxopyrido[1,2-a]pyrimidine-2-carboxylate (6.57 g, 32.2 mmol) was dissolved in HCl (aq) (~8M, 7.5 mL) at room temperature and the solution was heated at reflux for 2 hours.

The mixture was cooled to room temperature and the precipitate was collected by filtration and dried on the filter to give the title compound (5.03 g, 81%) as a white solid.

Method A: LC-MS (electrospray): m/z=191.1 (M+H)+, RT=0.29 min

Compound 266: 4-[1-[[6-[(cyclobutylmethylamino)methyl]imidazo[1,2-a]pyridin-2-yl]methyl]triazol-4-yl]-1H-indazol-6-ol

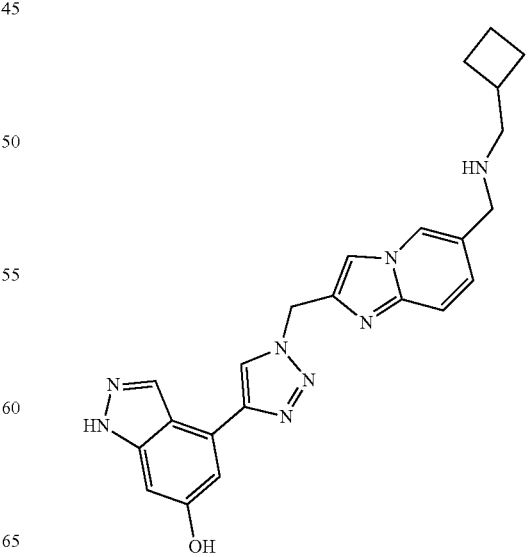

Step 1: {[2-({4-[6-bromo-1-(oxan-2-yl)-1H-indazol-4-yl]-1H-1,2,3-triazol-1-yl}methyl)imidazo[1,2-a]pyridin-6-yl]methyl}(cyclobutylmethyl)amine

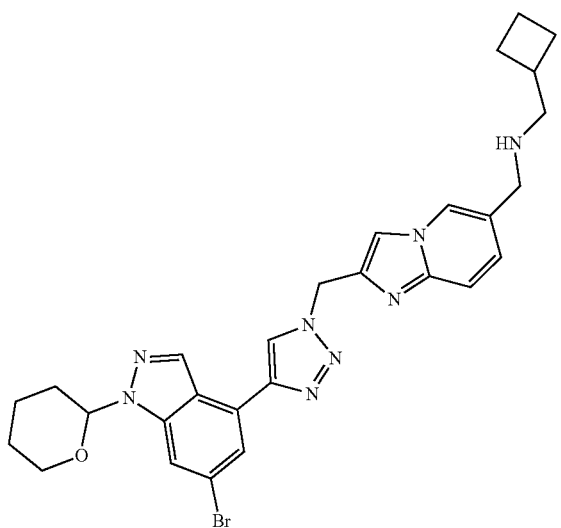 [SMILES: Brc1cc(-c2cn(Cc3cn4cc(CNCC5CCC5)ccc4n3)nn2)c2cnn(C3CCCCO3)c2c1]

The title compound was prepared from Intermediate 35 using the method described in Compound 250 to afford (487 mg, 48%) as a pale yellow solid.

Method B: LC-MS (electrospray): m/z=508.3/510.3 (M+H)+, RT=1.49 min

Step 2: 4-[1-[[6-[(cyclobutylmethylamino)methyl]imidazo[1,2-a]pyridin-2-yl]methyl]triazol-4-yl]-1H-indazol-6-ol

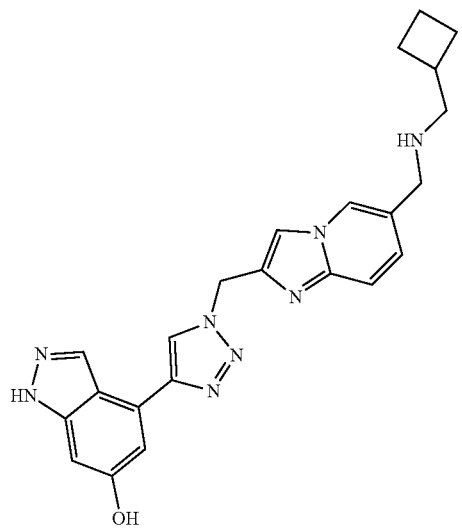 [SMILES: Oc1cc(-c2cn(Cc3cn4cc(CNCC5CCC5)ccc4n3)nn2)c2cn[nH]c2c1]

A microwave vial was charged with {[2-({4-[6-bromo-1-(oxan-2-yl)-1H-indazol-4-yl]-1H-1,2,3-triazol-1-yl}methyl)imidazo[1,2-a]pyridin-6-yl]methyl}(cyclobutylmethyl)amine (85 mg, 0.148 mmol), copper (1+) iodide (2.8 mg, 0.0148 mmol) and quinolin-8-ol 1-oxide (10 mg, 0.0591 mmol) in DMSO (1.3 mL) and water (1.3 mL), the mixture was degassed via a stream of N₂ before a solution of caesium hydroxide (66 mg, 0.443 mmol) in water was added, the mixture was further de-oxygenated before the vial was sealed and irradiated in a microwave at 110° C. for 4.5 h.

The mixture was purified by ion exchange (SCX-2 10 g) washed with MeOH and eluted with ammonia solution (3M in MeOH). The eluted fraction was evaporated under vacuum.

1. The residue was diluted with MeOH (0.5 mL) and 4M HCl in dioxane (1.7 mL), and was stirred at RT for 1 h and at 40° C. for 18 hours.
2. The solvent was removed under vacuum and purified by Basic reverse phase chromatography and the relevant fractions were freeze dried to give the title compound (12 mg, 19%) as a white solid.

Method D: LC-MS (electrospray): m/z=429.3 (M+H)+, RT=3.02 min

Compound 267: 4-[1-[[6-[[(1-hydroxycyclobutyl)methylamino]methyl]imidazo[1,2-a]pyridin-2-yl]methyl]triazol-4-yl]-1H-indazol-6-ol

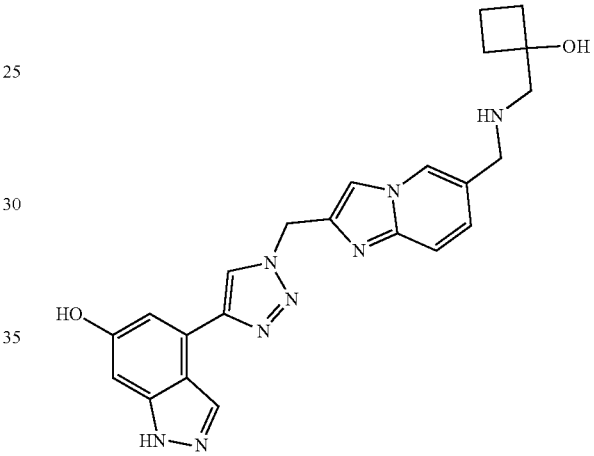

Step 1: 1-[({[2-({4-[6-bromo-1-(oxan-2-yl)-1H-indazol-4-yl]-1H-1,2,3-triazol-1-yl}methyl)imidazo[1,2-a]pyridin-6-yl]methyl}amino)methyl]cyclobutan-1-ol

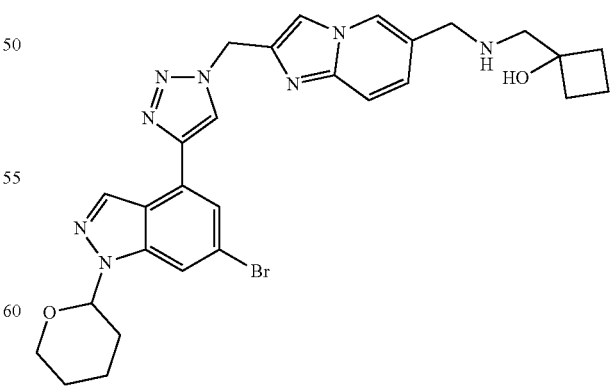

The title compound was prepared from Intermediate 35 using the method described in Compound 250 to afford (357 mg, 66%) as a brown solid.

Method B: LC-MS (electrospray): m/z=591.3/593.3 (M+H)+, RT=1.57 min

Step 2: 4-[1-[[6-[[(1-hydroxycyclobutyl)methyl-amino]methyl]imidazo[1,2-a]pyridin-2-yl]methyl]triazol-4-yl]-1H-indazol-6-ol

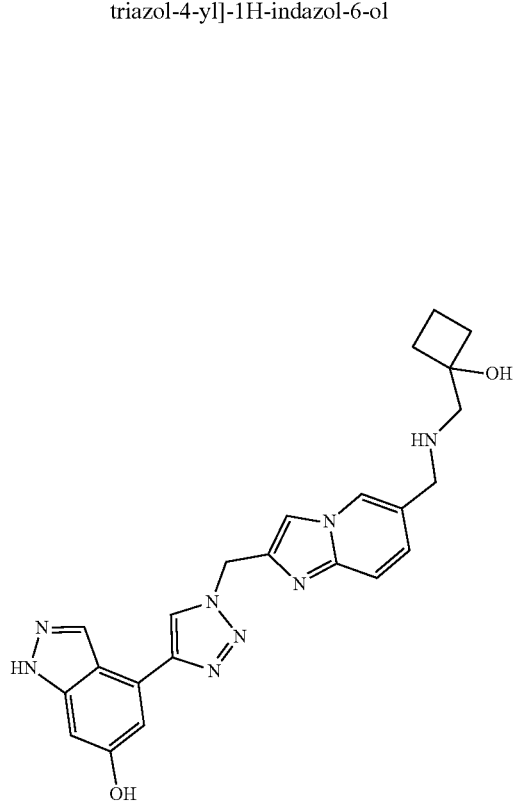

1-[[[2-[[4-(6-bromo-1-tetrahydropyran-2-yl-indazol-4-yl)triazol-1-yl]methyl]imidazo[1,2-a]pyridin-6-yl]methyl-amino]methyl]cyclobutanol (150 mg, 0.25 mmol), tBuBrett-Phos Pd G3 (22 mg, 0.03 mmol) and NaOtBu (29 mg, 0.30 mmol) were combined in 1,4-Dioxane-Anhydrous (10 ml) and the mixture was sparged with nitrogen for 5 mins. Propan-2-ol (0.4 ml, 5.26 mmol) was added, the mixture further sparged briefly and the vessel sealed and the mixture was heated at 100° C. for 2 hours.

The reaction mixture was cooled to RT and evaporated under vacuum. The residue was redissolved in MeOH (3 ml) and treated with HCl in Dioxane (4M, 3 ml) and incubated at room temperature for 18 hours.

The reaction mixture was evaporated under vacuum and the residue purified by basic reverse phase chromatography. The product-containing fractions combined and evaporated under vacuum to afford crude material.

The residue was further purified by preparative HPLC [method B] to afford the title compound (7 mg, 6%) as an off-white solid.

Method C: LC-MS (electrospray): m/z=445.4 (M+H)+, RT=1.53 min

Compound 268: 1-[[[2-[[4-(5-methoxy-1H-indazol-4-yl)triazol-1-yl]methyl]imidazo[1,2-a]pyridin-6-yl]methylamino]methyl]cyclobutanol

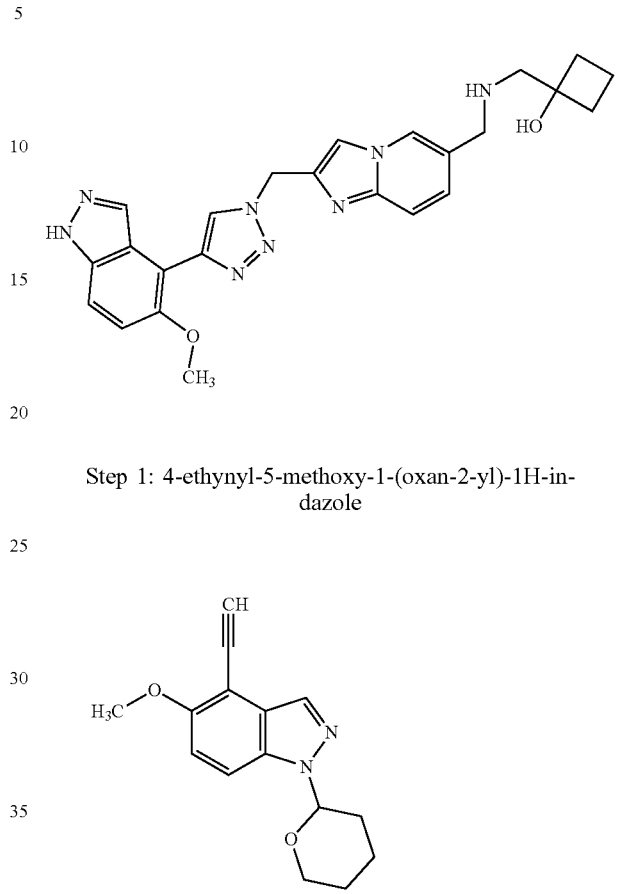

Step 1: 4-ethynyl-5-methoxy-1-(oxan-2-yl)-1H-indazole

Prepared in a similar manner to Intermediate 24 from commercial 4-bromo-5-methoxy-1H-indazole to give the title compound (296 mg, 34%) as a brown oil.

Method B: LC-MS (electrospray): m/z=257.3 (M+H)+, RT=1.62 min

Step 2: [2-({4-[5-methoxy-1-(oxan-2-yl)-1H-indazol-4-yl]-1H-1,2,3-triazol-1-yl}methyl)imidazo[1,2-a]pyridin-6-yl]methanol

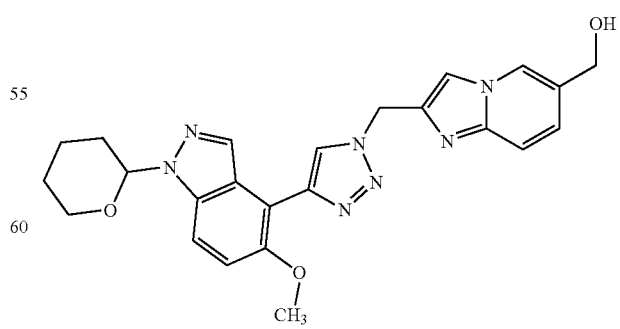

Prepared using 4-ethynyl-5-methoxy-1-(oxan-2-yl)-1H-indazole and Intermediate 34 Step 3 using the method described in Intermediate 34 Step 4 to give the title compound (264 mg, 45%) as an off white solid.

Method F: LC-MS (electrospray): m/z=460.4 (M+H)+, RT=0.48 min

Step 3: 2-({4-[5-methoxy-1-(oxan-2-yl)-1H-indazol-4-yl]-1H-1,2,3-triazol-1-yl}methyl)imidazo[1,2-a]pyridine-6-carbaldehyde

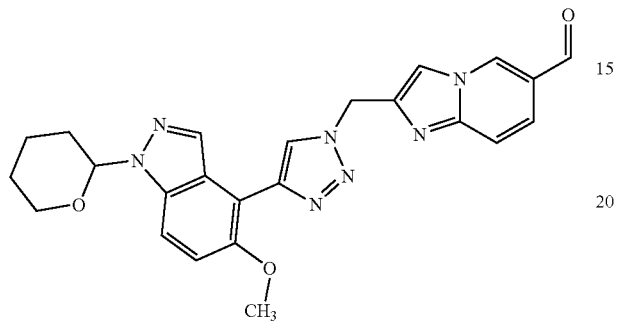

[2-[[4-(5-methoxy-1-tetrahydropyran-2-yl-indazol-4-yl)triazol-1-yl]methyl]imidazo[1,2-a]pyridin-6-yl]methanol (264 mg, 0.57 mmol) and MnO2 (499 mg, 5.75 mmol) were combined in DCE (10 ml) and the mixture heated at reflux for an hour.

The reaction mixture was cooled to RT and filtered through Celite. The residue was rinsed with MeOH and 3:1 chloroform/isopropanol and the combined filtrates were evaporated under vacuum to afford 265 mg (80% yield, 79% purity) of the title compound as a grey solid.

Method F: LC-MS (electrospray): m/z=458.4 (M+H)+, RT=0.52 min

Step 4: 1-[[[2-[[4-(5-methoxy-1H-indazol-4-yl)triazol-1-yl]methyl]imidazo[1,2-a]pyridin-6-yl]methylamino]methyl]cyclobutanol

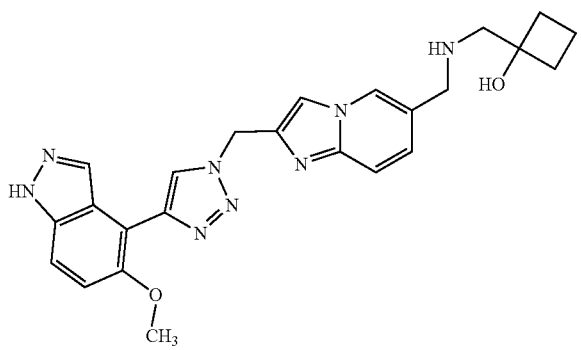 [SMILES: COc1ccc2[nH]ncc2c1-c1cn(Cc2cn3cc(CNCC4(O)CCC4)ccc3n2)nn1]

The title compound was prepared in a similar fashion to Compound 252 and purified by phase chromatography (method B) to give (23 mg, 30%) as a white solid.

Method D: LC-MS (electrospray): m/z=459.3 (M+H)+, RT=2.97 min

Compound 269: 1-[[[2-[[4-(6-methoxy-1H-indazol-4-yl)triazol-1-yl]methyl]imidazo[1,2-a]pyridin-6-yl]methylamino]methyl]cyclobutanol

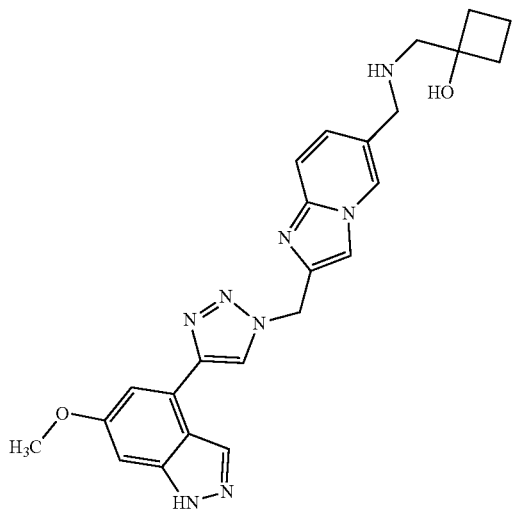 [SMILES: COc1cc(-c2cn(Cc3cn4cc(CNCC5(O)CCC5)ccc4n3)nn2)c2cn[nH]c2c1]

1-[[[2-[[4-(6-bromo-1-tetrahydropyran-2-yl-indazol-4-yl)triazol-1-yl]methyl]imidazo[1,2-a]pyridin-6-yl]methylamino]methyl]cyclobutanol (Compound 267 Step 1) (400 mg, 0.68 mmol), tBuBrettPhos Pd G3 (58 mg, 0.07 mmol) and NaOtBu (78 mg, 0.81 mmol) were combined in 1,4-Dioxane (15 ml) and the mixture sparged with nitrogen for 5 mins. Anhydrous methanol-(0.3 ml, 7.41 mmol) was added and the mixture further sparged briefly and the mixture was heated at 100° C. for 2 hours.

The reaction mixture was cooled to room temperature and left standing overnight.

The reaction mixture was concentrated under vacuum. The residue was redissolved in methanol (10 ml), treated with HCl in Dioxane (4M, 10 ml) and heated at 50° C. for an hour.

The reaction mixture was cooled to RT and evaporated under vacuum. The residue was purified by ion exchange (SCX-2 (10 g) washing with DCM and MeOH. The system was eluted with ammonia (7N in MeOH) and the basic eluent evaporated under vacuum.

The residue was purified by basic reverse phase chromatography and the product-containing fractions combined and evaporated under vacuum. The residue was triturated with MeOH/Et2O and the solids collected by filtration to afford the title compound (87 mg, 28%) as an off-white solid Method C: LC-MS (electrospray): m/z=459.4 (M+H)+, RT=2.10 min The filtrates were evaporated under vacuum to afford a second crop of desired product (72 mg) as pale yellow solid which was further purified by preparative HPLC (method B) to afford further title compound (50 mg, 16%) as an off-white solid.

Compound 270: N-(cyclobutylmethyl)-1-[2-[[4-(6-methoxy-1H-indazol-4-yl)triazol-1-yl]methyl]imidazo[1,2-a]pyridin-6-yl]methanamine

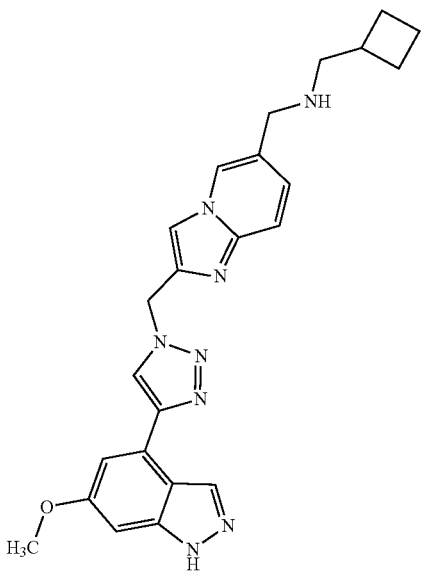 [SMILES: COc1cc(-c2cn(Cc3cn4cc(CNCC5CCC5)ccc4n3)nn2)c2cn[nH]c2c1]

The title compound was prepared in a similar manner to Compound 269 from {[2-({4-[6-bromo-1-(oxan-2-yl)-1H-indazol-4-yl]-1H-1,2,3-triazol-1-yl}methyl)imidazo[1,2-a]pyridin-6-yl]methyl}(cyclobutylmethyl)amine (Compound 266 step 1) to give (7 mg, 30%) as a white solid.

Method D: LC-MS (electrospray): m/z=443.3 (M+H)+, RT=3.55 min

Compound 271: N-(cyclobutylmethyl)-1-[2-[[4-(5-methoxy-1H-indazol-4-yl)triazol-1-yl]methyl]imidazo[1,2-a]pyridin-6-yl]methanamine

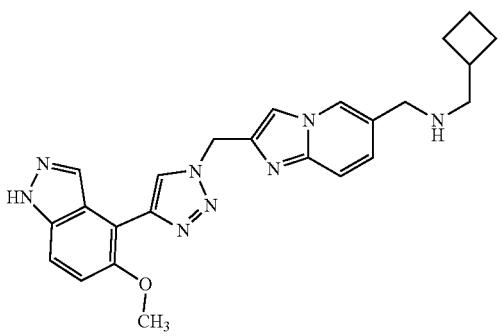 [SMILES: COc1ccc2[nH]ncc2c1-c1cn(Cc2cn3cc(CNCC4CCC4)ccc3n2)nn1]

The title compound was prepared using the intermediate from Compound 268 Step 3 in a similar manner to Compound 252 and purified by basic reverse phase chromatography to give (88 mg, 68%) as a pale yellow solid.

Method D: LC-MS (electrospray): m/z=443.3 (M+H)+, RT=3.55 min

Compound 272: 4-[1-[(6-methylimidazo[1,2-a]pyridin-2-yl)methyl]triazol-4-yl]-1H-indazol-3-amine

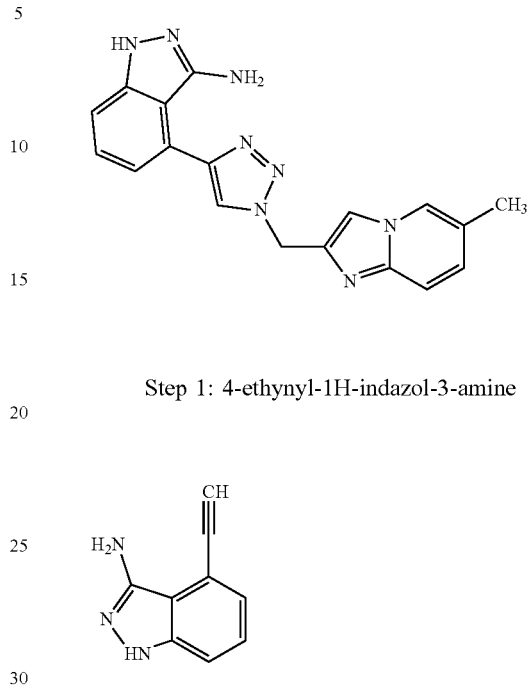

Step 1: 4-ethynyl-1H-indazol-3-amine

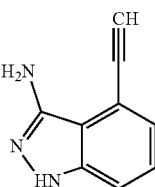

The title compound was prepared in a similar fashion Intermediate 24 starting from 4-iodo-1H-indazol-3-amine to give (92 mg, 31%) as a pale brown solid.

Method B: LC-MS (electrospray): m/z=158.2 (M+H)+, RT=1.23 min

Step 2: 4-[1-[(6-methylimidazo[1,2-a]pyridin-2-yl)methyl]triazol-4-yl]-1H-indazol-3-amine

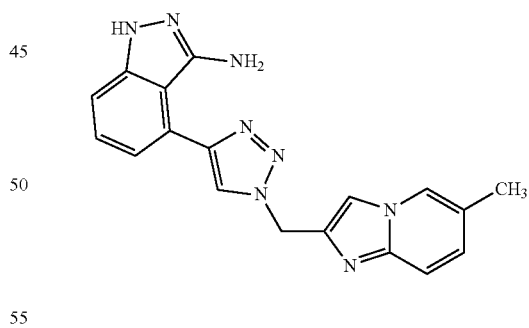

Prepared using the method described in Intermediate 34 Step 4 using 4-ethynyl-1H-indazol-3-amine and Intermediate 23 to give the title compound (38 mg, 41%) as an off white solid.

Method E: LC-MS (electrospray): m/z=345.2 (M+H)+, RT=1.10 min

The intermediates in Table 14 were prepared from commercial reagents and Intermediate Step 2 in the same manner as Intermediate 48.

TABLE 14

| Intermediate | Name | Structure | LCMS method | LCMS Retention time | Mass ion |
|---|---|---|---|---|---|
| 50 | tert-butyl N-[[6-(1,4-oxazepan-3-yl)imidazo[1,2-a]pyridin-2-yl]methyl]carbamate | 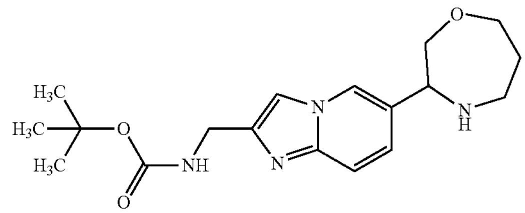 [SMILES: CC(C)(C)OC(=O)NCc1cn2cc(C3COCCCN3)ccc2n1] | C | 2.18 | 347.3 |
| 62 | tert-butyl N-[[6-[rac-(3S,6S)-6-methylmorpholin-3-yl]imidazo[1,2-a]pyridin-2-yl]methyl]carbamate | 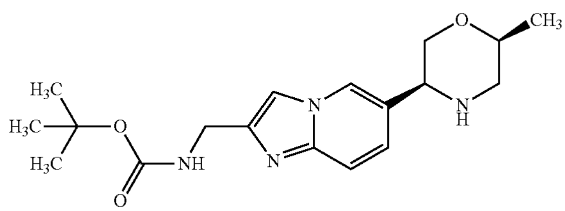 [SMILES: C[C@H]1CN[C@@H](c2ccc3nc(CNC(=O)OC(C)(C)C)cn3c2)CO1] | C | 2.23 | 347.3 |
| 63 | tert-butyl N-[[6-(7-bromo-9-methoxy-2,3,4,5-tetrahydro-1,4-benzoxazepin-3-yl)imidazo[1,2-a]pyridin-2-yl]methyl]carbamate | 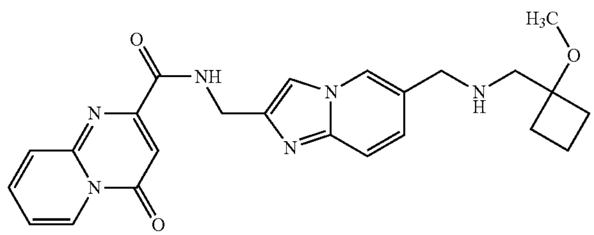 [SMILES: COC1(CNCc2ccc3nc(CNC(=O)c4cc(=O)n5ccccc5n4)cn3c2)CCC1] | C | 3.26 | 503.2/ 505.2 |

The Examples in Table 15 were prepared from Intermediate 4 and the appropriate intermediate from Table 15 in the same manner as Compound 233

TABLE 15

| Example | Name | Structure | LCMS method | LCMS Retention time | Mass ion |
|---|---|---|---|---|---|
| 274 | : N-[[6-(1,4-oxazepan-3-yl)imidazo[1,2-a]pyridin-2-yl]methyl]-4-oxo-pyrido[1,2-a]pyrimidine-2-carboxamide | 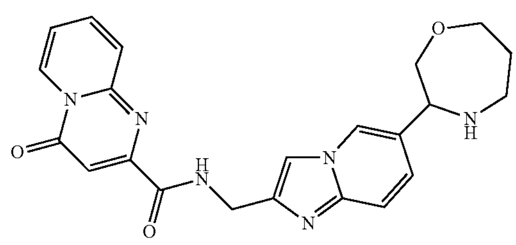 [SMILES: O=C(NCc1cn2cc(C3COCCCN3)ccc2n1)c1cc(=O)n2ccccc2n1] | C | 1.73 | 429.2 |
| 331 | N-[[6-(6-methylmorpholin-3-yl)imidazo[1,2-a]pyridin-2-yl]methyl]-4-oxo-pyrido[1,2-a]pyrimidine-2-carboxamide | 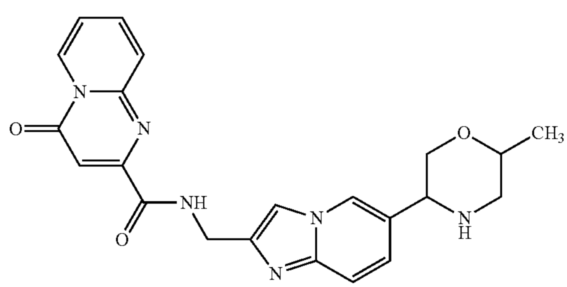 [SMILES: CC1CNC(c2ccc3nc(CNC(=O)c4cc(=O)n5ccccc5n4)cn3c2)CO1] | C | 1.77 | 419.3 |

TABLE 15-continued

| Example | Name | Structure | LCMS method | LCMS Retention time | Mass ion |
|---|---|---|---|---|---|
| 332 | N-[[6-(7-bromo-9-methoxy-2,3,4,5-tetrahydro-1,4-benzoxazepin-3-yl)imidazo[1,2-a]pyridin-2-yl]methyl]-4-oxo-pyrido[1,2-a]pyrimidine-2-carboxamide | 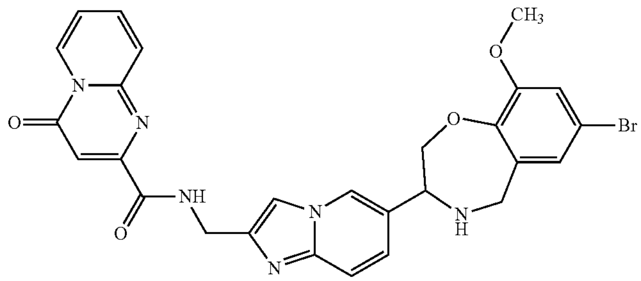 [SMILES: COc1cc(Br)cc2c1OCC(c1ccc3nc(CNC(=O)c4cc(=O)n5ccccc5n4)cn3c1)NC2] | C | 2.78 | 575.2/ 577.1 |

The compounds in Table 16 were prepared from Intermediate 35 in a similar manner to Compound 252.

TABLE 16

| Example No | Name | Structure | LCMS method | LCMS Retention time | Mass ion |
|---|---|---|---|---|---|
| 294 | 1-[[[2-[[4-(6-bromo-1H-indazol-4-yl)triazol-1-yl]methyl]imidazo[1,2-a]pyridin-6-yl]methylamino]methyl]cyclohexanol | 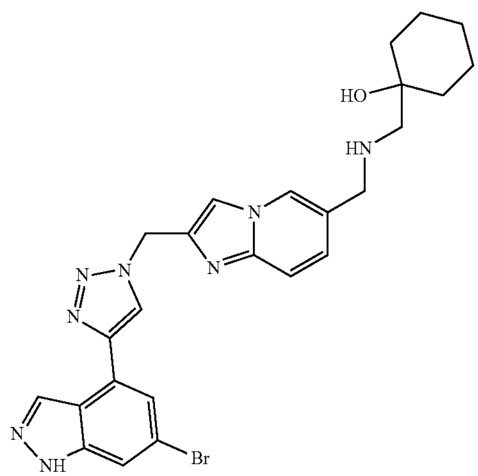 [SMILES: OC1(CNCc2ccc3nc(Cn4cc(-c5cc(Br)cc6[nH]ncc56)nn4)cn3c2)CCCCC1] | C | 2.83 | 535.2/ 537.2 |
| 295 | 1-[[[2-[[4-(6-bromo-1H-indazol-4-yl)triazol-1-yl]methyl]imidazo[1,2-a]pyridin-6-yl]methylamino]methyl]cyclobutanol | 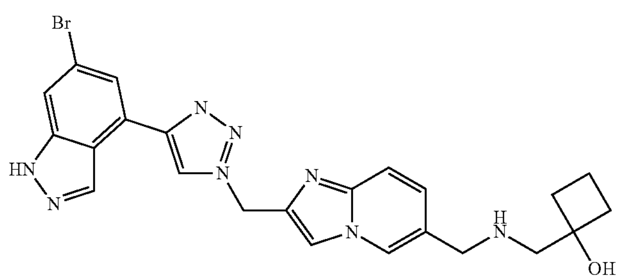 | C | 2.42 | 507.3/ 509.3 |

TABLE 16-continued

| Example No | Name | Structure | LCMS method | LCMS Retention time | Mass ion |
|---|---|---|---|---|---|
| 296 | 1-[2-[[4-(6-bromo-1H-indazol-4-yl)triazol-1-yl]methyl]imidazo[1,2-a]pyridin-6-yl]-N-(cyclobutylmethyl)methanamine | 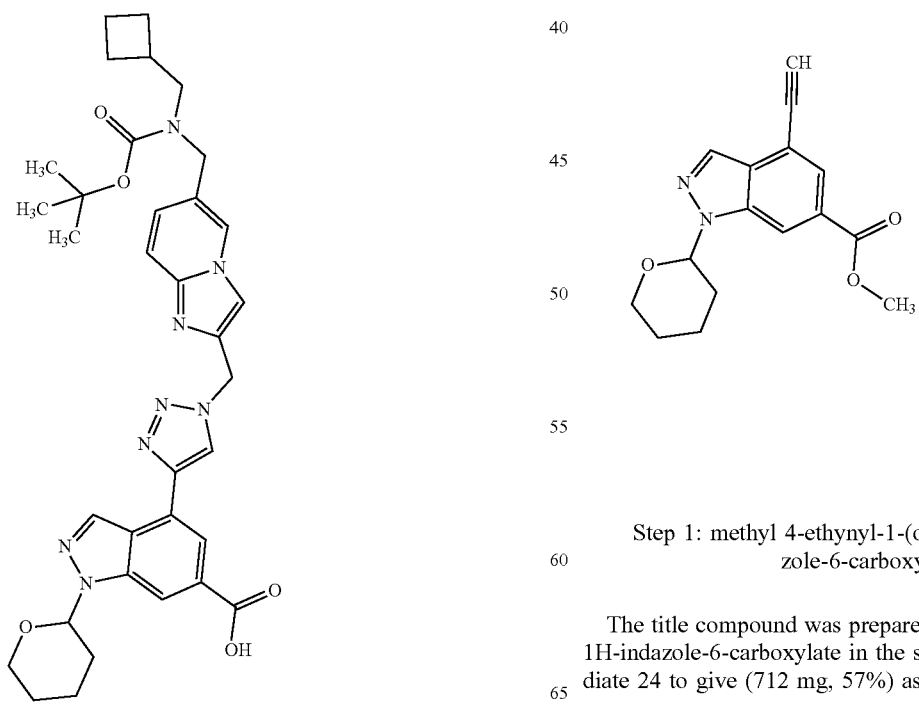 | D | 3.82 | 491.2/ 493.2 |

Intermediate 51: 4-[1-[[6-[[tert-butoxycarbonyl(cyclobutylmethyl)amino]methyl]imidazo[1,2-a]pyridin-2-yl]methyl]triazol-4-yl]-1-tetrahydropyran-2-yl-indazole-6-carboxylic acid Step 1:

Step 1: methyl 4-ethynyl-1-(oxan-2-yl)-1H-indazole-6-carboxylate

The title compound was prepared from methyl 4-bromo-1H-indazole-6-carboxylate in the same manner as intermediate 24 to give (712 mg, 57%) as a brown solid.

Method A: LC-MS (electrospray): m/z=285.05 (M+H)+, RT=1.27 min

Step 2: methyl 4-[1-({6-formylimidazo[1,2-a]pyridin-2-yl}methyl)-1H-1,2,3-triazol-4-yl]-1-(oxan-2-yl)-1H-indazole-6-carboxylate

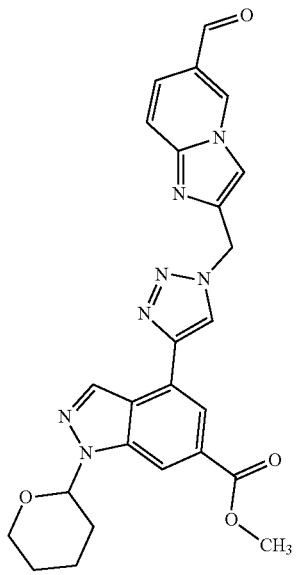 [SMILES: COC(=O)c1cc(-c2cn(Cc3cn4cc(C=O)ccc4n3)nn2)c2cnn(C3CCCCO3)c2c1]

Prepared from intermediate 51 step 1 using the procedure described in Intermediate 34 to provide the title compound (867 mg, 62%) as a pale brown solid.

Method B: LC-MS (electrospray): m/z=486.3 (M+H)+, RT=1.50 min

Step 3: methyl 4-[1-[[6-[[tert-butoxycarbonyl(cyclobutylmethyl)amino]methyl]imidazo[1,2-a]pyridin-2-yl]methyl]triazol-4-yl]-1-tetrahydropyran-2-yl-indazole-6-carboxylate

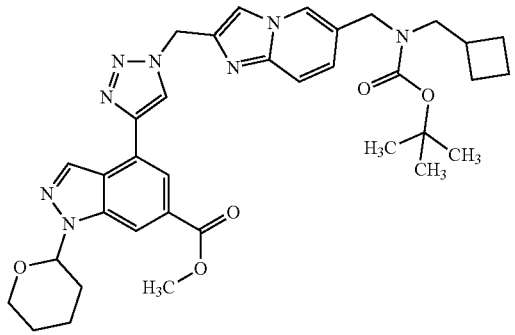 [SMILES: COC(=O)c1cc(-c2cn(Cc3cn4cc(CN(CC5CCC5)C(=O)OC(C)(C)C)ccc4n3)nn2)c2cnn(C3CCCCO3)c2c1]

Methyl 4-[1-[(6-formylimidazo[1,2-a]pyridin-2-yl)methyl]triazol-4-yl]-1-tetrahydropyran-2-yl-indazole-6-carboxylate (860 mg, 1.77 mmol) and 1-cyclobutylmethanamine (302 mg, 3.54 mmol) were combined in 1,1,1,3,3,3-Hexafluoro-2-propanol (8 ml) and the mixture stirred at room temperature for 30 minutes before further 1-cyclobutylmethanamine (302 mg, 3.54 mmol) added and the stir was continued for 1.5 hours.

Sodium borohydride (536 mg, 1.42 mmol) was added along with a few drops MeOH—gas evolution—and the mixture stirred briefly at room temperature.

The reaction mixture evaporated under vacuum and the residue was suspended in NaHCO₃ (sat, 50 ml) and extracted with chloroform/isopropanol (3:1, 3×80 ml). The combined organic extracts were dried over sodium sulfate and evaporated under vacuum.

The residue was dissolved in MeOH (20 ml) and treated with Boc2O (773 mg, 3.54 mmol) and the mixture stirred at room temperature for 30 minutes before further Boc2O (773 mg, 3.54 mmol) added and the mixture stirred for 16 hours.

Further Boc2O (773 mg, 3.54 mmol) added and the stir was continued for 2 hours.

The reaction mixture was evaporated under vacuum and the residue was dissolved in EtOAc (80 ml), washed with NaHCO₃ (sat, 2×50 ml) and brine (50 ml), and the organic layer dried over sodium sulfate and evaporated under vacuum.

The residue was purified by flushing through a short pad of silica, eluting with 0-100% EtOAc/heptane [DP elutes at ~80%] to afford the title compound (360 mg, 26%) as a pale brown solid.

Method B: LC-MS (electrospray): m/z=655.5 (M+H)+, RT=2.02 min

Step 4: 4-[1-[[6-[[tert-butoxycarbonyl(cyclobutylmethyl)amino]methyl]imidazo[1,2-a]pyridin-2-yl]methyl]triazol-4-yl]-1-tetrahydropyran-2-yl-indazole-6-carboxylic acid

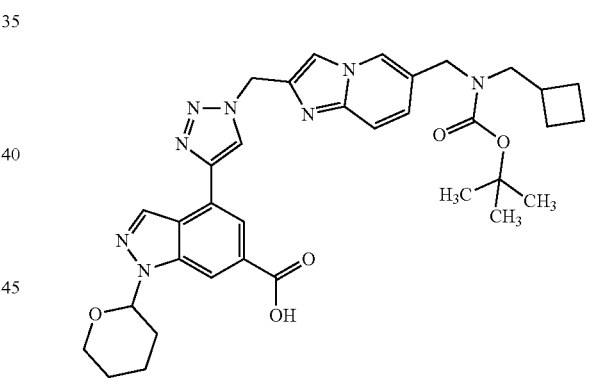

Methyl 4-[1-[[6-[[tert-butoxycarbonyl(cyclobutylmethyl)amino]methyl]imidazo[1,2-a]pyridin-2-yl]methyl]triazol-4-yl]-1-tetrahydropyran-2-yl-indazole-6-carboxylate (360 mg, 0.55 mmol) and lithium hydroxide (120 mg, 5.01 mmol) were combined in THF (10 ml) and Water (5 ml) and the mixture stirred was at room temperature for 18 hours.

The reaction mixture was concentrated under vacuum, diluted with water (15 ml) and acidified with HCl (1M). The mixture was extracted with chloroform/isopropanol (3:13× 40 ml) and the combined organic extracts dried over sodium sulfate and evaporated under vacuum to afford the title compound (279 mg, 72%) as a pale brown solid.

Method B: LC-MS (electrospray): m/z=641.6 (M+H)+, RT=1.27 min

Compound 297: 4-[1-[[6-[(cyclobutylmethylamino)methyl]imidazo[1,2-a]pyridin-2-yl]methyl]triazol-4-yl]-1H-indazole-6-carboxylic acid

Compound 298: 4-[1-[[6-[(cyclobutylmethylamino)methyl]imidazo[1,2-a]pyridin-2-yl]methyl]triazol-4-yl]-1H-indazole-6-carboxamide

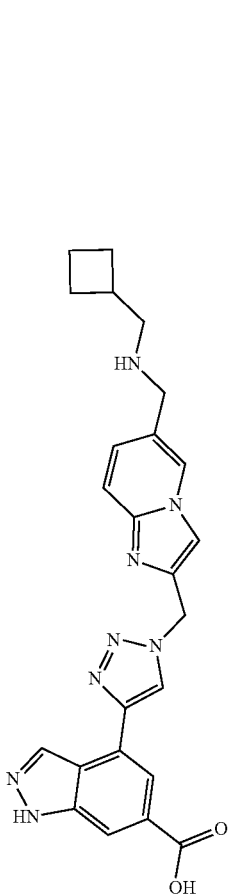 [SMILES: O=C(O)c1cc(-c2cn(Cc3cn4cc(CNCC5CCC5)ccc4n3)nn2)c2cn[nH]c2c1]

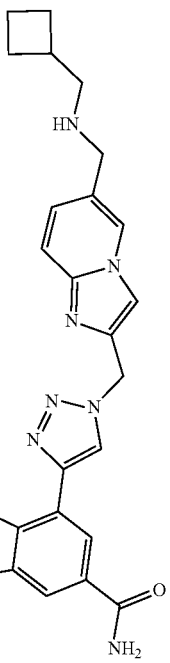

4-[1-[[6-[[tert-butoxycarbonyl(cyclobutylmethyl)amino]methyl]imidazo[1,2-a]pyridin-2-yl]methyl]triazol-4-yl]-1-tetrahydropyran-2-yl-indazole-6-carboxylic acid Intermediate 51 (50 mg, 0.08 mmol) was suspended in methanol (1 ml) and HCl (4M in dioxane, 1 ml, 4 mmol) was added and the mixture was incubated at room temperature for two hours.

The reaction mixture was concentrated under vacuum and the residue was purified by basic preparative HPLC (method B) to afford the title compound (18 mg, 51%) as a pale yellow solid.

Method D: LC-MS (electrospray): m/z=457.3 (M+H)+, RT=2.26 min

4-[1-[[6-[[tert-butoxycarbonyl(cyclobutylmethyl)amino]methyl]imidazo[1,2-a]pyridin-2-yl]methyl]triazol-4-yl]-1-tetrahydropyran-2-yl-indazole-6-carboxylic acid Intermediate 51 (70 mg, 0.099 mmol) and triethylamine (42 µl, 0.298 mmol) were combined in THF-Anhydrous (5 ml) and isobutyl chloroformate (19 µl, 0.149 mmol) was added. The resultant solution was stirred at RT for 5 mins, then ammonia (28% aqueous, 0.2 ml, 1.4 mmol) was added, and the mixture further stirred at room temperature for 15 mins.

The reaction mixture was quenched with NaHCO$_3$ (sat, 30 ml) and extracted with chloroform/isopropanol (3:1, 3×30 ml). The combined organic extracts were dried over sodium sulfate and evaporated under vacuum.

The residue was suspended in methanol (2 ml) and treated with HCl (4M in Dioxane, 2 ml). The mixture was incubated at room temperature for two hours.

The reaction mixture was evaporated under vacuum. The residue was purified by preparative HPLC (method B) to afford the title compound (19 mg, 42%) as a pale brown solid.

Method D: LC-MS (electrospray): m/z=456.3 (M+H)+, RT=3.09 min

The Examples in Table 17 were prepared in a similar manner Compound 298 using the appropriate amine.

TABLE 17

| Example No | Name | Structure | LCMS method | Retention time | Mass ion |
|---|---|---|---|---|---|
| 299 | 4-[1-[[6-[(cyclobutylmethylamino)methyl]imidazo[1,2-a]pyridin-2-yl]methyl]triazol-4-yl]-N,N-dimethyl-1H-indazole-6-carboxamide | 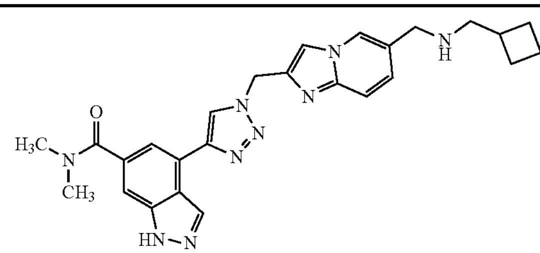 | C | 2.42 | 484.4 |
| 300 | [4-[1-[[6-[(cyclobutylmethylamino)methyl]imidazo[1,2-a]pyridin-2-yl]methyl]triazol-4-yl]-1H-indazol-6-yl]-morpholino-methanone | 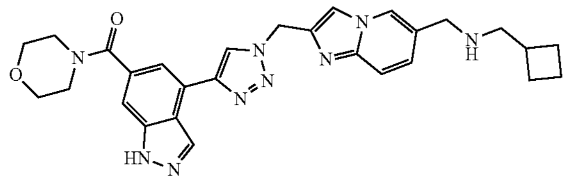 [SMILES: O=C(c1cc(-c2cn(Cc3cn4cc(CNCC5CCC5)ccc4n3)nn2)c2cn[nH]c2c1)N1CCOCC1] | C | 2.41 | 526.5 |
| 301 | 4-[1-[6-[(cyclobutylmethylamino)methyl]imidazo[1,2-a]pyridin-2-yl]methyl]triazol-4-yl]-N-(2-hydroxyethyl)-1H-indazole-6-carboxamide | 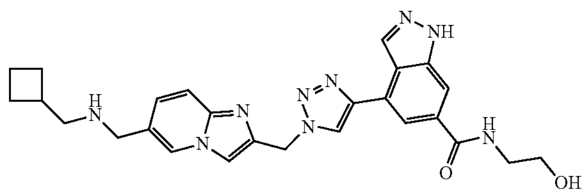 [SMILES: O=C(NCCO)c1cc(-c2cn(Cc3cn4cc(CNCC5CCC5)ccc4n3)nn2)c2cn[nH]c2c1] | C | 2.24 | 500.6 |

Intermediate 52: 2-[[4-(6-chloro-1-tetrahydropyran-2-yl-indazol-4-yl)triazol-1-yl]methyl]imidazo[1,2-a]pyridine-6-carbaldehyde

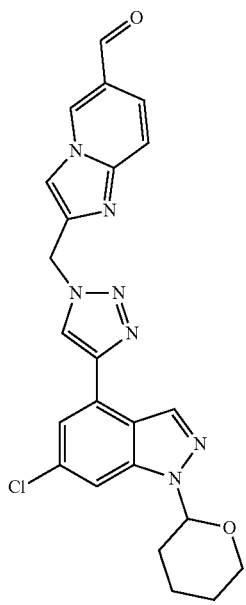 [SMILES: O=Cc1ccc2nc(Cn3cc(-c4cc(Cl)cc5c4cnn5C4CCCCO4)nn3)cn2c1]

The title compound was prepared from 6-chloro-4-iodo-1H-indazole in a similar fashion to Intermediate 34 giving (370 mg, 36%) as a beige solid.

Method B: LC-MS (electrospray): m/z=462.3 (M+H)+, RT=1.58 min

Example 302: 1-[2-[[4-(6-chloro-1H-indazol-4-yl)triazol-1-yl]methyl]imidazo[1,2-a]pyridin-6-yl]-N-(cyclobutylmethyl)methanamine

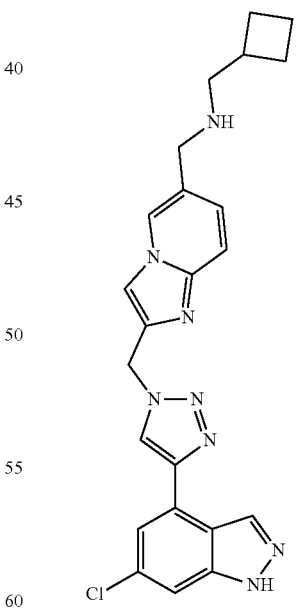

The title compound was prepared from intermediate 52 using the procedure described for Compound 250 to give (41 mg, 34%) as an off-white solid.

Method D: LC-MS (electrospray): m/z=447.3 (M+H)+, RT=3.86 min

The compounds in Table 18 were prepared from Intermediate 52 using the procedure described for Example 302.

TABLE 18

| Example No | Name | Structure | LCMS method | LCMS Retention time | Mass ion |
|---|---|---|---|---|---|
| 303 | 1-[[[2-[[4-(6-chloro-1H-indazol-4-yl)triazol-1-yl]methyl]imidazo[1,2-a]pyridin-6-yl]methylamino]methyl]cyclobutanol | 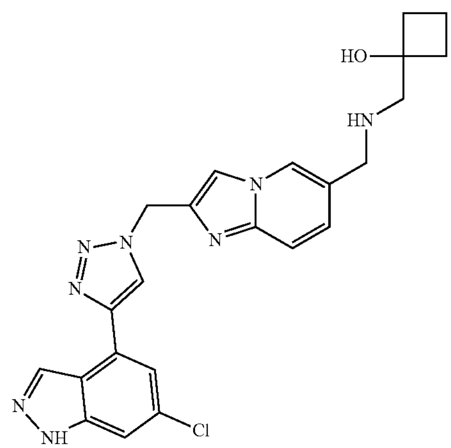 | C | 2.40 | 463.3 |
| 304 | N-[[2-[[4-(6-chloro-1H-indazol-4-yl)triazol-1-yl]methyl]imidazo[1,2-a]pyridin-6-yl]methyl]-2,2-dimethyl-propan-1-amine | 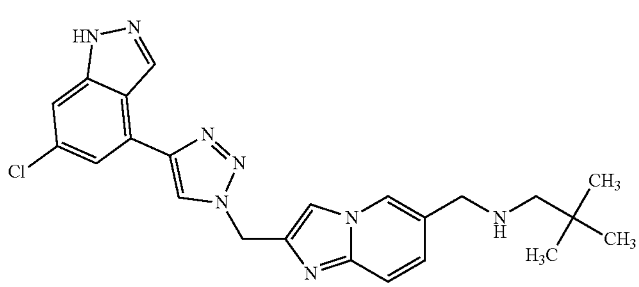 [SMILES: CC(C)(C)CNCc1ccc2nc(Cn3cc(-c4cc(Cl)cc5[nH]ncc45)nn3)cn2c1] | C | 3.24 | 449.4 |

Intermediate 53: 2-({4-[6-chloro-1-(oxan-2-yl)-1H-indazol-4-yl]-1H-1,2,3-triazol-1-yl}methyl)imidazo[1,2-a]pyridine-6-carbaldehyde

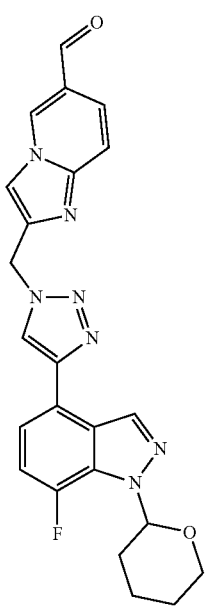

The title compound was prepared from 4-bromo-7-fluoro-1H-indazole in a similar fashion to Intermediate 34 giving (739 mg, 95%) as a pale brown solid.

Method B: LC-MS (electrospray): m/z=446.2 (M+H)+, RT=1.50 min

Example 305: N-(cyclobutylmethyl)-1-[2-[[4-(7-fluoro-1H-indazol-4-yl)triazol-1-yl]methyl]imidazo[1,2-a]pyridin-6-yl]methanamine The title compound was prepared from intermediate 53 using the procedure described for Compound 250 to give (15 mg, 23%) as a white solid.

Method D: LC-MS (electrospray): m/z=431.3 (M+H)+, RT=3.55 min

The compounds in Table 19 were prepared from Intermediate 53 using the procedure described for Example 305.

TABLE 19

| Example No | Name | Structure | LCMS method | LCMS Retention time | Mass ion |
|---|---|---|---|---|---|
| 306 | 1-[[[2-[[4-(7-fluoro-1H-indazol-4-yl)triazol-1-yl]methyl]imidazo[1,2-a]pyridin-6-yl]methylamino]methyl]cyclohexanol | 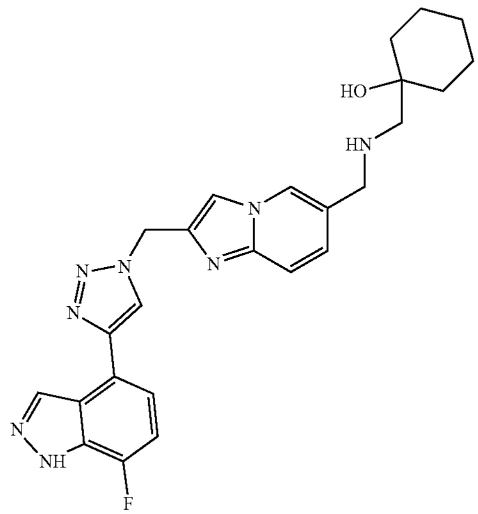 [SMILES: OC1(CNCc2ccc3nc(Cn4cc(-c5ccc(F)c6[nH]ncc56)nn4)cn3c2)CCCCC1] | D | 3.32 | 475.3 |
| 307 | N-(cyclohexylmethyl)-1-[2-[[4-(7-fluoro-1H-indazol-4-yl)triazol-1-yl]methyl]imidazo[1,2-a]pyridin-6-yl]methanamine | 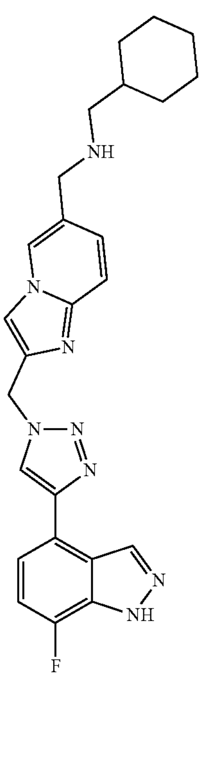 [SMILES: Fc1ccc(-c2cn(Cc3cn4cc(CNCC5CCCCC5)ccc4n3)nn2)c2cn[nH]c12] | D | 4.03 | 459.3 |

TABLE 19-continued

| Example No | Name | Structure | LCMS method | LCMS Retention time | Mass ion |
|---|---|---|---|---|---|
| 308 | 1-[[[2-[[4-(7-fluoro-1H-indazol-4-yl)triazol-1-yl]methyl]imidazo[1,2-a]pyridin-6-yl]methylamino]methyl]cyclobutanol | 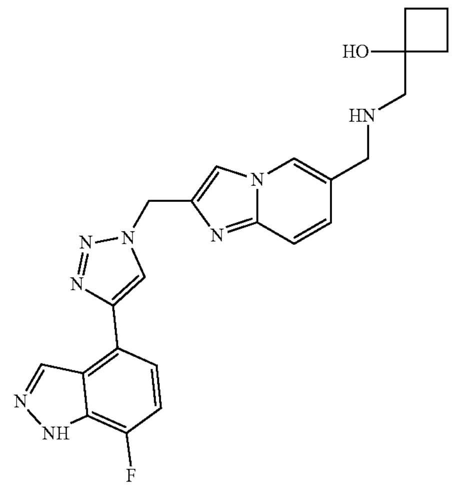 [SMILES: OC1(CNCc2ccc3nc(Cn4cc(-c5ccc(F)c6[nH]ncc56)nn4)cn3c2)CCC1] | D | 3.00 | 447.2 |

Example 309: 1-[[[2-[[4-(7-fluoro-1H-indazol-4-yl)triazol-1-yl]methyl]imidazo[1,2-a]pyridin-6-yl]methylamino]methyl]cyclopentanamine

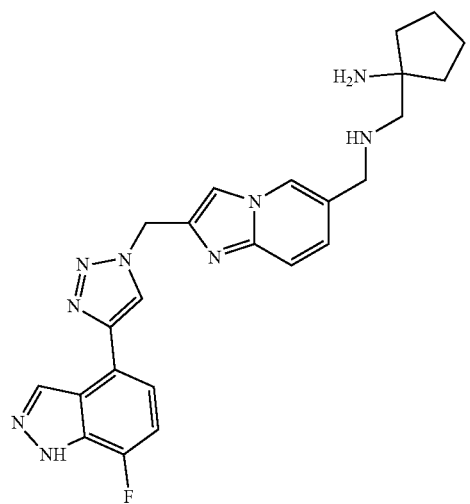 [SMILES: NC1(CNCc2ccc3nc(Cn4cc(-c5ccc(F)c6[nH]ncc56)nn4)cn3c2)CCCC1]

2-[[4-(7-fluoro-1-tetrahydropyran-2-yl-indazol-4-yl)triazol-1-yl]methyl]imidazo[1,2-a]pyridine-6-carbaldehyde Intermediate 53 (90 mg, 0.19 mmol) and tert-butyl [1-(aminomethyl)cyclopentyl]carbamate (81 mg, 0.38 mmol) were combined in 1,1,1,3,3,3-Hexafluoro-2-propanol (3 ml) and the mixture stirred at room temperature for an hour.

NaBH4 (50 mg, 1.32 mmol) was added along with a few drop MeOH-gas evolution—and the mixture stirred briefly at room temperature The reaction mixture was quenched with MeOH (30 ml)—gas evolution—and evaporated under vacuum. The residue was suspended in NaHCO₃ (sat, 30 ml) and extracted with chloroform/isopropanol (3:1, 3×30 ml). The combined organic extracts were dried over sodium sulfate and evaporated under vacuum.

The residue was purified by chromatography on SiO₂ (28 g kp-NH, eluting with EtOAc/heptane 0-100% followed by MeOH/EtOAc 0-20%) to afford the title compound (70 mg (54%) as a colourless residue which was dissolved in methanol (3 ml) and treated with HCl (4M in dioxane, 2 ml) and incubated at room temperature for 16 hours.

The reaction mixture was evaporated under vacuum. The residue was purified by ion exchange (SCX-2 5 g) washed with DCM and MeOH and eluted with NH₃/MeOH (7N). The eluent was evaporated under vacuum and the residue dried to afford the title compound (25 mg, 50%) as a pale yellow solid.

Method E: LC-MS (electrospray): m/z=460.2 (M+H)⁺, RT=0.96 min

Example 310: N-[[6-[(4,4-dimethyl-1-piperidyl)methyl]imidazo[1,2-a]pyridin-2-yl]methyl]-5-fluoro-4-oxo-chromene-2-carboxamide

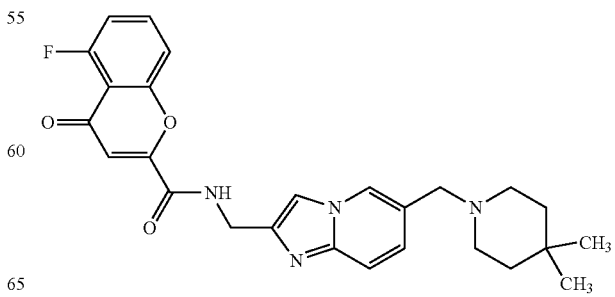

Step 1: ethyl 5-fluoro-4-oxo-chromene-2-carboxylate

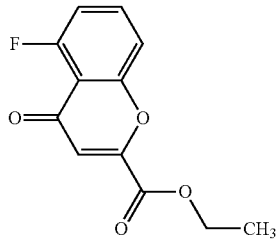 [SMILES: CCOC(=O)c1cc(=O)c2c(F)cccc2o1]

A solution of 1-(2-fluoro-6-hydroxyphenyl)ethanone (700 mg, 4.54 mmol) and diethyl oxalate (1.4 mL, 10.4 mmol) in ethanol (23 ml) was treated with NaOEt (21% wt solution, 7.3 mL, 19.5 mmol) which gave a dark brown solution. The mixture was heated at reflux for 30 minutes during which time a Yellow precipitate formed.

The mixture was cooled in ice and acidified (c.HCl) during which the yellow precipitate dissolved and a white precipitate formed. The solids were removed by filtration and washed with a little EtOH and the filtrate was evaporated under vacuum.

The residue was dissolved in EtOAc (20 mL), washed with brine/water (1:1, 20 ml). The aqueous phase was extracted with EtOAc (2×20 ml). The combined organics were dried over sodium sulfate and evaporated under vacuum. The residue was purified by chromatography on $SiO_2$ (Biotage, 50 g kp-Sil, eluting with EtOAc/heptane 0-50%) to afford a title compound (600 mg, 56%) as an off white solid.

Method B: LC-MS (electrospray): m/z=237.1 (M+H)+, RT=1.42 min

Step 2: 5-fluoro-4-oxo-chromene-2-carboxylic acid

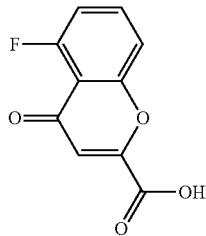 [SMILES: O=C(O)c1cc(=O)c2c(F)cccc2o1]

To a solution of ethyl 5-fluoro-4-oxo-chromene-2-carboxylate (600 mg, 2.54 mmol) in acetic acid (8 mL) was added hydrogen chloride (6M, 4.0 mL, 24.0 mmol) at room temperature and the reaction was stirred at 90° C. for 16 hours.

The mixture was cooled to room temperature and evaporated under vacuum. The residue was suspended in $CH_3CN$-water (1:1, 5 mL) and the solid was collected by filtration, washed with a little water and $CH_3CN$, and dried under vacuum to provide the title compound (520 mg, 98%) as a beige solid.

Method E: LC-MS (electrospray): m/z=209.0 (M+H)+, RT=1.50 min

Step 3: N-[[6-[(4,4-dimethyl-1-piperidyl)methyl]imidazo[1,2-a]pyridin-2-yl]methyl]-5-fluoro-4-oxo-chromene-2-carboxamide

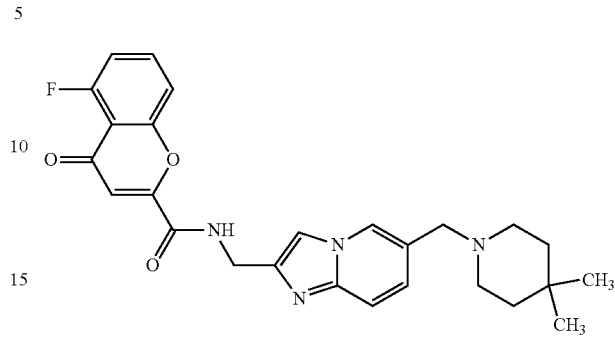

The title compound was prepared by coupling 5-fluoro-4-oxo-chromene-2-carboxylic acid with Intermediate 43 using the procedure described in Example 1 with DMF as solvent to give (4.6 mg, 2%) as an off-white solid.

Method D: LC-MS (electrospray): m/z=463.3 (M+H)+, RT=4.03 min

Intermediate 54: 2-({4-[6-chloro-1-(oxan-2-yl)-1H-indazol-4-yl]-1H-1,2,3-triazol-1-yl}methyl)imidazo[1,2-a]pyridine-6-carbaldehyde

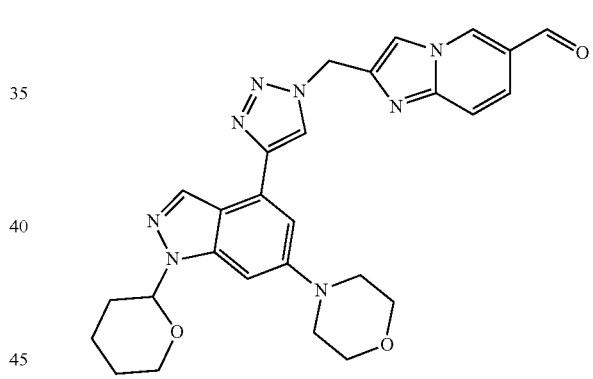

Step 1: 4-(3-bromo-5-fluoro-phenyl)morpholine

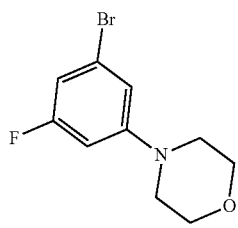 [SMILES: Fc1cc(Br)cc(N2CCOCC2)c1]

A solution of 3-bromo-5-fluoroaniline (1.00 g, 5.26 mmol), 1-bromo-2-(2-bromoethoxy)ethane (0.79 mL, 6.32 mmol) and N-ethyl-N-isopropyl-propan-2-amine (2.8 mL, 15.8 mmol) in DMF (20 mL) were stirred at 90° C. deg C. for 16 hours.

More 1-bromo-2-(2-bromoethoxy)ethane (0.40 mL, 3.16 mmol) was added and mixture was heated at 110° C. for 4 hours.

The reaction was cooled to room temperature, diluted with ethyl acetate (100 mL) and washed with water (1×50 mL) followed by brine (5×50 mL). The organic layer was dried over sodium sulfate, concentrated in vacuo to give the crude material as a black oil.

The residue was purified by chromatography on SiO$_2$ (Biotage KP—NH 30 g, eluting with EtOAc:Heptane 5 to 50%) gave a mixture of desired product and starting material as an orange oil which crystallised upon standing. Further chromatography on SiO$_2$ (Biotage KP-Sil 25 g eluting with EtOAc:Heptane, 0 to 30%) which gave the title product (740 mg, 50%) as a pale yellow solid.

Method B: LC-MS (electrospray): m/z=260.4/262.4 (M+H)$^+$, RT=1.74 min

Step 2:
2-bromo-6-fluoro-4-morpholino-benzaldehyde

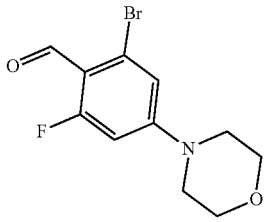 [SMILES: O=Cc1c(F)cc(N2CCOCC2)cc1Br]

A cold (0° C.) solution of 4-(3-bromo-5-fluoro-phenyl)morpholine (300 mg, 1.15 mmol) in DMF (anhydrous, 5 mL) was treated dropwise with phosphoryl trichloride (0.13 mL, 1.27 mmol). Once the addition was complete the mixture was warmed 60° C. and stirred for 16 hours.

The reaction was quenched via dropwise addition of the reaction mixture into an ice cold saturated solution of sodium bicarbonate (10 mL). The aqueous was extracted with ethyl acetate (3×10 mL) and the combined organics were washed with brine (3×10 mL) dried over sodium sulfate and concentrated in vacuo to give the title compound (268 mg, 65%) as a pale yellow solid.

Method A: LC-MS (electrospray): m/z=287.9/289.9 (M+H)$^+$, RT=1.10 min

Step 3: 4-(4-bromo-1H-indazol-6-yl)morpholine

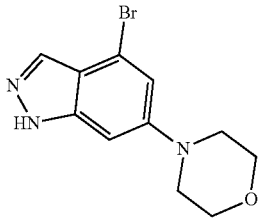 [SMILES: Brc1cc(N2CCOCC2)cc2[nH]ncc12]

Hydrazine (55%, 10 mL, 0.132 mol) was added to a solution of 2-bromo-6-fluoro-4-morpholino-benzaldehyde (4.30 g, 12.1 mmol) in 1,4-Dioxane (50 mL) and the reaction was stirred at 100° C. for 16 hours.

The reaction was cooled to room temperature and evaporated under vacuum. The residue was dissolved in EtOAc (100 ml), washed with water (100 mL) followed by brine (100 mL), dried (Na$_2$SO$_4$) and evaporated under reduced pressure to give a pale yellow solid, which was purified by chromatography on SiO$_2$ (Biotage 25 g eluting by 10-90% EtOAc in Heptane) to give the title compound (2.90 g, 76%) as a pale yellow solid.

Method B: LC-MS (electrospray): m/z=282.1/284.1 (M+H)$^+$, RT=1.41 min

Step 4: 2-({4-[6-chloro-1-(oxan-2-yl)-1H-indazol-4-yl]-1H-1,2,3-triazol-1-yl}methyl)imidazo[1,2-a]pyridine-6-carbaldehyde

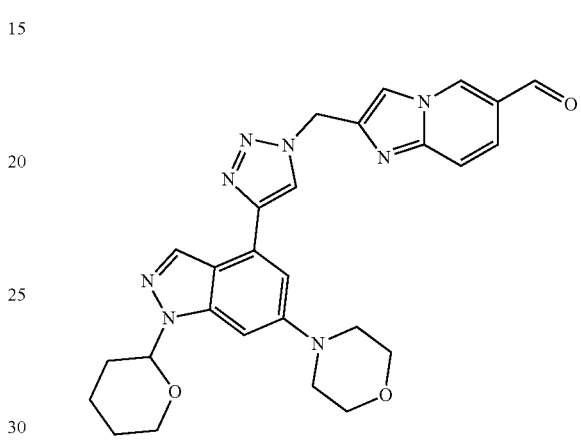

The title compound was prepared from 4-(4-bromo-1H-indazol-6-yl)morpholine using the procedures described in Intermediate 24 steps 1, 2 and 3 and intermediate 34 steps 4 and 5 to give (1.0 g, 83%) as a beige solid.

Method B: LC-MS (electrospray): m/z=513.3 (M+H)$^+$, RT=1.41 min

Example 311: N-(cyclobutylmethyl)-1-[2-[[4-(6-morpholino-1H-indazol-4-yl)triazol-1-yl]methyl]imidazo[1,2-a]pyridin-6-yl]methanamine

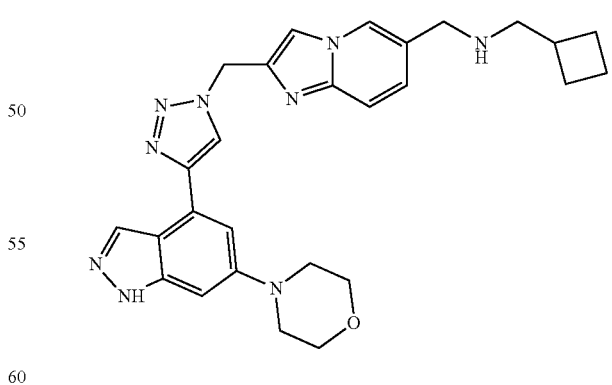

The title compound was prepared from intermediate 53 using the method described for Compound 250 giving (104 mg, 26%) as a white powder.

Method C: LC-MS (electrospray): m/z=498.4 (M+H)$^+$, RT=2.56 min

Example 312: 6-[2-(2-aminoethoxy)ethoxy]-N-[[6-[(4,4-dimethyl-1-piperidyl)methyl]imidazo[1,2-a]pyridin-2-yl]methyl]-1H-indazole-4-carboxamide trihydrochloride

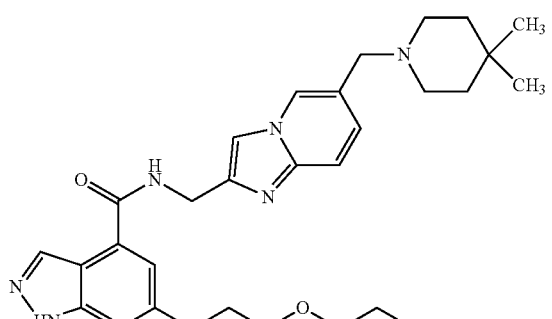

HCl (4M in dioxane, 3.1 mL, 12.4 mmol) was added to tert-butyl N-[2-[2-[4-[[6-[(4,4-dimethyl-1-piperidyl)methyl]imidazo[1,2-a]pyridin-2-yl]methylcarbamoyl]-1-tetrahydropyran-2-yl-indazol-6-yl]oxyethoxy]ethyl]carbamate (30 mg, 0.0426 mmol) and the mixture was stirred at room temperature for 1 hour and at 50° C. for 1 hour. The solvent was removed under vacuum to give the title compound (20 mg, 72%) as a tan solid.

Method D: LC-MS (electrospray): m/z=520.3 (M+H)$^+$, RT=4.11 min

Intermediate 55: tert-butyl N-[[6-[(Z)-tert-butylsulfinyliminomethyl]imidazo[1,2-a]pyridin-2-yl]methyl]carbamate

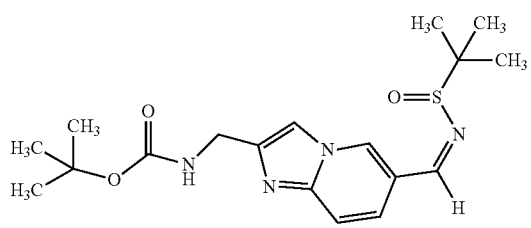 [SMILES: CC(C)(C)OC(=O)NCc1cn2cc(/C=N\S(=O)C(C)(C)C)ccc2n1]

A solution of tert-butyl N-[(6-formylimidazo[1,2-a]pyridin-2-yl)methyl]carbamate Intermediate 25 Step 2 (1.00 g, 3.63 mmol) and 2-methylpropane-2-sulfinamide (533 mg, 4.40 mmol) in DCE (Anhydrous, 97 mL), under a nitrogen atmosphere, was treated with CuSO$_4$ (1.76 g, 10.9 mmol) and the resultant blue solution was heated at reflux for 44 hours and left standing at room temperature for a further 5 days.

The dark green suspension was filtered through Celite washing with DCM and the filtrate was concentrated under vacuum and purified by chromatography on SiO2 [Biotage KPNH 28 g eluting with 50-100% EtOAc/heptane] to give the title compound (725 mg, 53%) as a pale yellow solid.

Method B: LC-MS (electrospray): m/z=379.3 (M+H)$^+$, RT=1.49 min

Example 313: N-[[6-[1-(cyclobutylmethylamino)-2-phenyl-ethyl]imidazo[1,2-a]pyridin-2-yl]methyl]-4-oxo-pyrido[1,2-a]pyrimidine-2-carboxamide

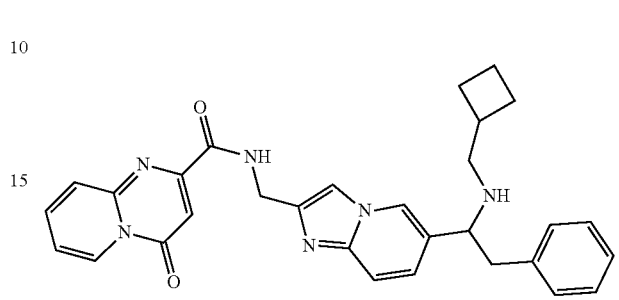

Step 1: tert-butyl N-[[6-[1-(tert-butylsulfinylamino)-2-phenyl-ethyl]imidazo[1,2-a]pyridin-2-yl]methyl]carbamate

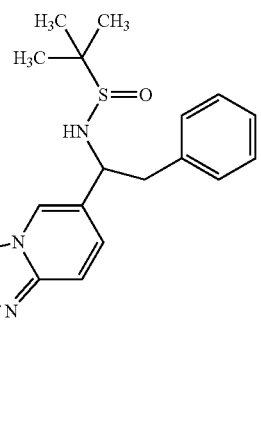

A solution of benzylmagnesium chloride (1.5M in THF, 969 uL, 1.45 mmol) was added dropwise over 1 min to a solution of tert-butyl N-[[6-[(E)-tert-butylsulfinyliminomethyl]imidazo[1,2-a]pyridin-2-yl]methyl]carbamate Intermediate 54 (110 mg, 0.291 mmol) in dry DCM (14 mL) at room temperature and the solution was stirred for 16 hours. The reaction mixture became turbid upon the addition of the first few drops but became clear after the addition was complete.

The reaction was quenched by the addition of NH$_4$Cl (sat) and extracted with DCM (phase sep cartridge). The organics were evaporated under vacuum to a pale gum which was purified by chromatography on SiO$_2$ [Biotage KPNH 11 g eluting with EtOAc] to give the title compound (2:1 mixture of diastereoisomers, 102 mg, 75%) as a beige foam.

Method B: LC-MS (electrospray): m/z=471.3 (M+H)$^+$, RT=1.54 & 1.59 min

Step 2: tert-butyl N-[[6-(1-amino-2-phenyl-ethyl)imidazo[1,2-a]pyridin-2-yl]methyl]carbamate

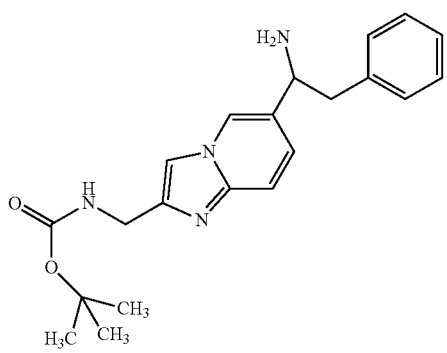 [SMILES: CC(C)(C)OC(=O)NCc1cn2cc(C(N)Cc3ccccc3)ccc2n1]

A solution of tert-butyl N-[[6-[1-(tert-butylsulfinylamino)-2-phenyl-ethyl]imidazo[1,2-a]pyridin-2-yl]methyl]carbamate (185 mg, 0.39 mmol) in THF (9.25 mL) and Water (1.85 mL) was treated with molecular iodine (20 mg, 0.08 mmol) and the mixture was warmed at 60° C. for 16 hours.

The mixture was cooled to room temperature, quenched by the addition of sodium thiosulfate (sat 10 ml) and extracted with DCM (phase sep cartridge). The organics were evaporated under vacuum and purified by chromatography on SiO₂ [Biotage KPNH 11 g eluting with 50 to 100% EtOAc in heptane followed by 0 to 20% MeOH in DCM]. To give the title compound (30 mg, 7% Yield) as a white powder.

During the separation a white solid was seen between the layers. The solid was collected by filtration, washed with ether and dried to give the title compound (40 mg, 28%) as a white powder.

Method B: LC-MS (electrospray): m/z=367.3 (M+H)⁺, RT=1.46 min

Step 3: tert-butyl N-[[6-[1-(cyclobutylmethylamino)-2-phenyl-ethyl]imidazo[1,2-a]pyridin-2-yl]methyl]carbamate

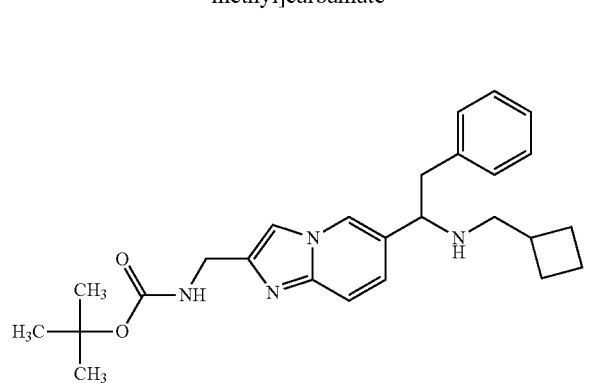

The title compound was prepared from tert-butyl N-[[6-(1-amino-2-phenyl-ethyl)imidazo[1,2-a]pyridin-2-yl]methyl]carbamate using the procedure described in Compound 250 to give (21 mg, 22%) as a white powder along with the doubly alkylated product (30 mg, 31%).

Method B: LC-MS (electrospray): m/z=435.4 (M+H)⁺, RT=1.78 min

Step 4: N-[[6-[1-(cyclobutylmethylamino)-2-phenyl-ethyl]imidazo[1,2-a]pyridin-2-yl]methyl]-4-oxo-pyrido[1,2-a]pyrimidine-2-carboxamide

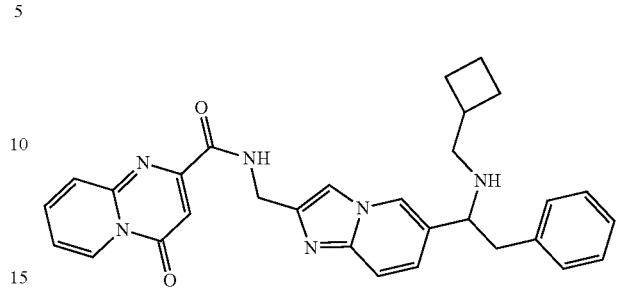

tert-butyl N-[[6-[1-(cyclobutylmethylamino)-2-phenyl-ethyl]imidazo[1,2-a]pyridin-2-yl]methyl]carbamate (30 mg, 0.07 mmol) was dissolved in hydrogen chloride (4M in dioxane, 0.17 mL, 0.7 mmol) and stirred at room temperature for 1 hour.

The solvent was removed in vacuo and the resulting crude material dissolved in DMF (1 mL), N-ethyl-N-isopropyl-propan-2-amine (0.06 mL, 0.35 mmol) was added and the mixture was stirred at room temperature for 10 minutes.

In a separate flask tert-butyl N-[[6-[1-(cyclobutylmethylamino)-2-phenyl-ethyl]imidazo[1,2-a]pyridin-2-yl]methyl]carbamate (30 mg, 0.07 mmol), HATU (39 mg, 0.1 mmol) and N-ethyl-N-isopropyl-propan-2-amine (0.06 mL, 0.35 mmol) in DMF (1 mL) were combined at room temperature and stirred for 5 minutes before the amine solution was added and the mixture was stirred at room temperature for 2 hours.

Water (2 mL) and IPA/CHCl3 (1/4, 5 mL) were added and the layers separated (phase sep cartridge). The organic filtrate was concentrated in vacuo to give a brown oil. Purification by reverse phase chromatography (Biotage 12 g, water/MeCN+0.1% NH3, 10 to 90%) and subsequent freeze-drying overnight gave the title compound (8.0 mg, 23%) a pale yellow solid.

Method D: LC-MS (electrospray): m/z=507.3 (M+H)+, RT=4.13 min

Example 314

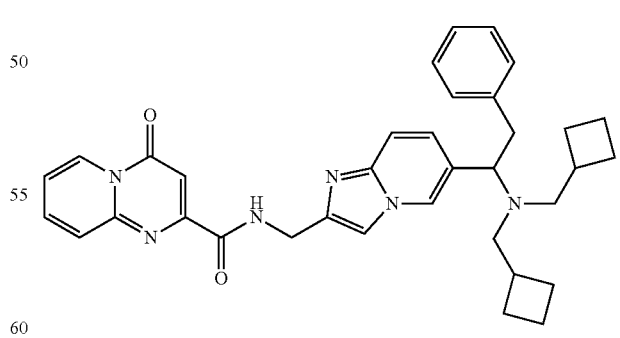

The title compound was prepared from the bis alkylated product isolated in Example 313 Step 3 in the same manner as Example 313 Step 4 to give (10 mg, 25%) as a white powder.

Method C: LC-MS (electrospray): m/z=575.4 (M+H)+, RT=4.86 min

Intermediate 56: 2-({4-[7-chloro-1-(oxan-2-yl)-1H-indazol-4-yl]-1H-1,2,3-triazol-1-yl}methyl)imidazo[1,2-a]pyridine-6-carbaldehyde

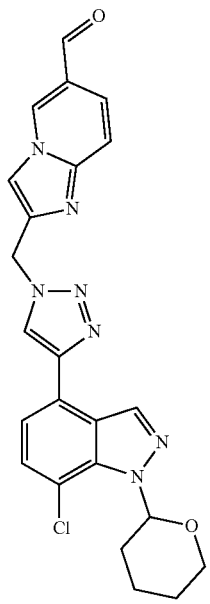 [SMILES: O=Cc1ccc2nc(Cn3cc(-c4ccc(Cl)c5c4cnn5C4CCCCO4)nn3)cn2c1]

The title compound was prepared from 4-bromo-7-chloro-1H-indazole in a similar fashion to Intermediate 34 using the oxidation described in Compound 268 Step 3 for the final step giving (388 mg, 75%) as a grey solid.

Method B: LC-MS (electrospray): m/z=462.2 (M+H)$^+$, RT=1.54 min

Example 315: 1-[2-[[4-(7-chloro-1H-indazol-4-yl)triazol-1-yl]methyl]imidazo[1,2-a]pyridin-6-yl]-N-(cyclobutylmethyl)methanamine

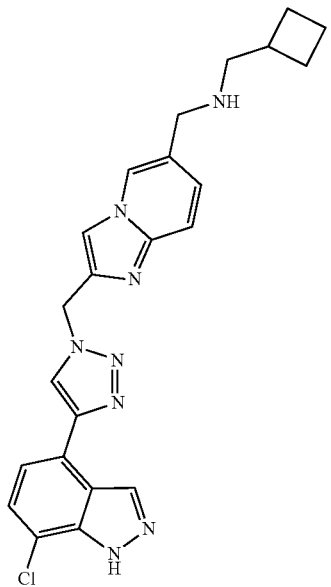 [SMILES: Clc1ccc(-c2cn(Cc3cn4cc(CNCC5CCC5)ccc4n3)nn2)c2cn[nH]c12]

The title compound was prepared from Intermediate 56 in a similar manner to Example 305 to give (58 mg, 40%) as a white solid.

Method E: LC-MS (electrospray): m/z=447.2 (M+H)$^+$, RT=1.37 min

Example 316: 1-[[[2-[[4-(7-chloro-1H-indazol-4-yl)triazol-1-yl]methyl]imidazo[1,2-a]pyridin-6-yl]methylamino]methyl]cyclobutanol

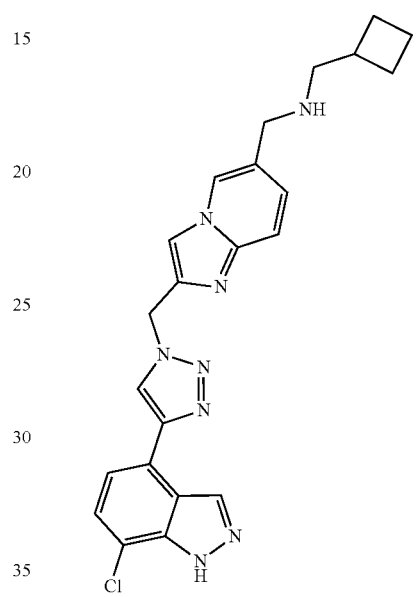

The title compound was prepared in the same manner as Example 315 to give (20 mg, 14%) as a white solid.

Method D: LC-MS (electrospray): m/z=463.2 (M+H)$^+$, RT=3.09 min

Example 317: [2-[[4-(6-fluoro-1H-indazol-4-yl)triazol-1-yl]methyl]imidazo[1,2-a]pyridin-6-yl]methanol

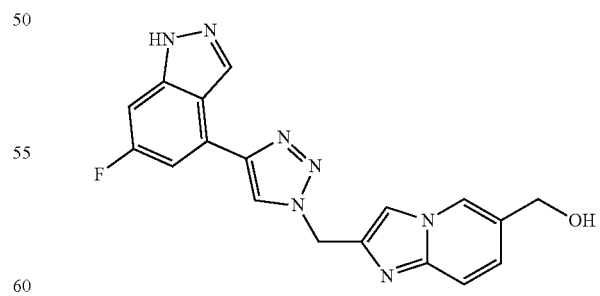

The title compound was prepared from 4-bromo-6-fluoro-1H-indazole in a similar fashion to Compound 253 giving (20 mg, 6%) as a white solid.

Method D: LC-MS (electrospray): m/z=364.6 (M+H)$^+$, RT=2.71 min

Intermediate 57: 2-({4-[6-fluoro-1-(oxan-2-yl)-1H-indazol-4-yl]-1H-1,2,3-triazol-1-yl}methyl)imidazo[1,2-a]pyridine-6-carbaldehyde

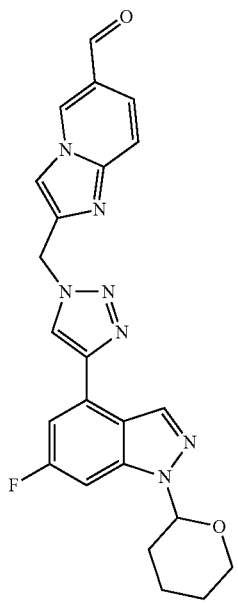 [SMILES: O=Cc1ccc2nc(Cn3cc(-c4cc(F)cc5c4cnn5C4CCCCO4)nn3)cn2c1]

The title compound was prepared from 4-bromo-6-fluoro-1H-indazole in a similar fashion to Intermediate 34 giving (472 mg, 96%) as a sandy solid.

Method B: LC-MS (electrospray): m/z=446.7 (M+H)$^+$, RT=1.49 min

Example 318: N-(cyclobutylmethyl)-1-[2-[[4-(6-fluoro-1H-indazol-4-yl)triazol-1-yl]methyl]imidazo[1,2-a]pyridin-6-yl]methanamine

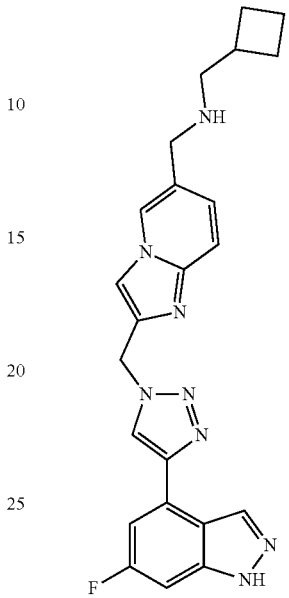

The title compound was prepared from Intermediate 57 in a similar fashion to Compound 250 giving (30 mg, 29%) as an off white solid.

Method C: LC-MS (electrospray): m/z=431.4 (M+H)$^+$, RT=2.79 min

The compounds in Table 20 were prepared from Intermediate 57 using the procedure described for Example 318.

TABLE 20

| Example No | Name | Structure | LCMS method | LCMS Retention time | Mass ion |
|---|---|---|---|---|---|
| 319 | 1-[[[2-[[4-(6-fluoro-1H-indazol-4-yl)triazol-1-yl]methyl]imidazo[1,2-a]pyridin-6-yl]methylamino]methyl]cyclobutanol | 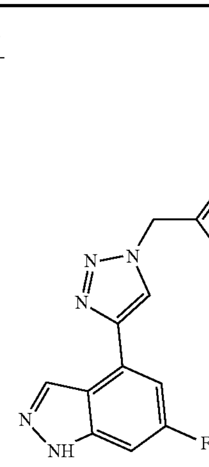 | C | 2.21 | 447.3 |

TABLE 20-continued

| Example No | Name | Structure | LCMS method | LCMS Retention time | Mass ion |
|---|---|---|---|---|---|
| 320 | N-(cyclohexylmethyl)-1-[2-[[4-(6-fluoro-1H-indazol-4-yl)triazol-1-yl]methyl]imidazo[1,2-a]pyridin-6-yl]methanamine | 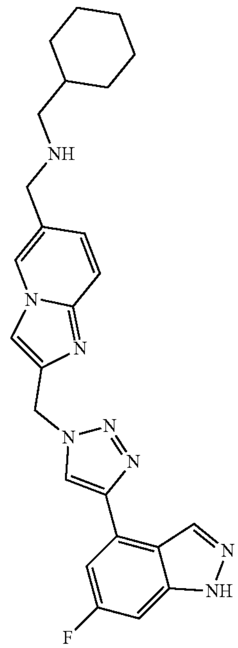 [SMILES: Fc1cc(-c2cn(Cc3cn4cc(CNCC5CCCCC5)ccc4n3)nn2)c2cn[nH]c2c1] | C | 3.23 | 459.5 |

Example 321: N-[[2-[[4-(6-cyclopropyl-1H-indazol-4-yl)triazol-1-yl]methyl]imidazo[1,2-a]pyridin-6-yl]methyl]-2,2-dimethyl-propan-1-amine

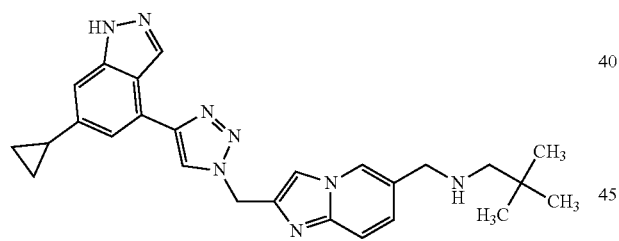

A pressure vial charged with bromo(cyclopropyl)zinc (0.5M in THF, 0.38 mL, 0.188 mmol), THF (0.3 mL) and N-[[2-[[4-(6-bromo-1H-indazol-4-yl)triazol-1-yl]methyl]imidazo[1,2-a]pyridin-6-yl]methyl]-2,2-dimethyl-propan-1-amine (31 mg, 0.0628 mmol) Compound 229 was degassed with nitrogen. Tetrakis(triphenylphosphine)palladium(0) (3.6 mg, 3.14 µmol) was added and the reaction degassed with nitrogen for 2 minutes before the reaction was heated to 50° C.

Further. Tetrakis(triphenylphosphine)palladium(0) (3.6 mg, 3.14 µmol) and bromo(cyclopropyl)zinc (0.5M in THF, 0.38 mL, 0.188 mmol) were added and the reaction degassed for 5 minutes before heating to 65° C. for 2 hours.

[1,1'-Bis(diphenylphosphino)ferrocene]dichloropalladium(II), complex with dichloromethane (2.6 mg, 3.14 µmol) was added and the reaction heated to 70° C. for 18 hours.

The reaction was cooled to room temperature, filtered through a pad of Celite washing with MeOH (10 mL). The solvent was removed in vacuo to give a red/brown oil. The crude mixture was purified by reverse phase chromatography [water/MeCN+0.1% NH3, 0 to 100%] gave partially clean fractions containing product. Concentration of these fractions in vacuo gave a yellow residue (5 mg)

Repurification by reverse phase chromatography [water/MeCN+0.1% NH3, 0 to 100%] followed by freeze drying overnight gave the title compound (1.2 mg, 3.8% Yield) as a white solid.

Method C: LC-MS (electrospray): m/z=455.4 (M+H)+, RT=3.15 min

Intermediate 58: [6-[(cyclobutylmethylamino)methyl]imidazo[1,2-a]pyridin-2-yl]methanamine trihydrochloride

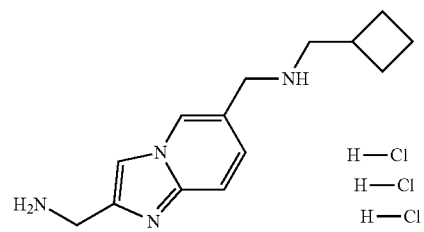

The title compound was prepared in a similar fashion to Intermediate 25 to give (953 mg, 95%) as a pale yellow solid.

Method C: LC-MS (electrospray): m/z=245.1 (M+H)+, RT=2.02 min

Example 322: N-[[6-[(cyclobutylmethylamino)methyl]imidazo[1,2-a]pyridin-2-yl]methyl]-1H-indazole-4-carboxamide

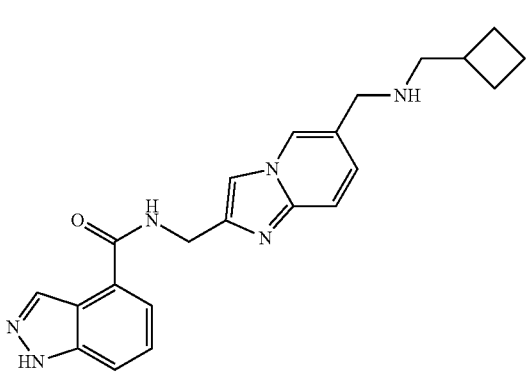 [SMILES: O=C(NCc1cn2cc(CNCC3CCC3)ccc2n1)c1cccc2[nH]ncc12]

The title compound was prepared in the same manner as Example 1 by coupling of 1-tetrahydropyran-2-ylindazole-4-carboxylic acid and Intermediate 58 followed by deprotection to give (7.8 mg, 10%) as a white powder.

Method C: LC-MS (electrospray): m/z=389.4 (M+H)$^+$, RT=2.38 min

Intermediate 59: 6-methylimidazo[1,2-a]pyridin-2-amine

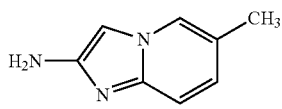

Step 1: 4-methyl-N-(5-methyl-2-pyridyl)benzenesulfonamide

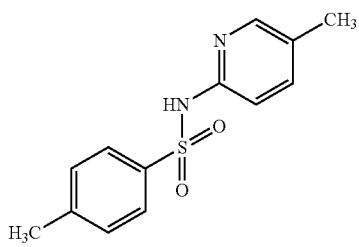

A solution of 5-methylpyridin-2-amine (5.00 g, 46.2 mmol) in Pyridine (50 mL) was treated with (p-toluenesulfonyl chloride (11.47 g, 55.5 mmol) and the mixture was stirred at room temperature for 20 hours. The addition caused an orange colouration and a slight exotherm.

The solvent was removed under vacuum and the residue was triturated with MeOH, the solids were collected by filtration, washed with MeOH and dried under vacuum to provide the title compound (10.9 g, 90%) as a white solid.

Method A: LC-MS (electrospray): m/z=263.2 (M+H)$^+$, RT=0.96 min

Step 2: 2-[5-methyl-2-(4-methylbenzenesulfonamido)-1,2-dihydropyridin-1-yl]acetamide

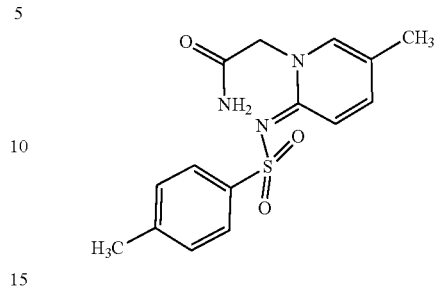

A suspension of 4-methyl-N-(5-methyl-2-pyridyl)benzenesulfonamide (3.00 g, 11.4 mmol) and N-ethyl-N-isopropyl-propan-2-amine (2.2 mL, 12.6 mmol) in DMF-Anhydrous (36 mL), under a nitrogen atmosphere, was treated with idoacetamide (2.33 g, 12.6 mmol) and the mixture was stirred at room temperature for 20 hours.

The solvent was removed under vacuum and the residue was triturated with DCM/EtOAc (30 mL) but the product was too soluble. EtOAc was added until cloud point and the mixture was aged. The solids were collected by filtration and dried on the sinter to give the title compound (5.3 g, >100%) as a white solid. The material was used without further purification.

Method A: LC-MS (electrospray): m/z=320.0 (M+H)$^+$, RT=0.88 min

Step 3: 6-methylimidazo[1,2-a]pyridin-2-amine

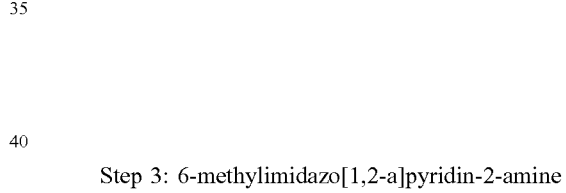

A suspension of 2-[5-methyl-2-(4-methylbenzenesulfonamido)-1,2-dihydropyridin-1-yl]acetamide (3.60 g, 11.3 mmol) in DCM (40 mL), under a nitrogen atmosphere, was slowly treated with (2,2,2-trifluoroacetyl) 2,2,2-trifluoroacetate (7.9 mL, 56.4 mmol) and the mixture was stirred at room temperature for 16 hours. During the addition, the solids dissolved and the solution darkened to nearly black.

The dark solution was cautiously quenched by the addition of NaHCO$_3$ (sat). The solvent was removed under vacuum and the residue was extracted with EtOAc (×2). The organics were washed with brine, dried (MgSO$_4$) and evaporated under vacuum to a dark gum which was purified by ion exchange [SCX-2 (5 g) washing with methanol and eluting with ammonia in MeOH) to give the title compound (476 mg, 29%) as a dark gum.

Method A: LC-MS (electrospray): m/z=147.9 (M+H)$^+$, RT=0.17 min

Intermediate 60: 4-ethynyl-1-tetrahydropyran-2-yl-pyrazolo[4,3-c]pyridine

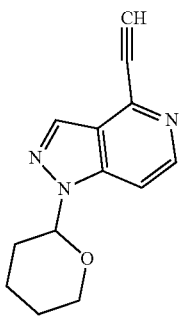 [SMILES: C#Cc1nccc2c1cnn2C1CCCCO1]

The title compound was prepared from 4-chloro-1H-pyrazolo[4,3-c]pyridine using the procedures described for Intermediate 24 to give the title compound (243 mg, 33%) as a brown oil.
Method B: LC-MS (electrospray): m/z=228.3 (M+H)$^+$, RT=1.40 min Intermediate 61: 2-[[4-(1-tetrahydropyran-2-ylpyrazolo[4,3-c]pyridin-4-yl)triazol-1-yl]methyl]imidazo[1,2-a]pyridine-6-carbaldehyde

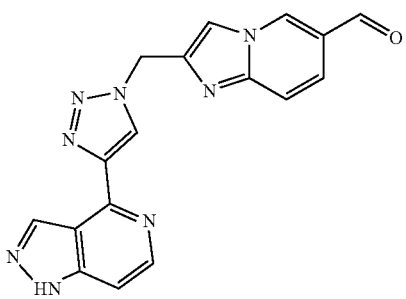 [SMILES: O=Cc1ccc2nc(Cn3cc(-c4nccc5[nH]ncc45)nn3)cn2c1]

The title compound was prepared from Intermediate 60 using the procedures described for Intermediate 34 to give the title compound (290 mg, 95%) as a very pale yellow solid.
Method B: LC-MS (electrospray): m/z=429.3 (M+H)$^+$, RT=1.39 min Example 324: N-(cyclobutylmethyl)-1-[2-[[4-(1H-pyrazolo[4,3-c]pyridin-4-yl)triazol-1-yl]methyl]imidazo[1,2-a]pyridin-6-yl]methanamine

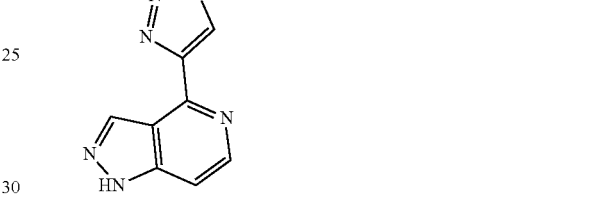

The title compound was prepared from Intermediate 61 in a similar manner to Compound 250 to give (45 mg, 47%) as a white solid.
Method D: LC-MS (electrospray): m/z=414.3 (M+H)$^+$, RT=3.20 min The compounds in Table 21 were prepared in a similar manner to Example 324.

TABLE 21

| Example No | Name | Structure | LCMS method | LCMS Retention time | Mass ion |
|---|---|---|---|---|---|
| 325 | N-(cyclohexylmethyl)-1-[2-[[4-(1H-pyrazolo[4,3-c]pyridin-4-yl)triazol-1-yl]methyl]imidazo[1,2-a]pyridin-6-yl]methanamine | 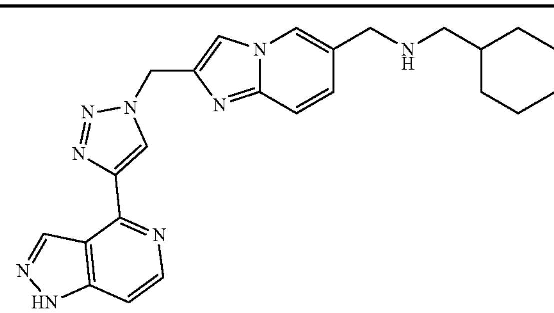 | D | 3.66 | 442.3 |

TABLE 21-continued

| Example No | Name | Structure | LCMS method | LCMS Retention time | Mass ion |
|---|---|---|---|---|---|
| 326 | 1-[[[2-[[4-(1H-pyrazolo[4,3-c]pyridin-4-yl)triazol-1-yl]methyl]imidazo[1,2-a]pyridin-6-yl]methylamino]methyl]cyclobutanol | 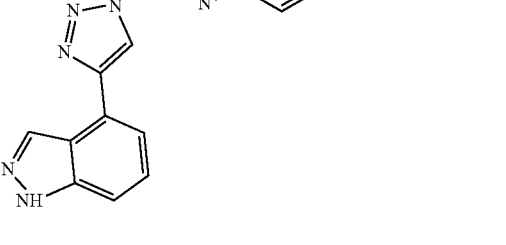 | D | 2.66 | 430.3 |

The Compounds in Table 22 were prepared from Intermediate 34 in a similar fashion to Compound 250.

TABLE 22

| Example No | Name | Structure | LCMS Retention time | Mass ion |
|---|---|---|---|---|
| 327 | N-(cyclobutylmethyl)-1-[2-[[4-(1H-indazol-4-yl)triazol-1-yl]methyl]imidazo[1,2-a]pyridin-6-yl]methanamine | 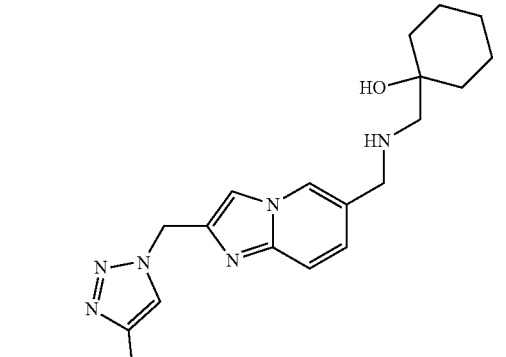 | 2.62 | 413.4 |
| 328 | 1-[[[2-[[4-(1H-indazol-4-yl)triazol-1-yl]methyl]imidazo[1,2-a]pyridin-6-yl]methylamino]methyl]cyclohexanol | 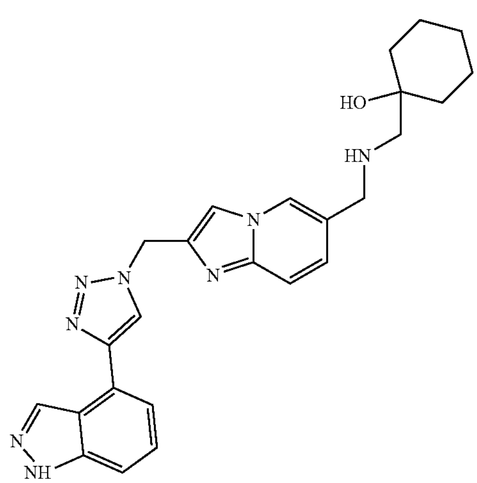 [SMILES: OC1(CNCc2ccc3nc(Cn4cc(-c5cccc6[nH]ncc56)nn4)cn3c2)CCCCC1] | 2.42 | 457.4 |

Example 329: 2-[[4-(1H-indazol-4-yl)imidazol-1-yl]methyl]-6-methyl-imidazo[1,2-a]pyridine formate

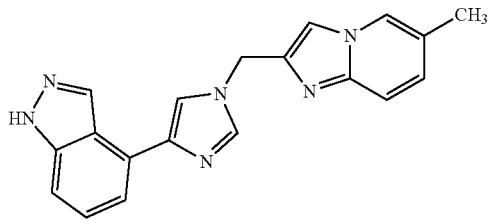 [SMILES: Cc1ccc2nc(Cn3cnc(-c4cccc5[nH]ncc45)c3)cn2c1]

Step 1: 4-bromo-1-({6-methylimidazo[1,2-a]pyridin-2-yl}methyl)-1H-imidazole

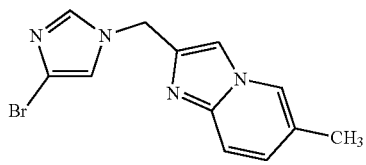 [SMILES: Cc1ccc2nc(Cn3cnc(Br)c3)cn2c1]

A mixture of 4-bromo-1H-imidazole (500 mg, 3.40 mmol), K$_2$CO$_3$ (1.41 g, 10.2 mmol) and 2-(chloromethyl)-6-methyl-imidazo[1,2-a]pyridine hydrochloride (886 mg, 4.08 mmol) were combined in DMF (8 ml) and stirred at room temperature for 1.5 hours before NaI (30 mg, 0.20 mmol) was added and the stir was continued for 19 hours.

The reaction mixture was diluted with NaHCO$_3$ (sat, 50 ml) and extracted with chloroform/isopropanol (3:1, 3×50 ml). The combined organic extracts were dried over sodium sulfate and evaporated under vacuum.

The residue was purified by chromatography on SiO$_2$ (Biotage 28 g kp-NH, eluting with EtOAc/heptane 0-100% followed by MeOH/EtOAc 0-20%) to afford the title compound (836 mg, 84%) as a white solid which contained a small amount of the regioisomeric product.

Method B: LC-MS (electrospray): m/z=291.1/293.1 (M+H)$^+$, RT=1.31 min

Step 2: 4-[1-({6-methylimidazo[1,2-a]pyridin-2-yl}methyl)-1H-imidazol-4-yl]-1-(oxan-2-yl)-1H-indazole

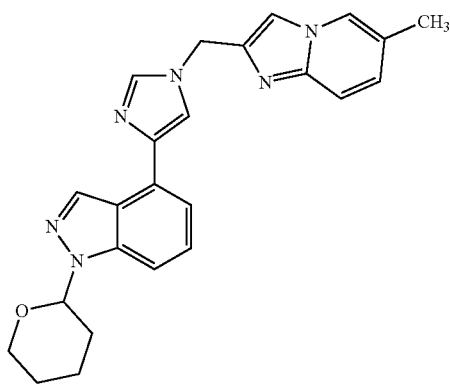 [SMILES: Cc1ccc2nc(Cn3cnc(-c4cccc5c4cnn5C4CCCCO4)c3)cn2c1]

1-tetrahydropyran-2-yl-4-(4,4,5,5-tetramethyl-1,3,2-dioxaborolan-2-yl)indazole (300 mg, 0.91 mmol), 2-[(4-bromoimidazol-1-yl)methyl]-6-methyl-imidazo[1,2-a]pyridine (319 mg, 1.10 mmol) and K$_2$CO$_3$ (1.2M aqueous, 2.28 ml, 2.74 mmol) were combined in 1,4-Dioxane (6 ml) and the mixture sparged with nitrogen for 5 mins. PdCl$_2$dppf (67 mg, 0.09 mmol) was added and the mixture further sparged briefly and the vessel sealed. The mixture was heated at 90° C. for 2 hours.

Further PdCl$_2$dppf (67 mg, 0.09 mmol) was added, mixture briefly sparged with nitrogen and further heated at 100° C. for 4 hours. The reaction mixture was cooled to room temperature and stood over the weekend.

The reaction mixture was diluted with NaHCO$_3$ (sat, 50 ml) and extracted with chloroform/isopropanol (3:1, 3×50 ml). The combined organic extracts were dried over sodium sulfate and evaporated under vacuum.

The residue was purified by chromatography on SiO$_2$ (Biotage 28 g kp-NH, eluting with EtOAc/heptane 0-100% followed by MeOH/EtOAc 0-20%) to afford the crude title compound (229 mg, 27% yield, 45% purity) as a brown oil. No further purification attempted; carried direct to next step.

Method A: LC-MS (electrospray): m/z=413.2 (M+H)$^+$, RT=0.87 min

Step 3: 2-[[4-(1H-indazol-4-yl)imidazol-1-yl]methyl]-6-methyl-imidazo[1,2-a]pyridine formate

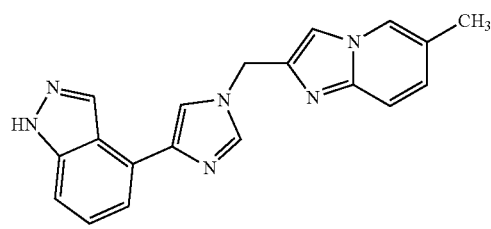 [SMILES: Cc1ccc2nc(Cn3cnc(-c4cccc5[nH]ncc45)c3)cn2c1]

A solution of 4-[1-[(6-methylimidazo[1,2-a]pyridin-2-yl)methyl]imidazol-4-yl]-1-tetrahydropyran-2-yl-indazole (229 mg, 0.56 mmol) in methanol (5 ml) was treated with HCl (4M in dioxane, 5 ml) and the mixture was incubated at room temperature for 18 hours.

The reaction mixture was evaporated under vacuum and the residue was purified by reverse phase chromatography on SiO$_2$ (12 g C18-Ultra, eluting with Acetonitrile+0.1% NH3/Water+0.1% NH3 10-100%) the relevant fractions were combined to afford crude material which was triturated with MeOH/EtOAc/heptane. The solids were collected by filtration to give a grey solid 100 mg.

The material was purified by preparative HPLC [Acidic method A] to give the title compound (20 mg, 9%) as a white solid.

Method E: LC-MS (electrospray): m/z=329.1 (M+H)$^+$, RT=1.00 min

Example 330: N-[[6-[2-cyano-1-(cyclobutylmethyl-amino)ethyl]imidazo[1,2-a]pyridin-2-yl]methyl]-4-oxo-pyrido[1,2-a]pyrimidine-2-carboxamide

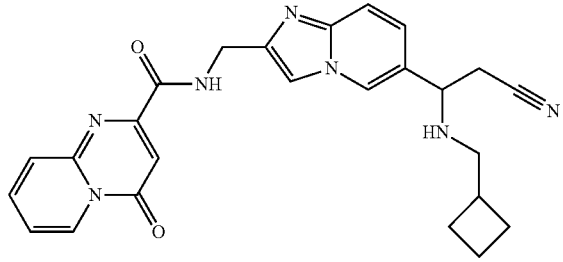 [SMILES: N#CCC(NCC1CCC1)c1ccc2nc(CNC(=O)c3cc(=O)n4ccccc4n3)cn2c1]

Step 1: tert-butyl N-[(6-{2-cyano-1-[(2-methylpropane-2-sulfinyl)amino]ethyl}imidazo[1,2-a]pyridin-2-yl)methyl]carbamate

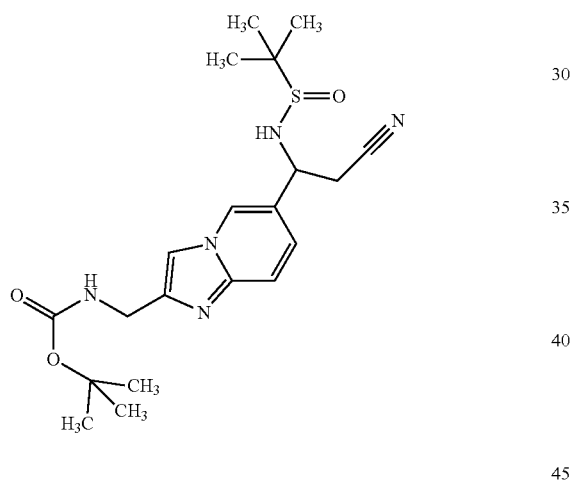

An oven dried flask containing N-(propan-2-yl)propan-2-amine (0.28 mL, 2.00 mmol) in THF (2.5 mL) was cooled to −78° C. and a solution of n-butyllithium (1.6 M in hexanes, 1.3 mL, 2.00 mmol) was added whilst maintaining the temperature at −78° C. Once the addition was complete, the mixture was stirred at ambient temperature for 20 minutes.

The mixture was cooled to −78° C. and a solution of acetonitrile (0.10 mL, 2.00 mmol) in THF (1 mL) was added and the mixture was stirred at −78 C for 10 minutes before a quarter of the mixture was syringed into a separate oven dried flask and cooled to −78° C. and stirred for 20 minutes before a solution of tert-butyl N-[[6-[(E)-tert-butylsulfinyliminomethyl]imidazo[1,2-a]pyridin-2-yl]methyl]carbamate Intermediate 55 (190 mg, 0.502 mmol) in THF (0.5 mL) was added dropwise. The reaction was stirred at −78° C. for 20 minutes.

A further quarter of the LDA mixture was added dropwise and the reaction was stirred for at −78° C. for 15 minutes.

A further quarter of the LDA mixture was added dropwise and the reaction was stirred for at −78° C. for 15 minutes.

The remaining LDA mixture was added dropwise and the reaction was stirred for at −78° C. for 15 minutes.

The reaction was quenched via dropwise addition of $NH_4Cl$ (sat) and the reaction was warmed to room temperature. The mixture was diluted with EtOAc (5 mL) and the layers separated. The aqueous layer was extracted with ethyl acetate (5 mL). The organic layers were washed with brine (5 mL), dried over magnesium sulfate and concentrated in vacuo to give a red viscous oil.

The crude product was purified by reverse phase chromatography on $SiO_2$ (Biotage 12 g, water/MeCN (+0.1% NH3) at a gradient of 90:10 to 20:80) concentration of product fractions in vacuo and subsequent freeze drying overnight gave the desired product (110 mg, 52%) as an off-white solid.

Method B: LC-MS (electrospray): m/z=420.3 (M+H)$^+$, RT=1.35 min

Step 2: tert-butyl N-{[6-(1-amino-2-cyanoethyl)imidazo[1,2-a]pyridin-2-yl]methyl}carbamate

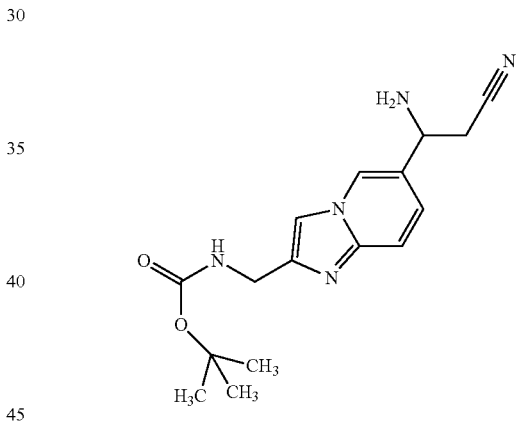

A solution of tert-butyl N-[[6-[1-(tert-butylsulfinylamino)-2-cyano-ethyl]imidazo[1,2-a]pyridin-2-yl]methyl]carbamate (110 mg, 0.26 mmol) in THF (2 mL) and Water (0.2 mL) was treated with iodine (13 mg, 0.052 mmol) and the mixture was warmed at 60° C. for 18 hours.

Further iodine (13 mg, 0.052 mmol) was added and the heating was continued for a further 4 hours.

The mixture was cooled to room temperature, quenched by the addition of sodium thiosulfate (sat 10 ml) and extracted with EtOAc, dried over sodium sulfate and concentrated in vacuo Purification by reverse phase chromatography on $SiO_2$ (12 g C18 cartridge, water/MeCN+0.1% NH3 gradient) gave the desired product (20 mg, 23%) as a yellow oil.

Method B: LC-MS (electrospray): m/z=316.3 (M+H)$^+$, RT=1.23 min

Step 3: tert-butyl N-[(6-{2-cyano-1-[(cyclobutylmethyl)amino]ethyl}imidazo[1,2-a]pyridin-2-yl)methyl]carbamate

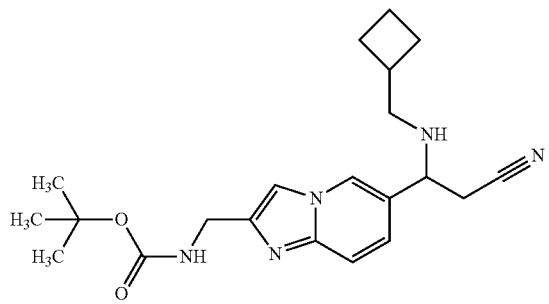 [SMILES: CC(C)(C)OC(=O)NCc1cn2cc(C(CC#N)NCC3CCC3)ccc2n1]

tert-butyl N-[[6-(1-amino-2-cyano-ethyl)imidazo[1,2-a]pyridin-2-yl]methyl]carbamate (20 mg, 0.06 mmol) and N-ethyl-N-isopropyl-propan-2-amine (0.055 mL, 0.32 mmol) were combined in DCM (0.3 mL) and methanol (0.06 mL). To the yellow suspension was added cyclobutanecarbaldehyde (6.4 mg, 0.0761 mmol) and the reaction was stirred at room temperature for an hour.

The reaction was concentrated in vacuo to remove any excess aldehyde and the resulting crude yellow oil was dissolved in DCM (0.5 mL). sodium borohydride (22 mg, 0.57 mmol) was added followed by a drop of methanol and the reaction was stirred at room temperature for 30 minutes. The reaction was quenched with dropwise addition of water (3 mL). IPA/CHCl3 (1:4, 5 mL) was added and the separated (phase sep cartridge). The organic filtrate was concentrated in vacuo to give the title compound (21 mg, 75%) as a pale yellow residue, which was used without further purification.

Method B: LC-MS (electrospray): m/z=384.4 (M+H)+, RT=1.53 min

Step 4: N-[[6-[2-cyano-1-(cyclobutylmethylamino)ethyl]imidazo[1,2-a]pyridin-2-yl]methyl]-4-oxopyrido[1,2-a]pyrimidine-2-carboxamide

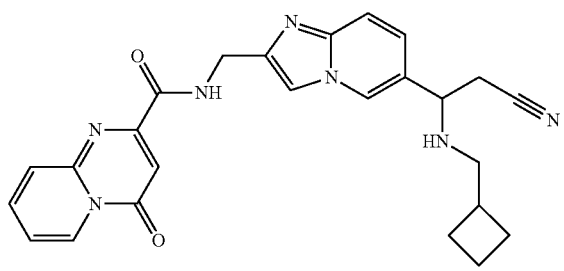 [SMILES: N#CCC(NCC1CCC1)c1ccc2nc(CNC(=O)c3cc(=O)n4ccccc4n3)cn2c1]

tert-butyl N-[[6-[2-cyano-1-(cyclobutylmethylamino)ethyl]imidazo[1,2-a]pyridin-2-yl]methyl]carbamate (21 mg, 0.06 mmol) was dissolved in hydrogen chloride solution (4 M in dioxane, 0.14 mL, 0.55 mmol) and stirred at room temperature for an hour.

The solvent was removed in vacuo and the resulting crude material was dissolved in DMF (1 mL) and treated with N-ethyl-N-isopropyl-propan-2-amine (0.048 mL, 0.274 mmol) and stirred at room temperature for 10 minutes.

In a separate flask were combined (4-oxopyrido[1,2-a]pyrimidine-2-carbonyl)oxylithium (11 mg, 0.0548 mmol), HATU (31 mg, 0.0821 mmol) and N-ethyl-N-isopropyl-propan-2-amine (0.048 mL, 0.274 mmol) in DMF (1 mL) at room temperature. The mixture was stirred for 5 minutes before the amine solution was added and resultant mixture was stirred at RT for 2 hours.

Water (2 mL) and IPA/CHCl3 (1:4, 5 mL) were added and the layers separated (phase sep cartridge). The organic filtrate was concentrated in vacuo to give a green oil. Purification over silica (Reversed phase, 12 g cartridge, water/MeCN+0.1% formic acid, 10 to 90%) and concentration of the fractions containing product in vacuo gave impure material.

The compound was further purified over silica (reversed phase 12 g cartridge, water/MeCN+0.1% NH3, 10 to 90%). And freeze dried to give the title compound (4.5 mg, 18%) as a white solid.

Method C: LC-MS (electrospray): m/z=456.4 (M+H)+, RT=2.53 min

Example 333: 4-oxo-N-[(6-piperazin-2-ylimidazo[1,2-a]pyridin-2-yl)methyl]pyrido[1,2-a]pyrimidine-2-carboxamide

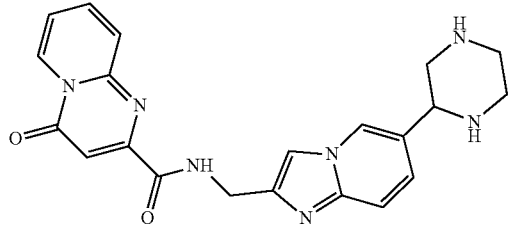 [SMILES: O=C(NCc1cn2cc(C3CNCCN3)ccc2n1)c1cc(=O)n2ccccc2n1]

The title compound was prepared from Example 49 using the procedure described for Compound 231 to give (12 mg, 15%) as a white solid.

Method C: LC-MS (electrospray): m/z=404.2 (M+H)+, RT=1.39 min

Example 334: N-[[6-(6-cyclohexyl-4-oxo-2-piperidyl)imidazo[1,2-a]pyridin-2-yl]methyl]-4-oxopyrido[1,2-a]pyrimidine-2-carboxamide

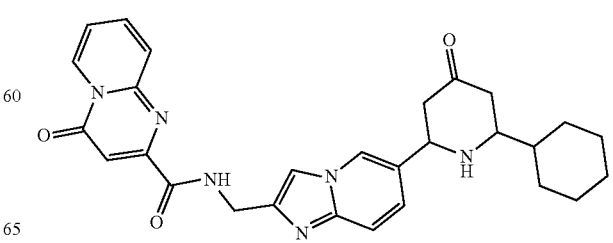

Step 1: tert-butyl N-[cyclohexyl(p-tolylsulfonyl)methyl]carbamate

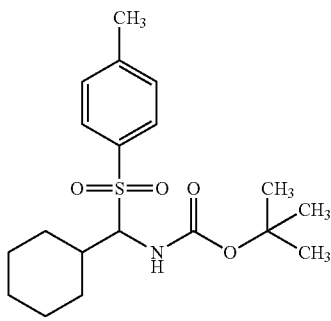 [SMILES: Cc1ccc(S(=O)(=O)C(NC(=O)OC(C)(C)C)C2CCCCC2)cc1]

A mixture of cyclohexanecarbaldehyde (2.24 g, 20.0 mmol), tert-butyl carbamate (2.34 g, 20.0 mmol), sodium; 4-methylbenzenesulfinate (3.56 g, 20.0 mmol), water (40 mL), methanol (20 mL) and formic acid (5 mL) was stirred for 15 minutes (until it became homogenous) and then left standing for 18 hours at RT. The crystalline product was filtered off with suction, washed successively with water (30 mL) and diethyl ether (30 mL) and dried in the vacuum oven at 45° C. for 4 hours to afford The title compound (4.81 g, 65%) as a white solid.

$^1$HNMR (500 MHz, Chloroform-d) δ 1.03-1.45 (m, 14H), 1.58-1.72 (m, 2H), 1.74-1.80 (m, 2H), 2.06-2.20 (m, 1H), 2.35-2.49 (m, 4H), 4.44-4.70 (m, 1H), 4.87-5.21 (m, 1H), 7.28-7.36 (m, 2H), 7.73-7.80 (m, 2H).

Step 2: 4-amino-4-cyclohexyl-butan-2-one hydrochloride

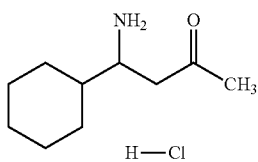

To a solution tert-butyl N-[cyclohexyl(p-tolylsulfonyl)methyl]carbamate (1.84 g, 5.00 mmol) in THF-Anhydrous (30 mL) was added potassium; 2-methylpropan-2-olate (95%, 1.18 g, 10.0 mmol) at 0° C. The mixture was stirred for 10 minutes before a solution of tert-butyl 3-oxobutanoate (0.79 g, 5.00 mmol) in THF-Anhydrous (10 mL) was added dropwise via syringe. The reaction was allowed to warm slowly to room temperature and was stirred for 2 hours. The reaction was then cooled to 0° C. (ice-bath) and quenched with NH4Cl (sat, 12.5 mL). Diethyl ether (50 mL) was added and the organic layer was separated. The aqueous layer was extracted with diethyl ether (25 mL). The combined organic layers were washed with brine (30 mL), dried (MgSO4) and concentrated at reduced pressure to give a clear colourless oil. The oil was treated with HCl (3M, 15 mL) and the mixture was heated at reflux with efficient stirring for 2 hours. Water and the excess HCl were removed at reduced pressure to afford the title compound (0.86 g, 79%) as a brown oil that was used without further purification.

$^1$HNMR (500 MHz, Methanol-d4) δ 1.05-1.90 (m, 11H), 2.23 (s, 3H), 2.80 (dd, J=19.0, 9.1 Hz, 1H), 3.01 (dd, J=19.0, 3.2 Hz, 1H), 3.38-3.48 (m, 1H).

Step 3: N-[[6-(6-cyclohexyl-4-oxo-2-piperidyl)imidazo[1,2-a]pyridin-2-yl]methyl]-4-oxo-pyrido[1,2-a]pyrimidine-2-carboxamide

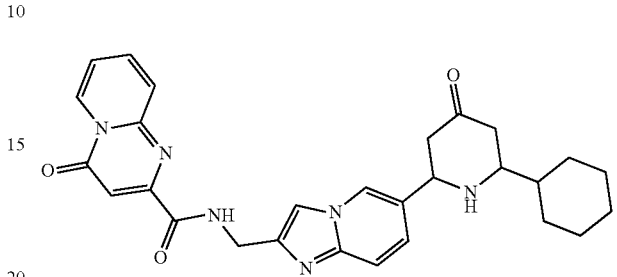

To a solution of 4-amino-4-cyclohexyl-butan-2-one hydrochloride (54 mg, 0.24 mmol) in ethanol (2 mL) was added DL-Proline (5.5 mg, 0.0477 mmol), magnesium sulfate (29 mg, 0.24 mmol), triethylamine (0.033 mL, 0.24 mmol) and N-[(6-formylimidazo[1,2-a]pyridin-2-yl)methyl]-4-oxo-pyrido[1,2-a]pyrimidine-2-carboxamide Example 49 (92 mg, 0.24 mmol) and the mixture was stirred at room temperature for 6 hours. NaHCO$_3$ (sat, 10 mL) was added and the mixture was extracted with EtOAc (3×15 mL). The combined extracts were washed with brine (10 mL), dried (Na$_2$SO$_4$), and concentrated at reduced pressure.

The residue was purified by open access preparative HPLC (Method B) The product containing fractions were combined and concentrated to dryness under reduced pressure.

The residue was dissolved acetonitrile and water (1:1, 4 mL) and lyophilised to afford the title compound (24 mg, 19%) as an off-white solid as a 7:3 mixture of cis and trans diastereoisomers.

Method C: LC-MS (electrospray): m/z=499.4 (M+H)$^+$, RT=2.99 min

Example 335: 1-[2-(1H-indazol-4-yl)thiazol-5-yl]-1-(6-methylimidazo[1,2-a]pyridin-2-yl)ethanol

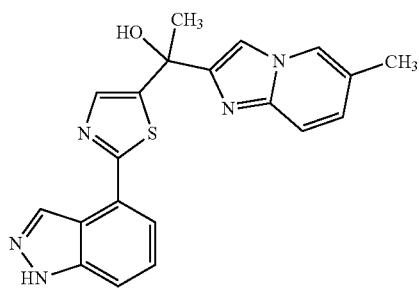 [SMILES: Cc1ccc2nc(C(C)(O)c3cnc(-c4cccc5[nH]ncc45)s3)cn2c1]

Step 1: (6-methylimidazo[1,2-a]pyridin-2-yl)-[2-(1-tetrahydropyran-2-ylindazol-4-yl)thiazol-5-yl]methanone

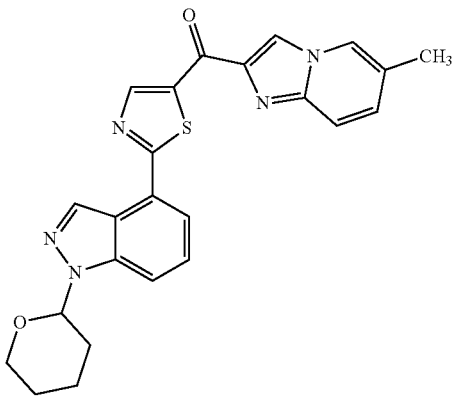 [SMILES: Cc1ccc2nc(C(=O)c3cnc(-c4cccc5c4cnn5C4CCCCO4)s3)cn2c1]

A solution of (6-methylimidazo[1,2-a]pyridin-2-yl)-[2-(1-tetrahydropyran-2-ylindazol-4-yl)thiazol-5-yl]methanol Compound 258 Step 1 (190 mg, 0.43 mmol) was dissolved in DCM (5 ml) was treated with Dess-Martin periodinane (271 mg, 0.64 mmol) and the mixture was stirred at room temperature for 2 hours.

The reaction was quenched with NaHCO$_3$ (sat, 20 ml) and extracted with chloroform/isopropanol (3:1, 3×20 ml). The combined organic extracts were dried over sodium sulfate and evaporated under vacuum.

The residue was purified by chromatography on SiO$_2$ (Biotage 25 g kp-Sil, eluting with EtOAc/heptane 0-100%) to afford the title compound (117 mg 53%) as a yellow solid Method A: LC-MS (electrospray): m/z=444.2 (M+H)$^+$, RT=1.35 min Step 2: 1-[2-(1H-indazol-4-yl)thiazol-5-yl]-1-(6-methylimidazo[1,2-a]pyridin-2-yl)ethanol

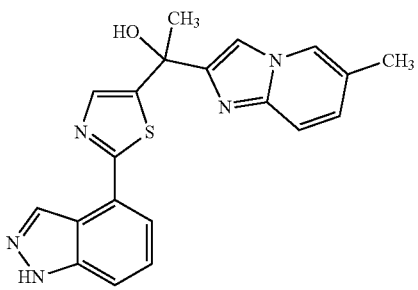 [SMILES: Cc1ccc2nc(C(C)(O)c3cnc(-c4cccc5[nH]ncc45)s3)cn2c1]

A suspension of (6-methylimidazo[1,2-a]pyridin-2-yl)-[2-(1-tetrahydropyran-2-ylindazol-4-yl)thiazol-5-yl]methanone (110 mg, 0.25 mmol) in THF (Anhydrous, 10 ml) was cooled in an ice/water bath. MeMgBr (3M in Et2O, 165 μl, 0.496 mmol) was added dropwise and the dark red mixture was stirred under cooling for 45 minutes.

The reaction mixture was quenched with NH$_4$Cl (sat, 20 ml), warmed to room temperature and extracted with chloroform/isopropanol (3:1, 3×20 ml). The combined organic extracts were dried over sodium sulfate and evaporated under vacuum.

The residue was dissolved in methanol (3 ml), treated with HCl (4M in Dioxane, 3 ml) and incubated at room temperature for 3 hours.

The reaction mixture was evaporated under vacuum. The residue was purified by ion exchange (SCX-2 cartridge (5 g) washed with DCM and MeOH and eluted with NH$_3$/MeOH (7M) and the basic eluent evaporated under vacuum.

The residue was purified by Preparative HPLC (method B) and the clean product-containing fractions combined and evaporated under vacuum. The residue was triturated with EtOAc/heptane to afford the title compound (32 mg, 34%) as an off-white solid.

Method D: LC-MS (electrospray): m/z=376.3 (M+H)$^+$, RT=3.24 min

Intermediate 62: 4-azido-1H-indazole

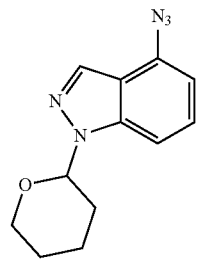 [SMILES: [N-]=[N+]=Nc1cccc2c1cnn2C1CCCCO1]

Step-1: 1H-indazol-4-amine

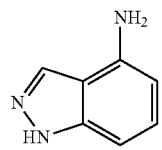

To a solution of 4-nitro-1H-indazole (50.0 g, 153.33 mmol) in MeOH (500 ml) was added Pd/C (50% wet) (10%, 5.00 g) at room temperature. The reaction mixture was placed under a an atmosphere of hydrogen and stirred at room temperature for 5 hours. The reaction mixture was filtered through celite pad and washed with additional methanol (3×200 ml). The combined filtrate was concentrated under vacuum to afford the title compound (14.0 g, 34%).

Method G: LC-MS (electrospray): m/z=134.0 (M+H)$^+$, RT=0.49 min

Step-2: 4-azido-1H-indazole

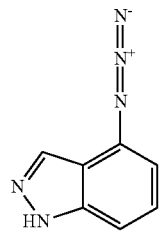 [SMILES: [N-]=[N+]=Nc1cccc2[nH]ncc12]

To a solution of 1H-indazol-4-amine (0.50 g, 3.14 mmol) in acetonitrile (5 ml) was added tert butyl nitrite (1.16 g, 12.57 mmol) followed by addition of sodium azide (0.97 g, 15.7 mmol) at 0° C. The resulting reaction mixture was stirred at 60° C. for 16 h. The reaction mixture was cooled to room temperature. This procedure was repeated five times and the combined reactions were poured into water (250 ml). The mixture was extracted with ethyl acetate (3×100 mL). The combined organic layer were dried (Na$_2$SO$_4$) and concentrated under vacuum. The crude material was purified by chromatography on SiO$_2$ (60-120) eluting with 15% EtOAc in hexane to afford the title compound (0.90 g, 25%). LCMS: 1.504 min, MS: ES+160.1 (M+1);

Method G: LC-MS (electrospray): m/z=160.1 (M+H)$^+$, RT=1.50 min

Step-3: 4-azido-1-(tetrahydro-2H-pyran-2-yl)-1H-indazole

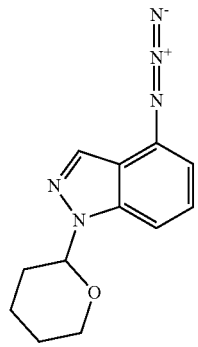 [SMILES: [N-]=[N+]=Nc1cccc2c1cnn2C1CCCCO1]

To a solution of 4-azido-1H-indazole (1.0 g, 6.3 mmol) in EtOAc (10 ml) was added dihydropyran (1.30 g, 15.5 mmol) followed by TFA (0.07 g, 0.63 mmol) at 0° C. and the resulting reaction mixture was stirred at 70° C. temperature for 4 hours.

The reaction mixture was allowed to cool to room temperature, poured into saturated NaHCO$_3$ (sat, 100 ml) and extracted with ethyl acetate (2×50 ml). The organic layer was dried (Na$_2$SO$_4$) and concentrated under vacuum. The crude material was purified by chromatography on SiO$_2$ (60-120) eluting with 8% EtOAc in hexane to afford the title compound (0.9 g, 59%).

Method G: LC-MS (electrospray): m/z=244.1 (M+H)$^+$, RT=2.07 min

Intermediate 63: 2-(prop-2-yn-1-yl)imidazo[1,2-a]pyridine

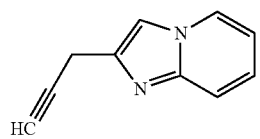

Step-1: imidazo[1,2-a]pyridin-2-ylmethanol

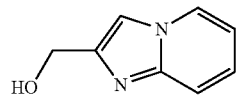 [SMILES: OCc1cn2ccccc2n1]

A solution of ethyl imidazo[1,2-a]pyridine-2-carboxylate (10.00 g, 52.5 mmol) in THF (40 ml) was added dropwise to a cold (0° C.) solution of LiAlH$_4$ (2M in THF, 34.2 ml, 68.3 mmol) in THF (60 ml) and the resulting reaction mixture was stirred at 0° C. for 1 hour. The reaction mixture was quenched with NaOH (10%, 50 ml) and the slurry was filtered through Celite. The filtrate was extracted with methanol in DCM (10% 7×50 ml). The combined organic layers were dried (Na$_2$SO$_4$) and concentrated under reduced pressure to afford the title compound (7.5 g, 96%).

Method H: LC-MS (electrospray): m/z=149.3 (M+H)$^+$, RT=1.22 min

Step-2: 2-(chloromethyl)imidazo[1,2-a]pyridine

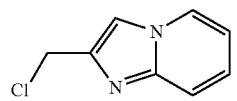 [SMILES: ClCc1cn2ccccc2n1]

To a solution of imidazo[1,2-a]pyridin-2-ylmethanol (7.50 g, 50.7 mmol) in DCM (100 ml) was added SOCl$_2$ (4.4 ml, 60.7 mmol) at 0° C. dropwise and the mixture was stirred at 0° C. for 1 hour. The mixture was diluted with NaHCO$_3$ (sat, 200 ml) and extracted with DCM (4×50 ml). The combined organics were dried (Na$_2$SO$_4$) and concentrated under reduced pressure to afford the title compound (6.5 g, 39.14 mmol).

Method G: LC-MS (electrospray): m/z=166.9 (M+H)$^+$, RT=1.10 min

Step-3: 2-(3-(trimethylsilyl)prop-2-yn-1-yl)imidazo[1,2-a]pyridine

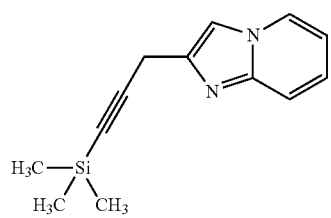 [SMILES: C[Si](C)(C)C#CCc1cn2ccccc2n1]

A mixture of 2-(chloromethyl)imidazo[1,2-a]pyridine (1.50 g, 9.0 mmol), potassium carbonate (3.72 g, 27.0 mmol) and Cu—I (0.17 g, 0.9 mmol) in DMF (15 ml) was de-oxygenated via a stream of N$_2$ for 15 minutes. TMS acetylene (6.3 ml, 45.0 mmol) was added and the resulting mixture was heated at 70° C. temperature for 10 hours. The mixture was diluted with ice cold water (300 ml) and extracted with EtOAc (3×150 ml). The combined organic layers were dried (Na$_2$SO$_4$) filtered and concentrated under reduced pressure. The crude was purified by column chromatography on SiO2 eluting with 5% EtOAc in hexane to afford the title compound (0.13 g, 6.3%).

Method G: LC-MS (electrospray): m/z=229.1 (M+H)$^+$, RT=1.31 min

Step-4: 2-(prop-2-yn-1-yl)imidazo[1,2-a]pyridine

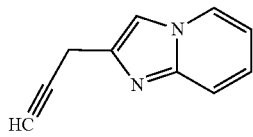

To a solution of 2-(3-(trimethylsilyl)prop-2-yn-1-yl)imidazo[1,2-a]pyridine (0.23 g, 1.0 mmol) in THF (3 ml) was added TBAF (1M in THF, 0.10 ml, 1.0 mmol) at −20° C. temperature dropwise and the mixture was stirred at −10° C. for 15 minutes before it was diluted with NaHCO$_3$ (sat, 50 ml) and extracted with EtOAc (4×30 ml). The extracts were dried (Na$_2$SO$_4$) and concentrated under reduced pressure to afford the title compound (0.15 g, 96%).

Method I: LC-MS (electrospray): m/z=157.28 (M+H)$^+$, RT=1.62 min

Example 336: 4-(4-(imidazo[1,2-a]pyridin-2-ylmethyl)-1H-1,2,3-triazol-1-yl)-1H-indazole

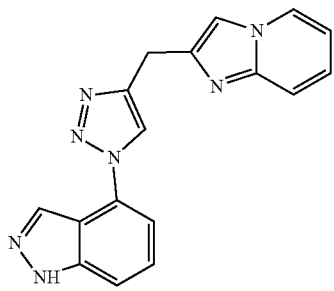 [SMILES: c1cc(-n2cc(Cc3cn4ccccc4n3)nn2)c2cn[nH]c2c1]

A mixture of 2-(prop-2-yn-1-yl)imidazo[1,2-a]pyridine Intermediate 63 (0.10 g, 0.64 mmol), 4-azido-1H-indazole Intermediate 62 (0.1 g, 0.64 mmol), sodium ascorbate (0.013 g, 0.064 mmol) and CuSO4 (0.037 g, 0.230 mmol) in tert-butanol: water (1:1, 3 ml) was heated in a microwave reactor at 100° C. for 30 minutes. The resultant mixture was concentrated under reduced pressure and the residue was purified by reverse phase column chromatography using C18 silica gel and product (eluted at 30% MeCN in water) to afford the title product (32 mg, 16%).

Method D: LC-MS (electrospray): m/z=316.3 (M+H)$^+$, RT=2.94 min

Example 337: [(3,3-difluorocyclobutyl)methyl][(2-{[1-(1H-indazol-4-yl)-1H-1,2,3-triazol-4-yl]methyl}imidazo[1,2-a]pyridin-6-yl)methyl]amine

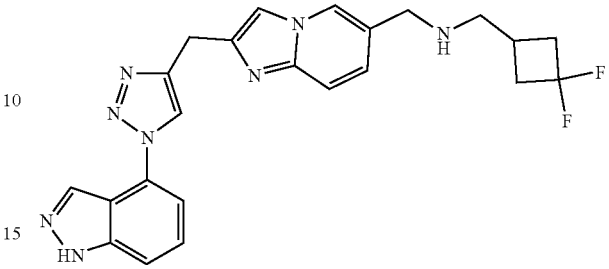

Step 1: methyl 2-(chloromethyl)imidazo[1,2-a]pyridine-6-carboxylate

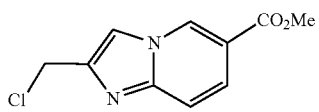 [SMILES: COC(=O)c1ccc2nc(CCl)cn2c1]

To a stirred Solution of methyl 6-aminonicotinate (40.0 g, 262.8 mmol) in acetonitrile (400 ml) was added 1, 3-dichloropropan-2-one (66.73 g, 525.6 mmol) at room temperature under a nitrogen atmosphere and the resulting reaction mixture was heated at 80° C. temperature for 16 hours. The mixture was cooled to room temperature, diluted with NaHCO$_3$ (sat, 500 ml) and extracted with DCM (3×500 ml). The combined organics were dried (Na$_2$SO$_4$), concentrated under reduced pressure and purified by column chromatography on SiO$_2$ (60-120) eluting with 5% acetone/DCM to afford the title compound (28.0 g, 64%).

Method G: LC-MS (electrospray): m/z=225.2 (M+H)$^+$, RT=0.95 min

Step 2: (2-(chloromethyl)imidazo[1,2-a]pyridin-6-yl)methanol

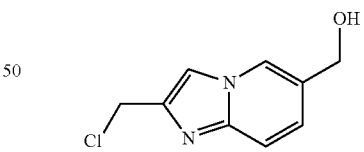

To a stirred Solution of methyl 2-(chloromethyl)imidazo[1,2-a]pyridine-6-carboxylate (9.50 g, 42.3 mmol) in THF (dry, 200 ml) was added DIBAL-H (1M in THF, 168.8 ml, 168.8 mmol) at 0° C., under a nitrogen atmosphere, and the resulting mixture was stirred at room temperature for 2 hours. The mixture was cooled at 0° C., quenched with MeOH (70 ml) and diluted with DCM (500 ml). The resulting slurry was filtered through a Celite bed washing with DCM (3×250 ml). The filtrate was washed with NaHCO$_3$ (sat, 2×100 ml), dried (Na$_2$SO$_4$), concentrated under reduced pressure and purified by column chromatography on SiO$_2$ (60-120) eluting with 5% MeOH in DCM to give the title compound (4.0 g, 42%).

Method H: LC-MS (electrospray): m/z=197.4 (M+H)+, RT=1.42 min

Step 3: (2-(prop-2-yn-1-yl)imidazo[1,2-a]pyridin-6-yl)methanol

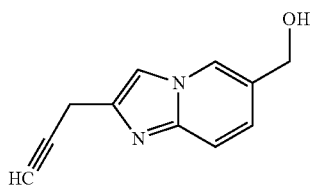

To a stirred Solution of (2-(chloromethyl)imidazo[1,2-a]pyridin-6-yl)methanol (0.50 g, 2.5 mmol) in THF (dry, 10 ml) in a sealed tube was added ethynylmagnesium bromide (0.5 M in THF, 40 ml, 20 mmol) at room temperature, under a nitrogen atmosphere and the mixture was heated at 70° C. for 16 hours. The resulting reaction mixture was cooled at room temperature, diluted with ammonium bicarbonate (sat, 25 ml) and extracted with DCM (3×30 ml). The extracts were dried ($Na_2SO_4$), concentrated under reduced pressure and purified by column chromatography on (neutral alumina) eluting with 5% MeOH in DCM to give the title compound (0.197 g, 42%).

Method G: LC-MS (electrospray): m/z=187.1 (M+H)+, RT=0.63 min

Step 4: (2-((1-(1-(tetrahydro-2H-pyran-2-yl)-1H-indazol-4-yl)-1H-1,2,3-triazol-4-yl)methyl)imidazo[1,2-a]pyridin-6-yl)methanol

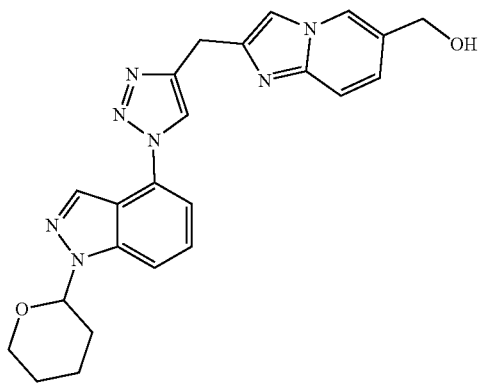 [SMILES: OCc1ccc2nc(Cc3cn(-c4cccc5c4cnn5C4CCCCO4)nn3)cn2c1]

To a stirred solution of (2-(prop-2-yn-1-yl)imidazo[1,2-a]pyridin-6-yl)methanol (0.19 g, 1.0 mmol) in tert-BuOH:water (1:1, 10 ml) was added 4-azido-1-(tetrahydro-2H-pyran-2-yl)-1H-indazole Intermediate 62 (0.24 g, 1.0 mmol), sodium ascorbate (0.019 g, 0.10 mmol) and CuSO4 (0.063 g, 0.4 mmol) at room temperature under nitrogen atmosphere and the resulting mixture was heated at 100° C. for 16 hours. The mixture was cooled to room temperature, diluted with water (25 ml) and extracted with MeOH:DCM (10%, 3×30 ml). The extracts were dried ($Na_2SO_4$), concentrated under reduced pressure and purified by column chromatography (neutral alumina) eluting with 5% MeOH in DCM to give the title compound (0.25 g, 67%).

Method G: LC-MS (electrospray): m/z=430.2 (M+H)+, RT=1.20 min

Step 5: 2-((1-(1-(tetrahydro-2H-pyran-2-yl)-1H-indazol-4-yl)-1H-1,2,3-triazol-4-yl)methyl)imidazo[1,2-a]pyridine-6-carbaldehyde

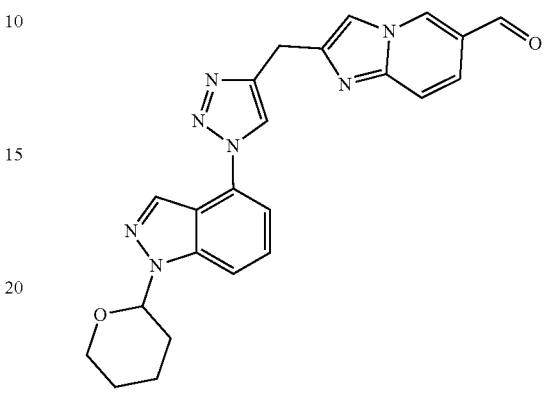

To a stirred solution of (2-((1-(1-(tetrahydro-2H-pyran-2-yl)-1H-indazol-4-yl)-1H-1,2,3-triazol-4-yl)methyl)imidazo[1,2-a]pyridin-6-yl)methanol (0.25 g, 0.58 mmol) in DCM (10 ml) was added Dess-Martin periodinane (0.424 g, 1.164 mmol) at 0° C. under a nitrogen atmosphere and the reaction mixture was stirred at room temperature for an hour.

The mixture was diluted with NaHCO3 (sat, 25 ml) and extracted with DCM (3×30 ml). The extracts were dried ($Na_2SO_4$) and concentrated under reduced pressure to give the title compound (0.25 g, 100%).

Method G: LC-MS (electrospray): m/z=428.2 (M+H)+, RT=1.34 min

Step 6: 1-(2-((1-(1H-indazol-4-yl)-1H-1,2,3-triazol-4-yl)methyl)imidazo[1,2-a]pyridin-6-yl)-N-((3,3-difluorocyclobutyl)methyl)methan amine

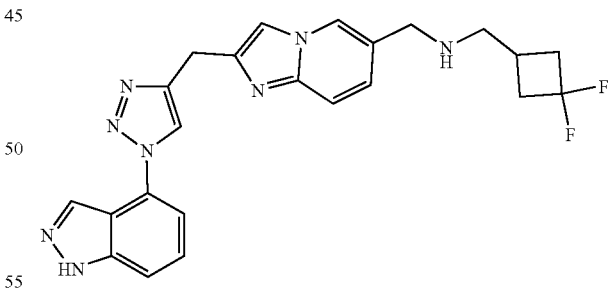

To a stirred solution of 3,3-difluorocyclobutyl)methanamine hydrochloride (0.118 g, 0.878 mmol) in DCE (10 ml) was added $Et_3N$ (0.140 ml, 1.170 mmol) at room temperature. 2-((1-(1-(tetrahydro-2H-pyran-2-yl)-1H-indazol-4-yl)-1H-1,2,3-triazol-4-yl)methyl)imidazo[1,2-a]pyridine-6-carbaldehyde (0.250 g, 0.585 mmol) was added followed by AcOH (0.003 g, 0.058 mmol) at room temperature and the mixture was stirred for 10-15 min before the mixture was cooled to 0° C., Na(OAc)3BH (0.42 g, 2.340 mmol) was added and the mixture was stirred at room temperature for 15 hours.

The mixture was cooled to 0° C., NaBH₄ (0.018 g, 0.585 mmol) was added and the mixture was stirred at room temperature for an hour. The mixture was diluted with water (25 ml) and extracted with DCM (3×30 ml). The extracts were dried (Na₂SO₄) and concentrated under reduced pressure to give the intermediate product.

The intermediate product was dissolved in 1,4-dioxane (5.0 ml), cooled to 0° C. and HCl (4M in dioxane, 0.400 ml, 1.652 mmol) was added dropwise and the resulting mixture was stirred at room temperature for 1 hour.

The mixture was diluted with DCM (15 ml) quenched with NaHCO₃ (sat, 50 ml) and extracted with DCM (3×50 ml). The extracts were dried (Na2SO4), concentrated under reduced pressure and purified by reverse phase flash chromatography using C18 silica eluting with 30% acetonitrile in water to give the title compound (37 mg, 14%) as a white solid.

Method C: LC-MS (electrospray): m/z=449.4 (M+H)⁺, RT=2.48 min

Intermediate 64: 4-[1-({6-formylimidazo[1,2-a]pyridin-2-yl}methyl)-1H-1,2,3-triazol-4-yl]-1-(oxan-2-yl)-1H-indazole-6-carbonitrile

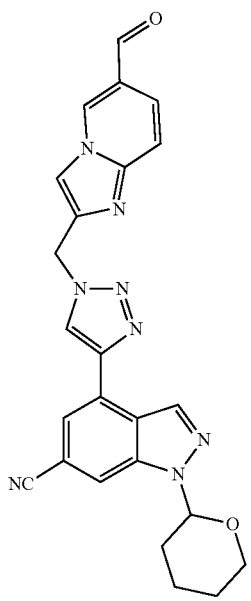 [SMILES: N#Cc1cc(-c2cn(Cc3cn4cc(C=O)ccc4n3)nn2)c2cnn(C3CCCCO3)c2c1]

The title compound was prepared from 4-bromo-1H-indazole-6-carbonitrile in a similar fashion to Intermediate 34 giving (313 mg, 78%) as a beige powder.

Method C: LC-MS (electrospray): m/z=453.3 (M+H)⁺, RT=2.96 min

Example 338: 4-{1-[(6-{[(cyclobutylmethyl)amino]methyl}imidazo[1,2-a]pyridin-2-yl)methyl]-1H-1,2,3-triazol-4-yl}-1H-indazole-6-carbonitrile

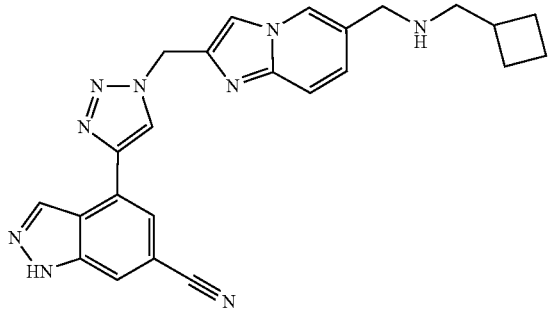 [SMILES: N#Cc1cc(-c2cn(Cc3cn4cc(CNCC5CCC5)ccc4n3)nn2)c2cn[nH]c2c1]

The title compound was prepared from intermediate 64 using the procedure described for Compound 250 to give (42 mg, 38%) as an off-white solid.

Method C: LC-MS (electrospray): m/z=438.4 (M+H)⁺, RT=2.73 min

Example 339: N-(cyclobutylmethyl)-1-[2-[[4-(1H-indazol-4-yl)imidazol-1-yl]methyl]imidazo[1,2-a]pyridin-6-yl]methanamine

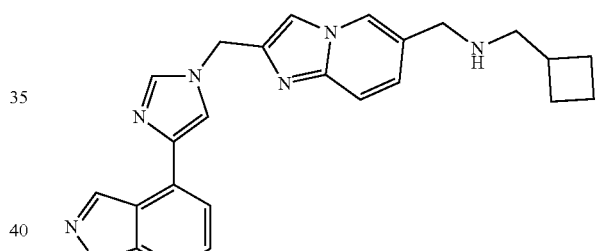

Step 1: 4-(1H-imidazol-4-yl)-1-tetrahydropyran-2-yl-indazole

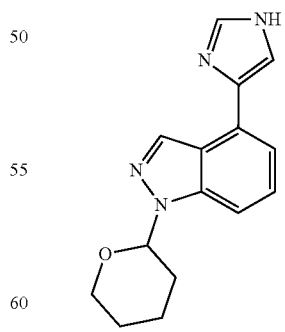

1-tetrahydropyran-2-yl-4-(4,4,5,5-tetramethyl-1,3,2-dioxaborolan-2-yl)indazole (700 mg, 1.75 mmol), 4-bromo-1H-imidazole (397 mg, 2.62 mmol), Pd(OAc)₂ (39 mg, 0.17 mmol), A-ta-Phos (111 mg, 0.42 mmol) and K₂CO₃ (1.2M aqueous, 4.4 ml, 5.25 mmol) were combined in 1,4-Dioxane (10 ml) and the mixture was sparged with nitrogen for 5 minutes. The vessel was sealed and the mixture was heated at 115° C. for 3 hours. The mixture was cooled to room temperature and more K₂CO₃ (1.2M aqueous, 1 ml, 1.2 mmol), Pd(OAc)₂ 39 mg, 0.17 mmol) and A-ta-Phos (111 mg, 0.42 mmol) were added the mixture was sparged with nitrogen for 5 minutes and heated at 115° C. for 3 hours. The mixture was cooled to room temperature and more K₂CO₃ (1.2M aqueous, 1 ml, 1.2 mmol), Pd(OAc)₂ 39 mg, 0.17 mmol) and A-ta-Phos (111 mg, 0.42 mmol) were added the mixture was sparged with nitrogen for 5 minutes and heated at 115° C. for 17 hours.

The reaction mixture was cooled to room temperature, diluted with water (40 ml) and extracted with chloroform/isopropanol (3:1, 3×40 ml). The organic extracts were dried over sodium sulfate and evaporated under vacuum. The residue was purified chromatography on SiO₂ (Biotage kp-NH 28 g, eluting with EtOAc/heptane 0-100% followed by MeOH/EtOAc 0-20%) to afford the title compound 405 mg, 73%) as a white solid.

Method B: LC-MS (electrospray): m/z=269.2 (M+H)⁺, RT=1.35 min

Step 2: [2-[[4-(1-tetrahydropyran-2-ylindazol-4-yl)imidazol-1-yl]methyl]imidazo[1,2-a]pyridin-6-yl]methanol

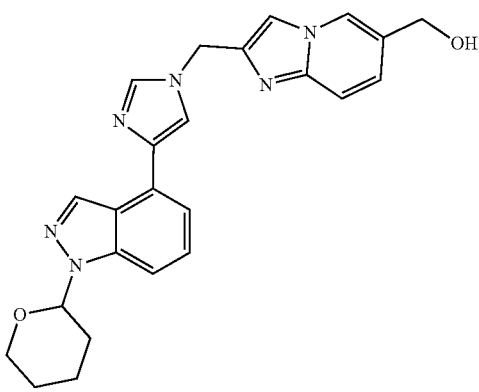 [SMILES: OCc1ccc2nc(Cn3cnc(-c4cccc5c4cnn5C4CCCCO4)c3)cn2c1]

4-(1H-imidazol-4-yl)-1-tetrahydropyran-2-yl-indazole (400 mg, 1.27 mmol), [2-(chloromethyl)imidazo[1,2-a]pyridin-6-yl]methanol Intermediate 34 Step 2 (274 mg, 1.39 mmol), Cs₂CO₃ (1.24 g, 3.80 mmol) and NaI (19 mg, 0.13 mmol) were combined in DMF (10 ml) and the mixture was at heated at 80° C. for an hour. The mixture was cooled to room temperature, further [2-(chloromethyl)imidazo[1,2-a]pyridin-6-yl]methanol (274 mg, 1.39 mmol) was added the mixture was at heated at 80° C. for 16 hours.

The reaction mixture was cooled to room temperature, diluted with water (80 ml) and extracted with chloroform/isopropanol (3:1, 3×50 ml) and the combined organic extracts dried over sodium sulfate and evaporated under vacuum. The residue was purified by chromatography on SiO₂ (Biotage, 28 g kp-NH, eluting with EtOAc/heptane 0-100% followed by MeOH/EtOAc 0-20%) to afford the title compound (259 mg, 31%) as a pale pink solid.

Method B: LC-MS (electrospray): m/z=429.3 (M+H)⁺, RT=1.33 min

Step 3: 2-[[4-(1-tetrahydropyran-2-ylindazol-4-yl)imidazol-1-yl]methyl]imidazo[1,2-a]pyridine-6-carbaldehyde

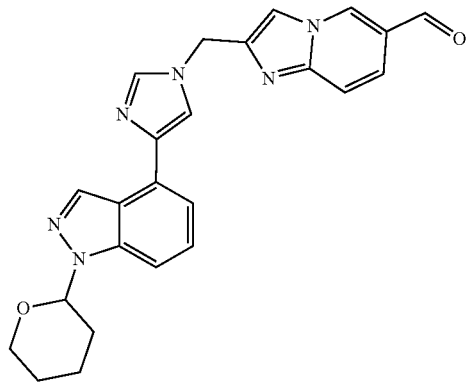 [SMILES: O=Cc1ccc2nc(Cn3cnc(-c4cccc5c4cnn5C4CCCCO4)c3)cn2c1]

The title compound was prepared from 2-[[4-(1-tetrahydropyran-2-ylindazol-4-yl)imidazol-1-yl]methyl]imidazo[1,2-a]pyridin-6-yl]methanol using the method described in Compound 268 Step 3 to afford the crude title compound (241 mg, 57%) as a pink solid which was used directly without further purification.

Method B: LC-MS (electrospray): m/z=427.2 (M+H)⁺, RT=1.40 min

Step 4: N-(cyclobutylmethyl)-1-[2-[[4-(1-tetrahydropyran-2-ylindazol-4-yl)imidazol-1-yl]methyl]imidazo[1,2-a]pyridin-6-yl]methanamine

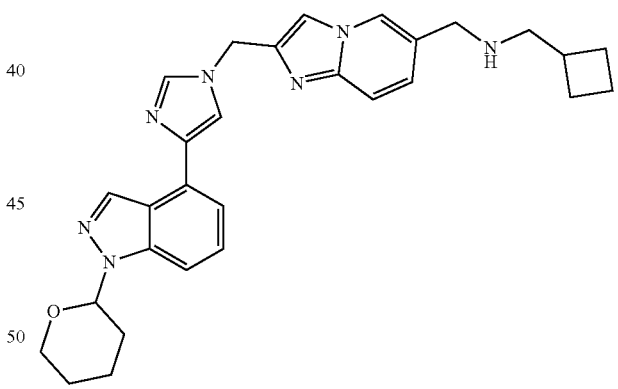

2-[[4-(1-tetrahydropyran-2-ylindazol-4-yl)imidazol-1-yl]methyl]imidazo[1,2-a]pyridine-6-carbaldehyde (250 mg, 0.59 mmol) and 1-cyclobutylmethanamine (100 mg, 1.17 mmol) were combined in 1,1,1,3,3,3-Hexafluoro-2-propanol (3 ml) and the mixture was incubated at room temperature for 1.5 hours. NaBH4 (67 mg, 1.76 mmol) was added along with a few drops of MeOH and the mixture was stood for 5 minutes before being quenched with MeOH (20 ml). The mixture was evaporated under vacuum and the residue was diluted NaHCO₃ (sat, 20 ml), extracted with chloroform/isopropanol (3:1, 3×30 ml) and the combined organic extracts dried over sodium sulfate and evaporated under vacuum. The residue was purified by chromatography on SiO₂ (Biotage 28 g kp-NH, eluting with EtOAc/heptane 0-100% followed by MeOH/EtOAc 0-20%) followed by further purification by reverse phase chromatography (30 g C18 Ultra, eluting with Acetonitrile+0.1% NH3/Water+0.1% NH3 10-100%) to afford the title compound (83 mg, 27%) as a yellow residue.

Method B: LC-MS (electrospray): m/z=496.3 (M+H)+, RT=1.59 min

Step 5: N-(cyclobutylmethyl)-1-[2-[[4-(1H-indazol-4-yl)imidazol-1-yl]methyl]imidazo[1,2-a]pyridin-6-yl]methanamine

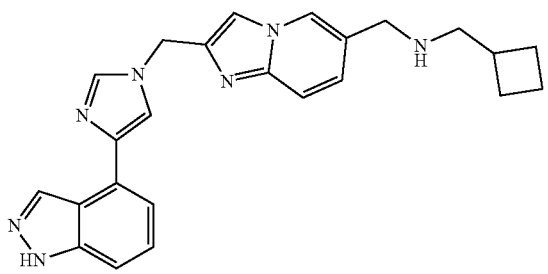 [SMILES: c1cc(-c2cn(Cc3cn4cc(CNCC5CCC5)ccc4n3)cn2)c2cn[nH]c2c1]

N-(cyclobutylmethyl)-1-[2-[[4-(1-tetrahydropyran-2-ylindazol-4-yl)imidazol-1-yl]methyl]imidazo[1,2-a]pyridin-6-yl]methanamine (83 mg, 0.17 mmol) was dissolved in MeOH (3 ml) and treated with HCl (4M in dioxane, 3 ml, 12 mmol) and the mixture was incubated at room temperature for 2 hours. The reaction mixture was filtered and the residue was purified by preparative HPLC (method B) to afford the title compound (16 mg, 27%) as a white solid.

Method D: LC-MS (electrospray): m/z=412.3 (M+H)+, RT=3.30 min

Example 340: N-[(6-{[N-(cyclobutylmethyl)acetamido]methyl}imidazo[1,2-a]pyridin-2-yl)methyl]-4-oxo-4H-pyrido[1,2-a]pyrimidine-2-carboxamide

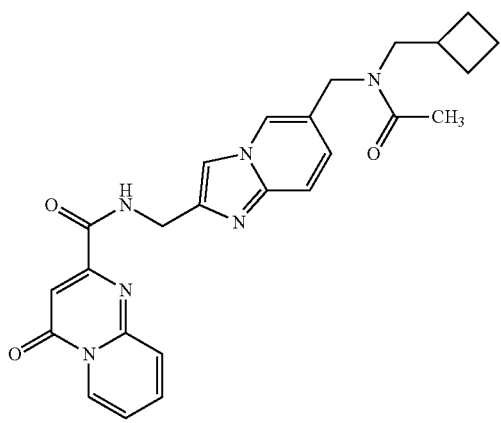 [SMILES: CC(=O)N(Cc1ccc2nc(CNC(=O)c3cc(=O)n4ccccc4n3)cn2c1)CC1CCC1]

A solution of N-[[6-[(cyclobutylmethylamino)methyl]imidazo[1,2-a]pyridin-2-yl]methyl]-4-oxo-pyrido[1,2-a]pyrimidine-2-carboxamide Compound 212 (72 mg, 0.17 mmol) in DCE (5 ml) was treated with acetic anhydride (162 μl, 1.71 mmol) and the mixture was stirred at room temperature for an hour.

The reaction was quenched with NaHCO3 (sat, 20 ml) and extracted with chloroform/isopropanol (3:1, 3×10 ml). The combined organic extracts were dried over sodium sulfate and evaporated under vacuum. The residue was purified by ion exchange (SCX-2, 2 g) washing with DCM and MeOH, and eluted with NH3 (7M in MeOH). The basic eluent was evaporated under a stream of nitrogen.

The residue was purified by preparative HPLC (Method B) and evaporated under vacuum to afford the title compound (59 mg, 75%) as a pale yellow solid.

Method D: LC-MS (electrospray): m/z=459.3 (M+H)+, RT=3.18 min

Example 341: N-(cyclobutylmethyl)-1-[2-[[3-(1H-indazol-4-yl)-1,2,4-triazol-1-yl]methyl]imidazo[1,2-a]pyridin-6-yl]methanamine

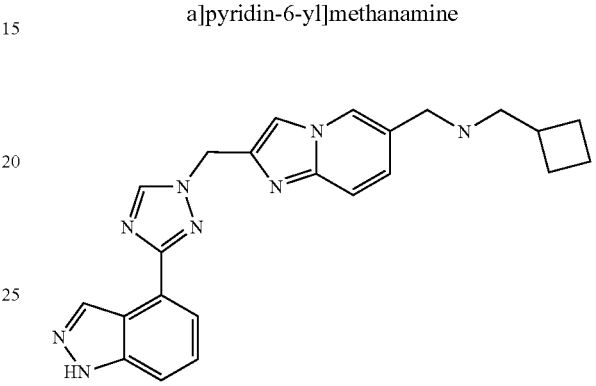

Step 1: 1-tetrahydropyran-2-ylindazole-4-carbonitrile

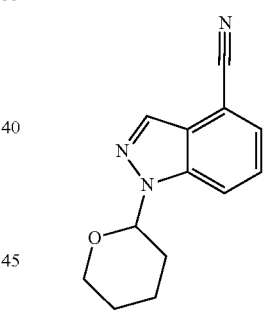

An oven-dried three-neck 25 mL RBF was charged with zinc cyanide (459 mg, 3.91 mmol), 4-bromo-1-tetrahydropyran-2-yl-indazole (1.00 g, 3.56 mmol), Pd(PPh3)4 (206 mg, 0.178 mmol) and anhydrous DMF (9 mL). The flask was equipped with a reflux condenser, the assembly flushed with nitrogen and then the reaction mixture was de-oxygenated by passing a stream of nitrogen gas for 5 min. The reaction was placed in a pre-heated heating block at 100° C. and stirred at this temperature for 3 hours. The reaction was cooled to room temperature and diluted with EtOAc (30 mL) and water (20 mL). The aqueous phase was extracted with EtOAc (2×30 mL). The combined organics were washed with brine (10 mL), dried over magnesium sulfate and concentrated to give a reddish oily solid which was purified by chromatography on SiO2 (Biotage 25 g) eluting with EtOAc/heptane (0-100%) to give the title compound (697 mg, 86%) as a white solid.

Method B: LC-MS (electrospray): m/z=228.3, (M+H)+, RT=1.6 min.

Step 2: 1-tetrahydropyran-2-yl-4-(1H-1,2,4-triazol-3-yl)indazole

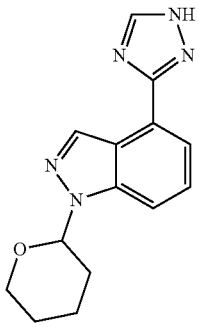

A flask was charged with 1-tetrahydropyran-2-ylindazole-4-carbonitrile (627 mg, 2.76 mmol), sodium methoxide (1.34 g, 24.8 mmol) and anhydrous methanol (10 mL) and the resulting suspension was stirred at room temperature for an hour before formic hydrazide (4.81 g, 80.0 mmol) was added and the reaction was heated at 65° C. for 16 hours. The mixture was cooled to room temperature and concentrated. The residue was partitioned between water (50 mL) and EtOAc (50 mL), the phases were separated and the aqueous was extracted with EtOAc (20 mL). The combined organic phases were washed with water (20 mL) and brine (20 mL), dried (MgSO$_4$) and concentrated under vacuum. The residue was purified by chromatography on SiO$_2$ (Biotage 25 g) eluting with EtOAc/heptane 0-100% followed by MeOH/DCM (0-50%) to give the title compound (113 mg, 12%) as a yellow solid.

Method B: LC-MS (electrospray): m/z=270.2, (M+H)+, RT=1.22 min.

Step 3: N-(cyclobutylmethyl)-1-[2-[[3-(1H-indazol-4-yl)-1,2,4-triazol-1-yl]methyl]imidazo[1,2-a]pyridin-6-yl]methanamine

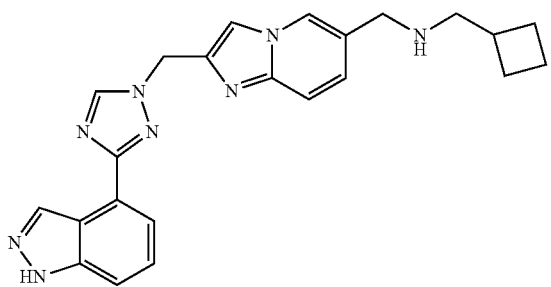

A suspension of 1-tetrahydropyran-2-yl-4-(1H-1,2,4-triazol-3-yl)indazole 113 mg, 0.344 mmol), sodium hydride (60%, 14 mg, 0.344 mmol) and DMF (anhydrous 2 mL) was stirred at room temperature for 20 minutes during which time it developed a deep red-brown colouration. A solution containing tert-butyl N-[[2-(chloromethyl)imidazo[1,2-a]pyridin-6-yl]methyl]-N-(cyclobutylmethyl)carbamate (138 mg, 0.378 mmol) in DMF (anhydrous 2 mL) was added, the flask was equipped with a reflux condenser and the reaction was stirred at 90° C. for 2 hours.

The mixture was cooled to room temperature, diluted with water (1 mL) and concentrated to a brown oil which was diluted with water (5 mL) and extracted with DCM (20 mL and 2×5 mL). The combined organics were washed with brine (5 mL) dried (MgSO$_4$) and concentrated to give a brown oil (303 mg). The residue was dissolved in ethanol (5 mL) treated with HCl (4M in dioxane 6 mL) and the resulting solution was stirred at room temperature for 16 hours. The mixture was concentrated and the resulting residue was suspended in HCl (4M in 1,4-dioxane 4 mL) and stirred at room temperature for 45 minutes. The mixture was concentrated under vacuum to give a brown solid which was dissolved in methanol (~50 mL) and the resulting solution was diluted with NaHCO$_3$ (sat, 10 mL), DCM (20 mL) and IPA/CHCl$_3$ (1:3, 20 mL). The organic phase was separated and the aqueous was extracted with IPA/CHCl$_3$ (1:3, 20+10 mL). The combined organics were washed with brine (5 mL), dried (MgSO$_4$) and concentrated to give the crude product as a brown oil (240 mg) which was purified by preparative HPLC (method B). The product containing fractions were combined and diluted with brine (10 mL) and extracted with DCM (3×10 mL). The combined organics were washed with brine (2×5 mL), dried (MgSO$_4$) and concentrated to give the title compound (60 mg, 42%) as a yellow solid.

Method C: LC-MS (electrospray): m/z=413.4, (M+H)+, RT=2.57 min.

Intermediate 65: tert-butyl N-{[2-(azidomethyl)imidazo[1,2-a]pyridin-6-yl]methyl}-N-(cyclobutylmethyl)carbamate

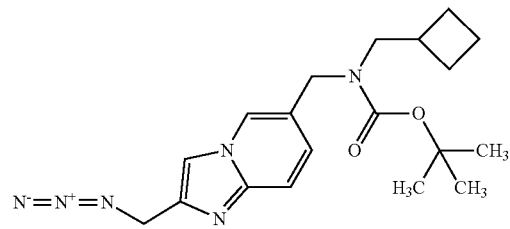 [SMILES: CC(C)(C)OC(=O)N(Cc1ccc2nc(CN=[N+]=[N-])cn2c1)CC1CCC1]

Step 1: [(6-chloropyridin-3-yl)methyl](cyclobutylmethyl)amine

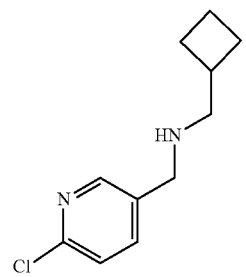 [SMILES: Clc1ccc(CNCC2CCC2)cn1]

A solution of 1-cyclobutylmethanamine (1.80 g, 21.2 mmol) in DCE (30 mL). was treated with 6-chloropyridine-3-carbaldehyde (2.50 g, 17.7 mmol) followed by magnesium sulfate (1.06 g, 8.83 mmol) and the reaction was stirred at room temperature for 1.5 hours. Sodium borohydride (0.67 g, 17.7 mmol) and MeOH (0.5 mL) were added and the mixture was stirred at room temperature for 17 hours. More Sodium borohydride (1.54 g, 40.7 mmol) and methanol (1.5 mL) were added and the mixture was stirred at room temperature for 5 hours and at 40° C., for 1.5 hours. The mixture was poured into NaHCO$_3$ (sat, 50 mL) and stirred for 20 minutes. The phases were separated and the aqueous phase extracted with DCM (2×25 mL). The combined organics were washed with brine (25 mL). The combined aqueous phases were extracted with DCM (25 mL). All the organic phases were combined, dried MgSO$_4$ and concentrated. to give a yellow oil which was purified by chromatography on SiO$_2$ (Biotage Kp-Sil 50 g) eluting with EtOAc. to give the title compound (1.89 g, 46%) as a pale yellow oil.

Method C: LC-MS (electrospray): m/z=210.9, (M+H)+, RT=2.95 min.

Step 2: tert-butyl N-[(6-chloro-3-pyridyl)methyl]-N-(cyclobutylmethyl) carbamate

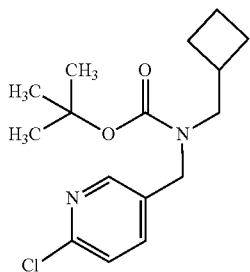 [SMILES: CC(C)(C)OC(=O)N(Cc1ccc(Cl)nc1)CC1CCC1]

A solution of Di-tert-butyl dicarbonate (3.76 g, 17.2 mmol) in MeCN (30 mL) was added to a flask containing 1-(6-chloro-3-pyridyl)-N-(cyclobutylmethyl)methanamine (3.44 g, 14.4 mmol) and the mixture was refluxed at 80° C. for 2 hours. The mixture was cooled to room temperature and concentrated to a yellow oil which was purified by chromatography on SiO$_2$ (Biotage Kp-Sil 100 g) eluting with EtOAc in heptane (0-15%) to give the title compound (4.47 g, 100%) as a colourless oil.

Method C: LC-MS (electrospray): m/z=311.2, (M+H)+, RT=4.32 min.

Step 3: tert-butyl N-[(6-amino-3-pyridyl)methyl]-N-(cyclobutylmethyl)carbamate

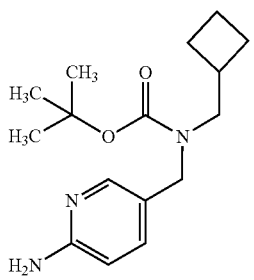 [SMILES: CC(C)(C)OC(=O)N(Cc1ccc(N)nc1)CC1CCC1]

An oven-dried 100 mL two-neck RBF was charged with tert-butyl N-[(6-chloro-3-pyridyl)methyl]-N-(cyclobutylmethyl)carbamate (4.40 g, 14.2 mmol), XPhos (1350 mg, 2.83 mmol) and Pd$_2$dba$_3$ (648 mg, 0.708 mmol). The flask was equipped with a reflux condenser and the assembly was flushed with nitrogen. THF (anhydrous, 47 mL) was added and the resulting solution was de-oxygenated by bubbling nitrogen for 30 minutes. [Bis(trimethylsilyl)amino]lithium (1M in THF, 21 mL, 21.2 mmol) was added with vigorous stirring dropwise over 5 minutes and the mixture was placed in a pre-heated heating block at 70° C. and stirred for 2 hours.

The mixture was cooled to room temperature, poured into NaHCO$_3$ (sat, 50 mL) and stirred for 5 minutes before the mixture was extracted with DCM (2×50 mL). The aqueous phase was diluted with brine (30 mL) and extracted with DCM (2×50 mL). The combined organics were washed with brine (30 mL). The brine washings were extracted with DCM (50 mL). All the organics were combined, dried (MgSO$_4$) and concentrated to give the crude product as a viscous brown oil which was purified by chromatography on SiO$_2$ (Biotage, Amino Duo D 55 g) eluting with EtOAc in heptane (0-100%) to give the title compound (3.25 g, 75%) as a light orange solid.

Method D: LC-MS (electrospray): m/z=292.3, (M+H)+, RT=4.24 min.

Step 4: tert-butyl N-[[2-(chloromethyl)imidazo[1,2-a]pyridin-6-yl]methyl]-N-(cyclobutylmethyl)carbamate

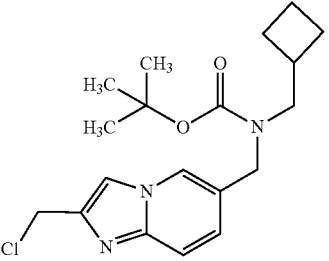 [SMILES: CC(C)(C)OC(=O)N(Cc1ccc2nc(CCl)cn2c1)CC1CCC1]

A mixture of tert-butyl N-[(6-amino-3-pyridyl)methyl]-N-(cyclobutylmethyl)carbamate (3.16 g, 10.3 mmol) in DME (anhydrous, 45 mL) was treated with 1,3-dichloropropan-2-one (1.44 g, 11.3 mmol) and the mixture was heated, with stirring, at 80° C. for 1.5 hours. More 1,3-dichloropropan-2-one (260 mg, 2 mmol) was added and the mixture was heated at 80° C. for 30 minutes. The mixture was cooled to room temperature and washed with NaHCO$_3$ (sat, 2×15 mL). The aqueous was extracted with EtOAc (2×20 mL) and the combined organics were dried (MgSO4) and concentrated to give the crude product as an orange-brown semi-solid. The product was purified by chromatography on neutral alumina (~250 g) eluting in a step gradient of EtOAc/heptane: 1:3 (500 mL), 1:2 (500 mL), 1:1 (1.5 L) to give the title compound (1.90 g, 49%) as a light yellow solid.

Method C: LC-MS (electrospray): m/z=364.2, (M+H)+, RT=3.89 min.

Step 5: tert-butyl N-[[2-(azidomethyl)imidazo[1,2-a]pyridin-6-yl]methyl]-N-(cyclobutylmethyl)carbamate

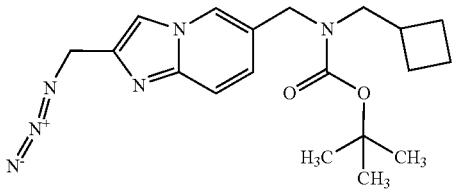 [SMILES: CC(C)(C)OC(=O)N(Cc1ccc2nc(CN=[N+]=[N-])cn2c1)CC1CCC1]

A vial was charged with sodium azide (300 mg, 4.62 mmol), sodium iodide (28 mg, 0.185 mmol), tert-butyl N-[[2-(chloromethyl)imidazo[1,2-a]pyridin-6-yl]methyl]-N-(cyclobutylmethyl)carbamate (700 mg, 1.85 mmol) and DMF (3.7 mL). The resulting suspension was stirred at room temperature for 2 hours. The mixture was diluted with water (3 mL) and extracted with EtOAc (3×10 mL). The combined organics were washed with brine (5 mL), dried (MgSO₄) and concentrated to give the crude product as a yellow oil which partially solidifies on standing. The material was purified by chromatography on SiO₂ (Botage 25 g) eluting with EtOAc/heptane (0-50%). The product to give the title compound (719 mg, 99%) as a yellow oil.

Method C: LC-MS (electrospray): m/z=371.4, (M+H)+, RT=3.91 min.

Example 342: 2-[1-[[6-[(cyclobutylmethylamino)methyl]imidazo[1,2-a]pyridin-2-yl]methyl]triazol-4-yl]pyrido[1,2-a]pyrimidin-4-one

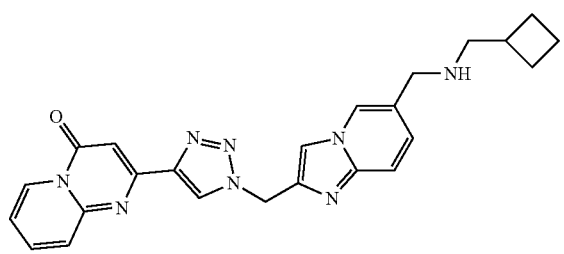 [SMILES: O=c1cc(-c2cn(Cc3cn4cc(CNCC5CCC5)ccc4n3)nn2)nc2ccccn12]

Step 1: 2-ethynylpyrido[1,2-a]pyrimidin-4-one

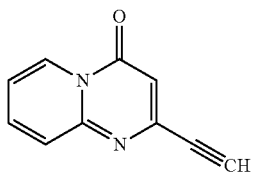

A mixture of 2-chloropyrido[1,2-a]pyrimidin-4-one (700 mg, 3.88 mmol), PdCl₂dppf (284 mg, 0.39 mmol), copper iodide (74 mg, 0.39 mmol) and trimethylamine (2.6 mL, 18.5 mmol) were combined in DMF (anhydrous, 4 mL) and sparged with nitrogen. Ethynyl(trimethyl)silane (1.6 mL, 11.6 mmol) was added and the mixture was briefly sparged with nitrogen and stirred at 100° C. for 16 hours.

The reaction mixture was cooled to room temperature diluted with NaHCO₃ (sat, 50 mL) and extracted with DCM (3×50 mL). The combined organic extracts were washed with NaHCO₃ (sat, 50 mL), dried over Na₂SO₄, and concentrated under vacuum. The residue was purified by chromatography on SiO₂ (Biotage 28 g SNAP NH, eluting with 0-50% EtOAc in heptane) to afford the title compound (302 mg, 46%) as a brown solid.

Method B: LC-MS (electrospray): m/z=171.2 (M+H)+, RT=1.14 min

Step 2: 2-[1-[[6-[(cyclobutylmethylamino)methyl]imidazo[1,2-a]pyridin-2-yl]methyl]triazol-4-yl]pyrido[1,2-a]pyrimidin-4-one

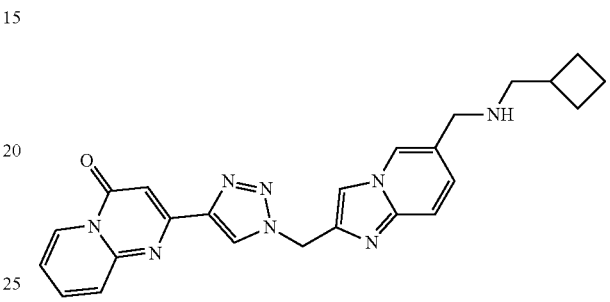

2-ethynylpyrido[1,2-a]pyrimidin-4-one (86 mg, 0.505 mmol), tert-butyl N-[[2-(azidomethyl)imidazo[1,2-a]pyridin-6-yl]methyl]-N-(cyclobutylmethyl)carbamate Intermediate 65 (170 mg, 0.459 mmol) and CuSO4 (4.6 mg, 0.0282 mmol) were combined in DMF (2 mL) and water (0.5 mL). Sodium ascorbate (137 mg, 0.688 mmol) was added and the mixture was stirred at room temperature for one and a half hours.

The mixture was diluted with chloroform/isopropanol (3:1, 40 ml) and water (30 ml) the phases were separated and the aqueous was extracted with CHCl3/IPA (3; 1, 3×20 mL). The combined organics were washed with water (50 mL), dried (Na₂SO₄) and concentrated under vacuum to a residue.

The material was dissolved in methanol (0.5 mL), HCl (4M in dioxane, 5 mL) was added and the mixture was stirred for an hour before the solvent was removed under vacuum.

The residue was purified by preparative HPLC (method B) to give the title compound (92 mg, 46%) as an off-white solid.

Method C: LC-MS (electrospray): m/z=441.4 (M+H)+, RT=2.49 min.

Example 343: N-[(1-methoxycyclobutyl)methyl]-1-[2-[[4-(6-methoxy-1H-indazol-4-yl)triazol-1-yl]methyl]imidazo[1,2-a]pyridin-6-yl]methanamine

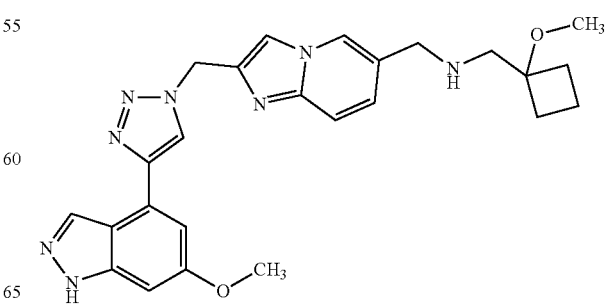

Step 1: 2-bromo-6-fluoro-4-methoxy-benzaldehyde

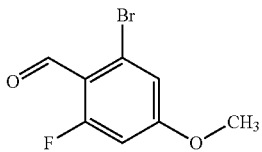

To a solution of N-isopropylpropan-2-amine (3.4 mL, 24.4 mmol) in THF (80 mL) at −78° C. was added n-butyl-lithium (2.5M in hexanes, 10 mL, 24.4 mmol) dropwise and the mixture was stirred for 15 minutes before a solution of 1-bromo-3-fluoro-5-methoxybenzene (5.00 g, 24.4 mmol) in THF (10 ml) was added dropwise, and the mixture was stirred at −78° C. for 20 minutes. DMF (1.1 mL, 12.2 mmol) was added dropwise and the mixture was stirred at −78° C. for an hour, then quenched with HCl (1M, 50 ml) and allowed to warm to room temperature. The mixture was extracted with EtOAc (3×50 ml) and the combined organic layers were washed with brine, dried ($Na_2SO_4$) and evaporated under reduced pressure. The residue was purified by chromatography on $SiO_2$ (Biotage, 340 g) eluting with EtOAc/heptane 0-30% to afford the title compound (3.20 g, 56%) as a yellow solid.

Method A: LC-MS (electrospray): m/z=232.9/234.9 (M+H)+, RT=1.13 min.

Step 2: 4-bromo-6-methoxy-1H-indazole

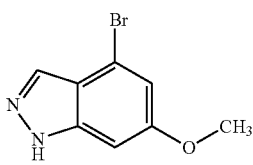

Hydrazine (55%, 2.6 mL, 34.8 mmol) was added to a solution of 2-bromo-6-fluoro-4-methoxy-benzaldehyde (2.70 g, 11.6 mmol) in 1,4-dioxane (55 mL) and the mixture was stirred at 100° C. for 42 hours. The mixture was cooled to room temperature, and the solvent was removed under vacuum. The residue was dissolved in EtOAc (60 ml) and washed with water and brine, dried ($Na_2SO_4$) and evaporated under reduced pressure. The residue was purified by chromatography on $SiO_2$ (Biotage 100 g) eluting with EtOAc/heptane 10-50% to afford the title compound (750 mg, 26%) as an off-white solid Method A: LC-MS (electrospray): m/z=226.9/228.9 (M+H)+, RT=1.08 min.

Step 3: 4-bromo-6-methoxy-1-tetrahydropyran-2-yl-indazole

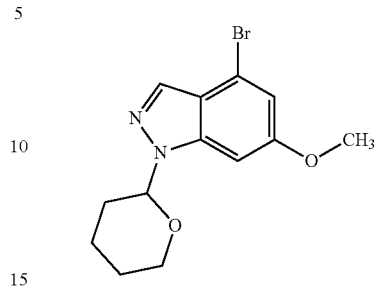

To a mixture of 4-bromo-6-methoxy-1H-indazole (620 mg, 2.65 mmol) and tosic acid monohydrate (50 mg, 0.26 mmol) in DCM (20 mL) was added 3,4-dihydro-2H-pyran (0.75 mL, 7.95 mmol) and the reaction mixture was stirred at room temperature for 2 days then concentrated under vacuum. The residue was dissolved in EtOAc (60 ml) and washed with water and $NaHCO_3$ (sat). The organic layer was dried ($Na_2SO_4$) and evaporated under reduced pressure. The residue was purified by chromatography on $SiO_2$ (Biotage 100 g kp-Sil) eluting with EtOAc/heptane 0-25% to afford the title compound (720 mg, 81%) as a white gum.

Method A: LC-MS (electrospray): m/z=310.95/313.00 (M+H)+, RT=1.43 min.

Step 4: 4-ethynyl-6-methoxy-1-tetrahydropyran-2-yl-indazole

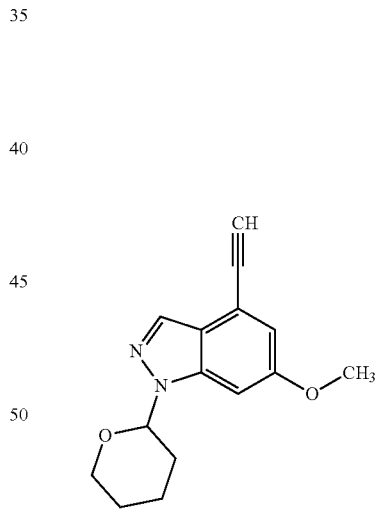

The title compound was prepared from 4-bromo-6-methoxy-1-tetrahydropyran-2-yl-indazole using the chemistry described in Intermediate 24 Steps 2 and 3 to give (210 mg, 34%) as a colourless oil which solidified on standing to a white solid.

Method A: LC-MS (electrospray): m/z=257.1 (M+H)+, RT=1.22 min.

Step 5: N-[(1-methoxycyclobutyl)methyl]-1-[2-[[4-(6-methoxy-1H-indazol-4-yl)triazol-1-yl]methyl]imidazo[1,2-a]pyridin-6-yl]methanamine

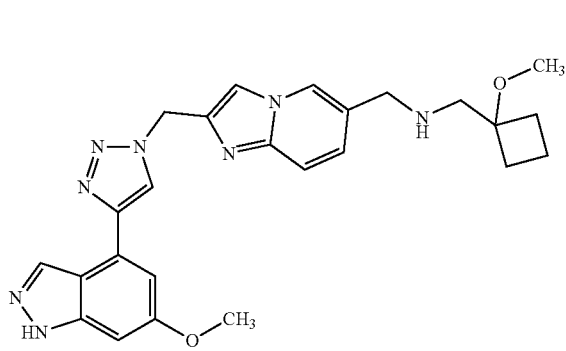 [SMILES: COc1cc(-c2cn(Cc3cn4cc(CNCC5(OC)CCC5)ccc4n3)nn2)c2cn[nH]c2c1]

The title compound was prepared from 4-ethynyl-6-methoxy-1-tetrahydropyran-2-yl-indazole and [2-(azidomethyl)imidazo[1,2-a]pyridin-6-yl]methanol using the chemistry described in Compound 268 Steps 2, 3 and 4 to give (95 mg, 65%) as a white solid.

Method C: LC-MS (electrospray): m/z=473.5 (M+H)+, RT=2.43 min.

Example 344: 4-[1-[(6-methylimidazo[1,2-a]pyridin-2-yl)methyl]triazol-4-yl]isoquinoline

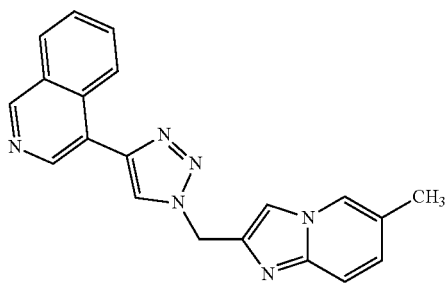 [SMILES: Cc1ccc2nc(Cn3cc(-c4cncc5ccccc45)nn3)cn2c1]

2-(azidomethyl)-6-methyl-imidazo[1,2-a]pyridine Intermediate 23 (50 mg, 0.27 mmol), 4-ethynylisoquinoline (49 mg, 0.32 mmol) and sodium ascorbate (80 mg, 0.40 mmol) were combined in DMF (2 ml) and Water (0.5 ml), CuSO4 (4 mg, 0.03 mmol) was added and the mixture was stirred at room temperature for 30 minutes during which time a precipitate formed.

The mixture was diluted with water (15 ml) and the solids were collected by filtration. The residue was purified by reverse phase chromatograpghy (method B) to afford the title compound (24 mg, 26%) as an off-white solid.

Method D: LC-MS (electrospray): m/z=341.3 (M+H)+, RT=3.33 min.

Intermediate 66: tert-butyl N-{[2-(azidomethyl)imidazo[1,2-a]pyridin-6-yl]methyl}carbamate

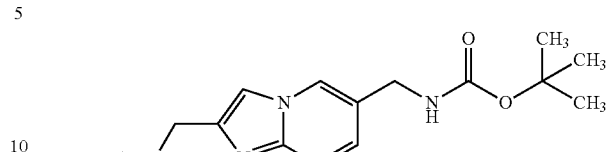

Step 1: tert-butyl N-[(6-aminopyridin-3-yl)methyl]carbamate

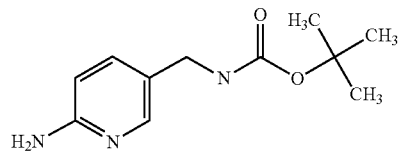

A solution of 6-aminopyridine-3-carbonitrile (1.00 g, 8.39 mmol) and tert-butoxycarbonyl tert-butyl carbonate (3.66 g, 16.8 mmol) in MeOH (32 mL) was cooled to 0° C. and treated with nickel (II) chloride (1.10 g, 8.39 mmol) followed by the addition of sodium borohydride (2.86 g, 75.6 mmol) in small portions. The mixture was stirred and allowed to warm to room temperature overnight.

The stir was continued for 24 hours before the black suspension was evaporated under vacuum, quenched by the addition of NaHCO3 (sat) and EtOAc was added. The solids were removed by filtration through Celite (washing with EtOAc). The phases were separated and the aqueous extracted with EtOAc. The organics were washed with brine, dried (MgSO4) and evaporated under vacuum to a brown foam which was purified by chromatography on SiO2 (Biotage KPNH 28 g) eluting with 0-100% EtOAc in heptane to give the title compound (734 mg, 28%) as a beige foam along with an earlier eluting product (178 mg).

Method B: LC-MS (electrospray): m/z=224.3 (M+H)+, RT=1.24 min.

Step 2: tert-butyl N-[[2-(chloromethyl)imidazo[1,2-a]pyridin-6-yl]methyl]carbamate

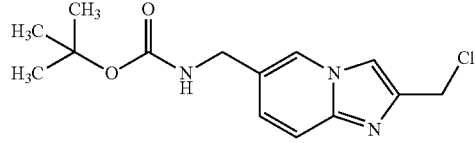 [SMILES: CC(C)(C)OC(=O)NCc1ccc2nc(CCl)cn2c1]

A solution of tert-butyl N-[(6-amino-3-pyridyl)methyl]carbamate (730 mg, 3.27 mmol) and 1,3-dichloropropan-2-one (450 uL, 4.90 mmol) in MeCN (20 mL) was stirred at 80° C. for 20 hours.

The mixture was cooled to room temperature, evaporated to dryness and purified by chromatography on SiO2 (Biotage; 28 g KP—NH) eluting with EtOAc in heptane 50-100% to afford the title compound (581 mg, 52%) as a beige solid.

Method B: LC-MS (electrospray): m/z=296.2 (M+H)+, RT=1.53 min.

Step 3: tert-butyl N-{[2-(azidomethyl)imidazo[1,2-a]pyridin-6-yl]methyl}carbamate

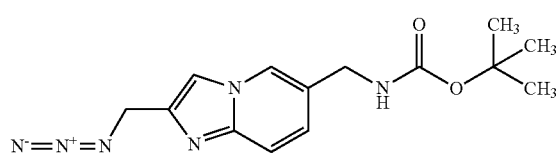 [SMILES: CC(C)(C)OC(=O)NCc1ccc2nc(CN=[N+]=[N-])cn2c1]

A solution of tert-butyl N-[[2-(chloromethyl)imidazo[1,2-a]pyridin-6-yl]methyl]carbamate (581 mg, 1.96 mmol) and NaI (30 mg, 0.196 mmol) in DMF (4 mL) was treated with NaN3 (255 mg, 3.93 mmol) and the mixture was stirred at room temperature 17 hours.

The brown suspension was quenched with NaHCO₃ (sat, 10 ml) and extracted with chloroform/isopropanol (3:1, 3×80 ml). The combined organic extracts were dried (Na₂SO₄) and evaporated under vacuum. The residue was triturated with EtOAc/heptane and the solids were collected by filtration to afford the title compound (400 mg, 67%) as a beige solid.

Method B: LC-MS (electrospray): m/z=303.2 (M+H)+, RT=1.42 min.

Example 345: N-(cyclobutylmethyl)-1-[2-[[4-(4-isoquinolyl)triazol-1-yl]methyl]imidazo[1,2-a]pyridin-6-yl]methanamine

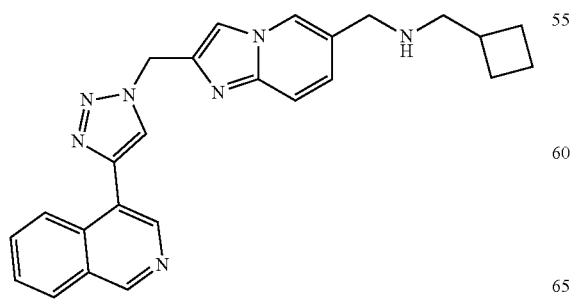

Step 1: tert-butyl N-[[2-[[4-(4-isoquinolyl)triazol-1-yl]methyl]imidazo[1,2-a]pyridin-6-yl]methyl]carbamate

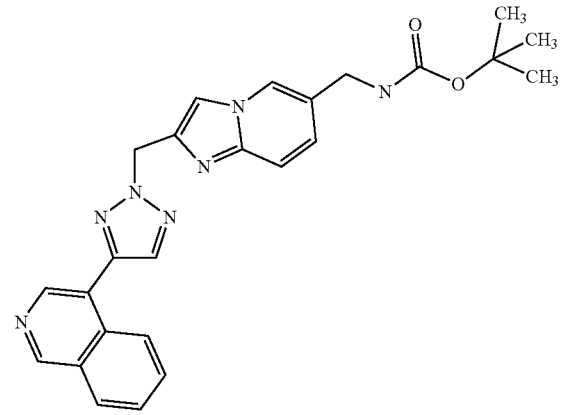

Under nitrogen atmosphere, isoquinoline-4-carbaldehyde (100 mg, 0.636 mmol) was suspended in MeOH (anhydrous, 1 mL) and THF (anhydrous, 1 mL), dimethyl (1-diazo-2-oxopropyl)phosphonate (245 mg, 1.28 mmol) and K₂CO₃ (264 mg, 1.91 mmol) were added to the reaction mixture and stirred for 5 hours.

Tert-butyl N-[[2-[[4-(4-isoquinolyl)triazol-1-yl]methyl]imidazo[1,2-a]pyridin-6-yl]methyl]carbamate Intermediate 66 (193 mg, 0.636 mmol) and copper (1) iodide (25 mg, 0.131 mmol) were added and the mixture was stirred at room temperature for 2 hours.

Water was added and the mixture was extracted with CHCl₃/IPA×3. The organic extracts were combined, dried (MgSO₄) and evaporated under vacuum to give the crude material which was Purified by chromatography on SiO₂ (Botage, KP—NH) eluting with Heptane/EtOAc 50 to 100% followed by 5% MeOH in EtOAc) to give the title compound (84 mg, 29%) as an off-white solid.

Method B: LC-MS (electrospray): m/z=456.4 (M+H)+, RT=1.42 min.

Step 2: N-(cyclobutylmethyl)-1-[2-[[4-(4-isoquinolyl)triazol-1-yl]methyl]imidazo[1,2-a]pyridin-6-yl]methanamine

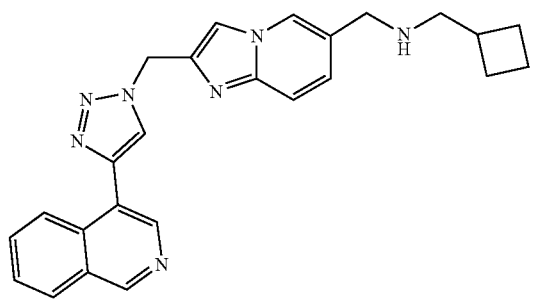 [SMILES: c1ccc2c(-c3cn(Cc4cn5cc(CNCC6CCC6)ccc5n4)nn3)cncc2c1]

To a solution of [2-[[4-(4-isoquinolyl)triazol-1-yl]methyl]imidazo[1,2-a]pyridin-6-yl]methanamine (13 mg, 0.0368 mmol) in DCE (1.0 ml) was added cyclobutanecarbaldehyde (3.1 mg, 0.0368 mmol) and the reaction was stirred at room temperature for 30 minutes, before sodium triacetoxyborhydride (16 mg, 0.0737 mmol) was added and the reaction was stirred at 40° C. for 2 hours.

The reaction was cooled to room temperature and the solvent was removed in vacuo. Water (5 ml) and NaOH (1M, 2.0 ml) were added and the aqueous was extracted with IPA-CHCl$_3$ (1:4, 3×3 ml). The organics dried (Na$_2$SO$_4$) and evaporated under reduced pressure to give a yellow gum, which was purified by preparative HPLC (method B) to give the title compound (2.1 mg, 13%) as an off white solid along with the bis alkylated by-product.

Method C: LC-MS (electrospray): m/z=424.4 (M+H)+, RT=2.87 min.

Intermediate 67: [rel-(1S,2R,4S)-7-oxabicyclo[2.2.1]hept-5-en-2-yl]methanamine and [rel-(1S,2S,4S)-7-oxabicyclo[2.2.1]hept-5-en-2-yl]methanamine

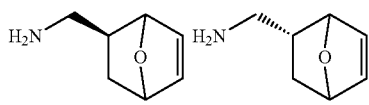

Prepared according to Tetrahedron, 49 (8), 1649-1664, 1993.

Abbreviations

HATU—[dimethylamino(triazolo[4,5-b]pyridin-3-yloxy)methylene]-dimethyl-ammonium-hexafluorophosphate
DCM—Dichloromethane
DIPEA—N-ethyl-N-isopropyl-propan-2-amine
DEAD—Diethylazodicarboxylate
DMF—Dimethylformamide
EtOAc—Ethyl acetate
EtOH—Ethanol
MeCN—Acetonitrile
RT—Retention Time
Phase separation cartridge—Telos phase separator 6 mL
STAB—Sodium triacetoxyborohydride
THF—Tetrahydrofuran
XPHOS—dicyclohexyl-[2-(2,4,6-triisopropylphenyl)phenyl]phosphane Example 3: METTL3/14 Methyltransferase Assay Biochemical Assay—METTL3_14 RFMS The enzymatic assay was established to determine IC50 values for inhibition of RNA methyltransferase activity. The enzyme used was full-length his-tagged METTL3 co-expressed with full length FLAG-tagged METTL14 in a baculovirus expression system. Enzymatic reactions were performed at room temperature in 384-well plates using a final reaction volume of 20 µL containing 20 mM TrisCl pH 7.6, 1 mM DTT, 0.01% Tween-20. 5 nM final concentration of METTL3/14 was pre-incubated with various compound concentrations for 10 minutes, followed by addition of 0.2 µM final concentration synthetic RNA substrate (5'P-uacacucgaucuggacuaaagcugcuc-3') and 0.5 µM final concentration S-adenosyl-methionine (SAM). The reaction was incubated for further 60 minutes at room temperature, and then quenched by the addition of 40 µL 7.5% TCA with two internal product standards (D$_4$-SAH and $^{13}$C$_{10}$-SAH). After termination, plates were sealed, centrifuged and stored at 4° C. until analysis. Note: the lower limit of the assay is IC50=5 nM.

Mass Spectrometry Analysis

RNA methyltransferase activity was measured label free using the RapidFire™ mass spectrometry (RF/MS) platform. Stopped and stable assay plates were analyzed on the Agilent RF300 integrated autosampler/solid-phase extraction (SPE) system coupled to an ABSciex 4000 mass spectrometer for the generation of the product S-adenosyl homocysteine (SAH) and normalized to the ratio of signal of the two internal product standards, respectively. Solvent A was water containing 0.1% (v/v) TCA. Solvent B was acetonitrile/0.1% ammonium acetate (8:2, v/v). More specifically, plates were centrifuged at 4350 rpm for 10 min, samples were aspirated under vacuum for 600 ms, then loaded onto a C18 solid-phase extraction cartridge and washed for 3 s with solvent A at a flow rate of 1.5 mL/min. Retained product and internal standards were eluted with solvent B at a flow rate of 1 mL/min for 3 s and finally the cartridge was reequilibrated with solvent A for 500 ms. The mass transition for the product (SAH) was 384.9/135.9 Da. Transitions of the two internal product standards (IS1: D$_4$-SAH and IS2: $^{13}$C$_{10}$-SAH) were 389.1/135.8 Da and 395.0/134.2 Da, respectively. Ratios of SAH/IS1 and SAH/IS2 were used for normalization of matrix effects. IC50 values were calculated based on dilution series of individual compounds. Potency of a compound was measured at varied inhibitor concentrations and normalized to control wells without RNA substrate and without inhibition (DMSO only).

Results:

| Compound No | METTL3_14 RFMS IC50 nM |
|---|---|
| 1 | 5600 |
| 2 | 9840 |
| 3 | 4660 |
| 4 | 6070 |
| 5 | 9450 |
| 6 | 9120 |
| 7 | 2670 |
| 8 | 4560 |
| 9 | 2710 |
| 10 | 1610 |
| 11 | 4100 |
| 12 | 1410 |
| 13 | 4180 |
| 14 | 5900 |
| 15 | 536 |
| 16 | 8010 |
| 17 | 2240 |
| 18 | 1859 |
| 19 | 2600 |
| 20 | 8410 |
| 21 | 3060 |
| 22 | 2210 |
| 23 | 1790 |
| 24 | 6770 |
| 25 | 543 |
| 26 | 2060 |
| 27 | 6610 |
| 28 | 5340 |
| 29 | 2780 |
| 30 | 8520 |
| 31 | 9350 |
| 32 | 7340 |
| 33 | 5870 |
| 34 | 5350 |

| Compound No | METTL3_14 RFMS IC50 nM |
|---|---|
| 35 | 15820 |
| 36 | 3910 |
| 37 | 4740 |
| 38 | 5440 |
| 39 | 1470 |
| 40 | 7390 |
| 41 | 1340 |
| 42 | 6260 |
| 43 | 1290 |
| 44 | 5050 |
| 45 | 2580 |
| 46 | 2210 |
| 47 | 3980 |
| 48 | 2040 |
| 49 | 1040 |
| 50 | 272 |
| 51 | 1220 |
| 52 | 267 |
| 53 | 38 |
| 54 | 16 |
| 55 | 87 |
| 56 | 945 |
| 57 | 702 |
| 58 | 299 |
| 59 | 939 |
| 60 | 700 |
| 61 | 695 |
| 62 | 8760 |

| Compound No | METTL3_14 RFMS IC50 nM |
|---|---|
| 63 | 299 |
| 64 | 7326 |
| 65 | 6600 |
| 66 | 1350 |
| 67 | 8140 |
| 68 | 5090 |
| 69 | 1340 |
| 70 | 143 |
| 71 | 206 |
| 72 | 18.52 |
| 73 | 64.9 |
| 74 | 122 |
| 75 | 48.1 |
| 76 | 30 |
| 77 | 84 |
| 78 | 163 |
| 79 | 62.5 |
| 80 | 16.5 |
| 81 | 27.67 |
| 82 | 354 |
| 83 | 10.64 |
| 84 | 36.5 |
| 85 | 25.5 |
| 86 | 23.1 |
| 87 | 48.5 |
| 88 | 114 |
| 89 | 1860 |
| 90 | 79.2 |
| 91 | 57.6 |
| 92 | 112 |
| 93 | 13 |
| 94 | 131 |
| 95 | 74.4 |
| 96 | 947 |
| 97 | 1020 |
| 98 | 45.6 |
| 99 | 318 |
| 100 | 1380 |
| 101 | 18.1 |
| 102 | 429 |

| Compound No | METTL3_14 RFMS IC50 nM |
|---|---|
| 103 | 13.7 |
| 104 | 69.07 |
| 105 | 1200 |
| 106 | 15 |
| 107 | 143 |
| 108 | 241 |
| 109 | 350 |
| 110 | 102 |
| 111 | 109 |
| 112 | 755 |
| 113 | 16.42 |
| 114 | 244 |
| 115 | 43.5 |
| 116 | 280 |
| 117 | 83.7 |
| 118 | 87.2 |
| 119 | 578 |
| 120 | 24.7 |
| 121 | 16.8 |
| 122 | 110 |
| 123 | 332 |
| 124 | 119 |
| 125 | 221 |
| 126 | 79.8 |
| 127 | 429 |
| 128 | 333 |
| 129 | 84.3 |
| 130 | 206 |
| 131 | 87.7 |
| 132 | 917 |
| 133 | 480 |
| 134 | 440 |
| 135 | 18.3 |
| 136 | 99 |
| 137 | 17.8 |
| 138 | 31.4 |
| 139 | 32.6 |
| 140 | 18.7 |
| 141 | 14.5 |
| 142 | 48.8 |
| 143 | 136 |
| 144 | 59.7 |
| 145 | 276 |
| 146 | 25.1 |
| 147 | 224 |
| 148 | 28.5 |
| 149 | 40.21 |
| 150 | 29.9 |
| 151 | 16.3 |
| 152 | 104 |
| 153 | 1580 |
| 154 | 1180 |
| 155 | 177 |
| 156 | 61.7 |
| 157 | 42.9 |
| 158 | 3810 |
| 159 | 19.5 |
| 160 | 93.2 |
| 161 | 99.1 |
| 162 | 225 |
| 163 | 80.1 |
| 166 | 10500 |
| 167 | 8070 |
| 168 | 114 |
| 169 | 391 |
| 170 | 29.4 |
| 171 | 293 |
| 172 | 309 |
| 175 | 214 |
| 176 | 909 |
| 177 | 1890 |
| 178 | 209 |
| 180 | 889 |
| 181 | 179 |
| 182 | 179 |
| 185 | 1070 |

-continued

| Compound No | METTL3_14 RFMS IC50 nM |
|---|---|
| 187 | 44.1 |
| 188 | 1190 |
| 189 | 132 |
| 190 | 56.1 |
| 191 | 4790 |
| 193 | 12.4 |
| 194 | 305 |
| 195 | 32.4 |
| 196 | 597 |
| 197 | 84.8 |
| 198 | 44.1 |
| 199 | 1860 |
| 200 | 1260 |
| 202 | 61.1 |
| 203 | 32 |
| 204 | 61.5 |
| 205 | 197 |
| 206 | 15.6 |
| 207 | 37.9 |
| 208 | 5730 |
| 209 | 10 |
| 210 | 20.3 |
| 211 | 19.3 |
| 212 | 6.25 |
| 213 | 41.8 |
| 214 | 15.8 |
| 215 | 54.3 |
| 216 | 14.9 |
| 217 | 7.58 |
| 218 | 26.4 |
| 219 | 247 |
| 220 | 168 |
| 221 | 46.7 |
| 222 | 33.9 |
| 223 | 2170 |
| 224 | 1870 |
| 225 | 6.69 |
| 226 | 8.145 |
| 227 | 7.898 |
| 228 | 239 |
| 229 | 100 |
| 230 | 81.26 |
| 231 | 1220 |
| 232 | 8370 |
| 233 | 1390 |
| 234 | 3440 |
| 235 | 111 |
| 236 | 28.7 |
| 237 | 742 |
| 238 | 850 |
| 239 | 513 |
| 240 | 260 |
| 241 | 2110 |
| 242 | 68 |
| 243 | 1450 |
| 245 | 735 |
| 247 | 1080 |
| 248 | 12.7 |
| 249 | 229 |
| 250 | 11.34 |
| 251 | 5.76 |
| 252 | 8.02 |
| 253 | 207 |
| 254 | 10100 |
| 255 | 25.8 |
| 256 | 246 |
| 257 | 4440 |
| 263 | 2730 |
| 264 | 195 |
| 265 | 50.6 |

| Compound | METTL3_14 RFMS IC50 nM |
|---|---|
| 266 | 4.23 |
| 267 | 6.95 |
| 268 | 10.6 |
| 269 | 8.05 |
| 270 | 3.63 |
| 271 | 6.1 |
| 272 | 9020 |
| 273 | 27.7 |
| 274 | 1510 |
| 275 | 1240 |
| 276 | 6.1 |
| 277 | 76.3 |
| 278 | 27.6 |
| 279 | 6.19 |
| 280 | 13.14 |
| 281 | 98.7 |
| 282 | 10.6 |
| 283 | 29.3 |
| 284 | 11.53 |
| 285 | 15.01 |
| 286 | 19.3 |
| 287 | 69.5 |
| 288 | 13.89 |
| 289 | 103 |
| 290 | 17.98 |
| 291 | 62.2 |
| 292 | 19.96 |
| 293 | 12.77 |
| 294 | 5.8 |
| 295 | 6.1 |
| 296 | 4.44 |
| 297 | 737 |
| 298 | 42.1 |
| 299 | 112 |
| 300 | 511 |
| 301 | 233 |
| 302 | 4.35 |
| 303 | 5.92 |
| 304 | 6.1 |
| 305 | 6.009 |
| 306 | 9.46 |
| 307 | 6.721 |
| 308 | 11.4 |
| 309 | 120 |
| 310 | 186 |
| 311 | 19 |
| 312 | 52.1 |
| 313 | 37.6 |
| 314 | 7110 |
| 315 | 19.3 |
| 316 | 38.4 |
| 317 | 462 |
| 318 | 5.67 |
| 319 | 7.838 |
| 320 | 6.156 |
| 321 | 13.2 |
| 322 | 32.5 |
| 324 | 8.857 |
| 325 | 14.49 |
| 326 | 76.6 |
| 327 | 5.776 |
| 328 | 8.837 |
| 329 | 1640 |
| 330 | 202 |
| 331 | 3440 |
| 332 | 1700 |
| 333 | 1230 |
| 334 | 122 |
| 335 | 7290 |
| 336 | 4160 |
| 337 | 16.3 |
| 338 | 7.49 |
| 339 | 10.1 |
| 340 | 6810 |
| 341 | 64.4 |
| 342 | 18.4 |
| 343 | 6.1 |
| 346 | 7.68 |

-continued

| Compound | METTL3_14 RFMS IC50 nM |
|---|---|
| 347 | 7.5 |
| 348 | 9.02 |
| 349 | 303 |
| 350 | 56.2 |
| 351 | 24.1 |

MOLM-13 and MOLM-14 Cell Culture

MOLM-13 and MOLM-14 cells (Purchased from Leibniz-Institut DSMZ-Deutsche Sammlung von Mikroorganismen und Zellkulturen GmbH) were established from the blood of a 20 year old man with acute myeloid leukaemia (AML) in 1995 and are of a round morphology which grow in suspension. These are regularly maintained in aseptic tissue culture conditions, and grown in RPMI 1640 media containing 10% FBS at a density of $0.4$-$2\times10^6$/ml.

Treatment of MOLM-13 and MOLM-14 Cells with METTL3 Inhibitors

MOLM-13 or MOLM-14 cells were plated, in suspension, in 24 well tissue culture plates at final concentration of 200,000/ml, with or without 50 ng/ml IFNγ. METTL3 inhibitors (Compound 15, Compound 54, Compound 55, and Compound 53) were dissolved in DMSO, titration curve generated at 200× final concentration, compounds were then diluted in tissue culture media (RPMI 1640, 10% FBS) before being added to MOLM-13 or MOLM-14 cells in a final DMSO concentration of 0.5%, final volume 1 ml. Cells were incubated for 4 days at 37° C. at which point 600 µl of cell suspension was removed for Mass spectrometry analysis of m6A. 600 µl of fresh media containing the appropriate concentration of METTL3 inhibitor/IFNγ was added to remaining cell suspensions. Cells where then cultured for a further 7 days, cell suspension was sampled for analysis of proliferation and Cell surface markers periodically.

Analysis of Cell Proliferation

At regular time points (4, 5, 6 &7) days cells were mixed to maintain a homogenous cell suspension. 25 µl of this cell suspension was removed and added to a white 384 well plate, 25 µl of Cell Titre Glo reagent (Promega) was added, and incubated for 10 mins at room temperature before measurement of luminescence intensity, as per the manufacturers instructions.

Analysis of Cell Surface Markers

Cell surface CD markers were measured via flow cytometry. 300 µl of a homogenous cell suspension was removed after 6 days. Samples were washed in PBS containing 0.5% BSA, and resuspended in 1 ml PBS 0.5% BSA. 5 µl of anti-CD14-FITC, 5 µl of anti-CD11 b-APC and 2 µl of DAPI were added to all samples and incubated in the dark at room temperature for 15 mins. Samples were analysed on Becton Dickinson LSRII.

Isolation of Individual Nucleosides from Cellular Samples.

Compound-treated cells were harvested by centrifugation and the total RNA content was extracted using a silica filter-based method (PureLink™ Pro 96 total RNA Purification Kit ThermoFisher Scientific Catalog number: 12173011A). Up to 10 µg of RNA was digested by adding 1 µl digestion enzyme mix per well in a digest buffer, final concentrations: Tris-HCl pH 8 (4 mM), $MgCl_2$ (5 mM), NaCl (20 mM) in a total volume of up to 100 µl.

The digestion enzyme mix was made by mixing benzonase (250 U/µl, Sigma Aldrich Cat #E1014-25KU), phosphodiesterase I from *Crotalus adamanteus* venom (10 mU/µl, Sigma Aldrich Cat #P3243) and Antarctic phosphatase (5 U/µl, NEB Cat #M0289L) in a ratio of 1:10:20. This was incubated overnight at 37 C.

The following day an equal volume of $^{13}C$, $^{15}N$-labelled Uridine (Sigma Aldrich Cat #645672 that had been previously dephosphorylated) in 0.1% formic acid was added to each reaction and this was subsequently prepared for LC-MSMS by filtration through 30 kDa molecular weight cut-off filters (Sigma, Cat #UFC503096).

Mass Spectrometric Analysis of m6A

Samples were resolved using a Thermo Scientific U3000 UPLC system on a gradient of 2-98% [0.1% formic acid/acetonitrile] through an Acquity 100 mm×2.1 mm C-18 HSS T3 column and analysed on a QExactive-HF Orbitrap High Resolution Mass Spectrometer (ThermoFisher Scientific Cat #IQLAAEGAAPFALGMBFZ) in positive full-scan mode and the results were deconvoluted using the accompanying Xcalibur Software. Nucleosides of interest (including adenosine, cytidine, guanosine, uridine, $^{13}C$, $^{15}N$-labelled uridine and m6A) were identified by both retention time and accurate masses and compared to purified standards and quantified accordingly.

A schematic of the timings of the processes outlined about is showing in FIG. 1.

Results

Figure 2:
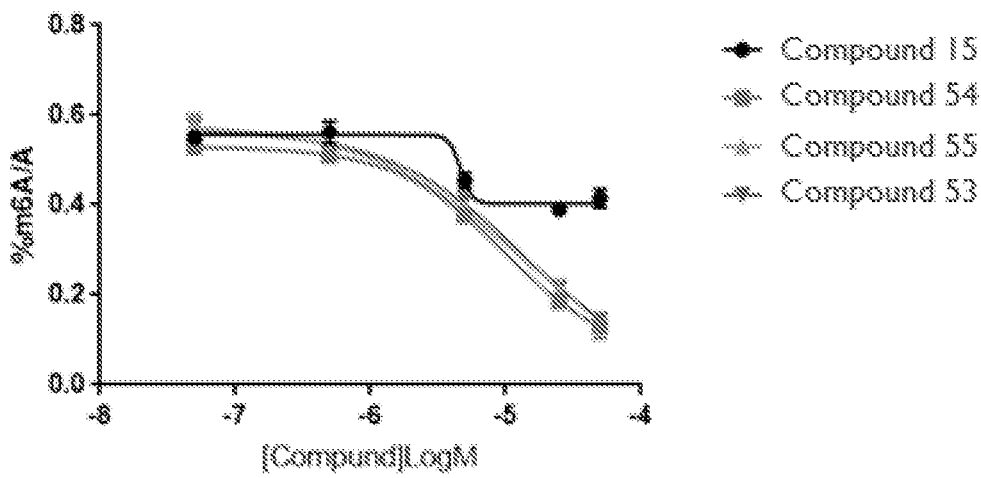
FIG. 2: m6A levels in total RNA from MOLM13 (+IFNy) day 4

METTL3 inhibitors Compound 15 (IC50 520 nM), Compound 54 (16 nM), Compound 55 (66 nM), Compound 53 (27 nM) tested in MOLM13 cells at concentrations ranging from 50-0.1 µM Total RNA isolated at day 4. METTL3 inhibitors show dose dependent decrease in m6A which correlates with their activity from primary enzyme screen, see FIG. 2.

Figure 3:
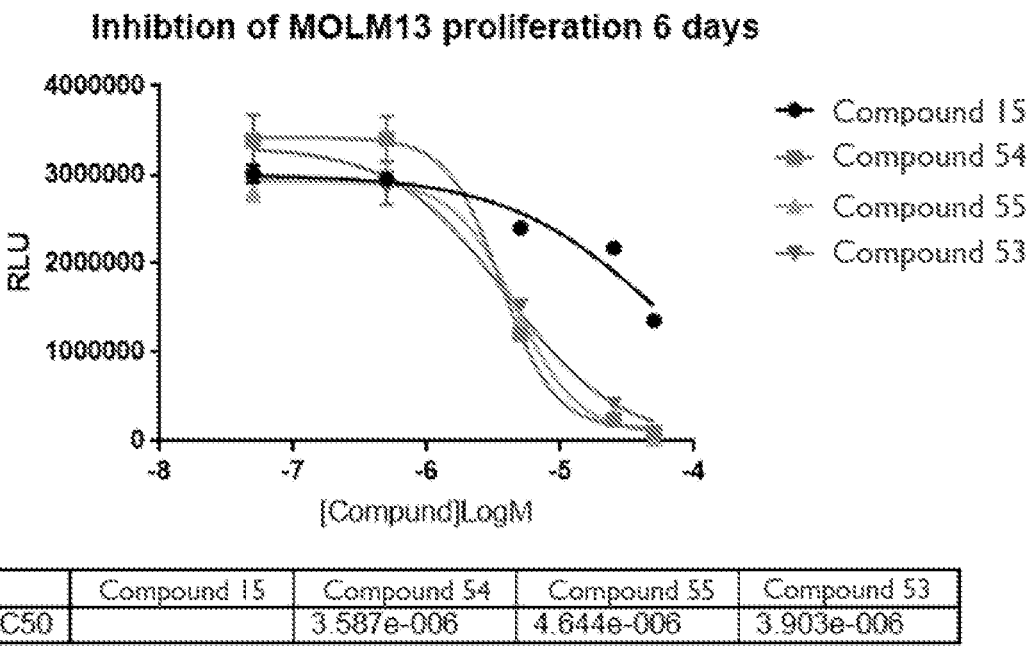
FIG. 3: Inhibition of MOLM13 proliferation 6 days

Proliferation measured every 24 hours (Day 3-Day 7). METTL3 inhibitors show dose dependent decrease in MOLM13 proliferation which correlates with their activity from primary enzyme screen and m6A levels, see FIG. 3.

Figure 4:
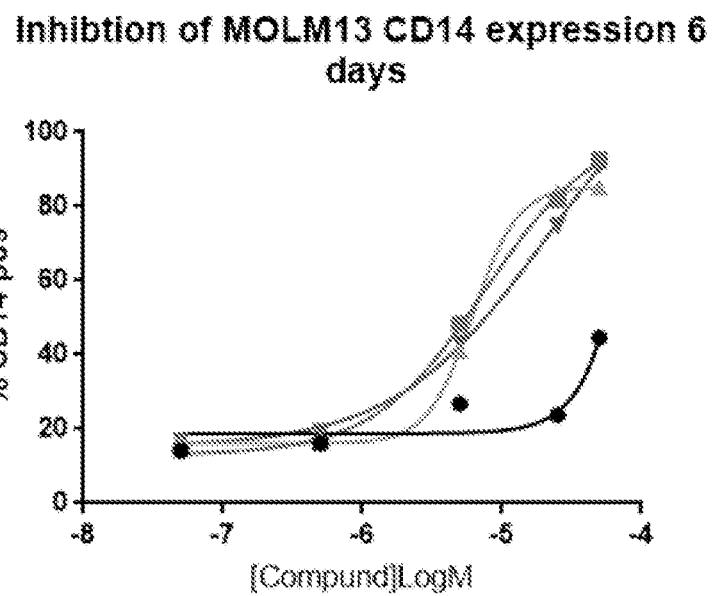
FIG. 4: Inhibition of MOLM13 CD14 expression 6 days

Expression of CD14 measured at day 6 via flow cytometry. METTL3 inhibitors show dose dependent increase of CD14 cell surface expression in MOLM13 cells which correlates with their activity from primary enzyme screen and m6A levels, see FIG. 4.

Figure 5:
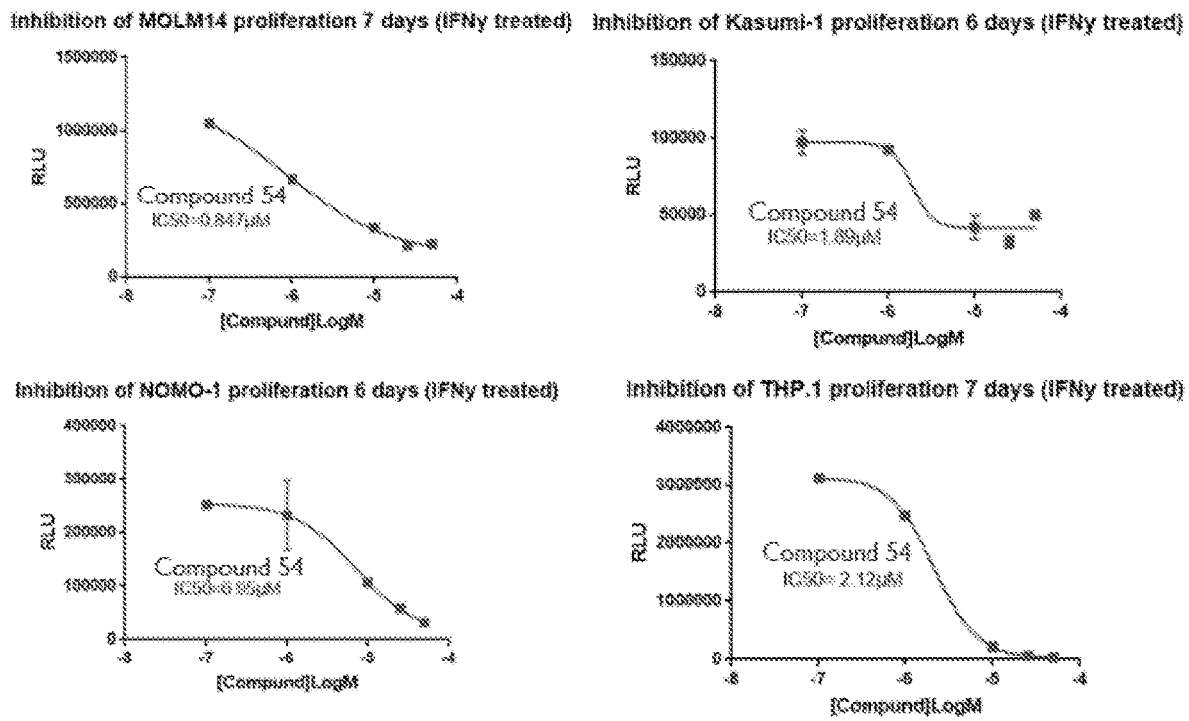
FIG. 5: Inhibition of MOLM14, Kasumi-1, NOMO-1 and THP.1 proliferation 7 days (IFNy treated)
Figure 6:
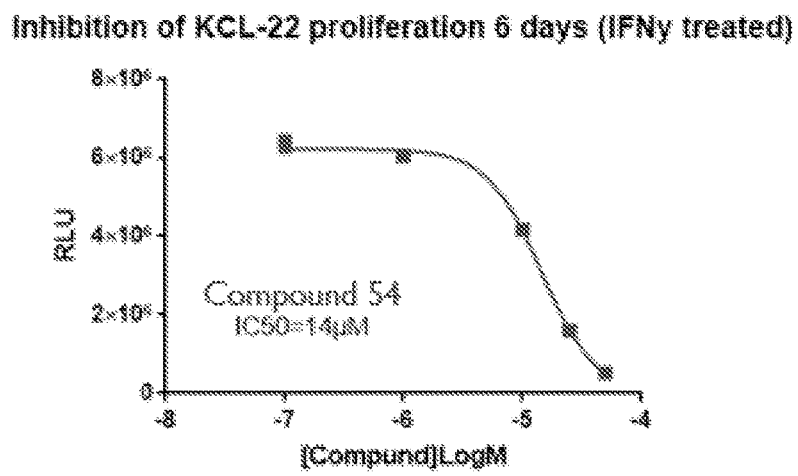
FIG. 6: Inhibition of KCL-22 proliferation 6 days (IFNy treated)

Proliferation in other cell lines (MOLM14, Kasumi-1, NOMO-1, THP.1, and KCL-22) was investigated for Compound 54, see FIGS. 5 and 6. A similar potency profile was observed in other AML cell lines, indicating that this is not specific to one particular AML cell line.

MOLM13 CTG—Analysis of Cell Proliferation

| Example No | CTG MOLM13 cells IC50 GEOMEAN (nM) |
|---|---|
| 72 | 8699 |
| 74 | 30000 |
| 78 | 6040 |
| 83 | 4117 |
| 87 | 30000 |
| 89 | 13090 |
| 93 | 6254 |
| 103 | 6796 |
| 104 | 8729 |
| 112 | 12700 |
| 114 | 2800 |
| 126 | 30000 |
| 127 | 30000 |
| 178 | 9890 |
| 193 | 2462 |
| 195 | 9768 |
| 203 | 8741 |
| 206 | 9134 |
| 207 | 10250 |

437 -continued

| Example No | CTG MOLM13 cells IC50 GEOMEAN (nM) |
|---|---|
| 209 | 6577 |
| 210 | 5019 |
| 211 | 11390 |
| 212 | 1819 |
| 213 | 30000 |
| 214 | 7338 |
| 216 | 3508 |
| 217 | 2931 |
| 218 | 4708 |
| 225 | 649.3 |
| 226 | 1475 |
| 227 | 338 |
| 235 | 30000 |
| 236 | 11770 |
| 237 | 12900 |
| 248 | 1927 |
| 250 | 2999 |
| 251 | 727.1 |
| 252 | 714.5 |
| 253 | 2790 |
| 254 | 30000 |
| 255 | 9612 |
| 263 | 13850 |
| 265 | 12980 |
| 266 | 11140 |
| 267 | 30000 |
| 268 | 5334 |
| 269 | 1392 |
| 270 | 430.9 |
| 271 | 1167 |
| 273 | 9021 |
| 276 | 657.4 |
| 278 | 30000 |
| 279 | 1334 |
| 280 | 4505 |
| 281 | 30000 |
| 282 | 3423 |
| 283 | 10740 |
| 284 | 7402 |
| 285 | 7372 |
| 286 | 12320 |
| 287 | 30000 |
| 288 | 7315 |
| 290 | 6975 |
| 292 | 7191 |
| 293 | 4725 |
| 294 | 998.1 |
| 295 | 905.9 |
| 296 | 362.5 |
| 297 | 30000 |
| 298 | 30000 |
| 299 | 30000 |
| 300 | 30000 |
| 302 | 628.6 |
| 303 | 1440 |
| 304 | 1474 |
| 305 | 1831 |
| 306 | 3926 |
| 307 | 3681 |
| 308 | 5614 |
| 311 | 3680 |
| 313 | 11310 |
| 315 | 8360 |
| 316 | 12630 |
| 318 | 1183 |
| 319 | 4377 |
| 320 | 2762 |
| 322 | 11020 |
| 324 | 3276 |
| 325 | 7503 |
| 326 | 10680 |
| 327 | 1616 |
| 328 | 3253 |
| 330 | 30000 |
| 334 | 17930 |
| 337 | 5166 |

438 -continued

| Example No | CTG MOLM13 cells IC50 GEOMEAN (nM) |
|---|---|
| 338 | 1189 |
| 339 | 3071 |
| 342 | 6710 |
| 343 | 929.8 |

CTG Assay (Caov3 Cell Line)

Cell culture: Caov-3 cells (HTB-75, Lot number: 70016791, ATCC) were grown in DMEM (11960-04431053-028, Gibco) supplemented with 10% fetal bovine serum (1600-44, Gibco), 1 mM sodium pyruvate (11360-039, Gibco) and 2 mM Glutamax (35050-038, Gibco) at 37° C. with 5% C02.

Cell treatment and cell growth assessment: 18 hours post-seeding in white 384-Viewplate (6007480, PerkinElmer) at 1500 cells/well, Caov3 cells were treated for 120 hours with compounds inhibiting the METTL3/14 activity (10 serial semi-log dilutions, 30 μM as top concentration). Upon treatment, Coav-3 cells were incubated for 10 min at RT with the CellTiter-Glo reagent (G7571, Promega). Measurement of the luminescence signal was performed on a microplate reader (Ensight, PerkinElmer).

Caov3 CTG Assay—Proliferation Assay

| Example No | CTG Caov3 cells IC50 GEOMEAN nM |
|---|---|
| 212 | 320 |
| 227 | 182 |
| 269 | 692 |
| 270 | 161 |
| 271 | 558 |
| 276 | 248 |
| 279 | 296 |
| 302 | 211 |
| 307 | 1770 |
| 327 | 572 |
| 337 | 3210 |
| 338 | 1110 |
| 339 | 849 |
| 343 | 554 |

Numbered Paragraphs

The following numbered paragraphs serve to define particular aspects and embodiments of the invention.

Paragraph 1. A compound of the formula (I), or a pharmaceutically acceptable salt thereof,

X—Y—Z (I)

wherein:

X is selected from:

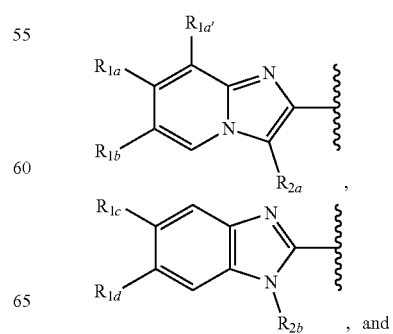

, and

-continued

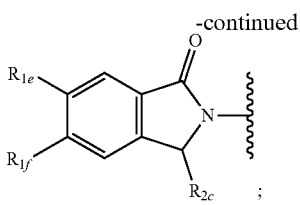

wherein:

$R_{1a}$, $R_{1b}$, $R_{1c}$, $R_{1d}$, $R_{1e}$ and $R_{1f}$ are independently selected from hydrogen, cyano, halo or a group of the formula:

-$L_{1a}$-$L_{1b}$-$Q_1$ wherein $L_{1a}$ is absent or $C_{1-3}$alkylene, $C_{3-4}$cycloalkylene, optionally substituted by one or more substituents selected from $C_{1-2}$alkyl, halo, hydroxy, or oxo;

$L_{1b}$ is absent or selected from O, S, SO, $SO_2$, $N(R_r)$, C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or $C_{1-2}$alkyl; and $Q_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), C(O)N($R_v$), N($R_v$)C(O), N($R_v$)C(O)N($R_w$), S(O)$_2$N($R_v$), or N($R_v$)SO$_2$, wherein $R_v$ and $R_w$ are each independently selected from hydrogen or $C_{1-2}$alkyl; and $Z_1$ is $C_{3-8}$cycloalkyl, heterocyclyl, phenyl or 5-6 membered heteroaryl; wherein $Z_1$ is optionally substituted by one or more substituents selected from $C_{1-4}$alkyl, $C_{3-6}$cycloalkyl, heterocyclyl halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl; $NR_{t1}R_{u1}$, $OR_{t1}$, $C(O)R_{t1}$, $C(O)OR_{t1}$, $OC(O)R_{t1}$, $C(O)N(R_{t1})R_{u1}$, $N(R_{t1})C(O)R_{u1}$, $S(O)_yR_{t1}$ (where y is 0, 1 or 2), $SO_2N(R_{t1})R_{u1}$, $N(R_{t1})SO_2R_{u1}$ or $(CH_2)_zNR_{t1}R_{u1}$ (where z is 1, 2 or 3), wherein $R_{t1}$ and $R_{u1}$ are each independently selected from hydrogen or $C_{1-4}$alkyl; and when $Z_1$ is $C_{3-8}$cycloalkyl or heterocyclyl, $Z_1$ is optionally spro-fused to a $C_{3-6}$cycloalkyl or heterocyclyl;

$R_{1a'}$ is selected from hydrogen and methyl;

$R_{2a}$, $R_{2b}$ and $R_{2c}$ are selected from hydrogen or a group of the formula:

-$L_{2a}$-$L_{2b}$-$Q_2$ wherein $L_{2a}$ is absent or $C_{1-3}$alkylene optionally substituted by $C_{1-2}$ alkyl or oxo;

$L_{2b}$ is selected from O, S, SO, $SO_2$, $N(R_n)$, C(O), C(O)O, OC(O), C(O)N($R_n$), N($R_n$)C(O), N($R_n$)C(O)N($R_o$), S(O)$_2$N($R_n$), or N($R_n$)SO$_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

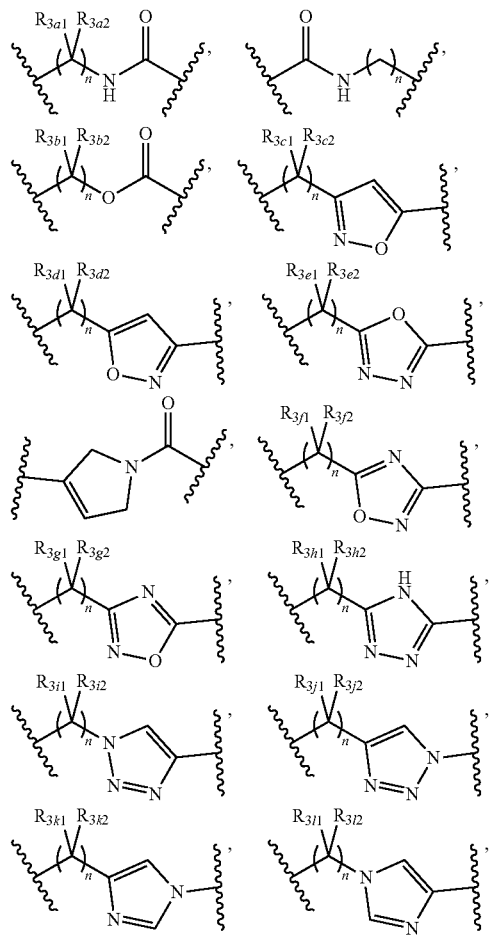

-continued

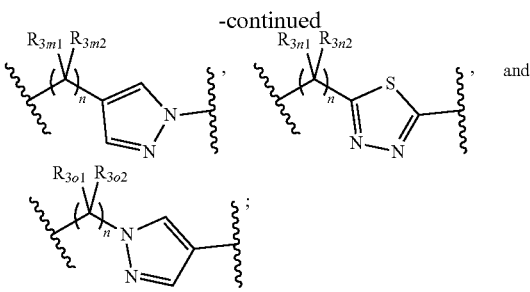

wherein
$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen, $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$ are hydrogen;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, or $R_{3o1}$ and $R_{3o2}$ may be linked to form a spiro-fused $C_{3-4}$cycloalkyl which is optionally substituted with one or more substituents selected from halo, amino, cyano, and hydroxy;

Z is selected from:

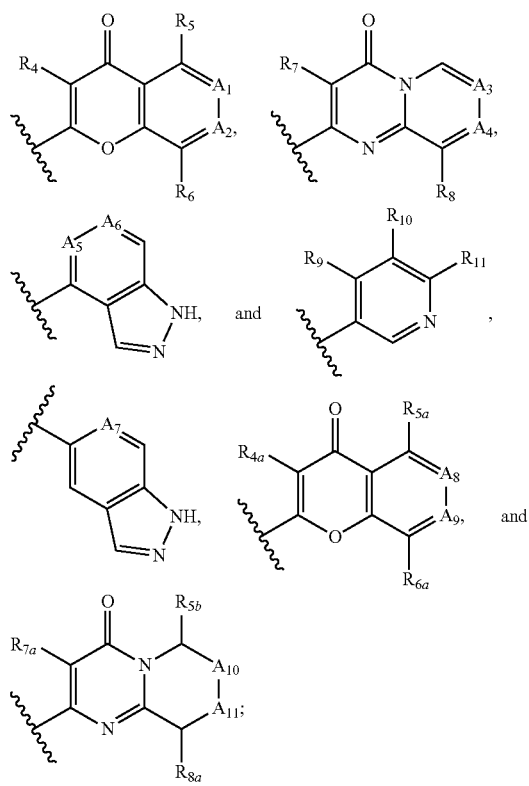

wherein:
$R_4$, $R_7$ $R_{4a}$ and $R_{7a}$ are independently selected from hydrogen and methyl;

$R_5$, $R_{5a}$ and $R_{5b}$ are independently selected from hydrogen and halo;

$R_6$, $R_8$, $R_{6a}$ and $R_{8a}$ are independently selected from hydrogen, halo and methyl;

$R_9$, $R_{10}$ and $R_{11}$ are independently selected from hydrogen, $NH_2$, halo, cyano, and $C_{1-6}$ alkyl; or $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system;

$A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;

$R_{12}$ and $R_{14}$ are independently selected from hydrogen, halo, cyano and $C_{1-4}$ alkyl;
$R_{13}$ is selected from hydrogen, halo, cyano and methyl;
$R_{15}$ is selected from hydrogen, methoxy and methyl;
$R_{16}$ is selected from hydrogen, halo, cyano and $C_{1-4}$ alkyl;
$R_{17}$ is selected from hydrogen, halo, cyano, $C_{1-4}$ alkyl, $C_{2-4}$ alkenyl, $C_{2-4}$ alkynyl and a 5- or 6-membered heteroaryl;
$R_{18}$ is selected from hydrogen, halo, cyano, $C_{1-4}$ alkyl, $C_{2-4}$ alkenyl, $C_{2-4}$ alkynyl and a 5- or 6-membered heteroaryl;
$R_{19}$, $R_{20}$, $R_{25}$ and $R_{26}$ are selected from hydrogen, halo, cyano and $C_{1-4}$ alkyl;
$R_{22}$ and $R_{23}$ are selected from hydrogen, halo, cyano and methyl;
$R_{28}$ and $R_{29}$ are selected from hydrogen, methoxy and methyl;
$R_{21}$, $R_{24}$, $R_{27}$ and $R_{30}$ are hydrogen; and
n is 0, 1 or 2.

Paragraph 2. A compound of the formula (I), or a pharmaceutically acceptable salt thereof, according to Paragraph 1, wherein:

X is selected from:

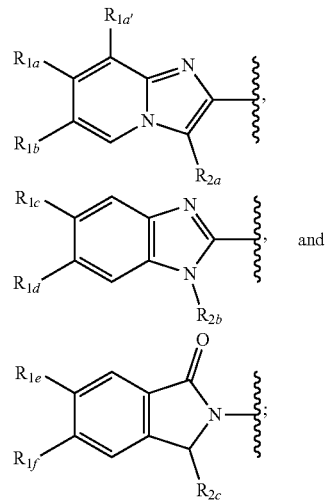

wherein:
R$_{1a}$, R$_{1b}$, R$_{1c}$, R$_{1d}$, R$_{1e}$ and R$_{1f}$ are independently selected from hydrogen, cyano, halo or a group of the formula:

-L$_{1a}$-L$_{1b}$-Q$_1$   5 wherein
L$_{1a}$ is absent or C$_{1-3}$alkylene, C$_{3-4}$cycloalkylene, optionally substituted by one or more substituents selected from C$_{1-2}$alkyl, halo, hydroxy, or oxo;   10
L$_{1b}$ is absent or selected from O, S, SO, SO$_2$, N(R$_r$), C(O), C(O)O, OC(O), C(O)N(R$_r$), N(R$_r$)C(O), N(R$_r$)C(O)N(R$_s$), S(O)$_2$N(R$_r$), or N(R$_r$)SO$_2$, wherein R$_r$ and R$_s$ are each independently selected from hydrogen or C$_{1-2}$alkyl; and   15
Q$_1$ is hydrogen, cyano, C$_{1-6}$alkyl, C$_{3-6}$cycloalkyl, C$_{2-3}$alkenyl, C$_{2-3}$alkynyl, aryl, heterocyclyl or heteroaryl; and wherein Q$_1$ is optionally substituted by one or more substituents selected from C$_{1-4}$alkyl, halo, trifluoromethyl, trifluoromethoxy,   20 amino, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and   25 R$_u$ are each independently selected from hydrogen or C$_{1-4}$alkyl; or
Q$_1$ is optionally substituted by a group of the formula:

-L$_{1c}$-L$_{1d}$-Z$_1$   30 wherein
L$_{1c}$ is absent or C$_{1-3}$alkylene optionally substituted by C$_{1-2}$alkyl or oxo;
L$_{1d}$ is absent or selected from C(O), C(O)O, OC(O),   35 C(O)N(R$_v$), N(R$_v$)C(O), N(R$_v$)C(O)N(R$_w$), S(O)$_2$N(R$_v$), or N(R$_v$)SO$_2$, wherein R$_v$ and R$_w$ are each independently selected from hydrogen or C$_{1-2}$alkyl; and
Z$_1$ is phenyl or 5-6 membered heteroaryl; wherein Z$_1$   40 is optionally substituted by one or more substituents selected from C$_{1-4}$alkyl, halo, C$_{1-4}$haloalkyl, C$_{1-4}$haloalkoxy, C$_{1-4}$alkoxy, C$_{1-4}$alkylamino, amino, cyano, hydroxyl, carboxy, carbamoyl or sulphamoyl;   45
R$_{1a'}$ is selected from hydrogen and methyl;
R$_{2a}$, R$_{2b}$ and R$_{2c}$ are selected from hydrogen or a group of the formula:

-L$_{2a}$-L$_{2b}$-Q$_2$   50 wherein
L$_{2a}$ is absent or C$_{1-3}$alkylene optionally substituted by C$_{1-2}$ alkyl or oxo;
L$_{2b}$ is selected from O, S, SO, SO$_2$, N(R$_n$), C(O), C(O)O, OC(O), C(O)N(R$_n$), N(R$_n$)C(O), N(R$_n$)C   55 (O)N(R$_o$), S(O)$_2$N(R$_n$), or N(R$_n$)SO$_2$, wherein R$_n$ and R$_o$ are each independently selected from hydrogen or C$_{1-2}$alkyl; and
Q$_2$ is hydrogen, cyano, C$_{1-6}$alkyl, C$_{3-6}$cycloalkyl, aryl, heterocyclyl or heteroaryl, each of which is   60 optionally substituted by one or more substituents selected from halo, trifluoromethyl, trifluoromethoxy, amino, cyano, hydroxy, amino, carboxy, carbamoyl, sulphamoyl, C$_{1-4}$alkyl, NR$_p$R$_q$, OR$_p$, C(O)R$_p$, C(O)OR$_p$, OC(O)R$_p$, C(O)N(R$_p$)   65 R$_q$, N(R$_r$)C(O)R$_p$, S(O)$_y$R$_p$ (where y is 0, 1 or 2), SO$_2$N(R$_p$)R$_q$, N(R$_r$)SO$_2$R$_p$ or (CH$_2$)$_z$NR$_p$R$_q$ (where z is 1, 2 or 3), wherein R$_p$ and R$_q$ are each independently selected from hydrogen or C$_{1-4}$alkyl;
Y is selected from:

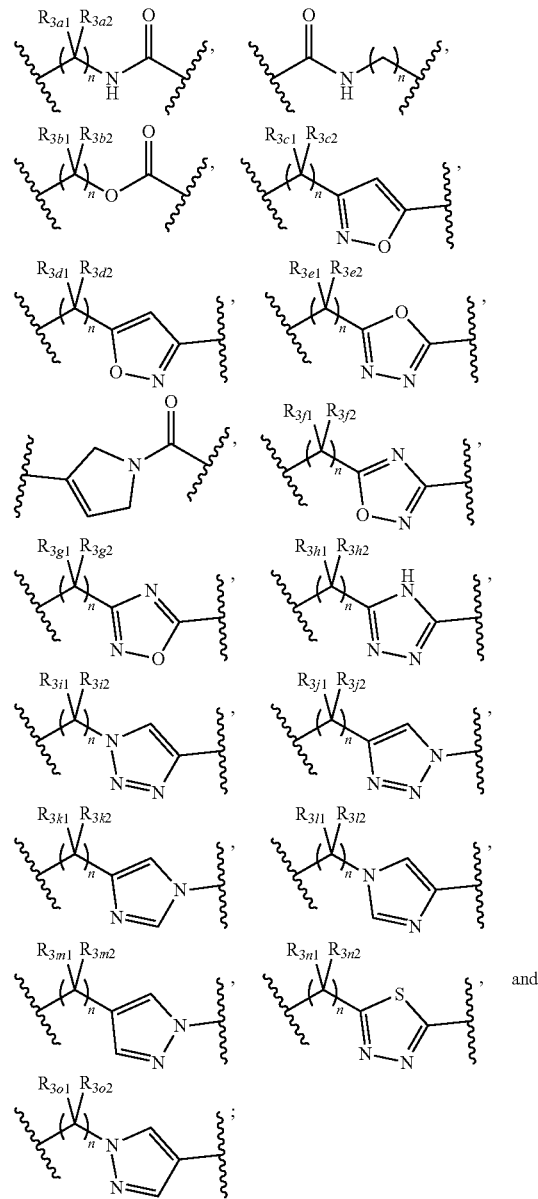

wherein
R$_{3a1}$, R$_{3b1}$, R$_{3c1}$, R$_{3d1}$, R$_{3e1}$, R$_{3f1}$, R$_{3g1}$, R$_{3h1}$, R$_{3i1}$, R$_{3j1}$, R$_{3k1}$, R$_{3l1}$, R$_{3m1}$, R$_{3n1}$ and R$_{3o1}$ are independently selected from hydrogen, C$_{1-6}$alkyl, C$_{3-4}$ cycloalkyl, hydroxy, and halo; and wherein C$_{1-6}$alkyl, or C$_{3-4}$ cycloalkyl is optionally substituted with one or more substituents selected from halo, amino, cyano, and hydroxy;
R$_{3a2}$, R$_{3b2}$, R$_{3c2}$, R$_{3d2}$, R$_{3e2}$, R$_{3f2}$, R$_{3g2}$, R$_{3h2}$, R$_{3i2}$, R$_{3j2}$, R$_{3k2}$, R$_{3l2}$, R$_{3m2}$, R$_{3n2}$ and R$_{3o2}$ are hydrogen;
or R$_{3a1}$ and R$_{3a2}$, R$_{3b1}$ and R$_{3b2}$, R$_{3c1}$ and R$_{3c2}$, R$_{3d1}$ and R$_{3d2}$, R$_{3e1}$ and R$_{3e2}$, R$_{3f1}$ and R$_{3f2}$, R$_{3g1}$ and R$_{3g2}$, R$_{3h1}$ and R$_{3h2}$, R$_{3i1}$ and R$_{3i2}$, R$_{3j1}$ and R$_{3j2}$, R$_{3k1}$ and R$_{3k2}$, R$_{3l1}$ and R$_{3l2}$, R$_{3m1}$ and R$_{3m2}$, R$_{3n1}$ and $R_{3n2}$, or $R_{3o1}$ and $R_{3o2}$ may be linked to form a spiro-fused $C_{3-4}$cycloalkyl which is optionally substituted with one or more substituents selected from halo, amino, cyano, and hydroxy;

Z is selected from:

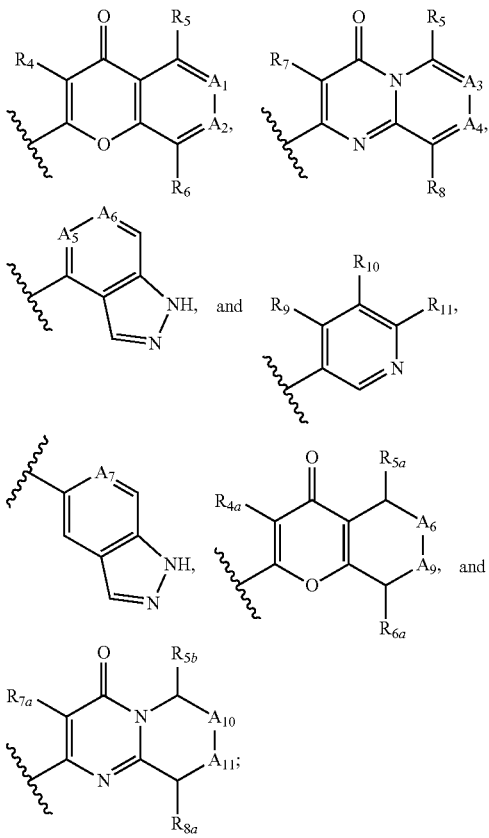

wherein $R_4$, $R_7$ $R_{4a}$ and $R_{7a}$ are independently selected from hydrogen and methyl;

$R_5$, $R_{5a}$ and $R_{5b}$ are independently selected from hydrogen and halo;

$R_6$, $R_8$, $R_{6a}$ and $R_{8a}$ are independently selected from hydrogen, halo and methyl;

$R_9$, $R_{10}$ and $R_{11}$ are independently selected from hydrogen, $NH_2$, halo, cyano, and $C_{1-6}$ alkyl; or $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system;

$A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;
$R_{12}$ and $R_{14}$ are independently selected from hydrogen, halo, cyano and $C_{1-4}$ alkyl;
$R_{13}$ is selected from hydrogen, halo, cyano and methyl;
$R_{15}$ is selected from hydrogen, methoxy and methyl;
$R_{16}$ is selected from hydrogen, halo, cyano and $C_{1-4}$ alkyl;
$R_{17}$ is selected from hydrogen, halo, cyano, $C_{1-4}$ alkyl, $C_{2-4}$ alkenyl, $C_{2-4}$ alkynyl and a 5- or 6-membered heteroaryl;
$R_{18}$ is selected from hydrogen, halo, cyano, $C_{1-4}$ alkyl, $C_{2-4}$ alkenyl, $C_{2-4}$ alkynyl and a 5- or 6-membered heteroaryl;
$R_{19}$, $R_{20}$, $R_{25}$ and $R_{26}$ are selected from hydrogen, halo, cyano and $C_{1-4}$ alkyl;
$R_{22}$ and $R_{23}$ are selected from hydrogen, halo, cyano and methyl;
$R_{28}$ and $R_{29}$ are selected from hydrogen, methoxy and methyl;
$R_{21}$, $R_{24}$, $R_{27}$ and $R_{30}$ are hydrogen; and
n is 0, 1 or 2.

Paragraph 3. A compound according to Paragraph 1, or a pharmaceutically acceptable salt thereof, wherein X is:

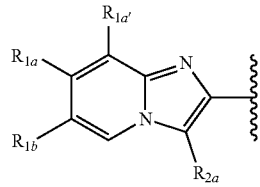

and $R_{1a}$, $R_{1b}$, $R_{1a'}$ and $R_{2a}$ are each as defined in claim 1.

Paragraph 4. A compound according to any one of the preceding Paragraphs, or a pharmaceutically acceptable salt thereof, wherein one of $R_{1a}$ and $R_{1b}$, $R_{1c}$ and $R_{1d}$, $R_{1e}$ and $R_{1f}$ is selected from hydrogen, halo, $C_{1-6}$alkyl, $C_{2-3}$alkenyl or —O—$C_{1-6}$alkyl, and the other is selected from hydrogen, cyano, halo or a group of the formula:

-$L_{1a}$-$L_{1b}$-$Q_1$ wherein $L_{1a}$ is absent or $C_{1-3}$alkylene, $C_{3-4}$cycloalkylene, optionally substituted by one or more substituents selected from $C_{1-2}$alkyl, halo, hydroxy, or oxo;

$L_{1b}$ is absent or selected from O, S, SO, $SO_2$, N($R_r$), C(O), C(O)O, OC(O), C(O)N($R_r$), N($R_r$)C(O), N($R_r$)C(O)N($R_s$), S(O)$_2$N($R_r$), or N($R_r$)$SO_2$, wherein $R_r$ and $R_s$ are each independently selected from hydrogen or $C_{1-2}$alkyl; and $Q_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or $Q_1$ is optionally substituted by one or more groups of the formula:

-$L_{1c}$-$L_{1d}$-$Z_1$ wherein
$L_{1c}$ is absent or $C_{1-3}$alkylene optionally substituted by $C_{1-2}$alkyl or oxo;
$L_{1d}$ is absent or selected from C(O), C(O)O, OC(O), C(O)N($R_v$), N($R_v$)C(O), N($R_v$)C(O)N($R_w$), S(O)$_2$N ($R_v$), or N($R_v$)SO$_2$, wherein $R_v$ and $R_w$ are each independently selected from hydrogen or $C_{1-2}$alkyl; and
$Z_1$ is phenyl or 5-6 membered heteroaryl; wherein $Z_1$ is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl.

Paragraph 5. A compound according to Paragraph 4, or a pharmaceutically acceptable salt thereof, wherein $R_{1a}$, $R_{1c}$ and $R_{1e}$ are selected from hydrogen, halo, $C_{1-6}$alkyl, $C_{2-3}$alkenyl or —O—$C_{1-6}$alkyl
and $R_{1b}$, $R_{1d}$, and $R_{1f}$ are selected from hydrogen, cyano, halo or a group of the formula:

-$L_{1a}$-$L_{1b}$-$Q_1$ wherein
$L_{1a}$ is absent or $C_{1-3}$alkylene, $C_{3-4}$cycloalkylene, optionally substituted by one or more substituents selected from $C_{1-2}$alkyl, halo, hydroxy, or oxo;
$L_{1b}$ is absent or selected from O, S, SO, SO$_2$, N($R_r$), C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or $C_{1-2}$alkyl; and
$Q_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and R$_u$ are each independently selected from hydrogen or $C_{1-4}$alkyl; or
$Q_1$ is optionally substituted by one or more groups of the formula:

-$L_{1c}$-$L_{1d}$-$Z_1$ wherein
$L_{1c}$ is absent or $C_{1-3}$alkylene optionally substituted by $C_{1-2}$alkyl or oxo;
$L_{1d}$ is absent or selected from C(O), C(O)O, OC(O), C(O)N($R_v$), N($R_v$)C(O), N($R_v$)C(O)N($R_w$), S(O)$_2$N($R_v$), or N($R_v$)SO$_2$, wherein $R_v$ and $R_w$ are each independently selected from hydrogen or $C_{1-2}$alkyl; and
$Z_1$ is phenyl or 5-6 membered heteroaryl; wherein $Z_1$ is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl.

Paragraph 6. A compound according to any one of the preceding Paragraphs, or a pharmaceutically acceptable salt thereof, wherein $R_{1a}$, $R_{1c}$ and $R_{1e}$ are selected from hydrogen, halo, $C_{1-4}$alkyl, $C_{2-3}$alkenyl and —O-$C_{14}$alkyl.

Paragraph 7. A compound according to any one of the preceding Paragraphs, or a pharmaceutically acceptable salt thereof, wherein:
$R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent or $C_{1-3}$alkylene, optionally substituted by one or more hydroxy;
$L_{1b}$ is absent or N($R_r$) wherein $R_r$ is hydrogen; and
$Q_1$ is $C_{1-6}$alkyl, $C_{2-3}$alkenyl, $C_{3-6}$cycloalkyl, aryl, heterocyclyl or heteroaryl; and wherein
$Q_1$ is optionally substituted by one or more substituents selected from halo, carboxy, trifluromethyl, NR$_t$R$_u$, OR$_t$ wherein R$_t$ and R$_u$ are independently selected from hydrogen or $C_{1-4}$alkyl; or
$Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is 5-6 membered heteroaryl; wherein $Z_1$ is optionally substituted by one or more $C_{1-4}$alkyl.

Paragraph 8. A compound according to any one of the preceding Paragraphs, or a pharmaceutically acceptable salt thereof, wherein:
$R_{1b}$, $R_{1d}$ and $R_{1f}$ are selected from hydrogen, halo, cyano or from a group of formula:

-$L_{1a}$-$L_{1b}$-$Q_1$ wherein
$L_{1a}$ is absent or $C_{1-3}$alkylene;
$L_{1b}$ is absent or N($R_r$) wherein $R_r$ is hydrogen; and
$Q_1$ is $C_{1-6}$alkyl, and wherein
$Q_1$ is substituted by a group of the formula:

-$L_{1c}$-$L_{1d}$-$Z_1$ wherein
$L_{1c}$ is absent;
$L_{1d}$ is absent; and
$Z_1$ is phenyl.

Paragraph 9. A compound according to any one of Paragraphs 1 to 8, or a pharmaceutically acceptable salt thereof, wherein $Q_1$ is a 5- or 6-membered aryl, a 5- or 6-membered heteroaryl, or a 5- or 6-membered heterocyclyl, wherein $Q_1$ is optionally substituted by one or more substituents selected from halo, NR$_t$R$_u$, OR$_t$ wherein R$_t$ and R$_u$ are independently selected from hydrogen or $C_{1-4}$alkyl; or
$Q_1$ is optionally substituted by one or more groups of the formula:

-$L_{1c}$-$L_{1d}$-$Z_1$ wherein
$L_{1c}$ is absent;
$L_{1d}$ is absent; and
$Z_1$ is 5-6 membered heteroaryl; wherein $Z_1$ is optionally substituted by one or more $C_{1-4}$alkyl.

Paragraph 10. A compound according to any one of the preceding Paragraphs, or a pharmaceutically acceptable salt thereof, wherein $R_{2a}$, $R_{2b}$ and $R_{2c}$ are hydrogen.

Paragraph 11. A compound according to any one of the preceding Paragraphs, or a pharmaceutically acceptable salt thereof, wherein X is selected from

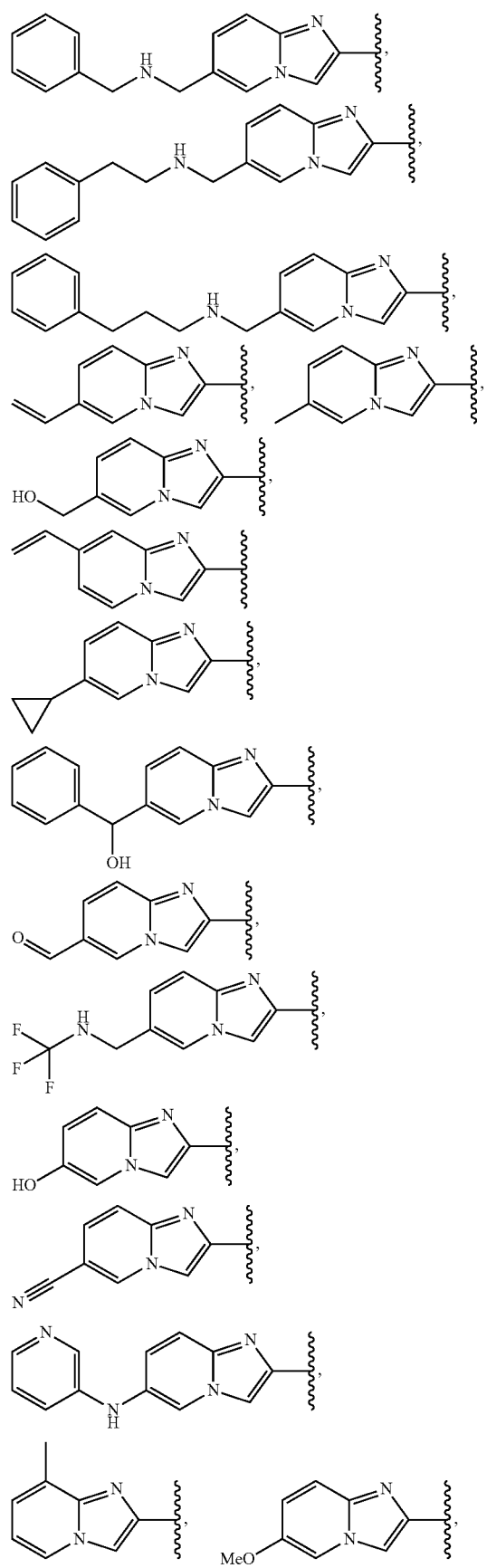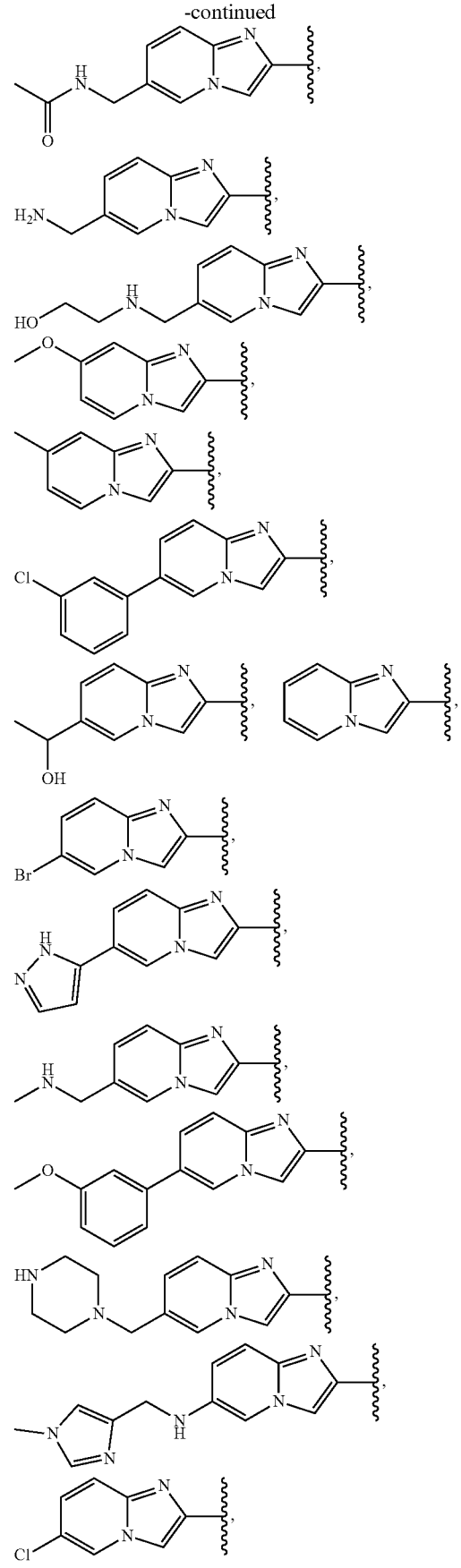

-continued

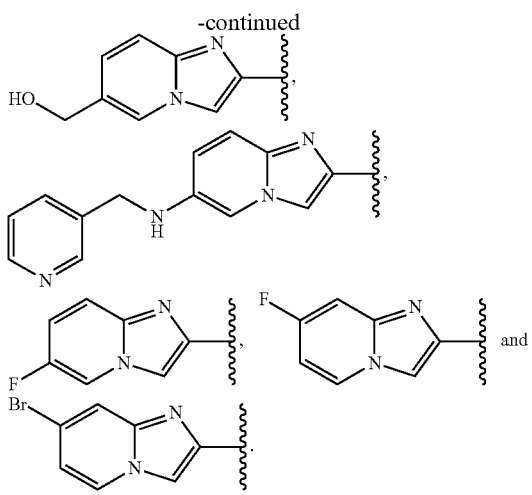

Paragraph 12. A compound according to any one of the preceding Paragraphs, or a pharmaceutically acceptable salt thereof, wherein X is

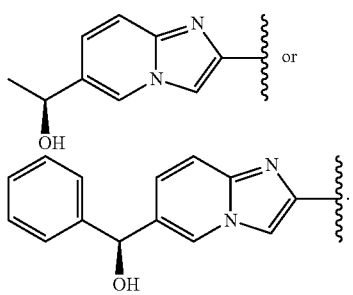 or

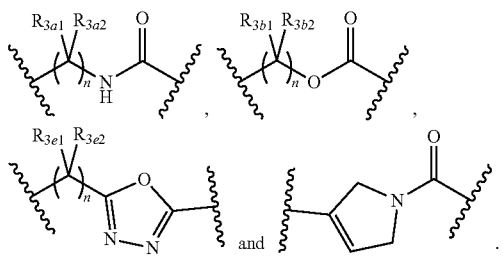

Paragraph 13. A compound according to any one of the preceding Paragraphs, or a pharmaceutically acceptable salt thereof, wherein Y is selected from:

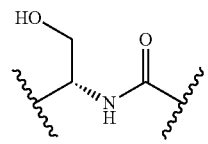

Paragraph 14. A compound according to any one of the preceding Paragraphs, or a pharmaceutically acceptable salt thereof, wherein $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen and $C_{1-6}$alkyl; and wherein $C_{1-6}$alkyl is optionally substituted with one or more hydroxy substituents.

Paragraph 15. A compound according to any one of the preceding Paragraphs, or a pharmaceutically acceptable salt thereof, wherein $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$ are hydrogen.

Paragraph 16. A compound according to any one of the preceding Paragraphs, or a pharmaceutically acceptable salt thereof, wherein n is 1.

Paragraph 17. A compound according to any one of the preceding Paragraphs, or a pharmaceutically acceptable salt thereof, wherein Y is selected from:

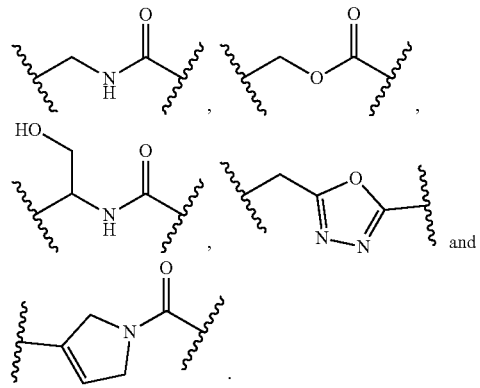

Paragraph 18. A compound according to any one of the preceding Paragraphs, or a pharmaceutically acceptable salt thereof, wherein Y is

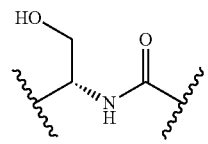

Paragraph 19. A compound according to any one of the preceding Paragraphs, or a pharmaceutically acceptable salt thereof, wherein Z is selected from:

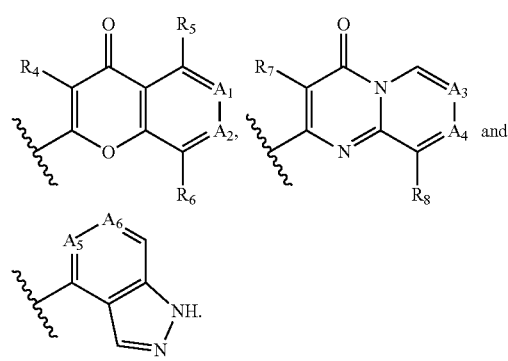

Paragraph 20. A compound according to any one of the preceding Paragraphs, or a pharmaceutically acceptable salt thereof, wherein $R_4$, $R_5$, $R_6$, $R_7$, $R_8$, $R_{4a}$, $R_{5a}$, $R_{5b}$, $R_{6a}$, $R_{7a}$ and $R_{8a}$ are hydrogen.

Paragraph 21. A compound according to any one of the preceding Paragraphs, or a pharmaceutically acceptable salt thereof, wherein $A_1$ is $CR_{12}$ and wherein $R_{12}$ is hydrogen.

Paragraph 22. A compound according to any one of the preceding Paragraphs, or a pharmaceutically acceptable salt thereof, wherein $A_2$ is $CR_{13}$ and wherein $R_{13}$ is hydrogen.

Paragraph 23. A compound according to any one of the preceding Paragraphs, or a pharmaceutically acceptable salt thereof, wherein $A_3$ is $CR_{14}$ and wherein $R_{14}$ is hydrogen or chloro.

Paragraph 24. A compound according to any one of the preceding Paragraphs, or a pharmaceutically acceptable salt thereof, wherein $A_4$ is $CR_{15}$ and wherein $R_{15}$ is hydrogen or methoxy.

Paragraph 25. A compound according to any one of the preceding Paragraphs, or a pharmaceutically acceptable salt thereof, wherein $A_5$ is $CR_{16}$ and wherein $R_{16}$ is hydrogen.

Paragraph 26. A compound according to any one of the preceding Paragraphs, or a pharmaceutically acceptable salt thereof, wherein $A_6$ is $CR_{17}$ and wherein $R_{17}$ is selected from hydrogen, halo, $C_{1-4}$ alkynyl and a 5- or 6-membered heteroaryl.

Paragraph 27. A compound according to Paragraph 26, or a pharmaceutically acceptable salt thereof, wherein $R_{17}$ is a 5-membered heteroaryl.

Paragraph 28. A compound according to any one of the preceding Paragraphs, or a pharmaceutically acceptable salt thereof, wherein Z is selected from:

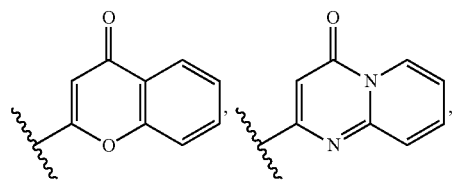

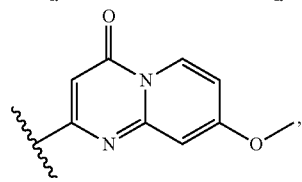

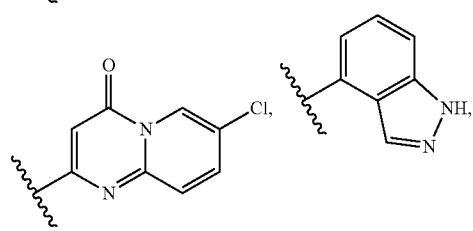

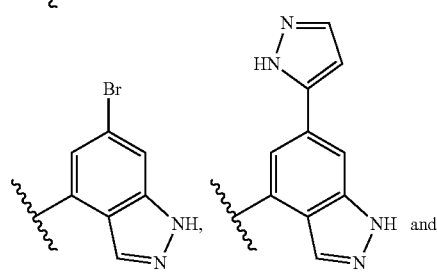

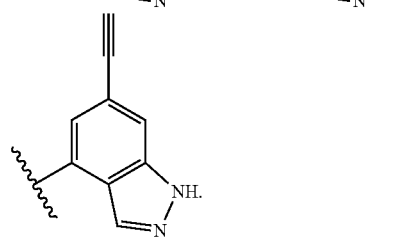

Paragraph 29. A compound according to Paragraph 1 or Paragraph 2, or a pharmaceutically acceptable salt thereof, wherein:

X is

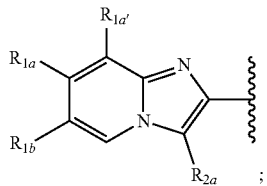

Y is selected from

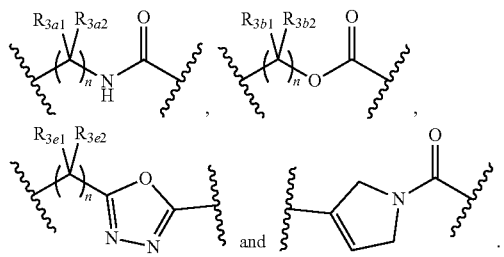

and

Z is selected from

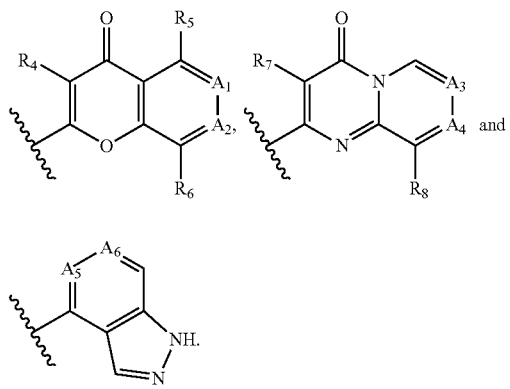

Paragraph 30. A compound according to Paragraph 29, or a pharmaceutically acceptable salt thereof, wherein:

X is

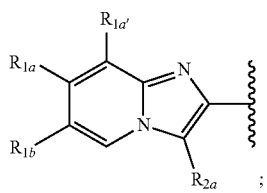

Y is

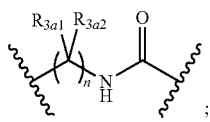
;

Z is

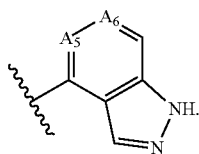

Paragraph 31. A compound according to Paragraph 29, or a pharmaceutically acceptable salt thereof, wherein:
X is

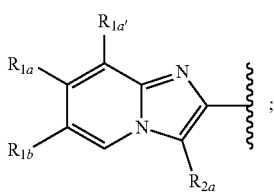
;

Y is

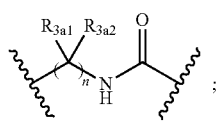
;

Z is

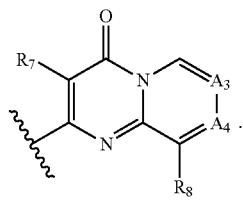

Paragraph 32. A compound according to Paragraph 1 or Paragraph 2, or a pharmaceutically acceptable salt thereof, wherein:
$R_9$ and $R_{10}$ are linked together to form a fused 5- or 6-membered unsaturated ring system or $R_{10}$ and $R_{11}$ may be linked together to form a fused 5- or 6-membered unsaturated ring system.

Paragraph 33. A compound according to Paragraph 1, or a pharmaceutically acceptable salt thereof, wherein:
$R_{1a}$, $R_{1c}$ and $R_{1e}$ are independently selected from hydrogen, $C_{2-3}$alkenyl, cyano, halo, $C_{1-6}$alkyl, $OR^t$, wherein $R^t$ is $C_{1-4}$alkyl; and $R_{1b}$, $R_{1d}$ and $R_{1f}$ are independently selected from hydrogen, cyano, halo, and a group of the formula:

$-L_{1a}-L_{1b}-Q_1$ wherein
$L_{1a}$ is absent or $C_{1-3}$alkylene, $C_{3-4}$cycloalkylene, optionally substituted by one or more substituents selected from $C_{1-2}$alkyl, halo, hydroxy, or oxo;
$L_{1b}$ is absent or selected from O, S, SO, $SO_2$, $N(R_r)$, C(O), C(O)O, OC(O), $C(O)N(R_r)$, $N(R_r)C(O)$, $N(R_r)C(O)N(R_s)$, $S(O)_2N(R_r)$, or $N(R_r)SO_2$, wherein $R_r$ and $R_s$ are each independently selected from hydrogen or $C_{1-2}$alkyl; and
$Q_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from hydrogen or $C_{1-4}$alkyl; or
$Q_1$ is optionally substituted by one or more groups of the formula:

$-L_{1c}-L_{1d}-Z_1$ wherein
$L_{1c}$ is absent or $C_{1-3}$alkylene optionally substituted by $C_{1-2}$alkyl or oxo;
$L_{1d}$ is absent or selected from C(O), C(O)O, OC(O), $C(O)N(R_v)$, $N(R_v)C(O)$, $N(R_v)C(O)N(R_w)$, $S(O)_2N(R_v)$, or $N(R_v)SO_2$, wherein $R_v$ and $R_w$ are each independently selected from hydrogen or $C_{1-2}$alkyl; and
$Z_1$ is phenyl or 5-6 membered heteroaryl; wherein $Z_1$ is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl.

Paragraph 34. A compound, or a pharmaceutically acceptable salt thereof, selected from any one of the following:
N-({6-methylimidazo[1,2-a]pyridin-2-yl}methyl)-1H-indazole-4-carboxamide;
N-({7-bromoimidazo[1,2-a]pyridin-2-yl}methyl)-1H-indazole-4-carboxamide;
N-({6-bromoimidazo[1,2-a]pyridin-2-yl}methyl)-1H-indazole-4-carboxamide;
N-({6-chloroimidazo[1,2-a]pyridin-2-yl}methyl)-1H-indazole-4-carboxamide;
N-({7-fluoroimidazo[1,2-a]pyridin-2-yl}methyl)-1H-indazole-4-carboxamide;
N-({6-fluoroimidazo[1,2-a]pyridin-2-yl}methyl)-1H-indazole-4-carboxamide;
N-({7-methoxyimidazo[1,2-a]pyridin-2-yl}methyl)-1H-indazole-4-carboxamide;
N-({6-methylimidazo[1,2-a]pyridin-2-yl}methyl)-6-(1H-pyrazol-5-yl)-1H-indazole-4-carboxamide;
N-({7-methylimidazo[1,2-a]pyridin-2-yl}methyl)-1H-indazole-4-carboxamide;
6-bromo-N-({6-methylimidazo[1,2-a]pyridin-2-yl}methyl)-1H-indazole-4-carboxamide;
6-bromo-N-({7-methylimidazo[1,2-a]pyridin-2-yl}methyl)-1H-indazole-4-carboxamide;
N-({6-methylimidazo[1,2-a]pyridin-2-yl}methyl)-4-oxo-4H-chromene-2-carboxamide;
N-({imidazo[1,2-a]pyridin-2-yl}methyl)-4-oxo-4H-chromene-2-carboxamide;

6-ethynyl-N-({6-methylimidazo[1,2-a]pyridin-2-yl}methyl)-1H-indazole-4-carboxamide;
N-({6-methylimidazo[1,2-a]pyridin-2-yl}methyl)-4-oxo-4H-pyrido[1,2-a]pyrimidine-2-carboxamide;
N-({7-methylimidazo[1,2-a]pyridin-2-yl}methyl)-4-oxo-4H-chromene-2-carboxamide;
N-({7-methylimidazo[1,2-a]pyridin-2-yl}methyl)-4-oxo-4H-pyrido[1,2-a]pyrimidine-2-carboxamide;
N-({6-cyanoimidazo[1,2-a]pyridin-2-yl}methyl)-4-oxo-4H-pyrido[1,2-a]pyrimidine-2-carboxamide;
8-methoxy-N-({6-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-indazole-5-carboxamide;
7-chloro-N-({6-methylimidazo[1,2-a]pyridin-2-yl}methyl)-4-oxo-4H-pyrido[1,2-a]pyrimidine-2-carboxamide;
N-({6-fluoroimidazo[1,2-a]pyridin-2-yl}methyl)-4-oxo-4H-pyrido[1,2-a]pyrimidine-2-carboxamide;
N-({6-bromoimidazo[1,2-a]pyridin-2-yl}methyl)-4-oxo-4H-pyrido[1,2-a]pyrimidine-2-carboxamide;
N-({6-methoxyimidazo[1,2-a]pyridin-2-yl}methyl)-4-oxo-4H-pyrido[1,2-a]pyrimidine-2-carboxamide;
N-({7-methoxyimidazo[1,2-a]pyridin-2-yl}methyl)-4-oxo-4H-pyrido[1,2-a]pyrimidine-2-carboxamide;
N-({imidazo[1,2-a]pyridin-2-yl}methyl)-4-oxo-4H-pyrido[1,2-a]pyrimidine-2-carboxamide;
N-({8-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-pyrazolo[4,3-c]pyridine-4-carboxamide;
N-({7-bromoimidazo[1,2-a]pyridin-2-yl}methyl)-4-oxo-4H-pyrido[1,2-a]pyrimidine-2-carboxamide;
N-(2-hydroxy-1-{6-methylimidazo[1,2-a]pyridin-2-yl}ethyl)-1H-indazole-4-carboxamide;
4-(3-{imidazo[1,2-a]pyridin-2-yl}-2,5-dihydro-1H-pyrrole-1-carbonyl)-1H-indazole;
N-[(6-{[(pyridin-3-yl)methyl]amino}imidazo[1,2-a]pyridin-2-yl)methyl]-1H-indazole-4-carboxamide;
N-[(6-{[(1-methyl-1H-imidazol-4-yl)methyl]amino}imidazo[1,2-a]pyridin-2-yl)methyl]-1H-indazole-4-carboxamide;
N-{[6-(3-methoxyphenyl)imidazo[1,2-a]pyridin-2-yl]methyl}-1H-indazole-4-carboxamide;
N-{[6-(1H-pyrazol-5-yl)imidazo[1,2-a]pyridin-2-yl]methyl}-1H-indazole-4-carboxamide;
N-[[6-(3-chlorophenyl)imidazo[1,2-a]pyridin-2-yl]methyl]-1H-indazole-4-carboxamide;
N-({6-[(pyridin-3-yl)amino]imidazo[1,2-a]pyridin-2-yl}methyl)-1H-indazole-4-carboxamide;
N-({6-[(piperazin-1-yl)methyl]imidazo[1,2-a]pyridin-2-yl}methyl)-1H-indazole-4-carboxamide;
N-{[6-(aminomethyl)imidazo[1,2-a]pyridin-2-yl]methyl}-1H-indazole-4-carboxamide;
N-{[6-(acetamidomethyl)imidazo[1,2-a]pyridin-2-yl]methyl}-1H-indazole-4-carboxamide;
{6-methylimidazo[1,2-a]pyridin-2-yl}methyl 1H-indazole-4-carboxylate;
{6-methylimidazo[1,2-a]pyridin-2-yl}methyl 1H-indazole-4-carboxylate hydrochloride;
N-{[6-(hydroxymethyl)imidazo[1,2-a]pyridin-2-yl]methyl}-1H-indazole-4-carboxamide;
N-({6-hydroxyimidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide dihydrochloride;
N-[(6-{[(2-hydroxyethyl)amino]methyl}imidazo[1,2-a]pyridin-2-yl)methyl]-1H-indazole-4-carboxamide;
N-[(6-{[(2,2,2-trifluoroethyl)amino]methyl}imidazo[1,2-a]pyridin-2-yl)methyl]-1H-indazole-4-carboxamide;
N-{[6-(1-hydroxyethyl)imidazo[1,2-a]pyridin-2-yl]methyl}-1H-indazole-4-carboxamide;
N-({6-[hydroxy(phenyl)methyl]imidazo[1,2-a]pyridin-2-yl}methyl)-1H-indazole-4-carboxamide;
N-({6-formylimidazo[1,2-a]pyridin-2-yl}methyl)-4-oxo-4H-pyrido[1,2-a]pyrimidine-2-carboxamide;
N-{[6-(aminomethyl)imidazo[1,2-a]pyridin-2-yl]methyl}-4-oxo-4H-pyrido[1,2-a]pyrimidine-2-carboxamide;
4-oxo-N-[(6-{[(2,2,2-trifluoroethyl)amino]methyl}imidazo[1,2-a]pyridin-2-yl)methyl]-4H-pyrido[1,2-a]pyrimidine-2-carboxamide;
N-[(6-{[(2-hydroxyethyl)amino]methyl}imidazo[1,2-a]pyridin-2-yl)methyl]-4-oxo-4H-pyrido[1,2-a]pyrimidine-2-carboxamide;
4-oxo-N-[(6-{[(2-phenylethyl)amino]methyl}imidazo[1,2-a]pyridin-2-yl)methyl]-4H-pyrido[1,2-a]pyrimidine-2-carboxamide;
N-({6-[(benzylamino)methyl]imidazo[1,2-a]pyridin-2-yl}methyl)-4-oxo-4H-pyrido[1,2-a]pyrimidine-2-carboxamide;
4-oxo-N-[(6-{[(3-phenylpropyl)amino]methyl}imidazo[1,2-a]pyridin-2-yl)methyl]-4H-pyrido[1,2-a]pyrimidine-2-carboxamide;
N-({6-[hydroxy(phenyl)methyl]imidazo[1,2-a]pyridin-2-yl}methyl)-4-oxo-4H-pyrido[1,2-a]pyrimidine-2-carboxamide;
N-{[6-(1-hydroxyethyl)imidazo[1,2-a]pyridin-2-yl]methyl}-4-oxo-4H-pyrido[1,2-a]pyrimidine-2-carboxamide;
N-({6-ethenylimidazo[1,2-a]pyridin-2-yl}methyl)-4-oxo-4H-pyrido[1,2-a]pyrimidine-2-carboxamide;
N-({6-cyclopropylimidazo[1,2-a]pyridin-2-yl}methyl)-4-oxo-4H-pyrido[1,2-a]pyrimidine-2-carboxamide;
N-({7-ethenylimidazo[1,2-a]pyridin-2-yl}methyl)-4-oxo-4H-pyrido[1,2-a]pyrimidine-2-carboxamide;
N-{[6-(hydroxymethyl)imidazo[1,2-a]pyridin-2-yl]methyl}-4-oxo-4H-pyrido[1,2-a]pyrimidine-2-carboxamide;
2-(1H-indazol-4-yl)-5-[(6-methylimidazo[1,2-a]pyridin-2-yl)methyl]-1,3,4-oxadiazole;
N-{[6-(2-aminoethyl)imidazo[1,2-a]pyridin-2-yl]methyl}-4-oxo-4H-pyrido[1,2-a]pyrimidine-2-carboxamide;
N-({6-methylimidazo[1,2-a]pyridin-2-yl}methyl)-4-oxo-4H,6H,7H,8H,9H-pyrido[1,2-a]pyrimidine-2-carboxamide;
4-oxo-N-{[6-(trifluoromethyl)imidazo[1,2-a]pyridin-2-yl]methyl}-4H-pyrido[1,2-a]pyrimidine-2-carboxamide;
tert-butyl N-(2-{2-[({4-oxo-4H-pyrido[1,2-a]pyrimidin-2-yl}formamido)methyl]imidazo[1,2-a]pyridin-6-yl}ethyl)carbamate;
N-benzyl-2-[({4-oxo-4H-pyrido[1,2-a]pyrimidin-2-yl}formamido)methyl]imidazo[1,2-a]pyridine-6-carboxamide;
N-[(6-{[(cyclohexylmethyl)amino]methyl}imidazo[1,2-a]pyridin-2-yl)methyl]-4-oxo-4H-chromene-2-carboxamide;
7-chloro-N-[(6-{[(cyclohexylmethyl)amino]methyl}imidazo[1,2-a]pyridin-2-yl)methyl]-4-oxo-4H-chromene-2-carboxamide;

6-chloro-N-[(6-{[(cyclohexylmethyl)amino]methyl}imidazo[1,2-a]pyridin-2-yl)methyl]-4-oxo-4H-chromene-2-carboxamide;

N-[(6-{[(cyclohexylmethyl)amino]methyl}imidazo[1,2-a]pyridin-2-yl)methyl]-4-oxo-4H,6H,7H,8H,9H-pyrido[1,2-a]pyrimidine-2-carboxamide;

6-amino-N-[(6-{[(cyclohexylmethyl)amino]methyl}imidazo[1,2-a]pyridin-2-yl)methyl]pyridine-3-carboxamide;

N-({6-[(benzyloxy)methyl]imidazo[1,2-a]pyridin-2-yl}methyl)-4-oxo-4H-pyrido[1,2-a]pyrimidine-2-carboxamide;

N-({6-[(benzylamino)methyl]imidazo[1,2-a]pyridin-2-yl}methyl)-1H-indazole-4-carboxamide;

N-[(6-{[(cyclohexylmethyl)amino]methyl}imidazo[1,2-a]pyridin-2-yl)methyl]-7-fluoro-4-oxo-4H-chromene-2-carboxamide;

N-[(6-{[(cyclohexylmethyl)amino]methyl}imidazo[1,2-a]pyridin-2-yl)methyl]-7-methyl-4-oxo-4H-chromene-2-carboxamide;

N-[(6-{[(cyclohexylmethyl)amino]methyl}imidazo[1,2-a]pyridin-2-yl)methyl]-1H-indazole-4-carboxamide;

8-chloro-N-[(6-{[(cyclohexylmethyl)amino]methyl}imidazo[1,2-a]pyridin-2-yl)methyl]-4-oxo-4H-chromene-2-carboxamide;

6-bromo-N-[(6-{[(cyclohexylmethyl)amino]methyl}imidazo[1,2-a]pyridin-2-yl)methyl]-1H-indazole-4-carboxamide;

N-[(6-{[(cyclohexylmethyl)amino]methyl}imidazo[1,2-a]pyridin-2-yl)methyl]quinoline-3-carboxamide;

N-[(6-{1-[(cyclohexylmethyl)amino]ethyl}imidazo[1,2-a]pyridin-2-yl)methyl]-4-oxo-4H-pyrido[1,2-a]pyrimidine-2-carboxamide;

6-chloro-N-[(6-{[(cyclohexylmethyl)amino]methyl}imidazo[1,2-a]pyridin-2-yl)methyl]-1H-indazole-4-carboxamide;

4-[5-({6-methylimidazo[1,2-a]pyridin-2-yl}methyl)-1,3,4-thiadiazol-2-yl]-1H-indazole;

4-[1-({6-methylimidazo[1,2-a]pyridin-2-yl}methyl)-1H-1,2,3-triazol-4-yl]-1H-indazole;

N-[(6-{[(3-chlorophenyl)amino]methyl}imidazo[1,2-a]pyridin-2-yl)methyl]-4-oxo-4H-pyrido[1,2-a]pyrimidine-2-carboxamide;

N-[(6-{[(1-cyclohexyl-2-hydroxyethyl)amino]methyl}imidazo[1,2-a]pyridin-2-yl)methyl]-4-oxo-4H-pyrido[1,2-a]pyrimidine-2-carboxamide;

4-oxo-N-{[6-({[(pyridin-3-yl)methyl]amino}methyl)imidazo[1,2-a]pyridin-2-yl]methyl}-4H-pyrido[1,2-a]pyrimidine-2-carboxamide;

N-{[6-({[(4-methoxyphenyl)methyl]amino}methyl)imidazo[1,2-a]pyridin-2-yl]methyl}-4-oxo-4H-pyrido[1,2-a]pyrimidine-2-carboxamide;

N-[(6-{[(cyclohexylmethyl)amino]methyl}imidazo[1,2-a]pyridin-2-yl)methyl]-4-oxo-4H-pyrido[1,2-a]pyrimidine-2-carboxamide;

N-{[6-({[(4-chlorophenyl)methyl]amino}methyl)imidazo[1,2-a]pyridin-2-yl]methyl}-4-oxo-4H-pyrido[1,2-a]pyrimidine-2-carboxamide;

N-[(6-{[benzyl(methyl)amino]methyl}imidazo[1,2-a]pyridin-2-yl)methyl]-4-oxo-4H-pyrido[1,2-a]pyrimidine-2-carboxamide;

4-oxo-N-{[6-({[(1R)-1-phenylethyl]amino}methyl)imidazo[1,2-a]pyridin-2-yl]methyl}-4H-pyrido[1,2-a]pyrimidine-2-carboxamide;

4-oxo-N-{[6-({[(1S)-1-phenylethyl]amino}methyl)imidazo[1,2-a]pyridin-2-yl]methyl}-4H-pyrido[1,2-a]pyrimidine-2-carboxamide;

N-{[6-({[(2-fluorophenyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(2-phenylpropan-2-yl)amino]methyl}imidazo[1,2-a]pyridin-2-yl)methyl]-4H-pyrido[1,2-a]pyrimidine-2-carboxamide;

N-{[6-({[(3-fluorophenyl)methyl]amino}methyl)imidazo[1,2-a]pyridin-2-yl]methyl}-4-oxo-4H-pyrido[1,2-a]pyrimidine-2-carboxamide;

N-{[6-({[(4-fluorophenyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(4,4,4-trifluorobutyl)amino]methyl}imidazo[1,2-a]pyridin-2-yl)methyl]-4H-pyrido[1,2-a]pyrimidine-2-carboxamide;

N-{[6-({[(oxan-4-yl)methyl]amino}methyl)imidazo[1,2-a]pyridin-2-yl]methyl}-4-oxo-4H-pyrido[1,2-a]pyrimidine-2-carboxamide;

N-{[6-({[(3,3-difluorocyclobutyl)methyl]amino}methyl)imidazo[1,2-a]pyridin-2-yl]methyl}-4-oxo-4H-pyrido[1,2-a]pyrimidine-2-carboxamide;

N-[(6-{[(cyclopropylmethyl)amino]methyl}imidazo[1,2-a]pyridin-2-yl)methyl]-4-oxo-4H-pyrido[1,2-a]pyrimidine-2-carboxamide;

4-oxo-N-[(6-{[(3,3,3-trifluoropropyl)amino]methyl}imidazo[1,2-a]pyridin-2-yl)methyl]-4H-pyrido[1,2-a]pyrimidine-2-carboxamide;

N-({6-[(cyclohexylamino)methyl]imidazo[1,2-a]pyridin-2-yl}methyl)-4-oxo-4H-pyrido[1,2-a]pyrimidine-2-carboxamide;

4-oxo-N-({6-[({[3-(trifluoromethyl)bicyclo[1.1.1]pentan-1-yl]methyl}amino)methyl]imidazo[1,2-a]pyridin-2-yl}methyl)-4H-pyrido[1,2-a]pyrimidine-2-carboxamide;

N-{[6-({[(oxan-2-yl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(3-phenyloxetan-3-yl)amino]methyl}imidazo[1,2-a]pyridin-2-yl)methyl]-4H-pyrido[1,2-a]pyrimidine-2-carboxamide;

N-{[6-({[(oxan-3-yl)methyl]amino}methyl)imidazo[1,2-a]pyridin-2-yl]methyl}-4-oxo-4H-pyrido[1,2-a]pyrimidine-2-carboxamide;

N-{[6-({[(1-fluorocyclohexyl)methyl]amino}methyl)imidazo[1,2-a]pyridin-2-yl]methyl}-4-oxo-4H-pyrido[1,2-a]pyrimidine-2-carboxamide;

N-{[6-({[(3-cyclopropylphenyl)methyl]amino}methyl)imidazo[1,2-a]pyridin-2-yl]methyl}-4-oxo-4H-pyrido[1,2-a]pyrimidine-2-carboxamide;

N-[(6-{[(3,3-dimethylbutyl)amino]methyl}imidazo[1,2-a]pyridin-2-yl)methyl]-4-oxo-4H-pyrido[1,2-a]pyrimidine-2-carboxamide;

4-oxo-N-{[6-({[2-(trifluoromethoxy)ethyl]amino}methyl)imidazo[1,2-a]pyridin-2-yl]methyl}-4H-pyrido[1,2-a]pyrimidine-2-carboxamide;

4-oxo-N-{[6-({[(oxolan-2-yl)methyl]amino}methyl)imidazo[1,2-a]pyridin-2-yl]methyl}-4H-pyrido[1,2-a]pyrimidine-2-carboxamide;

N-[(6-{[(2-methanesulfonylethyl)amino]methyl}imidazo[1,2-a]pyridin-2-yl)methyl]-4-oxo-4H-pyrido[1,2-a]pyrimidine-2-carboxamide;

4-oxo-N-({6-[(3-phenylpyrrolidin-1-yl)methyl]imidazo[1,2-a]pyridin-2-yl}methyl)-4H-pyrido[1,2-a]pyrimidine-2-carboxamide;

N-[(6-{[(1-cyclohexylcyclopropyl)amino]methyl}imidazo[1,2-a]pyridin-2-yl)methyl]-4-oxo-4H-pyrido[1,2-a]pyrimidine-2-carboxamide;

4-oxo-N-{[6-({[(1,3-thiazol-5-yl)methyl]amino}methyl)imidazo[1,2-a]pyridin-2-yl]methyl}-4H-pyrido[1,2-a]pyrimidine-2-carboxamide;

tert-butyl 3-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;

N-{[6-({[(4,4-difluorocyclohexyl)methyl]amino}methyl)imidazo[1,2-a]pyridin-2-yl]methyl}-4-oxo-4H-pyrido[1,2-a]pyrimidine-2-carboxamide;

tert-butyl 2-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;

N-[(6-{[(2-cyclopropylethyl)amino]methyl}imidazo[1,2-a]pyridin-2-yl)methyl]-4-oxo-4H-pyrido[1,2-a]pyrimidine-2-carboxamide;

4-oxo-N-({6-[(piperidin-1-yl)methyl]imidazo[1,2-a]pyridin-2-yl}methyl)-4H-pyrido[1,2-a]pyrimidine-2-carboxamide;

4-oxo-N-({6-[({[1-(2,2,2-trifluoroethyl)-1H-pyrazol-3-yl]methyl}amino)methyl]imidazo[1,2-a]pyridin-2-yl}methyl)-4H-pyrido[1,2-a]pyrimidine-2-carboxamide;

N-{[6-({[(1-methylcyclohexyl)methyl]amino}methyl)imidazo[1,2-a]pyridin-2-yl]methyl}-4-oxo-4H-pyrido[1,2-a]pyrimidine-2-carboxamide;

4-oxo-N-{[6-({[2-(pyridin-3-yl)ethyl]amino}methyl)imidazo[1,2-a]pyridin-2-yl]methyl}-4H-pyrido[1,2-a]pyrimidine-2-carboxamide;

N-{[6-({[(1,4-dioxan-2-yl)methyl]amino}methyl)imidazo[1,2-a]pyridin-2-yl]methyl}-4-oxo-4H-pyrido[1,2-a]pyrimidine-2-carboxamide;

N-({6-[(cyclopropylamino)methyl]imidazo[1,2-a]pyridin-2-yl}methyl)-4-oxo-4H-pyrido[1,2-a]pyrimidine-2-carboxamide;

N-[(6-{[(3,3-difluorocyclobutyl)amino]methyl}imidazo[1,2-a]pyridin-2-yl)methyl]-4-oxo-4H-pyrido[1,2-a]pyrimidine-2-carboxamide;

N-{[6-({[(oxetan-3-yl)methyl]amino}methyl)imidazo[1,2-a]pyridin-2-yl]methyl}-4-oxo-4H-pyrido[1,2-a]pyrimidine-2-carboxamide;

4-oxo-N-{[6-({[(1R,2R)-2-(trifluoromethyl)cyclopropyl]amino}methyl)imidazo[1,2-a]pyridin-2-yl]methyl}-4H-pyrido[1,2-a]pyrimidine-2-carboxamide;

N-[(6-{[(2,2-dimethylpropyl)amino]methyl}imidazo[1,2-a]pyridin-2-yl)methyl]-4-oxo-4H-pyrido[1,2-a]pyrimidine-2-carboxamide;

N-[(6-{[(cyclohexylmethyl)(methyl)amino]methyl}imidazo[1,2-a]pyridin-2-yl)methyl]-4-oxo-4H-pyrido[1,2-a]pyrimidine-2-carboxamide;

N-[(6-{[(4,4-difluorocyclohexyl)amino]methyl}imidazo[1,2-a]pyridin-2-yl)methyl]-4-oxo-4H-pyrido[1,2-a]pyrimidine-2-carboxamide;

N-({6-[({bicyclo[1.1.1]pentan-1-yl}amino)methyl]imidazo[1,2-a]pyridin-2-yl}methyl)-4-oxo-4H-pyrido[1,2-a]pyrimidine-2-carboxamide;

4-oxo-N-({6-[({[(2S)-oxolan-2-yl]methyl}amino)methyl]imidazo[1,2-a]pyridin-2-yl}methyl)-4H-pyrido[1,2-a]pyrimidine-2-carboxamide;

4-oxo-N-({6-[({[(2R)-oxolan-2-yl]methyl}amino)methyl]imidazo[1,2-a]pyridin-2-yl}methyl)-4H-pyrido[1,2-a]pyrimidine-2-carboxamide;

N-[(6-{[(2,2-difluoroethyl)amino]methyl}imidazo[1,2-a]pyridin-2-yl)methyl]-4-oxo-4H-pyrido[1,2-a]pyrimidine-2-carboxamide;

4-oxo-N-{[6-({[(oxolan-3-yl)methyl]amino}methyl)imidazo[1,2-a]pyridin-2-yl]methyl}-4H-pyrido[1,2-a]pyrimidine-2-carboxamide;

N-{[6-({[(1-methylcyclopropyl)methyl]amino}methyl)imidazo[1,2-a]pyridin-2-yl]methyl}-4-oxo-4H-pyrido[1,2-a]pyrimidine-2-carboxamide;

4-oxo-N-[(6-{[(oxolan-3-yl)amino]methyl}imidazo[1,2-a]pyridin-2-yl)methyl]-4H-pyrido[1,2-a]pyrimidine-2-carboxamide;

methyl 3-methyl-2-[({2-[({4-oxo-4H-pyrido[1,2-a]pyrimidin-2-yl}formamido)methyl]imidazo[1,2-a]pyridin-6-yl}methyl)amino]butanoate;

N-[(6-{[(oxan-3-yl)amino]methyl}imidazo[1,2-a]pyridin-2-yl)methyl]-4-oxo-4H-pyrido[1,2-a]pyrimidine-2-carboxamide;

4-oxo-N-{[6-({[(2S)-3,3,3-trifluoro-2-hydroxypropyl]amino}methyl)imidazo[1,2-a]pyridin-2-yl]methyl}-4H-pyrido[1,2-a]pyrimidine-2-carboxamide;

N-({6-[(cyclobutylamino)methyl]imidazo[1,2-a]pyridin-2-yl}methyl)-4-oxo-4H-pyrido[1,2-a]pyrimidine-2-carboxamide;

N-({6-[(tert-butylamino)methyl]imidazo[1,2-a]pyridin-2-yl}methyl)-4-oxo-4H-pyrido[1,2-a]pyrimidine-2-carboxamide;

N-[(6-{[(2-fluoroethyl)amino]methyl}imidazo[1,2-a]pyridin-2-yl)methyl]-4-oxo-4H-pyrido[1,2-a]pyrimidine-2-carboxamide;

N-({6-[(4,4-difluoropiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenylpiperazin-1-yl)methyl]imidazo[1,2-a]pyridin-2-yl}methyl)-4H-pyrido[1,2-a]pyrimidine-2-carboxamide;

4-oxo-N-({6-[(1,2,3,4-tetrahydroisoquinolin-2-yl)methyl]imidazo[1,2-a]pyridin-2-yl}methyl)-4H-pyrido[1,2-a]pyrimidine-2-carboxamide;

N-({6-[(diethylamino)methyl]imidazo[1,2-a]pyridin-2-yl}methyl)-4-oxo-4H-pyrido[1,2-a]pyrimidine-2-carboxamide;

4-oxo-N-({6-[(pyrrolidin-1-yl)methyl]imidazo[1,2-a]pyridin-2-yl}methyl)-4H-pyrido[1,2-a]pyrimidine-2-carboxamide;

4-oxo-N-[(6-{[3-(pyridin-2-yl)azetidin-1-yl]methyl}imidazo[1,2-a]pyridin-2-yl)methyl]-4H-pyrido[1,2-a]pyrimidine-2-carboxamide;

N-[(6-{[(dicyclopropylmethyl)amino]methyl}imidazo[1,2-a]pyridin-2-yl)methyl]-4-oxo-4H-pyrido[1,2-a]pyrimidine-2-carboxamide;

N-[(6-{[(cyclopropylmethyl)(methyl)amino]methyl}imidazo[1,2-a]pyridin-2-yl)methyl]-4-oxo-4H-pyrido[1,2-a]pyrimidine-2-carboxamide;

N-({6-[(4-methylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[4-(trifluoromethyl)piperidin-1-yl]methyl}imidazo[1,2-a]pyridin-2-yl)methyl]-4H-pyrido[1,2-a]pyrimidine-2-carboxamide;

N-({6-[(3-methylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[({spiro[2.2]pentan-1-yl}methyl)amino]methyl}imidazo[1,2-a]pyridin-2-yl)methyl]-4H-pyrido[1,2-a]pyrimidine-2-carboxamide;

N-({6-[(3,3-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[3-(trifluoromethyl)piperidin-1-yl]methyl}imidazo[1,2-a]pyridin-2-yl)methyl]-4H-pyrido[1,2-a]pyrimidine-2-carboxamide;

N-{[6-({[(5,5-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-({6-[(4-fluoropiperidin-1-yl)methyl]imidazo[1,2-a]pyridin-2-yl}methyl)-4-oxo-4H-pyrido[1,2-a]pyrimidine-2-carboxamide;

N-[(6-{[(3-methoxypropyl)amino]methyl}imidazo[1,2-a]pyridin-2-yl)methyl]-4-oxo-4H-pyrido[1,2-a]pyrimidine-2-carboxamide;

N-(6-{[(1-methylcyclohexyl)amino]methyl}imidazo[1,2-a]pyridin-2-yl)methyl]-4-oxo-4H-pyrido[1,2-a]pyrimidine-2-carboxamide;

N-{[6-({[(4,4-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(1-methylcyclopentyl)amino]methyl}imidazo[1,2-a]pyridin-2-yl)methyl]-4-oxo-4H-pyrido[1,2-a]pyrimidine-2-carboxamide;

4-oxo-N-({6-[(propylamino)methyl]imidazo[1,2-a]pyridin-2-yl}methyl)-4H-pyrido[1,2-a]pyrimidine-2-carboxamide;

N-{[6-({[(3,3-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(2-methylpropyl)amino]methyl}imidazo[1,2-a]pyridin-2-yl)methyl]-4-oxo-4H-pyrido[1,2-a]pyrimidine-2-carboxamide;

N-{[6-({[2-(tert-butoxy)ethyl]amino}methyl)imidazo[1,2-a]pyridin-2-yl]methyl}-4-oxo-4H-pyrido[1,2-a]pyrimidine-2-carboxamide;

N-[(6-{[(4-chlorophenyl)amino]methyl}imidazo[1,2-a]pyridin-2-yl)methyl]-4-oxo-4H-pyrido[1,2-a]pyrimidine-2-carboxamide;

N-{[6-({[2-(oxan-2-yl)ethyl]amino}methyl)imidazo[1,2-a]pyridin-2-yl]methyl}-4-oxo-4H-pyrido[1,2-a]pyrimidine-2-carboxamide;

N-({6-[(4-benzylpiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenoxypiperidin-1-yl)methyl]imidazo[1,2-a]pyridin-2-yl}methyl)-4H-pyrido[1,2-a]pyrimidine-2-carboxamide;

N-{[6-({[(2,2-difluorocyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2,2-dimethylcyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2-methyloxolan-2-yl)methyl]amino}methyl)imidazo[1,2-a]pyridin-2-yl]methyl}-4-oxo-4H-pyrido[1,2-a]pyrimidine-2-carboxamide;

N-({6-[(4-tert-butylpiperidin-1-yl)methyl]imidazo[1,2-a]pyridin-2-yl}methyl)-4-oxo-4H-pyrido[1,2-a]pyrimidine-2-carboxamide;

N-[(6-{[(4-tert-butylcyclohexyl)amino]methyl}imidazo[1,2-a]pyridin-2-yl)methyl]-4-oxo-4H-pyrido[1,2-a]pyrimidine-2-carboxamide;

N-[(6-{[(2-cyclopentylethyl)amino]methyl}imidazo[1,2-a]pyridin-2-yl)methyl]-4-oxo-4H-pyrido[1,2-a]pyrimidine-2-carboxamide;

N-[(6-{[4-(2,2-dimethylpropanoyl)piperazin-1-yl]methyl}imidazo[1,2-a]pyridin-2-yl)methyl]-4-oxo-4H-pyrido[1,2-a]pyrimidine-2-carboxamide;

N-({6-[(4-acetylpiperazin-1-yl)methyl]imidazo[1,2-a]pyridin-2-yl}methyl)-4-oxo-4H-pyrido[1,2-a]pyrimidine-2-carboxamide;

N-{[6-({7-azabicyclo[2.2.1]heptan-7-yl}methyl)imidazo[1,2-a]pyridin-2-yl]methyl}-4-oxo-4H-pyrido[1,2-a]pyrimidine-2-carboxamide;

N-({6-[(4,4-dimethylpiperidin-1-yl)methyl]imidazo[1,2-a]pyridin-2-yl}methyl)-4-oxo-4H-pyrido[1,2-a]pyrimidine-2-carboxamide;

N-({6-[(2,2-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-(6-{[(2,3,3-trimethylbutan-2-yl)amino]methyl}imidazo[1,2-a]pyridin-2-yl)methyl]-4H-pyrido[1,2-a]pyrimidine-2-carboxamide;

N-[(6-{[(5-fluoropyridin-2-yl)amino]methyl}imidazo[1,2-a]pyridin-2-yl)methyl]-4-oxo-4H-pyrido[1,2-a]pyrimidine-2-carboxamide;

N-({6-[({[1,1'-bi(cyclopropane)]-1-yl}amino)methyl]imidazo[1,2-a]pyridin-2-yl}methyl)-4-oxo-4H-pyrido[1,2-a]pyrimidine-2-carboxamide;

N-{[6-({[(1-fluorocyclopentyl)methyl]amino}methyl)imidazo[1,2-a]pyridin-2-yl]methyl}-4-oxo-4H-pyrido[1,2-a]pyrimidine-2-carboxamide;

N-({6-[(2,6-dimethylmorpholin-4-yl)methyl]imidazo[1,2-a]pyridin-2-yl}methyl)-4-oxo-4H-pyrido[1,2-a]pyrimidine-2-carboxamide;

methyl 1-({2-[({4-oxo-4H-pyrido[1,2-a]pyrimidin-2-yl}formamido)methyl]imidazo[1,2-a]pyridin-6-yl}methyl)piperidine-3-carboxylate;

N-[(6-{[(2-fluoro-2-methylpropyl)amino]methyl}imidazo[1,2-a]pyridin-2-yl)methyl]-4-oxo-4H-pyrido[1,2-a]pyrimidine-2-carboxamide;

N-[(6-{[(1-cyclohexylethyl)amino]methyl}imidazo[1,2-a]pyridin-2-yl)methyl]-4-oxo-4H-pyrido[1,2-a]pyrimidine-2-carboxamide;

N-[(6-{[(2-cyclopropylethyl)(methyl)amino]methyl}imidazo[1,2-a]pyridin-2-yl)methyl]-4-oxo-4H-pyrido[1,2-a]pyrimidine-2-carboxamide;

N-[(6-{[(2,2-dimethylpropyl)(methyl)amino]methyl}imidazo[1,2-a]pyridin-2-yl)methyl]-4-oxo-4H-pyrido[1,2-a]pyrimidine-2-carboxamide;

N-{[6-({[(1-fluorocyclobutyl)methyl]amino}methyl)imidazo[1,2-a]pyridin-2-yl]methyl}-4-oxo-4H-pyrido[1,2-a]pyrimidine-2-carboxamide;

N-({6-[(4-fluoro-4-methylpiperidin-1-yl)methyl]imidazo[1,2-a]pyridin-2-yl}methyl)-4-oxo-4H-pyrido[1,2-a]pyrimidine-2-carboxamide;

N-({6-[(3,3-difluoropiperidin-1-yl)methyl]imidazo[1,2-a]pyridin-2-yl}methyl)-4-oxo-4H-pyrido[1,2-a]pyrimidine-2-carboxamide;

N-{[6-({[(1-hydroxycyclohexyl)methyl]amino}methyl)imidazo[1,2-a]pyridin-2-yl]methyl}-4-oxo-4H-pyrido[1,2-a]pyrimidine-2-carboxamide;

N-[(6-{[(cyclopentylmethyl)amino]methyl}imidazo[1,2-a]pyridin-2-yl)methyl]-4-oxo-4H-pyrido[1,2-a]pyrimidine-2-carboxamide;

N-{[6-({[(3,3-difluorocyclopentyl)methyl]amino}methyl)imidazo[1,2-a]pyridin-2-yl]methyl}-4-oxo-4H-pyrido[1,2-a]pyrimidine-2-carboxamide;

N-[(6-{[(cyclobutylmethyl)amino]methyl}imidazo[1,2-a]pyridin-2-yl)methyl]-4-oxo-4H-pyrido[1,2-a]pyrimidine-2-carboxamide;

N-{[6-({[2-(3,3-difluorocyclobutyl)ethyl]amino}methyl)imidazo[1,2-a]pyridin-2-yl]methyl}-4-oxo-4H-pyrido[1,2-a]pyrimidine-2-carboxamide;

N-{[6-({[(2-fluorocyclobutyl)methyl]amino}methyl)imidazo[1,2-a]pyridin-2-yl]methyl}-4-oxo-4H-pyrido[1,2-a]pyrimidine-2-carboxamide;

N-{[6-({[(2S)-3,3-dimethylbutan-2-yl]amino}methyl)imidazo[1,2-a]pyridin-2-yl]methyl}-4-oxo-4H-pyrido[1,2-a]pyrimidine-2-carboxamide;

N-{[6-({6-azaspiro[2.5]octan-6-yl}methyl)imidazo[1,2-a]pyridin-2-yl]methyl}-4-oxo-4H-pyrido[1,2-a]pyrimidine-2-carboxamide;

4-oxo-N-({6-[({[(1r,3r)-3-fluorocyclobutyl]methyl}amino)methyl]imidazo[1,2-a]pyridin-2-yl}methyl)-4H-pyrido[1,2-a]pyrimidine-2-carboxamide;

4-oxo-N-({6-[(2-phenylethyl)amino]imidazo[1,2-a]pyridin-2-yl}methyl)-4H-pyrido[1,2-a]pyrimidine-2-carboxamide;

N-({6-[2-(benzylamino)ethyl]imidazo[1,2-a]pyridin-2-yl}methyl)-4-oxo-4H-pyrido[1,2-a]pyrimidine-2-carboxamide;

N-({6-[2-(cyclohexylamino)ethyl]imidazo[1,2-a]pyridin-2-yl}methyl)-4-oxo-4H-pyrido[1,2-a]pyrimidine-2-carboxamide;

4-oxo-N-({6-[(phenylformamido)methyl]imidazo[1,2-a]pyridin-2-yl}methyl)-4H-pyrido[1,2-a]pyrimidine-2-carboxamide;

N-({6-[(cyclohexylformamido)methyl]imidazo[1,2-a]pyridin-2-yl}methyl)-4-oxo-4H-pyrido[1,2-a]pyrimidine-2-carboxamide;

4-oxo-N-{[6-({[(piperidin-3-yl)methyl]amino}methyl)imidazo[1,2-a]pyridin-2-yl]methyl}-4H-pyrido[1,2-a]pyrimidine-2-carboxamide;

4-oxo-N-{[6-({[(piperidin-2-yl)methyl]amino}methyl)imidazo[1,2-a]pyridin-2-yl]methyl}-4H-pyrido[1,2-a]pyrimidine-2-carboxamide;

N-[(6-{[(azetidin-3-yl)amino]methyl}imidazo[1,2-a]pyridin-2-yl)methyl]-4-oxo-4H-pyrido[1,2-a]pyrimidine-2-carboxamide;

N-({6-[(cyclohexylamino)methyl]imidazo[1,2-a]pyridin-2-yl}methyl)-4-oxo-4H-chromene-2-carboxamide;

N-[(6-{[(2-cyclopropylethyl)amino]methyl}imidazo[1,2-a]pyridin-2-yl)methyl]-4-oxo-4H-chromene-2-carboxamide;

4-oxo-N-({6-[(piperidin-1-yl)methyl]imidazo[1,2-a]pyridin-2-yl}methyl)-4H-chromene-2-carboxamide;

N-{[6-({[(4-chlorophenyl)methyl]amino}methyl)imidazo[1,2-a]pyridin-2-yl]methyl}-4-oxo-4H-chromene-2-carboxamide;

N-({6-[(benzylamino)methyl]imidazo[1,2-a]pyridin-2-yl}methyl)-4-oxo-4H-chromene-2-carboxamide;

N-{[6-({[(1-methylcyclohexyl)methyl]amino}methyl)imidazo[1,2-a]pyridin-2-yl]methyl}-4-oxo-4H-chromene-2-carboxamide;

N-[(6-{[(2,2-dimethylpropyl)amino]methyl}imidazo[1,2-a]pyridin-2-yl)methyl]-4-oxo-4H-chromene-2-carboxamide;

4-oxo-N-[(7-{[(2-phenylethyl)amino]methyl}imidazo[1,2-a]pyridin-2-yl)methyl]-4H-pyrido[1,2-a]pyrimidine-2-carboxamide;

N-[(7-{[(cyclohexylmethyl)amino]methyl}imidazo[1,2-a]pyridin-2-yl)methyl]-4-oxo-4H-pyrido[1,2-a]pyrimidine-2-carboxamide;

N-[(7-{[(cyclopropylmethyl)amino]methyl}imidazo[1,2-a]pyridin-2-yl)methyl]-4-oxo-4H-pyrido[1,2-a]pyrimidine-2-carboxamide;

N-[(6-{1-[(cyclohexylmethyl)amino]cyclopropyl}imidazo[1,2-a]pyridin-2-yl)methyl]-4-oxo-4H-pyrido[1,2-a]pyrimidine-2-carboxamide;

N-{[6-(2-amino-3-phenylpropyl)imidazo[1,2-a]pyridin-2-yl]methyl}-4-oxo-4H-pyrido[1,2-a]pyrimidine-2-carboxamide;

(cyclohexylmethyl)[(2-{[4-(1H-indazol-4-yl)-1H-1,2,3-triazol-1-yl]methyl}imidazo[1,2-a]pyridin-6-yl)methyl]amine;

N-(cyclohexylmethyl)-2-{[4-(1H-indazol-4-yl)-1H-1,2,3-triazol-1-yl]methyl}imidazo[1,2-a]pyridine-6-carboxamide;

(2,2-dimethylpropyl)[(2-{[4-(1H-indazol-4-yl)-1H-1,2,3-triazol-1-yl]methyl}imidazo[1,2-a]pyridin-6-yl)methyl]amine;

4-[1-({6-[(4,4-dimethylpiperidin-1-yl)methyl]imidazo[1,2-a]pyridin-2-yl}methyl)-1H-1,2,3-triazol-4-yl]-1H-indazole;

[(2-{[4-(6-bromo-1H-indazol-4-yl)-1H-1,2,3-triazol-1-yl]methyl}imidazo[1,2-a]pyridin-6-yl)methyl][(3,3-difluorocyclobutyl)methyl]amine;

[(2-{[4-(6-bromo-1H-indazol-4-yl)-1H-1,2,3-triazol-1-yl]methyl}imidazo[1,2-a]pyridin-6-yl)methyl](2,2-dimethylpropyl)amine;

[(2-{[4-(6-bromo-1H-indazol-4-yl)-1H-1,2,3-triazol-1-yl]methyl}imidazo[1,2-a]pyridin-6-yl)methyl](cyclohexylmethyl)amine;

6-bromo-4-[1-({6-[(4,4-dimethylpiperidin-1-yl)methyl]imidazo[1,2-a]pyridin-2-yl}methyl)-1H-1,2,3-triazol-4-yl]-1H-indazole;

(2-{[4-(6-bromo-1H-indazol-4-yl)-1H-1,2,3-triazol-1-yl]methyl}imidazo[1,2-a]pyridin-6-yl)methanol;

(2,2-dimethylpropyl)[(2-{[4-(1H-indazol-5-yl)-1H-1,2,3-triazol-1-yl]methyl}imidazo[1,2-a]pyridin-6-yl)methyl]amine;

((cyclohexylmethyl)[1-(2-{[4-(1H-indazol-4-yl)-1H-1,2,3-triazol-1-yl]methyl}imidazo[1,2-a]pyridin-6-yl)ethyl]amine;

(2,2-dimethylpropyl)({2-[(4-{1H-pyrazolo[3,4-c]pyridin-4-yl}-1H-1,2,3-triazol-1-yl)methyl]imidazo[1,2-a]pyridin-6-yl}methyl)amine;

{2-[(4-{1H-pyrazolo[3,4-c]pyridin-4-yl}-1H-1,2,3-triazol-1-yl)methyl]imidazo[1,2-a]pyridin-6-yl}methanol;

N-({6-[(3R,5S)-5-tert-butylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-tert-butylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-cyclohexylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-cyclohexylmorpholin-3-yl]imidazo[1,2-a]pyridin-2-yl}methyl)-1H-indazole-4-carboxamide;

N-({6-[(3S,5R)-5-cyclohexylmorpholin-3-yl]imidazo[1,2-a]pyridin-2-yl}methyl)-4-oxo-4H-chromene-2-carboxamide;

N-({6-[4-(2,2-dimethylpropyl)morpholin-3-yl]imidazo[1,2-a]pyridin-2-yl}methyl)-4-oxo-4H-pyrido[1,2-a]pyrimidine-2-carboxamide;

N-({6-[(3S,5R)-5-methylmorpholin-3-yl]imidazo[1,2-a]pyridin-2-yl}methyl)-4-oxo-4H-pyrido[1,2-a]pyrimidine-2-carboxamide; and N-{[6-(9-methoxy-2,3,4,5-tetrahydro-1,4-benzoxazepin-3-yl)imidazo[1,2-a]pyridin-2-yl]methyl}-4-oxo-4H-pyrido[1,2-a]pyrimidine-2-carboxamide.

Paragraph 35. A pharmaceutical composition comprising a compound according to any one of Paragraphs 1 to 34, or a pharmaceutically acceptable salt thereof, and one or more pharmaceutically acceptable excipients.

Paragraph 36. A compound according to any one of Paragraphs 1 to 34, or a pharmaceutically acceptable salt thereof, or a pharmaceutical composition according to Paragraph 35, for use in therapy.

Paragraph 37. A compound according to any one of Paragraphs 1 to 34, or a pharmaceutically acceptable salt thereof, or a pharmaceutical composition according to Paragraph 35, for use in the treatment of a proliferative condition.

Paragraph 38. A compound according to any one of Paragraphs 1 to 34, or a pharmaceutically acceptable salt thereof, or a pharmaceutical composition according to Paragraph 35, for use in the treatment of cancer.

Paragraph 39. A compound according to any one of Paragraphs 1 to 34 or a pharmaceutically acceptable salt there, or a pharmaceutical composition according to Paragraph 35, for use in the treatment of leukaemia.

Paragraph 40. A compound according to any one of Paragraphs 1 to 34, or a pharmaceutically acceptable salt thereof, or a pharmaceutical composition according to Paragraph 35, for use in the treatment of AML leukaemia or chronic myeloid leukaemia.

Paragraph 41. A compound according to any one of Paragraphs 1 to 34, or a pharmaceutically acceptable salt thereof, or a pharmaceutical composition according to Paragraph 35, for use in the inhibition of METTL3 activity.

Paragraph 42. A compound according to any one of Paragraphs 1 to 34, or a pharmaceutically acceptable salt thereof, or a pharmaceutical composition according to Paragraph 35, for use in the treatment of an autoimmune disease, a neurological disease, an inflammatory disease or an infectious disease.

Paragraph 43. Use of a compound according to any one of Paragraphs 1 to 34, or a pharmaceutically acceptable salt thereof, in the manufacture of a medicament for the treatment of a proliferative condition.

Paragraph 44. Use of a compound according to any one of Paragraphs 1 to 34, or a pharmaceutically acceptable salt thereof, in the manufacture of a medicament for the treatment of cancer.

Paragraph 45. Use of a compound according to any one of Paragraphs 1 to 34, or a pharmaceutically acceptable salt thereof, in the manufacture of a medicament for the treatment of leukaemia.

Paragraph 46. Use of a compound according to any one of Paragraphs 1 to 34, or a pharmaceutically acceptable salt thereof, in the manufacture of a medicament for the treatment of AML leukaemia or chronic myeloid leukaemia.

Paragraph 47. Use of a compound according to any one of Paragraphs 1 to 34, or a pharmaceutically acceptable salt thereof, in the manufacture of a medicament for the treatment of an autoimmune disease, a neurological disease, an inflammatory disease or an infectious disease.

Paragraph 48. Use of a compound according to any one of Paragraphs 1 to 34, or a pharmaceutically acceptable salt thereof, in the manufacture of a medicament for the inhibition of METTL3 activity.

Paragraph 49. A method of treating a proliferative disorder, said method comprising administering to a subject in need thereof a therapeutically effective amount of a compound according to any one of Paragraphs 1 to 34, or a pharmaceutically acceptable salt thereof, or a pharmaceutical composition according to Paragraph 35.

Paragraph 50. A method of treating cancer, said method comprising administering to a subject in need thereof a therapeutically effective amount of a compound according to any one of Paragraphs 1 to 34, or a pharmaceutically acceptable salt thereof, or a pharmaceutical composition according to Paragraph 35.

Paragraph 51. A method of treating leukaemia, said method comprising administering to a subject in need thereof a therapeutically effective amount of a compound according to any one of Paragraphs 1 to 34, or a pharmaceutically acceptable salt thereof, or a pharmaceutical composition according to Paragraph 35.

Paragraph 52. A method of treating AML leukaemia or chronic myeloid leukaemia, said method comprising administering to a subject in need thereof a therapeutically effective amount of a compound according to any one of Paragraphs 1 to 34, or a pharmaceutically acceptable salt thereof, or a pharmaceutical composition according to Paragraph 35.

Paragraph 53. A method of treating an autoimmune disease, a neurological disease, an inflammatory disease or an infectious disease, said method comprising administering to a subject in need thereof a therapeutically effective amount of a compound according to any one of Paragraphs 1 to 34, or a pharmaceutically acceptable salt thereof, or a pharmaceutical composition according to Paragraph 35.

Paragraph 54. A method of inhibiting METTL3 activity in vitro or in vivo, said method comprising contacting a cell with an effective amount of a compound according to any one of Paragraphs 1 to 34, or a pharmaceutically acceptable salt thereof, or a pharmaceutical composition according to Paragraph 35.

Paragraph 55. A method of inhibiting metastasis in vitro or in vivo, said method comprising contacting a cell with an effective amount of a compound according to any one of Paragraphs 1 to 34, or a pharmaceutically acceptable salt thereof, or a pharmaceutical composition according to Paragraph 35.

Paragraph 56. A combination comprising a compound according to any one of Paragraphs 1 to 34, or a pharmaceutically acceptable salt there, with one or more additional therapeutic agents.

The invention claimed is:

1. A compound of the formula (I), or a pharmaceutically acceptable salt thereof, $$X-Y-Z \quad (I)$$

wherein:

X is

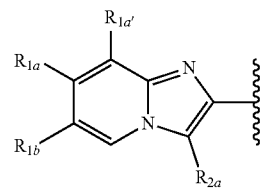

wherein:

$R_{1a}$ and $R_{1b}$ are independently selected from hydrogen, cyano, halo or a group of the formula:

-$L_{1a}$-$L_{1b}$-$Q_1$ wherein $L_{1a}$ is absent or selected from $C_{1-3}$alkylene and $C_{3-5}$cycloalkylene, wherein $C_{1-3}$alkylene and $C_{3-5}$ cycloalkylene are optionally substituted by one or more substituents selected from aryl, aryl-(1-2C)alkyl, heteroaryl, aryl-(1-2C)alkyl, $C_{1-3}$alkyl, cyano, $C_{1-3}$alkoxy, halo, hydroxy, $C_{1-3}$-haloalkoxy, —O—$C_{3-4}$cycloalkyl, $NH_2$ or oxo; wherein any —O—$C_{3-6}$cycloalkyl aryl, aryl-(1-2C)alkyl, heteroaryl, aryl-(1-2C)alkyl or $C_{1-3}$alkyl is optionally further substituted by one or more substituents selected from cyano, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally further substituted with halo, cyano or hydroxy; or $C_{1-3}$alkylene is optionally spiro-fused to a a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$L_{1b}$ is absent or selected from O, S, SO, $SO_2$, $N(R_r)$, C(O), C(O)O, OC(O), $C(O)N(R_r)$, $N(R_r)C(O)$, $N(R_r)C(O)N(R_s)$, $S(O)_2N(R_r)$, or $N(R_r)SO_2$, wherein $R_r$ and $R_s$ are each independently selected from hydrogen or $C_{1-3}$alkyl, wherein $C_{1-3}$alkyl is optionally further substituted by cyano, hydroxy, $C_{1-2}$alkoxy, halo, $C_{1-2}$haloalkoxy, $NH_2$, $C_{3-6}$cycloalkyl or a 3 to 6 membered heterocyclyl, wherein the $C_{3-6}$cycloalkyl or a 3 to 6 membered heterocyclyl in turn are optionally further substituted by halo, hydroxy, $C_{1-2}$alkoxy or $C_{1-2}$haloalkoxy; and $Q_1$ is hydrogen, cyano, $C_{1-6}$alkyl, $C_{3-8}$cycloalkyl (e.g. $C_{3-6}$cycloalkyl), $C_{2-3}$alkenyl, $C_{2-3}$alkynyl, aryl, heterocyclyl or heteroaryl; and wherein $Q_1$ is optionally substituted by one or more substituents selected from $C_{1-4}$alkyl, halo, trifluoromethyl, trifluoromethoxy, amino, oxo, cyano, hydroxy, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, —$S(O)_{0-2}R_tR_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $C_{1-4}$alkyl is in turn optionally substituted by one more substituents selected from cyano, hydroxy, $C_{1-2}$alkoxy, halo, $C_{1-2}$-haloalkoxy, —O—$C_3$cycloalkyl, wherein —O—$C_3$cycloalkyl is optionally substituted with halo, cyano or hydroxy; and wherein $R_t$ and $R_u$ are each independently selected from hydrogen or $C_{1-4}$alkyl; or $Q_1$ is optionally substituted by one or more groups of the formula:

-$L_{1c}$-$L_{1d}$-$Z_1$ wherein $L_{1c}$ is absent or $C_{1-3}$alkylene optionally substituted by $C_{1-2}$alkyl or oxo;

$L_{1d}$ is absent or selected from C(O), O, C(O)O, OC(O), $C(O)N(R_v)$, $N(R_v)C(O)$, $N(R_v)C(O)N(R_w)$, $S(O)_2N(R_v)$, or $N(R_v)SO_2$, wherein $R_v$ and $R_w$ are each independently selected from hydrogen or $C_{1-2}$alkyl; and $Z_1$ is $C_{3-8}$cycloalkyl (including a spirocyclic carbocyclic and a bridged $C_{3-8}$cycloalkyl), heterocyclyl (including a mono- or bicyclic-heterocyclic ring system, a spirocyclic heterocyclic ring system, or a bridged heterocyclic ring system), aryl or heteroaryl; wherein $Z_1$ is optionally substituted by one or more substituents selected from $C_{1-4}$alkyl, $C_{3-6}$cycloalkyl, heterocyclyl, halo, $C_{1-4}$haloalkyl, $C_{1-4}$haloalkoxy, $C_{1-4}$alkoxy, cyano, hydroxyl, $NR_{r1}R_{u1}$, $OR_{r1}$, $C(O)R_{r1}$, $C(O)OR_{r1}$, $OC(O)R_{r1}$, $C(O)N(R_{r1})R_{u1}$, $N(R_{r1})C(O)R_{u1}$, —$S(O)_{0-2}R_{r1}R_{u1}$, $S(O)_yR_{r1}$ (where y is 0, 1 or 2), $SO_2N(R_{r1})R_{u1}$, $N(R_{r1})SO_2R_{u1}$ or $(CH_2)_zNR_{r1}R_{u1}$ (where z is 1, 2 or 3), wherein $R_{r1}$ and $R_{u1}$ are each independently selected from hydrogen or $C_{1-4}$alkyl;

and when $Z_1$ is $C_{3-8}$cycloalkyl or heterocyclyl, $Z_1$ is optionally spiro-fused to a $C_{3-6}$cycloalkyl or heterocyclyl ring;

$R_{1a'}$ is selected from hydrogen, halo and methyl;

$R_{2a}$ is selected from hydrogen, halo or a group of the formula:

-$L_{2a}$-$L_{2b}$-$Q_2$ wherein $L_{2a}$ is absent or $C_{1-3}$alkylene optionally substituted by $C_{1-2}$ alkyl or oxo;

$L_{2b}$ is absent or selected from O, S, SO, $SO_2$, $N(R_n)$, C(O), C(O)O, OC(O), $C(O)N(R_n)$, $N(R_n)C(O)$, $N(R_n)C(O)N(R_o)$, $S(O)_2N(R_n)$, or $N(R_n)SO_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

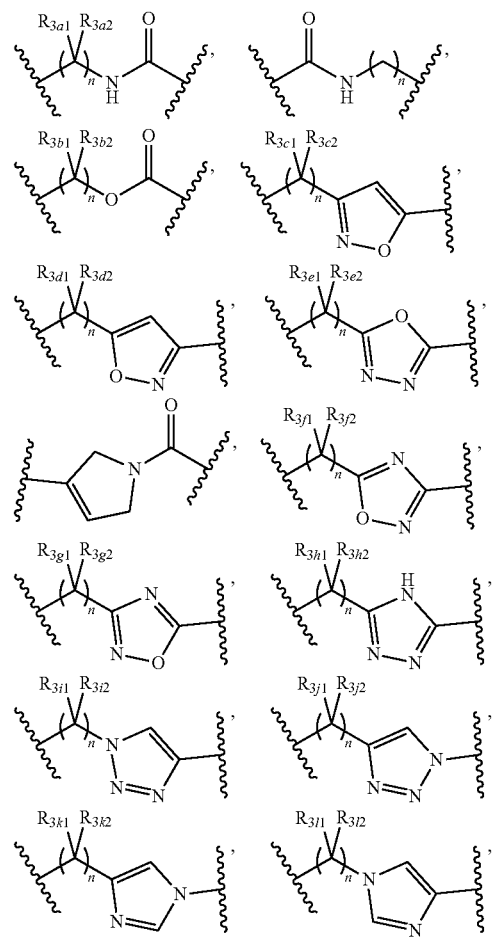

-continued

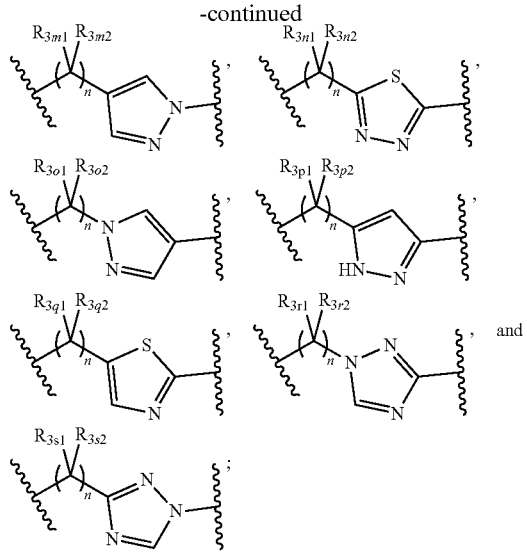

wherein:
$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen (including deuterium), $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen or halo;

with the proviso that $R_{3a1}$, $R_{3b1}$, $R_{3i1}$, $R_{3l1}$, $R_{3o1}$, $R_{3r1}$, $R_{3a2}$, $R_{3b2}$, $R_{3i2}$, $R_{3l2}$, $R_{3o2}$ and $R_{3s1}$ cannot be halo when n=1 or when n=2 and the carbon atom to which they are attached is linked to an oxygen or nitrogen atom;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$, or $R_{3r1}$ and $R_{3r2}$ or $R_{3s1}$ and $R_{3s2}$ may be linked such that, together with the carbon atom to which they are attached, they form a spiro-fused $C_{3-4}$cycloalkyl which is optionally substituted with one or more substituents selected from halo, methyl, amino, cyano, and hydroxy;

Z is selected from:

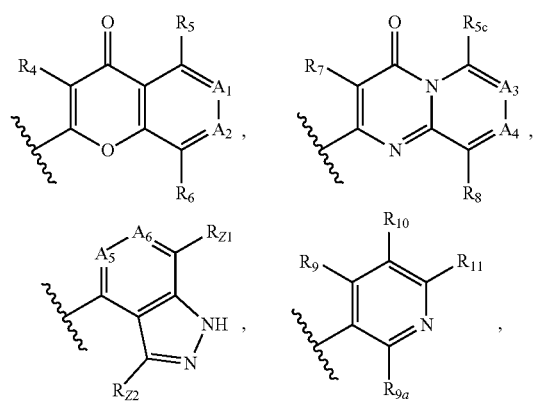

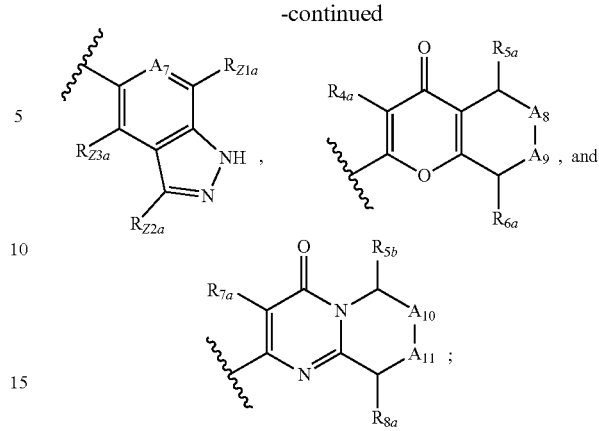

wherein:
$R_4$, $R_7$, $R_{4a}$ and $R_{7a}$ are independently selected from hydrogen, halo, cyano and methyl;
$R_5$, $R_{5a}$, $R_{5b}$ and $R_{5c}$ are independently selected from hydrogen, halo, cyano and methyl;
$R_6$, $R_8$, $R_{6a}$ and $R_{8a}$ are independently selected from hydrogen, halo, cyano and methyl;
$R_9$, $R_{9a}$, $R_{10}$ and $R_{11}$ are independently selected from hydrogen, $NH_2$, halo, cyano, and $C_{1-6}$ alkyl; or
$R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system; wherein either of the fused 5- or 6-membered saturated or unsaturated ring system may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ia}R_{1ja}$ or $—S(O)_{0-2}R_{1ia}R_{1ja}$, wherein $R_{1ia}$ and $R_{1ja}$ are H or $C_{1-2}$alky;

$R_{Z1}$ and $R_{Z1a}$ are selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-6}$cycloalkyl, wherein $C_{3-6}$cycloalkyl and —O—$C_{3-6}$cycloalkyl are optionally substituted by one or more of halo, methyl or methoxy;

$R_{Z2}$ and $R_{Z2a}$ are selected from hydrogen, $C_{1-4}$alkyl, cyano, halo, $NH_2$ and $C_{1-4}$alkoxy;

$R_{Z3a}$ is selected from hydrogen, $C_{1-4}$alkyl, cyano, halo, $NH_2$ and $C_{1-4}$alkoxy $A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;
$R_{12}$ and $R_{14}$ are independently selected from hydrogen, halo, cyano and $C_{1-4}$ alkyl;
$R_{13}$ is selected from hydrogen, halo, cyano, methoxy and methyl;
$R_{15}$ is selected from hydrogen, halo, cyano methoxy and methyl;
$R_{16}$ is selected from hydrogen, halo, cyano, $C_{1-4}$ alkyl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;

$R_{17}$ is selected from hydrogen, hydroxy, halo, cyano, $C_{1-5}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, —O—$C_{3-6}$cycloalkyl, heterocyclyl, —O-heterocyclyl (carbon-linked), —(OCH$_2$CH$_2$)$_m$—NR$_q$R$_r$, —(OCH$_2$CH$_2$)$_m$—OCH$_3$ wherein m is an integer from 1 to 6, NR$_q$R$_r$, —C(O)—NR$_q$R$_r$, —C(O)OR$_q$;

wherein $R_q$ and $R_r$ are each independently hydrogen, $C_{1-5}$ alkyl, $C_{3-6}$cycloalkyl, a 3- to 6-membered carbon-linked heterocyclyl, wherein $C_{1-5}$ alkyl, $C_{3-6}$cycloalkyl, a 3- to 6-membered carbon-linked heterocyclyl may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or $C_{1-2}$alkyl;

or $R_q$ and $R_r$ are linked together such that, together with the nitrogen atom to which they are attached, they form a 3- to 6-membered heterocyclic ring, which may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy;

wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$-haloalkyl, hydroxy, $C_{1-2}$alkoxy, halo, $C_{1-2}$haloalkoxy, NR$_{1ea}$R$_{1fa}$ or —S(O)$_{0-2}$R$_{1ea}$R$_{1fa}$, wherein Rea and R$_{1fa}$ are H or $C_{1-2}$alkyl;

$R_{18}$ is selected from hydrogen, halo, cyano, $C_{1-4}$ alkyl, $C_{2-4}$ alkenyl, $C_{2-4}$ alkynyl, a 5- or 6-membered heteroaryl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;

$R_{19}$, $R_{20}$, $R_{25}$ and $R_{26}$ are selected from hydrogen, halo, cyano and $C_{1-4}$ alkyl;

$R_{22}$ and $R_{23}$ are selected from hydrogen, halo, cyano and methyl;

$R_{28}$ and $R_{29}$ are selected from hydrogen, methoxy and methyl;

$R_{21}$, $R_{24}$, $R_{27}$ and $R_{30}$ are hydrogen; and n is 0, 1 or 2;

with the proviso that the compound is not:
2-((1H-benzo[d]imidazol-2-yl)methyl)-5-(pyridin-3-yl)-1,3,4-oxadiazole;
2-((6-chloro-1-phenyl-1H-benzo[d]imidazol-2-yl)methyl)-5-(pyridin-3-yl)-1,3,4-oxadiazole;
N-({6-methylimidazo[1,2-a]pyridin-2-yl}methyl)-1H-indazole-5-carboxamide.

2. The compound of the formula (I), or a pharmaceutically acceptable salt thereof, according to claim 1, wherein X is

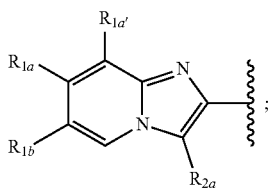

wherein:
$R_{1a}$ and $R_{1b}$ are independently selected from hydrogen, cyano, halo or a group of the formula:

-L$_{1a}$-L$_{1b}$-Q$_1$ wherein
L$_{1a}$ is absent or $C_{1-3}$alkylene, $C_{3-4}$cycloalkylene, optionally substituted by one or more substituents selected from $C_{1-2}$alkyl, halo, hydroxy, or oxo;
L$_{1b}$ is absent or selected from O, S, SO, SO$_2$, N(R$_r$), C(O), C(O)O, OC(O), C(O)N(R$_r$), N(R$_r$)C(O), N(R$_r$)C(O)N (R$_s$), S(O)$_2$N(R$_r$), or N(R$_r$)SO$_2$, wherein R$_r$ and R$_s$ are each independently selected from hydrogen or $C_{1-2}$alkyl; and
Q$_1$ is hydrogen, cyano, $C_{1-6}$alkyl, $C_{3-6}$cycloalkyl, $C_{2-3}$alkenyl, $C_{2-3}$alkynyl, aryl, heterocyclyl or heteroaryl; and wherein Q$_1$ is optionally substituted by one or more substituents selected from $C_{1-4}$alkyl, halo, trifluoromethyl, trifluoromethoxy, amino, cyano, hydroxy, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and R$_u$ are each independently selected from hydrogen or $C_{1-4}$alkyl; or Q$_1$ is optionally substituted by a group of the formula:
-L$_{1c}$-L$_{1d}$-Z$_1$ wherein
L$_{1c}$ is absent or $C_{1-3}$alkylene optionally substituted by $C_{1-2}$alkyl or oxo;
L$_{1d}$ is absent or selected from C(O), C(O)O, OC(O), C(O)N(R$_v$), N(R$_v$)C(O), N(R$_v$)C(O)N(R$_w$), S(O)$_2$N (R$_v$), or N(R$_v$)SO$_2$, wherein R$_v$ and R$_w$ are each independently selected from hydrogen or $C_{1-2}$alkyl; and
Z$_1$ is phenyl or 5-6 membered heteroaryl; wherein Z$_1$ is optionally substituted by one or more substituents selected from $C_{1-4}$alkyl, halo, $C_{1-4}$haloalkyl, $C_{1-4}$haloalkoxy, $C_{1-4}$alkoxy, $C_{1-4}$alkylamino, amino, cyano, hydroxyl, carboxy, carbamoyl or sulphamoyl;

$R_{1a'}$ is selected from hydrogen and methyl;
$R_{2a}$ is selected from hydrogen or a group of the formula:
-L$_{2a}$-L$_{2b}$-Q$_2$ wherein
L$_{2a}$ is absent or $C_{1-3}$alkylene optionally substituted by $C_{1-2}$ alkyl or oxo;
L$_{2b}$ is selected from O, S, SO, SO$_2$, N(R$_n$), C(O), C(O)O, OC(O), C(O)N(R$_n$), N(R$_n$)C(O), N(R$_n$)C(O)N(R$_o$), S(O)$_2$N(R$_n$), or N(R$_n$)SO$_2$, wherein R$_n$ and R$_o$ are each independently selected from hydrogen or $C_{1-2}$alkyl; and
Q$_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, NR$_p$R$_q$, OR$_p$, C(O)R$_p$, C(O)OR$_p$, OC(O)R$_p$, C(O)N(R$_p$)R$_q$, N(R$_r$)C(O)R$_p$, S(O)$_y$R$_p$ (where y is 0, 1 or 2), SO$_2$N(R$_p$)R$_q$, N(R$_r$)SO$_2$R$_p$ or (CH$_2$)$_z$NR$_p$R$_q$ (where z is 1, 2 or 3), wherein R$_p$ and R$_q$ are each independently selected from hydrogen or $C_{1-4}$alkyl;

Y is selected from:

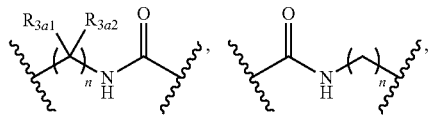

-continued

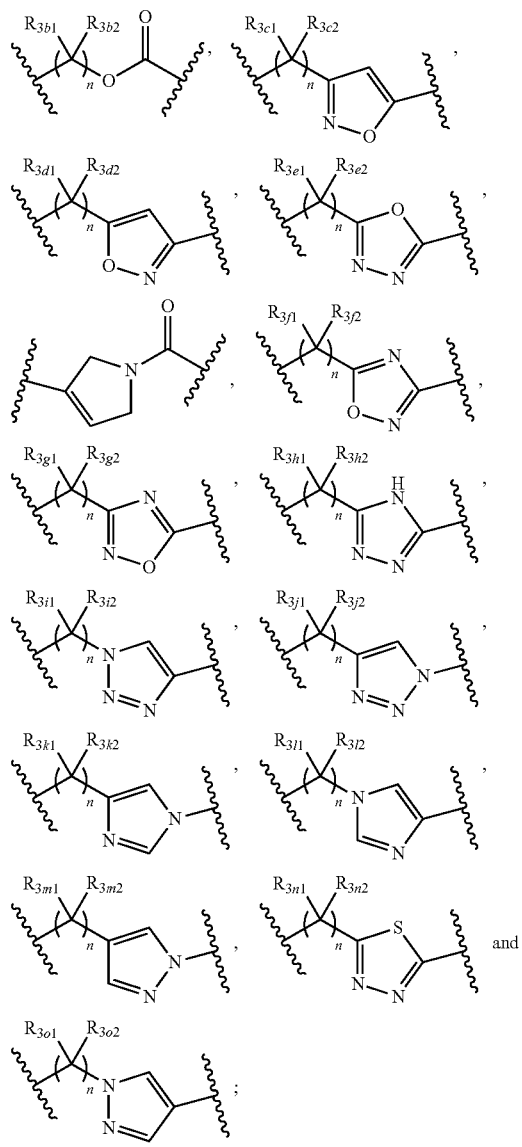

Z is selected from:

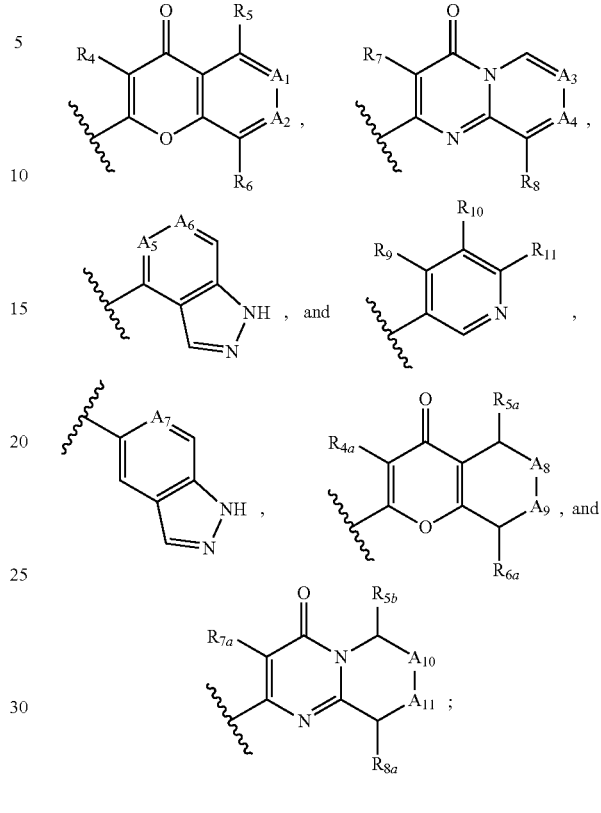

wherein:

$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$ and $R_{3o1}$ are independently selected from hydrogen, $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$ and $R_{3o2}$ are hydrogen;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, or $R_{3o1}$ and $R_{3o2}$ may be linked to form a spiro-fused $C_{3-4}$cycloalkyl which is optionally substituted with one or more substituents selected from halo, amino, cyano, and hydroxy;

wherein:

$R_4$, $R_7$ $R_{4a}$ and $R_{7a}$ are independently selected from hydrogen and methyl;

$R_5$, $R_{5a}$ and $R_{5b}$ are independently selected from hydrogen and halo;

$R_6$, $R_8$, $R_{6a}$ and $R_{8a}$ are independently selected from hydrogen, halo and methyl;

$R_9$, $R_{10}$ and $R_{11}$ are independently selected from hydrogen, $NH_2$, halo, cyano, and $C_{1-6}$ alkyl; or $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system;

$A_1$ is selected from $CR_{12}$ and N;
$A_2$ is selected from $CR_{13}$ and N;
$A_3$ is selected from $CR_{14}$ and N;
$A_4$ is selected from $CR_{15}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{10}$ is selected from $CR_{25}R_{26}$ and $NR_{27}$;
$A_{11}$ is selected from $CR_{28}R_{29}$ and $NR_{30}$;
$R_{12}$ and $R_{14}$ are independently selected from hydrogen, halo, cyano and $C_{1-4}$ alkyl;
$R_{13}$ is selected from hydrogen, halo, cyano and methyl;
$R_{15}$ is selected from hydrogen, methoxy and methyl;
$R_{16}$ is selected from hydrogen, halo, cyano and $C_{1-4}$ alkyl;
$R_{17}$ is selected from hydrogen, halo, cyano, $C_{1-4}$ alkyl, $C_{2-4}$ alkenyl, $C_{2-4}$ alkynyl and a 5- or 6-membered heteroaryl;
$R_{18}$ is selected from hydrogen, halo, cyano, $C_{1-4}$ alkyl, $C_{2-4}$ alkenyl, $C_{2-4}$ alkynyl and a 5- or 6-membered heteroaryl;

$R_{19}$, $R_{20}$, $R_{25}$ and $R_{26}$ are selected from hydrogen, halo, cyano and $C_{1-4}$ alkyl;

$R_{22}$ and $R_{23}$ are selected from hydrogen, halo, cyano and methyl;

$R_{28}$ and $R_{29}$ are selected from hydrogen, methoxy and methyl;

$R_{21}$, $R_{24}$, $R_{27}$ and $R_{30}$ are hydrogen; and n is 0, 1 or 2.

3. The compound according to claim 1, or a pharmaceutically acceptable salt thereof, wherein $R_{1a}$ is selected from hydrogen, halo, $C_{1-4}$-alkyl, $C_{2-3}$alkenyl and —O—$C_{1-4}$alkyl.

4. The compound according to claim 1, or a pharmaceutically acceptable salt thereof, wherein:

$R_{1b}$ is selected from hydrogen, halo, cyano, hydroxy, $C_{1-4}$-alkyl, $C_{1-4}$alkoxy, $C_{1-4}$haloalkoxy, or a group of the formula:

$(CR_{1c'}R_{1d'})_p$—$NR_{1e'}R_{1f'}$;

wherein p is an integer selected from 1 or 2;

$R_{1c'}$ and $R_{1d'}$ are independently selected from:
(i) hydrogen (including deuterium),
(ii) $C_{1-3}$alkyl which is optionally substituted by one more substituents selected from cyano, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally substituted with halo, cyano or hydroxy,
(iii) or $R_{1c'}$ and $R_{1d'}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$R_{1e'}$ is selected from:
(i) hydrogen (including deuterium);
(ii) $C_{1-3}$alkyl which is optionally substituted by one more substituents selected from cyano, hydroxy, $C_{1-2}$alkoxy, halo, $C_{1-2}$haloalkoxy and $NH_2$;

$R_{1f'}$ is a group with the formula:

—$(CR_{1g}R_{1h})_q$-$T_1$ wherein:

q is 0, 1 or 2;

$R_{1g}$ and $R_{1h}$ are independently selected from:
a) hydrogen (including deuterium); or
b) $C_{1-3}$alkyl, which is optionally substituted by one more substituents selected from cyano, hydroxy, $C_{1-2}$alkoxy, halo, $C_{1-2}$haloalkoxy, —O—$C_3$cycloalkyl, wherein —O—$C_3$cycloalkyl is optionally substituted with halo, cyano or hydroxy;

and $T_1$ is selected from $C_{3-8}$cycloalkyl, aryl, heterocyclyl, heteroaryl, a spirocyclic carbocyclic or heterocyclic ring system, a bridged $C_3$-cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo or $C_{1-2}$haloalkoxy;

or $R_{1e'}$ and $R_{1f'}$ are linked such that, together with the nitrogen atom to which they are attached, they form a mono- or bicyclic-heterocyclic ring, which is optionally substituted by one or more substituents selected from $C_{1-2}$alkoxy, $C_{1-2}$haloalkoxy, cyano, hydroxy, $C_{1-2}$alkoxy, halo, $C_{1-2}$haloalkoxy, $NR_{1i}R_{1j}$ or —$S(O)_{0-2}R_{1i}R_{1j}$, wherein $R_{1i}$ and $R_{1j}$ are H or $C_{1-2}$alkyl, and/or the mono- or bicyclic heterocyclic ring formed by $R_{1e'}$ and $R_{1f'}$ is optionally spiro-fused to a $C_{3-6}$cycloalkyl or a heterocyclic ring, which in turn is optionally substituted by one or more substituents selected from $C_{1-2}$alkyl, cyano, hydroxy, $C_{1-2}$alkoxy, halo, $C_{1-2}$haloalkoxy, $NR_{1i}R_{1j}$ or —$S(O)_{0-2}R_{1i}R_{1j}$, wherein $R_{1i}$ and $R_{1j}$ are H or $C_{1-2}$alkyl.

5. The compound according to claim 1, or a pharmaceutically acceptable salt thereof, wherein $R_{1b}$ is a group of the formula:

$(CR_{1c'}R_{1d'})_p$—$NR_{1e'}R_{1f'}$;

wherein p is 1;

$R_{1c'}$ and $R_{1d'}$ are independently selected from hydrogen (including deuterium) or $C_{1-2}$alkyl;

$R_{1e'}$ is selected from hydrogen (including deuterium) or $C_{1-2}$alkyl; and $R_{1f'}$ is a group with the formula:

—$(CR_{1g}R_{1h})_q$-$T_1$ wherein:

q is 1;

$R_{1g}$ and $R_{1h}$ are independently selected from hydrogen (including deuterium) or $C_{1-2}$alkyl;

and $T_1$ is selected from $C_{3-4}$cycloalkyl, heterocyclyl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

6. The compound according to claim 1, or a pharmaceutically acceptable salt thereof, wherein $R_{2a}$ is hydrogen.

7. The compound according to claim 1, or a pharmaceutically acceptable salt thereof, wherein $R_{1b}$ is selected from hydrogen; bromo; chloro; fluoro; cyano; methyl; methoxy;

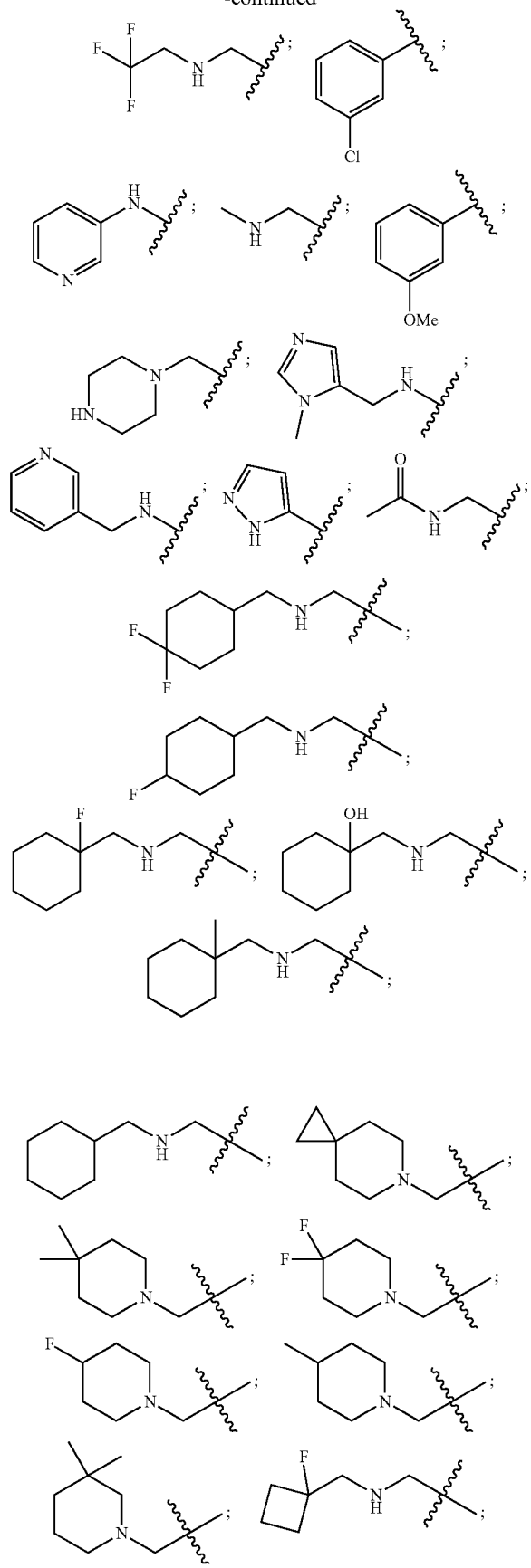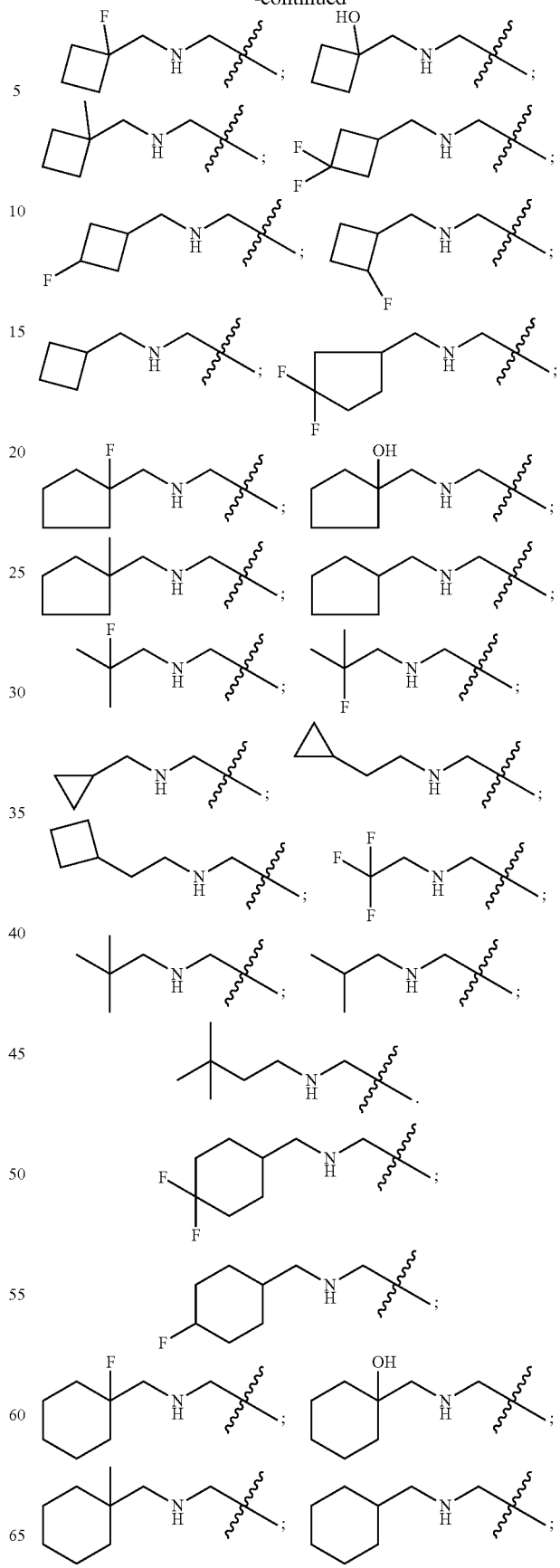

481
-continued
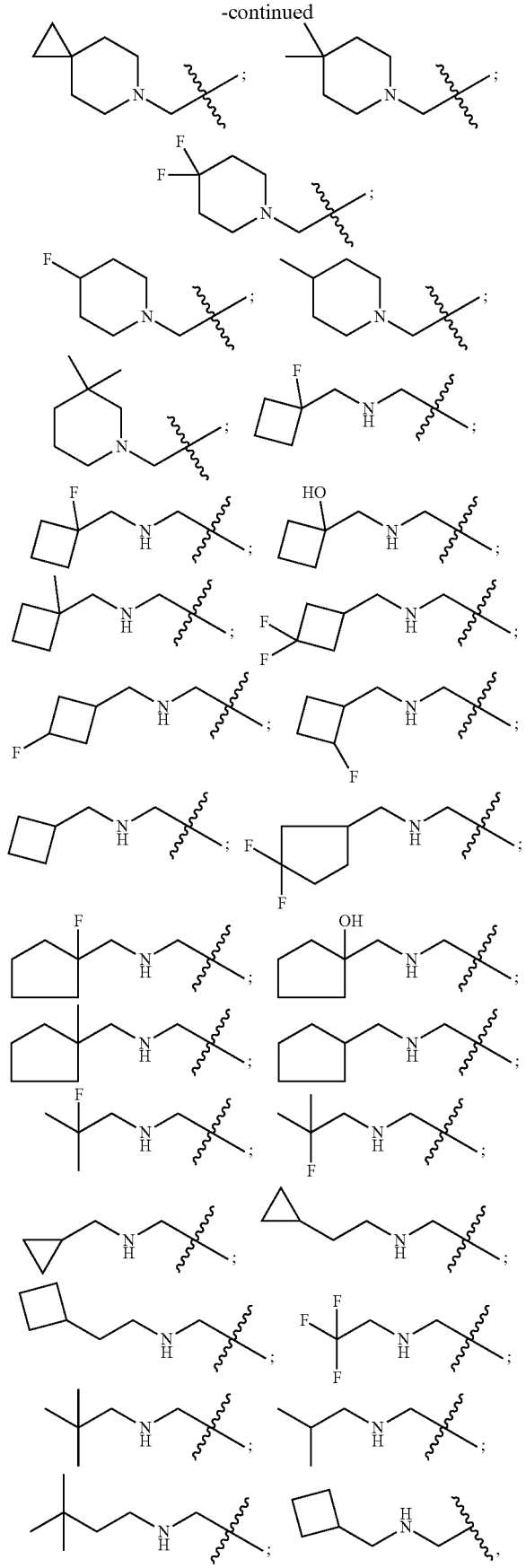
482
-continued
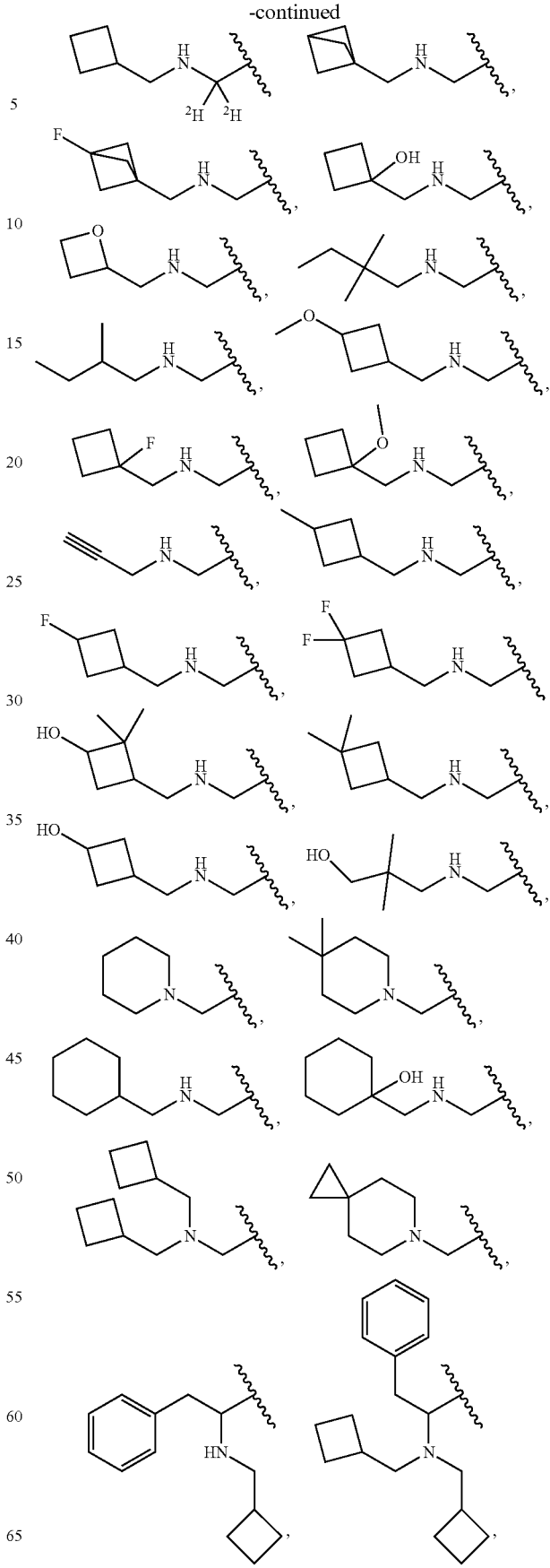

483
-continued

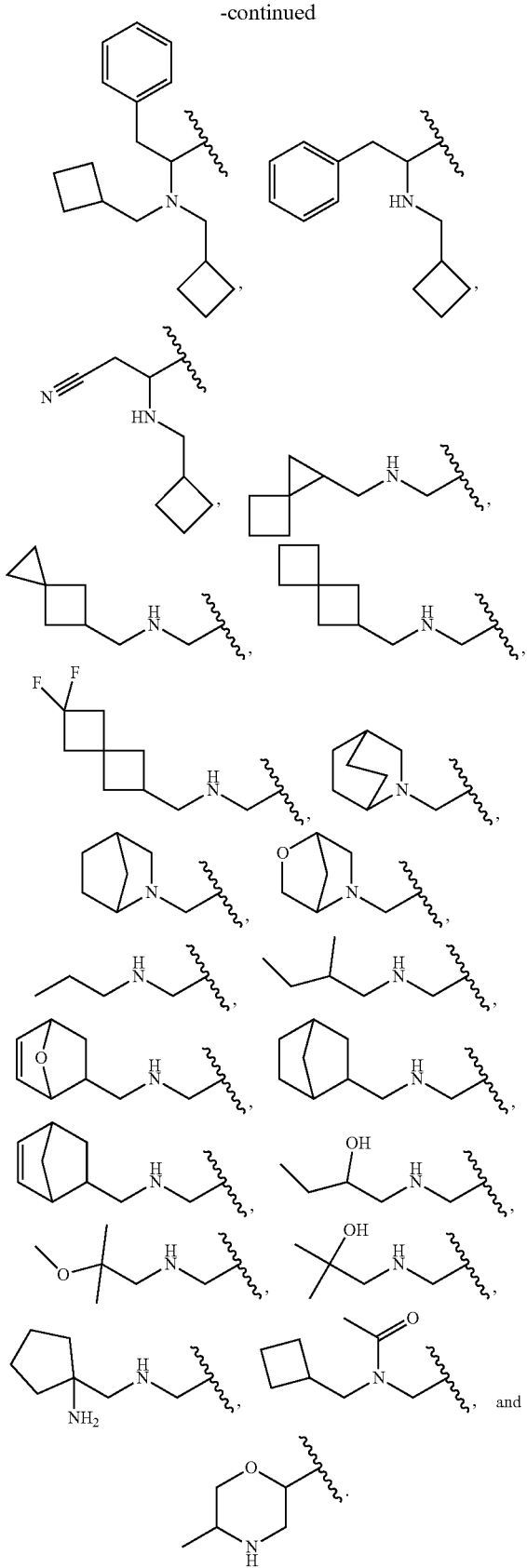

8. The compound according to claim 1, or a pharmaceutically acceptable salt thereof, wherein $R_{1b}$ is selected from

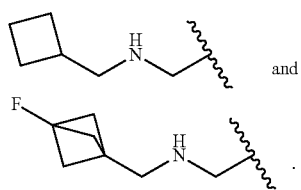

9. The compound according to claim 1, or a pharmaceutically acceptable salt thereof, wherein Y is selected from:

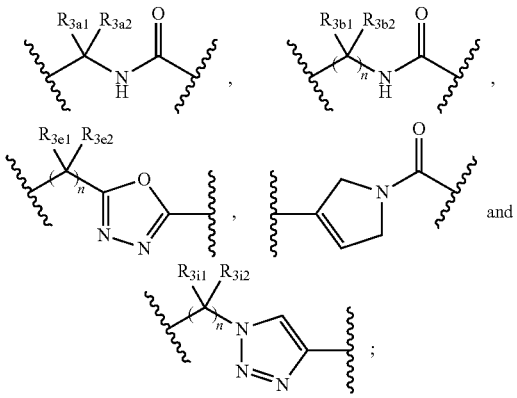

wherein $R_{3a1}$, $R_{3b1}$, $R_{3e1}$, $R_{3i1}$, $R_{3a2}$, $R_{3b2}$, $R_{3e2}$, and $R_{3i2}$ are as defined in claim 1.

10. The compound according to claim 1, or a pharmaceutically acceptable salt thereof, wherein $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen and $C_{1-6}$alkyl; and wherein $C_{1-6}$alkyl is optionally substituted with one or more hydroxy substituents;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen; and n is 1.

11. The compound according to claim 1, or a pharmaceutically acceptable salt thereof, wherein Y is selected from:

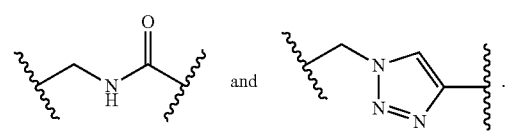 [SMILES: *CNC(*)=O ; *Cn1cc(*)nn1]

12. The compound according to claim 1, or a pharmaceutically acceptable salt thereof, wherein Z is selected from:

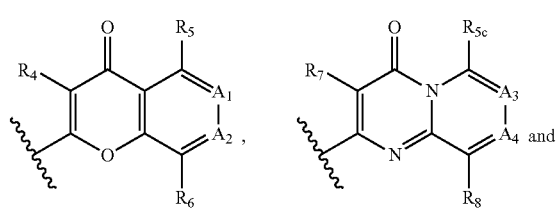

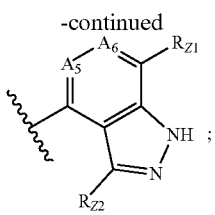

wherein $R_4$, $R_5$, $R_{5c}$ $R_6$, $R_7$, $R_8$, $A_1$, $A_2$, $A_3$, $A_4$, $A_5$, $A_6$ $R_{Z1}$ and $R_{Z2}$ are as defined in claim 1.

13. The compound according to claim 1, or a pharmaceutically acceptable salt thereof, wherein:

$R_4$, $R_{4a}$ $R_5$, $R_{5a}$ $R_{5b}$ $R_{5c}$ $R_6$, $R_{6a}$, $R_7$, $R_{7a}$ $R_8$, $R_{8a}$, $R_9$, $R_{10}$ and $R_{11}$ are hydrogen;

$A_1$ is $CR_{12}$ and wherein $R_{12}$ is hydrogen;

$A_2$ is $CR_{13}$ and wherein $R_{13}$ is hydrogen;

$A_3$ is $CR_{14}$ and wherein $R_{14}$ is hydrogen or chloro;

$A_4$ is $CR_{15}$ and wherein $R_{15}$ is hydrogen or methoxy;

$A_5$ is $CR_{16}$ and wherein $R_{16}$ is hydrogen;

$A_6$ is $CR_{17}$ and wherein $R_{17}$ is selected from selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{3-6}$cycloalkyl, —O—$C_{3-4}$ cycloalkyl, heterocyclyl, —(OCH$_2$CH$_2$)$_m$—OCH$_3$ wherein m is 1, 2 or 3, NR$_q$R$_r$, wherein R$_q$ and R$_r$ are each independently hydrogen or $C_{1-2}$ alkyl;

wherein any $C_{1-4}$ alkyl, $C_{2-4}$ alkenyl, $C_{2-4}$ alkynyl, $C_{3-6}$cycloalkyl, —O—$C_{3-4}$cycloalkyl, heterocyclyl, system is optionally further substituted by one or more substituents selected from $C_{1-2}$alkyl, $C_{1-2}$haloalkyl, cyano, hydroxy, $C_{1-2}$alkoxy, halo and $C_{1-2}$haloalkoxy.

14. The compound according to claim 13, or a pharmaceutically acceptable salt thereof, wherein $R_{17}$ is is selected from hydrogen, halo, $C_{1-4}$ alkoxy or $C_{1-4}$ haloalkoxy.

15. The compound according to claim 1, or a pharmaceutically acceptable salt thereof, wherein Z is selected from:

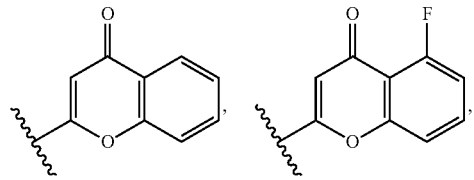

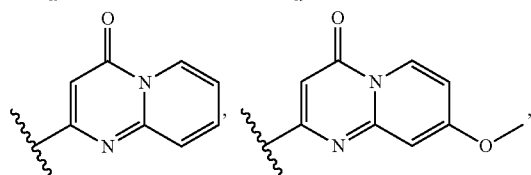

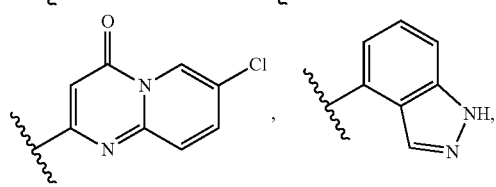

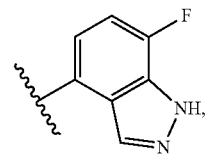

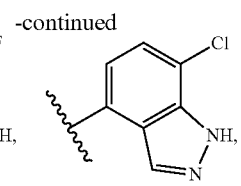

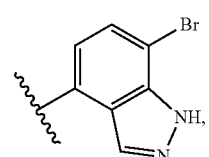

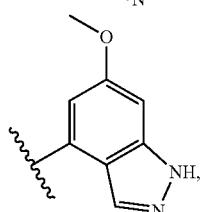

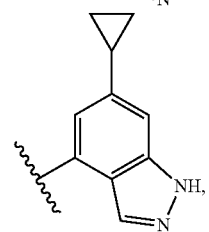

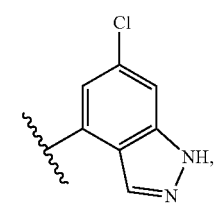

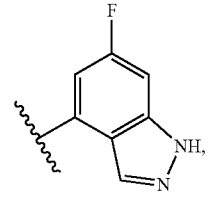

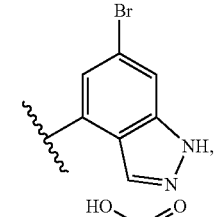

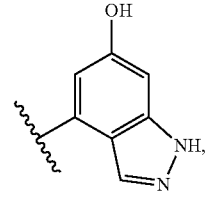

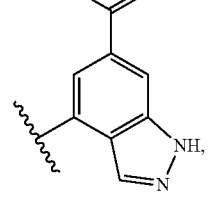

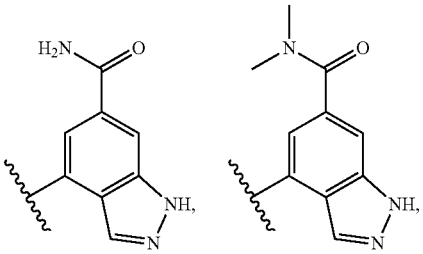

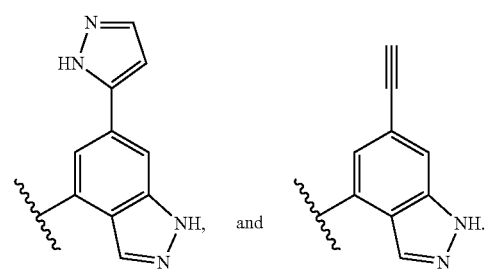

16. The compound according to claim 1, or a pharmaceutically acceptable salt thereof, wherein:
X is

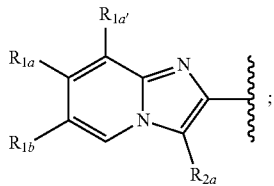

Y is selected from

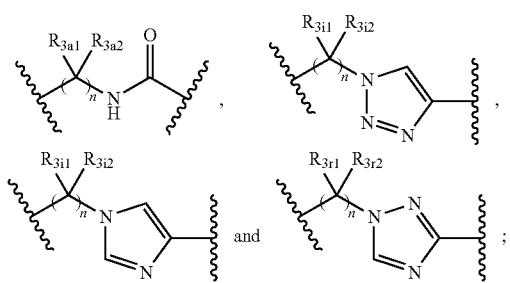

and
Z is selected from:

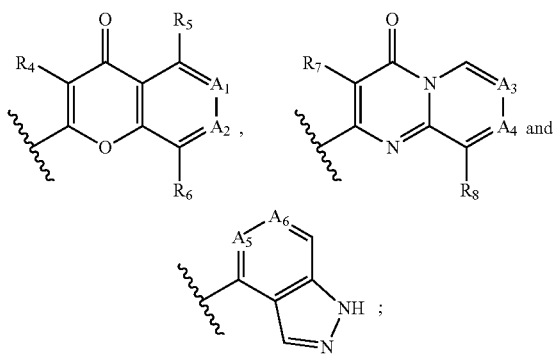

wherein $R_{1a}$, $R_{1a'}$, $R_{1b}$, $R_{2a}$, $R_{3a1}$, $R_{3a2}$, $R_{3i1}$, $R_{3i2}$, $R_{3t1}$, $R_{3t2}$, $R_{3r1}$, $R_{3r2}$, $R_4$, $R_5$, $R_6$, $R_7$, $R_8$, $A_1$, $A_2$, $A_3$, $A_4$, $A_5$ and $A_6$ are as defined in claim 1.

17. A compound, or a pharmaceutically acceptable salt thereof, selected from any one of the following:

N-({6-methylimidazo[1,2-a]pyridin-2-yl}methyl)-1H-indazole-4-carboxamide;
N-({7-bromoimidazo[1,2-a]pyridin-2-yl}methyl)-1H-indazole-4-carboxamide;
N-({6-bromoimidazo[1,2-a]pyridin-2-yl}methyl)-1H-indazole-4-carboxamide;
N-({6-chloroimidazo[1,2-a]pyridin-2-yl}methyl)-1H-indazole-4-carboxamide;
N-({7-fluoroimidazo[1,2-a]pyridin-2-yl}methyl)-1H-indazole-4-carboxamide;
N-({6-fluoroimidazo[1,2-a]pyridin-2-yl}methyl)-1H-indazole-4-carboxamide;
N-({7-methoxyimidazo[1,2-a]pyridin-2-yl}methyl)-1H-indazole-4-carboxamide;
N-({6-methylimidazo[1,2-a]pyridin-2-yl}methyl)-6-(1H-pyrazol-5-yl)-1H-indazole-4-carboxamide;
N-({7-methylimidazo[1,2-a]pyridin-2-yl}methyl)-1H-indazole-4-carboxamide;
6-bromo-N-({6-methylimidazo[1,2-a]pyridin-2-yl}methyl)-1H-indazole-4-carboxamide;
6-bromo-N-({7-methylimidazo[1,2-a]pyridin-2-yl}methyl)-1H-indazole-4-carboxamide;
N-({6-methylimidazo[1,2-a]pyridin-2-yl}methyl)-4-oxo-4H-chromene-2-carboxamide;
N-({imidazo[1,2-a]pyridin-2-yl}methyl)-4-oxo-4H-chromene-2-carboxamide;
6-ethynyl-N-({6-methylimidazo[1,2-a]pyridin-2-yl}methyl)-1H-indazole-4-carboxamide;
N-({6-methylimidazo[1,2-a]pyridin-2-yl}methyl)-4-oxo-4H-pyrido[1,2-a]pyrimidine-2-carboxamide;
N-({7-methylimidazo[1,2-a]pyridin-2-yl}methyl)-4-oxo-4H-chromene-2-carboxamide;
N-({7-methylimidazo[1,2-a]pyridin-2-yl}methyl)-4-oxo-4H-pyrido[1,2-a]pyrimidine-2-carboxamide;
N-({6-cyanoimidazo[1,2-a]pyridin-2-yl}methyl)-4-oxo-4H-pyrido[1,2-a]pyrimidine-2-carboxamide;
8-methoxy-N-({6-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-indazole-5-carboxamide;
7-chloro-N-({6-methylimidazo[1,2-a]pyridin-2-yl}methyl)-4-oxo-4H-pyrido[1,2-a]pyrimidine-2-carboxamide;
N-({6-fluoroimidazo[1,2-a]pyridin-2-yl}methyl)-4-oxo-4H-pyrido[1,2-a]pyrimidine-2-carboxamide;
N-({6-bromoimidazo[1,2-a]pyridin-2-yl}methyl)-4-oxo-4H-pyrido[1,2-a]pyrimidine-2-carboxamide;
N-({6-methoxyimidazo[1,2-a]pyridin-2-yl}methyl)-4-oxo-4H-pyrido[1,2-a]pyrimidine-2-carboxamide;
N-({7-methoxyimidazo[1,2-a]pyridin-2-yl}methyl)-4-oxo-4H-pyrido[1,2-a]pyrimidine-2-carboxamide;
N-({imidazo[1,2-a]pyridin-2-yl}methyl)-4-oxo-4H-pyrido[1,2-a]pyrimidine-2-carboxamide;
N-({8-methylimidazo[1,2-a]pyridin-2-yl}methyl)-4-oxo-4H-pyrido[1,2-a]pyrimidine-2-carboxamide;
N-({6-methylimidazo[1,2-a]pyridin-2-yl}methyl)-1H-pyrazolo[4,3-c]pyridine-4-carboxamide;
N-({7-bromoimidazo[1,2-a]pyridin-2-yl}methyl)-4-oxo-4H-pyrido[1,2-a]pyrimidine-2-carboxamide;
N-(2-hydroxy-1-{6-methylimidazo[1,2-a]pyridin-2-yl}ethyl)-1H-indazole-4-carboxamide;
4-(3-{imidazo[1,2-a]pyridin-2-yl}-2,5-dihydro-1H-pyrrole-1-carbonyl)-1H-indazole;
N-[(6-{[(pyridin-3-yl)methyl]amino}imidazo[1,2-a]pyridin-2-yl)methyl]-1H-indazole-4-carboxamide;
N-[(6-{[(1-methyl-1H-imidazol-4-yl)methyl]amino}imidazo[1,2a]pyridin-2-yl)methyl]-1H-indazole-4-carboxamide;
N-{[6-(3-methoxyphenyl)imidazo[1,2-a]pyridin-2-yl]methyl}-1H-indazole-4-carboxamide;
N-{[6-(1H-pyrazol-5-yl)imidazo[1,2-a]pyridin-2-yl]methyl}-1H-indazole-4-carboxamide;
N-[[6-(3-chlorophenyl)imidazo[1,2-a]pyridin-2-yl]methyl]-1H-indazole-4-carboxamide;
N-({6-[(pyridin-3-yl)amino]imidazo[1,2-a]pyridin-2-yl}methyl)-1H-indazole-4-carboxamide;
N-({6-[(piperazin-1-yl)methyl]imidazo[1,2-a]pyridin-2-yl}methyl)-1H-indazole-4-carboxamide;
N-{[6-(aminomethyl)imidazo[1,2-a]pyridin-2-yl]methyl}-1H-indazole-4-carboxamide;
N-{[6-(acetamidomethyl)imidazo[1,2-a]pyridin-2-yl]methyl}-1H-indazole-4-carboxamide;

{6-methylimidazo[1,2-a]pyridin-2-yl}methyl 1H-indazole-4-carboxylate;
{6-methylimidazo[1,2-a]pyridin-2-yl}methyl 1H-indazole-4-carboxylate hydrochloride;
N-{[6-(hydroxymethyl)imidazo[1,2-a]pyridin-2-yl]methyl}-1H-indazole-4-carboxamide;
N-({6-hydroxyimidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide;
N-({6-[(methylamino)methyl]imidazo[1,2-a]pyridin-2-yl}methyl)-1H-indazole-4-carboxamide dihydrochloride;
N-[(6-{[(2-hydroxyethyl)amino]methyl}imidazo[1,2-a]pyridin-2-yl)methyl]-1H-indazole-4-carboxamide;
N-[(6-{[(2,2,2-trifluoroethyl)amino]methyl}imidazo[1,2-a]pyridin-2-yl)methyl]-1H-indazole-4-carboxamide;
N-{[6-(1-hydroxyethyl)imidazo[1,2-a]pyridin-2-yl]methyl}-1H-indazole-4-carboxamide;
N-({6-[hydroxy (phenyl)methyl]imidazo[1,2-a]pyridin-2-yl}methyl)-1H-indazole-4-carboxamide;
N-({6-formylimidazo[1,2-a]pyridin-2-yl}methyl)-4-oxo-4H-pyrido[1,2-a]pyrimidine-2-carboxamide;
N-{[6-(aminomethyl)imidazo[1,2-a]pyridin-2-yl]methyl}-4-oxo-4H-pyrido[1,2-a]pyrimidine-2-carboxamide;
4-oxo-N-[(6-{[(2,2,2-trifluoroethyl)amino]methyl}imidazo[1,2-a]pyridin-2-yl)methyl]-4H-pyrido[1,2-a]pyrimidine-2-carboxamide;
N-[(6-{[(2-hydroxyethyl)amino]methyl}imidazo[1,2-a]pyridin-2-yl)methyl]-4-oxo-4H-pyrido[1,2-a]pyrimidine-2-carboxamide;
4-oxo-N-[(6-{[(2-phenylethyl)amino]methyl}imidazo[1,2-a]pyridin-2-yl)methyl]-4H-pyrido[1,2-a]pyrimidine-2-carboxamide;
N-({6-[(benzylamino)methyl]imidazo[1,2-a]pyridin-2-yl}methyl)-4-oxo-4H-pyrido[1,2-a]pyrimidine-2-carboxamide;
4-oxo-N-[(6-{[(3-phenylpropyl)amino]methyl}imidazo[1,2-a]pyridin-2-yl)methyl]-4H-pyrido[1,2-a]pyrimidine-2-carboxamide;
N-({6-[hydroxy (phenyl)methyl]imidazo[1,2-a]pyridin-2-yl}methyl)-4-oxo-4H-pyrido[1,2-a]pyrimidine-2-carboxamide;
N-{[6-(1-hydroxyethyl)imidazo[1,2-a]pyridin-2-yl]methyl}-4-oxo-4H-pyrido[1,2-a]pyrimidine-2-carboxamide;
N-({6-ethenylimidazo[1,2-a]pyridin-2-yl}methyl)-4-oxo-4H-pyrido[1,2-a]pyrimidine-2-carboxamide;
N-({6-cyclopropylimidazo[1,2-a]pyridin-2-yl}methyl)-4-oxo-4H-pyrido[1,2-a]pyrimidine-2-carboxamide;
N-({7-ethenylimidazo[1,2-a]pyridin-2-yl}methyl)-4-oxo-4H-pyrido[1,2-a]pyrimidine-2-carboxamide;
N-{[6-(hydroxymethyl)imidazo[1,2-a]pyridin-2-yl]methyl}-4-oxo-4H-pyrido[1,2-a]pyrimidine-2-carboxamide;
2-(1H-indazol-4-yl)-5-[(6-methylimidazo[1,2-a]pyridin-2-yl)methyl]-1,3,4-oxadiazole;
N-{[6-(2-aminoethyl)imidazo[1,2-a]pyridin-2-yl]methyl}-4-oxo-4H-pyrido[1,2-a]pyrimidine-2-carboxamide;
N-({6-methylimidazo[1,2-a]pyridin-2-yl}methyl)-4-oxo-4H,6H,7H,8H,9H-pyrido[1,2-a]pyrimidine-2-carboxamide;
4-oxo-N-{[6-(trifluoromethyl)imidazo[1,2-a]pyridin-2-yl]methyl}-4H-pyrido[1,2-a]pyrimidine-2-carboxamide;
tert-butylN-(2-{2-[({4-oxo-4H-pyrido[1,2-a]pyrimidin-2-yl}formamido)methyl]imidazo[1,2-a]pyridin-6-yl}ethyl) carbamate;
N-benzyl-2-[({4-oxo-4H-pyrido[1,2-a]pyrimidin-2-yl}formamido)methyl]imidazo[1,2-a]pyridine-6-carboxamide;
N-[(6-{[(cyclohexylmethyl)amino]methyl}imidazo[1,2-a]pyridin-2-yl)methyl]-4-oxo-4H-chromene-2-carboxamide;
7-chloro-N-[(6-{[(cyclohexylmethyl)amino]methyl}imidazo[1,2-a]pyridin-2-yl)methyl]-4-oxo-4H-chromene-2-carboxamide;
6-chloro-N-[(6-{[(cyclohexylmethyl)amino]methyl}imidazo[1,2-a]pyridin-2-yl)methyl]-4-oxo-4H-chromene-2-carboxamide;
N-[(6-{[(cyclohexylmethyl)amino]methyl}imidazo[1,2-a]pyridin-2-yl)methyl]-4-oxo-4H,6H,7H,8H,9H-pyrido[1,2-a]pyrimidine-2-carboxamide;
6-amino-N-[(6-{[(cyclohexylmethyl)amino]methyl}imidazo[1,2-a]pyridin-2-yl)methyl]pyridine-3-carboxamide;
N-({6-[(benzyloxy)methyl]imidazo[1,2-a]pyridin-2-yl}methyl)-4-oxo-4H-pyrido[1,2-a]pyrimidine-2-carboxamide;
N-({6-[(benzylamino)methyl]imidazo[1,2-a]pyridin-2-yl}methyl)-1H-indazole-4-carboxamide;
N-[(6-{[(cyclohexylmethyl)amino]methyl}imidazo[1,2-a]pyridin-2-yl)methyl]-7-fluoro-4-oxo-4H-chromene-2-carboxamide;
N-[(6-{[(cyclohexylmethyl)amino]methyl}imidazo[1,2-a]pyridin-2-yl)methyl]-7-methyl-4-oxo-4H-chromene-2-carboxamide;
N-[(6-{[(cyclohexylmethyl)amino]methyl}imidazo[1,2-a]pyridin-2-yl)methyl]-1H-indazole-4-carboxamide;
8-chloro-N-[(6-{[(cyclohexylmethyl)amino]methyl}imidazo[1,2-a]pyridin-2-yl)methyl]-4-oxo-4H-chromene-2-carboxamide;
6-bromo-N-[(6-{[(cyclohexylmethyl)amino]methyl}imidazo[1,2-a]pyridin-2-yl)methyl]-1H-indazole-4-carboxamide;
N-[(6-{[(cyclohexylmethyl)amino]methyl}imidazo[1,2-a]pyridin-2-yl)methyl]quinoline-3-carboxamide;
N-[(6-{1-[(cyclohexylmethyl)amino]ethyl}imidazo[1,2-a]pyridin-2-yl)methyl]-4-oxo-4H-pyrido[1,2-a]pyrimidine-2-carboxamide;
6-chloro-N-[(6-{[(cyclohexylmethyl)amino]methyl}imidazo[1,2-a]pyridin-2-yl)methyl]-1H-indazole-4-carboxamide;
4-[5-({6-methylimidazo[1,2-a]pyridin-2-yl}methyl)-1,3,4-thiadiazol-2-yl]-1H-indazole;
4-[1-({6-methylimidazo[1,2-a]pyridin-2-yl}methyl)-1H-1,2,3-triazol-4-yl]-1H-indazole;
N-[(6-{[(3-chlorophenyl)amino]methyl}imidazo[1,2-a]pyridin-2-yl)methyl]-4-oxo-4H-pyrido[1,2-a]pyrimidine-2-carboxamide;
N-[(6-{[(1-cyclohexyl-2-hydroxyethyl)amino]methyl}imidazo[1,2-a]pyridin-2-yl)methyl]-4-oxo-4H-pyrido[1,2-a]pyrimidine-2-carboxamide;
4-oxo-N-{[6-({[(pyridin-3-yl)methyl]amino}methyl)imidazo[1,2-a]pyridin-2-yl]methyl}-4H-pyrido[1,2-a]pyrimidine-2-carboxamide;
N-{[6-({[(4-methoxyphenyl)methyl]amino}methyl)imidazo[1,2-a]pyridin-2-yl]methyl}-4-oxo-4H-pyrido[1,2-a]pyrimidine-2-carboxamide;
N-[(6-{[(cyclohexylmethyl)amino]methyl}imidazo[1,2-a]pyridin-2-yl)methyl]-4-oxo-4H-pyrido[1,2-a]pyrimidine-2-carboxamide;

N-{[6-({[(4-chlorophenyl)methyl]amino}methyl)imidazo[1,2-a]pyridin-2-yl]methyl}-4-oxo-4H-pyrido[1,2-a]pyrimidine-2-carboxamide;
N-[(6-{[benzyl(methyl)amino]methyl}imidazo[1,2-a]pyridin-2-yl)methyl]-4-oxo-4H-pyrido[1,2-a]pyrimidine-2-carboxamide;
4-oxo-N-{[6-({[(1R)-1-phenylethyl]amino}methyl)imidazo[1,2-a]pyridin-2-yl]methyl}-4H-pyrido[1,2-a]pyrimidine-2-carboxamide;
4-oxo-N-{[6-({[(1S)-1-phenylethyl]amino}methyl)imidazo[1,2-a]pyridin-2-yl]methyl}-4H-pyrido[1,2-a]pyrimidine-2-carboxamide;
N-{[6-({[(2-fluorophenyl)methyl]amino}methyl)imidazo[1,2-a]pyridin-2-yl]methyl}-4-oxo-4H-pyrido[1,2-a]pyrimidine-2-carboxamide;
4-oxo-N-[(6-{[(2-phenylpropan-2-yl)amino]methyl}imidazo[1,2-a]pyridin-2-yl)methyl]-4H-pyrido[1,2-a]pyrimidine-2-carboxamide;
N-{[6-({[(3-fluorophenyl)methyl]amino}methyl)imidazo[1,2-a]pyridin-2-yl]methyl}-4-oxo-4H-pyrido[1,2-a]pyrimidine-2-carboxamide;
N-{[6-({[(4-fluorophenyl)methyl]amino}methyl)imidazo[1,2-a]pyridin-2-yl]methyl}-4-oxo-4H-pyrido[1,2-a]pyrimidine-2-carboxamide;
4-oxo-N-[(6-{[(4,4,4-trifluorobutyl)amino]methyl}imidazo[1,2-a]pyridin-2-yl)methyl]-4H-pyrido[1,2-a]pyrimidine-2-carboxamide;
N-{[6-({[(oxan-4-yl)methyl]amino}methyl)imidazo[1,2-a]pyridin-2-yl]methyl}-4-oxo-4H-pyrido[1,2-a]pyrimidine-2-carboxamide;
N-{[6-({[(3,3-difluorocyclobutyl)methyl]amino}methyl)imidazo[1,2-a]pyridin-2-yl]methyl}-4-oxo-4H-pyrido[1,2-a]pyrimidine-2-carboxamide;
N-[(6-{[(cyclopropylmethyl)amino]methyl}imidazo[1,2-a]pyridin-2-yl)methyl]-4-oxo-4H-pyrido[1,2-a]pyrimidine-2-carboxamide;
4-oxo-N-[(6-{[(3,3,3-trifluoropropyl)amino]methyl}imidazo[1,2-a]pyridin-2-yl)methyl]-4H-pyrido[1,2-a]pyrimidine-2-carboxamide;
N-({6-[(cyclohexylamino)methyl]imidazo[1,2-a]pyridin-2-yl}methyl)-4-oxo-4H-pyrido[1,2-a]pyrimidine-2-carboxamide;
4-oxo-N-({6-[({[3-(trifluoromethyl)bicyclo[1.1.1]pentan-1-yl]methyl}amino)methyl]imidazo[1,2-a]pyridin-2-yl}methyl)-4H-pyrido[1,2-a]pyrimidine-2-carboxamide;
N-{[6-({[(oxan-2-yl)methyl]amino}methyl)imidazo[1,2-a]pyridin-2-yl]methyl}-4-oxo-4H-pyrido[1,2-a]pyrimidine-2-carboxamide;
4-oxo-N-[(6-{[(3-phenyloxetan-3-yl)amino]methyl}imidazo[1,2-a]pyridin-2-yl)methyl]-4H-pyrido[1,2-a]pyrimidine-2-carboxamide;
N-{[6-({[(oxan-3-yl)methyl]amino}methyl)imidazo[1,2-a]pyridin-2-yl]methyl}-4-oxo-4H-pyrido[1,2-a]pyrimidine-2-carboxamide;
N-{[6-({[(1-fluorocyclohexyl)methyl]amino}methyl)imidazo[1,2-a]pyridin-2-yl]methyl}-4-oxo-4H-pyrido[1,2-a]pyrimidine-2-carboxamide;
N-{[6-({[(3-cyclopropylphenyl)methyl]amino}methyl)imidazo[1,2-a]pyridin-2-yl]methyl}-4-oxo-4H-pyrido[1,2-a]pyrimidine-2-carboxamide;
N-[(6-{[(3,3-dimethylbutyl)amino]methyl}imidazo[1,2-a]pyridin-2-yl)methyl]-4-oxo-4H-pyrido[1,2-a]pyrimidine-2-carboxamide;
4-oxo-N-{[6-({[2-(trifluoromethoxy)ethyl]amino}methyl)imidazo[1,2-a]pyridin-2-yl]methyl}-4H-pyrido[1,2-a]pyrimidine-2-carboxamide;
4-oxo-N-{[6-({[(oxolan-2-yl)methyl]amino}methyl)imidazo[1,2-a]pyridin-2-yl]methyl}-4H-pyrido[1,2-a]pyrimidine-2-carboxamide;
N-[(6-{[(2-methanesulfonylethyl)amino]methyl}imidazo[1,2-a]pyridin-2-yl)methyl]-4-oxo-4H-pyrido[1,2-a]pyrimidine-2-carboxamide;
4-oxo-N-({6-[(3-phenylpyrrolidin-1-yl)methyl]imidazo[1,2-a]pyridin-2-yl}methyl)-4H-pyrido[1,2-a]pyrimidine-2-carboxamide;
N-[(6-{[(1-cyclohexylcyclopropyl)amino]methyl}imidazo[1,2-a]pyridin-2-yl)methyl]-4-oxo-4H-pyrido[1,2-a]pyrimidine-2-carboxamide;
4-oxo-N-{[6-({[(1,3-thiazol-5-yl)methyl]amino}methyl)imidazo[1,2-a]pyridin-2-yl]methyl}-4H-pyrido[1,2-a]pyrimidine-2-carboxamide;
tert-butyl 3-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;
N-{[6-({[(4,4-difluorocyclohexyl)methyl]amino}methyl)imidazo[1,2-a]pyridin-2-yl]methyl}-4-oxo-4H-pyrido[1,2-a]pyrimidine-2-carboxamide;
tert-butyl 2-{[({2-[({4-oxo-4H-pyrido[1,2-a]pyrimidin-2-yl}formamido)methyl]imidazo[1,2-a]pyridin-6-yl}methyl)amino]methyl}piperidine-1-carboxylate;
N-[(6-{[(2-cyclopropylethyl)amino]methyl}imidazo[1,2-a]pyridin-2-yl)methyl]-4-oxo-4H-pyrido[1,2-a]pyrimidine-2-carboxamide;
4-oxo-N-({6-[(piperidin-1-yl)methyl]imidazo[1,2-a]pyridin-2-yl}methyl)-4H-pyrido[1,2-a]pyrimidine-2-carboxamide;
4-oxo-N-({6-[({[1-(2,2,2-trifluoroethyl)-1H-pyrazol-3-yl]methyl}amino)methyl]imidazo[1,2-a]pyridin-2-yl}methyl)-4H-pyrido[1,2-a]pyrimidine-2-carboxamide;
N-{[6-({[(1-methylcyclohexyl)methyl]amino}methyl)imidazo[1,2-a]pyridin-2-yl]methyl}-4-oxo-4H-pyrido[1,2-a]pyrimidine-2-carboxamide;
4-oxo-N-{[6-({[2-(pyridin-3-yl)ethyl]amino}methyl)imidazo[1,2-a]pyridin-2-yl]methyl}-4H-pyrido[1,2-a]pyrimidine-2-carboxamide;
N-{[6-({[(1,4-dioxan-2-yl)methyl]amino}methyl)imidazo[1,2-a]pyridin-2-yl]methyl}-4-oxo-4H-pyrido[1,2-a]pyrimidine-2-carboxamide;
N-({6-[(cyclopropylamino)methyl]imidazo[1,2-a]pyridin-2-yl}methyl)-4-oxo-4H-pyrido[1,2-a]pyrimidine-2-carboxamide;
N-[(6-{[(3,3-difluorocyclobutyl)amino]methyl}imidazo[1,2-a]pyridin-2-yl)methyl]-4-oxo-4H-pyrido[1,2-a]pyrimidine-2-carboxamide;
N-{[6-({[(oxetan-3-yl)methyl]amino}methyl)imidazo[1,2-a]pyridin-2-yl]methyl}-4-oxo-4H-pyrido[1,2-a]pyrimidine-2-carboxamide;
4-oxo-N-{[6-({[(1R,2R)-2-(trifluoromethyl)cyclopropyl]amino}methyl)imidazo[1,2-a]pyridin-2-yl]methyl}-4H-pyrido[1,2-a]pyrimidine-2-carboxamide;
N-[(6-{[(2,2-dimethylpropyl)amino]methyl}imidazo[1,2-a]pyridin-2-yl)methyl]-4-oxo-4H-pyrido[1,2-a]pyrimidine-2-carboxamide;
N-[(6-{[(cyclohexylmethyl)(methyl)amino]methyl}imidazo[1,2-a]pyridin-2-yl)methyl]-4-oxo-4H-pyrido[1,2-a]pyrimidine-2-carboxamide;
N-[(6-{[(4,4-difluorocyclohexyl)amino]methyl}imidazo[1,2-a]pyridin-2-yl)methyl]-4-oxo-4H-pyrido[1,2-a]pyrimidine-2-carboxamide;
N-({6-[({bicyclo[1.1.1]pentan-1-yl}amino)methyl]imidazo[1,2-a]pyridin-2-yl}methyl)-4-oxo-4H-pyrido[1,2-a]pyrimidine-2-carboxamide;

4-oxo-N-({6-[({[(2S)-oxolan-2-yl]methyl}amino) methyl]imidazo[1,2-a]pyridin-2-yl}methyl)-4H-pyrido[1,2-a]pyrimidine-2-carboxamide;

4-oxo-N-({6-[({[(2R)-oxolan-2-yl]methyl}amino) methyl]imidazo[1,2-a]pyridin-2-yl}methyl)-4H-pyrido[1,2-a]pyrimidine-2-carboxamide;

N-[(6-{[(2,2-difluoroethyl)amino]methyl}imidazo[1,2-a]pyridin-2-yl)methyl]-4-oxo-4H-pyrido[1,2-a]pyrimidine-2-carboxamide;

4-oxo-N-{[6-({[(oxolan-3-yl)methyl]amino}methyl)imidazo[1,2-a]pyridin-2-yl]methyl}-4H-pyrido[1,2-a]pyrimidine-2-carboxamide;

N-{[6-({[(1-methylcyclopropyl)methyl]amino}methyl) imidazo[1,2-a]pyridin-2-yl]methyl}-4-oxo-4H-pyrido[1,2-a]pyrimidine-2-carboxamide;

4-oxo-N-[(6-{[(oxolan-3-yl)amino]methyl}imidazo[1,2-a]pyridin-2-yl)methyl]-4H-pyrido[1,2-a]pyrimidine-2-carboxamide;

methyl 3-methyl-2-[({2-[({4-oxo-4H-pyrido[1,2-a]pyrimidin-2-yl}formamido)methyl]imidazo[1,2-a]pyridin-6-yl}methyl)amino]butanoate;

N-[(6-{[(oxan-3-yl)amino]methyl}imidazo[1,2-a]pyridin-2-yl)methyl]-4-oxo-4H-pyrido[1,2-a]pyrimidine-2-carboxamide;

4-oxo-N-{[6-({[(2S)-3,3,3-trifluoro-2-hydroxypropyl]amino}methyl)imidazo[1,2-a]pyridin-2-yl]methyl}-4H-pyrido[1,2-a]pyrimidine-2-carboxamide;

N-({6-[(cyclobutylamino)methyl]imidazo[1,2-a]pyridin-2-yl}methyl)-4-oxo-4H-pyrido[1,2-a]pyrimidine-2-carboxamide;

N-({6-[(tert-butylamino)methyl]imidazo[1,2-a]pyridin-2-yl}methyl)-4-oxo-4H-pyrido[1,2-a]pyrimidine-2-carboxamide;

N-[(6-{[(2-fluoroethyl)amino]methyl}imidazo[1,2-a]pyridin-2-yl)methyl]-4-oxo-4H-pyrido[1,2-a]pyrimidine-2-carboxamide;

N-({6-[(4,4-difluoropiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenylpiperazin-1-yl)methyl]imidazo[1,2-a]pyridin-2-yl}methyl)-4H-pyrido[1,2-a]pyrimidine-2-carboxamide;

4-oxo-N-({6-[(1,2,3,4-tetrahydroisoquinolin-2-yl) methyl]imidazo[1,2-a]pyridin-2-yl}methyl)-4H-pyrido[1,2-a]pyrimidine-2-carboxamide;

N-({6-[(diethylamino)methyl]imidazo[1,2-a]pyridin-2-yl}methyl)-4-oxo-4H-pyrido[1,2-a]pyrimidine-2-carboxamide;

4-oxo-N-({6-[(pyrrolidin-1-yl)methyl]imidazo[1,2-a]pyridin-2-yl}methyl)-4H-pyrido[1,2-a]pyrimidine-2-carboxamide;

4-oxo-N-[(6-{[3-(pyridin-2-yl) azetidin-1-yl]methyl}imidazo[1,2-a]pyridin-2-yl)methyl]-4H-pyrido[1,2-a]pyrimidine-2-carboxamide;

N-[(6-{[(dicyclopropylmethyl)amino]methyl}imidazo[1,2-a]pyridin-2-yl)methyl]-4-oxo-4H-pyrido[1,2-a]pyrimidine-2-carboxamide;

N-[(6-{[(cyclopropylmethyl)(methyl)amino]methyl}imidazo[1,2-a]pyridin-2-yl)methyl]-4-oxo-4H-pyrido[1,2-a]pyrimidine-2-carboxamide;

N-({6-[(4-methylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[4-(trifluoromethyl) piperidin-1-yl]methyl}imidazo[1,2-a]pyridin-2-yl)methyl]-4H-pyrido[1,2-a]pyrimidine-2-carboxamide;

N-({6-[(3-methylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[({spiro[2.2]pentan-1-yl}methyl)amino]methyl}imidazo[1,2-a]pyridin-2-yl)methyl]-4H-pyrido[1,2-a]pyrimidine-2-carboxamide;

N-({6-[(3,3-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[3-(trifluoromethyl) piperidin-1-yl]methyl}imidazo[1,2-a]pyridin-2-yl)methyl]-4H-pyrido[1,2-a]pyrimidine-2-carboxamide;

N-{[6-({[(5,5-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-({6-[(4-fluoropiperidin-1-yl)methyl]imidazo[1,2-a]pyridin-2-yl}methyl)-4-oxo-4H-pyrido[1,2-a]pyrimidine-2-carboxamide;

N-[(6-{[(3-methoxypropyl)amino]methyl}imidazo[1,2-a]pyridin-2-yl)methyl]-4-oxo-4H-pyrido[1,2-a]pyrimidine-2-carboxamide;

N-[(6-{[(1-methylcyclohexyl)amino]methyl}imidazo[1,2-a]pyridin-2-yl)methyl]-4-oxo-4H-pyrido[1,2-a]pyrimidine-2-carboxamide;

N-{[6-({[(4,4-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(1-methylcyclopentyl)amino]methyl}imidazo[1,2-a]pyridin-2-yl)methyl]-4-oxo-4H-pyrido[1,2-a]pyrimidine-2-carboxamide;

4-oxo-N-({6-[(propylamino)methyl]imidazo[1,2-a]pyridin-2-yl}methyl)-4H-pyrido[1,2-a]pyrimidine-2-carboxamide;

N-{[6-({[(3,3-dimethyloxolan-2-yl)methyl]amino}methyl)imidazo[1,2-a]pyridin-2-yl]methyl}-4-oxo-4H-pyrido[1,2-a]pyrimidine-2-carboxamide;

N-[(6-{[(2-methylpropyl)amino]methyl}imidazo[1,2-a]pyridin-2-yl)methyl]-4-oxo-4H-pyrido[1,2-a]pyrimidine-2-carboxamide;

N-{[6-({[2-(tert-butoxy)ethyl]amino}methyl)imidazo[1,2-a]pyridin-2-yl]methyl}-4-oxo-4H-pyrido[1,2-a]pyrimidine-2-carboxamide;

N-[(6-{[(4-chlorophenyl)amino]methyl}imidazo[1,2-a]pyridin-2-yl)methyl]-4-oxo-4H-pyrido[1,2-a]pyrimidine-2-carboxamide;

N-{[6-({[2-(oxan-2-yl)ethyl]amino}methyl)imidazo[1,2-a]pyridin-2-yl]methyl}-4-oxo-4H-pyrido[1,2-a]pyrimidine-2-carboxamide;

N-({6-[(4-benzylpiperidin-1-yl)methyl]imidazo[1,2-a]pyridin-2-yl}methyl)-4-oxo-4H-pyrido[1,2-a]pyrimidine-2-carboxamide;

4-oxo-N-({6-[(4-phenoxypiperidin-1-yl)methyl]imidazo[1,2-a]pyridin-2-yl}methyl)-4H-pyrido[1,2-a]pyrimidine-2-carboxamide;

N-{[6-({[(2,2-difluorocyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2,2-dimethylcyclopropyl)methyl]amino}methyl)imidazo[1,2-a]pyridin-2-yl]methyl}-4-oxo-4H-pyrido[1,2-a]pyrimidine-2-carboxamide;

N-{[6-({[(2-methyloxolan-2-yl)methyl]amino}methyl) imidazo[1,2-a]pyridin-2-yl]methyl}-4-oxo-4H-pyrido[1,2-a]pyrimidine-2-carboxamide;

N-({6-[(4-tert-butylpiperidin-1-yl)methyl]imidazo[1,2-a]pyridin-2-yl}methyl)-4-oxo-4H-pyrido[1,2-a]pyrimidine-2-carboxamide;

N-[(6-{[(4-tert-butylcyclohexyl)amino]methyl}imidazo[1,2-a]pyridin-2-yl)methyl]-4-oxo-4H-pyrido[1,2-a]pyrimidine-2-carboxamide;

N-[(6-{[(2-cyclopentylethyl)amino]methyl}imidazo[1,2-a]pyridin-2-yl)methyl]-4-oxo-4H-pyrido[1,2-a]pyrimidine-2-carboxamide;

N-[(6-{[4-(2,2-dimethylpropanoyl) piperazin-1-yl]methyl}imidazo[1,2-a]pyridin-2-yl)methyl]-4-oxo-4H-pyrido[1,2-a]pyrimidine-2-carboxamide;

N-({6-[(4-acetylpiperazin-1-yl)methyl]imidazo[1,2-a]pyridin-2-yl}methyl)-4-oxo-4H-pyrido[1,2-a]pyrimidine-2-carboxamide;

N-{[6-({7-azabicyclo[2.2.1]heptan-7-yl}methyl)imidazo[1,2-a]pyridin-2-yl]methyl}-4-oxo-4H-pyrido[1,2-a]pyrimidine-2-carboxamide;

N-({6-[(4,4-dimethylpiperidin-1-yl)methyl]imidazo[1,2-a]pyridin-2-yl}methyl)-4-oxo-4H-pyrido[1,2-a]pyrimidine-2-carboxamide;

N-({6-[(2,2-dimethylpiperidin-1-yl)methyl]imidazo[1,2-a]pyridin-2-yl}methyl)-4-oxo-4H-pyrido[1,2-a]pyrimidine-2-carboxamide;

4-oxo-N-[(6-{[(2,3,3-trimethylbutan-2-yl)amino]methyl}imidazo[1,2-a]pyridin-2-yl)methyl]-4H-pyrido[1,2-a]pyrimidine-2-carboxamide;

N-[(6-{[(5-fluoropyridin-2-yl)amino]methyl}imidazo[1,2-a]pyridin-2-yl)methyl]-4-oxo-4H-pyrido[1,2-a]pyrimidine-2-carboxamide;

N-({6-[({[1,1'-bi (cyclopropane)]-1-yl}amino)methyl]imidazo[1,2-a]pyridin-2-yl}methyl)-4-oxo-4H-pyrido[1,2-a]pyrimidine-2-carboxamide;

N-{[6-({[(1-fluorocyclopentyl)methyl]amino}methyl)imidazo[1,2-a]pyridin-2-yl]methyl}-4-oxo-4H-pyrido[1,2-a]pyrimidine-2-carboxamide;

N-({6-[(2,6-dimethylmorpholin-4-yl)methyl]imidazo[1,2-a]pyridin-2-yl}methyl)-4-oxo-4H-pyrido[1,2-a]pyrimidine-2-carboxamide;

methyl 1-({2-[({4-oxo-4H-pyrido[1,2-a]pyrimidin-2-yl}formamido)methyl]imidazo[1,2-a]pyridin-6-yl}methyl)piperidine-3-carboxylate;

N-[(6-{[(2-fluoro-2-methylpropyl)amino]methyl}imidazo[1,2-a]pyridin-2-yl)methyl]-4-oxo-4H-pyrido[1,2-a]pyrimidine-2-carboxamide;

N-[(6-{[(1-cyclohexylethyl)amino]methyl}imidazo[1,2-a]pyridin-2-yl)methyl]-4-oxo-4H-pyrido[1,2-a]pyrimidine-2-carboxamide;

N-[(6-{[(2-cyclopropylethyl)(methyl)amino]methyl}imidazo[1,2-a]pyridin-2-yl)methyl]-4-oxo-4H-pyrido[1,2-a]pyrimidine-2-carboxamide;

N-[(6-{[(2,2-dimethylpropyl)(methyl)amino]methyl}imidazo[1,2-a]pyridin-2-yl)methyl]-4-oxo-4H-pyrido[1,2-a]pyrimidine-2-carboxamide;

N-{[6-({[(1-fluorocyclobutyl)methyl]amino}methyl)imidazo[1,2-a]pyridin-2-yl]methyl}-4-oxo-4H-pyrido[1,2-a]pyrimidine-2-carboxamide;

N-({6-[(4-fluoro-4-methylpiperidin-1-yl)methyl]imidazo[1,2-a]pyridin-2-yl}methyl)-4-oxo-4H-pyrido[1,2-a]pyrimidine-2-carboxamide;

N-({6-[(3,3-difluoropiperidin-1-yl)methyl]imidazo[1,2-a]pyridin-2-yl}methyl)-4-oxo-4H-pyrido[1,2-a]pyrimidine-2-carboxamide;

N-{[6-({[(1-hydroxycyclohexyl)methyl]amino}methyl)imidazo[1,2-a]pyridin-2-yl]methyl}-4-oxo-4H-pyrido[1,2-a]pyrimidine-2-carboxamide;

N-[(6-{[(cyclopentylmethyl)amino]methyl}imidazo[1,2-a]pyridin-2-yl)methyl]-4-oxo-4H-pyrido[1,2-a]pyrimidine-2-carboxamide;

N-{[6-({[(3,3-difluorocyclopentyl)methyl]amino}methyl)imidazo[1,2-a]pyridin-2-yl]methyl}-4-oxo-4H-pyrido[1,2-a]pyrimidine-2-carboxamide;

N-[(6-{[(cyclobutylmethyl)amino]methyl}imidazo[1,2-a]pyridin-2-yl)methyl]-4-oxo-4H-pyrido[1,2-a]pyrimidine-2-carboxamide;

N-{[6-({[2-(3,3-difluorocyclobutyl)ethyl]amino}methyl)imidazo[1,2-a]pyridin-2-yl]methyl}-4-oxo-4H-pyrido[1,2-a]pyrimidine-2-carboxamide;

N-{[6-({[(2-fluorocyclobutyl)methyl]amino}methyl)imidazo[1,2-a]pyridin-2-yl]methyl}-4-oxo-4H-pyrido[1,2-a]pyrimidine-2-carboxamide;

N-{[6-({[(2S)-3,3-dimethylbutan-2-yl]amino}methyl)imidazo[1,2-a]pyridin-2-yl]methyl}-4-oxo-4H-pyrido[1,2-a]pyrimidine-2-carboxamide;

N-{[6-({6-azaspiro[2.5]octan-6-yl}methyl)imidazo[1,2-a]pyridin-2-yl]methyl}-4-oxo-4H-pyrido[1,2-a]pyrimidine-2-carboxamide;

4-oxo-N-({6-[({[(1r,3r)-3-fluorocyclobutyl]methyl}amino)methyl]imidazo[1,2-a]pyridin-2-yl}methyl)-4H-pyrido[1,2-a]pyrimidine-2-carboxamide;

4-oxo-N-({6-[(2-phenylethyl)amino]imidazo[1,2-a]pyridin-2-yl}methyl)-4H-pyrido[1,2-a]pyrimidine-2-carboxamide;

N-({6-[2-(benzylamino)ethyl]imidazo[1,2-a]pyridin-2-yl}methyl)-4-oxo-4H-pyrido[1,2-a]pyrimidine-2-carboxamide;

N-({6-[2-(cyclohexylamino)ethyl]imidazo[1,2-a]pyridin-2-yl}methyl)-4-oxo-4H-pyrido[1,2-a]pyrimidine-2-carboxamide;

4-oxo-N-({6-[(phenylformamido)methyl]imidazo[1,2-a]pyridin-2-yl}methyl)-4H-pyrido[1,2-a]pyrimidine-2-carboxamide;

N-({6-[(cyclohexylformamido)methyl]imidazo[1,2-a]pyridin-2-yl}methyl)-4-oxo-4H-pyrido[1,2-a]pyrimidine-2-carboxamide;

4-oxo-N-{[6-({[(piperidin-3-yl)methyl]amino}methyl)imidazo[1,2-a]pyridin-2-yl]methyl}-4H-pyrido[1,2-a]pyrimidine-2-carboxamide;

4-oxo-N-{[6-({[(piperidin-2-yl)methyl]amino}methyl)imidazo[1,2-a]pyridin-2-yl]methyl}-4H-pyrido[1,2-a]pyrimidine-2-carboxamide;

N-[(6-{[(azetidin-3-yl)amino]methyl}imidazo[1,2-a]pyridin-2-yl)methyl]-4-oxo-4H-pyrido[1,2-a]pyrimidine-2-carboxamide;

N-({6-[(cyclohexylamino)methyl]imidazo[1,2-a]pyridin-2-yl}methyl)-4-oxo-4H-chromene-2-carboxamide;

N-[(6-{[(2-cyclopropylethyl)amino]methyl}imidazo[1,2-a]pyridin-2-yl)methyl]-4-oxo-4H-chromene-2-carboxamide;

4-oxo-N-({6-[(piperidin-1-yl)methyl]imidazo[1,2-a]pyridin-2-yl}methyl)-4H-chromene-2-carboxamide;

N-{[6-({[(4-chlorophenyl)methyl]amino}methyl)imidazo[1,2-a]pyridin-2-yl]methyl}-4-oxo-4H-chromene-2-carboxamide;

N-({6-[(benzylamino)methyl]imidazo[1,2-a]pyridin-2-yl}methyl)-4-oxo-4H-chromene-2-carboxamide;

N-{[6-({[(1-methylcyclohexyl)methyl]amino}methyl)imidazo[1,2-a]pyridin-2-yl]methyl}-4-oxo-4H-chromene-2-carboxamide;

N-[(6-{[(2,2-dimethylpropyl)amino]methyl}imidazo[1,2-a]pyridin-2-yl)methyl]-4-oxo-4H-chromene-2-carboxamide;

4-oxo-N-[(7-{[(2-phenylethyl)amino]methyl}imidazo[1,2-a]pyridin-2-yl)methyl]-4H-pyrido[1,2-a]pyrimidine-2-carboxamide;

N-[(7-{[(cyclohexylmethyl)amino]methyl}imidazo[1,2-a]pyridin-2-yl)methyl]-4-oxo-4H-pyrido[1,2-a]pyrimidine-2-carboxamide;

N-[(7-{[(cyclopropylmethyl)amino]methyl}imidazo[1,2-a]pyridin-2-yl)methyl]-4-oxo-4H-pyrido[1,2-a]pyrimidine-2-carboxamide;

N-[(6-{1-[(cyclohexylmethyl)amino]cyclopropyl}imidazo[1,2-a]pyridin-2-yl)methyl]-4-oxo-4H-pyrido[1,2-a]pyrimidine-2-carboxamide;

N-{[6-(2-amino-3-phenylpropyl)imidazo[1,2-a]pyridin-2-yl]methyl}-4-oxo-4H-pyrido[1,2-a]pyrimidine-2-carboxamide;

(cyclohexylmethyl) [(2-{[4-(1H-indazol-4-yl)-1H-1,2,3-triazol-1-yl]methyl}imidazo[1,2-a]pyridin-6-yl)methyl]amine;

N-(cyclohexylmethyl)-2-{[4-(1H-indazol-4-yl)-1H-1,2,3-triazol-1-yl]methyl}imidazo[1,2-a]pyridine-6-carboxamide;

(2,2-dimethylpropyl)[(2-{[4-(1H-indazol-4-yl)-1H-1,2,3-triazol-1-yl]methyl}imidazo[1,2-a]pyridin-6-yl)methyl]amine;

4-[1-({6-[(4,4-dimethylpiperidin-1-yl)methyl]imidazo[1,2-a]pyridin-2-yl}methyl)-1H-1,2,3-triazol-4-yl]-1H-indazole;

[(2-{[4-(6-bromo-1H-indazol-4-yl)-1H-1,2,3-triazol-1-yl]methyl}imidazo[1,2-a]pyridin-6-yl)methyl][(3,3-difluorocyclobutyl)methyl]amine;

[(2-{[4-(6-bromo-1H-indazol-4-yl)-1H-1,2,3-triazol-1-yl]methyl}imidazo[1,2-a]pyridin-6-yl)methyl](2,2-dimethylpropyl)amine;

[(2-{[4-(6-bromo-1H-indazol-4-yl)-1H-1,2,3-triazol-1-yl]methyl}imidazo[1,2-a]pyridin-6-yl)methyl](cyclohexylmethyl)amine;

6-bromo-4-[1-({6-[(4,4-dimethylpiperidin-1-yl)methyl]imidazo[1,2-a]pyridin-2-yl}methyl)-1H-1,2,3-triazol-4-yl]-1H-indazole;

(2-{[4-(6-bromo-1H-indazol-4-yl)-1H-1,2,3-triazol-1-yl]methyl}imidazo[1,2-a]pyridin-6-yl)methanol;

(2,2-dimethylpropyl)[(2-{[4-(1H-indazol-5-yl)-1H-1,2,3-triazol-1-yl]methyl}imidazo[1,2-a]pyridin-6-yl)methyl]amine;

((cyclohexylmethyl) [1-(2-{[4-(1H-indazol-4-yl)-1H-1,2,3-triazol-1-yl]methyl}imidazo[1,2-a]pyridin-6-yl)ethyl]amine;

(2,2-dimethylpropyl) ({2-[(4-{1H-pyrazolo[3,4-c]pyridin-4-yl}-1H-1,2,3-triazol-1-yl)methyl]imidazo[1,2-a]pyridin-6-yl}methyl)amine;

{2-[(4-{1H-pyrazolo[3,4-c]pyridin-4-yl}-1H-1,2,3-triazol-1-yl)methyl]imidazo[1,2-a]pyridin-6-yl}methanol;

N-({6-[(3R,5S)-5-tert-butylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-tert-butylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-cyclohexylmorpholin-3-yl]imidazo[1,2-a]pyridin-2-yl}methyl)-4-oxo-4H-pyrido[1,2-a]pyrimidine-2-carboxamide;

N-({6-[(3S,5R)-5-cyclohexylmorpholin-3-yl]imidazo[1,2-a]pyridin-2-yl}methyl)-1H-indazole-4-carboxamide;

N-({6-[(3S,5R)-5-cyclohexylmorpholin-3-yl]imidazo[1,2-a]pyridin-2-yl}methyl)-4-oxo-4H-chromene-2-carboxamide;

N-({6-[4-(2,2-dimethylpropyl) morpholin-3-yl]imidazo[1,2-a]pyridin-2-yl}methyl)-4-oxo-4H-pyrido[1,2-a]pyrimidine-2-carboxamide;

N-({6-[(3S,5R)-5-methylmorpholin-3-yl]imidazo[1,2-a]pyridin-2-yl}methyl)-4-oxo-4H-pyrido[1,2-a]pyrimidine-2-carboxamide;

N-{6-(9-methoxy-2,3,4,5-tetrahydro-1,4-benzoxazepin-3-yl)imidazo[1,2-a]pyridin-2-yl]methyl}-4-oxo-4H-pyrido[1,2-a]pyrimidine-2-carboxamide;

4-[1-[[6-[(cyclobutylmethylamino)methyl]imidazo[1,2-a]pyridin-2-yl]methyl]triazol-4-yl]-1H-indazol-6-ol;

4-[1-[[6-[[(1-hydroxycyclobutyl)methylamino]methyl]imidazo[1,2-a]pyridin-2-yl]methyl]triazol-4-yl]-1H-indazol-6-ol;

1-[[[2-[[4-(5-methoxy-1H-indazol-4-yl)triazol-1-yl]methyl]imidazo[1,2-a]pyridin-6-yl]methylamino]methyl]cyclobutanol;

1-[[[2-[[4-(6-methoxy-1H-indazol-4-yl)triazol-1-yl]methyl]imidazo[1,2-a]pyridin-6-yl]methylamino]methyl]cyclobutanol;

N-(cyclobutylmethyl)-1-[2-[[4-(6-methoxy-1H-indazol-4-yl)triazol-1-yl]methyl]imidazo[1,2-a]pyridin-6-yl]methanamine;

N-(cyclobutylmethyl)-1-[2-[[4-(5-methoxy-1H-indazol-4-yl)triazol-1-yl]methyl]imidazo[1,2-a]pyridin-6-yl]methanamine;

4-[1-[(6-methylimidazo[1,2-a]pyridin-2-yl)methyl]triazol-4-yl]-1H-indazol-3-amine;

N-[[6-[[(1-methoxycyclobutyl)methylamino]methyl]imidazo[1,2-a]pyridin-2-yl]methyl]-4-oxo-pyrido[1,2-a]pyrimidine-2-carboxamide;

N-[[6-(1,4-oxazepan-3-yl)imidazo[1,2-a]pyridin-2-yl]methyl]-4-oxo-pyrido[1,2-a]pyrimidine-2-carboxamide;

N-[[6-[[(2-cyano-2-methyl-propyl)amino]methyl]imidazo[1,2-a]pyridin-2-yl]methyl]-4-oxo-pyrido[1,2-a]pyrimidine-2-carboxamide;

N-[[6-[[(3-fluoro-1-bicyclo[1.1.1]pentanyl)methylamino]methyl]imidazo[1,2-a]pyridin-2-yl]methyl]-4-oxo-pyrido[1,2-a]pyrimidine-2-carboxamide;

4-oxo-N-[[6-[(spiro[3.3]heptan-2-ylmethylamino)methyl]imidazo[1,2-a]pyridin-2-yl]methyl]pyrido[1,2-a]pyrimidine-2-carboxamide;

4-oxo-N-[[6-[(spiro[2.3]hexan-5-ylmethylamino)methyl]imidazo[1,2-a]pyridin-2-yl]methyl]pyrido[1,2-a]pyrimidine-2-carboxamide;

N-[[6-[(1-bicyclo[1.1.1]pentanylmethylamino)methyl]imidazo[1,2-a]pyridin-2-yl]methyl]-4-oxo-pyrido[1,2-a]pyrimidine-2-carboxamide;

4-oxo-N-[[6-[(spiro[2.3]hexan-2-ylamino)methyl]imidazo[1,2-a]pyridin-2-yl]methyl]pyrido[1,2-a]pyrimidine-2-carboxamide;

N-[[6-[[(2-methoxy-2-methyl-propyl)amino]methyl]imidazo[1,2-a]pyridin-2-yl]methyl]-4-oxo-pyrido[1,2-a]pyrimidine-2-carboxamide;

N-[[6-[[(1-methylcyclobutyl)methylamino]methyl]imidazo[1,2-a]pyridin-2-yl]methyl]-4-oxo-pyrido[1,2-a]pyrimidine-2-carboxamide;

N-[[6-(butylaminomethyl)imidazo[1,2-a]pyridin-2-yl]methyl]-4-oxo-pyrido[1,2-a]pyrimidine-2-carboxamide;

N-[[6-[[(1-hydroxycyclopentyl)methylamino]methyl]imidazo[1,2-a]pyridin-2-yl]methyl]-4-oxo-pyrido[1,2-a]pyrimidine-2-carboxamide;

N-[[6-[(2-methylbutylamino)methyl]imidazo[1,2-a]pyridin-2-yl]methyl]-4-oxo-pyrido[1,2-a]pyrimidine-2-carboxamide;

N-[[6-[(2-cyclobutylethylamino)methyl]imidazo[1,2-a]pyridin-2-yl]methyl]-4-oxo-pyrido[1,2-a]pyrimidine-2-carboxamide;

N-[[6-[[(2-hydroxy-2-methyl-propyl)amino]methyl]imidazo[1,2-a]pyridin-2-yl]methyl]-4-oxo-pyrido[1,2-a]pyrimidine-2-carboxamide;

N-[[6-[[(1-hydroxycyclobutyl)methylamino]methyl]imidazo[1,2-a]pyridin-2-yl]methyl]-4-oxo-pyrido[1,2-a]pyrimidine-2-carboxamide;

N-[[6-[(2-hydroxybutylamino)methyl]imidazo[1,2-a]pyridin-2-yl]methyl]-4-oxo-pyrido[1,2-a]pyrimidine-2-carboxamide;

N-[[6-[[(3-methylcyclobutyl)methylamino]methyl]imidazo[1,2-a]pyridin-2-yl]methyl]-4-oxo-pyrido[1,2-a]pyrimidine-2-carboxamide;

N-[[6-[[(3,3-dimethylcyclobutyl)methylamino]methyl]imidazo[1,2-a]pyridin-2-yl]methyl]-4-oxo-pyrido[1,2-a]pyrimidine-2-carboxamide;

N-[[6-[(2,2-dimethylbutylamino)methyl]imidazo[1,2-a]pyridin-2-yl]methyl]-4-oxo-pyrido[1,2-a]pyrimidine-2-carboxamide;

N-[[6-[[[(2S)-2-methylbutyl]amino]methyl]imidazo[1,2-a]pyridin-2-yl]methyl]-4-oxo-pyrido[1,2-a]pyrimidine-2-carboxamide;

1-[[[2-[[4-(6-bromo-1H-indazol-4-yl)triazol-1-yl]methyl]imidazo[1,2-a]pyridin-6-yl]methylamino]methyl]cyclohexanol;

1-[[[2-[[4-(6-bromo-1H-indazol-4-yl)triazol-1-yl]methyl]imidazo[1,2-a]pyridin-6-yl]methylamino]methyl]cyclobutanol;

1-[2-[[4-(6-bromo-1H-indazol-4-yl)triazol-1-yl]methyl]imidazo[1,2-a]pyridin-6-yl]-N-(cyclobutylmethyl)methanamine;

4-[1-[[6-[(cyclobutylmethylamino)methyl]imidazo[1,2-a]pyridin-2-yl]methyl]triazol-4-yl]-1H-indazole-6-carboxylic acid;

4-[1-[[6-[(cyclobutylmethylamino)methyl]imidazo[1,2-a]pyridin-2-yl]methyl]triazol-4-yl]-1H-indazole-6-carboxamide;

4-[1-[[6-[(cyclobutylmethylamino)methyl]imidazo[1,2-a]pyridin-2-yl]methyl]triazol-4-yl]-N,N-dimethyl-1H-indazole-6-carboxamide;

[4-[1-[[6-[(cyclobutylmethylamino)methyl]imidazo[1,2-a]pyridin-2-yl]methyl]triazol-4-yl]-1H-indazol-6-yl]-morpholino-methanone;

4-[1-[[6-[(cyclobutylmethylamino)methyl]imidazo[1,2-a]pyridin-2-yl]methyl]triazol-4-yl]-N-(2-hydroxyethyl)-1H-indazole-6-carboxamide;

1-[2-[[4-(6-chloro-1H-indazol-4-yl)triazol-1-yl]methyl]imidazo[1,2-a]pyridin-6-yl]-N-(cyclobutylmethyl)methanamine;

1-[[[2-[[4-(6-chloro-1H-indazol-4-yl)triazol-1-yl]methyl]imidazo[1,2-a]pyridin-6-yl]methylamino]methyl]cyclobutanol;

N-[[2-[[4-(6-chloro-1H-indazol-4-yl)triazol-1-yl]methyl]imidazo[1,2-a]pyridin-6-yl]methyl]-2,2-dimethyl-propan-1-amine;

N-(cyclobutylmethyl)-1-[2-[[4-(7-fluoro-1H-indazol-4-yl)triazol-1-yl]methyl]imidazo[1,2-a]pyridin-6-yl]methanamine;

1-[[[2-[[4-(7-fluoro-1H-indazol-4-yl)triazol-1-yl]methyl]imidazo[1,2-a]pyridin-6-yl]methylamino]methyl]cyclohexanol;

N-(cyclohexylmethyl)-1-[2-[[4-(7-fluoro-1H-indazol-4-yl)triazol-1-yl]methyl]imidazo[1,2-a]pyridin-6-yl]methanamine;

1-[[[2-[[4-(7-fluoro-1H-indazol-4-yl)triazol-1-yl]methyl]imidazo[1,2-a]pyridin-6-yl]methylamino]methyl]cyclobutanol;

1-[[[2-[[4-(7-fluoro-1H-indazol-4-yl)triazol-1-yl]methyl]imidazo[1,2-a]pyridin-6-yl]methylamino]methyl]cyclopentanamine;

N-[[6-[(4,4-dimethyl-1-piperidyl)methyl]imidazo[1,2-a]pyridin-2-yl]methyl]-5-fluoro-4-oxo-chromene-2-carboxamide;

N-(cyclobutylmethyl)-1-[2-[[4-(6-morpholino-1H-indazol-4-yl)triazol-1-yl]methyl]imidazo[1,2-a]pyridin-6-yl]methanamine;

6-[2-(2-aminoethoxy) ethoxy]-N-[[6-[(4,4-dimethyl-1-piperidyl)methyl]imidazo[1,2-a]pyridin-2-yl]methyl]-1H-indazole-4-carboxamide;

N-[[6-[1-(cyclobutylmethylamino)-2-phenyl-ethyl]imidazo[1,2-a]pyridin-2-yl]methyl]-4-oxo-pyrido[1,2-a]pyrimidine-2-carboxamide;

N-[[6-[1-[bis(cyclobutylmethyl)amino]-2-phenyl-ethyl]imidazo[1,2-a]pyridin-2-yl]methyl]-4-oxo-pyrido[1,2-a]pyrimidine-2-carboxamide;

1-[2-[[4-(7-chloro-1H-indazol-4-yl)triazol-1-yl]methyl]imidazo[1,2-a]pyridin-6-yl]-N-(cyclobutylmethyl)methanamine;

1-[[[2-[[4-(7-chloro-1H-indazol-4-yl)triazol-1-yl]methyl]imidazo[1,2-a]pyridin-6-yl]methylamino]methyl]cyclobutanol;

[2-[[4-(6-fluoro-1H-indazol-4-yl)triazol-1-yl]methyl]imidazo[1,2-a]pyridin-6-yl]methanol;

N-(cyclobutylmethyl)-1-[2-[[4-(6-fluoro-1H-indazol-4-yl)triazol-1-yl]methyl]imidazo[1,2-a]pyridin-6-yl]methanamine;

1-[[[2-[[4-(6-fluoro-1H-indazol-4-yl)triazol-1-yl]methyl]imidazo[1,2-a]pyridin-6-yl]methylamino]methyl]cyclobutanol;

N-(cyclohexylmethyl)-1-[2-[[4-(6-fluoro-1H-indazol-4-yl)triazol-1-yl]methyl]imidazo[1,2-a]pyridin-6-yl]methanamine;

N-[[2-[[4-(6-cyclopropyl-1H-indazol-4-yl)triazol-1-yl]methyl]imidazo[1,2-a]pyridin-6-yl]methyl]-2,2-dimethyl-propan-1-amine;

N-[[6-[(cyclobutylmethylamino)methyl]imidazo[1,2-a]pyridin-2-yl]methyl]-1H-indazole-4-carboxamide;

N-(cyclobutylmethyl)-1-[2-[[4-(1H-pyrazolo[4,3-c]pyridin-4-yl)triazol-1-yl]methyl]imidazo[1,2-a]pyridin-6-yl]methanamine;

N-(cyclohexylmethyl)-1-[2-[[4-(1H-pyrazolo[4,3-c]pyridin-4-yl)triazol-1-yl]methyl]imidazo[1,2-a]pyridin-6-yl]methanamine;

1-[[[2-[[4-(1H-pyrazolo[4,3-c]pyridin-4-yl)triazol-1-yl]methyl]imidazo[1,2-a]pyridin-6-yl]methylamino]methyl]cyclobutanol;

N-(cyclobutylmethyl)-1-[2-[[4-(1H-indazol-4-yl)triazol-1-yl]methyl]imidazo[1,2-a]pyridin-6-yl]methanamine;

1-[[[2-[[4-(1H-indazol-4-yl)triazol-1-yl]methyl]imidazo[1,2-a]pyridin-6-yl]methylamino]methyl]cyclohexanol;

2-[[4-(1H-indazol-4-yl)imidazol-1-yl]methyl]-6-methyl-imidazo[1,2-a]pyridine;

N-[[6-[2-cyano-1-(cyclobutylmethylamino)ethyl]imidazo[1,2-a]pyridin-2-yl]methyl]-4-oxo-pyrido[1,2-a]pyrimidine-2-carboxamide;

N-[[6-(6-methylmorpholin-3-yl)imidazo[1,2-a]pyridin-2-yl]methyl]-4-oxo-pyrido[1,2-a]pyrimidine-2-carboxamide;

N-[[6-(7-bromo-9-methoxy-2,3,4,5-tetrahydro-1,4-benzoxazepin-3-yl)imidazo[1,2-a]pyridin-2-yl]methyl]-4-oxo-pyrido[1,2-a]pyrimidine-2-carboxamide;

4-oxo-N-[(6-piperazin-2-ylimidazo[1,2-a]pyridin-2-yl)methyl]pyrido[1,2-a]pyrimidine-2-carboxamide;

N-[[6-(6-cyclohexyl-4-oxo-2-piperidyl)imidazo[1,2-a]pyridin-2-yl]methyl]-4-oxo-pyrido[1,2-a]pyrimidine-2-carboxamide;

1-[2-(1H-indazol-4-yl) thiazol-5-yl]-1-(6-methylimidazo[1,2-a]pyridin-2-yl) ethanol;

2-[[1-(1H-indazol-4-yl)triazol-4-yl]methyl]imidazo[1,2-a]pyridine;

N-[(3,3-difluorocyclobutyl)methyl]-1-[2-[[1-(1H-indazol-4-yl)triazol-4-yl]methyl]imidazo[1,2-a]pyridin-6-yl]methanamine;

4-[1-[[6-[(cyclobutylmethylamino)methyl]imidazo[1,2-a]pyridin-2-yl]methyl]triazol-4-yl]-1H-indazole-6-carbonitrile;

N-(cyclobutylmethyl)-1-[2-[[4-(1H-indazol-4-yl)imidazol-1-yl]methyl]imidazo[1,2-a]pyridin-6-yl]methanamine;

N-[[6-[[acetyl(cyclobutylmethyl)amino]methyl]imidazo[1,2-a]pyridin-2-yl]methyl]-4-oxo-pyrido[1,2-a]pyrimidine-2-carboxamide;

N-(cyclobutylmethyl)-1-[2-[[3-(1H-indazol-4-yl)-1,2,4-triazol-1-yl]methyl]imidazo[1,2-a]pyridin-6-yl]methanamine;

2-[1-[[6-[(cyclobutylmethylamino)methyl]imidazo[1,2-a]pyridin-2-yl]methyl]triazol-4-yl]pyrido[1,2-a]pyrimidin-4-one;

N-[[6-[(2-bicyclo[2.2.1]hept-5-enylmethylamino)methyl]imidazo[1,2-a]pyridin-2-yl]methyl]-4-oxo-pyrido[1,2-a]pyrimidine-2-carboxamide;

N-[[6-[[[(1R,2R,4S)-norbornan-2-yl]methylamino]methyl]imidazo[1,2-a]pyridin-2-yl]methyl]-4-oxo-pyrido[1,2-a]pyrimidine-2-carboxamide;

N-[[6-[[[(1R,2S,4S)-norbornan-2-yl]methylamino]methyl]imidazo[1,2-a]pyridin-2-yl]methyl]-4-oxo-pyrido[1,2-a]pyrimidine-2-carboxamide;

N-[[6-(2-oxa-5-azabicyclo[2.2.1]heptan-5-ylmethyl)imidazo[1,2-a]pyridin-2-yl]methyl]-4-oxo-pyrido[1,2-a]pyrimidine-2-carboxamide;

N-[[6-(2-azabicyclo[2.2.1]heptan-2-ylmethyl)imidazo[1,2-a]pyridin-2-yl]methyl]-4-oxo-pyrido[1,2-a]pyrimidine-2-carboxamide;

N-[[6-(2-azabicyclo[2.2.2]octan-2-ylmethyl)imidazo[1,2-a]pyridin-2-yl]methyl]-4-oxo-pyrido[1,2-a]pyrimidine-2-carboxamide;

N-[[6-[[(2,2-difluorospiro[3.3]heptan-6-yl)amino]methyl]imidazo[1,2-a]pyridin-2-yl]methyl]-4-oxo-pyrido[1,2-a]pyrimidine-2-carboxamide;

4-oxo-N-[[6-[[[rac-(1S,2S,4S)-7-oxabicyclo[2.2.1]hept-5-en-2-yl]methylamino]methyl]imidazo[1,2-a]pyridin-2-yl]methyl]pyrido[1,2-a]pyrimidine-2-carboxamide;

4-oxo-N-[6-[[[rac-(1S,2R,4S)-7-oxabicyclo[2.2.1]hept-5-en-2-yl]methylaminomethyl]imidazo[1,2-a]pyridin-2-yl]methyl]pyrido[1,2-a]pyrimidine-2-carboxamide; and N-[(1-methoxycyclobutyl)methyl]-1-[2-[[4-(6-methoxy-1H-indazol-4-yl)triazol-1-yl]methyl]imidazo[1,2-a]pyridin-6-yl]methanamine.

18. The pharmaceutical composition comprising a compound according to claim 1, or a pharmaceutically acceptable salt thereof, and one or more pharmaceutically acceptable excipients.

\* \* \* \* \*